(12) United States Patent
Gerlach et al.

(10) Patent No.: US 6,875,570 B2
(45) Date of Patent: Apr. 5, 2005

(54) PROTEINS AND NUCLEIC ACIDS ENCODING SAME

(75) Inventors: Valerie L. Gerlach, Branford, CT (US); John R. MacDougall, Hamden, CT (US); Glennda Smithson, Guilford, CT (US); Isabelle Millet, Milford, CT (US); David Stone, Guilford, CT (US); Erik Gunther, Branford, CT (US); Karen Ellerman, Branford, CT (US); William M. Grosse, Branford, CT (US); John P. Alsobrook, II, Madison, CT (US); Denise M. Lepley, Branford, CT (US); Catherine E. Burgess, Wethersfield, CT (US); Muralidhara Padigaru, Branford, CT (US); Ramesh Kekuda, Stamford, CT (US); Kimberly A. Spytek, New Haven, CT (US); Martin D. Leach, Madison, CT (US); Richard A. Shimkets, Guilford, CT (US)

(73) Assignee: CuraGen Corporation, New Haven, CT (US)

(*) Notice: Subject to any disclaimer, the term of this patent is extended or adjusted under 35 U.S.C. 154(b) by 114 days.

(21) Appl. No.: 09/964,956

(22) Filed: Sep. 26, 2001

(65) Prior Publication Data

US 2004/0043926 A1 Mar. 4, 2004

Related U.S. Application Data

(60) Provisional application No. 60/304,868, filed on Jul. 12, 2001, provisional application No. 60/294,823, filed on May 31, 2001, provisional application No. 60/276,667, filed on Mar. 16, 2001, provisional application No. 60/238,399, filed on Oct. 6, 2000, provisional application No. 60/238,396, filed on Oct. 6, 2000, provisional application No. 60/238,321, filed on Oct. 5, 2000, provisional application No. 60/237,434, filed on Oct. 3, 2000, provisional application No. 60/236,135, filed on Sep. 28, 2000, provisional application No. 60/236,066, filed on Sep. 27, 2000, provisional application No. 60/236,065, filed on Sep. 27, 2000, provisional application No. 60/236,064, filed on Sep. 27, 2000, provisional application No. 60/235,808, filed on Sep. 27, 2000, provisional application No. 60/235,633, filed on Sep. 27, 2000, and provisional application No. 60/235,631, filed on Sep. 27, 2000.

(51) Int. Cl.[7] .................................................. C12Q 1/68

(52) U.S. Cl. ...................... 435/6; 435/320.1; 435/252.3; 435/325; 514/44; 536/23.5; 536/23.1

(58) Field of Search .............................. 536/23.1, 23.5; 435/320.1, 325, 252.3, 6; 514/44

(56) References Cited

FOREIGN PATENT DOCUMENTS

| WO | WO 90/00569 | 1/1990 |
|---|---|---|
| WO | WO 01/81363 | 11/2001 |
| WO | WO 02/16593 | 2/2002 |
| WO | WO 02/29038 | 4/2002 |

OTHER PUBLICATIONS

GenBank Accession No.: XP_010150 (Dec. 11, 2001).
GenBank Accession No.: XP_043060 (Dec. 10, 2001).
GenBank Accession No.: XP_045786 (Dec. 10, 2001).
GenBank Accesion No.: B55886 (Nov. 11, 1997).
Baxter (1995). "Insulin–like growth factor binding proteins as glucoregulators." *Metabolism* 44(10 Suppl 4): 12–17.
Bouillet et al. (1997). "Development expression pattern of Stra6, a retinoic acid–responsive gene encoding a new type of membrane protein." *Mech Dev* 63(2): 173–186.
GenBank Accession No.: AAC60070 (Jan. 14, 1997).
GenBank Accession No.: BAB32241 (Jul. 5, 2001).
GenBank Accession No.: AAK07661 (Mar. 22, 2001).
GenBank Accession No.: O14578 (May 30, 2000).
Corse et al. (1999). "Preclinical testing of neuroprotective neurotrophic factors in a model of chronic motor neuron degeneration." *Neurobiol Dis* 6(5): 335–346.
Dearry et al. (1990). "Dopamine induces light–adaptive retinomotor movements in bullfrog cones via D2 receptors and in retinal pigment epithelium via D1 receptors." *J. Neurochem* 54(4): 1367–1378.
Deguchi et al. (2000). "PAPIN. A novel multiple PSD–95/Dlg–A/ZO–1 protein interacting with neural plakophilin–related armadillo repeat protein/delta–catenin and p0071." *J Biol Chem* 275(38): 29875–29880.
del Pozo et al. (1999). "Rho GTPases control migration and polarization of adhesion molecules and cytoskeletal ERM components in T lymphocytes." *Eur J Immunol* 29(11): 3609–3620.
Di Cunto et al. (1998). "Citron rho–interacting kinase, a novel tissue–specific ser/thr kinase encompassing the Rho-Rac–binding protein Citron." *J Biol Chem* 273(45): 29706–29711.
Di Cunto et al. (2000). "Defective neurogenesis in citron kinase knockout mice by altered cytokinesis and massive apoptosis." *Neuron* 28(1): 115–127.
GenBank Accession No.: O75882 (Aug. 20, 2001).
Duke–Cohan et al. (1998). "Attractin (DPPT–L), a member of the CUB family of cell adhesion and guidance proteins, is secreted by activated human T lymphocytes and modulates immune cell interactions." *Proc Natl Acad Sci U S A* 95(19): 11336–11341.

(Continued)

*Primary Examiner*—James Martinell
(74) *Attorney, Agent, or Firm*—Wendy Davis; Mei Benni; George Yahwak

(57) ABSTRACT

Disclosed herein are nucleic acid sequences that encode novel polypeptides. Also disclosed are polypeptides encoded by these nucleic acid sequences, and antibodies, which immunospecifically-bind to the polypeptide, as well as derivatives, variants, mutants, or fragments of the aforementioned polypeptide, polynucleotide, or antibody. The invention further discloses therapeutic, diagnostic and research methods for diagnosis, treatment, and prevention of disorders involving any one of these novel human nucleic acids and proteins.

11 Claims, No Drawings

OTHER PUBLICATIONS

Duke–Cohan et al. (2000). "Attractin: a cub–family protease involved in t cell–monocyte/macrophage interactions." *Adv. Exp Med Biol* 477: 173–185.

Fujisawa et al. (1997). "Function of a cell adhesion molecule, plexin, in neuron network formation." *Dev Neurosci* 19(1): 101–105.

Grandy et al. (1990). "A human D1 dopamine receptor gene is located on chromosome 5 at q35.1 and identifies an EcoRI RFLP." *Am J Hum Genet* 47(5): 828–834.

GenBank Accession No.: AAD25372 (Apr. 16, 1999).

GenBank Accession No.: AF119821 (Apr. 16, 1999).

Gunn et al. (1999). "The mouse mahogany locus encodes a transmembrane form of human attractin." *Nature* 398(6723): 152–156.

Hall et al. (1999), "Determinants of circulating insulin–like growth factor–1." *J Endocrinol Invest* 22(5): 48–57.

Hornig et al. (1999). "An infection–based model of neurodevelopmental damage." *Proc Natl Acad Sci U S A* 96(21): 12102–12107.

Isshiki and Anderson (1999). "Calcium signal transduction from caveolae." *Cell Calcium* 26: 201–208.

Jackson (1999). "The mahogany mouse mutation: further links between pigmentation, obesity and the immune system." *Trends Genet* 15(11): 429–431.

GenBank Accession No.: AK026427 (Sep. 29, 2000).

GenBank Accession No.: NP_115605 (Dec. 10, 2001).

Krieger, M. (1999). "Charting the fate of the "good cholesterol": identification and characterization of the high–density lipoprotein receptor SR–BI." *Annu Rev Biochem* 68: 523–558.

Krushkal et al. (1998). "Linkage and association of adrenergic and dopamine receptor genes in the distal portion of the long arm of chromosome 5 with systolic blood pressure variation." *Hum Mol Genet* 7(9): 1379–1383.

GenBank Accession No.: BAB21018 (Jan. 18, 2001).

Lu et al. (1999). "Distribution of Mahogany/Attractin mRNA in the rat central nervous system." *FEBS Lett* 462(1–2): 101–107.

GenBank Accession No.: AAL54730 (Dec. 28, 2001).

GenBank Accession No.: AAC27933 (Jul. 31, 1998).

GenBank Accession No.: P49025 (May 30, 2000).

Martins, V. R. (1999). "A receptor for infectious and cellular prion protein." *Braz J Med Biol Res* 32(7): 853–859.

GenBank Accession No.: AAK11226 (Feb. 19, 2001).

GenBank Accession No.: AF326591 (Feb. 19, 2001).

Mewar and McMorris (1997). "Expression of insulin–like growth factor–binding protein messenger RNAs in developing rat oligodendrocytes and astrocytes." *J. Neurosci Res* 50(5): 721–728.

GenBank Accession No.: AAF06741 (Nov. 9, 1999).

GenBank Accession No.: JC7160 (May 11, 2000).

SWALL(SPTR) Accession No.: Q9QYS2 (May 1, 2000).

Moller et al. (2000). "The acid–labile subunit of the ternary insulin–like growth factor complex in cirrhosis: relation to liver dysfunction." *J Hepatol* 32(3): 441–446.

Morita et al. (1998). "Expression of a 68kDa–glycoprotein (GP68) and laminin in the mesodermal tissue of the developing mouse embryo." *Okajimas Folia Anat Jpn* 75(4): 185–195.

Moroldo et al. (1998). "Cross–cultural adaptation and validation of an Argentine Spanish Version of the Stanford Childhood Health Assessment Questionnaire." *Arthritis Care Res* 11(5): 382–390.

GenBank Accession No.: BAA20760 (Oct. 6, 2001).

GenBank Accession No.: O94991 (Aug. 20, 2001).

GenBank Accession No.: NP_036202 (Feb. 3, 2001).

GenBank Accession No.: O94933 (Aug. 20, 2001).

Nagase et al. (1999). "Prediction of the coding sequences of unidentified human genes. XIII. The complete sequences of 100 new cDNA clones from brain which code for large proteins in vitro." *DNA Res* 6(1): 63–70.

GenBank Accession No.: BAA76793 (Jun. 16, 1999).

GenBank Accession No.: BAA96055 (Feb. 22, 2001).

GenBank Accession No.: BAB13376 (Feb. 22, 2001).

SWALL(SPTR) Accession No.: Q9WU60 (Oct. 16, 2001).

GenBank Accession No.: BAA32308 (Aug. 13, 1998).

GenBank Accession No.: 151553 (Jul. 21, 2000).

Ohta et al. (1995). "Plexin: a novel neuronal cell surface molecule that mediates cell adhesion via a homophilic binding mechanism in the presence of calcium ions." *Neuron* 14(6): 1189–1199.

Okamoto et al. (1998). "Expression and purification of the extracellular ligand binding region of metabotropic glutamate receptor subtype 1." *J Biol Chem* 273(21): 13089–13096.

Ostrom et al. (2000). "Stoichiometry and compartmentation in G protein–coupled receptor signaling: implications for therapeutic interventions involving G(s)." *J Pharmacol Exp Ther* 294(2): 407–412.

GenBank Accession No.: T46279 (Feb. 4, 2000).

Pardridge, W. M. (1999). "Blood–brain barrier biology and methodology." *J. Neurovirol* 5(6): 556–569.

Pasterkamp et al. (1999). "Semaphorins and their receptors in olfactory axon guidance." *Cell Mol Biol* (Noisy–le–grand) 45(6): 763–779.

Rosenfeld et al. (1999). "The insulin–like growth factor binding protein superfamily: new perspectives." *Pediatrics* 104(4 Pt 2): 1018–1021.

Shan et al. (1998). "Heterogeneity of anti–phospholipid and anti–endothelial cell antibodies." *J Autoimmun* 11(6): 651–660.

Smitt et al. (1998). "[Immunology in the clinical practice. XVI. Paraneoplastic syndromes of the nervous system: pathogenesis and diagnosis]." *Ned Tijdschr Geneeskd* 142(29): 1652–1658 (ABSTRACT ONLY).

Spriggs (1999). "Shared resources between the neural and immune systems: semaphorins join the ranks." *Curr Opin Immunol* 11(4): 387–391.

GenBank Accession No.: AF154831 (Aug. 13, 2001).

GenBank Accession No.: NP_064471 (Nov. 1, 2000).

SPTREMBL Accession No.: Q9WV78 (Nov. 1, 1999).

GenBank Accession No.: NP_112600 (Apr. 24, 2001).

GenBank Accession No.: NP_115774 (Jan. 8, 2002).

Stan et al. (1999). "Isolation, cloning, and localization of rat PV–1, a novel endothelial caveolar protein." *J Cell Biol* 145(6): 1189–1198.

Stan et al. (1999). "PV–1 is a component of the fenestral and stomatal diaphragms in fenestrated endothelia." *Proc Natl Acad Sci U S A* 96(23): 13203–13207.

Stan et al. (1997). "Immunoisolation and partial characterization of endothelial plasmalemmal vesicles (caveolae)." *Mol Biol of Cell* 8(4): 595–605.

GenBank Accession No.: AAH09343 (Jul. 12, 2001).

GenBank Accession No.: P42290 (Jul. 15, 1998).

GenBank Accession No.: NP_000789 (Oct. 26, 2001).

Sunahara et al. (1990). "Human dopamine D1 receptor encoded by an intronless gene on chromosome 5." *Nature* 347(6288): 80–83.

Takahashi et al. (1999). Plexin–neuropilin–1 complexes form functional semaphorin–3A receptor *Cell* 99(1): 59–69.

Tamagnone and Comoglio (2000). "Signalling by semaphorin receptors: cell guidance and beyond." *Trends Cell Biol* 10(9): 377–383.

Tamagnone et al. (1999). "Plexins are a large family of receptors for transmembrane, secreted, and GPI–anchored semaphorins in vertebrates." *Cell* 99(1): 71–80.

GenBank Accession No.: P31422 (Aug. 20, 2001).

Tang et al. (2000). "Secreted and membrane attractin result from alternative splicing of the human ATRN gene." *Proc Natl Acad Sci U S A* 97(11): 6025–6030.

GenBank Accession No.: NP_036900 (Nov. 1, 2000).

Ueki et al. (2000). "Inactivation of the acid labile subunit gene in mice results in mild retardation of postnatal growth despite profound disruptions in the circulating insulin–like growth factor system." *Proc Natl Acad Sci U S A* 97(12): 6868–6873.

GenBank Accession No.: NP_003182 (Jan. 7, 2002).

Wootton and Federhen (1996). "Analysis of compositionally biased regions in sequence databaes." *Methods Enzymol* 266: 554–571.

EBI Database Accession No.: AL137517 (Feb. 18, 2000).

Janosi, J.M.B. (1999). "The acid–labile subunit of the serum insulin–like growth factor–binding protein complexes" *The Journal of Biological Chemistry* 274(33):23328–23332.

Invitation to Pay Additional Fees report for PCT/US 01/42336, mailed Nov. 25, 2002.

GenBank Accession No.: AAK54730 (May 21, 2001).
GenBank Accession No.: AAL54730 (Mar. 27, 2003).
GenBank Accession No.: AB020655 (Jun. 16, 1999).
GenBank Accession No.: AB023166 (Jun. 16, 1999).
GenBank Accession No.: AC002563 (Sep. 26, 1997).
GenBank Accession No.: AF086824 (Nov. 11, 1998).
GenBank Accession No.: AF169411 (Sep. 19, 2000).
GenBank Accession No.: AF170701 (Nov. 9, 1999).
GenBank Accession No.: AF326591 (Feb. 19, 2001).
GenBank Accession No.: AF338650 (Mar. 22, 2001).
GenBank Accession No.: AF369900 (May 21, 2001).
GenBank Accession No.: AK026427 (Sep. 23, 2003).
GenBank Accession No.: BAA96055 (Jul. 5, 2002).
GenBank Accession No.: BAB13376 (May 10, 2002).
GenBank Accession No.: CAB65788 (Jan. 11, 2000).
GenBank Accession No.: CAC32456 (Feb. 23, 2001).
GenBank Accession No.: D86949 (Mar. 31, 2000).
GenBank Accession No.: M75867 (Dec. 31, 1994).
GenBank Accession No.: M92076 (Apr. 27, 1993).
GenBank Accession No.: NP_033182 (Dec. 24, 2003).
GenBank Accession No.: NP_115605 (Dec. 23, 2003).
GenBank Accession No.: O14578 (Jun. 15, 2002).
GenBank Accession No.: O75882 (Jun. 15, 2002).
GenBank Accession No.: O94933 (Jun. 15, 2002).
GenBank Accession No.: O94991 (Jun. 15, 2002).
SWALL (SPTR) Accession No.: Q9BX97 (Jun. 1, 2001).
SWALL (SPTR) Accession No.: Q9H5Y7 (Mar. 1, 2001).
GenBank Accession No.: Q9QYS2 (Sep. 15, 2003).
GenBank Accession No.: Q9WU60 (Jun. 15, 2002).
GenBank Accession No.: T46279 (Feb. 04, 2000).
GenBank Accession No.: XP_010150 (May 13, 2002).
GenBank Accession No.: XP_045786 (Apr. 28, 2003).

Adams, M. D. (1996). "Serial analysis of gene expression: ESTs get smaller." *Bioessays* 18(4): 261–2.

Alderborn, A., A. Kristofferson, et al. (2000). "Determination of single–nucleotide polymorphisms by real–time pyrophosphate DNA sequencing." *Genome Res* 10(8): 1249–58.

Arnold, P. M., J. Y. Ma, et al. (2000). "Selective developmental regulation of gene expression for insulin–like growth factor–binding proteins in mouse spinal cord." *Spine* 25(14): 1765–70.

Bonen, A. (2000). "Lactate transporters (MCT proteins) in heart and skeletal muscles." *Med Sci Sports Exerc* 32(4): 778–89.

Boultwood, J., K. Rack, et al. (1991). "Loss of both CSF1R (FMS) alleles in patients with myelodysplasia and a chromosome 5 deletion." *Proc Natl Acad Sci U S A* 88(14): 6176–80.

De Ferrari, G. V. and N. C. Inestrosa (2000). "Wnt signaling function in Alzheimer's disease." *Brain Res Brain Res Rev* 33(1): 1–12.

Fraser, P. E., G. Yu, et al. (2001). "Presenilin function: connections to Alzheimer's disease and signal transduction." *Biochem Soc Symp* 67: 89–100.

Jezior, J. R., J. D. Brady, et al. (2001). "Dependency of detrusor contractions on calcium sensitization and calcium entry through LOE–908–sensitive channels." *Br J Pharmacol* 134(1): 78–87.

Kone, B. C. (2000). "Protein–protein interactions controlling nitric oxide synthases." *Acta Physiol Scand* 168(1): 27–31.

Murakami, Y., F. Suto, et al. (2001). "Differential expression of plexin–A subfamily members in the mouse nervous system." *Dev Dyn* 220(3): 246–58.

Rohm, B., A. Ottemeyer, et al. (2000). "Plexin/neuropilin complexes mediate repulsion by the axonal guidance signal semaphorin 3A." *Mech Dev* 93(1–2): 95–104.

Walsh, S. V., A. M. Hopkins, et al. (2001). "Rho kinase regulates tight junction function and is necessary for tight junction assembly in polarized intestinal epithelia." *Gastroenterology* 121(3): 566–79.

Wassink, T. H., J. Piven, et al. (2001). "Evidence supporting WNT2 as an autism susceptibility gene." *Am J Med Genet* 105(5): 405–13.

PROTEINS AND NUCLEIC ACIDS ENCODING SAME

RELATED APPLICATIONS

This application claims priority from U.S. Ser. No. 60/235,631, filed Sep. 27, 2000; U.S. Ser. No. 60/235,633, filed Sep. 27, 2000; U.S. Ser. No. 60/235,808, filed Sep. 27, 2000; U.S. Ser. No. 60/236,064, filed Sep. 27, 2000; U.S. Ser. No. 60/236,065, filed Sep. 27, 2000; U.S. Ser. No. 60/236,066, filed Sep. 27, 2000; U.S. Ser. No. 60/236,135, filed Sep. 28, 2000; U.S. Ser. No. 60/237,434, filed Oct. 3, 2000; U.S. Ser. No. 60/238,321, filed Oct. 5, 2000; U.S. Ser. No. 60/238,399, filed Oct. 6, 2000; U.S. Ser. No. 60/238,396, filed Oct. 6, 2000; U.S. Ser. No. 60/276,667, filed Mar. 16, 2001; U.S. Ser. No. 60/294,823, filed May 31, 2001; and U.S. Ser. No. 60/304,868, filed Jul. 12, 2001 each of which is incorporated by reference in its entirety.

FIELD OF THE INVENTION

The invention generally relates to nucleic acids and polypeptides encoded thereby.

BACKGROUND OF THE INVENTION

The invention generally relates to nucleic acids and polypeptides encoded therefrom. More specifically, the invention relates to nucleic acids encoding cytoplasmic, nuclear, membrane bound, and secreted polypeptides, as well as vectors, host cells, antibodies, and recombinant methods for producing these nucleic acids and polypeptides.

SUMMARY OF THE INVENTION

The invention is based in part upon the discovery of nucleic acid sequences encoding novel polypeptides. The novel nucleic acids and polypeptides are referred to herein as NOVX, or NOV1, NOV2, NOV3, NOV4, NOV5, NOV6, NOV7, and NOV8 nucleic acids and polypeptides. These nucleic acids and polypeptides, as well as derivatives, homologs, analogs and fragments thereof, will hereinafter be collectively designated as "NOVX" nucleic acid or polypeptide sequences.

In one aspect, the invention provides an isolated NOVX nucleic acid molecule encoding a NOVX polypeptide that includes a nucleic acid sequence that has identity to the nucleic acids disclosed in SEQ ID NOS:1, 3, 4, 6, 8, 10, 12, 14, 16, 18, 20, 22, 24, and 26. In some embodiments, the NOVX nucleic acid molecule will hybridize under stringent conditions to a nucleic acid sequence complementary to a nucleic acid molecule that includes a protein-coding sequence of a NOVX nucleic acid sequence. The invention also includes an isolated nucleic acid that encodes a NOVX polypeptide, or a fragment, homolog, analog or derivative thereof. For example, the nucleic acid can encode a polypeptide at least 80% identical to a polypeptide comprising the amino acid sequences of SEQ ID NOS:2, 5, 7, 9, 11, 13, 15, 17, 19, 21, 23, 25, and 27. The nucleic acid can be, for example, a genomic DNA fragment or a cDNA molecule that includes the nucleic acid sequence of any of SEQ ID NOS:1, 3, 4, 6, 8, 10, 12, 14, 16, 18, 20, 22, 24, and 26.

Also included in the invention is an oligonucleotide, e.g., an oligonucleofide which includes at least 6 contiguous nucleotides of a NOVX nucleic acid (e.g., SEQ ID NOS:1, 3, 4, 6, 8, 10, 12, 14, 16, 18, 20, 22, 24, and 26) or a complement of said oligonucleotide.

Also included in the invention are substantially purified NOVX polypeptides (SEQ ID NOS:2, 5, 7, 9, 11, 13, 15, 17, 19, 21, 23, 25, and 27). In certain embodiments, the NOVX polypeptides include an amino acid sequence that is substantially identical to the amino acid sequence of a human NOVX polypeptide.

The invention also features antibodies that immunoselectively bind to NOVX polypeptides, or fragments, homologs, analogs or derivatives thereof.

In another aspect, the invention includes pharmaceutical compositions that include therapeutically- or prophylactically-effective amounts of a therapeutic and a pharmaceutically-acceptable carrier. The therapeutic can be, e.g., a NOVX nucleic acid, a NOVX polypeptide, or an antibody specific for a NOVX polypeptide. In a further aspect, the invention includes, in one or more containers, a therapeutically- or prophylactically-effective amount of this pharmaceutical composition.

In a further aspect, the invention includes a method of producing a polypeptide by culturing a cell that includes a NOVX nucleic acid, under conditions allowing for expression of the NOVX polypeptide encoded by the DNA. If desired, the NOVX polypeptide can then be recovered.

In another aspect, the invention includes a method of detecting the presence of a NOVX polypeptide in a sample. In the method, a sample is contacted with a compound that selectively binds to the polypeptide under conditions allowing for formation of a complex between the polypeptide and the compound. The complex is detected, if present, thereby identifying the NOVX polypeptide within the sample.

The invention also includes methods to identify specific cell or tissue types based on their expression of a NOVX.

Also included in the invention is a method of detecting the presence of a NOVX nucleic acid molecule in a sample by contacting the sample with a NOVX nucleic acid probe or primer, and detecting whether the nucleic acid probe or primer bound to a NOVX nucleic acid molecule in the sample.

In a further aspect, the invention provides a method for modulating the activity of a NOVX polypeptide by contacting a cell sample that includes the NOVX polypeptide with a compound that binds to the NOVX polypeptide in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

Also within the scope of the invention is the use of a therapeutic in the manufacture of a medicament for treating or preventing disorders or syndromes including, e.g., Cancer, Leukodystrophies, Breast cancer, Ovarian cancer, Prostate cancer, Uterine cancer, Hodgkin disease, Adenocarcinoma, Adrenoleukodystrophy, Cystitis, incontinence, Von Hippel-Lindau (VHL) syndrome, hypercalceimia, Endometriosis, Hirschsprung's disease, Crohn's Disease, Appendicitis, Cirrhosis, Liver failure, Wolfram Syndrome, Smith-Lemli-Opitz syndrome, Retinitis pigmentosa, Leigh syndrome; Congenital Adrenal Hyperplasia, Xerostomia; tooth decay and other dental problems; Inflammatory bowel disease, Diverticular disease, fertility, Infertility, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, Hemophilia, Hypercoagulation, Idiopathic thrombocytopenic purpura, obesity, Diabetes Insipidus and Mellitus with Optic Atrophy and Deafness, Pancreatitis, Metabolic Dysregulation, transplantation recovery, Autoimmune disease, Systemic lupus erythematosus, asthma, arthritis, psoriasis, Emphysema, Scleroderma, allergy, ARDS, Immunodeficiencies, Graft vesus host, Alzheimer's disease, Stroke, Parkinson's disease, Huntington's disease, Cerebral palsy, Epilepsy, Multiple sclerosis, Ataxia-telangiectasia, Behavioral disorders, Addiction, Anxiety, Pain, Neurodegeneration, Muscular dystrophy, Lesch-Nyhan syndrome, Myasthenia gravis, schizophrenia, and other dopamine-dysfunctional states, levodopa-induced dyskinesias, alcoholism, pileptic seizures and other neurological disorders, mental depression, Cerebellar ataxia, pure; Episodic ataxia, type 2; Hemiplegic migraine, Spinocerebellar ataxia-6, Tuberous sclerosis, Renal artery stenosis, Interstitial nephritis, Glomerulonephritis, Polycystic kidney disease, Renal tubular acidosis, IgA nephropathy, and/or other pathologies and disorders of the like.

The therapeutic can be, e.g., a NOVX nucleic acid, a NOVX polypeptide, or a NOVX-specific antibody, or biologically-active derivatives or fragments thereof.

For example, the compositions of the present invention will have efficacy for treatment of patients suffering from the diseases and disorders disclosed above and/or other pathologies and disorders of the like. The polypeptides can be used as immunogens to produce antibodies specific for the invention, and as vaccines. They can also be used to screen for potential agonist and antagonist compounds. For example, a cDNA encoding NOVX may be useful in gene therapy, and NOVX may be useful when administered to a subject in need thereof. By way of non-limiting example, the compositions of the present invention will have efficacy for treatment of patients suffering from the diseases and disorders disclosed above and/or other pathologies and disorders of the like.

The invention further includes a method for screening for a modulator of disorders or syndromes including, e.g., the diseases and disorders disclosed above and/or other pathologies and disorders of the like. The method includes contacting a test compound with a NOVX polypeptide and determining if the test compound binds to said NOVX polypeptide. Binding of the test compound to the NOVX polypeptide indicates the test compound is a modulator of activity, or of latency or predisposition to the aforementioned disorders or syndromes.

Also within the scope of the invention is a method for screening for a modulator of activity, or of latency or predisposition to disorders or syndromes including, e.g. the diseases and disorders disclosed above and/or other pathologies and disorders of the like by administering a test compound to a test animal at increased risk for the aforementioned disorders or syndromes. The test animal expresses a recombinant polypeptide encoded by a NOVX nucleic acid. Expression or activity of NOVX polypeptide is then measured in the test animal, as is expression or activity of the protein in a control animal which recombinantly-expresses NOVX polypeptide and is not at increased risk for the disorder or syndrome. Next, the expression of NOVX polypeptide in both the test animal and the control animal is compared. A change in the activity of NOVX polypeptide in the test animal relative to the control animal indicates the test compound is a modulator of latency of the disorder or syndrome.

In yet another aspect, the invention includes a method for determining the presence of or predisposition to a disease associated with altered levels of a NOVX polypeptide, a NOVX nucleic acid, or both, in a subject (e.g., a human subject). The method includes measuring the amount of the NOVX polypeptide in a test sample from the subject and comparing the amount of the polypeptide in the test sample to the amount of the NOVX polypeptide present in a control sample. An alteration in the level of the NOVX polypeptide in the test sample as compared to the control sample indicates the presence of or predisposition to a disease in the subject. Preferably, the predisposition includes, e.g., the diseases and disorders disclosed above and/or other pathologies and disorders of the like. Also, the expression levels of the new polypeptides of the invention can be used in a method to screen for various cancers as well as to determine the stage of cancers.

In a further aspect, the invention includes a method of treating or preventing a pathological condition associated with a disorder in a mammal by administering to the subject a NOVX polypeptide, a NOVX nucleic acid, or a NOVX-specific antibody to a subject (e.g., a human subject), in an amount sufficient to alleviate or prevent the pathological condition. In preferred embodiments, the disorder, includes, e.g., the diseases and disorders disclosed above and/or other pathologies and disorders of the like.

In yet another aspect, the invention can be used in a method to identity the cellular receptors and downstream effectors of the invention by any one of a number of techniques commonly employed in the art. These include but are not limited to the two-hybrid system, affinity purification, co-precipitation with antibodies or other specific-interacting molecules.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The present invention provides novel nucleotides and polypeptides encoded thereby. Included in the invention are the novel nucleic acid sequences and their encoded polypeptides. The sequences are collectively referred to herein as "NOVX nucleic acids" or "NOVX polynucleotides" and the corresponding encoded polypeptides are referred to as "NOVX polypeptides" or "NOVX proteins." Unless indicated otherwise, "NOVX" is meant to refer to any of the novel sequences disclosed herein. Table A provides a summary of the NOVX nucleic acids and their encoded polypeptides.

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

NOV1 is homologous to a Insulin Like Growth Factor Binding Protein Complex-Acid Labile Subunit-like family of proteins. Thus, the NOV1 nucleic acids, polypeptides, antibodies and related compounds according to the invention will be useful in therapeutic and diagnostic applications implicated in, for example; cancer, cystitis, incontinence, fertility, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation recovery, and/or other pathologies/disorders.

NOV2 is homologous to the Attractin-like family of proteins. Thus NOV2 nucleic acids, polypeptides, antibodies and related compounds according to the invention will be useful in therapeutic and diagnostic applications implicated in, for example; Von Hippel-Lindau (VHL) syndrome, Alzheimer's disease, Stroke, Tuberous sclerosis, hypercalceimia, Parkinson's disease, Huntington's disease, Cerebral palsy, Epilepsy, Multiple sclerosis, Ataxia-telangiectasia, Leukodystrophies, Behavioral disorders, Addiction, Anxiety, Pain, Neurodegeneration, Diabetes, Autoimmune disease, Renal artery stenosis, Interstitial nephritis, Glomermlonephritis, Polycystic kidney disease, Systemic lupus erythematosus, Renal tubular acidosis, IgA nephropathy, Hypercalceimia, Diabetes, Pancreatitis, Obesity, Endometriosis, Infertility, Hirschsprung's disease, Crohn's Disease, Appendicitis, Muscular dystrophy, Lesch-Nyhan syndrome, Myasthenia gravis, Cirrhosis, Liver failure, Breast cancer, Ovarian cancer, Prostate cancer, Uterine cancer and/or other pathologies/disorders.

NOV3 is homologous to a family of RHO/RAC-interacting citron kinase-like proteins. Thus, the NOV3 nucleic acids and polypeptides, antibodies and related compounds according to the invention will be useful in therapeutic and diagnostic applications implicated in, for example: asthma, arthritis, psoriasis, diabetes, and IBD, which require activated T cells, as well as diseases such as systemic lupus erythematosus that involve B cell activation, Autoimmune disease, Renal artery stenosis, Interstitial nephritis, Glomerulonephritis, Polycystic kidney disease, Renal tubular acidosis, IgA nephropathy, Hypercalceimia, Lesch-Nyhan syndrome, Von Hippel-Lindau (VHL) syndrome, Alzheimer's disease, Stroke, Tuberous sclerosis, hypercalceimia, Parkinson's disease, Huntington's disease, Cerebral palsy, Epilepsy, Multiple sclerosis, Ataxia-telangiectasia, Leukodystrophies, Behavioral disorders, Addiction, Anxiety, Pain, Neuroprotection, Endocrine dysfunctions, Obesity, Growth and Reproductive disorders Hemophilia, hypercoagulation, idiopathic thrombocytopenic purpura, allergies, immunodeficiencies, transplantation, Lymphaedema, Hemophilia, Hypercoagulation, Idiopathic thrombocytopenic purpura, Immunodeficiencies, Graft vesus host, Hirschsprung's disease, Crohn's Disease, Appendicitis Inflammatory bowel disease, Diverticular disease and/or other pathologies/disorders.

NOV4 is homologous to the Plexin-like family of proteins. Thus, NOV4 nucleic acids, polypeptides, antibodies and related compounds according to the invention will be useful in therapeutic and diagnostic applications implicated in, for example: Von Hippel-Lindau (VHL) syndrome, Alzheimer's disease, Stroke, Tuberous sclerosis, hypercalceimia, Parkinson's disease, Huntington's disease, Cerebral palsy, Epilepsy, Lesch-Nyhan syndrome, Multiple sclerosis, Ataxia-telangiectasia, Leukodystrophies, Behavioral disorders, Addiction, Anxiety, Pain, Neurodegeneration, Systemic lupus erythematosus, Autoimmune disease, Asthma, Emphysema, Scleroderma, allergy, ARDS, Obesity, Metabolic Dysregulation, Infertility and/or other pathologies/disorders.

NOV5 is homologous to the Dopamine receptor-like family of proteins. Thus NOV5 nucleic acids, polypeptides, antibodies and related compounds according to the invention will be useful in therapeutic and diagnostic applications implicated in, for example: schizophrenia, and other dopamine-dysfunctional states, Hypertension, Huntington's disease, levodopa-induced dyskinesias, alcoholism, Diabetes Insipidus and Mellitus with Optic Atrophy and Deafness, Wolfram Syndrome and/or other pathologies/disorders.

NOV6 is homologous to the Metabotropic Glutamate Receptor-like family of proteins. Thus NOV6 nucleic acids, polypeptides, antibodies and related compounds according to the invention will be useful in therapeutic and diagnostic applications implicated in, for example: pileptic seizures and other neurological disorders, Hodgkin disease, polycystic kidney disease, mental depression, Adenocarcinoma, Smith-Lemli-Opitz syndrome, Retinitis pigmentosa and/or other pathologies/disorders.

NOV7 is homologous to members of the PV-1-like family of proteins. Thus, the NOV7 nucleic acids, polypeptides, antibodies and related compounds according to the invention will be useful in therapeutic and diagnostic applications implicated in, for example; Cerebellar ataxia, pure; Episodic ataxia, type 2; Hemiplegic migraine, familial; Leigh syndrome; Spinocerebellar ataxia-6; Psoriasis, susceptibility to; Autoimmune disease, Asthma, Emphysema, Scleroderma, allergy, ARDS, Von Hippel-Lindau (VHL) syndrome, Alzheimer's disease, Stroke, Tuberous sclerosis, hypercalceimia, Parkinson's disease, Huntington's disease, Cerebral palsy, Epilepsy, Lesch-Nyhan syndrome, Multiple sclerosis, Ataxia-telangiectasia, Leukodystrophies, Behavioral disorders, Addiction, Anxiety, Pain, Neuroprotection, Muscular dystrophy, Myasthenia gravis, Hemophilia, Hypercoagulation, Idiopathic thrombocytopenic purpura, Immunodeficiencies, Graft vesus host, Von Hippel-Lindau (VHL) syndrome, Cirrhosis, Transplantation, Cardiomyopathy, Atherosclerosis, Hypertension, Congenital heart defects, Aortic stenosis, Atrial septal defect (ASD), Atrioventricular (A-V) canal defect, Ductus arteriosus, Pulmonary stenosis, Subaortic stenosis, Ventricular septal defect (VSD), valve diseases, Scleroderma, Obesity, Transplantation; fertility; cancer; Renal artery stenosis, Interstitial nephritis, Glomerulonephritis, Polycystic kidney disease, Systemic lupus erythematosus, Renal tubular acidosis, IgA nephropathy, Hypercalceimia, Lesch-Nyhan syndrome, Adrenoleukodystrophy, Congenital Adrenal Hyperplasia, Xerostomia; tooth decay and other dental problems; Inflammatory bowel disease, Diverticular disease, Pancreatitis, and/or other pathologies/disorders.

NOV8 is homologous to the Papin-like family of proteins. Thus, NOV8 nucleic acids and polypeptides, antibodies and related compounds according to the invention will be useful in therapeutic and diagnostic applications implicated in, for example; cancer, cystitis, incontinence, fertility, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation recovery and/or other pathologies/disorders.

The NOVX nucleic acids and polypeptides can also be used to screen for molecules, which inhibit or enhance NOVX activity or function. Specifically, the nucleic acids and polypeptides according to the invention may be used as targets for the identification of small molecules that modulate or inhibit, e.g., neurogenesis, cell differentiation, cell proliferation, hematopoiesis, wound healing and angiogenesis.

Additional utilities for the NOVX nucleic acids and polypeptides according to the invention are disclosed herein.

NOV1

NOV1 includes three novel Insulin Like Growth Factor Binding Protein Complex-Acid Labile Subunit (IGFBP-ALS)-like proteins disclosed below. The disclosed sequences have been named NOV1a, NOV1b, and NOV1c. The nucleotide sequences for NOV1a and b both code for the NOV1a protein sequence. The NOV1c nucleic acid sequence codes for the NOV1c protein sequence.

NOV1a

A disclosed NOV1a nucleic acid of 2838 nucleotides (also referred to as 83420733_EXT) encoding a novel Insulin Like Growth Factor Binding Protein Complex-Acid Labile Subunit-like protein is shown in Table 1A. An open reading frame was identified beginning with an ATG initiation codon at nucleotides 184–186 and ending with a TAG codon at nucleotides 2707–2709. A putative untranslated region upstream from the initiation codon and downstream from the termination codon is underlined in Table 1A. The start and stop codons are in bold letters.

TABLE 1A

NOV1a nucleotide sequence (SEQ ID NO:1).

AACTTTATGAAGCTATGGGACTTGACAAAAAGTGATATTTGAGAAGAAAGTACGCAGTGGTTGGTGTTTTCT

TTTTTTTAATAAAGGAATTGAATTACTTTGAACACCTCTTCCAGCTGTGCATTACAGATAACGTCAGGAAGA

GTCTCTGCTTTACAGAATCGGATTTCATCACATGACAACATGAAGCTGTGGATTCATCTCTTTTATTCATCT

CTCCTTGCCTGTATATCTTTACACTCCCAAACTCCAGTGCTCTCATCCAGAGGCTCTTGTGATTCTCTTTGC

AATTGTGAGGAAAAAGATGGCACAATGCTAATAAATTGTGAAGCAAAAGGTATCAAGATGGTATCTGAAATA

AGTGTGCCACCATCACGACCTTTCCAACTAAGCTTATTAAATAACGGCTTGACGATGCTTCACACAAATGAC

TTTTCTGGGCTTACCAATGCTATTTCAATACACCTTGGATTTAACAATATTGCAGATATTGAGATAGGTGCA

TTTAATGGCCTTGGCCTCCTGAAACAACTTCATATCAATCACAATTCTTTAGAAATTCTTAAAGAGGATACT

TTCCATGGACTGGAAAACCTGGAATTCCTGCAAGCAGATAACAATTTTATCACAGTGATTGAACCAAGTGCC

TTTAGCAAGCTCAACAGACTCAAAGTGTTAATTTTAAATGACAATGCTATTGAGAGTCTTCCTCCAAACATC

TTCCGATTTGTTCCTTTAACCCATCTAGATCTTCGTGGAAATCAATTACAAACATTGCCTTATGTTGGTTTT

GTCGAACACATTGGCCGAATATTGGATCTTCAGTTGGAGGACAACAAATGGGCCTGCAATTGTGACTTATTG

CAGTTAAAAACTTGGTTGGAGAACATGCCTCCACAGTCTATAATTGGTGATGTTGTCTGCAACAGCCCTCCA

TTTTTTAAAGGAAGTATACTCAGTAGACTAAAGAAGGAATCTATTTGCCCTACTCCACCAGTGTATGAAGAA

CATGAGGATCCTTCAGGATCATTACATCTGGCAGCAACATCTTCAATAAATGATAGTCGCATGTCAACTAAG

ACCACGTCCATTCTAAAACTACCCACCAAAGCACCAGGTTTGATACCTTATATTACAAAGCCATCCACTCAA

CTTCCAGGACCTTACTGCCCTATTCCTTGTAACTGCAAAGTCCTATCCCCATCAGGACTTCTAATACATTGT

CAGGAGCGCAACATTGAAAGCTTATCAGATCTGAGACCTCCTCCGCAAAATCCTAGAAAGCTCATTCTAGCG

GGAAATATTATTCACAGTTTAATGAAGTCTGATCTAGTGGAATATTTCACTTTGGAAATGCTTCACTTGGGA

AACAATCGTATTGAAGTTCTTGAAGAAGGATCGTTTATGAACCTAACGAGATTACAAAAACTCTATCTAAAT

GGTAACCACCTGACCAAATTAAGTAAAGGCATGTTCCTTGGTCTCCATAATCTTGAATACTTATATCTTGAA

TACAATGCCATTAAGGAAATACTGCCAGGAACCTTTAATCCAATGCCTAAACTTAAAGTCCTGTATTTAAAT

AACAACCTCCTCCAAGTTTTACCACCACATATTTTTTCAGGGGTTCCTCTAACTAAGGTAAATCTTAAAACA

AACCAGTTTACCCATCTACCTGTAAGTAATATTTTGGATGATCTTGATTTACTAACCCAGATTGACCTTGAG

GATAACCCCTGGGACTGCTCCTGTGACCTGGTTGGACTGCAGCAATGGATACAAAAGTTAAGCAAGAACACA

GTGACAGATGACATCCTCTGCACTTCCCCCGGGCATCTCGACAAAAAGGAATTGAAAGCCCTAAATAGTGAA

ATTCTCTGTCCAGGTTTAGTAAATAACCCATCCATGCCAACACAGACTAGTTACCTTATGGTCACCACTCCT

GCAACAACAACAAATACGGCTGATACTATTTTACGATCTCTTACGGACGCTGTGCCACTGTCTGTTCTAATA

TTGGGACTTCTGATTATGTTCATCACTATTGTTTTCTGTGCTGCAGGGATAGTGGTTCTTGTTCTTCACCGC

TABLE 1A-continued

NOV1a nucleotide sequence (SEQ ID NO:1).

AGGAGAAGATACAAAAAGAAACAAGTAGATGAGCAAATGAGAGACAACAGTCCTGTGCATCTTCAGTACAGC

ATGTATGGCCATAAAACCACTCATCACACTACTGAAAGACCCTCTGCCTCACTCTATGAACAGCACATGGTG

AGCCCCATGGTTCATGTCTATAGAAGTCCATCCTTTGGTCCAAAGCATCTGGAAGAGGAAGAAGAGAGGAAT

GAGAAAGAAGGAAGTGATGCAAAACATCTCCAAAGAAGTCTTTTGGAACAGGAAAATCATTCACCACTCACA

GGGTCAAATATGAAATACAAAACCACGAACCAATCAACAGAATTTTTATCCTTCCAAGATGCCAGCTCATTG

TACAGAAACATTTTAGAAAAAGAAAGGGAACTTCAGCAACTGGGAATCACAGAATACCTAAGGAAAAACATT

GCTCAGCTCCAGCCTGATATGGAGGCACATTATCCTGGAGCCCACGAAGAGCTGAAGTTAATGGAAACATTA

ATGTACTCACGTCCAAGGAAGGTATTAGTGGAACAGACAAAAAAATGAGTATTTTGAACTTAAAGTAATTTA

CATGCTGAACCTGACTATTTAGAAGTCCTGGAGCAGCAAACATAG<u>ATGGAGAGTTTGAGGGCTTTCGCAGAA</u>

<u>ATGCTGTGATTCTGTTTTAAGTCCATACCTTGTAAATTAGTGCCTTACGTGAGTGTGTCATCCATCAGAACC</u>

<u>TAAGCACAGCAGTAAACTATGGAGAAAAAA</u>

In a search of public sequence databases, the NOV1a nucleic acid sequence, located on chromsome 13 has 1173 of 1932 bases (61%) identical to a KIAA0848 mRNA from human (gb:GENBANK-ID:AB020655|acc:AB020655). Public nucleotide databases include all GenBank databases and the GeneSeq patent database.

In all BLAST alignments herein, the "E-value" or "Expect" value is a numeric indication of the probability that the aligned sequences could have achieved their similarity to the BLAST query sequence by chance alone, within the database that was searched. For example, the probability that the subject ("Sbjct") retrieved from the NOV1 BLAST analysis, e.g., thioredoxin mRNA from *Ovis aries*, matched the Query NOV1 sequence purely by chance is $7.4e^{-68}$. The Expect value (E) is a parameter that describes the number of hits one can "expect" to see just by chance when searching a database of a particular size. It decreases exponentially with the Score (S) that is assigned to a match between two sequences. Essentially, the E value describes the random background noise that exists for matches between sequences.

The Expect value is used as a convenient way to create a significance threshold for reporting results. The default value used for blasting is typically set to 0.0001. In BLAST 2.0, the Expect value is also used instead of the P value (probability) to report the significance of matches. For example, an E value of one assigned to a hit can be interpreted as meaning that in a database of the current size one might expect to see one match with a similar score simply by chance. An E value of zero means that one would not expect to see any matches with a similar score simply by chance. See, e.g., http://www.ncbi.nlm.nih.gov/Education/BLASTinfo/. Occasionally, a string of X's or N's will result from a BLAST search. This is a result of automatic filtering of the query for low-complexity sequence that is performed to prevent artifactual hits. The filter substitutes any low-complexity sequence that it finds with the letter "N" in nucleotide sequence (e.g., "NNNNNNNNNNNNN") or the letter "X" in protein sequences (e.g., "XXXXXXXXX"). Low-complexity regions can result in high scores that reflect compositional bias rather than significant position-by-position alignment. (Wootton and Federhen, Methods Enzymol 266:554–571, 1996).

The disclosed NOV1a polypeptide (SEQ ID NO:2) encoded by SEQ ID NO:1 has 841 amino acid residues and is presented in Table 1B using the one-letter amino acid code. Signal P, Psort and/or Hydropathy results predict that NOV1a has a signal peptide and is likely to be localized in the plasma membrane with a certainty of 0.4600. In other embodiments, NOV1a may also be localized to the endoplasmic reticulum (membrane) with a certainty of 0.1000, the endoplasmic reticulum (membrane) with a certainty of 0.1000, or extracellularly with a certainty of 0.1000. The most likely cleavage site for a NOV1a peptide is between amino acids 20 and 21, at: LHS-QT.

SNP data for NOV1 a can be found below in Example 3. SAGE data can also be found below for NOV1a in Example 4.

TABLE 1B

Encoded NOV1a protein sequence (SEQ ID NO:2).

MKLWIHLFYSSLLACISLHSQTPVLSSRGSCDSLCNCEEDGTMLINCEAKGIKMVSEISVPPS

RPFQLSLLNNGLTMLHTNDFSGLTNAISIHLGFNNIADIEIGAFNGLGLLKQLHINHNSLEILK

EDTFHGLENLEFLQADNNFITVIEPSAFSKLNRLKVLILNDNAIESLPPNIFRFVPLTWLDLRG

NQLQTLPYVGFLEHIGRILDLQLEDNKEACNCDLLQLKTWLENMPPQSIIGDVVCNSPPFFKGS

ILSRLKKESICPTPPVYEEHEDPSGSLHLAATSSINDSRMSTKTTSILKLPTKAPGLIPYITKP

TABLE 1B-continued

Encoded NOV1a protein sequence (SEQ ID NO:2).

STQLPGPYCPIPCNCKVLSPSGLLIHCQERNIESLSDLRPPPQNPRKLILAGNIIHSLMKSDLV

EYEFTLEMLHLGNNRIEVLEEGSFMNLTRLQKLYLNGNHLTKLSKGMFLGLHLEYLYLEYNAIK

EILPGTFNPMPKLKVLYLNNNLLQVLPPHIFSGVPLTKVNLKTNQFTHLPVSNILDDLDLLTQI

DLEDNPWDCSCDLVGLQQWIQKLSKNTVTDDILCTSPGHLDKKELKALNSEILCPGLVNNPSMP

TQTSYLMVTTPATTTNTADTILRSLTADVPLSVLILGLLIMFITTIVFCAGGIVVLVLHRRRYK

KKQVDEQMRDNSPVHLQYSMYGHKTTHHTTERPSASLYEQHMVSOMVHVYRSPSFGPKHLEEEE

ERNEKEGSDAKHLQRSLLEQENHSPLTGSNMKYKTTNQSTEFLSFQDASSLYRNILEKERELQQ

LGITEYLRKNIAQLQPDMEAHYPGAHEELKLMETLMYSRPRKVLVEQTKNEYFELKANLHAEPD

YLEVLEQQT

A search of sequence databases reveals that the NOV1a amino acid sequence has 266 of 543 amino acid residues (49%) identical to, and 337 of 543 amino acid residues (62%) similar to the 977 amino acid residue KIAA0848 protein from human (SPTREMBL-ACC:O94933) (E=1.6e−165), and 350 of 841 amino acid residues (41%) identical to, and 511 of 841 amino acid residues (60%) similar to the 845 amino acid residue Human gene 1 encoded secreted protein HMIAJ30 (patp:AAE01232) (E=1.6e−156). Public amino acid databases include the GenBank databases, SwissProt, PDB and PIR.

NOV1a is expressed in at least the following tissues: breast, heart, bladder, colon, prostate, brain, lung and uterus.

TaqMan expression data for NOV1a is shown below in Example 2.

NOV1b

A disclosed NOV1b nucleic acid of 2526 nucleotides (also referred to as AL356413.6) encoding a novel Insulin Like Growth Factor Binding Protein Complex-Acid Labile Subunit-like protein is shown in Table 1C. An open reading frame was identified beginning with an ATG initiation codon at nucleotides 1–3 and ending with a TAG codon at nucleotides 2524–2526. A putative untranslated region upstream from the initiation codon is underlined in Table 1C. The start and stop codons are in bold letters.

TABLE 1C

NOV1b nucleotide sequence (SEQ ID NO:3).

ATGAAGCTGTGGATTCATCTCTTTTATTCATCTCTCCTTGCCTGTATATCTTTACACTCCCAAAC

TCCAGTGCTCTCATCCAGAGGCTCTTGTGATTCTCTTTGCAATTGTGAGGAAAAAGATGGCACAA

TGCTAATAAATTGTGAAGCAAAAGGTATCAAGATGGTATCTGAAATAAGTGTGCCACCATCACGA

CCTTTCCAACTAAGCTTATTAAATAACGGCTTGACGATGCTTCACACAAATGACTTTTCTGGGCT

TACCAATGCTATTTCAATACACCTTGGATTTAACAATATTGCAGATATTGAGATAGGTGCATTTA

ATGGCCTTGGCCTCCTGAAACAACTTCATATCAATCACAATTCTTTAGAAATTCTTAAAGAGGAT

ACTTTCCATGGACTGGAAAACCTGGAATTCCTGCAAGCAGATAACAATTTTATCACAGTGATTGA

ACCAAGTGCCTTTAGCAAGCTCAACAGACTCAAAGTGTTAATTTTAAATGACAATGCTATTGAGA

GTCTTCCTCCAAACATCTTCCGATTTGTTCCTTTAACCCATCTAGATCTTCGTGGAAATCAATTA

CAAACATTGCCTTATGTTGGTTTTCTCGAACACATTGGCCGAATATTGGATCTTCAGTTGGAGGA

CAACAAATGGGCCTGCAATTGTGACTTATTGCAGTTAAAAACTTGGTTGGAGAACATGCCTCCAC

AGTCTATAATTGGTGATGTTGTCTGCAACAGCCCTCCATTTTTTAAAGGAAGTATACTCAGTAGA

CTAAAGAAGGAATCTATTTGCCCTACTCCACCAGTGTATGAAGAACATGAGGATCCTTCAGGATC

ATTACATCTGGCAGCAACATCTTCAATAAATGATAGTCGCATGTCAACTAAGACCACGTCCATTC

TAAAACTACCCACCAAAGCACCAGGTTTGATACCTTATATTACAAAGCCATCCACTCAACTTCCA

GGACCTTACTGCCCTATTCCTTGTAACTGCAAAGTCCTATCCCCATCAGGACTTCTAATACATTG

TABLE 1C-continued

NOV1b nucleotide sequence (SEQ ID NO:3).

TCAGGAGCGCAACATTGAAAGCTTATCAGATCTGAGACCTCCTCCGCAAAATCCTAGAAAGCTCA

TTCTAGCGGGAAATATTATTCACAGTTTAATGAAGTCTGATCTAGTGGAATATTTCACTTTGGAA

ATGCTTCACTTGGGAAACAATCGTATTGAAGTTCTTGAAGAAGGATCGTTTATGAACCTAACGAG

ATTACAAAAACTCTATCTAAATGGTAACCACCTGACCAAATTAAGTAAAGGCATGTTCCTTGGTC

TCCATAATCTTGAATACTTATATCTTGAATACAATGCCATTAAGGAAATACTGCCAGGAACCTTT

AATCCAATGCCTAAACTTAAAGTCCTGTATTTAAATAACAACCTCCTCCAAGTTTTACCACCACA

TATTTTTTCAGGGGTTCCTCTAACTAAGGTAAATCTTAAAACAAACCAGTTTACCCATCTACCTG

TAAGTAATATTTTGGATGATCTTGATTTGCTAACCCAGATTGACCTTGAGGATAACCCCTGGGAC

TGCTCCTGTGACCTGGTTGGACTGCAGCAATGGATACAAAAGTTAAGCAAGAACACAGTGACAGA

TGACATCTCTGCACTTCCCCCGGGCATCTCGACAAAAAAGGAATTGAAAGCCCTAAATAGTGAAA

TTCTCTGTCCAGGTTTAGTAAATAACCCATCCATGCCAACACAGACTAGTTACCTTATGGTCACC

ACTCCTGCAACAACAACAAATACGGCTGATACTATTTTACGATCTCTTACGGACGCTGTGCCACT

GTCTGTTCTAATATTGGGACTTCTGATTATGTTCATCACTATTGTTTTCTGTGCTGCAGGGATAG

TGGTTCTTGTTCTTCACCGCAGGAGAAGATACAAAAAGAAACAAGTAGATGAGCAAATGAGAGAC

AACAGTCCTGTGCATCTTCAGTACAGCATGTATGGCCATAAAACCACTCATCACACTACTGAAAG

ACCCTCTGCCTCACTCTATGAACAGCACATGGTGAGCCCCATGGTTCATGTCTATAGAAGTCCAT

CCTTTGGTCCAAAGCATCTGGAAGAGGAAGAAGAGAGGAATGAGAAAGAAGGAAGTGATGCAAAA

CATCTCCAAAGAAGTCTTTTGGAACAGGAAAATCATTCACCACTCACAGGGTCAAATATGAAATA

CAAAACCACGAACCAATCAACAGAATTTTTATCCTTCCAAGATGCCAGCTCATTGTACAGAAACA

TTTTAGAAAAAGAAAGGGAACTTCAGCAACTGGGAATCACAGAATACCTAAGGAAAAACATTGCT

CAGCTCCAGCCTGATATGGAGGCACATTATCCTGGAGCCCACGAAGAGCTGAAGTTAATGGAAAC

ATTAATGTACTCACGTCCAAGGAAGGTATTAGTGGAACAGACAAAAAATGAGTATTTTGAACTTA

AAGCTAATTTACATGCTGAACCTGACTATTTAGAAGTCCTGGAGCAGCAAACATAG

The disclosed NOV1b nucleotide encodes the NOV1a protein sequence disclosed above in Table 1B.

NOV1c

In the present invention, the target sequence identified previously, NOV1b, was subjected to the exon linking process to confirm the sequence. PCR primers were designed by starting at the most upstream sequence available, for the forward primer, and at the most downstream sequence available for the reverse primer. In each case, the sequence was examined, walking inward from the respective termini toward the coding sequence, until a suitable sequence that is either unique or highly selective was encountered, or, in the case of the reverse primer, until the stop codon was reached. Such primers were designed based on in silico predictions for the full length cDNA, part (one or more exons) of the DNA or protein sequence of the target sequence, or by translated homology of the predicted exons to closely related human sequences or sequences from other species. These primers were then employed in PCR amplification based on the following pool of human cDNAs: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea, uterus. Usually the resulting amplicons were gel purified, cloned and sequenced to high redundancy. The resulting sequences from all clones were assembled with themselves, with other fragments in CuraGen Corporation's database and with public ESTs. Fragments and ESTs were included as components for an assembly when the extent of their identity with another component of the assembly was at least 95% over 50 bp. In addition, sequence traces were evaluated manually and edited for corrections if appropriate. These procedures provide the sequence reported below, which is designated NOV1c (also referred to as Accession Number CG52997-02). This is a mature protein with 100% identity to the previously identified sequence NOV1b.

A disclosed NOV1c nucleic acid of 2531 nucleotides (also referred to as CG52997-02) encoding a novel Insulin Like Growth Factor Binding Protein Complex-Acid Labile Subunit-like protein is shown in Table 1D. An open reading frame was identified beginning with a GAT initiation codon at nucleotides 24 and ending with a TAA codon at nucleotides 2513–2515. A putative untranslated region upstream from the initiation codon and downstream from the termination codon is underlined in Table 1D. The start and stop codons are in bold letters. Because the start codon is not a traditional ATG start codon, the reading frame shown below for NOV1c could be a partial reading frame that extends further in the 5' direction.

TABLE 1D

NOV1c nucleotide sequence (SEQ ID NO:4).

GGATTCTCTCTTTTATTCATCTCTCCTTGCCTGTATATCTTTACACTCCCAAACTCCAGTGCTCTCATCCAG
AGGCTCTTGTGATTCTCTTTGCAATTGTGAGGAAAAAGATGGCACAATGCTAATAAATTGTGAAGCAAAAGG
TATCAAGATGGTATCTGAAATAAGTGTGCTACCATCACGACCTTTCCAACTAAGCTTATTAAATAACGGCTT
GACGATGCTTCACACAAATGACTTTTCTGGGCTTACCAATGCTATTTCAATACACCTTGGATTTAACAATAT
TGCAGATATTGAGATAGGTGCATTTAATGGCCTTGGCCTCCTGAAACAACTTCATATCAATCACAATTCTTT
AGAAATTCTTAAAGAGGATACTTTCCATGGACTGGAAAACCTGGAATTCCTGCAAGCAGATAACAATTTTAT
CACAGTGATTGAACCAAGTGCCCTTTAGCAAGCTCACAGACTCAAAGTGTTAATTTTAAATGACAATGCTAT
TGAGAGTCTTCCTCCAAACATCTTCCGATTTGTTCCTTTAACCCATCTAGATCTTCGTGGAAATCAATTACA
AACATTGCCTTATGTTGGTTTTCTCGAACACATTGGCCGAATATTGGATCTTCAGTTGGAGGACAACAAATG
GGCCTGCAATTGTGACTTATTGCAGTTAAAAACTTGGTTGGAGAACATGCCTCCACAGTCTATAATTGGTGA
TGTTGTCTGCAACAGCCCTCCATTTTTTAAAGGAAGTATACTCAGTAGACTAAAGAAGGAATCTATTTGCCC
TACTCCACCAGTGTATGAAGAACATGAGGATCCTTCAGGATCATTACATCTGGCAGCAACATCTTCAATAAA
TGATAGTCGCATGTCAACTAAGACCACGTCCATTCTAAAACTACCCACCAAAGCACCAGGTTTGATACCTTA
TATTACAAAGCCATCCACTCAACTTCCAGGACCTTACTGCCCTATTCCTTGTAACTGCAAAGTCCTATCCCC
ATCAGGACTTCTAATACATTGTCAGGAGCGCAACATTGAAAGCTTATCAGATCTGAGACCTCCTCCGCAAAA
TCCTAGAAAGCTCATTCTAGCGGGAAATATTATTCACAGTTTAATGAAGTCTGATCTAGTGGAATATTTCAC
TTTGGAAATGCTTCACTTGGGAAACAATCGTATTGAAGTTCTTGAAGAAGGATCGTTTATGAACCTAACGAG
ATTACAAAAACTCTATCTAAATGGTAACCACCTGACCAAATTAAGTAAAGGCATGTTCCTTGGTCTCCATAA
TCTTGAATACTTATATCTTGAATACAATGCCATTAAGGAAATACTGCCAGGAACCTTTAATCCAATGCCTAA
ACTTAAAGTCCTGTATTTAAATAACAACCTCCTCCAAGTTTTACCACCACATATTTTTTCAGGGGTTCCTCT
AACTAAGGTAAATCTTAAAACAAACCAGTTTACCCATCTACCTGTAAGTAATATTTTGGATGATCTTGATTT
GCTAACCCAGATTGACCTTGAGGATAACCCCTGGGACTGCTCCTGTGACCTGGTTGGACTGCAGCAATGGAT
ACAAAAGTTAAGCAAGAACACAGTGACAGATGACATCCTCTGCACTTCCCCCGGGCATCTCGACAAAAAGGA
ATTGAAAGCCCTAAATAGTGAAATTCTCTGTCCAGGTTTAGTAAATAACCCATCCATGCCAACACAGACTAG
TTACCTTATGGTCACCACTCCTGCAACAACAACAAATACGGCTGATACTATTTTACGATCTCTTACGGACGC
TGTGCCACTGTCTGTTCTAATATTGGGACTTCTGATTATGTTCATCACTATTGTTTTCTGTGCTGCAGGGAT
AGTGGTTCTTGTTCTTCACCGCAGGAGAAGATACAAAAAGAAACAAGTAGATGAGCAAATGAGAGACAACAG
TCCTGTGCATCTTCAGTACAGCATGTATGGCCATAAAACCACTCATCACACTACTGAAAGACCCTCTGCCTC
ACTCTATGAACAGCACATGGTGAGCCCCATGGTTCATGTCTATAGAAGTCCATCCTTTGGTCCAAAGCATCT
GGAAGAGGAAGAAGAGAGGAATGAGAAAGAAGGAAGTGATGCAAAACATCTCCAAAGAAGTCTTTTGGAACA
GGAAAATCATTCACCACTCACAGGGTCAAATATGAAATACAAAACCACGAACCAATCAACAGAATTTTTATC
CCTTCCAGATGCCAGCTCATTGTACAGAAACATTTTAGAAAAAGAAAGGGAACTTCAGCAACTGGGAATCAC
AGAATACCTAAGGAAAAACATTGCTCAGCTCCAGCCTGATATGGAGGCACATTATCCTGGAGCCCACGAAGA
GCTGAAGTTAATGGAAACATTAATGTACTCACGTCCAAGGAAGGTATTAGTGGAACAGACAAAAAATGAGTA
TTTTGAACTTAAAGCTAATTTACATGCTGAACCTGACTATTTAGAAGTCCTGGAGCAGCAAACATAA<u>GGGCG
AATTCTGCTGT</u>

In a search of public sequence databases, the NOV1c nucleic acid sequence, located on chromsome 13 has 2471 of 2480 bases (99%) identical to a gb:GENBANK-ID:AK026427|acc:AK026427.1 mRNA from *Homo sapiens* (*Homo sapiens* cDNA: FLJ22774 fis, clone KAIA1575) (E=0.0). Public nucleotide databases include all GenBank databases and the GeneSeq patent database.

The disclosed NOV1c polypeptide (SEQ ID NO:5) encoded by SEQ ID NO:4 has 837 amino acid residues and is presented in Table 1E using the one-letter amino acid code. Signal P, Psort and/or Hydropathy results predict that NOV1c has no signal peptide and is likely to be localized in the plasma membrane with a certainty of 0.4600. In other embodiments, NOV1c may also be localized to the endoplasmic reticulum (membrane) with a certainty of 0.1000, the endoplasmic reticulum (membrane) with a certainty of 0.1000, or extracellularly with a certainty of 0.1000.

A search of public sequence databases reveals that the NOV1c amino acid sequence has 427 of 436 amino acid residues (97%) identical to, and 428 of 436 amino acid residues (98%) similar to, the 440 amino acid residue ptnr:SPTREMBL-ACC:Q9H5Y7 protein from *Homo sapiens* (Human) (cDNA: FLJ22774 FIS, CLONE KAIA1575) (E=5.7e$^{-230}$). Public amino acid databases include the GenBank databases, SwissProt, PDB and PIR.

NOV1c is expressed in at least the following tissues: Heart, Coronary Artery, Pancreas, Small Intestine, Peripheral Blood, Brain, Mammary gland/Breast, Uterus, Vulva, Prostate, Lung, Trachea, Skin, Colon. Expression information was derived from the tissue sources of the sequences that were included in the derivation of the sequence of NOV1c.

The proteins encoded by the NOV1a, 1b and 1c nucleotides are very closely homologous as is shown in the alignment in Table 1F. As shown, the sequences encoded by the NOV1a and 1b nucleic acid sequences are 100% identical.

TABLE 1E

Encoded NOV1c protein sequence (SEQ ID NO:5).

DSLFYSSLLACISLHSQTPVLSSRGSCDSLCNCEEKDGTMLINCEAKGIKMVSEISVLPSRPFQLSLLNNGL

TMLHTNDFSGLTNAISIHLGFNNIADIEIGAFNGLGLLKQLHINHNSLEILKEDTFHGLENLEFLQADNNFI

TVIEPSAFSKLNRLKVLILNDNAIESLPPNIFRFVPLTHLDLRGNQLQTLPYVGFLEHIGRILDLQLEDNKW

ACNCDLLQLKTWLENMPPQSIIGDVVCNSPPFFKGSILSRLKKESICPTPPVYEEHEDPSGSLHLAATSSIN

DSRMSTKTTSLLKLPTKAPGLIPYITKPSTQLPGPYCPIPCNCKVLSPSGLLIHCQERNIESLSDLRPPPQN

PRKLELAGNIIHSLMKSKLVEYFTLEMLHLGNNRIEVLEEGSFMNLTRLQKLYLNGNHLTKLSKGMFLGLHN

LEYLYLEYNAIKEILPGTFNPMPKLKVLYLNNNLLQVLPPHIFSGVPLTKVNLKTNQFTHLPVSNILDDLDL

LTQIDLEDNPWDCSCDLVGLQQWIQKLSKNTVTDDILCTSPGHLDKKELKALNSEILCPGLVNNPSMPTQTS

YLMVTTPATTTNTAKTILRSLTDAVPLSVLILGLLIMFITIVFCAAGIVVLVLHRRRRYKKKQVDEQMRDNS

PVHLQYSMYGHKTTHHTTERPSASLYEQHMVSPMVHVYRSPSFGPKHLEEEEERNEKEGSDAKHLQRSLLEQ

ENHSPLTGSNMKYKTTNQSTEFLSFQDASSLYRNILEKERELQQLGITEYLRKNIAQLQPDMEAHYPGAHEE

LKLMETLMYSRPRKVLVEQTKEYFELKANLGAEPDYLEVLEQQT

TABLE 1F

Alignment of NOV1a, 1b, 1c.

```
                   10        20        30        40        50        60
              ....|....|....|....|....|....|....|....|....|....|....|....|
        NOV1a MKLWIHLFYSSLLACISLHSQTPVLSSRGSCDSLCNCEEKDGTMLINCEAKGIKMVSEIS
        NOV1b MKLWIHLFYSSLLACISLHSQTPVLSSRGSCDSLCNCEEKDGTMLINCEAKGIKMVSEIS
        NOV1c ----DSLFYSSLLACISLHSQTPVLSSRGSCDSLCNCEEKDGTMLINCEAKGIKMVSEIS 70        80        90       100       110       120
              ....|....|....|....|....|....|....|....|....|....|....|....|
        NOV1a VPPSRPFQLSLLNNGLTMLHTNDFSGLTNAISIHLGFNNIADIEIGAFNGLGLLKQLHIN
        NOV1b VPPSRPFQLSLLNNGLTMLHTNDFSGLTNAISIHLGFNNIADIEIGAFNGLGLLKQLHIN
        NOV1c VLPSRPFQLSLLNNGLTMLHTNDFSGLTNAISIHLGFNNIADIEIGAFNGLGLLKQLHIN 130       140       150       160       170       180
              ....|....|....|....|....|....|....|....|....|....|....|....|
        NOV1a HNSLEILKEDTFHGLENLEFLQADNNFITVIEPSAFSKLNRLKVLILNDNAIESLPPNIF
        NOV1b HNSLEILKEDTFHGLENLEFLQADNNFITVIEPSAFSKLNRLKVLILNDNAIESLPPNIF
        NOV1c HNSLEILKEDTFHGLENLEFLQADNNFITVIEPSAFSKLNRLKVLILNDNAIESLPPNIF
```

TABLE 1F-continued

Alignment of NOV1a, 1b, 1c.

```
                 190       200       210       220       230       240
             ....|....|....|....|....|....|....|....|....|....|....|....|
NOV1a        RFVPLTHLDLRGNQLQTLPYVGFLEHIGRILDLQLEDNKWACNCDLLQLKTWLENMPPQS
NOV1b        RFVPLTHLDLRGNQLQTLPYVGFLEHIGRILDLQLEDNKWACNCDLLQLKTWLENMPPQS
NOV1c        RFVPLTHLDLRGNQLQTLPYVGFLEHIGRILDLQLEDNKWACNCDLLQLKTWLENMPPQS 250       260       270       280       290       300
             ....|....|....|....|....|....|....|....|....|....|....|....|
NOV1a        IIGDVVCNSPPFFKGSILSRLKKESICPTPPVYEEHEDPSGSLHLAATSSINDSRMSTKT
NOV1b        IIGDVVCNSPPFFKGSILSRLKKESICPTPPVYEEHEDPSGSLHLAATSSINDSRMSTKT
NOV1c        IIGDVVCNSPPFFKGSILSRLKKESICPTPPVYEEHEDPSGSLHLAATSSINDSRMSTKT 310       320       330       340       350       360
             ....|....|....|....|....|....|....|....|....|....|....|....|
NOV1a        TSILKLPTKAPGLIPYITKPSTQLPGPYCPIPCNCKVLSPSGLLIHCQERNIESLSDLRP
NOV1b        IIGDVVCNSPPFFKGSILSRLKKESICPTPPVYEEHEDPSGSLHLAATSSINDSRMSTKT
NOV1c        IIGDVVCNSPPFFKGSILSRLKKESICPTPPVYEEHEDPSGSLHLAATSSINDSRMSTKT 370       380       390       400       410       420
             ....|....|....|....|....|....|....|....|....|....|....|....|
NOV1a        PPQNPRKLILAGNIIHSLMKSDLVEYFTLEMLHLGNNRIEVLEEGSFMNLTRLQKLYLNG
NOV1b        PPQNPRKLILAGNIIHSLMKSDLVEYFTLEMLHLGNNRIEVLEEGSFMNLTRLQKLYLNG
NOV1c        PPQNPRKLILAGNIIHSLMKSDLVEYFTLEMLHLGNNRIEVLEEGSFMNLTRLQKLYLNG 430       440       450       460       470       480
             ....|....|....|....|....|....|....|....|....|....|....|....|
NOV1a        NHLTKLSKGMFLGLHNLEYLYLEYNAIKEILPGTFNPMPKLKVLYLNNNLLQVLPPHIFS
NOV1b        NHLTKLSKGMFLGLHNLEYLYLEYNAIKEILPGTFNPMPKLKVLYLNNNLLQVLPPHIFS
NOV1c        NHLTKLSKGMFLGLHNLEYLYLEYNAIKEILPGTFNPMPKLKVLYLNNNLLQVLPPHIFS 490       500       510       520       530       540
             ....|....|....|....|....|....|....|....|....|....|....|....|
NOV1a        GVPLTKVNLKTNQFTHLPVSNILDDLDLLTQIDLEDNPWDCSCDLVGLQQWIQKLSKNTV
NOV1b        GVPLTKVNLKTNQFTHLPVSNILDDLDLLTQIDLEDNPWDCSCDLVGLQQWIQKLSKNTV
NOV1c        GVPLTKVNLKTNQFTHLPVSNILDDLDLLTQIDLEDNPWDCSCDLVGLQQWIQKLSKNTV 550       560       570       580       590       600
             ....|....|....|....|....|....|....|....|....|....|....|....|
NOV1a        TDDILCTSPGHLDKKELKALNSEILCPGLVNNPSMPTQTSYLMVTTPATTTNTADTILRS
NOV1b        TDDILCTSPGHLDKKELKALNSEILCPGLVNNPSMPTQTSYLMVTTPATTTNTADTILRS
NOV1c        TDDILCTSPGHLDKKELKALNSEILCPGLVNNPSMPTQTSYLMVTTPATTTNTADTILRS 610       620       630       640       650       660
             ....|....|....|....|....|....|....|....|....|....|....|....|
NOV1a        LTDAVPLSVLILGLLIMFITIVFCAAGIVVLVLHRRRRYKKKQVDEQMRDNSPVHLQYSM
NOV1b        LTDAVPLSVLILGLLIMFITIVFCAAGIVVLVLHRRRRYKKKQVDEQMRDNSPVHLQYSM
NOV1c        LTDAVPLSVLILGLLIMFITIVFCAAGIVVLVLHRRRRYKKKQVDEQMRDNSPVHLQYSM 670       680       690       700       710       720
             ....|....|....|....|....|....|....|....|....|....|....|....|
NOV1a        YGHKTTHHTTERPSASLYEQHMVSPMVHVYRSPSFGPKHLEEEEERNEKEGSDAKHLQRS
NOV1b        YGHKTTHHTTERPSASLYEQHMVSPMVHVYRSPSFGPKHLEEEEERNEKEGSDAKHLQRS
NOV1c        YGHKTTHHTTERPSASLYEQHMVSPMVHVYRSPSFGPKHLEEEEERNEKEGSDAKHLQRS 730       740       750       760       770       780
             ....|....|....|....|....|....|....|....|....|....|....|....|
NOV1a        LLEQENHSPLTGSNMKYKTTNQSTEFLSFQDASSLYRNILEKERELQQLGITEYLRKNIA
NOV1b        LLEQENHSPLTGSNMKYKTTNQSTEFLSFQDASSLYRNILEKERELQQLGITEYLRKNIA
NOV1c        LLEQENHSPLTGSNMKYKTTNQSTEFLSFQDASSLYRNILEKERELQQLGITEYLRKNIA 790       800       810       820       830       840
             ....|....|....|....|....|....|....|....|....|....|....|....|
NOV1a        QLQPDMEAHYPGAHEELKLMETLMYSRPRKVLVEQTKNEYFELKANLHAEPDYLEVLEQQ
NOV1b        QLQPDMEAHYPGAHEELKLMETLMYSRPRKVLVEQTKNEYFELKANLHAEPDYLEVLEQQ
NOV1c        QLQPDMEAHYPGAHEELKLMETLMYSRPRKVLVEQTKNEYFELKANLHAEPDYLEVLEQQ

NOV1a   T (SEQ ID NO:2)
NOV1b   T (SEQ ID NO:2)
NOV1c   T (SEQ ID NO:5)
```

Homologies to any of the above NOV1 proteins will be shared by the other two NOV1 proteins insofar as they are homologous to each other as shown above. Any reference to NOV1 is assumed to refer to all three of the NOV1 proteins in general, unless otherwise noted.

The disclosed NOV1a polypeptide has homology to the amino acid sequences shown in the BLASTP data listed in Table 1G.

TABLE 1G

BLAST results for NOV1a

| Gene Index/Identifier | Protein/Organism | Length (aa) | Identity (%) | Positives (%) | Expect |
|---|---|---|---|---|---|
| gi\|14758126\|ref\|XP_033182.1\| | hypothetical protein FLJ22774 [Homo sapiens] | 798 | 798/798 (100%) | 798/798 (100%) | 0.0 |
| gi\|14149932\|ref\|NP_115605.1\| | hypothetical protein FLJ22774 [Homo sapiens] | 440 | 425/425 (100%) | 425/425 (100%) | 0.0 |
| gi\|6691962\|emb\|CAB65788.1\| | bG256O22.1 (similar to IGFALS (insulin-like growth factor binding protein, acid labile subunit)) [Homo sapiens] | 853 | 354/866 (40%) | 504/866 (57%) | e-161 |
| gi\|11360190\|pir\|\|T46279 | hypothetical protein DKFZp56401278.1 - human (fragment) | 314 | 314/314 (100%) | 314/314 (100%) | e-160 |
| gi\|14424224\|sp\|094991\|Y918_HUMAN | HYPOTHETICAL PROTEIN KIAA0918 | 966 | 356/915 (38%) | 534/915 (57%) | e-158 |

The homology between these and other sequences is shown graphically in the ClustalW analysis shown in Table 1H. In the ClustalW alignment of the NOV1 protein, as well as all other ClustalW analyses herein, the black outlined amino acid residues indicate regions of conserved sequence (i.e., regions that may be required to preserve structural or functional properties), whereas non-highlighted amino acid residues are less conserved and can potentially be altered to a much broader extent without altering protein structure or function.

TABLE 1H

ClustalW Analysis of NOV1

1) Novel NOV1a (SEQ ID NO:2)
2) Novel NOV1b (SEQ ID NO:2) (Identical to NOV1a)
3) Novel NOV1c (SEQ ID NO:5)
4) gi|14758126|ref|XP_033182.1| hypothetical protein FLJ22774 [Homo sapiens] (SEQ ID NO:28)
5) gi|14149932|ref|NP_115605.1| hypothetical protein FLJ22774 [Homo sapiens] (SEQ ID NO:29)
6) gi|6691962|emb|CAB65788.1| bG256022.1 (similar to IGFALS (insulin-like growth factor binding protein, acid labile subunit)) [Homo sapiens] (SEQ ID NO:30)
7) gi|11360190|pir|T46279 hypothetical protein DKFZp56401278.1 - human (fragment (SEQ ID NO:31)
8) gi|14424224|sp|094991|Y918_Human HYPOTHETICAL PROTEIN KIAA0918 (SEQ ID NO:32)

```
                              10        20        30        40        50
                     ....|....|....|....|....|....|....|....|....|....|
          NOV1a      ------------------------MKLWIHLFYSSLLACSSLHSQTPVL
          NOV1b      ------------------------MKLWIHLFYSSLLACSSLHSQTPVL
          NOV1c      ------------------------DSLFYSSLLACSSLHSQTPVL
          gi|14758126| --------------------------------------------------
          gi|14149932| --------------------------------------------------
          gi|6691962|  --------YFSLFRSIQLFADCK-KMFLWLFLILS----ASISSTNADSD
          gi|11360190| --------------------------------------------------
          gi|14424224| RRGAQGGKMHTCCPPVTLEQDLHRKMHSWMLQTLAFAVTSSVLSCAETID 60        70        80        90       100
                     ....|....|....|....|....|....|....|....|....|....|
          NOV1a      SSRGSCSSLCNCEEKSGTMLINCEAKGIKMVSEISVPPSRPFQLSLLNNG
          NOV1b      SSRGSCSSLCNCEEKSGTMLINCEAKGIKMVSEISVPPSRPFQLSLLNNG
          NOV1c      SSRGSCSSLCNCEEKSGTMLINCEAKGIKMVSEISVLPSRPFQLSLLNNG
          gi|14758126| ------------------MLINCEAKGIKMVSEISVPPSRPFQLSLLNNG
          gi|14149932| ------------------MLINCEAKGIKMVSEISVPPSRPFQLSLLNNG
          gi|6691962|  ISVEICN-VCSCVSVSNVSYSNCEKVSSYRPSSSKPEWSNFSHLSFQNNF
          gi|11360190| --------------------------------------------------
          gi|14424224| YYGEICSNACPCEEKSGISTSSCENSGIISSSEISPERFPISHLLSGNL
```

TABLE 1H-continued

ClustalW Analysis of NOV1

```
                         110       120       130       140       150
                ....|....|....|....|....|....|....|....|....|....|
NOV1a           LTMLHTNDFSGLTNAISIHLGFNNIADIEIGAFNGLGLLKQLHINHNSLE
NOV1b           LTMLHTNDFSGLTNAISIHLGFNNIADIEIGAFNGLGLLKQLHINHNSLE
NOV1c           LTMLHTNDFSGLTNAISIHLGFNNIADIEIGAFNGLGLLKQLHINHNSLE
gi|14758126|    LTMLHTNDFSGLTNAISIHLGFNNIADIEIGAFNGLGLLKQLHINHNSLE
gi|14149932|    LTMLHTNDFSGLTNAISIHLGFNNIADIEIGAFNGLGLLKQLHINHNSLE
gi|6691962|     LNILYPNTFLNFSHAVSLHLGNNKLQNIEGGAFLGLSALKQLHLNNNELK
gi|11360190|    --------------------------------------------------
gi|14424224|    LNRLYPNEFVNYTGASIDHLGSNVIQDIETGAFHGLRGLKKLHLNKNKLE 160       170       180       190       200
                ....|....|....|....|....|....|....|....|....|....|
NOV1a           ILKEDTFHGLENLEFLQADNNFITVIEPSAFSKLNRLKVLILNDNAIESL
NOV1b           ILKEDTFHGLENLEFLQADNNFITVIEPSAFSKLNRLKVLILNDNAIESL
NOV1c           ILKEDTFHGLENLEFLQADNNFITVIEPSAFSKLNRLKVLILNDNAIESL
gi|14758126|    ILKEDTFHGLENLEFLQADNNFITVIEPSAFSKLNRLKVLILNDNAIESL
gi|14149932|    ILKEDTFHGLENLEFLQADNNFITVIEPSAFSKLNRLKVLILNDNAIESL
gi|6691962|     ILRADTFLGSENLEYLQADYNLIKYIERGAFNKLHKLKVLILNDNLISFL
gi|11360190|    --------------------------------------------------
gi|14424224|    ILRDDTFLGLENLEYLQVDYNYISVIEPNAFGKLHLLQVLILNDNLLSSL 210       220       230       240       250
                ....|....|....|....|....|....|....|....|....|....|
NOV1a           PPNIFRFVPLTHLDLRGNQLQTLPYVGFLEHIGRILDLQLEDNKWACNCD
NOV1b           PPNIFRFVPLTHLDLRGNQLQTLPYVGFLEHIGRILDLQLEDNKWACNCD
NOV1c           PPNIFRFVPLTHLDLRGNQLQTLPYVGFLEHIGRILDLQLEDNKWACNCD
gi|14758126|    PPNIFRFVPLTHLDLRGNQLQTLPYVGFLEHIGRILDLQLEDNKWACNCD
gi|14149932|    PPNIFRFVPLTHLDLRGNQLQTLPYVGFLEHIGRILDLQLEDNKWACNCD
gi|6691962|     PDNIFRFASLTHLDIRGNRIQKLPYIGVLEHIGRVVELQLEDNPWNCSCD
gi|11360190|    --------------------------------------------------
gi|14424224|    PNNLFRFVPLTHLDLRGNHLKLLPYVGLLQHMDKVVELQLESNPWNCSCE 260       270       280       290       300
                ....|....|....|....|....|....|....|....|....|....|
NOV1a           LLQLKTWLENMPPQSIIGDVVCNSPPFFKGSILSRLKKESICPTPPVYEE
NOV1b           LLQLKTWLENMPPQSIIGDVVCNSPPFFKGSILSRLKKESICPTPPVYEE
NOV1c           LLQLKTWLENMPPQSIIGDVVCNSPPFFKGSILSRLKKESICPTPPVYEE
gi|14758126|    LLQLKTWLENMPPQSIIGDVVCNSPPFFKGSILSRLKKESICPTPPVYEE
gi|14149932|    LLQ-----------------------------------------------
gi|6691962|     LLPLKAWLENMPYNIYIGEATCEIPSDLYGRLLKETNKQELCPMGTGSDF
gi|11360190|    --------------------------------------------------
gi|14424224|    LISLKDWLESISYSALVGDVVCEIPFRLHGRDLDEVSKQELCPRRLISDY 310       320       330       340       350
                ....|....|....|....|....|....|....|....|....|....|
NOV1a           HED---PSGSLHLAATSSINDSRMSTKTTSILKLPTKAPG----------
NOV1b           HED---PSGSLHLAATSSINDSRMSTKTTSILKLPTKAPG----------
NOV1c           HED---PSGSLHLAATSSINDSRMSTKTTSILKLPTKAPG----------
gi|14758126|    HED---PSGSLHLAATSSINDSRMSTKTTSILKLPTKAPG----------
gi|14149932|    --------------------------------------------------
gi|6691962|     DVR-ILPPSQLENGYTTPNGH----TTQTSLHRLVTKPPK-TTNPSK---
gi|11360190|    --------------------------------------------------
gi|14424224|    EMRPQTPLSTTGYLHTTPASVNSVATSSSAVYKPPLKPPKGTRQPNKPRV 360       370       380       390       400
                ....|....|....|....|....|....|....|....|....|....|
NOV1a           ---------------LIPYITKPSTQLPGPYCPIPCNCKVLS-PSGLLTH
NOV1b           ---------------LIPYITKPSTQLPGPYCPIPCNCKVLS-PSGLLTH
NOV1c           ---------------LIPYITKPSTQLPGPYCPIPCNCKVLS-PSGLLTH
gi|14758126|    ---------------LIPYITKPSTQLPGPYCPIPCNCKVLS-PSGLLTH
gi|14149932|    --------------------------------------------------
gi|6691962|     -ISGIVAGKALSNRNLSQIVSYQTRVPPLTPCPAPCFCKTHPSDLGLSVN
gi|11360190|    --------------------------------------------------
gi|14424224|    RPTSRQPSKDLGYSNYGPSIAYQTKSPVPLECPTACSCNLQISDLGLNVN 410       420       430       440       450
                ....|....|....|....|....|....|....|....|....|....|
NOV1a           CQERNIESLSDLRPPPQNPRKLILAGNIIHSLMKSDLVEYFTLEMLHLGN
NOV1b           CQERNIESLSDLRPPPQNPRKLILAGNIIHSLMKSDLVEYFTLEMLHLGN
NOV1c           CQERNIESLSDLRPPPQNPRKLILAGNIIHSLMKSDLVEYFTLEMLHLGN
gi|14758126|    CQERNIESLSDLRPPPQNPRKLILAGNIIHSLMKSDLVEYFTLEMLHLGN
gi|14149932|    --------------------------------------------------
gi|6691962|     CQEKNIQSMSELIPKPLNAKKLHVNGNSIKDVDVSDFTDFEGLDLLHLGS
gi|11360190|    --------------------------------------------------
gi|14424224|    CQERKIESIAELQPKPYNPKKMYLTENYIAVVRRTDFLEATGLDLLHLGN
```

TABLE 1H-continued

ClustalW Analysis of NOV1

```
                       460        470        480        490        500
                  ....|....|....|....|....|....|....|....|....|....|
NOV1a             NRIEVXXXGXFMNLTRLXXLYLNGNHXTXLSKGMXLGLHNLXYLYEYNA
NOV1b             NRIEVXXXGXFMNLTRLXXLYLNGNHXTXLSKGMXLGLHNLXYLYEYNA
NOV1c             NRIEVXXXGXFMNLTRLXXLYLNGNHXTXLSKGMXLGLHNLXYLYEYNA
gi|14758126|      NRIEVXXXGXFMNLTRLXXLYLNGNHXTXLSKGMXLGLHNLXYLYEYNA
gi|14149932|      ------------------------------------------------
gi|6691962|       NXITVXXXGDVFHNLTNLXXLYLNGNQXEXLYPEXFSGLHNLXYLYEYNL
gi|11360190|      ------------------------------------------------
gi|14424224|      NRISXXXXRAFGXLTNLXXLYLNGNRXEXLSPEXYGLQSLXYLXLXYNL 510        520        530        540        550
                  ....|....|....|....|....|....|....|....|....|....|
NOV1a             IKEILPGTEXPMPKLXXLYLNNNLLQVLPPXIFSGXPLTXXNLXXNXFTH
NOV1b             IKEILPGTEXPMPKLXXLYLNNNLLQVLPPXIFSGXPLTXXNLXXNXFTH
NOV1c             IKEILPGTEXPMPKLXXLYLNNNLLQVLPPXIFSGXPLTXXNLXXNXFTH
gi|14758126|      IKEILPGTEXPMPKLXXLYLNNNLLQVLPPXIFSGXPLTXXNLXXNXFTH
gi|14149932|      ------------------------------------------------
gi|6691962|       IKEISAGTEXSMPNLXXLYLNNNLLXSLEVXIFSGAPLAXXNLXNNXFMY
gi|11360190|      ------------------------------------------------
gi|14424224|      IREIQSGTEXEXVPNLXXLXLNNNLLQAXESGVFSGXTLLXXNLXXNHFIS 560        570        580        590        600
                  ....|....|....|....|....|....|....|....|....|....|
NOV1a             LPVSNXLDDXDLLTQIDLEDNPWDCXCDLVGLQQWIQKLSKNTVTDDILC
NOV1b             LPVSNXLDDXDLLTQIDLEDNPWDCXCDLVGLQQWIQKLSKNTVTDDILC
NOV1c             LPVSNXLDDXDLLTQIDLEDNPWDCXCDLVGLQQWIQKLSKNTVTDDILC
gi|14758126|      LPVSNXLDDXDLLTQIDLEDNPWDCXCDLVGLQQWIQKLSKNTVTDDILC
gi|14149932|      ------------------------LXTWXXNXPPQSXXIGDXXC
gi|6691962|       LPVSGXLDQLQSXLTQIDLEGNPWDCXCDLVALXLWXXKLSDGIVVKXXKC
gi|11360190|      ------------------------LQQWIQKLSKNTVTDDILC
gi|14424224|      LPVSGXLDQLKSLIQIDIHDNPWDCXCDRXVGXXLWXXXLKVGVXVDXXXC 610        620        630        640        650
                  ....|....|....|....|....|....|....|....|....|....|
NOV1a             TSPGHLDKKELKALNSEILCPG----LVNNPSMPTQT--SYLMVTTPATT
NOV1b             TSPGHLDKKELKALNSEILCPG----LVNNPSMPTQT--SYLMVTTPATT
NOV1c             TSPGHLDKKELKALNSEILCPG----LVNNPSMPTQT--SYLMVTTPATT
gi|14758126|      TSPGHLDKKELKALNSEILCPG----LVNNPSMPTQT--SYLMVTTPATT
gi|14149932|      NSEPFFKGSILSRLKKESXCP-----TPPVYEEHE--DPSGDLHLAAT
gi|6691962|       EXPVQFANIELKXLKKEILCP-----KLXNKPS--------XPFTSPAPAIT
gi|11360190|      TSPGHLDKKELKALNSEILCPG----LVNNPSMPTQT--SYLMVTTPATT
gi|14424224|      KAPKKFAXTPXXXTKSELLCPDYSDVXVXTPXPSSXIQVPARTSAVTPAVR 660        670        680        690        700
                  ....|....|....|....|....|....|....|....|....|....|
NOV1a             TNTADTILRSLTDAV----PLSVLILGLLIMFITIVFCAAGIVVLVLHRR
NOV1b             TNTADTILRSLTDAV----PLSVLILGLLIMFITIVFCAAGIVVLVLHRR
NOV1c             TNTADTILRSLTDAV----PLSVLILGLLIMFITIVFCAAGIVVLVLHRR
gi|14758126|      TNTADTILRSLTDAV----PLSVLILGLLIMFITIVFCAAGIVVLVLHRR
gi|14149932|      XXINDXRXSXKTTX-----------I--XXXPTKAPCXXXP--------
gi|6691962|       FTXPLGPXRSPPGG---PVPLSXLILSXXXLILTVFXAFCXXXVFVLRXN
gi|11360190|      TNTADTILRSLTDAV----PLSVLILGLLIMFITIVFCAAGIVVLVLHRR
gi|14424224|      LNXTGAPASLGAGGGASSVPLSVLILSLLXXFIMSVFVAAGXFVLVXKRR 710        720        730        740        750
                  ....|....|....|....|....|....|....|....|....|....|
NOV1a             RRYKKKQVDEQMRDNSPVHLQYSMYG-------HKTTHHTTERPSAS---
NOV1b             RRYKKKQVDEQMRDNSPVHLQYSMYG-------HKTTHHTTERPSAS---
NOV1c             RRYKKKQVDEQMRDNSPVHLQYSMYG-------HKTTHHTTERPSAS---
gi|14758126|      RRYKKKQVDEQMRDNSPVHLQYSMYG-------HKTTHHTTERPSAS---
gi|14149932|      --YITKPSTXLPGPYCPXPCNCKXLSP------SGLLIHCQERNIES---
gi|6691962|       XXPTVKHEGLGNPDCGSXQLQL-----------RKXHDXKTNXXDGLS---
gi|11360190|      RRYKKKQVDEQMRDNSPVHLQYSMYG-------HKTTHHTTERPSAS---
gi|14424224|      XXNXSDHTSTNNSDVXSFXXQYSXYGGGGGTGGHPHAXVHHRGPXLPKVK 760        770        780        790        800
                  ....|....|....|....|....|....|....|....|....|....|
NOV1a             ----LYEQHMVSPMVHVYRSPSFGPKHLE--------EEEERNRKEG---
NOV1b             ----LYEQHMVSPMVHVYRSPSFGPKHLE--------EEEERNRKEG---
NOV1c             ----LYEQHMVSPMVHVYRSPSFGPKHLE--------EEEERNRKEG---
gi|14758126|      ----LYEQHMVSPMVHVYRSPSFGPKHLE--------EEEERNRKEG---
gi|14149932|      ----LSX------X----RPPQNPXKLI---------LAGNIIHS----
gi|6691962|       -----TEAFXPQTXEQMSXSHXCGLKES---------ETGFMFSX----
gi|11360190|      ----LYEQHMVSPMVHVYRSPSFGPKHLE--------EEEERNRKEG---
gi|14424224|      TPAGHVYXXXPHPXGHXCXPIXRSXEGNSVEDYKDLHPLXVTYSSNHHL
```

TABLE 1H-continued

ClustalW Analysis of NOV1

```
                810       820       830       840       850
           ....|....|....|....|....|....|....|....|....|....|
NOV1a      --------SDAK------HLQRSLLEQENHSPLTGSNMKY--KTTNQST
NOV1b      --------SDAK------HLQRSLLEQENHSPLTGSNMKY--KTTNQST
NOV1c      --------SDAK------HLQRSLLEQENHSPLTGSNMKY--KTTNQST
gi|14758126 --------SDAK------HLQRSLLEQENHSPLTGSNMKY--KTTNQST
gi|14149932 ------------------LMKSDLVEYFTLEMIHLGNNKI--KVLEKG-
gi|6691962  --------PPGK------KVVMRNVADKEKDLIHVDTRKR-LSTIKKLD
gi|11360190 --------SDAK------HLQRSLLEQENHSPLTGSNMKY--KTTNQST
gi|14424224 QQQQQPPPPPQKPQQQPPPQLQLQPGEKERRESHHLRKPAYSVSTIEPRE 860       870       880       890       900
           ....|....|....|....|....|....|....|....|....|....|
NOV1a      EFL-SFQDASSLYRNILEKERELQQLGITEYLRK------NIA--QLQPD
NOV1b      EFL-SFQDASSLYRNILEKERELQQLGITEYLRK------NIA--QLQPD
NOV1c      EFL-SFQDASSLYRNILEKERELQQLGITEYLRK------NIA--QLQPD
gi|14758126 EFL-SFQDASSLYRNILEKERELQQLGITEYLRK------NIA--QLQPD
gi|14149932 ----SFMKLTRLQKLYLNGN-HLTKLSKGMRLG---------------LHK
gi|6691962  ELF-PSKDKKVFIKNFLEAKKEYNSKGKKG--------------------
gi|11360190 EFL-SFQDASSLYRNILEKERELQQLGITEYLRK------NIA--QLQPD
gi|14424224 KLKSPVQDADRFYRGILEPKKHCSTTPAGNSLPKYPKFPCKPAAYTFSEK 910       920       930       940       950
           ....|....|....|....|....|....|....|....|....|....|
NOV1a      MEAHYPGAH-----EELKLMETLMYSRPRKVLVEQTKNEYFELKANLHAE
NOV1b      MEAHYPGAH-----EELKLMETLMYSRPRKVLVEQTKNEYFELKANLHAE
NOV1c      MEAHYPGAH-----EELKLMETLMYSRPRKVLVEQTKNEYFELKANLHAE
gi|14758126 MEAHYPGAH-----EELKLMETLMYSRPRKVLVEQTKNEYFELKANLHAE
gi|14149932 KEYLMLEYK------AIKKKKPGTFNPMP-KKKVLYLNNTSSKFYHKKFFK
gi|6691962  FEIRVPEK--QP---KKKSKIKLIGGNHSKKVVEQRKKEYFELKAKLQKS
gi|11360190 MEAHYPGAH-----EELKLMETLMYSRPRKVLVEQTKNEYFELKANLHAE
gi|14424224 YKLRRKHQKLHPGAGKSKKREPKKYSPESAVFVEPNKNEYLELKAKLKVE

960
           ....|....|....|.
NOV1a      PDYLEVLEQQT-----
NOV1b      PDYLEVLEQQT-----
NOV1c      PDYLEVLEQQT-----
gi|14758126 PDYLEVLEQQT-----
gi|14149932 G-KL------------
gi|6691962  PDYLKVLEKQTALNKI
gi|11360190 PDYLEVLEQQT-----
gi|14424224 PDYLEVLEKQTTFSQF
```

The presence of identifiable domains in NOV1, as well as all other NOVX proteins, was determined by searches using software algorithms such as PROSITE, DOMAIN, Blocks, Pfam, ProDomain, and Prints, and then determining the Interpro number by crossing the domain match (or numbers) using the Interpro website (http:www.ebi.ac.uk/interpro). DOMAIN results for NOV1as disclosed in Tables 1I-IL, were collected from the Conserved Domain Database (CDD) with Reverse Position Specific BLAST analyses. This BLAST analysis software samples domains found in the Smart and Pfam collections. For Table 1E and all successive DOMAIN sequence alignments, fully conserved single residues are indicated by black shading or by the sign (|) and "strong" semi-conserved residues are indicated by grey shading or by the sign (+). The "strong" group of conserved amino acid residues may be any one of the following groups of amino acids: STA, NEQK, NHQK, NDEQ, QHRK, MILV, MILF, HY, FYW.

Tables 1I–1L lists the domain description from DOMAIN analysis results against NOV1. This indicates that the NOV1 sequence has properties similar to those of other proteins known to contain this domain.

TABLE 1I

Domain Analysis of NOV1 gnl|Smart|smart00082, LRRCT, Leucine rich repeat C-terminal domain.
(SEQ ID NO:65)
CD-Length = 51 residues, 100.0% aligned
Score = 49.7 bits (117), Expect = 7-07

```
Query:  517 NPWDCSCDLVGLQQWIQKLSKNTVTDDILCTSPGHLDKKELKALNSEILCP  567
                ||+ | |+|  | +|+|           |+ ||| |   |  |  ||
Sbjct:    1 NPFICDCELRWLLRWLQANRHLQDPVDLRCASPESLRGPLLLLLPSSFKCP   51
```

TABLE 1J

Domain Analysis of NOV1 gnl|Smart|smart00082, LRRCT, Leucine rich repeat C-terminal domain.
(SEQ ID NO:65)
CD-Length = 51 residues, 100.0% aligned
Score = 45.1 bits (105). Expect = 2-05

```
Query:  218 NKWACNCDLLQLKTWLENMPPQSIIGDVVCNSPPGGKGSILSRLKKESICP   268
              | + |+|+|   | ||+          |+ | ||   +| +|  |     ||
Sbjct:    1 NPFICDCELRWLLRWLQANRHLQDPVDLRCASPESLRGPLLLLLPSSFKCP    51
```

TABLE 1K

Domain Analysis of NOV1 gnl|Pfam|pfam01463, LRRCT, Leucine rich repeat C-terminal domain.
Leucine Rich Repeats pfam00560 are short sequence motifs present in
a number of proteins with diverse functions and cellular locations.
Leucine Rich Repeats are often flanked by cysteine rich domains.
This domain is often found at the C-terminus of tandem leucine rich
repeats (SEQ ID NO:66)
CD-Length = 51 residues, 100.0% aligned
Score = 47.8 bits (112), Expect = 3-06

```
Query:  517 NPWDCSCDLVGLQQWIQKLSKNTVTDDILCTSPGHLDKKELKALNSEILCP   567
            ||+ |  |+|   | +|+++    +    +|+ | ||   |   |+ | |+ ||
Sbjct:    1 NPFICDCELRWLLRWLREPRRLEDPEDLRCASPESLRGPLLELLPSDFSCP    51
```

TABLE 1L

Domain Analysis of NOV1 gnl|pfam|pfam01463, LRRCT, Leucine rich repeat C-terminal domain.
Leucine Rich Repeats pfam00560 are short sequence motifs present in
a number of proteins with diverse functions and cellular locations.
Leucine Rich Repeats are often flanked by cysteine rich domains.
This domain is often found at the C-terminus of tandem leucine rich
repeats. (SEQ ID NO:66)
CD-Length = 51 residues, 100.0% aligned
Score = 46.2 bits (108), Expect = 7e-06

```
Query:  218 NKWACNCDLLQLKTWLENMPPQSIIGDVVCNSPPFFKGSILSRLKKESICP   268
              | + |+|+|   | ||            |+ | ||   +| +|  |  + ||
Sbjct:    1 NPFICDCELRWLLRWLREPRRLEDPEDLRCASPESLRGPLLELLPSDFSCP    51
```

Proteins belonging to the IGFBP-ALS family of proteins play an important role in regulating the levels of circulating hormones. The acid labile subunit of the complex plays an important role in regulating the stability of the complex and ensuring high levels of circulating hormones that are regulated by the IGFBP family of proteins. This protein also has a leucine rich repeat that is a common domain in many proteins that are important for the developing embryo. As a result this protein may play an important role in development and disease.

Insulin-like growth factors (IGFs) I and II are important regulators of cell proliferation and differentiation (Ueki I et al., Proc Natl Acad Sci USA 2000 Jun. 6;97(12):6868–73). After birth, plasma IGFs, representing mostly liver-derived IGFs, circulate in ternary complexes of 150 kDa consisting of one molecule each of IGF, IGF-binding protein (IGFBP) 3, and an acid labile subunit (ALS). Onset of ALS synthesis after birth is the primary factor driving the formation of ternary complexes. Capture of IGFs by ALS is thought to allow the development of a plasma reservoir without negative effects such as hypoglycemia and cell proliferation. To evaluate the importance of ALS and ternary complexes, we have created mice in which the ALS gene has been inactivated. The mutation was inherited in a Mendelian manner, without any effects on survival rates and birth weights. A growth deficit was observed in null mice after 3 weeks of life and reached 13% by 10 weeks. This modest phenotype was observed despite reductions of 62 and 88% in the concentrations of plasma IGF-I and IGFBP-3, respectively. Increased turnover accounted for these reductions because indices of synthesis in liver and kidney were not decreased. Surprisingly, absence of ALS did not affect glucose and insulin homeostasis. Therefore, ALS is required for postnatal accumulation of IGF-I and IGFBP-3 but, consistent with findings supporting a predominant role for locally produced IGF-I, is not critical for growth. This model should be useful to determine whether presence of ALS is needed for other actions of liver-derived IGF-I and for maintenance of homeostasis in presence of high circulating levels of IGF-II.

In circulation, insulin-like growth factor-I (IGF-I) is bound in a trimeric complex of 150 kDa with IGF binding protein-3 (IGFBP-3) and the acid-labile subunit (ALS). (Moller S et al., J Hepatol 2000 March;32(3):441–6). Whereas circulating IGF-I and IGFBP-3 are reported to be low in patients with chronic liver failure, the level of ALS has not been described in relation to hepatic dysfunction. The aim of the present study was therefore to measure circulating and hepatic venous concentrations of ALS in relation to hepatic function and the IGF axis.

The insulin-like growth factor (IGF) binding proteins (IGFBPs) were initially identified as carrier proteins for IGF-I and IGF-II in a variety of biologic fluids. (Rosenfeld R G et al., Pediatrics 1999 October;104(4 Pt 2):1018–21). Their presumed function was to protect IGF peptides from degradation and clearance, increase the half-life of the IGFs, and deliver them to appropriate tissue receptors. The concept of IGFBPs as simple carrier proteins has been complicated, however, by a number of observations: 1) the six IGFBPs vary in their tissue expression and their regulation by other hormones and growth factors; 2) the IGFBPs are subjected to proteolytic degradation, thereby altering their affinities for the IGFs; 3) IGFBP-3 and IGFBP-5, in addition to binding IGFs, also can associate with an acid-labile subunit, thereby increasing further the half-life of the IGFs; 4) in addition to modifying the access of IGF peptides to IGF and insulin receptors, several of the IGFBPs may be capable of increasing IGF action; 5) some of the IGFBPs may be capable of IGF-independent regulation of cell growth; 6) some of the IGFBPs are associated with cell membranes or possibly with membrane receptors; and 7) some of the IGFBPs have nuclear recognition sites and may be found within the nucleus. Additionally, a number of cDNAs identified recently have been found to encode proteins that bind IGFs, but with substantially lower affinities than is the case with IGFBPs. The N-terminal regions of the predicted proteins are structurally homologous to the classic IGFBPs, with conservation of the cysteine-rich region. These observations suggest that these low-affinity binders are members of an IGFBP superfamily, capable of regulating cell growth by both IGF-dependent and IGF-independent mechanisms.insulin-like growth factor, insulin-like growth factor binding proteins.

Total IGF-I level in serum is a sensitive index during growth hormone (GH) replacement therapy of adults, since GH stimulates the hepatic expressions of both insulin-like growth factor (IGF-I) and acid-labile subunit (ALS) and the major part of IGF-I in the circulation is found in a ternary complex together with ALS and IGFBP-3. (Hall K et al., J Endocrinol Invest 1999;22(5 Suppl):48–57) However, other regulators of the proteins constituting the ternary complex may influence IGF-I levels. In healthy subjects the serum IGF-I levels are low at birth, rise during childhood, with peak levels during puberty, and decline with increasing age. This pattern has been attributed to the age-dependent GH production, but it is unknown whether the wide range of IGF-I levels within each age interval is due to GH production or GH sensitivity. In elderly twins approximately 60% of IGF-I levels are genetically determined. The remaining environmental dependency of IGF-I is partly due to nutrition. Both caloric and protein content of the diet is of importance. Thus, low IGF-I levels are found in GH deficient patients as well as in patients with GH resistance due to malnutrition or GH receptor defects. It is essential that IGF-I determination is performed by assays in which IGFBPs do not interfere, and that IGF-I concentration is evaluated in relation to age, i.e. expressed in SD score, and the number of individuals constituting the reference intervals improves the sensitivity and specificity. Although determination of IGF-I is recommended in assessing GH deficiency in children, its diagnostic value in patients with adult onset of GH deficiency is not agreed upon. In the age group above 40–80 years many patients with pituitary/hypothalamic disorders and GH peaks below 31 g/l during provocation tests have normal IGF-I levels. It is not clarified, whether the IGF-I levels within normal range for age is due to endogenous basal GH production being sufficient or other factors stimulating IGF-1, IGFBP-3 or ALS expressions.

Circulating insulin-like growth factors (IGFs) represent an important pool of potential hypoglycemic activity, which is largely inhibited by their sequestration in a heterotrimeric complex comprising growth factor, IGF-binding protein-3 (IGFBP-3), and acid-labile subunit (ALS). (Baxter R C Metabolism 1995 October;44(10 Suppl 4):12–7). Less than 1% of total IGFs circulate in the free form, yet even this amount might contribute significantly to circulating insulin-like activity. The ternary binding protein complex appears to inhibit insulin-like activity of bound IGFs by preventing their egress from the circulation. Although the integrity of this complex might be affected by limited proteolysis of IGFBP-3 in pregnancy and catabolic conditions, the evidence that this increases IGF bioavailability, and thus hypoglycemic potential, is as yet unclear. However, in patients with IGF-II-secreting tumors, hypoglycemia may result from a failure of the ternary complex to adequately sequester the IGFs. Improvement in complex formation, by treatment with corticosteroids or growth hormone, alleviates the hypoglycemia, even if (as seen with growth hormone treatment) IGF-II hypersecretion persists. In these patients, blood glucose levels are inversely correlated with IGFBP-2 levels, suggesting that this protein might play a part in transporting IGFs to their target tissues. Conversely, ALS levels correlate positively with blood glucose, emphasizing the importance of the ternary complex in preventing hypoglycemia. Unlike the other IGF-binding proteins, IGFBP-1 is acutely regulated in the circulation, in a manner consistent with its acting as a glucose counterregulator. It might act in this way by inhibiting the activity of free IGFs in the circulation.

Leucine-rich repeats (LRRS) are relatively short motifs (22–28 residues in length) found in a variety of cytoplasmic, membrane and extracellular proteins (InterPro). Although these proteins are associated with widely different functions, a common property involves protein-protein interaction. Little is known about the 3D structure of LRRs, although it is believed that they can form amphipathic structures with hydrophobic surfaces capable of interacting with membranes. In vitro studies of a synthetic LRR from *Drosophila* Toll protein have indicated that the peptides form gels by adopting beta-sheet structures that form extended filaments. These results are consistent with the idea that LRRs mediate protein-protein interactions and cellular adhesion. Other functions of LRR-containing proteins include, for example, binding to enzymes and vascular repair. The 3D structure of ribonuclease inhibitor, a protein containing 15 LRRs, has been determined, revealing LRRs to be a new class of alpha/beta fold. LRRs form elongated non-globular structures and are often flanked by cysteine rich domains.

The disclosed NOV1 nucleic acid of the invention encoding a Insulin Like Growth Factor Binding Protein Complex-Acid Labile Subunit-like protein includes the nucleic acid whose sequence is provided in Table 1A, C and E or a fragment thereof. The invention also includes a mutant or variant nucleic acid any of whose bases may be changed from the corresponding base shown in Table 1A, C, or E while still encoding a protein that maintains its Insulin Like Growth Factor Binding Protein Complex-Acid Labile Subunit-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 10% percent of the bases may be so changed.

The disclosed NOV1 protein of the invention includes the Insulin Like Growth Factor Binding Protein Complex-Acid Labile Subunit-like protein whose sequence is provided in Table 1B or 1E. The invention also includes a mutant or variant protein any of whose residues may be changed from the corresponding residue shown in Table 1B or 1E while still encoding a protein that maintains its Insulin Like Growth Factor Binding Protein Complex-Acid Labile Subunit-like activities and physiological functions, or a functional fragment thereof. In the mutant or variant protein, up to about 60% percent of the residues may be so changed.

The invention further encompasses antibodies and antibody fragments, such as $F_{ab}$ or $(F_{ab})_2$, that bind immuno-specifically to any of the proteins of the invention.

The above defined information for this invention suggests that this Insulin Like Growth Factor Binding Protein Complex-Acid Labile Subunit-like protein (NOV1) may function as a member of a "Insulin Like Growth Factor Binding Protein Complex-Acid Labile Subunit family". Therefore, the NOV1 nucleic acids and proteins identified here may be useful in potential therapeutic applications implicated in (but not limited to) various pathologies and disorders as indicated below. The potential therapeutic applications for this invention include, but are not limited to: protein therapeutic, small molecule drug target, antibody target (therapeutic, diagnostic, drug targeting/cytotoxic antibody), diagnostic and/or prognostic marker, gene therapy (gene delivery/gene ablation), research tools, tissue regeneration in vivo and in vitro of all tissues and cell types composing (but not limited to) those defined here.

The NOV1 nucleic acids and proteins of the invention are useful in potential therapeutic applications implicated in cancer including but not limited to various pathologies and disorders as indicated below. For example, a cDNA encoding the Insulin Like Growth Factor Binding Protein Complex-Acid Labile Subunit-like protein (NOV1) may be useful in gene therapy, and the Insulin Like Growth Factor Binding Protein Complex-Acid Labile Subunit-like protein (NOV1) may be useful when administered to a subject in need thereof. By way of nonlimiting example, the compositions of the present invention will have efficacy for treatment of patients suffering from cancer, cystitis, incontinence, fertility, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation recovery. The NOV1 nucleic acid encoding the Insulin Like Growth Factor Binding Protein Complex-Acid Labile Subunit-like protein of the invention, or fragments thereof, may further be useful in diagnostic applications, wherein the presence or amount of the nucleic acid or the protein are to be assessed.

NOV1 nucleic acids and polypeptides are further useful in the generation of antibodies that bind immuno-specifically to the novel NOV1 substances for use in therapeutic or diagnostic methods. These antibodies may be generated according to methods known in the art, using prediction from hydrophobicity charts, as described in the "Anti-NOVX Antibodies" section below. The disclosed NOV1 protein has multiple hydrophilic regions, each of which can be used as an immunogen. In one embodiment, a contemplated NOV1 epitope is from about amino acids 10 to 50. In another embodiment, a NOV1 epitope is from about amino acids 80 to 120. In additional embodiments, NOV1 epitopes are from about amino acids 180 to 220, from about amino acids 230 to 300, from about amino acid 330 to 350, from about amino acid 370 to 400, from about amino acid 480 to 540, from about amino acid 550 to 560, and from about amino acids 620 to 840. These novel proteins can be used in assay systems for functional analysis of various human disorders, which will help in understanding of pathology of the disease and development of new drug targets for various disorders.

NOV2

A disclosed NOV2 nucleic acid of 3609 nucleotides (also referred to as 101599929_EXT1) encoding a novel Attractin like protein is shown in Table 2A. An open reading frame was identified beginning with an ATG initiation codon at nucleotides 7–9 and ending with a TAA codon at nucleotides 3562–3564. A putative untranslated region upstream from the initiation codon and downstream from the termination codon is underlined in Table 2A, and the start and stop codons are in bold letters.

TABLE 2A

NOV2 nucleotide sequence (SEQ ID NO:6).

<u>CAGTGG</u>ATGCAGAAGGCAGACAGCAGCACCGAGACGATGAAGGAGAAGAGGACAGCGGCTGCGATACCGTG

CGGCACAGGACCGGCTCCTGCTTCTCGGGCCGCTGTGTCAACTCCACCTGCCTCTGCGACCCGGGCTGGGTG

GGGGACCAGTGCCAGCACTGCCAGGGCAGGTTCAGGTTAACAGAACCTTCTGGATATTTAACAGATGGCCCA

ATTAACTATAAATATAAAACTAAATGTACTTGGCTCATTGAAGGCCCAAATGCAGTGTTAAGATTAAGATTC

AATCATTTTGCTACAGAATGTAGCTGGGATCATATGTATGTTTATGATGGAGATTCAATATATGCACCTTTA

ATAGCTTCTTTTAGTGGTTTGATAGTCCCTGAAATAAGGGGCAATGAAACTGTGCCTGAAGTTGTTACTACA

TABLE 2A-continued

NOV2 nucleotide sequence (SEQ ID NO:6).

TCTGGCTATGCACTGTTACATTTTTTTAGTGATGCTGCGTATAATCTAACTGGTTTCAACATTTTCTATTCG
ATCAATTCTTGTCCTAACAATTGCTCTGGTCATGGGAAGTGTACAACTAGTGTCTCTGTTCCAAGTCAAGTA
TATTGTGAATGTGATAAATACTGGAAGGGTGAAGCTTGTGATATTCCTTACTGTAAAGCCAATTGCGGCAGT
CCAGATCACGGTTACTGTGACCTGACTGGAGAAAAATTATGTGTCTGCAATGATAGTTGGCAAGGTATAGGT
CCTGATTGTTCTTTGAATGTTCCCTCTACTGAGTCTTACTGGATTCTGCCAAACGTTAAACCCTTCAGTCCT
TCTGTAGGTCGGGCTTCACATAAAGCAGTTTTACACGGGAAATTTATGTGGGTGATTGGTGGATATACTTTT
AACTACAGTTCTTTTCAAATGGTCCTAAGTTACAATTTAGAAAGCAGTATATGGAATGTAGGAACTCCATCA
AGGGGACCTCTCCAGAGATATGGACACTCTCTTGCTTTATATCAGGAAAACATCTTTATGTATGGAGGCAGA
ATTGAAACAAATGATGGCAATGTCACAGATGAATTATGGGTTTTTAACATACATAGTCAGTCATGGAGTACA
AAAACTCCTACTGTTCTTGGACATGGTCAGCAGTATGCTGTGGAGGGACATTCAGCACATATTATGGAGTTG
GATAGTAGAGATGTTGTCATGATCATAATATTTGGATATTCTGCAATATATGGTTATACAAGCAGCATACAG
GAATACCATATCTGTTCAAACACTTGGCTTGTTCCAGAAACTAAAGGAGCTATTGTACAAGGTGGATATGGC
CATACTAGTGTGTATGATGAAATAACAAAGTCCATTTATGTTCATGGAGGGTATAAAGCATTGCCAGGGAAC
AAATATGGATTGGTTGATGATCTTTATAAATATGAAGTTAACACTAAGACTTGGACTATTTTGAAAGAAAGT
GGGTTTGCCAGATACCTTCATTCAGCTGTTCTTATCAATGGAGCTATGCTTATTTTTGGAGGAAATACCCAT
AATGACACTTCCTTGAGTAACGGTGCAAAATGTTTTTCTGCCGATTTCCTGGCATATGACATATGCCCAGGC
TGGAGTGCAGTGGCACGATCTCAGCTCACTGCCACCTCCACCTCCCACGTTCAAGCGATTCTCAATAGGTCC
ATGTATATATTTGGGGGATTTTCTAGTGTACTCCTTAATGATATCCTTGTATACAAGCCTCCAAATTGCAAG
GCTTTCAGAGATGAAGAACTTTGTAAAAATGCTGGTCCAGGGATAAAATGTGTTTGGAATAAAAATCACTGT
GAATCTTGGGAATCTGGGAATACTAATAATATTCTTAGAGCAAAGTGCTTTTCTAAAAGAAATCTCTGCAGT
GACAGATGTTACAGATATGCAGATTGTGCCAGCTGTACTGCCAATACAAATGGGTGCCAATGGTGTGATGAC
AAGAAATGCATTTCGGCAAATAGTAACTGCAGTATGGTTAGTATTTTTGGGTATATAACCTTGCCTTCACAG
TTCCCATTCTATTATTGCTACAGATATGCAGATTGTGCCAGCTGTACTGCCAATACAAATGGGTGCCAATGG
TGTGATGACAAGAAATGCATTGCTTTACCAGCTCATCTTTGTGGAGAAGGATGGAGTCATATTGGGGATGCT
TGTCTTAGAGTCAATTCCAGTAGAGAAAACTATGACAATGCAAAACTTTATTGCTATAATCTTAGTGGAAAT
CTTGCTTCATTAACAACCTCAAAAGAAGTAGAATTTGTTCTGGATGAAATACAGAAGTATACACAACAGAAA
GTATCACCTTGGGTAGGCTTGCGCAAGATCAATATATCCTATTGGGGATGGAAGACATGTCTCCTTTTACA
AACACAACACTACAGTGGCTTCCTGGCGAACCCAATGATTCTGGGTTTTGTGCATATCTGGAAAGGGCTGCA
GTGGCAGGCTTAAAAGCTAATCCTTGTACATCTATGGCAAATGGCCTTGTCTGTGAAAAACCTGTTAATCAA
AATGCGAGGCCGTGCAAAAAGCCATGCTCTCTGAGGACATCATGTTCCAACTGTACAAGCAATGGCATGGAG
TGTATGTGGTGCAGCAGTACGAAACGATGTGTTGACTCTAATGCCTATATCATCTCTTTTCCATATGGACAA
TGTCTAGAGTGGCAAACTGCCACCTGCTCCCGTGCTCAAAATTGTTCTGGATTGAGAACCTGTGGACAGTGT
TTGGAACAGCCTGAATGTGGCTGGTGCAATGATCCTAGTAATACAGGAAGAGGACATTGCATTGAAGGTTCT
TCACGGGACCAATGAAGCTTATTGGAATGCACCACAGTGAGATGGTTCTTGACACCAATCTTTGCCCCAAA
GAAAAGAACTATGAGTGGTCCTTTATCCAGTGTCCAGCTTGCCAGTGTAATGGACATAGCACTTGCATCAAT
AATAATGTGTGCGAACAGTGTAAAAATCTCACCACAGGAAAGCAGTGTCAAGATTGTATGCCAGGTTATTAT
GGAGATCCAACCAATGGTGGACAGTGCACAGCTTGTACATGCAGTGGCCATGCAAATATCTGTCATCTGCAC
ACAGGAAAATGTTTCTGCACAACTAAAGGAATAAAAGGTGACCAATGCCAATTGTGTGACTCTGAAAATCGC
TATGTTGGTAATCCACTTAGAGGAACATGTTATTGTAAGTATAGCCTTTTGATTGATTATCAATTTACCTTC

TABLE 2A-continued

NOV2 nucleotide sequence (SEQ ID NO:6).

AGCTTATTACAGGAAGATGATCGCCACCATACTGCCATAAACTTTATAGCAAACCCAGAACAGGTGAGGAAA

AATCTGGATATATCAATTAATGCATCAAACAACTTTAATCTCAACATTACGTGGTCTGTCGGTTCAGCTGGA

ACAATATCTGGGGAAGAGACTTCTATAGTTTCCAAGAATAATATAAAGGAATACAGAGATAGTTTTTCCTAT

GAAAAATTTAACTTTAGAAGCAATCCTAACATTACATTCTATGTGTACGTCAGCAACTTTTCCTGGCCTATT

AAAATACAGGTAAGTGTTAAGAGTATTTACTTCTAATGACCATAATATCATTAAGAAAAGAATGGTGCTTTT

GTCCAAAGT

The disclosed NOV2 nucleic acid sequence, localized to chromsome 10, has 494 of 694 bases (71%) identical to an Attractin protein mRNA from mouse (GENBANK-ID: AF119821) (E=2.9e$^{-204}$).

A NOV2 polypeptide (SEQ ID NO:7) encoded by SEQ ID NO:6 has 1185 amino acid residues and is presented using the one-letter code in Table 2B. Signal P, Psort and/or Hydropathy results predict that NOV2 does not contain a signal peptide and is likely to be localized in the mitochondrial membrane space with a certainty of 0.3600. In other embodiments, NOV2 may also be localized to the microbody (peroxisome) with a certainty of 0.3000, or the lysosome (lumen) with a certainty of 0.1000.

The disclosed NOV2 amino acid sequence has 703 of 1197 amino acid residues (58%) identical to, and 895 of 197 amino acid residues (74%) similar to, the 1198 amino acid residue Attractin protein from human (SPTREMBL-ID:O75882) (E=0.0), and 703 of 1197 amino acid residues (58%) identical to, and 895 of 1197 amino acid residues (74%) similar to, the 1198 amino acid residue human soluble Attractin-1 protein (patp:AAY70689) (E=0.0).

NOV2 is expressed in at least the following tissues: Brain, Kidney, Muscle, Pancreas, Prostate, Uterus, Breast, Colon, Ovary, and Liver. In addition, the sequence is predicted to be expressed in the following tissues because of the expression pattern of (GENBANK-ID: AF119821) a closely related attractin homolog in mouse: Brain, Heart, Kidney, Liver, Lung, Skin, Spinal cord, and Pituitary.

NOV2 also has homology to the amino acid sequences shown in the BLASTP data listed in Table 2C.

TABLE 2B

Encoded NOV2 protein sequence (SEQ ID NO:7).

MQKADSSTETMKEKRTAAAITVRHRTGSCFSGRCVNSTCLCDPGWVGDQCQHCQGRFRLTEPSGYLTDGPIN

YKYKTKCTWLIEGPNAVLRLRFNHFATECSWDHMYVYDGDSIYAPLIASFSGLIVPEIRGNETVPEVVTTSG

YALLHFFSDAAYNLTGFNIFYSINSCPNNCSGHGKCTTSVSVPSQVYCECDKYWKGEACDIPYCKANCGSPD

HGYCDLTGEKLCVDNDSWQGIGPDCSLNVPSTESYWILPNVKPFSPSVGRASHKAVLHGKFMWVIGGYTFNY

SSFQMVLSYNLESSIWNVGTPSRGPLQRYGHSLALYQENIFMYGGRIETNDGNVTDELWVFNIHSQSWSTKT

PTVLGHGQQYAVEGHSAHIMELDSRDVVMIIIFGYSAIYGYTSSIQEYHICSNTWLVPETKGAIVQGGYGHT

SVYDEITKSIYVHGGYKALPGNKYGLVDDLYKYEVNTKTWTILKESGFARYLHSAVLINGAMLIFGGNTHND

TSLSNGAKCFSADFLAYDICPGWSAVARSQLTATSTSHVQAILNRSMYIFGGFSSVLLNDILVYKPPNCKAF

RDEELCKNAGPGIKCVWNKNHCESWESGNTNNILRAKCFSKRNLCSDRCYRYADCASCTANTNGCQWCDDKK

CISANSNCSMVSIFGYITLPSQFPFYYCYRYADCASCTANTNGCQWCDDKKCIALPAHLCGEGWSHIGDACL

RVNSSRENYDNAKLYCYNLSGNLASLTTSKEVEFVLDEIQKYTQQKVSPWVGLRKINISYWGWEDMSPFTNT

TLQWLPGEPNDSGFCAYLERAAVAGLKANPCTSMANGLVCEKPVNQNARPCKKPCSLRTSCSNCTSNGMECM

WCSSTKRCVDSNAYIISFPYGQCLEWQTATCSRAQNCSGLRTCGQCLEQPECGWCNDPSNTGRGHCIEGSSR

GPMKLIGMHHSEMVLDTNLCPKEKNYEWSFIQCPACQCNGHSTCINNNVCEQCKNLTTGKQCQDCMPGYYGD

PTNGGQCTACTCSGHANICHLHTGKCFCTTKGIKGDQCQLCDSENRYVGNPLRGTCYCKYSLLIDYQFTFSL

LQEDDRHHTAINFIANPEQVRKNLDISINASNNFNLNITWSVGSAGTISGEETSIVSKNNIKEYRDSFSYEK

FNFRSNPNITFYVYVSNFSWPIKIQVSVKSIYF

TABLE 2C

BLAST results for NOV2

| Gene Index/ Identifier | Protein/Organism | Length (aa) | Identity (%) | Positives (%) | Expect |
|---|---|---|---|---|---|
| gi\|13160051\|emb\|CAC 32456.1\| | dJ741H3.1.1 (attractin (with dipeptidylpeptidase IV activity) secreted isoform) [*Homo sapiens*] | 1011 | 566/1015 (55%) | 739/1015 (72%) | 0.0 |
| gi\|4585307\|gb\| AAD25372.1\| AF119821_1 | attractin [*Mus musculus*] | 1428 | 677/1174 (57%) | 865/1174 (73%) | 0.0 |
| gi\|13431313\|sp\|Q9WU 60\|ATRN_MOUSE | ATTRACTIN PRECURSOR (MAHOGANY PROTEIN) | 1428 | 679/1174 (57%) | 871/1174 (73%) | 0.0 |
| gi\|6912258\|ref\|NP_ 036202.1\| | attractin; attractin (with dipeptidylpeptidase IV activity); mahogany protein [*Homo sapiens*] | 1198 | 703/1210 (58%) | 894/1210 (73%) | 0.0 |
| gi\|12275312\|dbj\| BAB21018.1\| | attractin [*Rattus norvegicus*] | 1275 | 680/1177 (57%) | 870/1177 (73%) | 0.0 |

The homology of these sequences is shown graphically in the ClustalW analysis shown in Table 2D.

TABLE 2D

ClustalW Analysis of NOV2

```
1) NOV2 (SEQ ID NO:7)
2) gi|13160051|emb|CAC32456.1| dJ741H3.1.1 (attractin (with
dipeptidylpeptidase IV activity) secreted isoform) [Homo sapiens]
(SEQ ID NO:127)
2) gi|4585307|gb|AAD25372.1|AF119821_1 attractin [Mus musculus]
(SEQ ID NO:33)
3) gi|13431313|sp|Q9WU60|ATRN_MOUSE ATTRACTIN PRECURSOR
(MAHOGANY PROTEIN) (SEQ ID NO:34)
4) gi|6912258|ref|NP_036202.1| attractin; attractin (with
dipeptidylpeptidase IV activity); mahogany protein [Homo
sapiens] (SEQ ID NO:35)
5) gi|12275312|dbj|BAB21018.1| attractin [Rattus norvegicus]
(SEQ ID NO:36)

10         20         30         40         50
              ....|....|....|....|....|....|....|....|....|....|
NOV2          ---MQKADSSTETMKEKRIAAAITVRHRTG---------------------
gi|13160051|  --------------------------------------------------
gi|4585307|   -MVAVAVASSTEARLRGSTTATAAPAGRKGRQHRPCTATGAWRPGPRARL
gi|13431313|  -MVAVAAASSTEARLRGSTTTTAAPAGRKGRQHRPCTATGAWRPGPRARL
gi|6912258|   ---MVAAASSTEARLRRTAATAALAGRSG--------------GP----
gi|12275312|  MVAAAAAAESTEARLRGYTTATAAPAGWKERQHRPCAATGAWRPWPRAGL 60         70         80         90        100
              ....|....|....|....|....|....|....|....|....|....|
NOV2          --------------------------------------------------
gi|13160051|  --------------------------------------------------
gi|4585307|   CLPRVLSRALPPP---PLLPLLFSLLLLPLPREAEAAAVAAAVSGSAAAE
gi|13431313|  CLPRVLSRALPPP---PLLPLLFSLLLLPLPREAEAAAVAAAVSGSAAAE
gi|6912258|   ---------------------------------------H----------
gi|12275312|  CLPRVLSRALPPPPLLPLLPLLFSLLLLPLPREAEAAAVAAAVSGSAAAE
```

TABLE 2D-continued

ClustalW Analysis of NOV2

```
              110        120        130        140        150
              ....|....|....|....|....|....|....|....|....|....|
NOV2          -------SCFSGRCVNSI--CSCDPGWVGSQCQHCQGRFRLTEPSGSSTD
gi|13160051|  --------------------------------------------------
gi|4585307|   AKECDRPCVNGGRCNPGTGQCVCETGWVGEQCQHCGGRFRLTGSSGFVTD
gi|13431313|  AKECDRPCVNGGRCNPGTGQCVCETGWVGEQCQHCGGRFRLTGSSGFVTD
gi|6912258|   -------CVNGGRCNPGTGQCVCEAGWVGEQCQHCGGRFRLTGSSGFVTD
gi|12275312|  AKECDRPCVNGGRCNPGTGQCVCETGWVGEQCQHCGGRFRLTGSSGFVTD 160        170        180        190        200
              ....|....|....|....|....|....|....|....|....|....|
NOV2          GPINYKYKTKCTWLIEG-PNASRLRFNHFATECSWDHSVYYDGDSIYAP
gi|13160051|  --------------------------------------------------
gi|4585307|   GPGNYKYKTKCTWLIEGYPNASRLRFNHFATECSWDHLYVYDGDSIYAP
gi|13431313|  GPGNYKYKTKCTWLIEGQPNRSRLRFNHFATECSWDHLYVYDGDSIYAP
gi|6912258|   GPGNYKYKTKCTWLIEGQPNRSRLRFNHFATECSWDHLYVYDGDSIYAP
gi|12275312|  GPGNYKYKTKCTWLIEGQPNKSRLRFNHFATECSWDHLYVYDGDSIYAP 210        220        230        240        250
              ....|....|....|....|....|....|....|....|....|....|
NOV2          LIASFSGLIVPEIRGNETVPEVVTTSGYALLHFFSDAAYNLTGFNIFYSI
gi|13160051|  --------------------------------------------------
gi|4585307|   LIAAFSGLIVPERDGNETAPEVTVTSGYALLHFFSDAAYNLTGFNITYSF
gi|13431313|  LIAAFSGLIVPERDGNETAPEVTVTSGYALLHFFSDAAYNLTGFNITYSF
gi|6912258|   LSAAFSGLIVPERDGNETVPEVVATSGYALLHFFSDAAYNLTGFNITYSF
gi|12275312|  LIAAFSGLIVPERDGNETAPEVTVTSGYALLHFFSDAAYNLTGFNITYSF 260        270        280        290        300
              ....|....|....|....|....|....|....|....|....|....|
NOV2          SCPNNCSGHGSCTSSVSVPSQVLCECDSYWKGEACDIPSCKANCGSPDH
gi|13160051|  -----------ISNSS-DTVECECSENWKGESCDIPHCTDNCGFPHR
gi|4585307|   DMCPNNCSARGECKSSNSS-SAVECECSENWKGESCDIPHCTDNCGFPHR
gi|13431313|  DMCPNNCSGRGECKSSNSS-SAVECECSENWKGESCDIPHCTDNCGFPHR
gi|6912258|   DMCPNNCSDVRGECKISNSS-DTVECECSENWKGESCDIPHCTDNCGFPHR
gi|12275312|  DMCPNNCSGRGECKSSNSS-STVECECSENWKGESCDIPHCTDNCGFPHR 310        320        330        340        350
              ....|....|....|....|....|....|....|....|....|....|
NOV2          GYCSLSGEKLCVCNDSWQGIGPDCSSNVPSTSSWILPNVKPFSPSSGRA
gi|13160051|  GICNSSDVRGCSCFSDWQ--GPGCSSPVPANQSFWTREEYS--SLKLPRA
gi|4585307|   GICNSSDTRGCSCFPHWQ--GPGCSSPVPANQSFWTREEYS--SLKLPRA
gi|13431313|  GICNSSDTRGCSCFPHWQ--GPGCSSPVPANQSFWTREEYS--SLKLPRA
gi|6912258|   GICNSSDVRGCSCFSDWQ--GPGCSSPVPANQSFWTREEYS--SLKLPRA
gi|12275312|  GICNSSDTRGCSCFPHWQ--GPGCSSPVPANQSFWTREEYS--SLKLPRA 360        370        380        390        400
              ....|....|....|....|....|....|....|....|....|....|
NOV2          SHKAVSSGKFMWVSGGYTFKSSSSQMVLSYSLESSIWN-SGTPSRGPSQR
gi|13160051|  SHKAVVNGNIMWVVGGYMFNHSDYSMVLAYDIASREWLPLNRSVNSVVVR
gi|4585307|   SHKAVVNGNIMWVVGGYMFNHSDYSMVLAYDLTSREWLPLNHSVNSVVVR
gi|13431313|  SHKAVVNGNIMWVVGGYMFNHSDYSMVLAYDLTSREWLPLNHSVNSVVVR
gi|6912258|   SHKAVVNGNIMWVVGGYMFNHSDYSMVLAYDIASREWLPLNRSVNSVVVR
gi|12275312|  SHKAEVNGNIMWVVGGYMFNHSDYSMVLAYDIASREWLSLNHSVNSVVVR 410        420        430        440        450
              ....|....|....|....|....|....|....|....|....|....|
NOV2          YGHSLALSSNISMYGGSISSNDGNVTSEIWVFSIHSSSSWSTKTPTVLGH
gi|13160051|  YGHSLALSKDKIYMYGGKIDS-TGNVTNILRVFHIHNESWVLLTPKAK--
gi|4585307|   YGHSLALSKDKIYMYGGKIDS-TGNVTNILRVFHIHNESWVLLTPKAK--
gi|13431313|  YGHSLALSKDKIYMYGGKIDS-TGNVTNILRVFHIHNESWVLLTPKAK--
gi|6912258|   YGHSLALSKDKIYMYGGKIDS-TGNVTNILRVFHIHNESWVLLTPKAK--
gi|12275312|  YGHSLALSKDKIYMYGGKIDS-TGNVTNILRVFHIHNESWVLLTPKAK--

460        470        480        490        500
              ....|....|....|....|....|....|....|....|....|....|
NOV2          GQQYAVEGHSAHISELDSRDVVMSSIFGYSASYGYTSSSQEYHSCSNTWL
gi|13160051|  -SQYAVVGHSAHIVTLKSGRVVMLVIFGHCPLYGYISNVQEYDLSKNTWS
gi|4585307|   -SQYAVVGHSAHIVTLASGRVVMLVIFGHCPLYGYISVVQEYDLSKNTWS
gi|13431313|  -SQYAVVGHSAHIVTLASGRVVMLVIFGHCPLYGYISVVQEYDLSKNTWS
gi|6912258|   -SQYAVVGHSAHIVTLKSGRVVMLVIFGHCPLYGYISNVQEYDLSKNTWS
gi|12275312|  -SQYAVVGHSAHIVTLASGRVVMLVIFGHCPLYGYISVVQEYDLSKNTWS 510        520        530        540        550
              ....|....|....|....|....|....|....|....|....|....|
NOV2          SPETSGASVQGGYGHTSVDEITKSSYVHGGYKALPGNKYGLSVDDLYSS
gi|13160051|  ILHTQGALVQGGYGHSSVYDHRTSKALYVHGGYKAFSANKYRLADDLYRYD
gi|4585307|   ILHTQGALVQGGYGHSSAYDHRTKALYVHGGYKAFSANKYRLADDLYRYD
gi|13431313|  ILHTQGALVQGGYGHSSVYDHRTKALYVHGGYKAFSANKYRLADDLYRYD
gi|6912258|   ILHTQGALVQGGYGHSSVYDHRTKALYVHGGYKAFSANKYRLADDLYRYD
gi|12275312|  ILQTQGALVQGGYGHSSVYDHRTKALYVHGGYKAFSANKYRLADDLYRYH
```

TABLE 2D-continued

ClustalW Analysis of NOV2

```
              560        570        580        590        600
              ....|....|....|....|....|....|....|....|....|....|
NOV2          VDTXTWTILKXSGXARYLHXAVXXXGAMLXFGGNTHNDTSXSXGAKCFSX
gi|13160051|  VDTQMWTILKDSRFFRYLHTAVIVSGTMLVFGGNTHNDTSMSHGAKCFSS
gi|4585307|   VDTQMWTILKDSRFFRYLHTAVIVSGTMLVFGGNTHNDTSMSHGAKCFSS
gi|13431313|  VDTQMWTILKDSRFFRYLHTAVIVSGTMLVFGGNTHNDTSMSHGAKCFSS
gi|6912258|   VDTQMWTILKDSRFFRYLHTAVIVSGTMLVFGGNTHNDTSMSHGAKCFSS
gi|12275312|  VDTQMWTILKDSRFFRYLHTAVIVSGTMLVFGGNTHNDTSMSHGAKCFSS 610        620        630        640        650
              ....|....|....|....|....|....|....|....|....|....|
NOV2          DFXAYDICPG-WSAXARSQXTATST--SXVQAXLNRXMYXIFGGFXSXLLX
gi|13160051|  DFMAYDIACDRWSVLPREXLHHDVNRFGHSAVLXNSTMYVFGGFNSLLLS
gi|4585307|   DFMAYDIACDRWSVLPREXLHHDVNRFGHSAVLXNSTMYVFGGFNSLLLS
gi|13431313|  DFMAYDIACDRWSVLPREXLHHDVNRFGHSAVLXNSTMYVFGGFNSLLLS
gi|6912258|   DFMAYDIACDRWSVLPREXSTMMSTDLAIPAVLXNSTMYVFGGFNSLLLS
gi|12275312|  DFMAYDIACDRWSVLPREXLHHDVNRFGHSAVLXNSTMYVFGGFNSLLLS 660        670        680        690        700
              ....|....|....|....|....|....|....|....|....|....|
NOV2          DXLVXKPPNCKAFRDEELCKNAGPGIXCXWXKN--HCESWEXSGNTNN--I
gi|13160051|  DXLVFTSEQCDAHRSEAACXAAGPGIRCXWXTGSSXCISWALATXEQAEK
gi|4585307|   DXLVFTSEQCDAHRSEAACXAAGPGIRCXWXTQSSXCISWELATXEQAEK
gi|13431313|  DXLVFTSEQCDAHRSEAACXAAGPGIRCXWXTQSSXCISWELATXEQAEK
gi|6912258|   DXLVFTSEQCDAHRSEAACXAAGPGIRCXWXTGSSXCISWALATXEQAEK
gi|12275312|  DXLVFTSEQCDAHRSEAACXAAGPGIRCXWXTQSSXCISWELATXEQAEK 710        720        730        740        750
              ....|....|....|....|....|....|....|....|....|....|
NOV2          LXAXCFSKRNXCSDRCYXXADCASCTANTNGCQWCXDKKCXSANXNCX--
gi|13160051|  LKSECFSKRTLDHDRCDQHTDCYSCTANTNDCHWCND-HCVPRNHSCXEG
gi|4585307|   LKSECFSKRTLDHDRCDQHTDCYSCTANTNDCHWCND-HCVPVNHSCXEG
gi|13431313|  LKSECFSKRTLDHDRCDQHTDCYSCTANTNDCHWCND-HCVPRNHSCXEG
gi|6912258|   LKSECFSKRTLDHDRCDQHTDCYSCTANTNDCHWCND-HCVPVNHSCXEG
gi|12275312|  LKSECFSKRTLDHDRCDQHTDCYSCTANTNDCHWCND-HCVPVNHSCXEG 760        770        780        790        800
              ....|....|....|....|....|....|....|....|....|....|
NOV2          MXSIFGYITLPSQFPFYYCYRYADCASCTANTNGCQWCD-XXXCIALEAX
gi|13160051|  QISIFRYEXCPKDNPMYYCNKKYSCRSCALDQN-CQWERPNQECIALPEN
gi|4585307|   QISIAXYEXCPKDNPMYYCNKKYSCRSCALDQN-CQWERPNQECIALPEN
gi|13431313|  QISIAXYEXCPKDNPMYYCNKKYSCRSCALDQN-CQWERPNQECIALPEN
gi|6912258|   QISIFRYEXCPKDNPMYYCNKKYSCRSCALDQN-CQWERPNQECIALPEN
gi|12275312|  QISIAXYXXCPKDNPMYYCNKKYSCRSCALDQN-CQWERPNQECIALPEN 810        820        830        840        850
              ....|....|....|....|....|....|....|....|....|....|
NOV2          XCGEGWSHIGXXCLXYNSXXENYDNAKLXCYNLXGNLASLTXSKXVEFVL
gi|13160051|  ICGIGWHLVGNSCLKITTAKENYDNAKLFCRNHNALLASLTXQKKVEFVL
gi|4585307|   ICGNGWHLVGNSCLKITTAKENYDNAKLSCRNHNAFLASLTXQKKVELVL
gi|13431313|  ICGIGWHLVGNSCLKITTAKENYDNAKLFCRNHNALLASLTXQKKVEFVL
gi|6912258|   ICGIGWHLVGNSCLKITTAKENYDNAKLFCRNHNALLASLTXQKKVEFVL
gi|12275312|  ICGIGWHLVGNSCLKITTAKENYDNAKLSCRNHNAFLASLTXQKKVEFVL 860        870        880        890        900
              ....|....|....|....|....|....|....|....|....|....|
NOV2          DXX------QKYXQKXXPWVGLRKINXSYWGWEDMSPFTNXITLQWXPGE
gi|13160051|  KQLRXMQSSQSMSKLTLTPWVGLRKINVSYWCWEDMSPFTNSLLQWMPSE
gi|4585307|   KQLRXMQSSQSMSKLTLTPWVGLRKINVSYWCWEDMSPFTNSLLQWMPSE
gi|13431313|  KQLRXMQSSQSMSKLTLTPWVGLRKINVSYWCWEDMSPFTNSLLQWMPSE
gi|6912258|   KQLRXMQSSQSMSKLTLTPWVGLRKINVSYWCWEDMSPFTNSLLQWMPSE
gi|12275312|  KQLRXMQSSQSTXSKLTLTPWVGLRKINVSYWCWEDMSPFTNSLLQWMPSE 910        920        930        940        950
              ....|....|....|....|....|....|....|....|....|....|
NOV2          PXDXGFCAYLERAXVAGLKANPCTXMANGLVCEXPVNQXAXPCXKPCXLR
gi|13160051|  PSDAGFCGILSEPSTRGLKAATCINPLNGSVCERPANHSAKQCRTPCALR
gi|4585307|   PSDAGFCGILSEPSTRGLKAATCINPLNGSVCERPANHSAKQCRTPCALR
gi|13431313|  PSDAGFCGILSEPSTRGLKAATCINPLNGSVCERPANHSAKQCRTPCALR
gi|6912258|   PSDAGFCGILSEPSTRGLKAATCINPLNGSVCERPANHSAKQCRTPCALR
gi|12275312|  PSDAGFCGILSEPSTRGLKAATCINPLNGSVCERPANHSAKQCRTPCALR 960        970        980        990        1000
              ....|....|....|....|....|....|....|....|....|....|
NOV2          TXCSNXCTSXGMECMWCSXTKXCVDSNAYXISFPXGQCXEWQXAXCSRAXN
gi|13160051|  TACCXCTSXSSECMWCSNMKQCVDSNAYVASFPFGQCMEWYTMSXCPPEN
gi|4585307|   TACCXCTSXSSECMWCSNMKQCVDSNAYVASFPFGQCMEWYTMSXCPPEN
gi|13431313|  TACCXCTSXSSECMWCSNMKQCVDSNAYVASFPFGQCMEWYTMSXCPPEN
gi|6912258|   TACCXCTSXSSECMWCSNMKQCVDSNAYVASFPFGQCMEWYTMSXCPPEN
gi|12275312|  TACCXCTSXSSECMWCSNMKQCVDSNAYVASFPFGQCMEWYTMSXCPPEN
```

TABLE 2D-continued

ClustalW Analysis of NOV2

```
              1010       1020       1030       1040       1050
              ....|....|....|....|....|....|....|....|....|....|
NOV2          CSGLRTCGQCLEQPECGWCNDPSNTGKGHCIEGSSKGEKK-----IGMH
gi|13160051|  CSGYCTCSHCLEQPGCGWCTDPSNTGKGKCIEGSYKGPVKMPSQAPTGNF
gi|4585307|   CSGYCTCSHCLEQPGCGWCTDPSNTGKGKCIEGSYKGPVKMPSQASAGNV
gi|13431313|  CSGYCTCSHCLEQPGCGWCTDPSNTGKGKCIEGSYKGPVKMPSQASAGNV
gi|6912258|   CSGYCTCSHCLEQPGCGWCTDPSNTGKGKCIEGSYKGPVKMPSQAPTGNF
gi|12275312|  CSGYCTCSHCLEQPGCGWCTDPSNTGKGKCIEGSYKGPVKMPSHASTGNV 1060       1070       1080       1090       1100
              ....|....|....|....|....|....|....|....|....|....|
NOV2          HSKMKLKKKCPKKKNYEWSFIQCPACQCNGHSTCINNKKCEKCKLTTG
gi|13160051|  YPQPLLNSSMCLEDSRYNWSFIHCPACQCNGHSKCINQSICEKCELTTG
gi|4585307|   YPQPLLNSSMCLEDSRYNWSFIHCPACQCNGHSKCINQSKCEKCELTTG
gi|13431313|  YPQPLLNSSMCLEDSRYNWSFIHCPACQCNGHSKCINQSICEKCELTTG
gi|6912258|   YPQPLLNSSMCLEDSRYNWSFIHCPACQCNGHSKCINQSICEKCELTTG
gi|12275312|  YPQPLLNSSMCLEDSRYNWSFIHCPACQCNGHSKCINQSICEKCELTTG 1110       1120       1130       1140       1150
              ....|....|....|....|....|....|....|....|....|....|
NOV2          KQCKDCKPCKYGDPTNGGKCTACKCKGHAKKCKLKTGKCFCTTKGKKGDK
gi|13160051|  KHCETCISGFYGDPTNGGKCQPCKCNGHASLCNTNTGKCFCTTKGVKGDE
gi|4585307|   KHCETCISGFYGDPTNGGKCQPCKCNGHASLCNTNTGKCFCTTKGVKGDE
gi|13431313|  KHCETCISGFYGDPTNGGKCQPCKCNGHASLCNTNTGKCFCTTKGVKGDE
gi|6912258|   KHCETCISGFYGDPTNGGKCQPCKCNGHASLCNTNTGKCFCTTKGVKGDE
gi|12275312|  KHCETCISGFYGDPTNGGKCQPCKCNGHASLCNTNTGKCFCTTKGVKGE 1160       1170       1180       1190       1200
              ....|....|....|....|....|....|....|....|....|....|
NOV2          CQLCKSENRYVGNPLKGTCYCKYKLLIDYQFTFSLLQRDDRKTAINFKA
gi|13160051|  CQLCEVENRYQGNPLKGTCY--YTLLIDYQFTFSLSQEDDRYYTAINFVA
gi|4585307|   CQLCKVENRYQGNPLKGTCY--YTLLIDYQFTFSLSQGDDRYYTAINFVA
gi|13431313|  CQLCEVENRYQGNPLKGTCY--YTLLIDYQFTFSLSQEDDRYYTAINFVA
gi|6912258|   CQLCEVENRYQGNPLKGTCY--YTLLIDYQFTFSLSQEDDRYYTAINFVA
gi|12275312|  CQLCEVENRYQGNPLKGTCY--YTLLIDYQFTFSLSQEDDRYYTAINFVA 1210       1220       1230       1240       1250
              ....|....|....|....|....|....|....|....|....|....|
NOV2          NEKKVRKKLDKSINASNNFNLNITWKVG-SAGTIKGEETSKVSKNNIKEY
gi|13160051|  TPDEQNRFLFMFINASKNFNLNITWAASFSAGTQAGEEKPVVSKTNIKEY
gi|4585307|   TPDEQNRFEFMFINASKKFNLNITWATSFPAGTQKGEEKPVVSKTNIKEY
gi|13431313|  TPDEQNRFLFMFINASKNFNLNITWAASFSAGTQAGEEKPVVSKTNIKEY
gi|6912258|   TPDEQNRFLFMFINASKNFNLNITWAASFSAGTQAGEEKPVVSKTNIKEY
gi|12275312|  TPDEQNRFLFMFINASKNFNLNITWATSFPAGTQKGEEKPVVSKTNIKEY 1260       1270       1280       1290       1300
              ....|....|....|....|....|....|....|....|....|....|
NOV2          RDSFSYEKFKFRKKPNITFKVYVSNFKWPIKIQVSVKSIYF---------
gi|13160051|  KDSFSNEKFDFRNHPNITFFVYVSNFTWPIKIQVQTEQ------------
gi|4585307|   KDSFSNEKFDFRNHPNITFFVYVSNFTWPIKIQKAFSQHSNFMDLVQFFV
gi|13431313|  KDSFSNEKFDFRNHPNITFFVYVSNFTWPIKIQKAFSQHSNFMDLVQFFV
gi|6912258|   KDSFSNEKFDFRNHPNITFFVYVSNFTWPIKIQVQTEQ------------
gi|12275312|  KDSFSNEKFDFRNHPNITFFVYVSNFTWPIKIQVRVTS------------

1310       1320       1330       1340       1350
              ....|....|....|....|....|....|....|....|....|....|
NOV2          --------------------------------------------------
gi|13160051|  --------------------------------------------------
gi|4585307|   TFFSCFLSLLLVAAVVWKIKQSCWASRRREQLLREMQQMASRPFASNVVA
gi|13431313|  TFFSCFLSLLLVAAVVWKIKQSCWASRRREQLLREMQQMASRPFASNVVA
gi|6912258|   --------------------------------------------------
gi|12275312|  --------------------------------------------------

1360       1370       1380       1390       1400
              ....|....|....|....|....|....|....|....|....|....|
NOV2          --------------------------------------------------
gi|13160051|  --------------------------------------------------
gi|4585307|   LETDEEPPDLIGGSIKTVPKPIALEPCFGNKAAVLSVFVRLPRGLGGIPP
gi|13431313|  LETDEEPPDLIGGSIKTVPKPIALEPCFGNKAAVLSVFVRLPRGLGGIPP
gi|6912258|   --------------------------------------------------
gi|12275312|  --------------------------------------------------
```

TABLE 2D-continued

ClustalW Analysis of NOV2

```
                  1410       1420       1430       1440
            ....|....|....|....|....|....|....|....|....|
NOV2        --------------------------------------------
gi|13160051| --------------------------------------------
gi|4585307|  PGQSGLAVASALVDISQQMPIVYKEKSGAVRNRKQQPPAQPGTCI
gi|13431313| PGQSGLAVASALVDISQQMPIVYKEKSGAVRNRKQQPPAQPGTCI
gi|6912258|  --------------------------------------------
gi|12275312| --------------------------------------------
```

Tables 2E–I list the domain description from DOMAIN analysis results against NOV2. This indicates that the NOV2 sequence has properties similar to those of other proteins known to contain this domain.

TABLE 2E

Domain Analysis of NOV2 gnl|Smart|smart00034, CLECT, C-type lectin (CTL) or carbohydrate-recognition domain (CRD); Many of these domains function as calcium-dependent carbohydrate binding modules. (SEQ ID NO:67)
CD-Length = 124 residues, 100.0% aligned
Score = 70.1 bits (170), Expect = 7e-13

```
Query:  708 CGEGW SHIGDACLRVNSSRENYDNAKLYCYNLSGNLASLTTSKEVEFVLDEIQKYTQQK  766
                ||  |+ |   | + ++ +6 + +|+ +|  +|  +|||+ + +| +|+|  ++
Sbjct:    1 CPSGWVSYPGGKCYKFSTEKKTWADAQAFCQSLGAHLASIHSEEENDFLLSLLKNSNSDY  60

Query:  767 VSPWVGLRKINI SYWGWEDMSPFTNTTLQWLPGEPNDSGFCAYLERAAVAGLKANPCTS  825
                |+|| + +    |||   + +  ||||  || |   +           |||
Sbjct:   61 Y--WIGLSRPDSNGSWQWSDGSGPVDYS NWAPGEPGGSGNCVVLSTSGGGKWNDVSCTS  117

Query:  826 MANGLVCE  833
                +||
Sbjct:  118 -KLPFICE  124
```

TABLE 2F

Domain Analysis of NOV2 gnl|Smart|smart00042, CUB, Domain first found in C1r, C1s, uEGF, and bone morphogenetic protein.; This domain is found mostly among developmentally-regulated proteins. Spermadhesins contain only this domain. (SEQ ID NO:68)
CD-Length = 114 residues, 96.5% aligned
Score = 66.2 bits (160), Expect = 1e-11

```
Query:   58 RLTEPSGYLT--DGPINYKYKTKCTWLIEGPNA-VLRLRFNHFATE----CSWDHMYVYD  110
            ||  || +|  + | +|     ||| |    + |+|  | |    |++|++ +||
Sbjct:    4 TLTASSGTITSPNYPNSYPNNLNCVWTISAPPGYRIELKFTDFDLESSDNCTYDVYEIYD  63

Query:  111 GDSIYAPLIASFSGLIVPEIRGNETVPEVVTTSGYALLHFFSDAAYNLTGFNIFYSI    167
            | |  +||+  |  +|      | + ++|    + |  |++    ||+  ||
Sbjct:   64 GPSTSSPLLGRFCGSELPP-------PIISSSSNSMTVTFVSDSSVQKRGFSARYSA    113
```

TABLE 2G

Domain Analysis of NOV2 gnl|Smart|smart00042, CUB, Domain first found in C1r, C1s, uEGF, and bone morphogenetic protein.; This domain is found mostly among developmentally-regulated proteins. Spermadhesins contain only this domain. (SEQ ID NO:68)
CD-Length = 114 residues, 96.5% aligned
Score = 66.2 bits (160), Expect = 1e-11

```
Query:   58 RLTEPSGYLT--DGPINYKYKTKCTWLIEGPNA-VLRLRFNHFATE----CSWDHMYVYD  110
            ||  || +|  + | +|     ||| |    + |+|  | |    |++|++ +||
Sbjct:    4 TLTASSGTITSPNYPNSYPNNLNCVWTISAPPGYRIELKFTDFDLESSDNCTYDVYEIYD  63

Query:  111 GDSIYAPLIASFSGLIVPEIRGNETVPEVVTTSGYALLHFFSDAAYNLTGFNIFYSI    167
```

TABLE 2G-continued

Domain Analysis of NOV2

```
             |  | +||+  |  | +|       | + ++|    + |  ||++   ||+  ||
Sbjct:   64  GPSTSSPLLGRFCGSELPP-------PIISSSSNSMTVTFVSDSSVQKRGFSARYSA    113
```

TABLE 2H

Domain Analysis of NOV2 gnl|Pfam|pfam00431, CUB, CUB domain. (SEQ ID NO:69)
CD-Length = 110 residues, 97.3% aligned
Score = 63.9 bits (154), Expect = 5e-11

```
Query:   58  RLTEPSGYLT--DGPINYKYKTKCTWLIEGPNAV-LRLRFNHFATE----CSWDHMYVYD   110
             ||| ||  ++  +  | +|      +|  |  |     + |  |   |     | +|++ + |
Sbjct:    4  VLTESSGSISSPNYPNDYPPNKECVWTIRAPPGYRVELTFQDFDLEDHTGCRYDYVEIRD   63

Query:  111  GDSIYAPLIASFSGLIVPEIRGNETVPEVVTTSGYALLHFFSDAAYNLTGFNIFY       165
             ||    +||+   |  |       |        ++|++|      + |  |||+ +  ||      |
Sbjct:   64  GDGSSSPLLGKFCGSGPP--------EDIVSSSNRMTIKFVSDASVSKRGFKATY       110
```

TABLE 2I

Domain Analysis of NOV2 gnl|Pfam|pfam00059, lectin_c, Lectin C-type domain. This family
includes both long and short form C-type (SEQ ID NO:70)
CD-Length = 107 residues, 100.0% aligned
Score = 49.3 bits (116), Expect = 1e-06

```
Query:  725  SRENYDNAKLYCYNLSGNLASLTTSKEVEFVLDEIQKYTQQKVSPWVGLRKINIS-YWGW   783
             + +   |+  |   |  |  |  |+ +++| +|+     +          |+||   ||      | |
Sbjct:    1  ESKTWAEAQAACQKLGGGLVSIQSAEEQDFLTSLTKAS---NSYAWIGLTDINTEGTWVW   57

Query:  784  EDMSPFTNTTLQWLPGEPND---SGFCAYLERAAVAGLKANPCTSMANGLVCEK        834
             |  ||    |     | ||||||+      |    +                ||  |        |||
Sbjct:   58  TDGSPVNYTN--WAPGEPNNRGNKEDCVEIYTDG-NKWNDEPCGSK-LPYVCEF        107
```

The protein of invention is highly homologous to the protein attractin, which is a membrane-associated or secreted molecule (depending upon the splice variant) in activated T cells. It has a protease activity and is thought to modify the N-terminals of cytokines and chemokines, enabling the cells to interact and form clusters. The mouse ortholog of soluble attractin has been demonstrated to play a role in obesity and metabolic regulation. The protein of invention shows characteristic domains involved in protein-protein interactions, such as the CUB domain and the kelch motif. It also shows the presence of 4 plexin repeats, a lectin C-type domain and two laminin EGF-like domains, thus sharing its domain structure with attractin. Although attractin is predicted to be localized in the mitochondrial matrix, like the protein of invention, it is either secreted or located as a transmembrane protein at the plasma membrane. The protein of invention may therefore have diverse physiological roles in the tissues that it is expressed.

Attractin is a rapidly upregulated membrane-associated molecule on activated T cells (Duke-Cohan J S, et al. Adv Exp Med Biol 2000;477:173–85). It is a member of the CUB family of extracellular guidance and development proteins, sharing with them a protease activity similar to that of Dipeptidyl peptidase IV (DPPIV/CD26). Most remarkably, and in sharp contrast to CD26, it is released from the T cell and is presumed to be a major source of a soluble serum-circulating attractin. Genomic sequencing reveals that the soluble form is not a proteolytic product of the membrane form, but is in fact the result of alternative splicing. Recent results prove that the loss of murine membrane attractin results in the mahogany mutation with severe repercussions upon skin pigmentation and control of energy metabolism. In each of these latter instances, there is a strong likelihood that attractin is moderating the interaction of cytokines with their respective receptors. Attractin is likely performing a similar function in the immune system through capture and proteolytic modification of the N-terminals of several cytokines and chemokines. This regulatory activity allows cells to interact and form immunoregulatory clusters and subsequently aids in downregulating chemokine/cytokine activity once a response has been initiated. These two properties are likely to be affected by the balance of membrane-expressed to soluble attractin.

Attractin was initially identified as a soluble human plasma protein with dipeptidyl peptidase IV activity that is expressed and released by activated T lymphocytes. It has also been identified as the product of the murine mahogany gene with connections to control of pigmentation and energy metabolism. (Tang W et al., Proc Natl Acad Sci USA 2000 May 23;97(11):6025–30). The mahogany product, however, is a transmembrane protein, raising the possibility of a human membrane attractin in addition to the secreted form. The genomic structure of human attractin reveals that soluble attractin arises from transcription of 25 sequential exons on human chromosome 20p13, where the 3' terminal exon contains sequence from a long interspersed nuclear element-1 (LINE-1) retrotransposon element that includes a stop codon and a polyadenylation signal. The mRNA isoform for membrane attractin splices over the LINE-1 exon and includes five exons encoding transmembrane and cytoplasmic domains with organization and coding potential almost identical to that of the mouse gene.

The relative abundance of soluble and transmembrane isoforms measured by reverse transcription-PCR is differentially regulated in lymphoid tissues. Because activation of peripheral blood leukocytes with phytohemagglutinin induces strong expression of cell surface attractin followed by release of soluble attractin, these results suggest that a genomic event unique to mammals, LINE-1 insertion, has provided an evolutionary mechanism for regulating cell interactions during an inflammatory reaction.

The Mahogany/Attractin gene (Atrn) has been proposed as a downstream mediator of Agouti signaling because yellow hair color and obesity in lethal yellow (A(y)) mice are suppressed by the mahogany (Atrn(mg)) mutation. (Lu Xy et al., FEBS Lett 1999 Nov. 26;462(1–2):101–7). The present study examined the distribution of Atrn mRNA in the brain and spinal cord by in situ hybridization. Atrn mRNA was found widely distributed throughout the central nervous system, with high levels in regions of the olfactory system, some limbic structures, regions of the brainstem, cerebellum and spinal cord. In the hypothalamus, Atrn mRNA was found in specific nuclei including the suprachiasmatic nucleus, the supraoptic nucleus, the medial preoptic nucleus, the paraventricular hypothalamic nucleus, the ventromedial hypothalamic nucleus, and the arcuate nucleus. These results suggest a broad spectrum of physiological functions for the Atrn gene product.

Completely different lines of experimentation have identified attractin, a protein that seems to have multiple roles in regulating physiological processes. (Jackson I J Trends Genet 1999 November;15(11):429–31). It affects the balance between agonist and antagonist at receptors on melanocytes, modifies behaviour and basal metabolic rate, and mediates an interaction between activated T cells and macrophages. It may well be a target for development of drugs to treat obesity.

Agouti protein and agouti-related protein are homologous paracrine signalling molecules that normally regulate hair colour and body weight, respectively, by antagonizing signalling through melanocortin receptors. (Gunn T M, et al., Nature 1999 Mar. 11;398(6723):152–6). Expression of Agouti is normally limited to the skin, but rare alleles from which Agouti is expressed ubiquitously, such as lethal yellow, have pleiotropic effects that include a yellow coat, obesity, increased linear growth, and immune defects. The mahogany (mg) mutation suppresses the effects of lethal yellow on pigmentation and body weight, and results of our previous genetic studies place mg downstream of transcription of Agouti but upstream of melanocortin receptors. Here positional cloning was used to identify a candidate gene for mahogany, Mgca. The predicted protein encoded by Mgca is a 1,428-amino-acid, single-transmembrane-domain protein that is expressed in many tissues, including pigment cells and the hypothalamus. The extracellular domain of the Mgca protein is the orthologue of human attractin, a circulating molecule produced by activated T cells that has been implicated in immune-cell interactions. These observations provide new insight into the regulation of energy metabolism and indicate a molecular basis for crosstalk between melanocortin-receptor signalling and immune function.

Attractin is a normal human serum glycoprotein of 175 kDa that is rapidly expressed on activated T cells and released extracellularly after 48–72 hr. (Duke-Cohan J S et al., Proc Natl Acad Sci USA 1998 Sep. 15;95(19):11336–41). Attractin has been cloned and, in its natural serum form, it mediates the spreading of monocytes that become the focus for the clustering of nonproliferating T lymphocytes. There are two mRNA species with hematopoietic tissue-specific expression that code for a 134-kDa protein with a putative serine protease catalytic serine, four EGF-like motifs, a CUB domain, a C type lectin domain, and a domain homologous with the ligand-binding region of the common gamma cytokine chain. Except for the latter two domains, the overall structure shares high homology with the *Caenorhabditis elegans* F33C8.1 protein, suggesting that attractin has evolved new domains and functions in parallel with the development of cell-mediated immunity.

The disclosed NOV2 nucleic acid of the invention encoding a Attractin-like protein includes the nucleic acid whose sequence is provided in Table 2A or a fragment thereof. The invention also includes a mutant or variant nucleic acid any of whose bases may be changed from the corresponding base shown in Table 2A while still encoding a protein that maintains its Attractin-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 29% percent of the bases may be so changed.

The disclosed NOV2 protein of the invention includes the Attractin-like protein whose sequence is provided in Table 2B. The invention also includes a mutant or variant protein any of whose residues may be changed from the corresponding residue shown in Table 2B while still encoding a protein that maintains its Attractin-like activities and physiological functions, or a functional fragment thereof. In the mutant or variant protein, up to about 43% percent of the residues may be so changed.

The NOV2 nucleic acids and proteins of the invention are useful in potential therapeutic applications implicated in Von Hippel-Lindau (VHL) syndrome, Alzheimer's disease, Stroke, Tuberous sclerosis, hypercalceimia, Parkinson's disease, Huntington's disease, Cerebral palsy, Epilepsy, Multiple sclerosis, Ataxia-telangiectasia, Leukodystrophies, Behavioral disorders, Addiction, Anxiety, Pain, Neurodegeneration, Diabetes, Autoimmune disease, Renal artery stenosis, Interstitial nephritis, Glomerulonephritis, Polycystic kidney disease, Systemic lupus erythematosus, Renal tubular acidosis, IgA nephropathy, Hypercalceimia, Diabetes, Pancreatitis, Obesity, Endometriosis, Infertility, Hirschsprung's disease, Crohn's Disease, Appendicitis, Muscular dystrophy, Lesch-Nyhan syndrome, Myasthenia gravis, Cirrhosis, Liver failure, Breast cancer, Ovarian cancer, Prostate cancer, Uterine cancer and/or other pathologies/disorders. The NOV2 nucleic acid encoding Attractin-like protein, and the Attractin-like protein of the invention, or fragments thereof, may further be useful in diagnostic applications, wherein the presence or amount of the nucleic acid or the protein are to be assessed.

NOV2 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. The disclosed NOV2 protein has multiple hydrophilic regions, each of which can be used as an immunogen. In one embodiment, a contemplated NOV2 epitope is from about amino acids 1 to 20. In another embodiment, a NOV2 epitope is from about amino acids 50 to 130. In additional embodiments, NOV2 epitopes are from about amino acids 140 to 150, from about 180 to 380, from about amino acids 400 to 500, from about amino acids 530 to 550, from about amino acids 580 to 680, from about amino acids 700 to 740, from about amino acids 760 to 780, from about amino acids 820 to 900, and from about amino acids 950 to 1200. These novel proteins can be used in assay systems for functional analysis of various human disorders, which are useful in understanding of pathology of the disease and development of new drug targets for various disorders.

NOV3

NOV3 includes three novel Insulin Like Growth Factor Binding Protein Complex-Acid Labile Subunit (IGFBP-ALS)-like proteins disclosed below. The disclosed sequences have been named NOV3a and NOV3b.

NOV3a

A disclosed NOV3a nucleic acid of 6201 nucleotides (also referred to as 124217931_EXT) encoding a novel Kinase-like protein is shown in Table 3a. An open reading frame was identified beginning with a ATG initiation codon at nucleotides 57–59 and ending with a TGA codon at nucleotides 6199–6201. The start and stop codons are in bold letters.

TABLE 3A

NOV3a Nucleotide Sequence (SEQ ID NO:8)

ATGTTGAAGTTCAAATATGGAGCGCGGAATCCTTTGGATGCTGGTGCTGCTGAACCCATTGCCAGCCGGGC

CTCCAGGCTGAATCTGTTCTTCCAGGGGAAACCACCCTTTATGACTCAACAGCAGATGTCTCCTCTTTCCC

GAGAAGGGATATTAGATGCCCTCTTTGTTCTCTTTGAAGAATGCAGTCAGCCTGCTCTGATGAAGATTAAG

CACGTGAGCAACTTTGTCCGGAAGTGTTCCGACACCATAGCTGAGTTACAGGAGCTCCAGCCTTCGGCAAA

GGACTTCGAAGTCAGAAGTCTTGTAGGTTGTGGTCACTTTGCTGAAGTGCAGGTGGTAAGAGAGAAAGCAA

CCGGGGACATCTATGCTATGAAAGTGATGAAGAAGAAGGCTTTATTGGCCCAGGAGCAGGTTTCATTTTTT

GAGGAAGAGCGGAACATATTATCTCGAAGCACAAGCCCGTGGATCCCCCAATTACAGTATGCCTTTCAGGA

CAAAAATCACCTTTATCTGGTGATGGAATATCAGCCTGGAGGGGACTTGCTGTCACTTTTGAATAGATATG

AGGACCAGTTAGATGAAAACCTGATACAGTTTTACCTAGCTGAGCTGATTTTGGCTGTTCACAGCGTTCAT

CTGATGGGATACGTGCATCGGGACATCAAGCCTGAGAACATTCTCGTTGACCGCACAGGACACATCAAGCT

GGTGGATTTTGGATCTGCCGCGAAAATGAATTCAAACAAGGTGAATGCCAAACTCCCGATTGGGACCCCAG

ATTACATGGCTCCTGAAGTGCTGACTGTGATGAACGGGGATGGAAAAGGCACCTACGGCCTGGACTGTGAC

TGGTGGTCAGTGGGCGTGATTGCCTATGAGATGATTTATGGGAGATCCCCCTTCGCAGAGGGAACCTCTGC

CAGAACCTTCAATAACATTATGAATTTCCAGCGGTTTTTGAAATTTCCAGATGACCCCAAAGTGAGCAGTG

ACTTTCTTGATCTGATTCAAAGCTTGTTGTGCGGCCAGAAAGAGAGACTGAAGTTTGAAGGTCTTTGCTGC

CATCCTTTCTTCTCTAAAATTGACTGGAACAACATTCGTAACGCTCCTCCCCCCTTCGTTCCCACCCTCAA

GTCTGACGATGACACCTCCAATTTTGATGAACCAGAGAAGAATTCGTGGGTTTCATCCTCTCCGTGCCAGC

TGAGCCCCTCAGGCTTCTCGGGTGAAGAACTGCCGTTTGTGGGGTTTTCGTACAGCAAGGCACTGGGGATT

CTTGGTAGATCTGAGTCTGTTGTGTCGGGTCTGGACTCCCCTGCCAAGACTAGCTCCATGGAAAAGAAACT

TCTCATCAAAAGCAAAGAGCTACAAGACTCTCAGGACAAGTGTCACAAGATGGAGCAGGAAATGACCCGGT

TACATCGGAGAGTGTCAGAGGTGGAGGCTGTGCTTAGTCAGAAGGAGGTGGAGCTGAAGGCCTCTGAGACT

CAGAGATCCCTCCTGGAGCAGGACCTTGCTACCTACATCACAGAATGCAGTAGCTTAAAGCGAAGTTTGGA

GCAAGCACGGATGGAGGTGTCCCAGGAGGATGACAAAGCACTGCAGCTTCTCCATGATATCAGAGAGCAGA

GCCGGAAGCTCCAAGAAATCAAAGAGCAGGAGTACCAGGCTCAAGTGGAAGAAATGAGGTTGATGATGAAT

CAGTTGGAAGAGGATCTTGTCTCAGCAAGAAGACGGAGTGATCTCTACGAATCTGAGCTGAGAGAGTCTCG

GCTTGCTGCTGAAGAATTCAAGCGGAAAGCGACAGAATGTCAGCATAAACTGTTGAAGGCTAAGGATCAGG

GGAAGCCTGAAGTGGGAGAATATGCGAAACTGGAGAAGATCAATGCTGAGCAGCAGCTCAAAATTCAGGAG

CTCCAAGAGAAACTGGAGAAGGCTGTAAAAGCCAGCACGGAGGCCACCGACGTGCTGCAGAATATCCGCCA

TABLE 3A-continued

NOV3a Nucleotide Sequence (SEQ ID NO:8)

```
GGCAAAGGAGCGAGCCGAGAGGGAGCTGGAGAAGCTGCAGAACCGAGAGGATTCTTCTGAAGGCATCAGAA
AGAAGCTGGTGGAAGCTGAGGAACGCCGCCATTCTCTGGAGAACAAGGTAAAGAGACTAGAGACCATGGAG
CGTAGAGAAAACAGACTGAAGGATGACATCCAGACAAAATCCCAACAGATCCAGCAGATGGCTGATAAAAT
TCTGGAGCTCGAAGAGAAACATCGGGAGGCCCAAGTCTCAGCCCAGCACCTAGAAGTGCACCTGAAACAGA
AAGAGCAGCACTATGAGGAAAAGATTAAAGTATTGGACAATCAGATAAAGAAAGACCTGGCTGACAAGGAG
ACACTGGAGAACATGATGCAGAGACACGAGGAGGAGGCCCATGAGAAGGGCAAAATTCTCAGCGAACAGAA
GGCGATGATCAATGCTATGGATTCCAAGATCAGATCCCTGGAACAGAGGATTGTGGAACTGTCTGAAGCCA
ATAAACTTGCAGCAAATAGCAGTCTTTTTACCCAAAGGAACATGAAGGCCCAAGAAGAGATGATTTCTGAA
CTCAGGCAACAGAAATTTTACCTGGAGACACAGGCTGGGAAGTTGGAGGCCCAGAACCGAAAACTGGAGGA
GCAGCTGGAGAAGATCAGCCACCAAGACCACAGTGACAAGAATCGGCTGCTGGAACTGGAGACAAGATTGC
GGGAGGTGAGTCTAGAGCACGAGGAGCAGAAACTGGAGCTCAAGCGCCAGCTCACAGAGCTACAGCTCTCC
CTGCAGGAGCGCGAGTCACAGTTGACAGCCCTGCAGGCTGCACGGGCGGCCCTGGAGAGCCAGCTTCGCCA
GGCGAAGACAGAGCTGGAAGAGACCACAGCAGAAGCTGAAGAGGAGATCCAGGCACTCACGGCACATAGAG
ATGAAATCCAGCGCAAATTTGATGCTCTTCGTAACAGCTGTACTGTGATCACAGACCTGGAGGAGCAGCTA
AACCAGCTGACCGAGGACAACGCTGAACTCAACAACCAAAACTTCTACTTGTCCAAACAACTCGATGAGGC
TTCTGGCGCCAACGACGAGATTGTACAACTGCGAAGTGAAGTGGACCATCTCCGCCGGGAGATCACGGAAC
GAGAGATGCAGCTTACCAGCCAGAAGCAAACGATGGAGGCTCTGAAGACCACGTGCACCATGCTGGAGGAA
CAGGTCATGGATTTGGAGGCCCTAAACGATGAGCTGCTAGAAAAAGAGCGGCAGTGGGAGGCCTGGAGGAG
CGTCCTGGGTGATGAGAAATCCCAGTTTGAGTGTCGGGTTCGAGAGCTGCAGAGGATGCTGGACACCGAGA
AACAGAGCAGGGCGAGAGCCGATCAGCGGATCACCGAGTCTCGCCAGGTGGTGGAGCTGGCAGTGAAGGAG
CACAAGGCTGAGATTCTCGCTCTGCAGCAGGCTCTCAAAGAGCAGAAGCTGAAGGCCGAGAGCCTCTCTGA
CAAGCTCAATGACCTGGAGAAGAAGCATGCTATGCTTGAAATGAATGCCCGAAGCTTACAGCAGAAGCTGG
AGACTGAACGAGAGCTCAAACAGAGGCTTCTGGAAGAGCAAGCCAAATTACAGCAGCAGATGGACCTGCAG
AAAAATCACATTTTCCGTCTGACTCAAGGACTGCAAGAAGCTCTAGATCGGGCTGATCTACTGAAGACAGA
AAGAAGTGACTTGGAGTATCAGCTGGAAAACATTCAGGTGCTCTATTCTCATGAAAAGGTGAAAATGGAAG
GCACTATTTCTCAACAAACCAAACTCATTGATTTTTCTGCAAGCCAAAATGGACCAACCTGCTAAAAAGAA
AAGGTGCCTCTGCAGTACAATGAGCTGAAGCTGGCCCTGGAGAAGGAGAAAGCTCGCTGTGCAGAGCTAGA
GGAAGCCCTTCAGAAGACCCGCATCGAGCTCCGGTCCGCCCGGGAGGAAGCTGCCCACCGCAAAGCAACGG
ACCACCCACACCCATCCACGCCAGCCACCGCGAGGCAGCAGATCGCCATGTCTGCCATCGTGCGGTCGCCA
GAGCACCAGCCCAGTGCCATGAGCCTGCTGGCCCCGCCATCCAGCCGCAGAAAGGAGTCTTCAACTCCAGA
GGAATTTAGTCGGCGTCTTAAGGAACGCATGCACCACAATATTCCTCACCGATTCAACGTAGGACTGAACA
TGCGAGCCACAAAGTGTGCTGTGTGTCTGGATACCGTGCACTTTGGACGCCAGGCATCCAAATGTCTAGAA
TGTCAGGTGATGTGTCACCCCAAGTGCTCCACGTGCTTGCCAGCCACCTGCGGCTTGCCTGCTGAATATGC
CACACACTTCACCGAGGCCTTCTGCCGTGACAAAATGAACTCCCCAGGTCTCCAGACCAAGGAGCCCAGCA
GCAGCTTGCACCTGGAAGGGTGGATGAAGGTGCCCAGGAATAACAAACGAGGACAGCAAGGCTGGGACAGG
AAGTACATTGTCCTGGAGGGATCAAAAGTCCTCATTTATGACAATGAAGCCAGAGAAGCTGGACAGAGGCC
GGTGGAAGAATTTGAGCTGTGCCTTCCCGACGGGGATGTATCTATTCATGGTGCCGTTGGTGCTTCCGAAC
TCGCAAATACAGCCAAAGCAGATGTCCCATACATACTGAAGATGGAATCTCACCCGCACACCACCTGCTGG
```

TABLE 3A-continued

NOV3a Nucleotide Sequence (SEQ ID NO:8)

CCCGGGAGAACCCTCTACTTGCTAGCTCCCAGCTTCCCTGACAAACAGCGCTGGGTCACCGCCTTAGAATC

AGTTGTCGCAGGTGGGAGAGTTTCTAGGGAAAAAGCAGAAGCTGATGCTAAACTGCTTGGAAACTCCCTGC

TGAAACTGGAAGGTGATGACCGTCTAGACATGAACTGCACGCTGCCCTTCAGTGACCAGGTAGTGTTGGTG

GGCACCGAGGAAGGGCTCTACGCCCTGAATGTCTTGAAAAACTCCCTAACCCATGTCCCAGGAATTGGAGC

AGTCTTCCAAATTTATATTATCAAGGACCTGGAGAAGCTACTCATGATAGCAGGTGAAGAGCGGGCACTGT

GTCTTGTGGACGTGAAGAAAGTGAAACAGTCCCTGGCCCAGTCCCACCTGCCTGCCCAGCCCGACATCTCA

CCCAACATTTTTGAAGCTGTCAAGGGCTGCCACTTGTTTGGGGCAGGCAAGATTGAGAACGGGCTCTGCAT

CTGTGCAGCCATGCCCAGCAAAGTCGTCATTCTCCGCTACAACGAAAACCTCAGCAAATACTGCATCCGGA

AAGAGATAGAGACCTCAGAGCCCTGCAGCTGTATCCACTTCACCAATTACAGTATCCTCATTGGAACCAAT

AAATTCTACGAAATCGACATGAAGCAGTACACGCTCGAGGAATTCCTGGATAAGAATGACCATTCCTTGGC

ACCTGCTGTGTTTGCCGCCTCTTCCAACAGCTTCCCTGTCTCAATCGTGCAGGTGAACAGCGCAGGGCAGC

GAGAGGAGTACTTGCTGTGTTTCCACGAATTTGGAGTGTTCGTGGATTCTTACGAAGACGTAGCCGCACA

GACGATCTCAAGTGGAGTCGCTTACCTTTGGCCTTTGCCTACAGAGAACCCTATCTGTTTGTGACCCACTT

CAACTCACTCGAAGTAATTGAGATCCAGGCACGCTCCTCAGCAGGGACCCCTGCCCGAGCGTACCTGGACA

TCCCGAACCCGCGCTACCTGGGCCCTGCCATTTCCTCAGGAGCGATTTACTTGGCGTCCTCATACCAGGAT

AAATTAAGGGTCATTTGCTGCAAGGGAAACCTCGTGAAGGAGTCCGGCACTGAACACCACCGGGCCCGTC

CACCTCCCGCAGCAGCCCCAACAAGCGAGGCCCACCCACGTACAACGAGCACATCACCAAGCGCGTGGCCT

CCAGCCCAGCGCCGCCCGAAGGCCCCAGCCACCCGCGAGAGCCAAGCACACCCCACCGCTACCGCGAGGGG

CGGACCGAGCTGCGCAGGGACAAGTCTCCTGGCCGCCCCCTGGAGCGAGAGAAGTCCCCCGGCCGGATGCT

CAGCACGCGGAGAGAGCGGTCCCCCGGGAGGCTGTTTGAAGACAGCAGCAGGGGCCGGCTGCCTGCGGGAG

CCGTGAGGACCCCGCTGTCCCAGGTGAACAAGGTGAGGCAGCATTCCGAGGCCTGTGTGTCTGTTGCGGAG

GCCAGGAGTGACTTGGGGAACTGA

The disclosed NOV3a nucleic acid sequence maps to chromosome 13 and has 5518 of 6158 bases (89%) identical to rho/rac-interacting citron kinase (Crik) mRNA from *Mus musculus* (GENBANK-ID:AF086824) (E=0.0).

A disclosed NOV3a protein (SEQ ID NO:9) encoded by SEQ ID NO:8 has 2066 amino acid residues, and is presented using the one-letter code in Table 3B. Signal P, Psort and/or Hydropathy results predict that NOV3a does not have a signal peptide, and is likely to be localized to the nucleus with a certainty of 0.9800. In other embodiments NOV3a is also likely to be localized to microbody (peroxisome) with a certainty of 0.3000, to the mitochondrial membrane space with a certainty of 0.1000, or to the lysosome (lumen) with a certainty of 0.1000.

TABLE 3B

Encoded NOV3a protein sequence (SEQ ID NO:9).

MLKFKYGARNPLDAGAAEPIASRASRLNLFFQGKPPFMTQQQMSPLSREGILDALFVLFEECSQPALMKIK

HVSNFVRKCSDTIAELQELQPSAKDFEVRSLVGCGHFAEVQVVREKATGDIYAMKVMKKKALLAQEQVSFF

EEERNILSRSTSPWIPQLQYAFQDKNHLYLVMEYQPGGDLLSLLNRYEDQLDENLIQFYLAELILAVHSVH

LMGYVHRDIKPENILVDRTGHIKLVDFGSAAKMNSNKVNAKLPIGTPDYMAPEVLTVMNGDGKGTYGLDCD

WWSVGVIAYEMIYGRSPFAEGTSARTFNNIMNFQRFLKFPDDPKVSSDFLDLIQSLLCGQKERLKFEGLCC

HPFFSKIDWNNIRNAPPPFVPTLKSDDDTSNFDEPEKNSWVSSSPCQLSPSGFSGEELPFVGFSYSKALGI

LGRSESVVSGLDSPAKTSSMEKKLLIKSKELQDSQDKCHKMEQEMTRLHRRVSEVEAVLSQKEVELKASET

QRSLLEQDLATYITECSSLKRSLEQARMEVSQEDDKALQLLHDIREQSRKLQEIKEQEYQAQVEEMRLMMN

TABLE 3B-continued

Encoded NOV3a protein sequence (SEQ ID NO:9).

QLEEDLVSARRRSDLYESELRESRLAAEEFKRKATECQHKLLKAKDQGKPEVGEYAKLEKINAEQQLKIQE

LQEKLEKAVKASTEATELLQNIRQAKERAERELEKLQNREDSSEGIRKKLVEAEERRHSLENKVKRLETME

RRENRLKDDIQTKSQQIQQMADKILELEEKHREAQVSAQHLEVHLKQKEQHYEEKIKVLDNQIKKDLADKE

TLENMMQRHEEEAHEKGKILSEQKAMINAMDSKIRSLEQRIVELSEANKLAANSSLFTQRNMKAQEEMISE

LRQQKFYLETQAGKLEAQNRKLEEQLEKISHQDHSDKNRLLELETRLREVSLEHEEQKLELKRQLTELQLS

LQERESQLTALQAARAALESQLRQAKTELEETTAEAEEEIQALTAHRDEIQRKFDALRNSCTVITDLEEQL

NQLTEDNAELNNQNFYLSKQLDEASGANDEIVQLRSEVDHLRREITEREMQLTSQKQTMEALKTTCTMLEE

QVMDLEALNDELLEKERQWEAWRSVLGDEKSQFECRVRELQRMLDTEKQSRLRADQRITESRQVVELAVKE

HKAEILALQQALKEQKLKAESLSDKLNDLEKKHAMLEMNARSLQQKLETERELKQRLLEEQAKLQQQMDLQ

KNHIFRLTQGLQEALDRADLLKTERSDLEYQLENIQVLYSHEKVKMEGTISQQTKLIDFLQAKMDQPAKKK

KVPLQYNELKLALEKEKARCAELEEALQKTRIELRSAREEAAHRKATDHPHPSTPATARQQIAMSAIVRSP

EHQPSAMSLLAPPSSRRKESSTPEEFSRRLKERMHHNIPHRFNVGLNMRATKCAVCLDTVHFGRQASKCLE

CQVMCHPKCSTCLPATCGLPAEYATHFTEAFCRDKMNSPGLQTKEPSSSLHLEGWMKVPRNNKRGQQGWDR

KYIVLEGSKVLIYDNEAREAGQRPVEEFELCLPDGDVSIHGAVGASELANTAKADVPYILKMESHPHTTCW

PGRTLYLLAPSFPDKQRWVTALESVVAGGRVSREKAEADAKLLGNSLLKLEGDDRLDMNCTLPFSDQVVLV

GTEEGLYALNVLKNSLTHVPGIGAVFQIYIIKDLEKLLMIAGEERALCLVDVKKVKQSLAQSHLPAQPDIS

PNIFEAVKGCHLFGAGKIENGLCICAAMPSKVVILRYNENLSKYVIRKEIETSEPCSCIHFTNYSILIGTN

KFYEIDMKQYTLEEFLDKNDHSLAPAVFAASSNSFPVSIVQVNSAGQREEYLLCFHEFGVFVDSYGRRSRT

DDLKWSRLPLAFAYREPYLEVTHFNSLEVIEIQARSSAGTPARAYLDIPNPRYLGPAISSGAIYLASSYQD

KLRVICCKGNLVKESGTEHHRGPSTSRSSPNKRGPPTYNEHITKRVASSPAPPEGFSHPREPSTPHRYREG

RTELRRDKSPGRPLEREKSPGRMLSTRRERSPGRLFEDSSRGRLPAGAVRTPLSQVNKVRQHSEACVSVAE

ARSDLGN

The disclosed NOV3a amino acid has 1969 of 2053 amino acid residues (95%) identical to, and 2009 of 2053 amino acid residues (97%) similar to, the 2055 amino acid residue rho/rac-interacting citron kinase (Crik) protein from *Mus musculus* (SPTREMBL-ACC:O88938) (E=0.0).

TaqMan expression data for NOV3a is found below is Example 2.

NOV3b

A disclosed NOV3b nucleic acid of 6189 nucleotides (designated CuraGen Acc. No. CG106764-01) encoding a novel RHO/RAC-interacting citron kinase-like is shown in Table 3C. An open reading frame was identified beginning with an ATG initiation codon at nucleotides 1–3 and ending with a TAA codon at nucleotides 6160–6162. A putative untranslated region downstream from the termination codon is underlined in Table 3C, and the start and stop codons are in bold letters.

TABLE 3C

NOV3b Nucleotide Sequence (SEQ ID NO:10)

ATGTTGAAGTTCAAATATGGAGCGCGGAATCCTTTGGATGCTGGTGCTGCTGAACCCATTGCCAGCCGGGCCTCC

AGGCTGAATCTGTTCTTCCAGGGGAAACCACCCTTTATGACTCAACAGCAGATGTCTCCTCTTTCCCGAGAAGGG

ATATTAGATGCCCTCTTTGTTCTCTTTGAAGAATGCAGTCAGCCTGCTCTGATGAAGATTAAGCACGTGAGCAAC

TTTGTCCGGAAGTGTTCCGACACCATAGCTGAGTTACAGGAGCTCCAGCCTTCGGCAAAGGACTTCGAAGTCAGA

AGTCTTGTAGGTTGTGGTCACTTTGCTGAAGTGCAGGTGGTAAGAGAGAAAGCAACCGGGGACATCTATGCTATG

AAAGTGATGAAGAAGAAGGCTTTATTGGCCCAGGAGCAGGTTTCATTTTTTGAGGAAGAGCGGAACATATTATCT

TABLE 3C-continued

| NOV3b Nucleotide Sequence (SEQ ID NO:10) |
| --- |

CGAAGCACAAGCCCGTGGATCCCCCAATTACAGTATGCCTTTCAGGACAAAAATCACCTTTATCTGGTGATGGAA

TATCAGCCTGGAGGGGACTTGCTGTCACTTTTGAATAGATATGAGGACCAGTTAGATGAAAACCTGATACAGTTT

TACCTAGCTGAGCTGATTTTGGCTGTTCACAGCGTTCATCTGATGGGATACGTGCATCGGGACATCAAGCCTGAG

AACATTCTCGTTGACCGCACAGGACACATCAAGCTGGTGGATTTTGGATCTGCCGCGAAAATGAATTCAAACAAG

GTGAATGCCAAACTCCCGATTGGGACCCCAGATTACATGGCTCCTGAAGTGCTGACTGTGATGAACGGGGATGGA

AAAGGCACCTACGGCCTGGACTGTGACTGGTGGTCAGTGGGCGTGATTGCCTATGAGATGATTTATGGGAGATCC

CCCTTCGCAGAGGGAACCTCTGCCAGAACCTTCAATAACATTATGAATTTCCAGCGGTTTTTGAAATTTCCAGAT

GACCCCAAAGTGAGCAGTGACTTTCTTGATCTGATTCAAAGCTTGTTGTGCGGCCAGAAAGAGAGACTGAAGTTT

GAAGGTCTTTGCTGCCATCCTTTCTTCTCTAAAATTGACTGGAACAACATTCGTAACGCTCCTCCCCCCTTCGTT

CCCACCCTCAAGTCTGACGATGACACCTCCAATTTTGATGAACCAGAGAAGAATTCGTGGGTTTCATCCTCTCCG

TGCCAGCTGAGCCCCTCAGGCTTCTCGGGTGAAGAACTGCCGTTTGTGGGGTTTTCGTACAGCAAGGCACTGGGG

ATTCTTGGTAGATCTGAGTCTGTTGTGTCGGGTCTGGACTCCCCTGCCAAGACTAGCTCCATGGAAAAGAAACTT

CTCATCAAAAGCAAAGAGCTACAAGACTCTCAGGACAAGTGTCACAAGATGGAGCAGGAAATGACCCGGTTACAT

CGGAGAGTGTCAGAGGTGGAGGCTGTGCTTAGTCAGAAGGAGGTGGAGCTGAAGGCCTCTGAGACTCAGAGATCC

CTCCTGGAGCAGGACCTTGCTACCTACATCACAGAATGCAGTAGCTTAAAGCGAAGTTTGGAGCAAGCACGGATG

GAGGTGTCCCAGGAGGATGACAAAGCACTGCAGCTTCTCCATGATATCAGAGAGCAGAGCCGGAAGCTCCAAGAA

ATCAAAGAGCAGGAGTACCAGGCTCAAGTGGAAGAAATGAGGTTGATGATGAATCAGTTGGAAGAGGATCTTGTC

TCAGCAAGAAGACGGAGTGATCTCTACGAATCTGAGCTGAGAGAGTCTCGGCTTGCTGCTGAAGAATTCAAGCGG

AAAGCGACAGAATGTCAGCATAAACTGTTGAAGGCTAAGGATCAGGGGAAGCCTGAAGTGGGAGAATATGCGAAA

CTGGAGAAGATCAATGCTGAGCAGCAGCTCAAAATTCAGGAGCTCCAAGAGAAACTGGAGAAGGCTGTAAAAGCC

AGCACGGAGGCCACCGAGCTGCTGCAGAATATCCGCCAGGCAAAGGAGCGAGCCGAGAGGGAGCTGGAGAAGCTG

CAGAACCGAGAGGATTCTTCTGAAGGCATCAGAAAGAAGCTGGTGGAAGCTGAGGAACGCCGCCATTCTCTGGAG

AACAAGGTAAAGAGACTAGAGACCATGGAGCGTAGAGAAAACAGACTGAAGGATGACATCCAGACAAAATCCCAA

CAGATCCAGCAGATGGCTGATAAAATTCTGGAGCTCGAAGAGAAACATCGGGAGGCCCAAGTCTCAGCCCAGCAC

CTAGAAGTGCACCTGAAACAGAAAGAGCAGCACTATGAGGAAAAGATTAAAGTATTGGACAATCAGATAAAGAAA

GACCTGGCTGACAAGGAGACACTGGAGAACATGATGCAGAGACACGAGGAGGAGGCCCATGAGAAGGGCAAAATT

CTCAGCGAACAGAAGGCGATGATCAATGCTATGGATTCCAAGATCAGATCCCTGGAACAGAGGATTGTGGAACTG

TCTGAAGCCAATAAACTTGCAGCAAATAGCAGTCTTTTTACCCAAAGGAACATGAAGGCCCAAGAAGAGATGATT

TCTGAACTCAGGCAACAGAAATTTTACCTGGAGACACAGGCTGGGAAGTTGGAGGCCCAGAACCGAAAACTGGAG

GAGCAGCTGGAGAAGATCAGCCACCAAGACCACAGTGACAAGAATCGGCTGCTGGAACTGGAGACAAGATTGCGG

GAGGTGAGTCTAGAGCACGAGGAGCAGAAACTGGAGCTCAAGCGCCAGCTCACAGAGCTACAGCTCTCCCTGCAG

GAGCGCGAGTCACAGTTGACAGCCCTGCAGGCTGCACGGGCGGCCCTGGAGAGCCAGCTTCGCCAGGCGAAGACA

GAGCTGGAAGAGACCACAGCAGAAGCTGAAGAGGAGATCCAGGCACTCACGGCACATAGAGATGAAATCCAGCGC

AAATTTGATGCTCTTCGTAACAGCTGTACTGTGATCACAGACCTGGAGGAGCAGCTAAACCAGCTGACCGAGGAC

AACGCTGAACTCAACAACCAAAACTTCTACTTGTCCAAACAACTCGATGAGGCTTCTGGCGCCAACGACGAGATT

GTACAACTGCGAAGTGAAGTGGACCATCTCCGCCGGGAGATCACGGAACGAGAGATGCAGCTTACCAGCCAGAAG

CAAACGATGGAGGCTCTGAAGACCACGTGCACCATGCTGGAGGAACAGGTCATGGATTTGGAGGCCCTAAACGAT

GAGCTGCTAGAAAAAGAGCGGCAGTGGGAGGCCTGGAGGAGCGTCCTGGGTGATGAGAAATCCCAGTTTGAGTGT

CGGGTTCGAGAGCTGCAGAGGATGCTGGACACCGAGAAACAGAGCAGGGCGAGAGCCGATCAGCGGATCACCGAG

TABLE 3C-continued

NOV3b Nucleotide Sequence (SEQ ID NO:10)

```
TCTCGCCAGGTGGTGGAGCTGGCAGTGAAGGAGCACAAGGCTGAGATTCTCGCTCTGCAGCAGGCTCTCAAAGAG
CAGAAGCTGAAGGCCGAGAGCCTCTCTGACAAGCTCAATGACCTGGAGAAGAAGCATGCTATGCTTGAAATGAAT
GCCCGAAGCTTACAGCAGAAGCTGGAGACTGAACGAGAGCTCAAACAGAGGCTTCTGGAAGAGCAAGCCAAATTA
CAGCAGCAGATGGACCTGCAGAAAAATCACATTTTCCGTCTGACTCAAGGACTGCAAGAAGCTCTAGATCGGGCT
GATCTACTGAAGACAGAAAGAAGTGACTTGGAGTATCAGCTGGAAAACATTCAGGTGCTCTATTCTCATGAAAAG
GTGAAAATGGAAGGCACTATTTCTCAACAAACCAAACTCATTGATTTTCTGCAAGCCAAAATGGACCAACCTGCT
AAAAAGAAAAAGGTGCCTCTGCAGTACAATGAGCTGAAGCTGGCCCTGGAGAAGGAGAAAGCTCGCTGTGCAGAG
CTAGAGGAAGCCCTTCAGAAGACCCGCATCGAGCTCCGGTCCGCCCGGGAGGAAGCTGCCCACCGCAAAGCAACG
GACCACCCACACCCATCCACGCCAGCCACCGCGAGGCAGCAGATCGCCATGTCTGCCATCGTGCGGTCGCCAGAG
CACCAGCCCAGTGCCATGAGCCTGCTGGCCCCGCCATCCAGCCGCAGAAAGGAGTCTTCAACTCCAGAGGAATTT
AGTCGGCGTCTTAAGGAACGCATGCACCACAATATTCCTCACCGATTCAACGTAGGACTGAACATGCGAGCCACA
AAGTGTGCTGTGTGTCTGGATACCGTGCACTTTGGACGCCAGGCATCCAAATGTCTAGAATGTCAGGTGATGTGT
CACCCCAAGTGCTCCACGTGCTTGCCAGCCACCTGCGGCTTGCCTGCTGAATATGCCACACACTTCACCGAGGCC
TTCTGCCGTGACAAAATGAACTCCCCAGGTCTCCAGACCAAGGAGCCCAGCAGCAGCTTGCACCTGGAAGGGTGG
ATGAAGGTGCCCAGGAATAACAAACGAGGACAGCAAGGCTGGGACAGGAAGTACATTGTCCTGGAGGGATCAAAA
GTCCTCATTTATGACAATGAAGCCAGAGAAGCTGGACAGAGGCCGGTGGAAGAATTTGAGCTGTGCCTTCCCGAC
GGGGATGTATCTATTCATGGTGCCGTTGGTGCTTCCGAACTCGCAAATACAGCCAAAGCAGATGTCCCATACATA
CTGAAGATGGAATCTCACCCGCACACCACCTGCTGGCCCGGGAGAACCCTCTACTTGCTAGCTCCCAGCTTCCCT
GACAAACAGCGCTGGGTCACCGCCTTAGAATCAGTTGTCGCAGGTGGGAGAGTTTCTAGGGAAAAAGCAGAAGCT
GATGCTAAACTGCTTGGAAACTCCCTGCTGAAACTGGAAGGTGATGACCGTCTAGACATGAACTGCACGCTGCCC
TTCAGTGACCAGGTAGTGTTGGTGGGCACCGAGGAAGGGCTCTACGCCCTGAATGTCTTGAAAAACTCCCTAACC
CATGTCCCAGGAATTGGAGCAGTCTTCCAAATTTATATTATCAAGGACCTGGAGAAGCTACTCATGATAGCAGGT
GAAGAGCGGGCACTGTGTCTTGTGGACGTGAAGAAAGTGAAACAGTCCCTGGCCCAGTCCCACCTGCCTGCCCAG
CCCGACATCTCACCCAACATTTTTGAAGCTGTCAAGGGCTGCCACTTGTTTGGGGCAGGCAAGATTGAGAACGGG
CTCTGCATCTGTGCAGCCATGCCCAGCAAAGTCGTCATTCTCCGCTACAACGAAAACCTCAGCAAATACTGCATC
CGGAAAGAGATAGAGACCTCAGAGCCCTGCAGCTGTATCCACTTCACCAATTACAGTATCCTCATTGGAACCAAT
AAATTCTACGAAATCGACATGAAGCAGTACACGCTCGAGGAATTCCTGGATAAGAATGACCATTCCTTGGCACCT
GCTGTGTTTGCCGCCTCTTCCAACAGCTTCCCTGTCTCAATCGTGCAGGTGAACAGCGCAGGGCAGCGAAAGGAG
TACTTGCTGTGTTTCCACGAATTTGGAGTGTTCGTGGATTCTTACGGAAGACGTAGCCGCACAGACGATCTCAAG
TGGAGTCGCTTACCTTTGGCCTTTGCCTACAGAGAACCCTATCTGTTTGTGACCCACTTCAACTCACTCGAAGTA
ATTGAGATCCAGGCACCCTCCTCAGCAGGGACCCCTGCCCGAGCGTACCTGGACATCCCGAACCCGCGCTACCTG
GGCCCTGCCATTTCCTCAGGAGCGATTTACTTGGCGTCCTCATACCAGGATAAATTAAGGGTCATTTGCTGCAAG
GGAAACCTCGTGAAGGAGTCCGGCACTGAACACCACCGGCGCCCGTCCACCTCCCGCAGCAGCCCCAACAAGCGA
GGCCCACCCACGTACAACGAGCACATCACCAAGCGCGTCGCCTCCAGCCCAGCGCCGCCCGAAGGCCCCAGCCAC
CCGCGAGAGCCAAGCACACCCCACCGCTACCGCGAGGGGCGGACCGAGCTGCGCAGGGACAAGTCTCCTGGCCGC
CCCCTGGAGCGAGAGAAGTCCCCCGGCCGGATGCTCAGCACGCGGAGAGAGCGGTCCCCCGGGAGGCTGTTTGAA
GACAGCAGCAGGGGCCGGCTGCCTGCGGGAGCCGTGAGGACCCCGCTGTCCCAGGTGAACAAGGTGTGGGACCAG
TCTTCAGTATAAATCTCAGCCAGAAAAACCAACTCCTCA
```

The disclosed NOV3b nucleic acid sequence of this invention has 2894 of 2908 bases (99%) identity with KLAA1531 mRNA from *Homo sapiens* (GENBANK-ID: AB040964) (E=0.0).

A NOV3b polypeptide (SEQ ID NO:11) encoded by SEQ ID NO:10 is 2053 amino acid residues and is presented using the one letter code in Table 3D. The SignalP, Psort and Hydropathy, Psort, and/or SignalP data suggest that the NOV3b protein has no signal peptide and may be localized to nucleus with a certainty of 0.9800. In other embodiments, NOV3b may also be localized to the microbody (peroxisome) with a certainty of 0.300, the mitochondrial matrix space with a certainty of 0.100 or the lysosome (lumen) with a certainty of 0.100.

TABLE 3D

Encoded NOV3b protein sequence (SEQ ID NO:11)

MLKFKYGARNPLDAGAAEPIASRASRLNLFFQGKPPFMTQQQMSPLSREGILDALFVLFEECSQPALMKIKHV
SNFVRKCSDTIAELQELQPSAKDFEVRSLVGCGHFAEVQVVREKATGDIYAMKVMKKKALLAQEQVSFFEEER
NILSRSTSPWIPQLQYAFQDKNHLYLVMEYQPGGDLLSLLNRYEDQLDENLIQFYLAELILAVHSVHLMGYVH
RDIKPENILVDRTGHIKLVDFGSAAKMNSNKVNAKLPIGTPDYMAPEVLTVMNGDGKGTYGLDCDWWSVGVIA
YEMIYGRSPFAEGTSARTFNNIMNFQRFLKFPDDPKVSSDFLDLIQSLLCGQKERLKFEGLCCHPFFSKIDWN
NIRNAPPPFVPTLKSDDDTSNFDEPEKNSWVSSSPCQLSPSGFSGEELPFVGFSYSKALGILGRSESVVSGLD
SPAKTSSMEKKLLIKSKELQDSQDKCHKNEQEMTRLHRRVSEVEAVLSQKEVELKASETQRSLLEQDLATYIT
ECSSLKRSLEQARMEVSQEDDKALQLLHDIREQSRKLQEIKEQEYQAQVEEMRLMMNQLEEDLVSARRRSDLY
ESELRESRLAAEEFKRKATECQHKLLKAKDQGKPEVGEYAKLEKINAEQQLKIQELQEKLEKAVKASTEATEL
LQNIRQAKERAERELEKLQNREDSSEGIRKKLVEAEERRHSLENKVKRLETMERRENRLKDDIQTKSQQIQQM
ADKILELEEKHREAQVSAQHLEVHLKQKEQHYEEKIKVLDNQIKKDLADKETLRNMMQRHEEEAHEKGKILSE
QKAMINAMDSKIRSLEQRIVELSEANKLAANSSLFTQRNMKAQEEMISELRQQKFYLETQAGKLEAQNRKLEE
QLEKISHQDHSDKNRLLELETRLREVSLEHEEQKLELKRQLTELQLSLQERESQLTALQAARAALESQLRQAK
TELEETTAEAEEEIQALTAHRDEIQRKFDALRNSCTVITDLEEQLNQLTEDNAELNNQNFYLSKQLDEASGAN
DEIVQLRSEVDHLRREITEREMQLTSQKQTMEALKTTCTMLEEQVMDLEALNDELLEKERQWEAWRSVLGDEK
SQFECRVRELQRMLDTEKQSRARADQRITESRQVVELAVKEHKAEILALQQALKEQKLKAESLSDKLNDLEKK
HAMLEMNARSLQQKLETERELKQRLLEEQAKLQQQMDLQKNHIFRLTQGLQEALDRADLLKTERSDLEYQLEN
IQVLYSHEKVKMEGTISQQTKLIDFLQAKMDQPAKKKKVPLQYNELKLALEKEKARCAELEEALQKTRIELRS
AREEAAHRKATDHPHPSTPATARQQIAMSAIVRSPEHQPSAMSLLAPPSSRRKESSTPEEFSRRLKERMHHNI
PHRFNVGLNMRATKCAVCLDTVHFGRQASKCLECQVMCHPKCSTCLPATCGLPAEYATHFTEAFCRDKMNSPG
LQTKEPSSSLHLEGWMKVPRNNKRGQQGWDRKYIVLEGSKVLIYDNEAREAGQRPVEEFELCLPDGDVSIHGA
VGASELANTAKADVPYILKMESHPHTTCWPGRTLYLLAPSFPDKQRWVTALESVVAGGRVSREKAEADAKLLG
NSLLKLEGDDRLDMNCTLPFSDQVVLVGTEEGLYALNVLKNSLTHVPGIGAVFQIYIIKDLEKLLMIAGEERA
LCLVDVKKVKQSLAQSHLPAQPDISPNIFEAVKGCHLFGAGKIENGLCICAAMPSKVVILRYNENLSKYCIRK
EIETSEQCSCIHFTNYSILIGTNKFYEIDMKQYTLEEFLDKNDHSLAPAVFAASSNSFPVSIVQVNSAGQREE
YLLCFHEFGVFVDSYGRRSRTDDLKWSRLPLAFAYREPYLFVTHFNSLEVIEIQARSSAGTPARAYLDIPNPR
YLGPAISSGAIYLASSYQDKLRVICCKGNLVKESGTEHHRGPSTSRSSPNKRGPPTYNEHITKRVASSPAPPE
GPSHPREPSTPHRYREGRTELRRDKSPGRPLEREKSPGRMLSTRRERSPGRLFEDSSRGRLPAGAVRTPLSQV
NKVWDQSSV

The disclosed NOV3b amino acid sequence has 638 of 647 amino acid residues (98%) identical to, and 643 of 647 amino acid residues (99%) similar to, the KIAA1531 PROTEIN of 1060 amino acid residue prekallikrein-like protein from *Homo sapiens* (BAA96055) (E=0.0).

NOV3b is expressed primarily in normal brain but not in other normal tissues. Lower expression is seen in several tumor types.

NOV3b also has homology to the amino acid sequences shown in the BLASTP data listed in Table 3E.

TABLE 3E

BLAST results for NOV3b

| Gene Index/Identifier | Protein/Organism | Length (aa) | Identity (%) | Positives (%) | Expect |
|---|---|---|---|---|---|
| gi\|14768010\|ref\|XP_045786.1\| | citron (rho-interacting, serine/threonine kinase 21) [*Homo sapiens*] | 883 | 849/883 (96%) | 849/883 (96%) | 0.0 |
| gi\|6225217\|sp\|O14578\|CTRO_HUMAN | CITRON PROTEIN | 1286 | 1165/1286 (90%) | 1165/1286 (90%) | 0.0 |
| gi\|4589542\|dbj\|BAA76793.1\| | KIAA0949 protein [*Homo sapiens*] | 940 | 887/940 (94%) | 887/940 (94%) | 0.0 |
| gi\|3360514\|gb\|AAC27933.1\| | Citron-K kinase [*Mus musculus*] | 1641 | 1476/1683 (87%) | 1490/1683 (87%) | 0.0 |
| gi\|1345860\|sp\|P49025\|CTRO_MOUSE | CITRON PROTEIN | 1597 | 1427/1589 (89%) | 1442/1589 (89%) | 0.0 |

The homology of these sequences is shown graphically in the ClustalW analysis shown in Table 3F.

TABLE 3F

```
                    ClustalW Analysis of NOV3

1) NOV3a (SEQ ID NO:9)
2) NOV3b (SEQ ID NO:11)
3) gi|14768010|ref|XP_045786.1| citron (rho-interaction, serine/threonine kinase
   21) [Homo sapiens] (SEQ ID NO:37)
4) gi|6225217|sp|O14578|CTRO_HUMAN CITRON PROTEIN (SEQ ID NO:38)
5) gi|4589542|dbj|BAA76793.1| KIAA0949 protein [Homo sapiens] (SEQ ID NO:39)
6) gi|3360514|gb|AAC27933.1| Citron-K kinase [Mus musculus] (SEQ ID NO:40)
7) gi|1345860|sp|P49025|CTRO_MOUSE CITRON PROTEIN (SEQ ID NO:41)

10        20        30        40        50        60
                   ....|....|....|....|....|....|....|....|....|....|....|....|
NOV3a              MLKFKYGARNPLDAGAAEPIASRASRLNLFFQGKPPFMTQQQMSPLSREGILDALFVLFE  60
NOV3b              MLKFKYGARNPLDAGAAEPIASRASRLNLFFQGKPPFMTQQQMSPLSREGILDALFVLFE  60
gi|14768010|ref    ------------------------------------------------------------   1
gi|6225217|sp|O    ------------------------------------------------------------   1
gi|4589542|dbj|    ------------------------------------------------------------   1
gi|3360514|gb|A    ------------------------------------------------------------   1
gi|1345860|sp|P    ------------------------------------------------------------   1

70        80        90       100       110       120
                   ....|....|....|....|....|....|....|....|....|....|....|....|
NOV3a              ECSQPALMKIKHVSNFVRKCSDTIAELQELQPSAKDFEVRSLVGCGHFAEVQVVREKATG 120
NOV3b              ECSQPALMKIKHVSNFVRKCSDTIAELQELQPSAKDFEVRSLVGCGHFAEVQVVREKATG 120
gi|14768010|ref    ------------------------------------------------------------   1
gi|6225217|sp|O    ------------------------------------------------------------   1
gi|4589542|dbj|    ------------------------------------------------------------   1
gi|3360514|gb|A    ------------------------------------------------------------   1
gi|1345860|sp|P    ------------------------------------------------------------   1

130       140       150       160       170       180
                   ....|....|....|....|....|....|....|....|....|....|....|....|
NOV3a              DIYAMKVMKKKALLAQEQVSFFEEERNILSRSTSPWIPQLQYAFQDKNHLYLVMEYQPGG 180
NOV3b              DIYAMKVMKKKALLAQEQVSFFEEERNILSRSTSPWIPQLQYAFQDKNHLYLVMEYQPGG 180
gi|14768010|ref    ------------------------------------------------------------   1
gi|6225217|sp|O    ------------------------------------------------------------   1
gi|4589542|dbj|    ------------------------------------------------------------   1
gi|3360514|gb|A    ------------------------------------------------------------   1
gi|1345860|sp|P    ------------------------------------------------------------   1
```

TABLE 3F-continued

ClustalW Analysis of NOV3

```
                          190       200       210       220       230       240
                     ....|....|....|....|....|....|....|....|....|....|....|....|
NOV3a                DLLSLLNRYEDQLDENLIQFYLAELILAVHSVHLMGYVHRDIKPENILVDRTGHIKLVDF 240
NOV3b                DLLSLLNRYEDQLDENLIQFYLAELILAVHSVHLMGYVHRDIKPENILVDRTGHIKLVDF 240
gi|14768010|ref      ------------------------------------------------------------ 1
gi|6225217|sp|O      ------------------------------------------------------------ 1
gi|4589542|dbj|      ------------------------------------------------------------ 1
gi|3360514|gb|A      ------------------------------------------------------------ 1
gi|1345860|sp|P      ------------------------------------------------------------ 1

250       260       270       280       290       300
                     ....|....|....|....|....|....|....|....|....|....|....|....|
NOV3a                GSAAKMNSNKVNAKLPIGTPDYMAPEVLTVMNGDGKGTYGLDCDWWSVGVIAYEMIYGRS 300
NOV3b                GSAAKMNSNKVNAKLPIGTPDYMAPEVLTVMNGDGKGTYGLDCDWWSVGVIAYEMIYGRS 300
gi|14768010|ref      ------------------------------------------------------------ 1
gi|6225217|sp|O      ------------------------------------------------------------ 1
gi|4589542|dbj|      ------------------------------------------------------------ 1
gi|3360514|gb|A      ------------------------------------------------------------ 1
gi|1345860|sp|P      ------------------------------------------------------------ 1

310       320       330       340       350       360
                     ....|....|....|....|....|....|....|....|....|....|....|....|
NOV3a                PFAEGTSARTFNNIMNFQRFLKFPDDPKVSSDFLDLIQSLLCGQKERLKFEGLCCHPFFS 360
NOV3b                PFAEGTSARTFNNIMNFQRFLKFPDDPKVSSDFLDLIQSLLCGQKERLKFEGLCCHPFFS 360
gi|14768010|ref      ------------------------------------------------------------ 1
gi|6225217|sp|O      ------------------------------------------------------------ 1
gi|4589542|dbj|      ------------------------------------------------------------ 1
gi|3360514|gb|A      ------------------------------------------------------------ 1
gi|1345860|sp|P      ------------------------------------------------------------ 1

370       380       390       400       410       420
                     ....|....|....|....|....|....|....|....|....|....|....|....|
NOV3a                KIDWNNIRNAPPPFVPTLKSDDDTSNFDEPEKNSWVSSSPCQLSPSGFSGEELPFVGFSY 420
NOV3b                KIDWNNIRNAPPPFVPTLKSDDDTSNFDEPEKNSWVSSSPCQLSPSGFSGEELPFVGFSY 420
gi|14768010|ref      ------------------------------------------------------------ 1
gi|6225217|sp|O      ------------------------------------------------------------ 1
gi|4589542|dbj|      ------------------------------------------------------------ 1
gi|3360514|gb|A      ------------PFVPTLKSDDDTSNFDEPEKNSWVSSSPCQLSPSGFSGEELPFVGFSY 48
gi|1345860|sp|P      ------------------------------------------------------------ 1

430       440       450       460       470       480
                     ....|....|....|....|....|....|....|....|....|....|....|....|
NOV3a                SKALGILGRSESVVSSLDSPAKTSSMEKKLLIKSKELQDSQDKCHKMEQEMTRLHRRVSE 480
NOV3b                SKALGILGRSESVVSSLDSPAKTSSMEKKLLIKSKELQDSQDKCHKMEQEMTRLHRRVSE 480
gi|14768010|ref      ------------------------------------------------------------ 1
gi|6225217|sp|O      ------------------------------------------------------------ 1
gi|4589542|dbj|      ------------------------------------------------------------ 1
gi|3360514|gb|A      SKALGYLGRSESVVSSLDSPAKVSSMEKKLLIKSKELQDSQDKCHKMEQEMTRLHRRVSE 108
gi|1345860|sp|P      --------------------------MLLGEEAM---------MEQEMTRLHRRVSE 22

490       500       510       520       530       540
                     ....|....|....|....|....|....|....|....|....|....|....|....|
NOV3a                VEAVLSQKEVELKASETQRSLLEQDLATYITECSSLKRSLEQARMEVSQEDDKALQLLHD 540
NOV3b                VEAVLSQKEVELKASETQRSLLEQDLATYITECSSLKRSLEQARMEVSQEDDKALQLLHD 540
gi|14768010|ref      ------------------------------------------------------------ 1
gi|6225217|sp|O      ------------------------------------------------------------ 1
gi|4589542|dbj|      ------------------------------------------------------------ 1
gi|3360514|gb|A      VEAVLSQKEVELKASETQRSLLEQDLATYITECSSLKRSLEQARMEVSQEDDKALQLLHD 168
gi|1345860|sp|P      VEAVLSQKEVELKASETQRSLLEQDLATYITECSSLKRSLEQARMEVSQEDDKALQLLHD 82

550       560       570       580       590       600
                     ....|....|....|....|....|....|....|....|....|....|....|....|
NOV3a                IREQSRKLQEIKEQEYQAQVEEMRLMMNQLEEDLVSARRRSDLYESELRESRLAAEEFKR 600
NOV3b                IREQSRKLQEIKEQEYQAQVEEMRLMMNQLEEDLVSARRRSDLYESELRESRLAAEEFKR 600
gi|14768010|ref      ------------------------------------------------------------ 1
gi|6225217|sp|O      ------------------------------------------------------------ 1
gi|4589542|dbj|      ------------------------------------------------------------ 1
gi|3360514|gb|A      IREQSRKLQEIKEQEYQAQVEEMRLMMNQLEEDLVSARRRSDLYESELRESRLAAEEFKR 228
gi|1345860|sp|P      IREQSRKLQEIKEQEYQAQVEEMRLMMNQLEEDLVSARRRSDLYESELRESRLAAEEFKR 142

610       620       630       640       650       660
                     ....|....|....|....|....|....|....|....|....|....|....|....|
NOV3a                KATECQHKLLKAKDQGKPEVGEYAKLEKINAEQQLKIQELQEKLEKAVKASTEATELLQN 660
NOV3b                KATECQHKLLKAKDQGKPEVGEYAKLEKINAEQQLKIQELQEKLEKAVKASTEATELLQN 660
gi|14768010|ref      ------------------------------------------------------------ 1
gi|6225217|sp|O      ------------------------------------------------------------ 1
gi|4589542|dbj|      ------------------------------------------------------------ 1
gi|3360514|gb|A      KATECQHKLLKAKDQGKPEVGEYAKLEKINAEQQLKIQELQEKLEKAVKASTEATELLQN 288
gi|1345860|sp|P      KATECQHKLLKAKDQGKPEVGEYAKLEKINAEQQLKIQELQEKLEKAVKASTEATELLQN 202
```

TABLE 3F-continued

ClustalW Analysis of NOV3

```
                          670        680        690        700        710        720
                     ....|....|....|....|....|....|....|....|....|....|....|....|
NOV3a                IRQAKERAERELEKLQNREDSSEGIRKKLVEAEERRHSLENKVKRLETMERRENRLKDDI 720
NOV3b                IRQAKERAERELEKLQNREDSSEGIRKKLVEAEERRHSLENKVKRLETMERRENRLKDDI 720
gi|14768010|ref      ------------------------------------------------------------ 1
gi|6225217|sp|O      ------------------------------------------------------------ 1
gi|4589542|dbj|      ------------------------------------------------------------ 1
gi|3360514|gb|A      IRQAKERAERELEKLQNREDSSEGIRKKLVEAEE-------------------------- 322
gi|1345860|sp|P      IRQAKERAERELEKLQNREDSSEGIRKKLVEAEERRHSLENKVKRLETMERRENRLKDDI 262

730        740        750        760        770        780
                     ....|....|....|....|....|....|....|....|....|....|....|....|
NOV3a                QTKSQQIQQMADKILELEEKHREAQVSAQHLEVHLKQKEQHYEEKIKVLDNQIKKDLADK 780
NOV3b                QTKSQQIQQMADKILELEEKHREAQVSAQHLEVHLKQKEQHYEEKIKVLDNQIKKDLADK 780
gi|14768010|ref      ------------------------------------------------------------ 1
gi|6225217|sp|O      ---------------------------------------------VLDNQIKKDLADK 13
gi|4589542|dbj|      ------------------------------------------------------------ 1
gi|3360514|gb|A      ----------------LEEKHREAQVSAQHLEVHLKQKEQHYEEKIKVLDNQIKKDLADK 366
gi|1345860|sp|P      QTKSQQIQQMADKILELEEKHREAQVSAQHLEVHLKQKEQHYEEKIKVLDNQIKKDLADK 222

790        800        810        820        830        840
                     ....|....|....|....|....|....|....|....|....|....|....|....|
NOV3a                ERLENMMQRHEEEAHEKGKILSEQKAMINAMDSKIRSLEQRIVELSEANKLAANSSLFTQ 840
NOV3b                ERLENMMQRHEEEAHEKGKILSEQKAMINAMDSKIRSLEQRIVELSEANKLAANSSLFTQ 840
gi|14768010|ref      ------------------------------------------------------------ 1
gi|6225217|sp|O      ERLENMMQRHEEEAHEKGKILSEQKAMINAMDSKIRSLEQRIVELSEANKLAANSSLFTQ 73
gi|4589542|dbj|      ------------------------------------------------------------ 1
gi|3360514|gb|A      ERLENMMQRHEEEAHEKGKILSEQKAMINAMDSKIRSLEQRIVELSEANKLAANSSLFTQ 426
gi|1345860|sp|P      ERLENMMQRHEEEAHEKGKILSEQKAMINAMDSKIRSLEQRIVELSEANKLAANSSLFTQ 382

850        860        870        880        890        900
                     ....|....|....|....|....|....|....|....|....|....|....|....|
NOV3a                RNMKAQEEMISELRQQKFYLETQAGKLEAQNRKLEEQLEKISHQDHSDKSRLLELETRLR 900
NOV3b                RNMKAQEEMISELRQQKFYLETQAGKLEAQNRKLEEQLEKISHQDHSDKSRLLELETRLR 900
gi|14768010|ref      ------------------------------------------------------------ 1
gi|6225217|sp|O      RNMKAQEEMISELRQQKFYLETQAGKLEAQNRKLEEQLEKISHQDHSDKSRLLELETRLR 133
gi|4589542|dbj|      ------------------------------------------------------------ 1
gi|3360514|gb|A      RNMKAQEEMISELRQQKFYLETQAGKLEAQNRKLEEQLEKISHQDHSDKSRLLELETRLR 486
gi|1345860|sp|P      RNMKAQEEMISELRQQKFYLETQAGKLEAQNRKLEEQLEKISHQDHSDKSRLLELETRLR 442

910        920        930        940        950        960
                     ....|....|....|....|....|....|....|....|....|....|....|....|
NOV3a                EVSLEHEEQKLELKRQLTELQLSLQERESQLTALQAATAALESQLRQAKTELEETTAEAE 960
NOV3b                EVSLEHEEQKLELKRQLTELQLSLQERESQLTALQAATAALESQLRQAKTELEETTAEAE 960
gi|14768010|ref      ------------------------------------------------------------ 1
gi|6225217|sp|O      EVSLEHEEQKLELKRQLTELQLSLQERESQLTALQAATAALESQLRQAKTELEETTAEAE 193
gi|4589542|dbj|      ------------------------------------------------------------ 1
gi|3360514|gb|A      EVSLEHEEQKLELKRQLTELQLSLQERESQLTALQAATAALESQLRQAKTELEETTAEAE 546
gi|1345860|sp|P      EVSLEHEEQKLELKRQLTELQLSLQERESQLTALQAATAALESQLRQAKTELEETTAEAE 502

970        980        990       1000       1010       1020
                     ....|....|....|....|....|....|....|....|....|....|....|....|
NOV3a                EEIQALTAHRDEIQRKFDALRNSCTVITDLEEQLNQLTEDNAELNNQNFYLSKQLDEASG 1020
NOV3b                EEIQALTAHRDEIQRKFDALRNSCTVITDLEEQLNQLTEDNAELNNQNFYLSKQLDEASG 1020
gi|14768010|ref      ------------------------------------------------------------ 1
gi|6225217|sp|O      EEIQALTAHRDEIQRKFDALRNSCTVITDLEEQLNQLTEDNAELNNQNFYLSKQLDEASG 253
gi|4589542|dbj|      ------------------------------------------------------------ 1
gi|3360514|gb|A      EEIQALTAHRDEIQRKFDALRNSCTVITDLEEQLNQLTEDNAELNNQNFYLSKQLDEASG 606
gi|1345860|sp|P      EEIQALTAHRDEIQRKFDALRNSCTVITDLEEQLNQLTEDNAELNNQNFYLSKQLDEASG 562

1030       1040       1050       1060       1070       1080
                     ....|....|....|....|....|....|....|....|....|....|....|....|
NOV3a                ANDEIVQLRSEVDHLRREITEREMQLTSQKQTMEALKTTCTMLEEQVSDLEALNDELLEK 1080
NOV3b                ANDEIVQLRSEVDHLRREITEREMQLTSQKQTMEALKTTCTMLEEQVSDLEALNDELLEK 1080
gi|14768010|ref      ------------------------------------------------------------ 1
gi|6225217|sp|O      ANDEIVQLRSEVDHLRREITEREMQLTSQKQTMEALKTTCTMLEEQVSDLEALNDELLEK 313
gi|4589542|dbj|      ------------------------------------------------------------ 1
gi|3360514|gb|A      ANDEIVQLRSEVDHLRREITEREMQLTSQKQTMEALKTTCTMLEEQVSDLEALNDELLEK 666
gi|1345860|sp|P      ANDEIVQLRSEVDHLRREITEREMQLTSQKQTMEALKTTCTMLEEQVSDLEALNDELLEK 562

1090       1100       1110       1120       1130       1140
                     ....|....|....|....|....|....|....|....|....|....|....|....|
NOV3a                ERQWEAQRSVLGDEKSQFECRVRELQRMLDTEKQSRARADQRITESRQVVELAVKEHKAE 1140
NOV3b                ERQWEAQRSVLGDEKSQFECRVRELQRMLDTEKQSRARADQRITESRQVVELAVKEHKAE 1140
gi|14768010|ref      ------------------------------------------------------------ 1
gi|6225217|sp|O      ERQWEAQRSVLGDEKSQFECRVRELQRMLDTEKQSRARADQRITESRQVVELAVKEHKAE 373
gi|4589542|dbj|      --------------------------------QSRARADQRITESRQVVELAVKEHKAE 27
gi|3360514|gb|A      ERQWEAQRSVLGDEKSQFECRVRELQRMLDTEKQSRARADQRITESRQVVELAVKEHKAE 726
gi|1345860|sp|P      ERQWEAQRSVLGDEKSQFECRVRELQRMLDTEKQSRARADQRITESRQVVELAVKEHKAE 682
```

TABLE 3F-continued

ClustalW Analysis of NOV3

```
                       1150       1160       1170       1180       1190       1200
                    ....|....|....|....|....|....|....|....|....|....|....|....|
NOV3a               ILALQQALKEQKLKAESLSDKLNDLEKKEAMLEMNARSLQQKLETERELKQRLLEEQAKL   1200
NOV3b               ILALQQALKEQKLKAESLSDKLNDLEKKEAMLEMNARSLQQKLETERELKQRLLEEQAKL   1200
gi|14768010|ref     ------------------------------MLEMNARSLQQKLETERELKQRLLEEQAKL     30
gi|6225217|sp|O     ILALQQALKEQKLKAESLSDKLNDLEKKEAMLEMNARSLQQKLETERELKQRLLEEQAKL    433
gi|4589542|dbj|     ILALQQALKEQKLKAESLSDKLNDLEKKEAMLEMNARSLQQKLETERELKQRLLEEQAKL     87
gi|3360514|gb|A     ILALQQALKEQKLKAESLSDKLNDLEKKEAMLEMNARSLQQKLETERELKQRLLEEQAKL    786
gi|1345860|sp|P     ILALQQALKEQKLKAESLSDKLNDLEKKEAMLEMNARSLQQKLETERELKQRLLEEQAKL    742

1210       1220       1230       1240       1250       1260
                    ....|....|....|....|....|....|....|....|....|....|....|....|
NOV3a               QQQMDLQKNHIFRLTQGLQEALDRADLLKTERSDLEYQLENIQVLYSHEKVKMEGTISQQ   1260
NOV3b               QQQMDLQKNHIFRLTQGLQEALDRADLLKTERSDLEYQLENIQVLYSHEKVKMEGTISQQ   1260
gi|14768010|ref     QQQMDLQKNHIFRLTQGLQEALDRADLLKTERSDLEYQLENIQVLYSHEKVKMEGTISQQ     90
gi|6225217|sp|O     QQQMDLQKNHIFRLTQGLQEALDRADLLKTERSDLEYQLENIQVLYSHEKVKMEGTISQQ    493
gi|4589542|dbj|     QQQMDLQKNHIFRLTQGLQEALDRADLLKTERSDLEYQLENIQVLYSHEKVKMEGTISQQ    147
gi|3360514|gb|A     QQQMDLQKNHIFRLTQGLQEALDRADLLKTERSDLEYQLENIQVLYSHEKVKMEGTISQQ    846
gi|1345860|sp|P     QQQMDLQKNHIFRLTQGLQEALDRADLLKTERSDLEYQLENIQVLYSHEKVKMEGTISQQ    802

1270       1280       1290       1300       1310       1320
                    ....|....|....|....|....|....|....|....|....|....|....|....|
NOV3a               TKLIDFLQAKMDQPAKKKKVPLQYNELKLALEKEKARCAELEEALQKTRIELRSAREEAA   1320
NOV3b               TKLIDFLQAKMDQPAKKKKVPLQYNELKLALEKEKARCAELEEALQKTRIELRSAREEAA   1320
gi|14768010|ref     TKLIDFLQAKMDQPAKKKKVPLQYNELKLALEKEKARCAELEEALQKTRIELRSAREEAA    150
gi|6225217|sp|O     TKLIDFLQAKMDQPAKKKKVPLQYNELKLALEKEKARCAELEEALQKTRIELRSAREEAA    553
gi|4589542|dbj|     TKLIDFLQAKMDQPAKKKKVPLQYNELKLALEKEKARCAELEEALQKTRIELRSAREEAA    207
gi|3360514|gb|A     TKLIDFLQAKMDQPAKKKKVPLQYNELKLALEKEKARCAELEEALQKTRIELRSAREEAA    906
gi|1345860|sp|P     TKLIDFLQAKMDQPAKKKKVPLQYNELKLALEKEKARCAELEEALQKTRIELRSAREEAA    862

1330       1340       1350       1360       1370       1380
                    ....|....|....|....|....|....|....|....|....|....|....|....|
NOV3a               HRKATDHPHPSTPATARQQLAMSAIVRSPEHQPSAMSLLAPPSSRRKESSTPEEFSRRLK   1380
NOV3b               HRKATDHPHPSTPATARQQLAMSAIVRSPEHQPSAMSLLAPPSSRRKESSTPEEFSRRLK   1380
gi|14768010|ref     HRKATDHPHPSTPATARQQLAMSAIVRSPEHQPSAMSLLAPPSSRRKESSTPEEFSRRLK    210
gi|6225217|sp|O     HRKATDHPHPSTPATARQQLAMSAIVRSPEHQPSAMSLLAPPSSRRKESSTPEEFSRRLK    613
gi|4589542|dbj|     HRKATDHPHPSTPATARQQLAMSAIVRSPEHQPSAMSLLAPPSSRRKESSTPEEFSRRLK    267
gi|3360514|gb|A     HRKATDHPHPSTPATARQQLAMSAIVRSPEHQPSAMSLLAPPSSRRKESSTPEEFSRRLK    966
gi|1345860|sp|P     HRKATDHPHPSTPATARQQLAMSAIVRSPEHQPSAMSLLAPPSSRRKESSTPEEFSRRLK    922

1390       1400       1410       1420       1430       1440
                    ....|....|....|....|....|....|....|....|....|....|....|....|
NOV3a               ERMHHNIPHRFNVGLNMPATKCAVCLDTVHFGRQASKCLECQVMCHPKCSTCLPATCGLP   1440
NOV3b               ERMHHNIPHRFNVGLNMPATKCAVCLDTVHFGRQASKCLECQVMCHPKCSTCLPATCGLP   1440
gi|14768010|ref     ERMHHNIPHRFNVGLNMPATKCAVCLDTVHFGRQASKCLECQVMCHPKCSTCLPATCGLP    270
gi|6225217|sp|O     ERMHHNIPHRFNVGLNMPATKCAVCLDTVHFGRQASKCLECQVMCHPKCSTCLPATCGLP    673
gi|4589542|dbj|     ERMHHNIPHRFNVGLNMPATKCAVCLDTVHFGRQASKCLECQVMCHPKCSTCLPATCGLP    327
gi|3360514|gb|A     ERMHHNIPHRFNVGLNMPATKCAVCLDTVHFGRQASKCLECQVMCHPKCSTCLPATCGLP   1026
gi|1345860|sp|P     ERMHHNIPHRFNVGLNMPATKCAVCLDTVHFGRQASKCLECQVMCHPKCSTCLPATCGLP    982

1450       1460       1470       1480       1490       1500
                    ....|....|....|....|....|....|....|....|....|....|....|....|
NOV3a               AEYATHFTEAFCRDKMNSPGLQTKEPSSSLHLEGWMKVPRNNKRGQQGWDRKYIVLEGSK   1500
NOV3b               AEYATHFTEAFCRDKMNSPGLQTKEPSSSLHLEGWMKVPRNNKRGQQGWDRKYIVLEGSK   1500
gi|14768010|ref     AEYATHFTEAFCRDKMNSPGLQTKEPSSSLHLEGWMKVPRNNKRGQQGWDRKYIVLEGSK    330
gi|6225217|sp|O     AEYATHFTEAFCRDKMNSPGLQTKEPSSSLHLEGWMKVPRNNKRGQQGWDRKYIVLEGSK    733
gi|4589542|dbj|     AEYATHFTEAFCRDKMNSPGLQTKEPSSSLHLEGWMKVPRNNKRGQQGWDRKYIVLEGSK    387
gi|3360514|gb|A     AEYATHFTEAFCRDKMNSPGLQEKEPGSSLHLEGWMKVPRNNKRGQQGWDRKYIVLEGSK   1086
gi|1345860|sp|P     AEYATHFTEAFCRDKMNSPGLQEKEPGSSLHLEGWMKVPRNNKRGQQGWDRKYIVLEGSK   1042

1510       1520       1530       1540       1550       1560
                    ....|....|....|....|....|....|....|....|....|....|....|....|
NOV3a               VLIYDNEAREAGQRPVEEFELCLPDGDVSIHGAVGASELANTAKADVPYILKMESHPHTT   1560
NOV3b               VLIYDNEAREAGQRPVEEFELCLPDGDVSIHGAVGASELANTAKADVPYILKMESHPHTT   1560
gi|14768010|ref     VLIYDNEAREAGQRPVEEFELCLPDGDVSIHGAVGASELANTAKADVPYILKMESHPHTT    390
gi|6225217|sp|O     VLIYDNEAREAGQRPVEEFELCLPDGDVSIHGAVGASELANTAKADVPYILKMESHPHTT    793
gi|4589542|dbj|     VLIYDNEAREAGQRPVEEFELCLPDGDVSIHGAVGASELANTAKADVPYILKMESHPHTT    447
gi|3360514|gb|A     VLIYDNEAREAGQRPVEEFELCLPDGDVSIHGAVGASELANTAKADVPYILKMESHPHTT   1146
gi|1345860|sp|P     VLIYDNEAREAGQRPVEEFELCLPDGDVSIHGAVGASELANTAKADVPYILKMESHPHTT   1102

1570       1580       1590       1600       1610       1620
                    ....|....|....|....|....|....|....|....|....|....|....|....|
NOV3a               CWPGRTLYLLAPSFPDKQRWVTALESVVAGGRVSREKAEADAKLLGNSLLKLEGDDRLDM   1620
NOV3b               CWPGRTLYLLAPSFPDKQRWVTALESVVAGGRVSREKAEADAKLLGNSLLKLEGDDRLDM   1620
gi|14768010|ref     CWPGRTLYLLAPSFPDKQRWVTALESVVAGGRVSREKAEADAKLLGNSLLKLEGDDRLDM    450
gi|6225217|sp|O     CWPGRTLYLLAPSFPDKQRWVTALESVVAGGRVSREKAEADAKLLGNSLLKLEGDDRLDM    853
gi|4589542|dbj|     CWPGRTLYLLAPSFPDKQRWVTALESVVAGGRVSREKAEADAKLLGNSLLKLEGDDRLDM    507
gi|3360514|gb|A     CWPGRTLYLLAPSFPDKQRWVTALESVVAGGRVSREKAEADAKLLGNSLLKLEGDDRLDM   1206
gi|1345860|sp|P     CWPGRTLYLLAPSFPDKQRWVTALESVVAGGRVSREKAEADAKLLGNSLLKLEGDDRLDM   1162
```

TABLE 3F-continued

ClustalW Analysis of NOV3

```
                        1630      1640      1650      1660      1670      1680
                    ....|....|....|....|....|....|....|....|....|....|....|....|
NOV3a               NCTLPFSDQVVLVGTEEGLYALNVLKNSLTHVPGIGAVFQIYIIKDLEKLLMIAGEERAL 1680
NOV3b               NCTLPFSDQVVLVGTEEGLYALNVLKNSLTHVPGIGAVFQIYIIKDLEKLLMIAGEERAL 1680
gi|14768010|ref     NCTLPFSDQVVLVGTEEGLYALNVLKNSLTHVPGIGAVFQIYIIKDLEKLLMIAGEERAL 510
gi|6225217|sp|O     NCTLPFSDQVVLVGTEEGLYALNVLKNSLTHVPGIGAVFQIYIIKDLEKLLMIAGEERAL 913
gi|4589542|dbj|     NCTLPFSDQVVLVGTEEGLYALNVLKNSLTHVPGIGAVFQIYIIKDLEKLLMIAGEERAL 567
gi|3360514|gb|A     NCTLPFSDQVVLVGTEEGLYALNVLKNSLTHAPGIGAVFQIYIIKDLEKLLMIAGEERAL 1266
gi|1345860|sp|P     NCTLPFSDQVVLVGTEEGLYALNVLKNSLTHAPGIGAVFQIYIIKDLEKLLMIAGEERAL 1222

1690      1700      1710      1720      1730      1740
                    ....|....|....|....|....|....|....|....|....|....|....|....|
NOV3a               CLVDVKKVKQSLAQSHLPAQPDISPNIFEAVKGCHLFGAGKIENGLCICAAMPSKVVILR 1740
NOV3b               CLVDVKKVKQSLAQSHLPAQPDISPNIFEAVKGCHLFGAGKIENGLCICAAMPSKVVILR 1740
gi|14768010|ref     CLVDVKKVKQSLAQSHLPAQPDISPNIFEAVKGCHLFGAGKIENGLCICAAMPSKVVILR 570
gi|6225217|sp|O     CLVDVKKVKQSLAQSHLPAQPDISPNIFEAVKGCHLFGAGKIENGLCICAAMPSKVVILR 973
gi|4589542|dbj|     CLVDVKKVKQSLAQSHLPAQPDISPNIFEAVKGCHLFGAGKIENGLCICAAMPSKVVILR 627
gi|3360514|gb|A     CLVDVKKVKQSLAQSHLPAQPDNSPNIFEAVKGCHLFAAGKIENSLCICAAMPSKVVILR 1326
gi|1345860|sp|P     CLVDVKKVKQSLAQSHLPAQPDNSPNIFEAVKGCHLFAAGKIENSLCICAAMPSKVVILR 1282

1750      1760      1770      1780      1790      1800
                    ....|....|....|....|....|....|....|....|....|....|....|....|
NOV3a               YNENLSKYCIRKEIETSEPCSCIHFTNYSILIGTNKFYEIDMKQYTLEEFLDKNDHSLAP 1800
NOV3b               YNENLSKYCIRKEIETSEPCSCIHFTNYSILIGTNKFYEIDMKQYTLEEFLDKNDHSLAP 1800
gi|14768010|ref     YNENLSKYCIRKEIETSEPCSCIHFTNYSILIGTNKFYEIDMKQYTLEEFLDKNDHSLAP 630
gi|6225217|sp|O     YNENLSKYCIRKEIETSEPCSCIHFTNYSILIGTNKFYEIDMKQYTLEEFLDKNDHSLAP 1033
gi|4589542|dbj|     YNENLSKYCIRKEIETSEPCSCIHFTNYSILIGTNKFYEIDMKQYTLEEFLDKNDHSLAP 687
gi|3360514|gb|A     YNNNLSKYCIRKEIETSEPCSCIHFTNYSILIGTNKFYEIDMKQYTLNEFLDKNDHSLAP 1386
gi|1345860|sp|P     YNNNLSKYCIRKEIETSEPCSCIHFTNYSILIGTNKFYEIDMKQYTLNEFLDKNDHSLAP 1342

1810      1820      1830      1840      1850      1860
                    ....|....|....|....|....|....|....|....|....|....|....|....|
NOV3a               AVFAASSMSFPVSIVQVNSAGQREEYLLCFHEFGVFVDSYGRRSRTDDLKWSRLPLAFAY 1860
NOV3b               AVFAASSMSFPVSIVQVNSAGQREEYLLCFHEFGVFVDSYGRRSRTDDLKWSRLPLAFAY 1860
gi|14768010|ref     AVFAASSMSFPVSIVQVNSAGQREEYLLCFHEFGVFVDSYGRRSRTDDLKWSRLPLAFAY 690
gi|6225217|sp|O     AVFAASSMSFPVSIVQVNSAGQREEYLLCFHEFGVFVDSYGRRSRTDDLKWSRLPLAFAY 1093
gi|4589542|dbj|     AVFAASSMSFPVSIVQVNSAGQREEYLLCFHEFGVFVDSYGRRSRTDDLKWSRLPLAFAY 747
gi|3360514|gb|A     AVFASSSMSFPVSIVQANSAGQREEYLLCFHEFGVFVDSYGRRSRTDDLKWSRLPLAFAY 1446
gi|1345860|sp|P     AVFASSSMSFPVSIVQANSAGQREEYLLCFHEFGVFVDSYGRRSRTDDLKWSRLPLAFAY 1402

1870      1880      1890      1900      1910      1920
                    ....|....|....|....|....|....|....|....|....|....|....|....|
NOV3a               REPYLFVTHFNSLEVIEIQARSSAGTPARAYLDIPNPRYLGPAISSGAIYLASSYQDKLR 1920
NOV3b               REPYLFVTHFNSLEVIEIQARSSAGTPARAYLDIPNPRYLGPAISSGAIYLASSYQDKLR 1920
gi|14768010|ref     REPYLFVTHFNSLEVIEIQARSSAGTPARAYLDIPNPRYLGPAISSGAIYLASSYQDKLR 750
gi|6225217|sp|O     REPYLFVTHFNSLEVIEIQARSSAGTPARAYLDIPNPRYLGPAISSGAIYLASSYQDKLR 1153
gi|4589542|dbj|     REPYLFVTHFNSLEVIEIQARSSAGTPARAYLDIPNPRYLGPAISSGAIYLASSYQDKLR 807
gi|3360514|gb|A     REPYLFVTHFNSLEVIEIQARSSLGAPARAYLAIPNPRYLGPAISSGAIYLASSYQDKLR 1506
gi|1345860|sp|P     REPYLFVTHFNSLEVIEIQARSSLGAPARAYLAIPNPRYLGPAISSGAIYLASSYQDKLR 1462

1930      1940      1950      1960      1970      1980
                    ....|....|....|....|....|....|....|....|....|....|....|....|
NOV3a               VICCKGNLVKESGTEHHRGPSTSRSSPNKRGPPTYNEHITKRVASSPAPPEGPSHPREPS 1980
NOV3b               VICCKGNLVKESGTEHHRGPSTSRSSPNKRGPPTYNEHITKRVASSPAPPEGPSHPREPS 1980
gi|14768010|ref     VICCKGNLVKESGTEHHRGPSTSRSSPNKRGPPTYNEHITKRVASSPAPPEGPSHPREPS 810
gi|6225217|sp|O     VICCKGNLVKESGTEHHRGPSTSRSSPNKRGPPTYNEHITKRVASSPAPPEGPSHPREPS 1213
gi|4589542|dbj|     VICCKGNLVKESGTEHHRGPSTSRSSPNKRGPPTYNEHITKRVASSPAPPEGPSHPREPS 867
gi|3360514|gb|A     VICCKGNLVKESGTEQHRVPSTSRSSPNKRGPPTYNEHITKRVASSPAPPEGPSHPREPS 1566
gi|1345860|sp|P     VICCKGNLVKESGTEQHRVPSTSRSSPNKRGPPTYNEHITKRVASSPAPPEGPSHPREPS 1522

1990      2000      2010      2020      2030      2040
                    ....|....|....|....|....|....|....|....|....|....|....|....|
NOV3a               TPHRYR--EGRTELRRDKSPGRPLEREKSPGRMLSTRRERSPGRLFEDSSRGRLPAGAVR 2040
NOV3b               TPHRYR--EGRTELRRDKSPGRPLEREKSPGRMLSTRRERSPGRLFEDSSRGRLPAGAVR 2040
gi|14768010|ref     TPHRYR--EGRTELRRDKSPGRPLEREKSPGRMLSTRRERSPGRLFEDSSRGRLPAGAVR 870
gi|6225217|sp|O     TPHRYR--EGRTELRRDKSPGRPLEREKSPGRMLSTRRERSPGRLFEDSSRGRLPAGAVR 1273
gi|4589542|dbj|     TPHRYR--EGRTELRRDKSPGRPLEREKSPGRMLSTRRERSPGRLFEDSSRGRLPAGAVR 927
gi|3360514|gb|A     TPHRYRDREGRTELRRDKSPGRPLEREKSPGRMLSTRRERSPGRLFEDSSRGRLPAGAVR 1626
gi|1345860|sp|P     TPHRYRDREGRTELRRDKSPGRPLEREKSPGRMLSTRRERSPGRLFEDSSRGRLPAGAVR 1582

2050      2060
                    ....|....|....|....|...
NOV3a               TPLSQVNKVRQHSEACVSVAEARSDLGN 2066
NOV3b               TPLSQVNKVWDQSSV------------- 2053
gi|14768010|ref     TPLSQVNKVWDQSSV------------- 863
gi|6225217|sp|O     TPLSQVNKVWDQSSV------------- 1286
gi|4589542|dbj|     TPLSQVNKVWDQSSV------------- 940
gi|3360514|gb|A     TPLSQVNKVWDQSSV------------- 1641
gi|1345860|sp|P     TPLSQVNKVWDQSSV------------- 1597
```

Tables 3G–K list the domain description from DOMAIN analysis results against NOV3b. This indicates that the NOV3 sequence has properties similar to those of other proteins known to contain this domain.

TABLE 3G

Domain Analysis of NOV3b gnl|Pfam|pfam00780, CNH, CNH domain. Domain found in NIK1-like kinase, mouse citron and yeast ROM1, ROM2. Unpublished observations
CD-Length = 304 residues, 99.7% aligned (SEQ ID NO:71)
Score = 238 bits (607), Expect = 2e-63

```
Query: 1619 DMNCTLPFSDQ--VVLVGTEEGLYALNVLKN--SLTHVPGIGAVFQIYIIKDLEKLLMIA 1674
              |  | +     +|||||||||  ||    +|  +    +| | |+++++   | | |+
Sbjct:    2 TAKCNHPITCDAKNLLVGTEEGLYVLNRSDQGGTLEKIISRRSVTQIWVLEENNVLLMIS 61

Query: 1675 GE---ERALCLVDVKKVKQSLAQSHLPAQPDISPNIFEAVKGCHLFGAGKIENGLCICAA 1731
              |+        |  |   +++ | +|  + |  + ++      |||||||   +  | +|||
Sbjct:   62 GKKPYLYAHPLSGLRE-KDALGSARLVIRKNVWVK-IEDVKGCHLFAVVNGKRILFLCAA 119

Query: 1732 MPSKVVIL-RYNENLSKYCIR-----KEIETSEPCSCIHFTNY---SILIGTNKFYEIDM 1782
             +|| | +|  ||         +      | |        +   ++   | |  +|     |+
Sbjct:  120 LPSSVQLLQWYNPLKKFKLFKSKFLKKLIVPVPLFVLLTSSSFELPKICIGVDK-NGFDV 178

Query: 1783 KQYTLEEFLDKNDHSLAPAVFAASSNSFPVSIVQVNSAGQREEYLLCFHEFGVFVDSYG- 1841
              |+      +|  | ||           ||    |  +    +|  ||||  |||||+  |
Sbjct:  179 VQFHQTSLVSKEDLSLPNLNEETSKKPIPVIQVPQSD----DELLLCFDEFGVFVNLQGM 234

Query: 1842 RRSRTDDLKWSRLPLAFAYREPYLFVTHFNSLEVIEIQARSSAGTPARAYLDIPNPRYLG 1901
             ||||   | |  +|   |||  ||||  | |  +|  |              |   +   | ||
Sbjct:  235 RRSRKPILTWEFMPEYFAYHEPYLLAFHSNGIEIRSIETGELLQELADR--EARKIRVLG 292

Query: 1902 PAISSGAIYLASSY 1915
               |   |  +||
Sbjct:  293 S--SDRKILVSSSP 304
```

TABLE 3H

Domain Analysis of NOV3b gnl|Smart|smart00220, S_TKc, Serine/Threonine protein kinases, catalytic domain; Phosphotransferases. Serine or threonine-specific kinase subfamily. (SEQ ID NO:72)
CD-Length = 256 residues. 100.0% aligned
Score = 230 bits (587), Expec = 5e-61

```
Query:   97 FEVRSLVGCGHFAEVQVVREKATGDIYAMKVMKKKALLAQEQVSFFEEERNILSRSTSPW 156
             +|+ ++| | | +| + |+|  ||   |+|+|+|+  +++          |  ||+    |
Sbjct:    1 YELLEVLGKGAFGKVYLARDKKTGKLVAIKVIKKEKLK-KKKRERILREIKILKKLDHPN 59

Query:  157 IPQLQYAFQDKNHLYLVMEYQPGGDLLSLLNRYEDQLDENLIQFYLAELILAVHSVHLMG 216
              | +|    |+| +  +||||||  ||||  || +   +| |+ +| +|| +++  |+  +|  |
Sbjct:   60 IVKLYDVFEDDDKLYLVMEYCEGGDLFDLLKKR-GRLSEDEARFYARQILSALEYLHSQG 118

Query:  217 YVHRDIKPENILVDRTGHIKLVDFGSAAKMNSNKVNAKLPIGTPDYMAPEVLTVMNGDGK 276
             +|||+||||||+| ||+|| ||| |+++|         +  +++|       +|||||||
Sbjct:  119 IIHRDLKPENILLDSDGHVKLADFGLAKQLDSGGTLLTTFVGTPEYMAPEVLL------G 172

Query:  277 GTYGLDCDWWSVGVIAYEMIYGRSPFAEGTSARTFNNIMNFQRFLKFPDDPKVSSDFLDL 336
             ||    |  ||+|||  ||+ |+ ||         +          | + +| +  +  ||
Sbjct:  173 KGYGKAVDIWSLGVILYELLTGKPPFPGDDQLLALFKKIGKPPPPFPPPEWKISPEAKDL 232

Query:  337 IQSLLC-GQKERLKFEGLCCHPFF 359
             |+ ||        ++||    |    ||||
Sbjct:  233 IKKLLVKDPEKRLTAEEALEHPFF 256
```

TABLE 3I

Domain Analysis of NOV3b gnl|Smart|smart00036, CNN, Domain found in NIK1-like kinases, mouse citron and yeast ROM1, ROM2; Unpublished observations. (SEQ ID NO: 73)
CD-Length = 301 residues, 99.7% aligned
Score = 226 bits (577), Expect = 8e-60

```
Query:  1619 DMNCTLPFSDQ--VVLVGTEEGLYALNVLKN--SLTNVPGIGAVFQIYIIKDLEKLLMIA  1674
                | +   ++|||||||||  ||+    +|  + |   | ||+++++   ||||+
Sbjct:     2 TAKWNHPITCDAKILLVGTEEGLYVLNISDQHGTLEKLIGRRSVTQIWVLEENNVLLMIS    61

Query:  1675 GEERALC---LVDVKKVKQSLAQSHLPAQPDISPNIFEAVKGCHLFGAGKIENGLCICAA  1731
                |++  |    |  + + +|  +  + ++  |||||     +  |+|  |
Sbjct:    62 GKKPQLYSHPLSALTE-KDALGSARLVIRKNVLTK-IPDVKGCHLCAVVNGKRILFLCHA   119

Query:  1732 MPSKVVIL-RYNENLSKYCIR-----KEIETSEPCSCIHFTNY---SILIGTNKFYEIDM  1782
                + |  ||+|  ||      +     |      +   +    |  |++|     |+
Sbjct:   120 LQSSVVLLQWYNPLKKFKLFKSKFLFPLISPVPVFVELVSSSFELPGICIGSDK-NGGDV   178

Query:  1783 KQYTLEEFLDKNDHSLAPAVFAASSNSFPVSIVQVNSAGQREEYLLCFHEFGVFVDSYG-  1841
                |+  +    |  ||         ||   |  |       +|  |||+ ||||||+  |
Sbjct:   179 VQFH-QSLVSKEDLSLPFLSEETSSKPISVVQVP------ADELLLCYDEFGVFVNLYGM   231

Query:  1842 RRSRTDDLKWSRLPLAFAYREPYLFVTHFNSLEVIEIQARSSAGTPARAYLDIPNPRYLG  1901
                ||||    | |   +| +|||   |||   | | +|+ +|     |        |  ||
Sbjct:   232 RRSRNPILHWEFMPESFAYHSPYLLAFHDNGIEIRSIKTGELLQELADR--KTRKIRLLG   289

Query:  1902 PAISSGAIYLASSY  1915
                |    |  |+||
Sbjct:   290 S--SDRKILLSSSP   301
```

TABLE 3J

Domain Analysis of NOV3b gnl|Pfam|pfam00069, pkinase, Protein kinase domain.
CD-Length = 256 residues, 100.0% aligned (SEQ ID NO:74)
Score = 189 bits (481), Expect = 1e-48

```
Query:    97 FEVRSLVGCGHFAEVQVVREKATGDIYAMKVMKKKALLAQEQVSFFEEERNILSRSTSPW   156
                +|+   +|  | | |  +    + |  ||+  |+|++||+|      |     |  ||   + |
Sbjct:     1 YELGEKLGSGAFGKVYKGKHKDTGEIVAIKILKKRSL--SEKKKRFLREIQILRRLSHPN    58

Query:   157 IPQLQYAFQDKNHLYLVMEYQPGGDLLSLLNRYEDQLDENLIQFYLAELILAVHSVHLMG   216
                | +|    |++ +|||||||||| ||||   | |     | |    +   +++    | |
Sbjct:    59 IVRLLGVFEEDDHLYLVMEYMEGGDLFDYLRRNGLLLSEKEAKKIALQILRGLEYLHSRG   118

Query:   217 YVHRDIKPENILVDRTGHIKLVDFGSAAKMNS-NKVNAKLPIGTPDYMAPEVLTVMNGDG   275
                |||||+|||||||+|  | |   |||  |   |  ++     +|||+|||||||||   || ||
Sbjct:   119 IVHRDLKPENILLDENGTVKIADFGLARKLESSSYEKLTTFVGTPEYMAPEVL---EGRG   175

Query:   276 KQTYGLDCDWWSVGVIAYEMIYGRSPF-AEGTSARTFNNIMNFQRFLKEPDDPKVSSDFL   334
                |   | ||+|||  ||++ +|   |     +  | |   | | |    |++
Sbjct:   176 ---YSSKVDVWSLGVILYELLTGKLPFPGIDPLEELFRIKERPRLRLPLP--PNCSEELK   230

Query:   335 DLIQSLLCGQ-KERLKFEGLCCHPFF  359
                |||+  |   ++|    ||+|
Sbjct:   231 DLIKKCLNKDPEKRPTAKEILNHPWF  256
```

TABLE 3K

Domain Analysis of NOV3b gnl|Smart|smart00219, TyrKc, Tyrosine kinase, catalytic domain;
Phosphotransferases. Tyrosine-specific kinase subfamily. (SEQ ID NO: 75)
CD-Length = 258 residues, 95.0% aligned
Score = 91.7 bits (226), Expect = 4e-19

```
Query:   104 GCGHFAEVQVVREKATGDIYAMKVMKKKALLAQE-QVSFFEEERNILSRSTSPWIPQLQY   162
                | |||   | | ||    |    +     +|      |+  ||  + +   ++ +   |+|
Sbjct:     8 GEGAFGEVYKGTLKGKGGVEVEVAVKTLKEDASEQQIEEFLREARLMRKLDHPNIVKLLG    67

Query:   163 AFQDKNHLYLVMEYQPGGDLLSLLNRYEDQLDENLIQFYLAELI-LAVHSVHLMGYVHRD   221
                  ++  | +||||   ||||  |++  +            |  |   + +    +||||
```

TABLE 3K-continued

Domain Analysis of NOV3b

```
Sbjct:  68 VCTEEEPLMIVMEYMEGGDLLDYLRKNRPKELSLSDLLSFALQIARGMEYLESKNFVHRD 127

Query: 222 IKPENILVDRTGHIKLVDFGSAAKMNSNKVNAKLPIGTPD--YMAPEVLTVMNGDKGTY 279
           | ||    +|+ ||| |  + +    |         +|||| |       | +
Sbjct: 128 LAARNCLVGENKTVKIADFGLARDLYDDDYYRKKKSPRLPIRWMAPESLK------DGKF 181

Query: 280 GLDCDWWSVGVIAYEMI-YGRSPFAEGTSARTFNNIMNFQRFLKFPDDPKVSSDFLDLIQ 338
           | ||  ||+ +|   | ||+   ++       |  + |+ |   +  ||+
Sbjct: 182 TSKSDVWSFGVLLWEIFTLGESPYPGMSNEEVLEYLKKGYRLPQPPNCP---DEIYDLML 238

Query: 339 SLLCGQ---KERLKFE 351
           |        ++|   |
Sbjct: 239 Q--CWAEDPEDRPTFS 252
```

PS

Recent data shows the identification of a novel serine/threonine kinase belonging to the myotonic dystrophy kinase family (DiCunto et al. Eur J Immunol 2000 December;30(12):3403–10.). The kinase can be produced in at least two different isoforms: a approximately 240-kDa protein (Citron Rho-interacting kinase, CRIK), in which the kinase domain is followed by the sequence of Citron, a previously identified Rho/Rac binding protein; a approximately 54-kDa protein (CRIK-short kinase (SK)), which consists mostly of the kinase domain. CRIK and CRIK-SK proteins are capable of phosphorylating exogenous substrates as well as of autophosphorylation, when tested by in vitro kinase assays after expression into COS7 cells. CRIK kinase activity is increased several fold by coexpression of costitutively active Rho, while active Rac has more limited effects. Kinase activity of endogenous CRIK is indicated by in vitro kinase assays after immunoprecipitation with antibodies recognizing the Citron moiety of the protein. When expressed in keratinocytes, full-length CRIK, but not CRIK-SK, localizes into corpuscular cytoplasmic structures and elicits recruitment of actin into these structures. The previously reported Rho-associated kinases ROCK I and II are ubiquitously expressed. In contrast, CRIK exhibits a restricted pattern of expression, suggesting that this kinase may fulfill a more specialized function in specific cell types.

T cell receptor (TCR) engagement increases integrin-mediated adhesion to APC, resulting in the stabilization of the T cell. APC interaction and the close apposition of the two cell membranes. Engagement of either the TCR or CD3 chimeras with immobilized antibodies causes the rapid spreading of T cells in an integrin-independent fashion (Borroto et al. Eur J Immunol 1999 November;29(11):3609–20). This effect concurs with the polymerization of the actin cytoskeleton and is dependent on the integrity of the immunoreceptor tyrosine-based activation motifs of the CD3 subunits. Expression of a dominant negative mutant of RhoA, as well as the Rho-specific inhibitor C3 toxin, abolished TCR-induced spreading. In contrast, constitutively active or dominant negative forms of Rac and Cdc42 did not affect cell spreading. Signals emanating from the TCR can directly induce T cell spreading, independently of integrins, and via a Rho-dependent reorganization of the actin cytoskeleton.

Motile lymphocytes adopt a polarized morphology with different adhesion molecules (ICAM, CD43 and CD44) and ERM actin-binding proteins concentrated on the uropod, a slender posterior appendage with important functions in cell-cell interactions and lymphocyte recruitment. The role of Rho family of GTPases (Rho, Rac and Cdc42) in the control of lymphocyte polarity and migration has been studied by analyzing the effects of exogenously introduced Rho GTPase mutants. Transfection of T cell lines that constitutively display a polarized motile morphology with activated mutants of RhoA, Rac1 and Cdc42 impaired cell polarization. A guanosine nucleotide exchange factor for Rac, Tiam-1, induced the same effect as activated Rac1. Conversely, dominant negative forms of the three GTP-binding proteins induced a polarized phenotype in constitutively round-shaped T cells with redistribution of ICAM-3 and moesin to the uropod in an integrin-dependent manner. On the other hand, overexpression of dominant negative Cdc42 and activated mutants of all three Rho GTPases significantly inhibited SDF-1 alpha-induced T cell chemotaxis. Together, these data demonstrate that Rho GTPases regulate lymphocyte polarization and chemokine-induced migration, and underscore the key role of Cdc42 in lymphocyte directional migration.

Activated Rho GTPases trigger distinctive kinase cascades. In particular, ROCK binds to Rho, and its kinase activity is moderately stimulated by this association. The citron molecule (Madaule et al., 1995), a specific interactor of Rho and Rac, shares a significant degree of structural homology with ROCK; however, its lack of a kinase domain raised the question of its biologic function. By PCR of a mouse primary keratinocyte cDNA library, Di Cunto et al. (1998) identified a novel serine/threonine kinase, CRIK (citron Rho-interacting kinase), belonging to the myotonic dystrophy kinase family. CRIK can be expressed as at least 2 isoforms, one of which encompasses the previously reported form of citron in almost its entirety. The long form of CRIK is a 240-kD protein in which the kinase domain is followed by the sequence of citron. The short form, CRIK-SK (short kinase), is an approximately 54-kD protein that consists mostly of the kinase domain. CRIK and CRIK-SK proteins are capable of phosphorylating exogenous substrates as well as of autophosphorylation, when tested by in vitro kinase assays after expression into COS-7 cells. CRIK kinase activity is increased several-fold by coexpression of constitutively active Rho, while active Rac has more limited effects. Kinase activity of the endogenous CRIK is indicated by in vitro kinase assays after immunoprecipitation with antibodies recognizing the citron moiety of the protein. When expressed in keratinocytes, full-length CRIK, but not CRIK-SK, localizes into corpuscular cytoplasmic structures and elicits recruitment of actin into these structures. The previously reported Rho-associated kinases ROCK1 and ROCK2 are ubiquitously expressed. Northern blot analysis of mouse tissues revealed a restricted pattern of expression limited to keratinocytes, brain, spleen, lung, kidney, and an especially strong signal in testis. No expression was detectable in heart, liver, or skeletal muscle. The CRIK protein contains a kinase domain, a coiled-coil domain, a leucine-rich domain, a Rho-Rac binding domain, a zinc finger region, a pleckstrin homology domain, and a putative SH3-binding domain. Di Cunto et al. (1998) reported cloning the human homolog of the CRIK kinase domain. They stated that the human homolog of citron is contained within a PAC clone (GenBank GENBANK AC002563) mapping to chromosome 12q. By screening size-fractionated human brain cDNA libraries for cDNAs encoding proteins larger than 50 kD, Nagase et al. (1999) identified CRIK as cDNA KIAA0949 (GenBank GENBANK AB023166). Di Cunto et al. (1998) mapped the human CRIK gene to chromosome 12q24.1–q24.3.

Di Cunto et al. (2000) generated mice deficient in citron kinase by targeted disruption. Citron-K–/– mice grow at slower rates, are severely ataxic, and die before adulthood as a consequence of fatal seizures. Their brains display defective neurogenesis, with dramatic depletion of microneurons in the olfactory bulb, hippocampus, and cerebellum. These abnormalities arise during development of the central nervous system due to altered cytokinesis and massive apoptosis. Di Cunto et al. (2000) concluded that citron-K is essential for cytokinesis in vivo, in specific neuronal precursors only. Moreover, they suggested a novel molecular mechanism for a subset of human malformation syndromes of the central nervous system.

The disclosed NOV3 nucleic acid of the invention encoding a RHO/RAC-interacting citron kinase-like protein includes the nucleic acid whose sequence is provided in Table 3A or 3C or a fragment thereof. The invention also includes a mutant or variant nucleic acid any of whose bases may be changed from the corresponding base shown in Table 3A or 3C while still encoding a protein that maintains its RHO/RAC-interacting citron kinase-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 10% percent of the bases may be so changed.

The disclosed NOV3 protein of the invention includes the RHO/RAC-interacting citron kinase-like protein whose sequence is provided in Table 3B or 3D. The invention also includes a mutant or variant protein any of whose residues may be changed from the corresponding residue shown in Table 3B or 3D while still encoding a protein that maintains its RHO/RAC-interacting citron kinase-like activities and physiological functions, or a functional fragment thereof. In the mutant or variant protein, up to about 13% percent of the residues may be so changed.

The protein similarity information, expression pattern, and map location for the RHO/RAC-interacting citron kinase-like protein and nucleic acid (NOV3) disclosed herein suggest that NOV3 may have important structural and/or physiological functions characteristic of the citron kinase-like family. Therefore, the NOV3 nucleic acids and proteins of the invention are useful in potential diagnostic and therapeutic applications. These include serving as a specific or selective nucleic acid or protein diagnostic and/or prognostic marker, wherein the presence or amount of the nucleic acid or the protein are to be assessed, as well as potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), and (v) a composition promoting tissue regeneration in vitro and in vivo.

The NOV3 nucleic acids and proteins of the invention are useful in potential diagnostic and therapeutic applications implicated in various diseases and disorders described below. For example, the compositions of the present invention will have efficacy for treatment of patients suffering from asthma, arthritis, psoriasis, diabetes, and IBD, which require activated T cells, as well as diseases such as systemic lupus erythematosus that involve B cell activation, Autoimmune disease, Renal artery stenosis, Interstitial nephritis, Glomerulonephritis, Polycystic kidney disease, Renal tubular acidosis, IgA nephropathy, Hypercalceimia, Lesch-Nyhan syndrome, Von Hippel-Lindau (VHL) syndrome, Alzheimer's disease, Stroke, Tuberous sclerosis, hypercalceimia, Parkinson's disease, Huntington's disease, Cerebral palsy, Epilepsy, Multiple sclerosis, Ataxia-telangiectasia, Leukodystrophies, Behavioral disorders, Addiction, Anxiety, Pain, Neuroprotection, Endocrine dysfunctions, Obesity, Growth and Reproductive disorders Hemophilia, hypercoagulation, idiopathic thrombocytopenic purpura, allergies, immunodeficiencies, transplantation, Lymphaedema, Hemophilia, Hypercoagulation, Idiopathic thrombocytopenic purpura, Imrnunodeficiencies, Graft vesus host, Hirschsprung's disease, Crohn's Disease, Appendicitis Inflammatory bowel disease, Diverticular disease, and/or other pathologies. The NOV3 nucleic acid, or fragments thereof, may further be useful in diagnostic applications, wherein the presence or amount of the nucleic acid or the protein are to be assessed.

NOV3 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV3 protein have multiple hydrophilic regions, each of which can be used as an immunogen. In one embodiment, contemplated NOV3 epitope is from about amino acids 1 to 20. In another embodiment, a NOV3 epitope is from about amino acids 40 to 45. In additional embodiments, NOV3 epitopes are from about amino acids 110 to 150, from about amino acids 210 to 300, from about amino acids 410 to 900, from about amino acids 950 to 1200, from about amino acids 1250 to 1300, from about amino acids 1310 to 1450, from about amino acids 1490 to 1520, from about amino acids 1650 to 1680, from about amino acids 1800 to 1820, from about amino acids 1900 to 1920 and from about amino acids 1980 to 2053. This novel protein also has value in development of powerful assay system for functional analysis of various human disorders, which will help in understanding of pathology of the disease and development of new drug targets for various disorders. NOV4

A disclosed NOV4 nucleic acid of 5691 nucleotides (designated CuraGen Acc. No. 105827550_EXT) encoding a novel Plexin-like protein is shown in Table 4A. An open reading frame was identified beginning with an ATG initiation codon at nucleotides 1–3 and ending with a TGA codon at nucleotides 5683–5685. A putative untranslated region downstream from the termination codon is underlined in Table 4A, and the start and stop codons are in bold letters.

TABLE 4A

NOV4 Nucleotide Sequence (SEQ ID NO:12)

ATGAAAGCCATGCCCTGCAACTGGACCTGCCTTCTCTCCCACCTCCTCATGGTGGGCATGGGCTCCTCCA
CTTTGCTCACCCGGCAGCCAGCCCCGCTGTCCCAGAAGCAGCGGTCATTTGTCACATTCCGAGGAGAGCC
CGCCGAGGGTTTCAATCACCTGGTGGTGGATGAGAGGACAGGACACATTTACTTGGGGGCCGTCAATCGG
ATTTACAAGCTCTCCAGCGACCTGAAGGTCTTGGTGACGCATGAGACAGGGCCGGACGAGGACAACCCCA
AGTGTTACCCACCCCGCATCGTCCAGACCTGCAATGACCCCCTGACCACCACCAACAATGTCAACAAGAT
GCTCCTCATAGACTACAAGGAGAACAGGCTGATTGCCTGTGGGAGCCTGTACCAAGGCATCTGCAAGCTG
CTGAGGCTGGAGGACCTCTTCAAGCTGGGGGAGCCTTATCATAAGAAGGAGCACTATCTGTCAGGTGTCA
ACGAGAGCGGCTCAGTCTTTGGAGTGATCGTCTCCTACAGCAACCTGGATGACAAGCTGTTCATTGCCAC
GGCAGTGGATGGGAAGCCCGAGTATTTTCCCACCATCTCCAGCCGGAAACTGACCAAGAACTCTGAGGCG
GATGGCATGTTCGCGTACGTCTTCCATGATGAGTTCGTGGCCTCGATGATTAAGATCCCTTCGGACACCT
TCACCATCATCCCTGACTTTGATATCTACTATGTCTATGGTTTTAGCAGTGGCAACTTTGTCTACTTTTT
GACCCTCCAACCTGAGATGGTGTCTCCACCAGGCTCCACCACCAAGGAGCAGGTGTATACATCCAAGCTC
GTGAGGCTTTGCAAGGAGGACACAGCCTTCAACTCCTATGTAGAGGTGCCCATTGGCTGTGAGCGCAGTG
GGGTGGAGTACCGCCTGCTGCACGCTGCCTACCTGTCCAAAGCGGGGGCCGTGCTTGGCAGGACCCTTGG
AGTCCATCCAGATGATGACCTGCTCTTCACCGTCTTCTCCAAGGGCCAGAAGCGGAAAATGAAATCCCTG
GATGAGTCGGCCCTGTGCATCTTCATCTTGAAGCAGATAAATGACCGCATTAAGGAGCGGCTGCAGTCTT
GTTACCGGGGCGAGGGCACGCTGGACCTGGCCTGGCTCAAGGTGAAGGACATCCCCTGCAGCAGTGCGCT
CTTAACCATTGACGATAACTTCTGTGGCCTGGACATGAATGCTCCCCTGGGAGTGTCCGACATGGTGCGT
GGAATTCCCGTCTTCACGGAGGACAGGGACCGCATGACGTCTGTCATCGCATATGTCTACAAGAACCACT
CTCTGGCCTTTGTGGGCACCAAAAGTGGCAAGCTGAAGAAGATCCGGGTGGATGGACCCAGGGGCAACGC
CCTCCAGTATGAGACGGTGCAGGTGGTGGACCCCGGCCCAGTCCTCCGGGATATGGCCTTCTCCAAGGAC
CACGAGCAACTCTACATCATGTCAGAGAGGCAGCTCACCAGAGTCCCTGTGGAGTCCTGTGGTCAGTATC
AGAGCTGCGGCGAGTGCCTTGGCTCAGGCGACCCCCACTGTGGCTGGTGTGTGCTGCACAACACGTGCAC
CCGGAAGGAGCGGTGTGAGCGGTCCAAGGAGCCCCGCAGGTTTGCCTCGGAGATGAAGCAGTGTGTCCGG
CTGACGGTCCATCCCAACAATATCTCCGTCTCTCAGTACAACGTGCTGCTGGTCCTGGAGACGTACAATG
TCCCCGGAGCTGTCAGCTGGCGTCAACTGCACCTTTGAGGACCTGTCAGAGATGGATGGGCTGGTCGTGGG
CAATCAGATCCAGTGCTACTCCCCTGCAGCCAAGGAGGTGCCCCGGATCATCACAGAGAATGGGGACCAC
CATGTCGTACAGCTTCAGCTCAAATCAAAGGAGACCGGCATGACCTTCGCCAGCACCAGCTTTGTCTTCT
ACAATTGCAGCGTCCACAATTCGTGCCTGTCCTGCGTGGAGAGTCCATACCGCTGCCACTGGTGTAAATA
CCGGCATGTCTGCACCCATGACCCCAAGACCTGCTCCTTCCAGGAAGGCCGAGTGAAGCTGCCCGAGGAC
TGCCCCCAGCTGCTGCGAGTGGACAAGATCCTGGTGCCCGTGGAGGTGATCAAGCCTATCACGCTGAAGG
CCAAGAACCTCCCCCAGCCCCAGTCTGGGCAGCGTGGCTACGAATGCATCCTCAACATTCAGGGCAGCGA
GCAGCGAGTGCCCGCCCTGCGCTTCAACAGCTCCAGCGTACAGTGCCAGAACACCTCTTATTCCTATGAA
GGGATGGAGATCAACAACCTGCCCGTGGAGTTGACAGTCGTGTGGAATGGGCACTTCAACATTGACAACC
CAGCTCAGAATAAAGTTCACCTCTACAAGTGTGGAGCCATGCGTGAGAGCTGCGGGCTGTCCCTCAAGGC
TGACCCAGACTTCGCATGTGGCTGGTGCCAGGGCCCAGGCCAGTGCACCCTGCGCCAGCACTGCCCTGCC

TABLE 4A-continued

NOV4 Nucleotide Sequence (SEQ ID NO:12)

CAGGAGAGCCAGTGGCTGGAGCTGTCTGGTGCCAAAAGCAAGTGCACAAACCCCCGCATCACAGAGATAA
TCCCGGTGACAGGCCCCCGGGAAGGGGGCACCAAGGTCACTATCCGAGGGGAGAACCTGGGCCTGGAATT
TCGCGACATCGCCTCCCATGTCAAGGTTGCTGGCGTGGAGTGCAGCCCTTTAGTGGATGGTTACATCCCT
GCAGAACAGATCGTGTGTGAGATGGGGGAGGCCAAGCCCAGCCAGCATGCAGGCTTCGTGGAGATCTGCG
TGGCTGTGTGTCGGCCTGAATTCATGGCCCGGTCCTCACAGCTCTATTACTTCATGACACTGACTCTCTC
AGATCTGAAGCCCAGCCGGGGGCCCATGTCCGGAGGGACCCAAGTGACCATCACAGGCACCAACCTGAAT
GCCGGAAGCAACGTGGTGGTGATGTTTGGAAAGCAGCCCTGTCTCTTCCACAGGCGATCTCCATCCTACA
TTGTCTGCAACACCACATCCTCAGATGAGGTGCTAGAGATGAAGGTGTCGGTGCAGGTGGACAGGGCCAA
GATCCACCAGGACCTGGTCTTTCAGTATGTGGAAGACCCCACCATCGTGCGGATTGAGCCAGAATGGAGC
ATTGTCAGTGGAAACACACCCATCGCCGTATGGGGGACCCACCTGGACCTCATACAGAACCCCCAGATCC
GTGCCAAGCATGGAGGGAAGGAGCACATCAATATCTGTGAGGTTCTGAACGCTACTGAGATGACCTGTCA
GGCGCCCGCCCTCGCTCTGGGTCCTGACCACCAGTCAGACCTGACCGAGAGGCCCGAGGAGTTTGGCTTC
ATCCTGGACAACGTCCAGTCCCTGCTCATCCTCAACAAGACCAACTTCACCTACTATCCCAACCCGGTGT
TTGAGGCCTTTCGTCCCTCAGGAATCCTGGAGCTCAAGCCTGGCACGCCCATCATCCTAAAGGGCAAGAA
CCTGATCCCGCCTGTGGCTGGGGGCAACGTGAAGCTGAACTACACTGTGCTGGTTGGGGAGAAGCCGTGC
ACCGTGACCGTGTCAGATGTCCAGCTGCTCTGCGAGTCCCCCAACCTCATCGGCAGGCACAAAGTGATGG
CCCGTGTCGGTGGCATGGAGTACTCCCCGGGGATGGTGTACATTGCCCCGGACAGCCCGCTCAGCCTGCC
CGCCATCGTCAGCATCGCAGTGGCTGGCGGCCTCCTCATCATTTTCATCGTGGCCGTGCTCATTGCCTAT
AAACGCAAGTCCCGCGAAAGTGACCTCACGCTGAAGCGGCTGCAGATGCAGATGGACAACCTGGAGTCCC
GTGTGGCCCTGGAGTGCAAGGAAGCCTTTGCCGAGCTGCAGACGGACATCCATGAGCTGACCAGTGACCT
GGATGGAGCCGGGATTCCGTTCCTGGACTATAGAACTTACACCATGCGGGTGCTGTTCCCAGGAATTGAA
GACCACCCTGTCCTCCGGGACCTTGAGGTCCCGGGCTACCGGCAGGAGCGTGTGGAGAAAGGCCTGAAGC
TCTTCGCCCAGCTCATCAACAACAAGGTGTTCCTGCTGTCCTTCATCCGCACGCTTGAGTCCCAGCGTAG
CTTCTCCATGCGCGACCGTGGCAACGTGGCCTCACTCATCATGACCGTGCTGCAGAGCAAGCTGGAGTAC
GCCACTGATGTGCTGAAGCAGCTGCTGGCCGACCTCATTGACAAGAACCTGGAGAGCAAGAACCACCCTA
AGCTGCTGCTCAGGAOGACTGAGTCAGTGGCTGAGAAGATGCTGACCAATTCGTTTACTTTCCTCCTCTA
CAAGTTCCTCAAGGAGTGTGCTGGGGAGCCCCTCTTCTCCCTGTTCTGTCCCATCAAGCAGCAGATGGAG
AAGGGCCCCATTGACGCCATCACGGGCGAGGCCCGCTACTCCTTGAGCGAGGACAAGCTCATCCGCCAGC
AGATTGACTACAAAACCCTGGTCCTGAGCTGTGTCAGCCCAGACAATGCCAACAGCCCCGAGGTCCCAGT
AAAGATCCTCAACTGTGACACCATCACTCAGGTCAAGGAGAAGATTCTGGATGCCATCTTCAAGAATGTG
CCTTGCTCCCACCGGCCCAAAGCTGCAGATATGGATCTGGAGTCGCGACAAGGAAGTGGCGCAAGGATGA
TCTTGCAGGATGAAGACATCACCACCAAGATTGAGAATGATTCGAAGCGACTGAACACACTGGCCCACTA
CCAGGTGCCAGATGGTTCCGTGGTGGCATTAGTGTCCAAGCAGGTGACAGCCTATAACGCAGTGAACAAC
TCCACCGTCTCCAGGACCTCAGCAAGTAAATATGAAAACATCATCCCGTACACGGGCAGCCCCGACAGCC
TCCCCTCACGGACACCTATGATCACTCCTGACCTGGAGAGTCGAGTCAAGATGTGGCACCTAGTGAAGAA
CCACGAGCACGGAGACCAGAAGGAGGGGACCGGGGGAGCAAGATGGTGTCTGAAATCTACCTGACCCGA
CTCCTCGCCACTAAGGGCACACTGCAGAAGTTTGTGGATGACCTCTTTGAGACCATCTTCAGCACGGCAC
ACCGTGGCTCTGCCCTGCCCCTGGCCATCAAGTACATGTTTGACTTCCTGGATGAGCAGGCTGATAAACA
TGGCATTCATGACCCGCACGTCCGCCATACCTGGAAGAGCAATTGCCTGCCCCTGAGGTTTTGGGTCAAC

TABLE 4A-continued

NOV4 Nucleotide Sequence (SEQ ID NO:12)

ATGATCAAGAACCCGCAGTTTGTGTTTGACATCCATAAGAACAGCATCACAGACGCCTGCCTCTCTGTGG

TGGCTCAGACCTTCATGGACTCTTGCTCCACGTCAGAGCACCGGCTGGGCAAGGACTCCCCCTCCAACAA

GCTGCTGTATGCCAAGGACATCCCCAGCTACAAGAATTGGGTGGAGAGGTATTACTCACACATAGGGAAG

ATGCCAGCCATCAGCGACCAAGACATGAACGCATACCTGGCTGAGCAGTCCCGGATGCACATGAATGACT

TCAACACCATGAGTGCACTCTCAGAGATCTTCTCCTATGTGGGCAAATACAGCGAGGAGATCCTTGCACC

TCTGGACCACGATGACCAGTGTGGCAAGCAGAAACTGGCCTACAAACTAGAACAAGTCATAACCCTCATG

AGCTTAGACAGCTGAAATAAA

The nucleic acid sequence of NOV4, localized on chromosome 7, has 4004 of 5567 bases (71%) identical to a plexin-2 mRNA from mouse (GENBANK-ID: D86949) (E=0.0).

A NOV4 polypeptide (SEQ ID NO:13) encoded by SEQ ID NO:12 is 1896 amino acid residues and is presented using the one letter code in Table 4B. Signal P, Psort and/or Hydropathy results predict that NOV4 has no signal peptide and is likely to be localized at the plasma membrane with a certainty of 0.46. In other embodiments, NOV4 may also be localized to the endoplasmic reticulum (membrane) with a certainty of 0.1000, the endoplasmic reticulum (lumen) with a certainty of 0.1000, or the outside with a certainty of 0.1000.

TABLE 4B

NOV4 protein sequence (SEQ ID NO:13)

MKAMPWNWTCLLSHLLMVGMGSSTLLTRQPAPLSQKQRSFVTFRGEPAEGFNHLVVDERTGHIYLGAVNRIYKL

SSDLKVLVTHETGPDEDNPKCYPPRIVQTCNEPLTTTNNVNKMLLIDYKENRLIACGSLYQGICKLLRLEDLFK

LGEPYHKKEHYLSGVNESGSVFGVIVSYSNLDDKLFIATAVDGKPEYFPTISSRKLTKNSEADGMFAYVFHDEF

VASMIKIPSDTFTIIPDFDIYYVYGFSSGNFVYFLTLQPEMVSPPGSTTKEQVYTSKLVRLCKEDTAFNSYVEV

PIGCERSGVEYRLLQAAYLSKAGAVLGRTLGVHPDDDLLFTVFSKGQKRKMKSLDESALCIFILKQINDRIKER

LQSCYRGEGTLDLAWLKVKDIPCSSALLTIDDNFCGLDMNAPLGVSDMVRGIPVFTEDRDRMTSVIAYVYKNHS

LAFVGTKSGKLKKIRVDGPRGNALQYETVQVVDPGPVLRDMAFSKDHEQLYIMSERQLTRVPVESCCQYQSCGE

CLGSGDPHCGWCVLHNTCTRKERCERSKEPRRFASEMKQCVRLTVHPNNISVSQYNVLLVLETYNVPELSAGVN

CTFEDLSEMDGLVVGNQIQCYSPAAKEVPRIITENGDHHVVQLQLKSKETGMTFASTSFVFYNCSVHNSCLSCV

ESPYRCHWCKYRHVCTHDPKTCSFQEGRVKLPEDCPQLLRVDKILVPVEVIKPITLKAKNLPQPQSGQRGYECI

LNIQGSEQRVPALRFNSSSVQCQNTSYSYEGMEINNLPVELTVVWNGHFNIDNPAQNKVHLYKCGAMRESCGLC

LKADPDFACGNCQGPGQCTLRQHCPAQESQWLELSGAKSKCTNPRITEIIPVTGPREGGTKVTIRGENLGLEFR

DIASHVKVAGVECSPLVDGYIPAEQIVCEMGEAKPSQHAGFVEICVAVCRPEFMARSSQLYYFMTLTLSDLKPS

RGPMSGGTQVTITGTNLNAGSNVVVMFGKQPCLFHRRSPSYIVCNTTSSDEVLENKVSVQVDRAKIHQDLVFQY

VEDPTIVRIEPEWSIVSGNTPIAVWGTHLDLIQNPQIRAKHGGKEHINICEVLNATEMTCQAPALALGPDHQSD

LTERPEEFGFILDNVQSLLILNKTNFTYYPNPVFEAFGPSGILELKPGTPIILKGKNLIPPVAGGNVKLNYTVL

VGEKPCTVTVSDVQLLCESPNLIGRHKVMARVGGMEYSPGMVYIAPDSPLSLPAIVSIAVAGGLLIIFIVAVLI

AYKRKSRESDLTLKRLQMQMDNLESRVALECKEAFAELQTDIHELTSDLDGAGIPFLDYRTYTMRVLFPGIEDH

PVLRDLEVPGYRQERVEKGLKLFAQLINNKVFLLSFIRTLESQRSFSMRDRGNVASLIMTVLQSKLEYATDVLK

QLLADLIDKNLESKNHPKLLLRRTESVAEKMLTNWFTFLLYKFLKECAGEPLFSLFCAIKQQMEKGPIDAITGE

ARYSLSEDKLIRQQIDYKTLVLSCVSPDNANSPEVPVKILNCDTITQVKEKILDAIFKNVPCSHRPKAADMDLE

WRQGSGARMILQDEDITTKIENDWKRLNTLAHYQVPDGSVVALVSKQVTAYNAVNNSTVSRTSASKYENMIRYT

GSPDSLRSRTPMITPDLESGVKMWHLVKNHEHGDQKEGDRGSKMVSEIYLTRLLATKGTLQKFVDDLFETIFST

TABLE 4B-continued

NOV4 protein sequence (SEQ ID NO:13)

AHRGSALPLAIKYMFDFLDEQADKHGIHDPHVRHTWKSNCLPLRFWVNMIKNPQFVFDIHKNSITDACLSVVAQ

TFMDSCSTSEHRLGKDSPSNKLLYAKDIPSYKNWVERYYSDIGKMPAISDQDMNAYLAEQSRMHMNEFNTMSAL

SEIFSYVGKYSEEILGPLDHDDQCGKQKLAYKLEQVITLMSLDSNK

The full amino acid sequence of the protein of the invention was found to have 1263 of 1857 amino acid residues (68%) identical to, and 1501 of 1857 amino acid residues (80%) similar to, the 1884 amino acid residue plexin-2 protein from mouse (SPTREMBL-P70207) (E=0.0), and 364 of 801 amino acid residues (45%) identical to, and 520 of 801 amino acid residues (64%) similar to, the 2135 amino acid residue Human Plexin protein (patp:AAU00019) (E=$2.6^{-283}$).

The disclosed NOV4 protein is expressed in at least the following tissues: fibroblast-like synoviocytes (normal), fetal brain, adipose, microvascular endothelial cells-lung, thalamus, fetal cerebral cortex, temporal lobe, parietal lobe, fetal cerebellum, and testis. TaqMan expression data for NOV4 is shown below in Example 2.

NOV4 also has homology to the amino acid sequences shown in the BLASTP data listed in Table 4C.

TABLE 4C

BLAST results for NOV4

| Gene Index/ Identifier | Protein/Organism | Length (aa) | Identity (%) | Positives (%) | Expect |
|---|---|---|---|---|---|
| gi\|13649119\|ref\|XP_010150.2\| | SEX gene [Homo sapiens] | 1871 | 1121/1846 (60%) | 1413/1846 (75%) | 0.0 |
| gi\|3413888\|dbj\|BAA32308.1\| | KIAA0463 protein [Homo sapiens] | 1963 | 1270/1870 (67%) | 1508/1870 (79%) | 0.0 |
| gi\|2134135\|pir\|\|I51553 | Plexin - African clawed frog | 1905 | 1220/1915 (63%) | 1468/1915 (75%) | 0.0 |
| gi\|14424639\|gb\|AAH09343.1\|AAH09343 | Unkown (protein for IMAGE:4130636) [Homo sapiens] | 813 | 641/810 (79%) | 717/810 (88%) | 0.0 |
| gi\|10047165\|dbj\|BAB13376.1\| | KIAA1550 protein [Homo sapiens] | 593 | 513/513 (100%) | 513/513 (100%) | 0.0 |

The homology of these sequences is shown graphically in the ClustalW analysis shown in Table 4D.

TABLE 4D

ClustalW Analysis of NOV4

```
1) NOV4 (SEQ ID NO:13)
2) gi|13649119|ref|XP_010150.2| SEX gene [Homo sapiens]
   (SEQ ID NO:42)
3) gi|3413888|dbj|BAA32308.1| KIAA0463 protein [Homo sapiens]
   (SEQ ID NO:43)
4) gi|2134135|pir||I51553 Plexin - African clawed frog
   (SEQ ID NO:44)
5) gi|14424639|gb|AAH09343 Unkown(protein for IMAGE:4130636)
   [Homo sapiens] (SEQ ID NO:45)
6) gi|10047165|dbj|BAB13376.1| KIAA1550 protein [Homo sapiens]
   (SEQ ID NO:46)
```

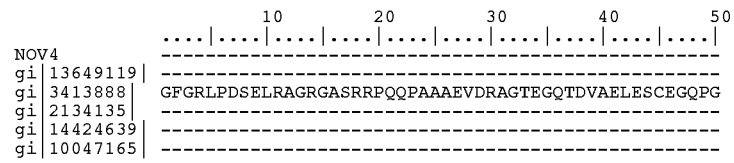

TABLE 4D-continued

ClustalW Analysis of NOV4

```
                         60         70         80         90        100
                   ....|....|....|....|....|....|....|....|....|....|
NOV4               ------------------------MKAMPWNWTCLLSHLSMVGMGSSTLLT
gi|13649119|       -------------------------MP--------SVCSLLLFLAVG-G
gi|3413888|        KVEQMSTHRSRLLTAAPLSMEQRRPWPRALEVDSRSVVSSVVWVLLAPP
gi|2134135|        ---------------MLLHAERPLP----FHLWSFLSSLGSWIATGDG
gi|14424639|       --------------------------------------------------
gi|10047165|       --------------------------------------------------

110        120        130        140        150
                   ....|....|....|....|....|....|....|....|....|....|
NOV4               RQPAPLSQKQRSFVTFRGEPAEGFSHLVVDERTCHSYLGAVNRIYKLSSD
gi|13649119|       ALGNRPFRAFVV--TDTTLTHLAVSRVTGEVFVCASNRVFKLAPNLTELR
gi|3413888|        AAGMPQFSTFHSENRDWTFNHLTVSQGTGAVYVCASNRVYKLTGNLTIQV
gi|2134135|        SP--KDFRTFTG--SDQSLTHLVVSNKTGEVYCASNRIYKLSNNLTLLR
gi|14424639|       --------------------------------------------------
gi|10047165|       --------------------------------------------------

160        170        180        190        200
                   ....|....|....|....|....|....|....|....|....|....|
NOV4               LKVLVTHETGPDEDNEKCYPPRIVQTCNEPLTTTNNYNKMLLIDYKENRL
gi|13649119|       AHVTGPVEDNARCYPPPSMRVCAHRLAPVDNINKLLEIDYAARRLVACGS
gi|3413888|        AHKTGPEEDNKSCYPPLIVQPCSEVLTLTNNVNKLLEIDYSENRLLACGS
gi|2134135|        THVTGPVEDNEKCYPPPSVQSCPHGLITTNNVNKLLEIDYSDNRLIACGS
gi|14424639|       --------------------------------------------------
gi|10047165|       --------------------------------------------------

210        220        230        240        250
                   ....|....|....|....|....|....|....|....|....|....|
NOV4               IACGSLYQGICKLDRLEDLFKLGEPSKKEHYLSGVNESGSYFGVIVSYS
gi|13649119|       IWQCICQFLRLDDDLFKLGEPHHRKESLSGAQEPDSMAGVIEEQGQGPSK
gi|3413888|        LYQCVCKLLRLDDDLFILVEPSHKKESLSSVNKTGTMYGVIERSEGEDGK
gi|2134135|        ASQCICQFLRLDDDLFKLGEPHHRKESLSSVNESGTMSGVIEEVPNGQNK
gi|14424639|       --------------------------------------------------
gi|10047165|       --------------------------------------------------

260        270        280        290        300
                   ....|....|....|....|....|....|....|....|....|....|
NOV4               NLDDKLFIATAVDGKPEYFPTSSSRKLTKNSEADGMFAYVFHDEFVASMI
gi|13649119|       LFVGTAVDGKSEYFPTLSSRKEISDEDSADMFSLVYQDEFVSSQIKIPSD
gi|3413888|        LFIGTAVDGKQDYFPTLSSRKSPRDPESSAMLDYELHSDFVSSLIKIPSD
gi|2134135|        LFVGTPIDGKSEYFPTLSSRKELGNEENAEMFGFVYQDEFVSSQLKIPSD
gi|14424639|       --------------------------------------------------
gi|10047165|       --------------------------------------------------

310        320        330        340        350
                   ....|....|....|....|....|....|....|....|....|....|
NOV4               KSPSDTFTIIPDFPISYVYGFSSGNFSYFLSLSPEMVSPPGSTTKEQVYT
gi|13649119|       TSSLYPAFDSIYYIYGSVSASFSVYFLTSQLDT-SQTLLDTAGEKFFTSKIV
gi|3413888|        TSALVSHFDSFYIYGSASGGSVYVLTSQPETPSGVAINSACDLFYTSRIV
gi|2134135|        TSSKFPTFDSIYYVYSSSSEQFSVYYLTSQLDT-SQLTSPDSTGEQFFTSKIV
gi|14424639|       --------------------------------------------------
gi|10047165|       --------------------------------------------------

360        370        380        390        400
                   ....|....|....|....|....|....|....|....|....|....|
NOV4               SKLVRLCSEDSAFNSYVEVPIGCERSGSEYRLLQSAYLSKAGAVLGRTLG
gi|13649119|       RMCAGDSSFYSYVEFPIGCSWRGVEYRSVQSAHLSKPGLLLAQALGVPAD
gi|3413888|        RLCKDDPSFHSYVSLPFGCTRAGVEYRSLQAAYLSKPGDSLAQAFNITSQ
gi|2134135|        RLCVDDPSFYSYVEFPIGCMKDGVEYRSIQDAYLSKPGKRLAKELGISER
gi|14424639|       --------------------------------------------------
gi|10047165|       --------------------------------------------------

410        420        430        440        450
                   ....|....|....|....|....|....|....|....|....|....|
NOV4               VHPDDDSLFTVFSKGQRKMKSLDESALCIFSLKQINDRSSERLGSCYRG
gi|13649119|       EDVLFTSFSQGQKNRASPPRQSILCLFTLSNSINAHSIRRRSSCYSGEGTL
gi|3413888|        DDVLFASFSKGQKQYHHPPDDSALCAFPIRASINLQIKGSSSCYQGEGNL
gi|2134135|        EDILFTSFSQGQKNRIKPPKESVLCLFTLKKSIKDKSIKERSSCYSGDGKL
gi|14424639|       --------------------------------------------------
gi|10047165|       --------------------------------------------------

460        470        480        490        500
                   ....|....|....|....|....|....|....|....|....|....|
NOV4               EGTLDSIAWLKVKDIPCSSALLTIDDNFCGLDSNAPLGYSDMVRGIPVFTE
gi|13649119|       ALPWLSNKELPCINTPMQINGNFCGLVLNQPSGGLHVSEGLPLLADSTDG
gi|3413888|        ELNWLSGKDVQCTKAPVPIDDNFCGLDINQPSGGSTPSEGLTLYTTSRDR
gi|2134135|        SLPQLSNKELGCINSPLQIDDNFCGQDFNQPSGGTVTSEGTPLFLDKEDG
gi|14424639|       --------------------------------------------------
gi|10047165|       --------------------------------------------------
```

TABLE 4D-continued

ClustalW Analysis of NOV4

```
                    510        520        530        540        550
                ....|....|....|....|....|....|....|....|....|....|
NOV4            DRDRMTSVIAYVYKNHSLAFVGTKSGKLKKIRVDGPRGNALQYETVQVVD
gi|13649119|    MASVAAYTYRQHSVVFIGTRSCSLKKVRVDGFQDAH----LYETVPVVDG
gi|3413888|     MTSVASYVYNGYSVVFVGTKSGKLKKIRADGPPHGG--VQYEMVSVLKDG
gi|2134135|     MTSVAAYDYRGHTVVFAGTRSGRVKKILVDLSASSSHLVQQYENVVVHEG
gi|14424639|    --------------------------------------------------
gi|10047165|    --------------------------------------------------

560        570        580        590        600
                ....|....|....|....|....|....|....|....|....|....|
NOV4            PGPYLRDMAFSKDHEQLYXMSERQLTRVPVESCGQYQSCGECLGSGDPHCG
gi|13649119|    SPIERDLLFSPDHRHIYLXSEKQVSQLPVETCEQYQSCAACLGSGDPHCG
gi|3413888|     SPIERDMAFSIDQRYLYVXSERQVTRVPVESCEQYTTCGECLSSGDPHCG
gi|2134135|     NAIERDLVLSPDRQYIYANTEKQVTRVPVESCEQYESCDTCLGSRDPHCG
gi|14424639|    --------------------------------------------------
gi|10047165|    --------------------------------------------------

610        620        630        640        650
                ....|....|....|....|....|....|....|....|....|....|
NOV4            GWCXLHNTCTRKERCERSKEPRRFASEMXQCVRLTVHPNNISVSQYNVXL
gi|13649119|    QCVERHRCCREGACLGASAPHGFAEELSXCVQVRVRPNXVSVTSPGVQXT
gi|3413888|     WCAHHMCSRRDKCQQAWEPNRFAASISXCVSLAVHPSXISVSEHSRLXS
gi|2134135|     WCVEHXMCSRKDKCERADELHRFTSDQRXCVQLTVHPKXISVTVSEVBXV
gi|14424639|    --------------------------------------------------
gi|10047165|    --------------------------------------------------

660        670        680        690        700
                ....|....|....|....|....|....|....|....|....|....|
NOV4            XLETYNVPELXAGVNCTFEDLSEMDGXVVGNXXCYSPAAKXXPRXITEN
gi|13649119|    XTLHNVPDLSXGVSCAFEAAAENEAVXLPSGXXLCPSPSLXXRAXTRGH
gi|3413888|     XVVSDAPDLSXGIACAFGNLTEVEGQXS-GSXXICISGPXXXPVXPLDQ
gi|2134135|     XQAWNVPDLSXGVNCSFEDFTEMEGRXL-DGXXYCTSPSAXXXIPXTRGH
gi|14424639|    --------------------------------------------------
gi|10047165|    --------------------------------------------------

710        720        730        740        750
                ....|....|....|....|....|....|....|....|....|....|
NOV4            GDHHVXQLQLXKSKETGMTXASTSXVFYNCSVHNSCXSCVESPXPCHWCKY
gi|13649119|    GATRTXRLQLXLSKETGVRXAGADXVFYNCSVLQSCXSCVGSPXPCHWCKY
gi|3413888|     -DWFGXELQLXRSKETGKIXVSTEXFYNCSAHQLCXSCVNSAXPCHWCKY
gi|2134135|     GDKRVXKXYLXKSKETGKKXASVDXVFYNCSVHQSCXSCVNGSXPCHWCKY
gi|14424639|    --------------------------------------------------
gi|10047165|    --------------------------------------------------

760        770        780        790        800
                ....|....|....|....|....|....|....|....|....|....|
NOV4            RXVCTHDPKTCSFQEGRXKLPEDCPQXXRVDKXLXPVEVXXPXTLKAXNL
gi|13649119|    RHTCTSRPHECSFQEGRXHSPEGCPXXPSGDXLXPVGVXXPXTLRAXNL
gi|3413888|     RXLCTHDPTTCSFQEGRXNISEDCPQXXPTEEXLXPVGEXXPXTLKAXNL
gi|2134135|     RXVCTHNAADCSFQEGRXNMSEDCPQXXPSSQXYXPVGVXXPXTLTAXNL
gi|14424639|    --------------------------------------------------
gi|10047165|    --------------------------------------------------

810        820        830        840        850
                ....|....|....|....|....|....|....|....|....|....|
NOV4            PSPQSGQXGYECXLNXQGSEQRVPAXRFNSXSXQCQNTSYSYXCMXINXL
gi|13649119|    PSPQSGQXKNYECXVRXQGRQQRVPAXRFNSXSXQCQNASYSYXGDXHGXT
gi|3413888|     PSPQSGQXGYECXLNXQGAIHRVPAXRFNSXSXQCQNSSYQYXCMXISXL
gi|2134135|     PSPQSGQXNYECXFHXPGSVTRVTAXRFNSXSXQCQNTSYNYXGNXISXL
gi|14424639|    --------------------------------------------------
gi|10047165|    --------------------------------------------------

860        870        880        890        900
                ....|....|....|....|....|....|....|....|....|....|
NOV4            PVXLXVVWNGXFNXIDNPAQNXVHLYKCGAMRESCGLCLKADPDXACGWCQ
gi|13649119|    EXXFXVVWXGDFPIDKPPSFXALLYKCWAQREPSCGLCLKADPRXNCQWCI
gi|3413888|     AVXFAVVWNGXFXIDNPQDLXVHLYKCAAQRESCGLCLKADRKXECGWCS
gi|2134135|     PVNLXVVWNGXFVIDNPQNIXAHLYKCSALRESCGLCLKXSDRRXECGWCV
gi|14424639|    --------------------------------------------------
gi|10047165|    -VXLXVVQNGXFNIFNEAQNXVHLYKCGAMRESCGLCLKADPDXACGWCQ 910        920        930        940        950
                ....|....|....|....|....|....|....|....|....|....|
NOV4            GPGXCTLRQHCPXQXXQWXELSGAKXXCXXPXITXIIEXXGPXEGGTXVT
gi|13649119|    SEHXCQLRITHCPXAPKXNWXHLSQKGXRCXXPXITXIHEXXVGPXEGGTXVT
gi|3413888|     GERXCTLXQHCTXPSSXPWXHLDWSSHNVKCXXPXITXILTXXGPPEGGTXVT
gi|2134135|     SEKXCTLRQKCPTLXXPWXHASTANXXCXXDPXITKXFPEXXGPXGGTXXT
gi|14424639|    --------------------------------------------------
gi|10047165|    GPGXCTLRQHCPXAQXXQWXELSGAKXXCXXPXITXIIPXXGPXEGGTXVT
```

TABLE 4D-continued

ClustalW Analysis of NOV4

```
                 960        970        980        990       1000
                  .    |    .    |    .    |    .    |    .    |
NOV4         IRGKNLGLEPREIASHVKVAGVRCSPKVDGYIPAEQIVCEMGKA-KPSQH
gi|13649119| IVGKNLGLLSRKKG--KKVAGVRCNSKPAEYISAEKIVCEMEKKLVPSPP
gi|3413888|  IHGVNLGLDESKIAHHVKVAGVPCTPKPGEYIIKAEQIVCEMGHA-LVGTT
gi|2134135|  ITGKNLGLRPEKIRFGVKVGHVMCVPKESEYISAEQIVCEKNKAGRTRVH
gi|14424639| --------------------------------------------------
gi|10047165| IRGKNLGLEPREIASHVKVAGVECSPKVDGYIPAEQIVCEMGKA-KPSQH 1010       1020       1030       1040       1050
                  .    |    .    |    .    |    .    |    .    |
NOV4         AGFVEKCVAVCRPKFMAKSSQLYYFKTLKLSDKKPSRGEMSGGTQKTIKG
gi|13649119| PGPVEKCVGDCSAKFRTKSEQVYSFKTPKFDQKSPSRGEASGGTRKTIKG
gi|3413888|  SGPVRKCKGECKPKFMTKSHQQYTFKNPKVLSKNPIRGEASGGTMVKTIKG
gi|2134135|  EAQVEKCVLDCSQKKRAISPKSKTFKVLPKFNRKTPSRGELSGGTWKSIKG
gi|14424639| --------------------------------------------------
gi|10047165| AGFVEKCVAVCRPKFMAKSSQLYYFKTLKLSDKKPSRGEMSGGTQKTIKG 1060       1070       1080       1090       1100
                  .    |    .    |    .    |    .    |    .    |
NOV4         TNLKAGSNVVMFGKQPCLFHRRKPSYIVCNKTSSDE-VLKMKKKQKDR
gi|13649119| SSLKAGSRVTVTVRDSECQFVRRDAKAIVCIKPLSTLGPSQAPKKKADR
gi|3413888|  HYLKAGSSVAVYLGNKTCEFYGRKMSEIVCKPPSSNGLGPVPKKVSKDR
gi|2134135|  NYLKAGSDVSVAICGKPCMFSWRKAKEIRCKKPQGPS-TGKAEKQILKKR
gi|14424639| --------------------------------------------------
gi|10047165| TNLKAGSNVVMFGKQPCLFHRRKPSYIVCNKTSSDE-VLKMKKKQKDR 1110       1120       1130       1140       1150
                  .    |    .    |    .    |    .    |    .    |
NOV4         AKKH-QDLVKQYVKDPTKVRIEPEWSIVSGNTPKAVWGTKLDLIQNPKIR
gi|13649119| ANKSSPGLIKTYTKDPTKTRKKEPTWSIIKGSTAKTVSGTKLLTKKEPKIR
gi|3413888|  AHKD-SNLQKEYIKDPRVQRIEPEWSIASCHTPKIKTGFKLDVIQEPKIR
gi|2134135|  ATKNNSEKVHKNYTKDPTKQRIEPEWSIASGGTPKIVTGMKLATIKEPKIR
gi|14424639| --------------------------------------------------
gi|10047165| AKKH-QDLVKQYVKDPTKVRIEPEWSIVSGNTPKAVWGTKLDLIQNPKIR 1160       1170       1180       1190       1200
                  .    |    .    |    .    |    .    |    .    |
NOV4         AKKGGKEHINKCKVKNATEMTCQAPKALALGPDHQSDLTERPKEFGFKKDN
gi|13649119| AKKRGIETTNTCKVKNDTAMLCKAPGTFLGRPQPRAQGEHPDEFGFKKDK
gi|3413888|  VKFNGKESVNKCKVKNTTITETCLAPKLTTDYRPGLDTVERPDEFGFKFKN
gi|2134135|  AKKGDVEKENNCTKYNDTTMVCLAPKKDNPLRSPPKNGKRPDEKGFKFKN
gi|14424639| ------GTRVKCKVKNTTITETCLAPKLTTDYRPGLDTVERPDEFGFKFKN
gi|10047165| AKKGGKEHINKCKVKNATEMTCQAPKALALGPDHQSDLTERPKEFGFKKDN 1210       1220       1230       1240       1250
                  .    |    .    |    .    |    .    |    .    |
NOV4         VQSLLIKNKIKFTYYPNPVFEAFGPSGKIKKPCTPIILKGKNLIPPVKG
gi|13649119| VQKARSKNRKKFTYYPKPSFEPLCPSGKLKKPCGSHKKLKGKNLIPAAKG
gi|3413888|  VQSLLIYNDTKFIYYPNPTFELLSPKGKIKQKPCSPIILKGKNLIPAAPG
gi|2134135|  VHKLLIKNTKSFLYYPKPVFEPLTASGNLKKPSSPKIKGKNLIPAAPG
gi|14424639| VQSLLIYNDTKFIYYPNPTFELLSPKGKIKQKPGSPIILKGKNLCPPAKG
gi|10047165| VQSLLIKNKIKFTYYPNPVFEAFGPSGKIKKPCTPIILKGKNLIPPVKG 1260       1270       1280       1290       1300
                  .    |    .    |    .    |    .    |    .    |
NOV4         GKVKLNYTVLKGEKPCTVTVSKVQLLCESPNLIKHKVMARVGGMEKSPG
gi|13649119| -KSKLNYTVLIGGQPCKKTVSKTQLLCKSPSQTGKQPVMKLVGGKEKWLG
gi|3413888|  -GAKLNYTVLIGETPCKVTVSKTQLLCEPPNLTCKHKVMKHVGGMVKSPG
gi|2134135|  -KFKLNYTVLIGEKPCKVTVSKTQLLCESPNLTCKHKVTKKAGGKEKSPG
gi|14424639| -GAKLNYTVLIGETPCKAVTVSKTQLLCEPPNLTCKHKVMKHVGGMVKSPG
gi|10047165| GKVKLNYTVLKGEKPCTVTVSKVQLLCESPNLICKHKVMARVGGMEKSPG 1310       1320       1330       1340       1350
                  .    |    .    |    .    |    .    |    .    |
NOV4         MVYIAPDSPLKLPAIVSIAVAGGLLKIFTVAVLIAYKRKSREKDLTLKRL
gi|13649119| TKHISKKRALTLPAKKGKAAGGGLLLLKAKTAVLKAYKRKKKKDRTLKRL
gi|3413888|  KVSKIKDSLLTLPAIVSIAAGGSLLLIKKKIEIVLIAYKRKSREKDRTLKRL
gi|2134135|  KQIYKDSLLTLPAIKCIKGGGGGLLLKIKIEIVLIAYKRKSREKDLTLKRL
gi|14424639| KVSKIKDSLLTLPAIVSIAAGGSLLLIKKKIVLIAYKRKSREKDLTLKRL
gi|10047165| MVYIAPDSPLKLPAIVSIAVAGGLLKIFTKAVLIAYKRKSREKDLTLKRL 1360       1370       1380       1390       1400
                  .    |    .    |    .    |    .    |    .    |
NOV4         QMQMDNLESRVALECKEAFAELQTDIKELTKDLDGKGIPKLDYRTYTMRV
gi|13649119| QKMMDNLESRVALECKEAFAELQTDIKELTKHKDEVQIPKLDYRTYAKRV
gi|3413888|  QMQMDNLESRVALECKEAFAELQTDIKELTKDLDRKGIPKLDYRTYAMRV
gi|2134135|  QKKMDNLESRVALECKEAFAELQTDIKELTKDLDRKGIPKLSYRTYAMRV
gi|14424639| QMQMDNLESRVALECKEAFAELQTDIKELTKDLDRKGIPKLDYRTYAMRV
gi|10047165| QMQMDNLESRVALECKEG----------T---------------------
```

TABLE 4D-continued

ClustalW Analysis of NOV4

```
                    1410       1420       1430       1440       1450
                 ....|....|....|....|....|....|....|....|....|....|
NOV4             LFPGIEDHPVLRELEVPGYRQERVEKGLLLFAQLHHHKVFLLSFIRTLES
gi|13649119|     LFPGIEAHPVLRELETPPN----VEKALLLFGQLHRRAFQLTFIHTLEA
gi|3413888|      LFPGIEDHPVLRELEVQGNGQQHVEKALLLFAQLHHHKVFLLTFIRTLEL
gi|2134135|      LFPGIEDHPVLREREVQAN----VEKSLILFGQLTKKHFLLTFIRTLEA
gi|14424639|     LFPGIEDHPVLRELEVQGNGQQHVEKALLLFAQLHHHKVFLLTFIRTLEL
gi|10047165|     EHPHAGGHVCHR-------------------------------------

1460       1470       1480       1490       1500
                 ....|....|....|....|....|....|....|....|....|....|
NOV4             QRSFSMRDRGNVASLIMTVLQSHLEYATDVLKQLLHDLIHKNLEHKNHPK
gi|13649119|     QSSFSMRDRGTVASLIMVALQSHLEYATGHLKQLLADLIHKNLEHKNHPK
gi|3413888|      QRSFSMRDRGNVASLIMTGLQGHLEYATDVLKQLLHDLIHKNLEHKNHPK
gi|2134135|      QRSFSMRDRGNVASLIMTALQGEMEYATGVLKQLLHDLIHKNLEHKNHPK
gi|14424639|     QRSFSMRDRGNVASLIMTGLQGHLEYATDVLKQLLHDLIHKNLEHKNHPK
gi|10047165|     -------------------------------------------------

1510       1520       1530       1540       1550
                 ....|....|....|....|....|....|....|....|....|....|
NOV4             LLLRRTESVAEKMLTNWFTFLLHKFLKECAGEPLFSLHCAIKQQMEKGPI
gi|13649119|     LLLRRTESVAEKMLTNWFTFLLHKFLKECAGEPLFHLHCAIKQQMEKGPI
gi|3413888|      LLLRRTESVAEKMLTNWFAPLLHKFLKECAGEPLFHLHCAIKQQMEKGPI
gi|2134135|      LLLRRTESVAEKMLTNWFTFLLHKFLKECAGEPLFHLHCAIKQQMEKGPI
gi|14424639|     LLLRRTESVAEKMLTNWFAPLLHKFLKECAGEPLFHLHCAIKQQMEKGPI
gi|10047165|     ----------------------VCHCVCMHICHCHCICFIYHCAGWAAH 1560       1570       1580       1590       1600
                 ....|....|....|....|....|....|....|....|....|....|
NOV4             DAITGEARYSLSEDKLIRQQIHYKTL-------------------VLHCV
gi|13649119|     DAITGEARYSLSEDKLIRQQIHYKTL--------------------TLHCV
gi|3413888|      DAITGEARYSLSEDKLIRQQIHYKTL-------------------ILHCV
gi|2134135|      DAITGEARYSLSEDKLIRQQIHYKTLNPCADDVGLSDESCCRSPQTLHCV
gi|14424639|     DAITGEARYSLSEDKLIRQQIHYKTL-------------------ILHCV
gi|10047165|     GHAGGWRCVCLCE------------------------------------CV 1610       1620       1630       1640       1650
                 ....|....|....|....|....|....|....|....|....|....|
NOV4             HPHNANSPEHPVKHLNCDTITQVKEKHLDAHHHKNVPCSHRPKAADMDLEW
gi|13649119|     CPHNEGSAHHPVKVLNCDSHITQAKHKHLDTVYKGHPYSQRPKAHVDMDLEW
gi|3413888|      HPHNENSPEHPVKVLNCDTITQVKEKHLDAVYKNVPYSQRPKAHDMDLEW
gi|2134135|      HPHNENHPEHPVKVLNCDTITQVKEKHLDAVYKGVPYSQRPKACDMDLEW
gi|14424639|     HPHNENSPRHPVKVLNCDTITQVKEKHLDAVYKNVPYSQRPKAHVDMDLEW
gi|10047165|     C---------HHVHCVCTHHC-----------HYVSYTSKQAGQQ---

1660       1670       1680       1690       1700
                 ....|....|....|....|....|....|....|....|....|....|
NOV4             RQGSGARHHLQDEDHTTKIENDWKRLNTLAHYQVPDGSHVALVSKQVHHY
gi|13649119|     RQGFMTRHHLQDEDHTTKIECDWKRLNLLAHYQVHDGSHVALVPKQVSHY
gi|3413888|      RQGHARVHLQDEDHTTKIENDWKRLNTLAHYQVHDGSHVALVPKQNSHY
gi|2134135|      RQGHAARHLQDEDHTTKIENDWKRLNTLAHYQVHDGSHVALVPKQNSHY
gi|14424639|     RQGFARHHLQDEDHTTKIEGDWKRLNTIMHYQVSDRSHVALVPKQTSHY
gi|10047165|     -------------------------------------------------

1710       1720       1730       1740       1750
                 ....|....|....|....|....|....|....|....|....|....|
NOV4             NAVNNHTVHRHSASHYHHMIRYTGSPDSLRSRTPMITPDLESGVKHWHLV
gi|13649119|     NHANSFHFHRS-HSRYHSLLRTASSPDSLRSRAPMITPDQEHGHKHWHLV
gi|3413888|      NHSNSHTFPHH-SRYHSMLRTASSPDSLRSRTPMITPDLESGTKHWHLV
gi|2134135|      NHPASAHIHRSHSRYHSFRYTGSPDSLRSRAPMITPDLESGVKHWHLV
gi|14424639|     NHPASAHIHRSHSRYHSFRYTGSPDSLRSRAPMITPDLESGVKHWHLV
gi|10047165|     -------------------------------------------------

1760       1770       1780       1790       1800
                 ....|....|....|....|....|....|....|....|....|....|
NOV4             KNHHHGDQHHEGDRGSKMVSEIYLTRLLATKGTLQKFVDDLFETHFSTAHR
gi|13649119|     KNHDHADHHHEGDRGSKMVSEIYLTRLLATKGTLQKFVDDLFETHFSTAHR
gi|3413888|      KNHDHGDQHEGDRGSKMVSEIYLTRLLATKGTLQKFVDDLFETHFSTAHR
gi|2134135|      KNHDHLDQHEGDRGSKMVSEIYLTRLLATKGTLQKFVDDLFETHFSTVHR
gi|14424639|     KNHDHGDQHEGDRGSKMVSEIYLTRLLATKGTLQKFVDDLFETHLSTVHR
gi|10047165|     -------------------------------------------------
```

TABLE 4D-continued

ClustalW Analysis of NOV4

```
                1810       1820       1830       1840       1850
             ....|....|....|....|....|....|....|....|....|....|
NOV4         GSALPLAIKYMFDFLDEQADKHGIHDPHVRHTWKSNCLPLRFEVNIIKNP
gi|13649119| GSALPLAIKYMFDFLDEQADERQISDPDVRHTWKSNCLPLRFEVNVIKNP
gi|3413888|  GSALPLAIKYMFDFLDEQADKHSIHDTDVRHTWKSNCLPLRFEVNVIKNP
gi|2134135|  GSALPLAIKYMFDFLDEQADKHQITDYDVRHTWKSNCLPLRFEVNVIKNP
gi|14424639| GSALPLAIKYMFDFLDEQADKHSIHDTDVRHTWKSNCLPLRFEVNVIKNP
gi|10047165| --------------------------------------------------

1860       1870       1880       1890       1900
             ....|....|....|....|....|....|....|....|....|....|
NOV4         QFVFDIHKNSITDACLSVVAQTFMDSCSTSEHRLGKDSPSNKLLYAKDIP
gi|13649119| QFVFDIHKNSITDACLSVVAQTFMDSCSTSEHRLGKDSPSNKLLYAKDIP
gi|3413888|  QFVFDIHKGSITDACLSVVAQTFMDSCSTSEHRLGKDSPSNKLLYAKDIP
gi|2134135|  QFVFDIHKNSITDACLSVVAQTFMDSCSTSEHRLGKDSPSNKLLYAKDIP
gi|14424639| QFVFDIHKGSITDACLSVVAQTFMDSCSTSEHRLGKDSPSNKLLYAKDIP
gi|10047165| --------------------------------------------------

1910       1920       1930       1940       1950
             ....|....|....|....|....|....|....|....|....|....|
NOV4         YKSWVERYYSDIGKMPAISDQDMKAYLAEQSRKHMNKFNTMSALSEIYS
gi|13649119| YKSWVERYYRDIAKNASISDQDMKAYIVEQSRLHASKFKVKSALEEYYF
gi|3413888|  YKSWVERYYADIAKLPKISDQDMKAYLAEQSRLHAVKFNMKSALEEIYS
gi|2134135|  YKSWVERYYADIAKPVISDQDMKAYLAEQSRLHLSKFNSKSALEEIYS
gi|14424639| YKSWVERYYSDIAKLPKISDQDMKAYLAEQSRLHAVKFNMKSALEEIYS
gi|10047165| --------------------------------------------------

1960       1970       1980       1990
             ....|....|....|....|....|....|....|....|....|.
NOV4         YVGKYSKEKGPLHDKQCGKQKLAYKEQKTTLMSLKSNK
gi|13649119| YVKKYRKEKTALKDASCRKHKLRQKEQKISLKSSKS--
gi|3413888|  YVKKYSKEKGALKDKQARQKLAYKEQKINAMSIKS--
gi|2134135|  YKKKYRKEKTALKDKQARQKLRSKKEQKIDTMAQSS--
gi|14424639| YVKKYSKEKGALKDKQARQKLAYKEQKINAMSIKS--
gi|10047165| --------------------------------------
```

Tables 4E–K list the domain description from DOMAIN analysis results against NOV4. This indicates that the NOV4 sequence has properties similar to those of other proteins known to contain this domain.

TABLE 4E

Domain Analysis of NOV4

```
gnl|Smart|smart00630, Sema, semaphorin domain (SEQ ID NO:76)
CD-Length = 430 residues, 100.0% aligned
Score = 226 bits (575), Expect = 1e-59

Query:    51 FNHLVVDERTGHIYLGAVNRIYKLSSDLKVLVTHETGPDEDNPKCYPPRIVQTCNEPLTT 110
             +|++||   |  +|+||  ||+|  || +|      +|||   +| |
Sbjct:     1 LQNLLLDEDNGTLYVGARNRLYVLSLNLISEAEVKTGPVLSSPDCEECV----SKCKDPP  56

Query:   111 TNNVNKM-LLIDYKENRLIACGS-LYQGICKLLRLEDLFKLGEPYHKKEHYLSGVNESGS 168
             |+ || + ||+||   + |+  ||  +| +|+|+  +| +|    +      +   +
Sbjct:    57 TDCVNFIRLLLDYNADHLLVCGTNAFQPVCRLINLGNLDRL-EVGRESGRGRCPFDPQHN 115

Query:   169 VFGVIVSYSNLDDKLFIATAVD--GKPEYFPTISSRKLTIQSEADGMFAYVFHDEFVASM 226
             |+|        | +|++ |    |        |  +  | +   |
Sbjct:   116 STAVLV-----DGELYVGTVADFSGSDPAIYRSLSVRRLKGT-------SGPSLRTVLYD 163

Query:   227 IKIPSDTFTIIPDFDIYYVYGFSSGNPVYFLTLQPEMVSPPGSTTKEQVYTSKLVRLCKE 286
              + +          +    +||     |   ||+|| +  +   +      |++ |+||
Sbjct:   164 SRWLN---------EPNFVYAFESGDFVYFFFRETAVEDENC----GKAVVSRVARVCKN 210

Query:   287 DTA--------FNSYVEVPIGC---ERSGVEYRLLQAAYLSKAGAVLGRTLGVHPDDDLL 335
             |         +  |+++   +         +    |||||+|   ||+|       ||+|
Sbjct:   211 DVGGPRSLSKKWTSFLKARLECSVPGEFPFYFNELQAAFLLPAGS---------ESDDVL 261

Query:   336 FTVFSKGQKRKMKSLDESALCIFILKQINDRIKERLQSCYRGEGTLDL----AWLKVKDI 391
             + |||        +  ||+| |  ||    |  +|  |
Sbjct:   262 YGVFSTSS----NPIPGSAVCAFSLSDINAVFNEPFKECETGNSQWLPYPRGLVPFPRPG 317

Query:   392 PC-----SSALLTIDDNFCGLDMNAPLGVSDMVRGIPVF--TEDRDRMTSV----IAYVY 440
             |       ||   |             |  + |+|  |+    +||+     +
Sbjct:   318 TCPNTPLSSKDLPDDVLNFIKTHPLMDEVVQPLTGRPLFVKTDSNYLLTSIAVDRVRTDG 377
```

TABLE 4E-continued

Domain Analysis of NOV4

```
Query:   441 KNHSLAFVGTKSGKLKKIRVDCPRGN--ALQYETVQVVDPGPVLRDMAFSKDH 491
             |+++ |+||   |++ |+ +        + ++  | + |  ||| + |+  |
Sbjct:   378 GNYTVLFLGTSDGRILKVVISRSSSSSESVVLEEISVFDPGSPVSDLVLSPKK 430
```

TABLE 4F

Domain Analysis of NOV4 gnl|Pfam|pfam01403, Sema, Sema domain. The Sema domain occurs in semaphorins, which are a large family of secreted and transmembrane proteins, some of which function as repellent signals during axon guidance. Sema domains also occur in the hepatocyte growth factor receptor. (SEQ ID NO:77)
CD-Length = 433 residues, 100.0% aligned
Score = 186 bits (471), Expect = 1e-47

```
Query:    51 FNHLVVDERTGIIYLGAVNRIYKLS----SDLKVLVTHETGPDEDNPKCYPPRIVQTCNE 106
              |  |++||   | +|+|| ||+| |+     |++  |   |    +|
Sbjct:     1 FVTLLLLDEDRGRLYVGARNRVYVLNLEDLSEVLNLKTGWPGSCETCEECNMKGKS----- 55

Query:   107 PLTTTNNVNKMLLIDYKENRLIACGS-LYQGICKLLRLEDLFKLGEPYHKKEEYLSGVNE 165
             |||   |  + +| | +  |   ||+ +| +| |+ ||| |       +          +
Sbjct:    56 PLTECTNFIR-VLQAYNDTHLYVCGTNAFQPVCTLINLGDLFSLDVDNEEDGCGDCPYDP 114

Query:   166 SGSVFGVIVSYSNLDDKLFIATAVDGKPEYFPTISSRKLTKNSEADGMFAYVFHDEFVAS 225
             |+    |+|      +|+   |+|            +      + +  +     |||  +
Sbjct:   115 LGNTTSVLVQ----GGELYSGTVID------FSGRDPSIRRLLGSHDGLRTEFHD---SK 161

Query:   226 MIKIPSDTFTIIPDFDIYYJYGFSSGNFVYFLTLQPEMVSPPGSTTKEQVYTSKLVRLCK 285
              + +|+    +  +|+||+  | + |||     +  +           |++ |+||
Sbjct:   162 WLNLPNFVDS----YPIHYVHSF-SDDKVYFFFRETAVEDSNCKT-----IHSRVARVCK 211

Query:   286 EDTAFNSYVEVPIG---------CERSGVE----YRLLQAAYLSKAGAVLGRTLGVHPDD 332
             |    ||+|+       |    |    + |||+++ ||              |
Sbjct:   212 NDPGGRSYLELNKWTTFLKARLNCSIPGEGTPFYFNELQAAFVLPTGA---------DTD 262

Query:   333 DLLFTVFSKGQKRKMKSLDESALCIPILKQIND--RIKERLQSCYRGEGTLDLAWLKVKD 390
             +|+ ||+    |   ||+| | +||     + ||           + +
Sbjct:   263 PVLYGVFTTSS----NSSAGSAVCAFSMSDINQVFEGPFKHQSPNSKWLPYRGKVPQPRP 318

Query:   391 IPCSSA-LLTIDDNFCGLDMNAPLG--VSDMVRGIPVFTEDRDR-------MTSVIAYVY 440
              | +|  | + +|         ||   | +  +| +|         +  | |
Sbjct:   319 GQCPNASGLNLPDDTLNFIRCHPLMDEVVPPLHNVPLFVGQSGNYRLTSIAVDRVRAGDG 378

Query:   441 KNHSLAFVGTKSGKLKKIRVDGPRGNA-----LQYETVQVV-DPGPVLRDMAFSKD 490
             +  +++ |+||   |++ | +|      ++        +  |  |  |||  + ||+
Sbjct:   379 QIYTVLFLGTDDGRVLK-QVVLSRSSSASYLVVVLEESLVFPDGEPVQRMVISSKN 433
```

TABLE 4G

Domain Analysis of NOV4 gnl|Pfam|pfam01833, TIG, IPT/TIG domain. This family consists of a domain that has an immunoglobulin like fold. These domains are found in cell surface receptors such as Met and Ron as well as in intracellular transcription factors where it is involved in DNA binding. CAUTION: This family does not currently recognise a significant number of members. (SEQ ID NO:78)
CD-Length = 85 residues, 98.8% aligned
Score 69.7 bits (169), Expect = 1e-12

```
Query:   955 TLSDLKPSRGPMSGGTQVTITGTNLNAGSNVVVMFGKQPCLFHRRSPSYIVCNTTSSDEV 1014
             ++ + || ||+|||++|||||+| +| ++ | ||    |   + | |||
Sbjct:     2 VITSISPSSGPLSGGTEITITGSNLGSEDIKVTFGGTECDVVSQEASQIVCKTPPYANG 61

Query:  1015 LENKVSVQVDRA-KIHQDLVFQYV 1037
              |+| +|    + | ||
Sbjct:    62 GPQPVTVSLDGGGLSSSPVTFTYV 85
```

TABLE 4H

Domain Analysis of NOV4 gnl|pfam|pfam01833, TIG, IPT/TIG domain. This family consists of a
domain that has an immunoglobulin like fold. These domains are found
in cell surface receptors such as Met and Ron as well as in
intracellular transcription factors where it is involved in DNA
binding. CAUTION: This family does not currently recognise a
significant number of members. (SEQ ID NO:79)
CD-Length = 85 residues, 91.8% aligned
Score = 54.3 bits (129), Expect = 6e-08

```
Query:  858 PRITEIIPVTGPREGGTKVTIRGENLGLEFRDIASHVKVAGVECSPLVDGYIPAEQIVCE  917
            | ||  | +||   |||++||  |||       |  ||| +        ||||+
Sbjct:    1 PVITSISPSSGPLSGGTEITITGSNLGSGED---IKVTFGGTECDVVSQEA---SQIVCK   54

Query:  918 MGE-AKPSQHAGFVEICVAVCRPE  940
            |         |         | +
Sbjct:   55 TPPYANCGPQPVTVSLDCGGLSSS   78
```

TABLE 4I

Domain Analysis of NOV4 gnl|Pfam|pfam01833, TIG, IPT/TIG domain. This family consists of a
domain that has an immunoglobulin like fold. These domains are found
in cell surface receptors such as Met and Ron as well as in
intracellular transcription factors where it is involved in DNA
binding. CAUTION: This family does not currently recognise a
significant number of members. (SEQ ID NO:80)
CD-Length = 85 residues, 100.0% aligned
Score = 45.8 bits (107), Expect 2e-05

```
Query: 1040 PTIVRIEPEWSIVSGNTPIAVWGTHLDLIQNPQIRAKHGGKEEINICEVLN--ATEMTCQ  1097
            | |  |    +|| |  | +  | ++|   ++  |+  ||  |     |+|++  |+++  |+
Sbjct:    1 PVITSISPSSGPLSGGTEITITGSNLGSGED--IKVTFGGTE----CDVVSQEASQIVCK   54

Query: 1098 APALALGPDEQSDLTERPEEFGFILDNVQSLLILNKTNFTYY  1139
            | |          |+    ||     |  +   |||
Sbjct:   55 TPPYA---------NGGPQPVTVSLDGGG--LSSSPVTFTYV   85
```

TABLE 4J

Domain Analysis of NOV4 gnl|Smart|smart00423, PSI, domain found in Plexins, Semaphorins
and Integrins (SEQ ID NO:81)
CD-Length = 47 residues, 100.0% aligned
Score = 46.6 bits (109), Expect = 1e-05

```
Query:  655 NCSVHNSCLSCVESPYR-CHWCKYRHVCTHDPKTCSFQEGRVKLPEDCP  702
            || + ||  |+ +      |  | + ||         |         ||
Sbjct:    1 RCSAYTSCSECLLARDPYCAWCSSQGRCTSGE-RCDSLRQNW-SSGQCP   47
```

TABLE 4K

Domain Analysis of NOV4 gnl|Smart|smart00429, IPT, ig-like, plexins, transcription factors
(SEQ ID NO:82)
CD-Length = 93 residues, 100.0% aligned
Score = 57.8 bits (138), Expect = 6e-09

```
Query: 1039 DPTIVRIEPEWSIVSGNTPIAVWGTHLDLIQNPQIRAKHGGKEHINICEVLNATEMTCQA    1098
            || | ||    +|| |  | + +||  |    +    |    +   ++ | + |+
Sbjct:    1 DPVITRISPNSGPLSGGTRITLCGKNLDSISVVFVEVGVGEVPCTFLPSDVSQTAIVCKT      60

Query: 1099 PALALGPDHQSDLTERPEEFGFILDNVQSLLILNKTNFTYY  1139
            |      |          ||   |           +  |||
Sbjct:   61 PPYHNIP----GSVPVRVEVGLRNGGVPGE----PSPFTYV   93
```

Semaphorins are a large family of secreted or cell-bound signals, known to guide axons in developing nervous tissue. They are expressed in a variety of adult and embryonic tissues and are thought to have a broader spectrum of functions. Recent evidence suggests that semaphorins and their receptors play a key role in the control of cellular interactions, most likely in cell-cell repulsion (Tamagnone and Comoglio. Trends Cell Biol 2000 September;10(9):377–83.). A subset of semaphorins interacts with neuropilins—cell-surface molecules lacking a signalling-competent cytoplasmic domain. Another large family of transmembrane molecules, namely plexins, bind specifically to semaphorins. Thus plexins, alone, or in association with neuropilins, behave as fully functional semaphorin receptors. The intracellular responses elicited by plexins are unknown, but their large cytoplasmic moiety, containing the strikingly conserved sex-plexin (SP) domain, is likely to trigger novel signal-transduction pathways.

Chemorepulsive signals such as the semaphorins play an essential role in navigating axons over large distances in the developing nervous system. The effects of one of these repulsive cues, semaphorin 3A (Sema3A), are mediated by the membrane protein neuropilin-1 (Npn-1). Recent work has shown that neuropilin-1 is essential but not sufficient to form functional Sema3A receptors and indicates that additional components are required to transduce signals from the cell surface to the cytoskeleton (Rohm et al. *Mech Dev* 2000 May;93(1–2):95–104). It has been shown that members of the plexin family interact with the neuropilins and act as co-receptors for Sema3A. Neuropilin/plexin interaction restricts the binding specificity of neuropilin-1 and allows the receptor complex to discriminate between two different semaphorins. Deletion of the highly conserved cytoplasmic domain of Plexin-A1 or -A2 creates a dominant negative Sema3A receptor that renders sensory axons resistant to the repulsive effects of Sema3A when expressed in sensory ganglia. These data suggest that functional semaphorin receptors contain plexins as signal-transducing and neuropilins as ligand-binding subunits.

Class 1 and 3 semaphorins repulse axons but bind to different cell surface proteins. Two known semaphorin-binding proteins, plexin 1 (Plex 1) and neuropilin-1 (NP-1), form a stable complex (Strittmatter. Cell 1999 October 1;99(1):59–69.). Plex 1 alone does not bind semaphorin-3A (Sema3A), but the NP-1/Plex 1 complex has a higher affinity for Sema3A than does NP-1 alone. While Sema3A binding to NP-1 does not alter normeuronal cell morphology, Sema3A interaction with NP-1/Plex 1 complexes induces adherent cells to round up. Expression of a dominant-negative Plex 1 in sensory neurons blocks Sema3A-induced growth cone collapse. Sema3A treatment leads to the redistribution of growth cone NP-1 and plexin into clusters. Thus, physiologic Sema3A receptors consist of NP-1/plexin complexes.

As mentioned previously, the semaphorin family of molecules contains members known to deliver guidance cues to migrating axons during development. Semaphorins also have been identified on the surface of hematopoietic cells and, interestingly, in the genomes of certain lytic viruses. Recent studies indicate that semaphorins bind with high affinity to at least two different receptor families and are biologically active on immune cells as well as neuronal cells (Spriggs. Curr Opin Immunol 1999 August;11(4):387–91.).

The mammalian olfactory system is capable of discriminating among a large variety of odor molecules and is therefore essential for the identification of food, enemies and mating partners. The assembly and maintenance of olfactory connectivity have been shown to depend on the combinatorial actions of a variety of molecular signals, including extracellular matrix, cell adhesion and odorant receptor molecules (Pasterkamp et al. Cell Mol Biol 1999 September;45(6):763–79). Recent studies have identified semaphorins and their receptors as putative molecular cues involved in olfactory pathfinding, plasticity and regeneration. Neuropilins were shown to serve as receptors for secreted class 3 semaphorins, whereas members of the plexin family are receptors for class 1 and V (viral) semaphorins.

In Drosophila, plexin A is a functional receptor for semaphorin-1 a. The human plexin gene family comprises at least nine members in four subfamilies (Goodman et al. Cell 1999 Oct. 1;99(1):71–80.). Plexin-B1 is a receptor for the transmembrane semaphorin Sema4D (CD100), and plexin-C1 is a receptor for the GPI-anchored semaphorin Sema7A (Sema-K1). Secreted (class 3) semaphorins do not bind directly to plexins, but rather plexins associate with neuropilins, coreceptors for these semaphorins. Plexins are widely expressed: in neurons, the expression of a truncated plexin-A1 protein blocks axon repulsion by Sema3A. The cytoplasmic domain of plexins associates with a tyrosine kinase activity. Plexins may also act as ligands mediating repulsion in epithelial cells in vitro. Plexins are receptors for multiple (and perhaps all) classes of semaphorins, either alone or in combination with neuropilins, and trigger a novel signal transduction pathway controlling cell repulsion.

Plexin is a type I membrane protein which was identified in *Xenopus* nervous system by hybridoma technique. Molecular cloning studies demonstrated that the extracellular segment of the plexin protein possesses three internal repeats of cysteine cluster which are homologous to the cysteine-rich domain of the c-met proto-oncogene protein product. A cell aggregation test revealed that the plexin protein mediated cell adhesion via a homophilic binding mechanism, in the presence of calcium ions (Fujisawa et al. Dev Neurosci 1997;19(1):101–5.). Plexin was expressed in the neuronal elements composing particular neuron circuits in *Xenopus* CNS and PNS. These findings indicate that plexin is a new member of the Ca(2+)-dependent cell adhesion molecules, and suggest that the molecule plays an important role in neuronal cell contact and neuron network formation.

Plexin (previously referred to as B2) is a neuronal cell surface molecule that has been identified in *Xenopus*. cDNA cloning reveals that plexin has no homology to known neuronal cell surface molecules but possesses, in its extracellular segment, three internal repeats of cysteine clusters that are homologous to the cysteine-rich domain of the c-met proto-oncogene protein product. The exogenous plexin proteins expressed on the surfaces of L cells by cDNA transfection mediate cell adhesion via a homophilic binding mechanism, under the presence of calcium ions (Fujisawa. Neuron 1995 June;14(6):1189–99.). Plexin is expressed in the receptors and neurons of particular sensory systems. These findings indicate that plexin is a novel calcium-dependent cell adhesion molecule and suggest its involvement in specific neuronal cell interaction and/or contact.

The disclosed NOV4 nucleic acid of the invention encoding a Plexin-like protein includes the nucleic acid whose sequence is provided in Table 4A or a fragment thereof. The invention also includes a mutant or variant nucleic acid any of whose bases may be changed from the corresponding base shown in Table 4A while still encoding a protein that maintains its Plexin-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 29% percent of the bases may be so changed.

The disclosed NOV4 protein of the invention includes the Plexin-like protein whose sequence is provided in Table 4B. The invention also includes a mutant or variant protein any of whose residues may be changed from the corresponding residue shown in Table 4B while still encoding a protein that maintains its Plexin-like activities and physiological functions, or a functional fragment thereof. In the mutant or variant protein, up to about 40% percent of the residues may be so changed.

The protein similarity information, expression pattern, and map location for the Plexin-like protein and nucleic acid (NOV4) disclosed herein suggest that this NOV4 protein may have important structural and/or physiological functions characteristic of the Plexin family. Therefore, the NOV4 nucleic acids and proteins of the invention are useful in potential diagnostic and therapeutic applications. These include serving as a specific or selective nucleic acid or protein diagnostic and/or prognostic marker, wherein the presence or amount of the nucleic acid or the protein are to be assessed, as well as potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), and (v) a composition promoting tissue regeneration in vitro and in vivo.

The NOV4 nucleic acids and proteins of the invention are useful in potential diagnostic and therapeutic applications implicated in various diseases and disorders described below. For example, the compositions of the present invention will have efficacy for treatment of patients suffering from Von Hippel-Lindau (VHL) syndrome, Alzheimer's disease, Stroke, Tuberous sclerosis, hypercalceimia, Parkinson's disease, Huntington's disease, Cerebral palsy, Epilepsy, Lesch-Nyhan syndrome, Multiple sclerosis, Ataxia-telangiectasia, Leukodystrophies, Behavioral disorders, Addiction, Anxiety, Pain, Neurodegeneration, Systemic lupus erythematosus, Autoimmune disease, Asthma, Emphysema, Scleroderma, allergy, ARDS, Obesity, Metabolic Dysregulation, Infertility, and/or other pathologies. The NOV4 nucleic acids, or fragments thereof, may further be useful in diagnostic applications, wherein the presence or amount of the nucleic acid or the protein are to be assessed.

NOV4 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example, the disclosed NOV4 protein has multiple hydrophilic regions, each of which can be used as an immunogen. In one embodiment, a contemplated NOV4 epitope is from about amino acids 20 to 30. In another embodiment, a NOV4 epitope is from about amino acids 180 to 190. In additional embodiments, NOV4 epitopes are from about amino acids 180 to 270, from about amino acids 310 to 320, from about amino acids 380 to 390, from about amino acids 400 to 405, from about amino acids 420 to 550, from about amino acids 620 to 630, from about amino acids 650 to 700, from about amino acids 790 to 900, from about amino acids 1040 to 1050, from about amino acids 1100 to 1120, from about amino acids 1220 to 1240, from about amino acids 1410 to 1420, from about amino acids 1450 to 1500, from about amino acids 1580 to 1600, from about amino acids 1620 to 1650, from about amino acids 1720 to 1730 and from about amino acids 1800 to 1900. These novel proteins can be used in assay systems for functional analysis of various human disorders, which will help in understanding of pathology of the disease and development of new drug targets for various disorders.

NOV5

A disclosed NOV5 nucleic acid of 1535 nucleotides (also referred to as GMAC027612_A) encoding a novel dopamine receptor-like protein is shown in Table 5A. An open reading frame was identified beginning with an ATG initiation codon at nucleotides 7–9 and ending with a TAA codon at nucleotides 1447–1449. A putative untranslated region upstream from the initiation codon and downstream from the termination codon is underlined in Table 5A, and the start and stop codons are in bold letters.

TABLE 5A

NOV5 Nucleotide Sequence (SEQ ID NO:14)

CCCGAAATGCTGCCGCCAACGAGCAACGACACCGCGTACCCGGGGCAGTTAGCGCTATACCA

GCAGCTGGCGCAGGGGAATGCCGTGGGGGGCTCGGCGGGGGCACCGCCACTGGGGCCCGTGC

AGGTGGTCACCGCCTGCCTGCTGACCCTACTCGTCATCTGGACCTTGCTGGGCAACGTGCTG

GTGTCCGCAGCCATCGTGTGGAGCCGCCACCTGCGCGCCAAGATGACCAACGTCTTCATCGT

GTCTCTACCTGTGTCAGACCTCTTCGTGGCGCTGCTGGTCATGTCCTGGAAGCCAGTCGCCG

AGGTGGCCGGTTACTGGCCCTTTGAAGCGTTCTGCGACGTCTGGGTGGCCTTCGACATCATG

TGCTCCACCGCCTCCATCCTGAACCTGTGCGTCATCAGCGTGGCCCGCTACTGGGCCATCTC

CAGGCCCTTCCGCTACGAGCGCAAGATGACCCAGCGCATGGCCTTGGTCATGGTCCGCCCGG

TABLE 5A-continued

NOV5 Nucleotide Sequence (SEQ ID NO:14)

```
CCTGGACCTTGTCCAGCCTCATCTCCTTCATTCCGGTCCAGCTCAACTGGCACAGGGACCAG
GCGGTCTCTTGGGGTGGGCTGGACCTGCCAAACAACCTGGCCAACTGGACGCCCTGGGAGGA
GGCCGTTTGGGAGCCCGACGTGAGGGCAGAGAACTGTGACTCCAGCCTGAATCGAACCTACG
CCATCCCTTCCTCGCTCATCAGCTTCTACATCCCCATGGCCATCATGATCGTGACCTACACG
CGCATCTACCGCATCGCCCAGGTGCAGATCCGCAGGATTTCCTCCCTGGAGAGCGCCGCAGA
GCACGTGCAGAGCTGCCGGAGCAGCGCAGGCTGCACGCCCGACACCAGCCTGCGGTTTTCCA
TCAAGAAGGAGACCGAGGTTCTCAAGACCCTGTCGGTGATCATGGGGGTCTTCGTGTGTTGC
TGGCTGCCCTTCTTCATCCTTAACTGCATGGTTCCTTTCTGCAGTGGACACCCCAAAGGCCC
TCCGGCCGGCTTCCCCTGCGTCAGTGAGACCACATTCGATGTCTTCATCTGGTTCTGCTGGG
CCAACTCCTCACTCAACCCAGTCCCCAGTCACTATGCCTTCAACGCCGACTTCCGGAAGGTG
TTTGCCCAGCTGCTGGGGTGCAGCCACGTCTGCTCCCGCACGCCGGTGGAGACGGTGAACAT
CAGCAATGAGCTCATCTCCTACAACCAAGACACGGTCTTCCACAAGGAAATCGCAGCTGCCT
ACATCCACATGATGCCCAACGCCATTCCCCCCGGGGACCGGGAGGTGGACAACGATGAGGAG
GAGGAGAGTCCTTTCGATCGCATGTCCCAGATCTATCAGACATCCCCAGATGGTGACCATGT
TGCAGAGTCTGTCTGGGACCTCGACTGCGAGGGGGAGATTTCTTTAGACAAAATAACACCTT
TCACCCCAAATGGATTCCATTAAACTGCATTAAGAAACCCCCTCATGGATCTGCATAACCAC
ACAGACATTGACAAGCATGCACACACAAGCAAATACATGGCTTTCCA
```

The NOV5 nucleic acid was identified on chromosome 4 and has 1494 of 1536 bases (97%) identical to a Human dopamine receptor (D5) transcribed pseudogene mRNA from Homo sapiens (GENBANK-ID: M75867) (E=0.0).

A disclosed NOV5 polypeptide (SEQ ID NO:15) encoded by SEQ ID NO:14 is 480 amino acid residues and is presented using the one-letter code in Table 5B. Signal P, Psort and/or Hydropathy results predict that NOV5 has a signal peptide and is likely to be localized in the plasma membrane with a certainty of 0.6400. In other embodiments, NOV5 may also be localized to the Golgi body with acertainty of 0.4600, the endoplasmic reticulum (membrane) with a certainty of 0.3700, or the endoplasmic reticulum (lumen) with a certainty of 0.1000.

The most likely cleavage site for a NOV5 peptide is between amino acids 63 and 64, at: VSA-AI.

The disclosed NOV5 amino acid sequence has 437 of 480 amino acid residues (91%) identical to, and 446 of 480 amino acid residues (92%) similar to, the 477 amino acid residue DOPAMINE RECEPTOR (D(5) DOPAMINE RECEPTOR) (DIBETA DOPAMINE RECEPTOR) protein from Homo sapiens (Human) (P21918) (E=$3.3e^{-237}$).

NOV5 is expressed in at least the following tissues: fetal heart, pooled human melanocyte, fetal heart, and pregnant uterus. TaqMan data for NOV5 is shown below in Example 2.

NOV5 also has homology to the amino acid sequences shown in the BLASTP data listed in Table 5C.

TABLE 5B

Encoded NOV5 protein sequence (SEQ ID NO:15)

```
MLPPRSNDTAYPGQLALYQQLAQGNAVGGSAGAPPLGPVQVVTACLLTLLVIWTLLGNVLVSAAIVWSRHLR
AKMTNVFIVSLPVSDLFVALLVMSWKAVAEVAGYWPFEAFCDVWVAFDIMCSTASILNLCVISVARYWAISR
PFRYERKMTQRMALVMVRPAWTLSSLISFIPVQLNWHRDQAVSWGGLDLPNNLANWTPWEEAVWEPDVRAEN
CDSSLNRTYAIPSSLISFYIPMAIMIVTYTRIYRIAQVQIRRISSLERAAEHVQSCRSSAGCTPDTSLRFSI
KKETEVLKTLSVIMGVFVCCWLPFFILNCMVPFCSGHPKGPPAGFPCVSETTFDVFIWFCWANSSLNPVPSH
YAFNADFRKVFAQLLGCSHVCSRTPVETVNISNELISYNQDTVFHKEIAAAYIHMMPNAIPPGDREVDNDEE
EESPFDRMSQIYQTSPDGDHVAESVWELDCEGEISLDKITPFTPNGFH
```

TABLE 5C

BLAST results for NOV5

| Gene Index/Identifier | Protein/Organism | Length (aa) | Identity (%) | Positives (%) | Expect |
|---|---|---|---|---|---|
| gi\|4503391\|ref\|NP_000789.1\| | dopamine receptor D5; Dopamine receptor D1B [Homo sapiens] | 477 | 437/480 (91%) | 446/480 (92%) | 0.0 |
| gi\|6978781\|ref\|NP_036900.1\| | D(1B) DOPAMINE RECEPTOR (D(5) DOPAMINE RECEPTOR) | 475 | 376/480 (78%) | 403/480 (83%) | 0.0 |
| gi\|1169230\|sp\|P42290\|DBDR_XENLA | D(1B) DOPAMINE RECEPTOR (D(5) DOPAMINE RECEPTOR) | 457 | 299/145 (67%) | 341/445 (76%) | e-158 |
| gi\|1362719\|pir\|\|B55886 | dopamine receptor D1B - chicken | 486 | 321/483 (66%) | 353/483 (72%) | e-157 |
| gi\|1518040\|gb\|AAC60070.1\| | dopamine D1B receptor [Anguilla anguilla] | 458 | 297/446 (66%) | 346/446 (76%) | e-154 |

The homology of these sequences is shown graphically in the ClustalW analysis shown in Table 5D.

TABLE 5D

Clustal W Sequence Alignment

1) NOV5 (SEQ ID NO:15)
2) gi|4503391|ref|NP_000789.1| dopamine receptor D5; Dopamine receptor D1B [Homo sapiens] (SEQ ID NO:47)
3) gi|6978781|ref|NP_036900.1| D(1B) DOPAMINE RECEPTOR (D(5) DOPAMINE RECEPTOR) (SEQ ID NO:48)
4) gi|1169230|sp|P42290|DBDR_XENLA D(1B) DOPAMINE RECEPTOR (D(5) DOPAMINE RECEPTOR (SEQ ID NO:49)
5) gi|1362719|pir||B55886 dopamine receptor D1B - chicken (SEQ ID NO:50)
6) gi|1518040|gb AAC60070.1| dopamine D1B receptor [Anguilla anguilla] (SEQ ID NO:51)

```
                        10         20         30         40         50
                 ....|....|....|....|....|....|....|....|....|....|
NOV5             MLPPRSNDKKYP-GKLALYQQLAQGNAVGCKAGAPPLG--PVQVVTACLL
gi|4503391       MLPPGSNGTKYP-GKFALYQQLAQGNAVGCSAGAPPLG--PSQVVTACLL
gi|6978781       MLPPGRKRKQP-AKLGLQRQLAQVKAPAGKA--TPLG--PAQVVTGSLL
gi|1169230       MYQPFQKLDK--DQVASWQSPEMLMNKSVSRESQRRKELVAGQKVTGSLL
gi|1362719       ------MLRG---GKSPLPPP---AGPPGCKRGQAGAG--AAQVAAGSLL
gi|1518040       MGSPAKYLKVHETQSVPFFIGEIMWNTSESKEKTDGKKELIVKTVTGCLL 60         70         80         90        100
                 ....|....|....|....|....|....|....|....|....|....|
NOV5             KLIKWTLLGNVLVSAAIVWSRHLRKKKINKFIVSLPVSDLFVALLVMSW
gi|4503391       KLLIKWTLLGNVLVCAAIVRSRHLRANKINKFIVSLAVSDLFVALLVMPW
gi|6978781       KLLIKWTLLGNVLVCAAIVRSRHLRKKKTNIFIVSLAVSDLFVALLVMPW
gi|1169230       LLLIEWTLFGNKLVCTAKKRFRHLRKKKTNIFIVSLAVSDLLVALLVMPW
gi|1362719       ALLIKWTLFGNVLVCAAIVRYRHLRKKKTNIFIVSLAVSDLLVAKLVMPW
gi|1518040       KLLIKWTLLGNKLVCKAKKKFRHLRTKKTNIFIVSLAVSDLFVAKLVMPW 110        120        130        140        150
                 ....|....|....|....|....|....|....|....|....|....|
NOV5             KAVAEVAGYWPFEAFCDKWVAFDIMCSTASILNLCVISVARYWAISRPFR
gi|4503391       KAVAEVAGYWPFGAFCDKWVAFDIMCSTASILNLCVISVDRYWAISRPFR
gi|6978781       KAVAEVAGYWPFGTFCDKWVAFDIMCSTASILNLCKISVDRYWAISRPFR
gi|1169230       KAVAEVAGKWPFGAFCDKWVAFDIMCSTASILNLCVISVDRYWAISSPFR
gi|1362719       KAVAEVAGYWPFGAFQKWVAFDIMCSTASILNLCVISVDRYWAISSPFR
gi|1518040       KAVAEVAGYWPFGPFCKKWVAFDIMCSTASILNLCKISVDRYWAISSPFR
```

TABLE 5D-continued

Clustal W Sequence Alignment

```
                 160        170        180        190        200
              ....|....|....|....|....|....|....|....|....|....|
NOV5          YERKMTQRIALVMKRPAWTLSSLISFIPVQLNWHRDQAVSWGG----L--
gi|4503391|   YERKMTQRIALVMGKAWTLSSLISFIPVQLNWHRDQAASWGG----L--
gi|6978781|   YERKMTQRIALVMGKAWTLSSLISFIPVQLSWHKAGSQG--------
gi|1169230|   YERKMTQRIALEMISTAWALSSLISFIPVQLSWHKSK-----------
gi|1362719|   YERKMTQRIALVMGVAWALSSLISFIPVQLNWHGGDAKTAAAAGDIED
gi|1518040|   YERKMTQRIAFVMKSVTWTLSKLISFIPVQLNWHKAS-----------

210        220        230        240        250
              ....|....|....|....|....|....|....|....|....|....|
NOV5          ----------------------D---------LPNNLANWIPNEEAVWEPD
gi|4503391|   ----------------------D---------LPNNLANWIPKEEDFWEPD
gi|6978781|   --------------------------------QEGLLSNGLPWEEG-WELE
gi|1169230|   --------------------------------TEDHLLSNHSTG------
gi|1362719|   GFDTGWEAAGAFTTWAEDMSTTWVALAAMTOSEGTSGKNNTVPGP-----
gi|1518040|   --------------------------------DEEVWINGISKGEK----

260        270        280        290        300
              ....|....|....|....|....|....|....|....|....|....|
NOV5          VRKENCDSSLNRTYAIPSSLISFYIPKAIMIVTYTRIYRIAQVQIRRISS
gi|4503391|   VRKENCDSSLNRTYAISSSLISFYIPVAIMIVTYTRIYRIAQVQIRRISS
gi|6978781|   GRTENCDSSLNRTYAISSSLISFYIPVAIMIVTYTRIYRIAQVQIRRISS
gi|1169230|   ----NCDSSLNRTYAISSSLISFYIPVAIMIVTYTRIYRIAQKQIKRISK
gi|1362719|   --SEKCDSSLNRTYAISSSLISFYIPVAIMIVTYTRIYRIAQVQIRRISS
gi|1518040|   --KENCDSSLNREYAISSSLISFYIPVAIMIVTYTRIYRIAQKQIRRISS 310        320        330        340        350
              ....|....|....|....|....|....|....|....|....|....|
NOV5          LERAAEHVQSCRSKAGCT----PDTSLRFSIKKETKVLKTLSKIMGVFVC
gi|4503391|   LERAAEHAQSCRSKAACA----PDTSLRASIKKETKVLKTLSKIMGVFVC
gi|6978781|   LERAAEHAQSCRSRGAYE----PDPSLRASIKKETKVFKTLSKIMGVFVC
gi|1169230|   LERAAEHAQSCRSKRVDSCSRHHQTSLRTSIKKETKVLKTLSKIMGVFVC
gi|1362719|   LERAAEHAQSCRCNHVDC----PDTSLKSSIKKETKVLKTLSKIMGVFVC
gi|1518040|   LERAAEHAQSCRTKRLEC---QHHNKLKTSIKKETKVFKTLSKIMGVFVC 360        370        380        390        400
              ....|....|....|....|....|....|....|....|....|....|
NOV5          CWLPFFILNCMVPFCS-GHPKGPPAGFPCVSETTFDVFVWFCWANSSLNP
gi|4503391|   CWLPFFILNCMVPFCS-GHPEGPPAGFPCVSETTFDKFVWFGWANSSLNP
gi|6978781|   CWLPFFILNCMVPFCSSGDAEGKPKTGFPCVSETTFDKFVWFGWANSSLNP
gi|1169230|   CWLPFFILNCMVPFCD-GHEGHPQAGLPCVSETTFDKFVWFGWANSSLNP
gi|1362719|   CWLPFFILNCMVPFCE-GHPSDPRAGLPCVSETTIKFVWFGWANSSLNP
gi|1518040|   CWLPFFILNCKVPFCD-GHPTDHTAGLPCVSKTTFDKFVWFGWTNSSLNP 410        420        430        440        450
              ....|....|....|....|....|....|....|....|....|....|
NOV5          KPSHYAFNADFRKVFAQLLGCSHVCSRTPVETVNISNELISYNQDTVFHK
gi|4503391|   I--IYAFNADFQKVFAQLLGCSHFCSRTPVETVNISNELISYNQDIVFHK
gi|6978781|   I--IYAFNADFRKVFAQLLGCSHFCFRTPVKTVNISNELISYNQDTVFHK
gi|1169230|   I--IYAFNADFRKVFKSLLGCGHKCSTTPVETVNISNELISYNQDTVFHK
gi|1362719|   I--IYAFNADFRKVFSNLLGCGQFCSSTPVETVNISNELISKQDT-FHK
gi|1518040|   I--IYAFNADFRKAFASLLGCRKFCSRTPVETVNISNELKSYNQDTVFHK 460        470        480        490        500
              ....|....|....|....|....|....|....|....|....|....|
NOV5          EIAAAYKVKPNAIPPGDRKVDKDEEKESPFDRMSQIYQLNPDGQHVAKS
gi|4503391|   EIAAAYKVKPNAVTPGNRKVDKDEEK-GPFDRMSQIYQLKPDGPVAKS
gi|6978781|   EIATAYVKMIPNAVSSGDRKVGKEEEK-GPFDHMSQISPTKRPDGEAAKS
gi|1169230|   EIVTAYVKMIPNVV-----KCIKDNKK--AFDHMSQISQLKAENSATKS
gi|1362719|   EIVTAYVKMIPNVV-----KCEKRED--PFDRMSQISP---DPKATKS
gi|1518040|   EIVTAYVKMIPNVV-----KVDKDNPK--TFDRKSQFSH---KNKEATKS 510        520
              ....|....|....|....|....|
NOV5          VWELDC-EGEISLDKITPFTPNGFH---
gi|4503391|   VWELDC-EGEISLDKITPFTPNGFH---
gi|6978781|   VWELDC-EEEKSLGKISPLTPNCFDKTA
gi|1169230|   KCELDS-EVKSLHKITPSMSNGIH---
gi|1362719|   VCELDC-EGEISLGKITPFTPNGLH---
gi|1518040|   VCKLDDCEAKICLDKKAPFTPNGLH---
```

Tables 5E list the domain description from DOMAIN analysis results against NOV5. This indicates that the NOV5 sequence has properties similar to those of other proteins known to contain this domain.

are indications of evolutionary relationship, but between which there is no statistically significant similarity in sequence. The currently known clan members include the rhodopsin-like GPCRs, the secretin-like GPCRs, the cAMP

TABLE 5E

Domain Analysis of NOV5

```
gnl|Pfam|pfam00001, 7tm_1, 7 transmembrane receptor (rhodopsin
family). (SEQ ID NO:83)
CD-Length = 254 residues, 99.2% aligned
Score = 188 bits (478), Expect = 5e-49

Query:   57 GNVLVSAAIVWSRHLRAKMTNVFIVSLPVSDLFVALLVMSWKAVAEVAGYWPF EAFCDV 115
            ||+||    |+ ++ ||   ||+|+++| |+||    | +  |    |  |  | +| | +
Sbjct:    1 GNLLVILVILRTKKLR TPTNIFLLNLAVADLLFLLTLPPWALYYLVGGDWVFGDALCKL  59

Query:  116 WVAFDIMCSTASILNLCVISVARYWAISRPERYERKMTQRMALVMVRPAWTLSSLISFIP 175
              |  ++    |||| |    ||+ || ||   ||| |    |   ++    | |+ |+|   |
Sbjct:   60 VGALFVVNGYASILLLTAISIDRYLAIVHPLRYRRIRTPRRAKVLILLVWVLALLLSLPP 119

Query:  176 VQLNWHRDQAVSWGGLDLPNNLANWTPWEEAVWEPDVRAENCDSSLNRTYAIPSSLISFY 235
              +  +|  |               |   + +             |+ |+|  +  |+|+ |
Sbjct:  120 LLFSWLR------------TVEEGNTTVCLIDFPEE--------SVKRSYVLLSTLVGFV 159

Query:  236 IPMAIMIVTYTRIYRIAQVQIRRISSLERAAEHVQSCRSSAGCTPDTSLRFSIKKETEVL 295
             +|+ +++|  ||||  | + +  |                              ||+      | +
Sbjct:  160 LPLLVILVCYTRILRTLRKRARSQ--------------------RSLKRRSSSERKAA 197

Query:  296 KTLSVIMGVFVCCWLPFFILNCMVPFCSGHPKGPPAGFPCVSETTFDVFIWFCWANSSLN 355
            |  |  |++  |||  ||||+  |+  +    |            |   |    + +|   + || ||
Sbjct:  198 KMLLVVVVVFVLCWLPYHIVLLLDSLC-------LLSIWRVLPTALLITLWLAYVNSCLN 250

Query:  356 PV 357
            |+
Sbjct:  251 PI 252
```

NOV5 also has homology to proteins found in the patp patent database as shown in Table 5E.

receptors, the fungal mating pheromone receptors, and the metabotropic glutamate receptor family.

TABLE 5E

BLAST results for NOV5 for patp Database

| Gene Index/ Identifier | Protein/Organism | Length (aa) | Identity (%) | Positives (%) | Expect |
| --- | --- | --- | --- | --- | --- |
| patp: AAR22546 | Truncated Dopamine D1 receptor encoded by pseudogene clone GL-39 Homo sapiens | 479 | 453/480 (94%) | 460/480 (95%) | 1.7e-244 |
| patp: AAR79381 | Dopamine receptor D5 - Homo sapiens | 477 | 436/480 (90%) | 445/480 (92%) | 2.0e-236 |

The rhodopsin-like GPCRs themselves represent a widespread protein family that includes hormone, neurotransmitter and light receptors, all of which transduce extracellular signals through interaction with guanine nucleotide-binding (G) proteins. Although their activating ligands vary widely in structure and character, the amino acid sequences of the receptors are very similar and are believed to adopt a common structural framework comprising 7 transmembrane (TM) helices.

G-protein-coupled receptors (GPCRs) constitute a vast protein family that encompasses a wide range of functions (including various autocrine, paracrine and endocrine processes). They show considerable diversity at the sequence level, on the basis of which they can be separated into distinct groups. The term clan is used to describe the GPCRs, as they embrace a group of families for which there The diverse physiologic actions of dopamine are mediated by its interaction with 2 types of G protein-coupled receptor, D1 and D2, which stimulate and inhibit, respectively, the enzyme adenylyl cyclase. Three groups reported the cloning of the D1 dopamine receptor gene (Dearry et al., 1990; Zhou et al., 1990; Sunahara et al., 1990). The gene encodes a protein of 446 amino acids having a predicted relative molecular mass of 49,300 and a transmembrane topology similar to that of other G protein-coupled receptors. Northern blot analysis and in situ hybridization showed that the mRNA for this receptor is most abundant in caudate, nucleus accumbens and olfactory tubercle, with little or no mRNA detectable in substantia nigra, liver, kidney, or heart (Dearry et al., 1990). Sunahara et al. (1990) reported that the DRD1 gene is intronless and, by Southern blot hybridization to DNAs from a hybrid cell panel, they mapped the gene to chromosome 5. Family linkage studies confirmed this assignment and suggested that it is in the same general region as the gene for glucocorticoid receptor and D5S22, a marker about 12 cM from GRL. This places it in the 5q31–q34 region near the structurally homologous genes for beta-2-adrenergic receptor and alpha-1-adrenergic Teceptor. Using pulsed field gel electrophoresis and a range of different restriction enzyme digests, Boultwood et al. (1991) established that GRL and DRD1 are on the same 300-kb genomic DNA fragment. Grandy et al. (1990) used the recently cloned DRD1 gene to map the locus to chromosome 5 in rodent-human somatic cell hybrids. Fluorescence in situ hybridization refined the localization to 5q35.1. A 2-allele EcoRI RFLP associated with DRD1 allowed confirmation of the localization by linkage analysis in CEPH families. The homologous gene in the mouse is located on chromosome 13.

The distal end of 5q, 5q31.1-qter, contains the genes for 2 adrenergic receptors, ADRB2 and ADRA1B and the dopamine receptor type 1A gene. Krushkal et al. (1998) used an efficient discordant sib-pair ascertainment scheme to investigate the impact of this region of the genome on variation in systolic blood pressure in young Caucasians. They measured 8 highly polymorphic markers spanning this positional candidate gene-rich region in 427 individuals from 55 3-generation pedigrees containing 69 discordant sib pairs, and calculated multipoint identity by descent probabilities. The results of genetic linkage and association tests indicated that the region between markers D5S2093 and D5S462 was significantly linked to 1 or more polymorphic genes influencing interindividual variation in systolic blood pressure levels. Since the ADRA1B and DRD1A genes are located close to these markers, the data suggested that genetic variation in 1 or both of these G protein-coupled receptors, which participate in the control of vascular tone, plays an important role in influencing interindividual variation in systolic blood pressure levels.

The disclosed NOV5 nucleic acid of the invention encoding a Dopamine receptor-like protein includes the nucleic acid whose sequence is provided in Table 5A or a fragment thereof. The invention also includes a mutant or variant nucleic acid any of whose bases may be changed from the corresponding base shown in Table 5A while still encoding a protein that maintains its Dopamine receptor-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 10% percent of the bases may be so changed.

The disclosed NOV5 protein of the invention includes the Dopamine receptor-like protein whose sequence is provided in Table 5B. The invention also includes a mutant or variant protein any of whose residues may be changed from the corresponding residue shown in Table SB while still encoding a protein that maintains its Dopamine receptor-like activities and physiological functions, or a functional fragment thereof. In the mutant or variant protein, up to about 34% percent of the residues may be so changed.

The NOV5 nucleic acids and proteins of the invention are useful in potential therapeutic applications implicated in schizophrenia, and other dopamine-dysfunctional states, Hypertension, Huntington's disease, levodopa-induced dyskinesias, alcoholism, Diabetes Insipidus and Mellitus with Optic Atrophy and Deafness, Wolfram Syndrome and/ or other pathologies and disorders. For example, a cDNA encoding the dopamine receptor-like protein may be useful in gene therapy, and the dopamine receptor-like protein may be useful when administered to a subject in need thereof. By way of nonlimiting example, the compositions of the present invention will have efficacy for treatment of patients suffering from schizophrenia, and other dopamine-dysfunctional states, Hypertension, Huntington's disease, levodopa-induced dyskinesias, alcoholism, Diabetes Insipidus and Mellitus with Optic Atrophy and Deafness, Wolfram Syndrome, as well as other diseases, disorders and conditions. The NOV5 nucleic acid, or fragments thereof, may further be useful in diagnostic applications, wherein the presence or amount of the nucleic acid or the protein are to be assessed.

NOV5 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV5 protein have multiple hydrophilic regions, each of which can be used as an immunogen. In one embodiment, contemplated NOV5 epitope is from about amino acids 1 to 10. In other embodiments, NOV5 epitope is from about amino acids 125 to 150, from about amino acids 175 to 230, from about amino acids 250 to 300, from about amino acids 320 to 330, from about amino acids 350 to 370, from about amino acids 380 to 410, or from about amino acids 420 to 460. This novel protein also has value in development of powerful assay system for functional analysis of various human disorders, which will help in understanding of pathology of the disease and development of new drug targets for various disorders.

NOV6

A disclosed NOV6 nucleic acid of 2657 nucleotides (also referred to as GM523_e_1_A) encoding a novel Metabotropic Glutamate Receptor-like protein is shown in Table 6A. An open reading frame was identified beginning with an ATG initiation codon at nucleotides 6–8 and ending with a TGA codon at nucleotides 2643–2645. A putative untranslated region upstream from the initiation codon and downstream from the termination codon is underlined in Table 6A, and the start and stop codons are in bold letters.

TABLE 6A

NOV6 Nucleotide Sequence (SEQ ID NO:16)

GATTCATGAAGATGTTGACAAGACTACAAGTTCTTATGTTAGCTTTGTTTTCAAAGGGATTTTTAGTCTC

TTTAGGAGATCACAACTTTATGAGGAGAGAAATTAAAATAGAAGGAGACCTTGTTTTAGGGGGCTTATTT

CCTATTAATGAAAAAGGCACTGGAACTGAAGAGTGTGGACGAATCAATGAAGACAGAGGTATCCAACGCC

TGGAGGCCATGTTGTTTGCCATTGATGAAATCAACAAAGACAATTACTTGCTTCCAGGAGTGAAGCTGGG

GGTTCACATTTTGGATACATGTTCAAGAGACACCTATGCATTAGAGCAGTCACTGGAGTTTGTCAGAGCA

TCGTTGACTAAAGTGGATGAAGCTGAATATATGTGTCCTGATGGATCATATGCTATTCAAGAAAACATCC

CACTACTCATTGCAGGAGTCATTGGCGGTTCGTACAGCAGTGTTTCCATACAGGTAGCAAACCTGCTGAG

GCTCTTCCAGATCCCTCAGATAAGCTACGCCTCCACCAGTGCCAAACTCAGCGACAAATCGCGCTATGAT

TATTTTGCCAGGACCGTCCCCCCTGACTTCTACCAGGCCAAAGCCATGGCCGAGATCTTGCGCTACTTTA

ACTGGACCTATGTGTCCACTGTTGCCTCTGAAGGTGACTATGGGAGACAGGGATTGAGGCCTTCGAGCA

GGAAGCAAGGCTACGCAACATCTGCATCGCCACTGCTGAAAAGGTGGGGCGCTCCAACATCCGCAAGTCC

TACGACAGCGTGATCCGTGAGCTCCTGCAGAAACCTAACGCGCGAGTTGTGGTCCTGTTCATGCGCAGTG

ATGACTCACGAGAGTTGATCGCTGCAGCCAGCCGCGTGAATGCTTCCTTCACCTGGGTGGCCAGCGATGG

CTGGGGTGCACAGGAGAGCATTGTCAAGGGCAGTGAGCACGTCGCCTATGGAGCCATCACCCTGGAGCTG

GCGTCCCACCCTGTTCGTCAGTTTGATCGCTACTTCCAGAGCCTCAACCCCTACAACAATCATCGTAACC

CCTGGTTCCGAGACTTCTGGGAGCAGAAGTTCCAGTGCAGCCTCCAGAACAAGAGAAACCACAGACAGAT

TTGTGACAAGCACCTGGCCATTGACAGCAGCAACTATGAACAAGAATCCAAGATCATGTTTGTGGTGAAT

GCAGTGTATGCCATGGCGCATGCGCTGCACAAAATGCAACGCACCCTCTGTCCCAACACCACCAAGCTCT

GTGATGCAATGAAGATCCTGGATGGAAAGAAGTTGTACAAAGATTATTTGCTGAAAATCAACTTCCTTGC

TCCATTCAACCCAAATAAAGGAGCAGACAGCATTGTGAAGTTTGACACTTACGGAGACGGGATGGGAAGA

TACAACGTGTTCAACTTCCAGCATATAGGTGGAAAGTATTCCTACTTAAAAGTTGGCCACTGGGCAGAAA

CTTTATATCTAGATGTGGACTCTATTCATTGGTCCCGGAACTCAGTCCCCACTTCCCAGTGCAGTGATCC

CTGTGCCCCCAATGAAATGAAAAACATGCAGCCAGGAGATGTTTGCTGCTGGATCTGCATCCCCATGTGAG

CCCTATGAATACCTGGTTGATGAGTTCACCTGCATGGATTGTGGCCCTGGCCAGTGGCCCACTGCAGACC

TATCTGGATGCTACAACCTTCCAGAGGATTACATCAGGTGGGAAGATGCCTGGGCAATAGGCCCAGTCAC

TATTGCCTGCCTGGGTTTTATGTGTACATGCATAGTCATAACTGTTTTTATCAAGCACAACAACACACCC

TTGGTCAAAGCATCAGGCCGAGAACTCTGCTACATCTTGTTATTTGGAGTTAGCCTGTCCTATTGCATGA

CATTCTTCTTCATTGCTAAGCCATCGCCTGTCATCTGTGCATTGCGCCGACTTGGGCTTGGGACCTCCTT

TGCCATCTGTTATTCAGCTCTCCTGACCAAGACAAACTGCATCGCTCGCATCTTTGATGGGGTCAAGAAT

GGCGCTCAGAGGCCAAAATTCATCAGCCCCAGTTCTCAGGTTTTTATCTGCCTGGGTTTGATACTGGTGC

AAATTGTGATGGTGTCTGTGTGGCTTATCTTGGAGACTCCAGGTACTAGAAGATACACCCTGCCAGAGAA

GCGGGAAACAGTCATCCTAAAATGCAATGTCAAAGATTCCAGCATGTTGATCTCTCTGACCTATGACGTG

GTTCTGGTGATTCTATGCACTGTGTATGCCTTCAAAACAAGGAAGTGTCCTGAAAACTTCAATGAAGCCA

AGTTCATAGGCTTCACCATGTACACCACCTGCATCATCTGGTTGGCATTCCTCCCTATATTTTATGTGAC

ATCAAGTGACTACAGAGTACAGACGACAACAATGTGCATCTCCGTTAGCTTGAGTGGTTTCGTGGTCTTG

GGCTGTTTGTTTGCCCCCAAGGTGCACATTGTCCTGTTCCAACCCCAGAAGAATGTGGTCACACACAGAC

TTCACCTCAACAGGTTCAGTGTCAGTGGAACTGCGACCACATATTCTCAGGCCTCTGCAAGCACGTATGT

GCCAACGGTGTGCAATGGGCGGGAAGTCCTCGACTCCACCACCTCATCTCTGTGA TTGTGAATTGCA

The disclosed NOV6 nucleic acid sequence has 2522 of 2658 bases (94%) identical to a Rat metabotropic glutamate receptor 3 mRNA from *Rattus norvegicus* (GENBANK-ID: M92076) (E=0.0).

A disclosed NOV6 polypeptide (SEQ ID NO:17) encoded by SEQ ID NO:16 is 879 amino acid residues and is presented using the one-letter amino acid code in Table 6B. Signal P, Psort and/or Hydropathy results predict that NOV6 contains a signal peptide and is likely to be localized in the endoplasmic reticulum (membrane) with a certainty of 0.6850. In other embodiments, NOV6 is also likely to be localized to the plasma membrane with a certainty of 0.6400, to the Golgi body with a certainty of 0.4600, or to the endoplasmic reticulum (lumen) with a certainty of 0.1000. The most likely cleavage site for a NOV6 peptide is between amino acids 24 and 25, at: SLG-DH.

The disclosed NOV6 amino acid sequence has 877 of 879 amino acid residues (99%) identical to, and 878 of 879 amino acid residues (99%) similar to, the 879 amino acid residue METABOTROPIC GLUTAMATE RECEPTOR 3 PROTEIN protein from *Mus musculus* (Mouse (Q9QYS2) (E=0.0).

NOV6 also has homology to the amino acid sequences shown in the BLASTP data listed in Table 6C.

TABLE 6B

Encoded NOV6 protein sequence (SEQ ID NO:17).

MKMLTRLQVLMLALFSKGFLVSLGDHNFMRREIKIEGDLVLGGLFPINEKGTGTEECGRINEDRGIQRLEAMLFA

IDEINKDNYLLPGVKLGVHILDTCSRDTYALEQSLEFVRASLTKVDEAEYMCPDGSYAIQENIPLLIAGVIGGSY

SSVSIQVANLLRLFQIPQISYASTSAKLSDKSRYDYFARTVPPDFYQAKAMAEILRYFNWTYVSTVASEGDYGET

GIEAFEQEARLRNICIATAEKVQRSNIRKSYDSVIRELLQKPNARVVVLFMRSDDSRELIAAASRVNASFTWVAS

DGWGAQESIVKGSEHVAYGAITLELASHPVRQFDRYFQSLNPYNNHRNPWFRDFWEQKFQCSLQNKRNHRQICDK

HLAIDSSNYEQESKIMFVVNAVYAMAHALHKMQRTLCPNTTKLCDAMKILDGKKLYKDYLLKINFLAPFNPNKGA

DSIVKFDTYGDGMGRYNVFNFQHIGGKYSYLKVGHWAETLYLDVDSIHWSRNSVPTSQCSDPCAPNEMKNMQPGD

VCCWICIPCEPYEYLVDEPTCMDCGPGQWPTADLSGCYNLPEDYIRWEDAWAIGPVTIACLGFMCTCIVITVFIK

HNNTPLVKASGRELCYILLFGVSLSYCMTFFFIAKPSPVICALRRLGLGTSFAICYSALLTKTNCIARIFDGVKN

GAQRPKFISPSSQVFICLGLILVQIVMVSVWLILETPGTRRYTLPEKRETVILKCNVKDSSMLISLTYDVVLVIL

CTVYAFKTRKCPENFNEAKFIGFTMYTTCIIWLAFLPIFYVTSSDYRVQTTTMCISVSLSGFVVLGCLFAPKVHI

VLFQPQKNVVTHRLHLNRFSVSGTATTYSQASASTYVPTVCNGREVLDSTTSSL

TABLE 6C

BLAST results for NOV6

| Gene Index/ Identifier | Protein/Organism | Length (aa) | Identity (%) | Positives (%) | Expect |
|---|---|---|---|---|---|
| gi\|400254\|sp\|P31422\| MGR3_RAT | METABOTROPIC GLUTAMATE RECEPTOR 3 PRECURSOR | 879 | 864/879 (98%) | 874/879 (99%) | 0.0 |
| gi\|6288800\|gb\| AAF06741.1\| AF170701_1 | metabotropic glutamate receptor 3 protein [*Mus musculus*] | 879 | 877/879 (99%) | 878/879 (99%) | 0.0 |
| gi\|11279202\|pir\|\| JC7160 | metabotropic glutamate receptor subtype 3 precursor - mouse | 879 | 875/879 (99%) | 876/879 (99%) | 0.0 |

The homology of these sequences is shown graphically in the ClustalW analysis shown in Table 6D.

TABLE 6D

Information for the ClustalW proteins

1) NOV6 (SEQ ID NO:17)
2) gi|400254|sp|P31422|MGR3_RAT METABOTROPIC GLUTAMATE RECEPTOR 3 PRECURSOR (SEQ ID NO:52)
3) gi|6288800|gb|AAF06741.1|AF170701_1 metabotropic glutamate receptor 3 protein [Mus musculus] (SEQ ID NO:53)
4) gi|11279202|pir||JC7160 metabotropic glutamate receptor subtype 3 precursor - mouse (SEQ ID NO:54)

```
                       10        20        30        40        50
                 ....|....|....|....|....|....|....|....|....|....|
NOV6             MKMLTRLQVLMLALFSKGFLVSLGDHNFMRREIKIEGDLVLGGLFPINEK
gi|400254|       MKMLTRLQ LMLALFSKGFL SLGDHNFMRREIKIEGDLVLGGLFPINEK
gi|6288800|      MKMLTRLQVLMLALFSKGFLVSLGDHNFMRREIKIEGDLVLGGLFPINEK
gi|11279202|     MKMLTRLQVLMLALFSKGFLVSLGDHNFMRREIKIEGDLVLGGLFPINEK 60        70        80        90       100
                 ....|....|....|....|....|....|....|....|....|....|
NOV6             GTGTEECGRINEDRGIQRLEAMLFAIDEINKDNYLLPGVKLGVHILDTCS
gi|400254|       GTGTEECGRINEDRGIQRLEAMLFAIDEINKDNYLLPGVKLGVHILDTCS
gi|6288800|      GTGTEECGRINEDRGIQRLEAMLFAIDEINKDNYLLPGVKLGVHILDTCS
gi|11279202|     GTGTEECRGINEDRGIQRLEAMLFAIDEINKDNYLLPGVKLGVHILDTCS 110       120       130       140       150
                 ....|....|....|....|....|....|....|....|....|....|
NOV6             RDTYALEQSLEFVRASLTKVDEAEYMCPDGSYAIQENIPLLIAGVIGGSY
gi|400254|       RDTYALEQSLEFVRASLTKVDEAEYMCPDGSYAIQENIPLLIAGVIGGSY
gi|6288800|      RDTYALEQSLEFVRASLTKVDEAEYMCPDGSYAIQENIPLLIAGVIGGSY
gi|11279202|     RDTYALEQSLEFVRASLTKVDEAEYMCPDGSYAIQENIPLLIAGVIGGSY 160       170       180       190       200
                 ....|....|....|....|....|....|....|....|....|....|
NOV6             SSVSIQVANLLRLFQIPQISYASTSAKLSDKSRYDYFARTVPPDFYQAKA
gi|400254|       SSVSIQVANLLRLFQIPQISYASTSAKLSDKSRYDYFARTVPPDFYQAKA
gi|6288800|      SSVSIQVANLLRLFQIPQISYASTSAKLSDKSRYDYFARTVPPDFYQAKA
gi|11279202|     SSVSIQVANLLRLFQIPQISYASTSAKLSDKSRYDYFARTVPPDFYQAKA 210       220       230       240       250
                 ....|....|....|....|....|....|....|....|....|....|
NOV6             MAEILRYFNWTYVSTVASEGDYGETGIEAFEQEARLRNICIATAEKVGRS
gi|400254|       MAEILR FNWTYVSTVASEGDYGETGIEAFEQEARLRNICIATAEKVGRS
gi|6288800|      MAEILRYFNWTYVSTVASEGDYGETGIEAFEQEARLRNICIATAEKVGRS
gi|11279202|     MAEILRYFNWTYVSTVASEGDYGETGIEAFEQEARLRNICIATAEKVGRS 260       270       280       290       300
                 ....|....|....|....|....|....|....|....|....|....|
NOV6             NIRKSYDSVIRELLQKPNARVVVLFMRSDDSRELIAAASRVNASFTWVAS
gi|400254|       MAEILRYFNWTYVSTVASEGDYGETGIEAFEQEARLRN CIATAEKVGRS
gi|6288800|      MAEILRYFNWTYVSTVASEGDYGETGIEAFEQEARLRNICIATAEKVGRS
gi|11279202|     MAEILRYFNWTYVSTVASEGDYGETGIEAFEQEARLRNICIATAEKVGRS 310       320       330       340       350
                 ....|....|....|....|....|....|....|....|....|....|
NOV6             DGWGAQESIVKGSEHVAYGAITLELASHPVRQFDRYFQSLNPYNNHRNPW
gi|400254|       DGWGAQESIVKGSEHVAYGAITLELASHPVRQFDRYFQSLNPYNNHRNPW
gi|6288800|      DGWGAQESIVKGSEHVAYGAITLELASHPVRQFDRYFQSLNPYNNHRNPW
gi|11279202|     DGWGAQESIVKGSEHVAYGAITLELASHPVRQFDRYFQSLNPYNNHRNPW 360       370       380       390       400
                 ....|....|....|....|....|....|....|....|....|....|
NOV6             FRDFWEQKFQCSLQNKRNHRQICDKHLAIDSSNYEQESKIMFVVNAVYAM
gi|400254|       FRDFWEQKFQCSLQNKRNHRQ CDKHLAIDSSNYEQESKIMFVVNAVYAM
gi|6288800|      FRDFWEQKFQCSLQNKRNHRQICDKHLAIDSSNYEQESKIMFVVNAVYAM
gi|11279202|     FRDFWEQKFQCSLQNKRNHRQICDKHLAIDSSNYEQESKIMFVVNAVYAM 410       420       430       440       450
                 ....|....|....|....|....|....|....|....|....|....|
NOV6             AHALHKMQRTLCPNTTKLCDAMKILDGKKLYKDYLLKINFLAPFNPNKGA
gi|400254|       AHALHKMQRTLCPNTTKLCDAMKILDGKKLYK YLLKINFTAPFNPNKGA
gi|6288800|      AHALHKMQRTLCPNTTKLCDAMKILDGKKLYKDYLLKINFTAPFNPNKGA
gi|11279202|     AHALHKMQRTLCPNTTKLCDAMKILDGKKLYKDYLLKINFTAPFNPNKGA
```

TABLE 6D-continued

Information for the ClustalW proteins

```
                460        470        480        490        500
             ....|....|....|....|....|....|....|....|....|....|
NOV6         DSIVKFDTYGDGMGRYNVFNFQHIGGKYSYLKVGHWAETLYLDVDSIHWS
gi|400254|   DSIVKFDTXGDGMGRYNVFNLQQTGGKYSYLKVGHWAETLSLDVDSIHWS
gi|6288800|  DSIVKFDTYGDGMGRYNVFNFQHIGGKYSYLKVGHWAETLYLDVDSIHWS
gi|11279202| DSIVKFDTYGDGMGRYNVFNFQHIGGKYSYLKVGHWAETLYLDVDSIHWS 510        520        530        540        550
             ....|....|....|....|....|....|....|....|....|....|
NOV6         RNSVPTSQCSDPCAPNEMKNMQPGDVCCWICIPCEPYEYLVDEFTCMDCG
gi|400254|   RNSVPTSQCSDPCAPNEMKNMQPGDVCCWICIPCEPYEYLVDEFTCMDCG
gi|6288800|  RNSVPTSQCSDPCAPNEMKNMQPGDVCCWICIPCEPYEYLVDEFTCMDCG
gi|11279202| RNSVPTSQCSDPCAPNEMKNMQPGDVCCWICIPCEPYEYLVDEFTCMDCG 560        570        580        590        600
             ....|....|....|....|....|....|....|....|....|....|
NOV6         PGQWPTADLSGCYNLPEDYIRWEDAWAIGPVTIACLGFMCTCIVITVFIK
gi|400254|   PGQWPTADLSGCYNLPEDYIXWEDAWAIGPVTIACLGFMCTCIVITVFIK
gi|6288800|  PGQWPTADLSGCYNLPEDYIRWEDAWAIGPVTIACLGFMCTCIVITVFIK
gi|11279202| PGQWPTADLSGCYNLPEDYIRWEDAWAIGPVTIACLGFMCTCIVITVFIK 610        620        630        640        650
             ....|....|....|....|....|....|....|....|....|....|
NOV6         HNNTPLVKASGRELCYILLFGVSLSYCMTFFFIAKPSPVICALRRLGLGT
gi|400254|   HNNTPLVKASGRELCYILLFGVSLSYCMTFFFIAKPSPVICALRRLGLGT
gi|6288800|  HNNTPLVKASGRELCYILLFGVSLSYCMTFFFIAKPSPVICALRRLGLGT
gi|11279202| HNNTPLVKASGRELCYILLFGVSLSYCMTFFFIAKPSPVICALRRLGLGT 660        670        680        690        700
             ....|....|....|....|....|....|....|....|....|....|
NOV6         SFAICYSALLTKTNCIARIFDGVKNGAQRPKFISPSSQVFICLGLILVQI
gi|400254|   SFAICYSALLTKTNCIARIFDGVKNGAQRPKFISPSSQVFICLGLILVQI
gi|6288800|  SFAICYSALLTKTNCIARIFDGVKNGAQRPKFISPSSQVFICLGLILVQI
gi|11279202| SFAICYSALLTKTNCIARIFDGVKNGAQRPKFISPSSQVFICLGLILVQI 710        720        730        740        750
             ....|....|....|....|....|....|....|....|....|....|
NOV6         VMVSVWLILETPGTRRYTLPEKRETVILKCNVKDSSMLISLTYDVVLVIL
gi|400254|   VMVSVWLILETPGTRRYTLPEKRETVILKCNVKDSSMLISLTYDVVLVIL
gi|6288800|  VMVSVWLILETPGTRRYTLPEKRETVILKCNVKDSSMLISLTYDVVLVIL
gi|11279202| VMVSVWLILETPGTRRYTLPEKRETVILKCNVKDSSMLISLTYDVVLVIL 760        770        780        790        800
             ....|....|....|....|....|....|....|....|....|....|
NOV6         CTVYAFKTRKCPENFNEAKFIGFTMYTTCIIWLAFLPIFYVTSSDYRVQT
gi|400254|   CTVYAFKTRKCPENFNEAKFIGFTMYTTCIIWLAFLPIFYVTSSDYRVQT
gi|6288800|  CTVYAFKTRKCPENFNEAKFIGFTMYTTCIIWLAFLPIFYVTSSDYRVQT
gi|11279202| CTVYAFKTRKCPENFNEAKFIGFTMYTTCIIWLAFLPIFYVTSSDYRVQT 810        820        830        840        850
             ....|....|....|....|....|....|....|....|....|....|
NOV6         TTMCISVSLSGFVVLGCLFAPKVHIVLFQPQKNVVTHRLHLNRFSVSGTA
gi|400254|   TTMCISVSLSGFVVLGCLFAPKVHIVLFQPQKNVVTHRLHLNRFSVSGTA
gi|6288800|  TTMCISVSLSGFVVLGCLFAPKVHIVLFQPQKNVVTHRLHLNRFSVSGTA
gi|11279202| TTMCISVSLSGFVVLGCLFAPKVHIVLFQPQKNVVTHRLHLNRFSVSGTA 860        870
             ....|....|....|....|....
NOV6         TTYSQXSASTYVPTVCNGREVLDSTTSSL
gi|400254|   TTYSQSSASTYVPTVCNGREVLDSTTSSL
gi|6288800|  TTYSQSSASTYVPTVCNGREVLDSTTSSL
gi|11279202| TTYSQSSASTYVPTVCNGREVLDSTTSSL
```

Table 6E–F lists the domain description from DOMAIN analysis results against NOV6. This indicates that the NOV6 sequence has properties similar to those of other proteins known to contain this domain.

G-protein-coupled receptors (GPCRs) constitute a vast protein family that encompasses a wide range of functions (including various autocnine, paracrine and endocrine processes). They show considerable diversity at the

TABLE 6E

Domain Analysis of NOV6 gnl|Pfam|pfam01094, ANF_receptor, Receptor family ligand binding region. This family includes extracellular ligand binding domains of a wide range of receptors. This family also includes the bacterial amino acid binding proteins of known structure. (SEQ ID NO:84)
CD-Length = 402 residues, 98.5% aligned
Score = 323 bits (827), Expect = 3e-89

```
Query:   62 EDRGIQRLEAMLFAIDEINKDNYLLPGVKLGVHILDTCSRDTYALEQSLEFVRASLTKVD 121
            |||  ||||||  |  |  ||  |   |||+  ||+ |||     |||||   ||    |||
Sbjct:    6 AVRGITRLEAMLGAFDRINADPALLPGLALGLAILDINSLRNVALEQSFTFVYGLLIKCD  65

Query:  122 EAEYMCPDGSYAIQENIPLLIAGVIGGSYSSVSIQVANLLRLFQIPQISYASTSAKLSDK 181
              +  |  |  |+   + +|         |    |   |||  |   || |||  ||+ +||||
Sbjct:   66 CSSVRCAGGDLALTHGVAGVIGPSCSSSAIQV----ANLASLLNIPMISYGSTAPELSDK 121

Query:  182 SRYDYFARTVPPDFYQAKAMAEILRYFNWTYVSTVASEGDYGETGIEAFEQEARLRNICI 241
             +||    |+||+|   |+|     ||   +|   ++|||   |||     |+|   |||    +       |     ||
Sbjct:  122 TRYPTFSRTIPSDAFQGLAMVDIFKHFNWNYVSVVYSDGTYGEEGCEAFIEALRARGGCI 181

Query:  242 ATAEKVGR--SNIRKSYDSVIRELLQKPNARVVVLFMRSDDSRELIAAASRVN--ASFTW 297
             |  +  |+|         +  +|  ++|||   +    ||||+      +    |||+   ||   |+
Sbjct:  182 ALSVKIGEFDRGDEEDFDKLLRELKR--RARVVVMCGHGETLRELLEAALRLGLTGEDYV 239

Query:  298 VASDGWGAQESIVKGSEHVAYGAITLELASHPVRQFDRYFQSLNPYNNHRNPWFRDFWEQ 357
             ||        +       |     |||    |||+  + +|   ||    +      ||  ||||||  +   ++
Sbjct:  240 FISDDLFNKSLPA---EPGAPGAI--ELANASMLRFAYYFVLVLTLNNPRNPWFLEFWKE 294

Query:  358 KFQCSLQNKRNHRQICDKHLAIDSSNYEQESKIMFVVNAVYAMAHALHKMQRTLCPNTT 416
             |   |+||+                 ||||  |   || +|||   |||||        |   +
Sbjct:  295 NFICALQDFLT------------LEPYEQEGKAGFVYDAVYLYAHALHNTTLALGGSWVD 342

Query:  417 --KLCDAMKILDGKKLYKDYLLKINFLAPFNPNKGADSIVKFDTYGDGMGRYNVFNFQHI 474
               ||   +              + |     |         |  ||  || | |  + +  |+
Sbjct:  343 GEKLVQHL-------------RNLTFEGVTGP-------VTFDENGDRDGDYVLLDTQNT 382

Query:  475 GGK-----YSYLKVGHWAE 488
                  +|   ||  | |
Sbjct:  383 ETGQLKVTGTYDGVGKWTE 401
```

TABLE 6F

Domain Analysis of NOV6 gnl|Pfam|pfam00003, 7tm_3, 7 transmembrane receptor (metabotropic E family). (SEQ ID NO:85)
CD-Length = 256 residues, 100.0% aligned
Score = 323 bits (827), Expect = 3e-89

```
Query:  576 WAIGPVTIACLGFMCTCIVITVFIKHNNTPLVKASGRELCYILLFGVSLSYCMTFFFIAK 635
            |   |  +|  || +   |+  ||+||  +|+||||   |||  |+||  |+  |    +| || |
Sbjct:    1 LGIVLVALAVLGIVLTLFVLVVFVKHRDTPIVKASNRELSYLLLIGLILCYLCSFLFIGK  60

Query:  636 PSPVICALRRLGLGTSFAICYSALLTKTNCIARIFDGVKNGAQRPKFISPSSQVFICLGL 695
            ||   |  |||+  |    |+||||||| ||| +  |||     | |+ +||||| +|| |||   |  |
Sbjct:   61 PSETSCILRRILFGLGFTLCYSALLAKTNRVLRIFRAKKPGSGKPKFISPWAQVLIVLIL 120

Query:  696 ILVQIVMVSVWLILETPGTRRYTLPEKRETVILKCNVKDS-SMLISLTYDVVLVILCTVY 754
            +|+|+++     +||++| |           || + +|+||        +  ++ |  ||  +| +|||
Sbjct:  121 VLIQVIICVIWLVVEPPRPTIDIYSEKEK-IILECNKGSMVAFVVVLGYDGLLAVLCTFL 179

Query:  755 AFKTRKCPENFNEAKFIGFTMYTTCIIWLAFLPIFYVTSSDYRVQTTTMCISVSLSGFVV 814
            || ||  ||||||||||||| ||+|  | ||+|+||+|+   |+  +||       |+   |   |+
Sbjct:  180 AFLTRNLPENFNEAKFIGFSMLTFCIVWVAFIPIYL--STPGKVQVAVEIFSILASSTVL 237

Query:  816 LGCLFAPKVHIVLFQPQKN 833
            |||||  ||  +|+||+|+||
Sbjct:  238 LGCLFVPKCYIILFRPEKN 256
``` sequence level, on the basis of which they can be separated into distinct groups. The term clan is used to describe the GPCRs, as they embrace a group of families for which there are indications of evolutionary relationship, but between which there is no statistically significant similarity in sequence. The currently known clan members include the rhodopsin-like GPCRs, the secretin-like GPCRs, the cAMP receptors, the fungal mating pheromone receptors, and the metabotropic glutamate receptor family.

The metabotropic glutamate receptors are functionally and pharmacologically distinct from the ionotropic glutamate receptors. They are coupled to G-proteins and stimulate the inositol phosphate/$Ca^{2+}$ intracellular signalling pathway. The amino acid sequences of the receptors contain high proportions of hydrophobic residues grouped into 7 domains, in a manner reminiscent of the rhodopsins and other receptors believed to interact with G-proteins. However, while a similar 3D framework has been proposed to account for this, there is no significant sequence identity between these and receptors of the rhodopsin-type family: the metabotropic glutamate receptors thus bear their own distinctive '7TM' signature. This 7TM signature is also shared by the calcium-sensing receptors, and GABA (gamma-ammno-butyric acid) type B (GABA(B)) receptors.

At least eight sub-types of metabotropic receptor (MGR1–8) have been identified in cloning studies. The sub-types differ in their agonist pharmacology and signal transduction pathways.

The mGluR3 gene consists of six exons and spans over 95 kb. Exon 1 and its preceding putative promoter are located distantly from the following protein-coding region. In the mGluR family, mGluR3 and mGluR5 are both expressed in neuronal and glial cells and are upregnlated during the early postnatal period. They are, however, coupled to two distinct signaling cascades and have been shown to exert opposite influences on some functions of cultured astrocytes. In cultured astrocytes, mGluR3 and mGluR5 mRNA levels were significantly increased by exposure to epidermal growth factor (EGF), basic fibroblast growth factor (bFGF), or transforming growth factor-alpha; and EGF was more efficacious than bFGF in producing this increase. Hence, mGluR3 and mGluR5 mRNAs are concertedly upregulated in cultured astrocytes by specific growth factors. This finding suggests that the two mGluR subtypes may play an important role in maintaining the proper balance of astrocyte functions via two distinct signal transduction mechanisms.

Glutamate receptors are divided into 2 distinct classes: ionotropic glutamate receptors (iGluRs) and metabotropic glutamate receptors (mGluRs). The iGluRs consist of N-methyl-D-aspartate (NMDA) receptors and non-NMDA receptors. Non-NMDA receptors are further subdivided into 2 groups: alpha-amino-3-hydroxy-5-methyl-4-isoxazolepropionic acid receptors and kainate receptors. The mGluRs are divided into 3 groups according to agonist selectivity, coupling to different effector systems, and sequence homology. Group I includes mGluR1 and mGluR5, which are coupled to inositol phospholipid metabolism. Group II, which includes mGluR2 and mGluR3, and group III, which includes mGluR4, mGluR6, mGluR7, and mGluR8, are negatively coupled to adenylate cyclase activity. Each mGluR possesses a large extracellular domain. Okamoto et al. (1998) expressed mGlur1-alpha (mGluR1A) in insect cells on a baculovirus system. They isolated a soluble mGluR that encodes only the extracellular domain and retains a ligand binding characteristic similar to that of the full-length receptor. Their observations demonstrated that a ligand binding event in mGluRs can be dissociated from the membrane domain.

Smitt et al. (2000) demonstrated that autoantibody against mGluR1A was responsible for severe paraneoplastic cerebellar ataxia in 2 patients. The disorder developed in both patients while they were in remission from Hodgkin disease. One, a teenager, had been in remission for 2 years when truncal ataxia, intention tremor, and gait ataxia developed. This patient improved clinically with loss of cells in the cerebrospinal fluid when treated with plasma exchanges, oral prednisone, and 2 courses of intravenous immune globulin. The second patient reported by Smitt et al. (2000) was in her late forties and, in addition to successfully treated Hodgkin disease, had polycystic kidney disease requiring hemodialysis for many years. Therapy was less successful in this patient, possibly because of delay in initiation.

The disclosed NOV6 nucleic acid of the invention encoding a Metabotropic Glutamate Receptor-like protein includes the nucleic acid whose sequence is provided in Table 6A or a fragment thereof. The invention also includes a mutant or variant nucleic acid any of whose bases may be changed from the corresponding base shown in Table 6A while still encoding a protein that maintains its Metabotropic Glutamate Receptor-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 10% percent of the bases may be so changed.

The disclosed NOV6 protein of the invention includes the Metabotropic Glutamate Receptor-like protein whose sequence is provided in Table 6B. The invention also includes a mutant or variant protein any of whose residues may be changed from the corresponding residue shown in Table 6B while still encoding a protein that maintains its Metabotropic Glutamate Receptor-like activities and physiological functions, or a functional fragment thereof. In the mutant or variant protein, up to about 10% percent of the residues may be so changed.

The above defined information for this invention suggests that these Metabotropic Glutamate Receptor-like proteins (NOV6) may function as a member of a "Metabotropic Glutamate Receptor family". Therefore, the NOV6 nucleic acids and proteins identified here may be useful in potential therapeutic applications implicated in (but not limited to) various pathologies and disorders as indicated below. The potential therapeutic applications for this invention include, but are not limited to: protein therapeutic, small molecule drug target, antibody target (therapeutic, diagnostic, drug targeting/cytotoxic antibody), diagnostic and/or prognostic marker, gene therapy (gene delivery/gene ablation), research tools, tissue regeneration in vivo and in vitro of all tissues and cell types composing (but not limited to) those defined here.

The nucleic acids and proteins of NOV6 are useful in potential therapeutic applications implicated in immune disorders and airway pathologies such as epileptic seizures and other neurological disorders, Hodgkin disease, polycystic kidney disease, mental depression, Adenocarcinoma, Smith-Lemli-Opitz syndrome, Retinitis pigmentosa, and/or other pathologies and disorders For example, a cDNA encoding NOV6 may be useful in gene therapy, and NOV6 may be useful when administered to a subject in need thereof. By way of nonlimiting example, NOV6 will have efficacy for treatment of patients suffering from epileptic seizures and other neurological disorders, Hodgkin disease, polycystic kidney disease, mental depression, Adenocarcinoma, Smith-Lemli-Opitz syndrome, Retinitis pigmentosa. The novel NOV6 nucleic acid encoding NOV6 protein, or fragments thereof, may further be useful in diagnostic applications, wherein the presence or amount of the nucleic acid or the protein are to be assessed. These materials are further useful in the generation of antibodies that bind immunospecifically to the novel substances of the invention for use in therapeutic or diagnostic methods.

NOV6 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV6 protein have multiple hydrophilic regions, each of which can be used as an immunogen. In one embodiment, contemplated NOV6 epitope is from about amino acids 20 to 30. In other embodiments, NOV6 epitope is from about amino acids 50 to 70, from about amino acids 100 to 140, from about amino acids 180 to 200, from about amino acids 210 to 280, from about amino acids 310 to 400, from about amino acids 450 to 510, from about amino acids 520 to 560, from about amino acids 600 to 610, from about amino acids 660 to 680, from about amino acids 700 to 720, from about amino acids 750 to 770, or from about amino acids 800 to 850. This novel protein also has value in development of powerful assay system for functional analysis of various human disorders, which will help in understanding of pathology of the disease and development of new drug targets for various disorders.

NOV7

NOV7 includes three novel PV-1-like proteins disclosed below. The disclosed proteins have been named NOV7a, NOV7b, and NOV7c.

NOV7a

A disclosed NOV7a nucleic acid of 1366 nucleotides (also referred to sggc_draft_ba560a15_20000723_da1) encoding a novel PV-1-like receptor protein is shown in Table 7A. An open reading frame was identified beginning with an ATG initiation codon at nucleotides 1–3 and ending with a TGA codon at nucleotides 1327–1329. In Table 7A, the 3' untranslated region is underlined and the start and stop codons are in bold letters.

TABLE 7A

NOV7a Nucleotide Sequence (SEQ ID NO:18)

ATGGGTCTGGCCATGGAGCACGGAGGGTCCTACGCTCGGGCGGGGGGCAGCTCTCGGGGCTGCTGGTATTA

CCTGCGCTACTTCTTCCTCTTCGTCTCCCTCATCCAATTCCTCATCATCCTGGGGCTCGTGCTCTTCATGG

TCTATGGCAACGTGCACGTGAGCACAGAGTCCAACCTGCAGGCCACCGAGCGCCGAGCCGAGGGCCTATAC

AGTCAGCTCCTAGGGCTCACGGCCTCCCAGTCCAACTTGACCAAGGAGCTCAACTTCACCACCCGCGCCAA

GGATGCCATCATGCAGATGTGGCTGAATGCTCGCCGCGACCTGGACCGCATCAATGCCAGCTTCCGCCAGT

GCCAGGGTGACCGGGTAATCTACACGAACAATCAGAGGTACATGGCTGCCATCATCTTGAGTGAGAAGCAA

TGCAGAGATCAATTCAAGGACATGAACAAGAGCTGCGATGCCTTGCTCTTCATGCTGAATCAGAAGGTGAA

GACGCTGGAGGTGGAGATAGCCAAGGAGAAGACCATTTGCACTAAGGATAAGGAAAGCGTGCTGCTGAACA

AACGCGTGGCGGAGGAACAGCTGGTTGAATGCGTGAAAACCCGGGAGCTGCAGCACCAAGAGCGCCAGCTG

GCCAAGGAGCAACTGCAAAAGGTGCAAGCCCTCTGCCTGCCCCTGGACAAGGACAAGTTTGAGATGGACCT

TCGTAACCTGTGGAGGGACTCCATTATCCCACGCAGCCTGGACAACCTGGGTTACAACCTCTACCATCCCC

TGGGCTCGGAATTGGCCTCCATCCGCAGAGCCTGCGACCACATGCCCAGCCTCATGAGCTCCAAGGTGGAA

GGTCAGTGCCGGAGCCTCCGGGCGGATATCGAACGCGTGGCCCGCGAGAACTCAGACCTCCAACGCCAGAA

GCTGGAAGCCCAGCAGGGCCTGCGGGCCAGTCAGGAGGCGAAACAGAAGGTGGAGAAGGAGGCTCAGGCCC

GGGAGGCCAAGCTCCAAGCTGAATGCTCCCGGCAGACCCAGCTAGCGCTGGAGGAGAAGGCGGTGCTGCGG

AAGGAACGAGACAACCTGGCCAAGGAGCTGGAAGAGAAGAAGAGGGAGGCGGAGCAGCTCAGGATGGAGCT

GGCCATCAGAAACTCAGCCCTGGACACCTGCATCAAGACCAAGTCGCAGCCAGATGATGCCAGTGTCAAGC

CCATGGGCCCTGTCCCCAACCCCCAGCCCATCGACCCAGCTAGCCTGGAGGAGTTCAAGAGGAAGATCCTG

GAGTCCCAGAGGCCCCCTGCAGGCATCCCTGTAGCCCCATCCAGTGGCTGAGGAGGCTCCGGCACTGACCT

AAGGGCGAATCCCAGCA

The disclosed NOV7a nucleic acid sequence, localized to chromosome 19, has 945 of 1345 bases (70%) identical to a 1968 bp PV-1 mRNA from *Rattus norvegicus* (GENBANK-ID: AF154831|acc:AF154831) (E=1.1e$^{-121}$).

A disclosed NOV7a polypeptide (SEQ ID NO:19) encoded by SEQ ID NO:18 is 442 amino acid residues and is presented using the one-letter amino acid code in Table 7B. Signal P, Psort and/or Hydropathy results predict that NOV7a has a signal peptide and is likely to be localized in the plasma membrane with a certainty of 0.7900. In other embodiments, NOV7a is also likely to be localized to the nucleus with a certainty of 0.6000, to the microbody (peroxisome) with a certainty of 0.3000, or the Golgi body with a certainty of 0.3000. The most likely cleavage site for a NOV7a peptide is between amino acids 50 and 51, at: YVG-NV.

SNP data for NOV7a can be found below in Example 3.

TaqMan data for NOV7a can be found below in Example 2.

NOV7b

TABLE 7B

Encoded NOV7a protein sequence (SEQ ID NO:19).

MGLAMEHGGSYARAGGSSRGCWYYLRYFFLFVSLIQFLIILGLVLFMVYGNVHVSTESNLQATE

RRAEGLYSQLLGLTASQSNLTKELNFTTRAKDAIMQMWLNARRDLDRINASFRQCQGDRVIYTN

NQRYMAAIILSEKQCRDQFKDMNKSCDALLFMLNQKVKTLEVEIAKEKTICTKDKESVLLNKRV

AEEQLVECVKTRELQHQERQLAKEQLQKVQALCLPLDKDKFEMDLRNLWRDSIIPRSLDNLGYN

LYHPLGSELASIRRACDHMPSLMSSKVEGQCRSLRADIERVARENSDLQRQKLEAQQGLRASQE

AKQKVEKEAQAREAKLQAECSRQTQLALEEKAVLRKERDNLAKELEEKKREAEQLRMELAIRNS

ALDTCIKTKSQPMMPVSRPMGPVPNPQPIDPASLEEFKRKILESQRPPAGIPVAPSSG

The disclosed NOV7a amino acid sequence has 266 of 442 amino acid residues (60%) identical to, and 347 of 442 amino acid residues (78%) similar to, the 438 amino acid residue PV-1 protein from *Rattus norvegicus* (SPTREMBL-ACC:Q9WV78) ($1.6e^{-142}$), and 439 of 442 amino acid residues (99%) identical to, and 439 of 442 amino acid residues (99%) similar to, the 479 amino acid residue Human ORFX ORF1918 polypeptide sequence (patp:AAB42154) ($3.2e^{-229}$).

A disclosed NOV7b nucleic acid of 1421 nucleotides (also referred to 2847264.0.32) encoding a novel PV-1-like receptor protein is shown in Table 7C. An open reading frame was identified beginning with an ATG initiation codon at nucleotides 55–57 and ending with a TGA codon at nucleotides 1381–1383. In Table 7C, the 5' and 3' untranslated regions are underlines and the start and stop codons are in bold letters.

TABLE 7C

NOV7b Nucleotide Sequence (SEQ ID NO:20)

<u>GAATTCTAGGTGGTGGTGAGCAGGGACGGTGCACCGGACGGCGGGATCGAGCAA</u>ATGGGTCTGGCCATGGA

GTACGGAGGGTCCTACGCTCGGGCGGGGGGCAGCTCTCGGGGCTGCTGGTATTACCTGCGCTACTTCTTCC

TCTTCGTCTCCCTCATCCAATTCCTCATCATCCTGGGGCTCGTGCTGTTCATGGTCTATGGCGACGTGCAC

GTGAGCACAGAGTCCAACCTGCAGGCCACCGAGCGCCGAGCCGAGGGCCTATACAGTCAGCTCCTAGGGCT

CACGGCCTCCCAGTCCAACTTGACCAAGGAGCTCAACTTCACCACCCGCGCCAAGGATGCCATCATGCAGA

TGTGGCTGAATGCTCGCCGCGACCTGGACCGCATCAATGCCAGCTTCCGCCAGTGCCAGGGTGACCGGGTC

ATCTACACGAACAATCAGAGGTACATGGCTGCCATCATCTTGAGTGAGAAGCAATGCAGAGATCAATTCAA

GGACATGAACAAGAGCTGCGATGCCTTGCTCTTCATGCTGAATCAGAAGGTGAAGACGCTGGAGGTGGAGA

TAGCCAAGGAGAAGACCATTTGCACTAAGGATAAGGAAAGCGTGCTGCTGAACAAACGCGTGGCGGAGGAA

CAGCTGGTTGAATGCGTGAAAACCCGGGAGCTGCAGCACCAAGAGCGCCAGCTGGCCAAGGAGCAACTGCA

AAAGGTGCAAGCCCTCTGCCTGCCCCTGGACAAGGACAAGTTTGAGATGGACCTTCGTAACCTGTGGAGGG

TABLE 7C-continued

NOV7b Nucleotide Sequence (SEQ ID NO:20)

ACTCCATTATCCCACGCAGCCTGGACAACCTGGGTTACAACCTCTACCATCCCCTGGGCTCGGAATTGGCC

TCCATCCGCAGAGCCTGCGACCACATGCCCAGCCTCATGAGCTCCAAGGTGGAGGAGCTGGCCCGGAGCCT

CCGGGCGGATATCGAACGCGTGGCCCGCGAGAACTCAGACCTCCAACGCCAGAAGCTGGAAGCCCAGCAGG

GCCTGCGGGCCAGTCAGGAGGCGAAACAGAAGGTGGAGAAGGAGGCTCAGGCCCGGGAGGCCAAGCTCCAA

GCTGAATGCTCCCGGCAGACCCAGCTAGCGCTGGAGGAGAAGGCGGTGCTGCGGAAGGAACGAGACAACCT

GGCCAAGGAGCTGGAAGAGAAGAAGAGGGAGGCGGAGCAGCTCAGGATGGAGCTGGCCATCAGAAACTCAG

CCCTGGACACCTGCATCAAGACCAAGTCGCAGCCGATGATGCCAGTGTCAAGGCCCATGGGCCCTGTCCCC

AACCCCAGCCCATCGACCCAGCTAGCCTGGAGGAGTTCAAGAGGAAGATCCTGGAGTCCCAGAGGCCCCC

TGCAGGCATCCCTGTAGCCCCATCCAGTGGCTGAGGAGGCTCCAGGCCTGAGGACCAAGGGATGGCCCGAC

T

The disclosed NOV7b nucleic acid sequence, localized to chromosome 19, has 969 of 1383 bases (70%) identical to a PV-1 mRNA from *Rattus norvegicus* (GENBANK-ID: AF154831) (E=$2.5e^{-123}$).

A disclosed NOV7b polypeptide (SEQ ID NO:21) encoded by SEQ ID NO:20 is 442 amino acid residues and is presented using the one-letter amino acid code in Table 7D. Signal P, Psort and/or Hydropathy results predict that NOV7b has a signal peptide and is likely to be localized in the plasma membrane with a certainty of 0.7900. In other embodiments, NOV7b is also likely to be localized to the nucleus with a certainty of 0.6000, to the microbody (peroxisome) with a certainty of 0.3000, or the Golgi body with a certainty of 0.3000. The most likely cleavage site for a NOV7b peptide is between amino acids 50 and 51, at: YVG-NV.

NOV7b is expressed in at least the following tissues: lymph node, bone marrow, spleen, mammary gland, thyroid, stomach, fetal kidney, heart, fetal liver. In addition, the sequence is predicted to be expressed in lung because of the expression pattern of (GENBANK-ID: Q9WV78) a closely related PV-1 homolog in species *Rattus norvegicus*. It has also been reported to be expressed in muscle and brain (J Cell Biol 1999 Jun. 14;145(6): 1189–98). Endothelium of the fenestrated peritubular capillaries of the kidney and those of the intestinal villi, pancreas, and adrenals have also been shown to express PV-1 (Proc Natl Acad Sci USA 1999 Nov. 9;96(23):13203–7) TaqMan data for NOV7b can be found below in Example 2.

TABLE 7D

Encoded NOV7b protein sequence (SEQ ID NO:21).

MGLAMEYGGSYARAGGSSRGCWYYLRYFFLFVSLIQFLIILGLVLFMVYGDVHVSTESNLQATERRAEGLY

SQLLGLTASQSNLTKELNFTTRAKDAIMQMWLNARRDLDRINASFRQCQGDRVIYTNNQRYMAAIILSEKQ

CRDQFKDMNKSCDALLFMLNQKVKTLEVEIAKEKTICTKDKESVLLNKRVAEEQLVECVKTRELQHQERQL

AKEQLQKVQALCLPLDKDKFEMDLRNLWRDSIIPRSLDNLGYNLYHPLGSELASIRRACDHMPSLMSSKVE

ELARSLRADIERVARENSDLQRQKLEAQQGLRASQEAKQKVEKEAQAREAKLQAECSRQTQLALEEKAVLR

KERDNLAKELEEKKREAEQLRMELAIRNSALDTCIKTKSQPMMPVSRPMGPVPNPQPIDPASLEEFKRKIL

ESQRPPAGIPVAPSSG

The disclosed NOV7b amino acid sequence has 268 of 442 amino acid residues (60%) identical to, and 350 of 442 amino acid residues (79%) similar to the 438 amino acid residue PV-1 protein from *Rattus norvegicus* (SPTREMBL-ACC:Q9WV78), and 454 of 457 amino acid residues (99%) identical to, and 457 of 457 amino acid residues (100%) similar to the 479 amino acid residue Human ORFX ORF1918 polypeptide sequence (patp:AAB42154) (E=$1.3e^{-237}$).

NOV7c

A disclosed NOV7c nucleic acid of 2024 nucleotides (also referred to CG51878-03) encoding a novel PV-1-like receptor protein is shown in Table 7E. An open reading frame was identified beginning with an ATG initiation codon at nucleotides 1–3 and ending with a TGA codon at nucleotides 1327–1329. In Table 7E, the 3' untranslated region is underlined and the start and stop codons are in bold letters.

TABLE 7A

NOV7c Nucleotide Sequence (SEQ ID NO:22)

ATGGGTCTGGCCATGGAGCACGGAGGGTCCTACGCTCGGCGGGGGGCAGCTCTCGGGGCTGCTGGTATTA
CCTGCGCTACTTCTTCCTCTTCGTCTCCCTCATCCAATTCCTCATCATCCTGGGGCTCGTGCTCTTCATGG
TCTATGGCAACGTGCACGTGAGCACAGAGTCCAACCTGCAGGCCACCGAGCGCCGAGCCGAGGGCCTATAC
AGTCAGCTCCTAGGGCTCACGGCCTCCCAGTCCAACTTGACCAAGGAGCTCAACTTCACCACCCGCGCCAA
GGATGCCATCATGCAGATGTGGCTGAATGCTCGTCGCGACCTGGACCGCATCAATGCCAGCTTCCGCCAGT
GCCAGGGTGACCGGGTCATCTACACGAACAATCAGAGGTACATGGCTGCCATCATCTTGAGTGAGAAGCAA
TGCAGAGATCAATTCAAGGACATGAACAAGAGCTGCGATGCCTTGCTCTTCATGCTGAATCAGAAGGTGAA
GACGCTGGAGGTGGAGATAGCCAAGGAGAAGACCATTTGCACTAAGGATAAGGAAAGCGTGCTGCTGAACA
AACGCGTGGCGGAGGAACAGCTGGTTGAATGCGTGAAAACCCGGGAGCTGCAGCACCAAGAGCGCCAGCTG
GCCAAGGAGCAACTGCAAAGGGTGCAAGCCCTCTGCCTGCCCCTGGACAAGGACAAGTTTGAGATGGACCT
TCGTAACCTGTGGAGGGACTCCATTATCCCACGCAGCCTGGACAACCTGGGTTACAACCTCTACCATCCCC
TGGGCTCGGAATTGGCCTCCATCCGCAGAGCCTGCGACCACATGCCCAGCCTCGTGAGCTCCAAGGTGGAG
GAGCTGGCCCGGAGCCTCCGGGCGGATATCGAACGCGTGGCCCGCGAGAACTCAGACCTCCAACGCCAGAA
GCTGGAAGCCCAGCAGGGCCTGCGGGCCAGTCAGGAGGCGAAACAGAAGGTGGAGAAGGAGGCTCAGGCCC
GGGAGGCCAAGCTCCAAGCTGAATGCTCCCGGCAGACCCAGCTAGCGCTGGAGGAGAAGGCGGTGCTGCGG
AAGGAACGAGACAACCTGGCCAAGGAGCTGGAAGAGAAGAAGAGGGAGGCGGAGCAGCTCAGGATGGAGCT
GGCCATCAGAAACTCAGCCCTGGACACCTGCATCAAGACCAAGTCGCAGCCGATGATGCCAGTGTCAAGGC
CCATGGGCCCTGTCCCCAACCCCCAGCCCATCGACCCAGCTAGCCTGGAGGAGTTCAAGAGGAAGATCCTG
GAGTCCCAGAGGCCCCCTGCAGGCATCCCTGTAGCCCCATCCAGTGGCTGAGGAGGCTCCAGGCCTGAGGA
CCAAGGGATGGCCCGACTCGGCGGTTTGCGGAGGATGCAGGGATATGCTCACAGCGCCCGACACAACCCCC
TCCCGCCGCCCCAACCACCCAGGGCCACCATCAGACAACTCCCTGCATGCAAACCCCTAGTACCCTCTCA
CACCCGCACCCGCGCCTCATGATCCCTCACCCAGAGCACACGGCCGCCGAGATGACGTCACGCAAGCAACG
GCGCTGACGTCACATATCACCGTGGTGATGGCGTCACGTGGCCATGTAGACGTCACGAAGAGATATAGCGA
TGGCGTCGTGCAGATGCAGCACGTCGCACACAGACATGGGGAACTTGGCATGACGTCACACCGAGATGCAG
CAACGACGTCACGGGCCATGTCGACGTCACACATATTAATGTCACACAGACGCGGCGATGGCATCACACAG
ACGGTGATGATGTCACACACAGACACAGTGACAACACACACCATGACAACGACACCTATAGATATGGCACC
AACATCACATGCACGCATGCCCTTTCACACACACTTTCTACCCAATTCTCACCTAGTGTCACGTTCCCCCG
ACCCTGGCACACGGGCCAACGTACCCACAGGATCCCATCCCCTCCCGCACAGCCCTGGGCCCCAGCACCTC
CCCTCCTCCAGCCTCCTGGCCTCCCGGTAGTACACG

The disclosed NOV7c nucleic acid sequence, localized to chromosome 19p 13, has 2009 of 2015 bases (99%) identical to a gb:GENBANK-ID:AF326591|acc:AF326591.1 mRNA from *Homo sapiens* (*Homo sapiens* fenestrated-endothelial linked structure protein (FELS) mRNA, complete cds) (E=0.0).

A disclosed NOV7c polypeptide (SEQ ID NO:23) encoded by SEQ ID NO:22 is 442 amino acid residues and is presented using the one-letter amino acid code in Table 7F.

Signal P, Psort and/or Hydropathy results predict that NOV7c has a signal peptide and is likely to be localized in the plasma membrane with a certainty of 0.7900. In other embodiments, NOV7c is also likely to be localized to the nucleus with a certainty of 0.6000, to the microbody (peroxisome) with a certainty of 0.3000, or the Golgi body with a certainty of 0.3000. The most likely cleavage site for a NOV7c peptide is between amino acids 50 and 51, at: YVG-NV.

TABLE 7F

Encoded NOV7c protein sequence (SEQ ID NO:23).

MGLAMEHGGSYARAGGSSRGCWYYLRYFFLFVSLIQFLIILGLVLFMVYGNVHVSTESNLQATERRAEGLY

SQLLGLTASQSNLTKELNFTTRAKDAIMQMWLNARRDLDRINASFRQCQGDRVIYTNNQRYMAAIILSEKQ

CRDQFKDMNKSCDALLFMLNQKVKTLEVEIAKEKTICTKDKESVLLNKRVAEEQLVECVKTRELQHQERQL

AKEQLQRVQALCLPLDKDKFEMDLRNLWRDSIIPRSLDNLGYNLYHPLGSELASIRRACDHMPSLVSSKVE

ELARSLRADIERVARENSDLQRQKLEAQQGLRASQEAKQKVEKEAQAREAKLQAECSRQTQLALEEKAVLR

KERDNLAKELEEKKREAEQLRMELAIRNSALDTCIKTKSQPMMPVSRPMGPVPNPQPIDPASLEEFKRKIL

ESQRPPAGIPVAPSSG

---

The disclosed NOV7c amino acid sequence has 440 of 442 amino acid residues (99%) identical to, and 442 of 442 amino acid residues (100%) similar to, the 442 amino acid residue ptnr:SPTREMBL-ACC:Q9BX97 protein from *Homo sapiens* (Human) (PV1 PROTEIN) ($E=6.9e^{-231}$).

NOV7c is expressed in at least the following tissues: Heart, Adrenal Gland/Suprarenal gland, Thyroid, Salivary Glands, Liver, Bone Marrow, Spleen, Lymph Node, Mammary gland/Breast, Placenta, Prostate, Lung, Kidney, Pancreas, Bone Marrow, and Small Intestine. Expression information was derived from the tissue sources of the sequences that were included in the derivation of the sequence of CuraGen Acc. No. CG51878-03. The sequence is predicted to be expressed in the following tissues because of the expression pattern of (GENBANK-ID: gb:GENBANK-ID:AF326591|acc:AF326591.1) a closely related *Homo sapiens* fenestrated-endothelial linked structure protein (FELS) mRNA.

The NOV7a, 7c and 7c are very closely homologous as is shown in the alignment in Table 7G.

TABLE 7G

Alignment of NOV7a, 7b, and 7c.

```
                10         20         30         40         50         60
        ....|....|....|....|....|....|....|....|....|....|....|....|
NOV7a   MGLAMEHGGSYARAGGSSRGCWYYLRYFFLFVSLIQFLIILGLVLFMVYGNVHVSTESNL  60
NOV7b   MGLAME GGSYARAGGSSRGCWYYLRYFFLFVSLIQFLIILGLVLFMVYG VHVSTESNL  60
NOV7c   MGLAMEHGGSYARAGGSSRGCWYYLRYFFLFVSLIQFLIILGLVLFMVYGNVHVSTESNL  60

70         80         90        100        110        120
        ....|....|....|....|....|....|....|....|....|....|....|....|
NOV7a   QATERRAEGLYSQLLGLTASQSNLTKELNFTTRAKDAIMQMWLNARRDLDRINASFRQCQ 120
NOV7b   QATERRAEGLYSQLLGLTASQSNLTKELNFTTRAKDAIMQMWLNARRDLDRINASFRQCQ 120
NOV7c   QATERRAEGLYSQLLGLTASQSNLTKELNFTTRAKDAIMQMWLNARRDLDRINASFRQCQ 120

130        140        150        160        170        180
        ....|....|....|....|....|....|....|....|....|....|....|....|
NOV7a   GDRVITYNNQRYMAAIILSEKQCRDQFKDMNKSCDALLFMLNQKVKTLEVEIAKEKTICT 180
NOV7b   GDRVITYNNQRYMAAIILSEKQCRDQFKDMNKSCDALLFMLNQKVKTLEVEIAKEKTICT 180
NOV7c   GDRVITYNNQRYMAAIILSEKQCRDQFKDMNKSCDALLFMLNQKVKTLEVEIAKEKTICT 180

190        200        210        220        230        240
        ....|....|....|....|....|....|....|....|....|....|....|....|
NOV7a   KDKESVLLNKRVAEEQLVECVKTRELQHQERQLAKEQLQKVQALCLPLDKDKFEMDLRNL 240
NOV7b   KDKESVLLNKRVAEEQLVECVKTRELQHQERQLAKEQLQKVQALCLPLDKDKFEMDLRNL 240
NOV7c   KDKESVLLNKRVAEEQLVECVKTRELQHQERQLAKEQLQ VQALCLPLDKDKFEMDLRNL 240

250        260        270        280        290        300
        ....|....|....|....|....|....|....|....|....|....|....|....|
NOV7a   WRDSIIPRSLDNLGYNLYHPLGSELASIRRACDHMPSLMSSKVEGQCRSLRADIERVARE 300
NOV7b   WRDSIIPRSLDNLGYNLYHPLGSELASIRRACDHMPSLMSSKVEELARSLRADIERVARE 300
NOV7c   WRDSIIPRSLDNLGYNLYHPLGSELASIRRACDHMPSL SSKVEELARSLRADIERVARE 300

310        320        330        340        350        360
        ....|....|....|....|....|....|....|....|....|....|....|....|
NOV7a   NSDLQRQKLEAQQGLRASQEAKQKVEKEAQAREAKLQAECSRQTQLALEEKAVLRKERDN 360
NOV7b   NSDLQRQKLEAQQGLRASQEAKQKVEKEAQAREAKLQAECSRQTQLALEEKAVLRKERDN 360
NOV7c   NSDLQRQKLEAQQGLRASQEAKQKVEKEAQAREAKLQAECSRQTQLALEEKAVLRKERDN 360

370        380        390        400        410        420
        ....|....|....|....|....|....|....|....|....|....|....|....|
NOV7a   LAKELEEKKREAEQLRMELAIRNSALDTCIKTKSQPMMPVSRPMGPVPNPQPIDPASLEE 420
NOV7b   LAKELEEKKREAEQLRMELAIRNSALDTCIKTKSQPMMPVSRPMGPVPNPQPIDPASLEE 420
NOV7c   LAKELEEKKREAEQLRMELAIRNSALDTCIKTKSQPMMPVSRPMGPVPNPQPIDPASLEE 420
```

Homologies to any of the above NOV7 proteins will be shared by the other two NOV7 proteins insofar as they are homologous to each other as shown above. Any reference to NOV7 is assumed to refer to all three of the NOV7 proteins in general, unless otherwise noted.

NOV7a also has homology to the amino acid sequence shown in the BLASTP data listed in Table 7H.

TABLE 7H

BLAST results for NOV7a

| Gene Index/ Identifier | Protein/Organism | Length (aa) | Identity (%) | Positives (%) | Expect |
|---|---|---|---|---|---|
| gi\|12963353\|gb\| AAK11226.1\| | fenestrated-endothelial linked structure protein [Homo sapiens] | 442 | 438/442 (99%) | 438/442 (99%) | 0.0 |
| gi\|13775238\|ref\|NP_112600.1\| | fenestrated-endothelial linked structure protein; PV-1 protein [Homo sapiens]) | 442 | 439/442 (99%) | 439/442 (99%) | 0.0 |
| gi\|9910520\|ref\|NP_064471.1\| | PV-1 [Rattus norvegicus] | 438 | 266/442 (60%) | 347/442 (78%) | e-131 |
| gi\|14161394\|gb\| AAK54730.1\| AF369900_1 | MECA32 [Mus musculus] | 438 | 270/442 (61%) | 348/442 (78%) | e-125 |
| gi\|14161698\|ref\|NP_115774.1\| | plasmalemma vesicle associated protein [Mus musculus] | 438 | 269/442 (60%) | 346/442 (77%) | e-125 |

The homology of these sequences is shown graphically in the ClustalW analysis shown in Table 7I.

TABLE 7I

Information for the ClustalW proteins

1) NOV7 (SEQ ID NO:19)
2) gi|12963353|gb|AAK11226.1| fenestrated-endothelial linked structure protein [Homo sapiens] (SEQ ID NO:55)
3) gi|13775238|ref|NP_112600.1| fenestrated-endothelial linked structure protein; PV-1 protein [Homo sapiens]) (SEQ ID NO:56)
4) gi|9910520|ref|NP_064471.1| PV-1 [Rattus norvegicus] (SEQ ID NO:57)
5) gi|14161394|gb|AAK54730.1|AF369900_1 MECA32 [Mus musculus] (SEQ ID NO:58)
6) gi|14161698|ref|NP_115774.1| plasmalemma vesicle associated protein [Mus musculus] (SEQ ID NO:59)

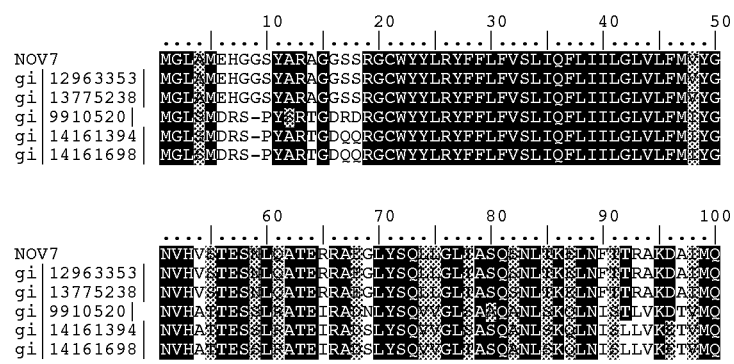

TABLE 7I-continued

Information for the ClustalW proteins

```
                110       120       130       140       150
              ....|....|....|....|....|....|....|....|....|....|
NOV7          MWLNARR  RINASFRQCQGDR IYTNNQR  AAIILSEKQC  QFK
gi|12963353|  MWLNARR  RINASFRQCQGDR IYTNNQR  AAIILSEKQC  QFK
gi|13775238|  MWLNARR  RINASFRQCQGDR IYTNNQR  AAIILSEKQC  QFK
gi|9910520|   QTLTTRR  RINASFRQCQGDL TYINYR   AAIILSEKQC  QLK G
gi|14161394|  QTLTTRR  RINASFRQCQGDL TYINYR   AAIILSEKQC  QLK
gi|14161698|  QTLTTRR  RINASFRQCQGDL TYINYR   AAIILSEKQC  QLK 160       170       180       190       200
              ....|....|....|....|....|....|....|....|....|....|
NOV7          NK C ALLEML N KVKTLE E AKEKT C KDKES L LNKRVAEEQLVEC
gi|12963353|  NK C ALLEML N KVKTLE E AKEKT C KDKES L LNKRVAEEQLVEC
gi|13775238|  NK C ALLEML N KVKTLE E AKEKT C KDKES L LNKRVAEEQLVEC
gi|9910520|   NK C ALLFKLG KVKTLE E VKEKA C KDK S L AGKRQAEMQQEAC
gi|14161394|  NK C ALLFKLG KVKTLE E AKEKA C KDKES L AGKRQTEEQLEAC
gi|14161698|  NK C ALLFKLG KVKTLE E AKEKA C KDKES L AGKRQAEEQLEAC 210       220       230       240       250
              ....|....|....|....|....|....|....|....|....|....|
NOV7          VKTRELQHQE Q A EQI KVQ LCLPLD KF MD RN WRDS IPRSL
gi|12963353|  VKTRELQHQE Q A EQI KVQ LCLPLD KF MD RN WRDS IPRSL
gi|13775238|  VKTRELQHQE Q A EQI KVQ LCLPLD KF MD RN WRDS IPRSL
gi|9910520|   GKAREQQE Q Q T EQL KVQ LCLPLD KF AD LN WRDS YRSL
gi|14161394|  GKARERQQE Q Q T ENL KVQ LCLPLD KF AD L AWRDS IYR L
gi|14161698|  GKARERQQE Q Q T ENL KVQ LCLPLD KF AD L AWRDS IYR L 260       270       280       290       300
              ....|....|....|....|....|....|....|....|....|....|
NOV7          DNLGYNL  PLGSELAS RRAC H PS M   KVEGQCRS LRAD IERV ARE
gi|12963353|  DNLGYNL  PLGSELAS RRAC H PS M   KVEELARS LRAD IERV ARE
gi|13775238|  DNLGYNL  PLGSELAS RRAC H PS M   KVEELARS LRAD IERV ARE
gi|9910520|   DN GY-- RYSLMPEF S  RRTC S PG M   KVEELARG LRAG IERV TRE
gi|14161394|  TLPY--  QLMPEYAS  RRTC S PG M   KEELARG LRAG IERV TRE
gi|14161698|  TLPY--  QLMPEYAS  RRTC S PG M PPK EE ARG RAG IERV TRE 310       320       330       340       350
              ....|....|....|....|....|....|....|....|....|....|
NOV7          N  L RQKLEA  G A QEA Q VEKEAQAREA L AEC RQTQLALEE
gi|12963353|  N  L RQKLEA  G A QEA Q VEKEAQAREA L AEC RQTQLALEE
gi|13775238|  N  L RQKLEA  G A QEA Q VEKEAQAREA L AEC RQTQLALEE
gi|9910520|   NG L RQKLEL  A GE EART AGTEAQARE T  EC RQTQLALEE
gi|14161394|  N  L RQKLEL  AA A QEA A AGTEAQARE T L AEC RQTQLALEE
gi|14161698|  N  L RQKLEL  AA R QEA A AGTEAQARE T L AEC RQTQLALEE 360       370       380       390       400
              ....|....|....|....|....|....|....|....|....|....|
NOV7          KAV LRK RDNLA ELE E KREAEQLRM  A RNSALDTC KTKSQPMM V
gi|12963353|  KAV LRK RDNLA ELE E KREAEQLRM  A RN SALDTC KTKSQPMM V
gi|13775238|  KAV LRK RDNLA ELE E KREAEQLRM  A RN SALDTC KTKSQPMM V
gi|9910520|   KAALRT R  LE  LEA KRELEQLRT  D RISALDTC KAKSLEA QP
gi|14161394|  KAALRA RDNLE ELEA KRELEQLRT  D RISALDTC KAKSLPA PP
gi|14161698|  KAV LRA RDNLE ELEA KRELEQLRT  D RISALDTC KAKSLPA PP 410       420       430       440
              ....|....|....|....|....|....|....|....|..
NOV7          SRPMGPVPNPQPIDPASLEEFK  ILESQRPPAGIPVAE SSG
gi|12963353|  SRPMGPVPNPQPIDPASLEEFK  ILESQRPPAGIPVAE SSG
gi|13775238|  SRPMGPVPNPQPIDPASLEEFK  ILESQRPPAGIPVAE SSG
gi|9910520|   -RLEGPPPNPPPIDPASLEEFK  ILESQRPPLVNPAVE PSG
gi|14161394|  -RVSGPPPNPPPIDPASLEEFK  ILESQRLPVVNPAA QPSG
gi|14161698|  -RVSGPPPNPPPIDPASLEEFK  ILESQRLPVVNPAA QPSG
```

PV-1 is a novel endothelial protein shown by immunocytochemical tests to be specifically associated with the stomatal diaphragms of caveolae in lung endothelium (Stan R V, et. al.; Proc Natl Acad Sci USA 1999 Nov. 9;96(23):13203–7). Although the highest expression levels of both mRNA and protein are in the lung, PV-1 also has been found to be expressed in other organs. Using a specific antibody to the extracellular domain of PV-1, the survey on the presence of this protein at light and electron microscope level has been extended in several rat organs. It has been shown by immunofluorescence the antibody recognizes with high specificity the endothelium of the fenestrated peritubular capillaries of the kidney and those of the intestinal villi, pancreas, and adrenals. By immunolocalization at electron microscope level, the antibody recognizes specifically the diaphragms of the fenestrae and the stomatal diaphragms of caveolae and transendothelial channels in the endothelia of these vascular beds. No signal was detected in the continuous endothelium of the heart, skeletal muscle, intestinal muscularis, or brain capillaries or the nondiaphragmed fenestrated endothelium of kidneyglomeruli. Taken together, the findings define the only antigen to be localized thus far in fenestral diaphragms. They also show that the stomatal diaphragms of caveolae and transendothelial channels and the fenestral diaphragms might be biochemically related, in addition to being morphologically similar structures.

By using an immunoisolation procedure (Stan, R.-V., W. G. Roberts, K. Ihida, D. Predescu, L., Saucan, L. Ghitescu, and G. E. Palade. 1997. Mol. Biol. Cell. 8:595–605) developed in our laboratory, a caveolar subfraction from rat lung endothelium has been isolated and the proteins of this subfraction have been partially characterized which include an apparently caveolae-specific glycoprotein is proposed to be called PV-1 (formerly known as gp68). The isolation and partial sequencing of PV-1, combined with the cloning of the full length PV-1 cDNA led to the following conclusions: (a) PV-1 is a novel single span type II integral membrane protein (438 amino acids long) which forms homodimers in situ; (b) the transmembrane domain of PV-1 is near the NH2 terminus defining a short cytoplasmic endodomain and a large COOH-terminal ectodomain exposed to the blood plasma; (c) PV-1 is N-glycosylated and its glycan antennae bear terminal nonreducing galactosyl residues in alpha 1–3 linkage. PV-1 is expressed mostly in the lung but both the messenger RNA and the protein can be detected at lower levels also in kidney, spleen, liver, heart, muscle, and brain. No signal could be detected in testis and two lower molecular weight forms were detected in brain. Immunocytochemical studies carried out by immunodiffusion on rat lung with an anti-PV-1 polyclonal antibody directed against a COOH-terminal epitope reveal a specific localization of PV-1 to the stomatal diaphragms of rat lung endothelial caveolae and confirm the extracellular orientation of the PV-1 COOH terminus (Stan, R. V. J. Cell. Biol., 1999, Jun. 14; 145(6): 189–98).

Immunohistochemistry revealed initial expression of the stage-specific glycoprotein, GP68, in various mesenchymal tissue substructures of mouse embryos (Morita T, et. al.; Okajimas Folia Anat Jpn 1998 October;75(4): 185–95). During the 11–15th days of gestation, GP68 was localized in the primitive meninges, chondroblasts and perichondrium of pre-cartilaginous vertebral bodies and ribs, connective tissue cells of the dermis, the epicardium and endocardium of the heart, the epimysium and perimysium of skeleton musclature, and the basement membranes of splanchnic organs. Double staining for laminin expression indicated coincidental expression in identical tissue substructures. However, laminin was expressed in days 10–18 embryos and the neonate. Therefore, GP68 is coincidentally expressed with laminin in mesenchymal tissues between the 11th and 15th day of gestation, and may play a role as a laminin-associated protein. In the light of these results, a hypothesis concerning the relationship between these two proteins and the mechanisms of non-integrin laminin-associated proteins during normal embryogenesis is discussed further.

The microvascular endothelium is organized as a highly differentiated squamous epithelium whose main function is to mediate the exchanges of water, macromolecules, and small solutes between the blood plasma and the interstitial fluid. The endothelial structures implicated so far in the transendothelial transport are the caveolae, transendothelial channels, intercellularjunctions, and the fenestrae. Caveolae are flask-shaped or spherical plasma membrane invaginations and associated vesicles of 70-nm average outer diameter that can occur singly or in chains or clusters. In invaginated form, their membranes is in continuity layer by layer with the plasmalemma proper, and, in some microvascular beds (e.g., the continuous endothelium of the lung and the fenestrated and sinusoidal endothelia), their introits or necks are provided with a stomatal diaphragm.

The transendothelial channels are channels of 60–70-nm diameter that run across the endothelial cell. They seem to be formed by the fusion of either one caveola with both luminal and abluminal aspects of the plasmalemma or by chains of usually two to four caveolae. These channels are provided with two diaphragms (one luminal and one abluminal) only in fenestrated endothelia and not in their continuous counterparts.

The diaphragmed fenestrae are characteristic structural elements of all fenestrated endothelia (e.g., kidney peritubular capillaries and ascending vasa recta, capillaries of intestinal villi, pancreas, adrenal cortex, endocrine glands, and choriocapillaries of the brain and eye). They are round openings or windows cutting through the endothelial cell, have a constant diameter of 63–68 nm, and occur only in the attenuated parts of the cell, in clusters referred to as "sieve plates". In en face electron microscopic images, the fenestrae appear circular, but several studies have shown that they have an 8-fold symmetry. The rim of the fenestra (where the abluminal plasmalemma is continuing the luminal plasmalemma) is the anchoring line for the fenestral diaphragm. In normal sections, the diaphragm appears as a very thin (5–6 nm) single-layer barrier provided with a central density or knob. Deep-etch rapid-freeze techniques have revealed the structure of the diaphragm to be composed of radial fibrils (7-nm diameter) starting at the rim and interweaving in a central mesh (the equivalent of the central knob in orthogonal sections).

Although the chemical composition of endothelial caveolae started to yield some insights, the molecular components of transendothelial channels and fenestrae remained elusive. The chemistry of these endothelial microdomains has been investigated with nonspecific "general" probes (charged molecules and lectins alone or in combination with various degrading enzymes), which yielded some information on the surface charge, type of molecules conferring the charge, and type of glycan antennae found on the glycoproteins and glycolipids. No specific component of the fenestral or transendothelial channels diaphragms has been identified so far.

Proteins reported to be contained within caveolae include G protein-coupled receptors (GPCR) (Ostrom R S, et al., J Pharmacol Exp Ther 2000 August;294(2):407–12), scavenger receptor class B type I (SR-BI) (Krieger M Annu Rev Biochem 1999;68:523–58), Monocarboxylate transporters (Bonen A, Med Sci Sports Exerc 2000 April;32(4):778–89), endothelial NOS (eNOS) (Kone BC Acta Physiol Scand 2000 January; 168(1):27–31). IP3 receptor-like protein, Ca2+ ATPase, several PKC isoforms. (Isshiki M, et al., Cell Calcium 1999 November;26(5):201–8). and GPI-anchored molecules (Martins V R, Braz J Med Biol Res 1999 July;32 (7):853–9).

The disclosed NOV7 nucleic acid of the invention encoding a PV-1-like protein includes the nucleic acid whose sequence is provided in Table 7A, 7C, or 7E or a fragment thereof. The invention also includes a mutant or variant nucleic acid any of whose bases may be changed from the corresponding base shown in Table 7A, 7C, or 7E while still encoding a protein that maintains its PV-1-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 30% percent of the bases may be so changed.

The disclosed NOV7 protein of the invention includes the PV-1-like protein whose sequence is provided in Table 7B, 7D, or 7F. The invention also includes a mutant or variant protein any of whose residues may be changed from the corresponding residue shown in Table 7B, 7D, or 7F while still encoding a protein that maintains its PV-1-like activities and physiological functions, or a functional fragment thereof. In the mutant or variant protein, up to about 40% percent of the residues may be so changed.

The protein similarity information, expression pattern, and map location for the PV-1-like protein and nucleic acid (NOV7) disclosed herein suggest that NOV7 may have important structural and/or physiological functions characteristic of the PV-1-like family. Therefore, the NOV7 nucleic acids and proteins of the invention are useful in potential diagnostic and therapeutic applications. These include serving as a specific or selective nucleic acid or protein diagnostic and/or prognostic marker, wherein the presence or amount of the nucleic acid or the protein are to be assessed, as well as potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), and (v) a composition promoting tissue regeneration in vitro and in vivo.

The NOV7 nucleic acids and proteins of the invention are useful in potential diagnostic and therapeutic applications implicated in various diseases and disorders described below and/or other pathologies. For example, the compositions of the present invention will have efficacy for treatment of patients suffering from Cerebellar ataxia, pure; Episodic ataxia, type 2; Hemiplegic migraine, familial; Leigh syndrome; Spinocerebellar ataxia-6; Psoriasis, susceptibility to; Autoimmune disease, Asthma, Emphysema, Scleroderma, allergy, ARDS, Von Hippel-Lindau (VHL) syndrome, Alzheimer's disease, Stroke, Tuberous sclerosis, hypercalceimia, Parkinson's disease, Huntington's disease, Cerebral palsy, Epilepsy, Lesch-Nyhan syndrome, Multiple sclerosis, Ataxia-telangiectasia, Leukodystrophies, Behavioral disorders, Addiction, Anxiety, Pain, Neuroprotection, Muscular dystrophy, Myasthenia gravis, Hemophilia, Hypercoagulation, Idiopathic thrombocytopenic purpura, Immunodeficiencies, Graft vesus host, Von Hippel-Lindau (VHL) syndrome, Cirrhosis, Transplantation, Cardiomyopathy, Atherosclerosis, Hypertension, Congenital heart defects, Aortic stenosis Atrial septal defect (ASD), Atrioventricular (A-V) canal defect, Ductus arteriosus, Pulmonary stenosis, Subaortic stenosis, Ventricular septal defect (VSD), valve diseases, Scleroderma, Obesity, Transplantation; fertility; cancer; Renal artery stenosis, Interstitial nephritis, Glomerulonephritis, Polycystic kidney disease, Systemic lupus erythematosus, Renal tubular acidosis, IgA nephropathy, Hypercalceimia, Lesch-Nyhan syndrome, Adrenoleukodystrophy, Congenital Adrenal Hyperplasia, Xerostomia; tooth decay and other dental problems; Inflammatory bowel disease, Diverticular disease, Pancreatitis, and/or other pathologies/disorders. The NOV7 nucleic acid, or fragments thereof, may further be useful in diagnostic applications, wherein the presence or amount of the nucleic acid or the protein are to be assessed.

NOV7 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV7 protein have multiple hydrophilic regions, each of which can be used as an immunogen. In one embodiment, contemplated NOV7 epitope is from about amino acids 5 to 25. In other embodiments, NOV7 epitope is from about amino acids 50 to 75, from about amino acids 80 to 160, from about amino acids 175 to 275, from about amino acids 280 to 380, or from about amino acids 385 to 430. This novel protein also has value in development of powerful assay system for functional analysis of various human disorders, which will help in understanding of pathology of the disease and development of new drug targets for various disorders.

NOV8

NOV8 includes two novel Papin-like proteins disclosed below. The disclosed proteins have been named NOV8a, and NOV8b.

NOV8a

A disclosed NOV8a nucleic acid of 8640 nucleotides (also referred to as SC134914330_A) encoding a novel papin-like protein is shown in Table 8A. An open reading frame was identified beginning with an ATG initiation codon at nucleotides 101–103 and ending with a TGA codon at nucleotides 8543–8545. A putative untranslated region upstream from the initiation codon and downstream from the termination codon is underlined in Table 8A. The start and stop codons are in bold letters.

TABLE 8A

NOV8a nucleotide sequence (SEQ ID NO:24).

AGCTGATGATGGCCAGGGACCCCAGGGGACGTGGGGCCCTGTGGGGTCTGGCCCCCAGGAGCAAGACCTCTG

ATGATGCTGGTGTCTGGGAGTGAGCACCATGCCCATCACCCAGGACAATGCCGTGCTGCACCTGCCCCTCCT

CTACCAGTGGCTGCAGAACAGCCTGCAGGAAGGTGGGGATGGGCCGGAGCAGCGGCTCTGCCAGGCGGCCAT

CCAGAAGCTGCAGGAGTACATCCAGCTGAACTTTGCTGTGGATGAGAGTACGGTCCCACCTGATCACAGCCC

CCCCGAAATGGAGATCTGTACTGTGTACCTCACCAAGGAGCTGGGGGACACAGAGACTGTGGGCCTGAGTTT

TGGGAACATCCCTGTTTTCGGGGACTATGGTGAAAAGCGCAGGGGGGGCAAGAAGAGGAAAACCCACCAGGG

TABLE 8A-continued

NOV8a nucleotide sequence (SEQ ID NO:24).

```
TCCTGTGCTGGATGTGGGCTGCATCTGGGTGACAGAGCTGAGGAAGAACAGCCCAGCAGGGAAGAGTGGGAA
GGTCCGACTGCGGGATGAGATCCTCTCACTGAATGGGCAGCTGATGGTTGGAGTTGATGTCAGTGGGGCCAG
TTACCTGGCTGAGCAGTGCTGGAATGGCGGCTTTATCTACCTGATCATGCTGCGTCGCTTTAAGCACAAAGC
CCACTCCACTTATAATGGCAACAGTAGCAACAGCTCTGAACCAGGAGAAACACCTACCTTGGAGCTGGGTGA
CCGAACTGCGAAAAAGGGGAAACGAACCAGAAAGTTTGGGGTCATCTCCAGGCCTCCTGCCAACAAGGCCCC
TGAAGAATCCAAGGGCAGCGCTGGCTGTGAGGTGTCCAGTGACCCCAGCACTGAGCTGGAGAACGGCCTGGA
CCCTGAACTTGGAAACGGCCATGTCTTTCAGCTAGAAAATGGCCCAGATTCTCTCAAGGAGGTGGCTGGACC
CCATCTAGAGAGGTCAGAAGTGGACAGAGGGACAGAGCATAGAATTCCAAAGACAGATGCTCCTCTGACCAC
AAGCAATGACAAACGCCGCTTCTCAAAAGGTGGGAAGACGGACTTCCAATCGAGTGACTGCCTGGCACGGTC
CAAGGAGGAAGTTGGCCGAATATGGAAGATGGAGCTGCTCAAAGAATCGGATGGGCTGGGAATTCAGGTTAG
TGGAGGCCGAGGATCAAAGCGCTCACCTCACGCTATCGTTGTCACTCAAGTGAAGGAAGGAGGTGCCGCTCA
CAGGCTCAGGGATGGCAGGCTGTCCTTAGGAGATGAGCTGCTGGTAATCAATGGTCATTTACTGGTCGGGCT
CTCCCACGAGGAAGCAGTGGCCATTCTTCGCTCCGCCACGGGAATGGTGCAGCTTGTGGTGGCCAGCAAGGT
AGGTGTGCTTTCTGCATTTCAGATGCCTGGGACAGATGAACCCCAAGATGTGTGCGGTGCTGAGGAATCCAA
GGGGAACTTGGAAAGTCCCAAACAGGGCAGCAATAAAATCAAGCTCAAGAGTCGCCTTTCAGGTAGGTGGGG
GCTCTACCTGATGCAGCCTGTCGGGGGTGTACACCGCCTTGAGTCAGTTGAAGAATATAACGAGCTGATGGT
GCGGAATGGGGACCCCCGGATCCGGATGTTGGAGGTCTCCCGAGATGGCCGGAAACACTCCCTCCCGCAGCT
GCTGGACTCTTCCAGTGCCTCACAGGAATACCACATTGTGAAGAAGTCTACCCGCTCCTTAAGCACGACTCA
GGTGGAATCTCCTTGGAGGCTCATTCGGCCATCCGTCATCTCGATCATTGGGTTGTACAAAGAAAAAGGCAA
GGGCCTTGGCTTTAGTATTGCTGGAGGTCGAGACTGCATTCGTGGACAGATGGGGATTTTTGTCAAGACCAT
CTTCCCAAATGGATCAGCTGCAGAGGACGGAAGACTTAAAGAAGGTGATGAAATCCTAGATGTAAATGGAAT
ACCAATAAAGGGCTTGACATTTCAAGAAGCCATTCATACCTTTAAGCAAATCCGGAGTGGATTATTTGTTTT
AACGGTACGCACAAAGTTGGTGAGCCCCAGCCTCACACCCTGCTCGACACCCACACACATGAGCAGATCCGC
CTCCCCGAACTTCAATACCAGTGGGGGAGCCTCGGCGGGAGGTTCCGATGAAGGCAGTTCTTCATCCCTGGG
TCGGAAGACCCCTGGGCCCAAGGACAGGATCGTCATGGAAGTAACACTCAACAAAGAGCCAAGAGTTGGATT
AGGCATTGGTGCCTGCTGCTTGGCTCTGGAAAACAGTCCTCCTGGCATCTACATTCACAGCCTTGCTCCAGG
ATCAGTGGCCAAGATGGAGAGCAACCTGTCGCGGGGATCAATCCTGGAAGTGAACTCCGTCAACGTCCGCCA
TGCTGCTTTAAGCAAAGTCCACGCCATCTTGAGTAAATGCCCTCCAGGACCCGTTCGCCTTGTCATCGGCCG
GCACCCTAATCCAAAGGTGAATCAGGTTTCCGAGCAGGAAATGGATGAAGTCATAGCACGCAGCACTTATCA
GGAGAGCAAAGAGGCCAATTCCTCTCCTGGCTTAGGTACTGTAATCTCAATCGGATGTTTTCTTCTTCAACA
GGACTCCCTTATTTCTGAATCTGAACTCTCCCAGTACTTTGCCCACGATGTCCCTGGCCCCTTGTCAGACTT
CATGGTGGCCGGTTCTGAGGACGAGGATCACCCGGGAAGTGGCTGCAGCACGTCGGAGGAGGGCAGCCTGCC
TCCCAGCACCTCCACTCACAAGGAGCCTGGAAAACCCAGAGCCAACAGCCTCGTGACTCTTGGGAGCCATCG
GGCTTCTGGGCTCTTCCACAAGCAGGTGACAGTTGCCAGACAAGCCAGTCTCCCCGGAAGCCCACAGGCCCT
CCGAAACCCTCTCCTCCGCCAGAGGAAGGTAGGCTGCTACGATGCCAACGATGCCAGTGATGAGGAAGAGTT
TGACAGAGAAGGGGACTGCATTTCACTCCCAGGGGCCCTCCCGGGTCCCATCAGGCCTCTGTCAGAGGATGA
CCCGAGGCGTGTCTCAATTTCCTCTTCCAAGGGCATGGACGTCCACAACCAAGAGGAACGACCCCGGAAAAC
ACTGGTGAGCAAGGCCATCTCGGCACCTCTTCTTGGTAGCTCAGTGGACTTAGAGGAGAGTATCCCAGAGGG
CATGGTGGATGCTGCGTCCTATGCAGCCAACCTCACGGACTCTGCAGAGGCCCCCAAGGGGAGCCCTGGAAG
```

TABLE 8A-continued

NOV8a nucleotide sequence (SEQ ID NO:24).

```
CTGGTGGAAGAAGGAACTGTCAGGATCAAGTAGCGCACCCAAATTGGAATACACAGTCCGTACAGACACCCA
GAGTCCGACAAACACTGGGAGCCCCAGTTCCCCCCAGCAAAAAAGTGAAGGCCTGGGCTCCAGGCACAGACC
AGTGGCCAGGGTAAGCCCCCACTGCAAGAGATCCGAGGCTGAGGCCAAGCCCAGTGGCTCACAGACAGTGAA
CCTGACTGGCAGAGCCAATGATCCATGCGATCTGGACTCGAGAGTCCAGGCCACTTCTGTCAAAGTGACTGT
CGCTGGCTTTCAGCCAGGTGGAGCTGTGGAGAAGGAATCTCTGGGAAAGCTGACCACTGGAGATGCTTGTGT
CTCTACCAGCTGTGAACTAGCCAGTGCTCTGTCCCATCTGGATGCCAGCCACCTCACAGAGAACCTGCCCAA
AGCTGCATCAGAGCTGGGGCAACAACCCATGACTGAACTGGACAGCTCCTCGGACCTCATCTCTTCCCCAGG
GAAGAAGGGGCCGCTCATCCTGACCCCAGAAGACCTCTGTAGACACAGGGAAAGTCAGTCGGCCAAGAGAA
TCCCAGCCAGCCTGCATCGCCCAGGGTCGCCAAGTGCAAGGCCAGGTGTCCAGTCAGGCTCCCCCATGAGGG
CAGCCCCTCCCCAGGGGAGAAAGCAGCGGCTCCCCCTGACTACAGCAAGACTCGATCAGCATCGGAAACCAG
CACACCCCACAATACCAGGAGGGTGGCTGCCCTCAGGGGAGCGGGACCTGGAGCAGAGGGAATGACACCAGC
TGGTGCTGTCCTGCCAGGAGACCCCCTCACATCCCAGGAGCAGAGACAGGGCGCTCCAGGTAACCACAGTAA
GGCTCTGGAAATGACAGGAATCCATGCACCTGAAAGCTCCCAGGAGCCTTCCCTGCTGGAGGGAGCAGATTC
TGTGTCCTCAAGGGCACCGCAGGCCAGCCTCTCCATGCTGCCATCCACTGACAACACCAAAGAAGCATGTGG
CCATGTCTCGGGGCACTGCTGCCCGGGGGGAGTAGAGAGAGCCCTGTGACGGACATTGACAGCTTCATCAA
GGAGCTGGATGCTTCTGCAGCAAGGTCTCCGTCTTCCCAGACGGGGACAGTGGCTCTCAGGAGGGCAGTGC
TCAGGGCCACCCACCAGCCGGGGCTGGAGGTGGGAGCTCCTGCCGTGCCGAACCAGTCCCGGGGGGCCAGAC
CTCCTCCCCGAGGAGGGCCTGGGCTGCTGGTGCCCCGCCTACCCACAATGGGCCTCCCAGCCTTCGGTTTT
AGATTCAATTAATCCCGACAAACATTTTACTGTGAACAAAAACTTTCTGAGCAACTACTCTAGAAATTTTAG
CAGTTTTCATGAAGACAGCACCTCCCTATCAGGCCTGGGTGACAGCACGGAGCCGTCTCTGTCATCCATGTA
TGGCGATGCTGAGGATTCTTCTTCTGACCCTGAGTCACTCACTGAAGCCCCACGAGCTTCTGCCAGGGACGG
CTGGTCCCCTCCTCGTTCCCGTGTGTCTTTGCACAAGGAAGATCCTTCGGAGTCAGAAGAGGAACAGATTGA
GATTTGTTCCACACGTGGCTGCCCCAATCCACCCTCGAGTCCTGCTCATCTTCCCACCCAGGCTGCCATCTG
TCCTGCCTCAGCCAAAGTTCTGTCATTAAAATACAGCACTCCGAGAGAGTCGGTGGCCAGTCCCCGTGAGAA
GGTCGCCTGCTTGCCAGGCTCATACACTTCAGGCCCAGACTCTTCCCAGCCATCATCACTCTTGGAGATGAG
CTCTCAGGAGCATGAAACTCATGCGGACATAAGCACTTCACAGAACCACAGGCCCTCGTGTGCAGAAGAAAC
CACAGAAGTCACCAGCGCTAGCTCAGCCATGGAAAACAGTCCGCTGTCTAAAGTAGCCAGGCATTTTCACAG
TCCGCCCATCATTCTCAGCTCCCCCAACATGGTAAATGGCTTGGAACATGACCTGCTAGATGACGAAACCCT
GAATCAATACGAAACAAGCATTAATGCAGCTGCCAGTCTGTCCTCCTTCAGTGTGGATGTCCCTAAGAATGG
AGAATCTGTTTTGGAAAACCTCCACATCTCTGAAAGTCAAGACCTGGATGACTTGCTACAGAAACCAAAAAT
GATCGCTAGGAGGCCCATCATGGCCTGGTTTAAAGAAATAAATAAACATAACCAAGGCACACATTTGAGGAG
CAAAACCGAGAAGGAACAACCTCTAATGCCTGCCAGAAGTCCCGACTCCAAGATTCAGATGGTGAGTTCAAG
CCAAAAAAAGGGCGTTACTGTGCCTCATAGCCCTCCTCAGCCGAAAACAAACCTGGAAAATAAGGACCTGTC
TAAGAAGAGTCCGGCAGAAATGCTTCTGACTAATGGTCAGAAGGCAAAGTGTGGTCCGAAGCTGAAGAGGCT
CAGCCTCAAGGGCAAGGCCAAAGTCAACTCTGAGGCCCCTGCTGCGAATGCTGTGAAGGCTGGGGGACGGA
CCACAGGAAACCCTTGATCTCACCCCAGACCTCCCACAAAACACTTTCTAAGGCAGTGTCACAGCGGCTCCA
TGTAGCCGACCACGAGGACCCTGACAGAAACACCACAGCTGCCCCCAGGTCCCCCCAGTGTGTGCTGGAAAG
CAAGCCACCTCTTGCCACCTCTGGGCCACTGAAACCCTCAGTGTCTGACACGAGCATCAGGACATTTGTCTC
```

TABLE 8A-continued

NOV8a nucleotide sequence (SEQ ID NO:24).

GCCCCTGACCTCTCCCAAGCCTGTTCCTGAGCAAGGCATGTGGAGCAGGTTCCACATGGCTGTCCTCTCTGA

ACCCGACAGAGGTTGCCCAACCACCCCTAAATCTCCTAAGTGTAGAGCAGAGGGCAGGGCGCCCCGTGCTGA

CTCCGGGCCGGTGAGTCCGGCAGCGTCTAGGAACGGCATGTCCGTGGCAGGGAACAGACAGAGTGAGCCGCG

CCTGGCCAGCCATGTGGCAGCAGACACAGCCCAACCCAGGCCGACTGGCGAAAAAGGAGGCAACATAATGGC

CAGCGATCGCCTCGAAAGAACAAACCAGCTGAAAATCGTGGAGATTTCTGCTGAAGCAGTGTCAGAGACTGT

ATGTGGTAACAAGCCAGCTGAAAGCGACAGACGGGGAGGGTGCTTGGCCCAGGGCAACTGTCAGGAGAAGAG

TGAAATCAGGCTCTATCGCCAGGTCGCAGAATCATCCACAAGTCATCCATCCTCACTCCCATCTCATGCCTC

CCAGGCAGAGCAGGAAATGTCACGATCATTCAGCATGGCAAAAGTGGCGTCCTCCTCCTCCTCCCTTCAAAC

AGCCATTAGAAAGGCAGAATACTCCCAGGGAAAATCAAGCCTGATGTCAGACTCCCGAGGGGTGCCCAGAAA

CAGCATTCCAGGGGCCCCTCGGGGGAGGACCATCTCTACTTCACCCCAAGGCCAGCGACCAGGACCTACTC

CATGCCAGCCCAGTTCTCAAGCCATTTTGGACGGGAGGGTCACCCCCCACACAGCCTGGGTCGCTCTCGGGA

CAGCCAGGTCCCTGTGACAAGCAGTGTTGTCCCCGAGGCAAAGGCATCCAGAGGTGGTCTTCCCAGCCTGGC

TAATGGACAGGGCATATATAGTGTAAAGCCGCTGCTGGACACATCGAGGAATCTTCCAGCCACAGATGAAGG

GGATATCATTTCAGTCCAGGAGACGAGCTGCCTAGTCACAGACAAAATCAAAGTCACCAGACGACACTACTG

CTATGAGCAGAACTGGCCCCATGAATCTACCTCATTTTTCTCTGTGAAGCAGCGGATCAAGTCTTTTGAGAA

CCTGGCCAATGCTGACCGGCCTGTAGCCAAGTCCGGGGCTTCCCCATTTTTGTCGGTGAGCTCCAAGCCTCC

CATTGGGAGGCGGTCTTCCGGCAGCATTGTTTCCGGGAGCCTGGGCCACCCAGGTGACGCAGCAGCAAGGTT

GTTGAGACGCAGCTTGAGTTCCTGCAGCGAAAACCAAAGCGAAGCCGGCACCCTCCTGCCCCAGATGGCCAA

GTCTCCCTCAATCATGACACTGACCATCTCTCGGCAGAACCCACCAGAGACCAGTAGCAAGGGCTCTGATTC

GGAACTAAAGAAATCACTTGGTCCTTTGGGAATTCCCACCCCAACGATGACCCTGGCTTCTCCTGTTAAGAG

GAACAAGTCCTCGGTACGCCACACGCAGCCCTCGCCCGTGTCCCGCTCCAAGCTCCAGGAGCTGAGAGCCTT

GAGCATGCCTGACCTTGACAAGCTCTGCAGCGAGGATTACTCAGCAGGGCCGAGCGCCGTGCTCTTCAAAAC

TGAGCTGGAGATCACCCCCAGGAGGTCACCTGGCCCTCCTGCTGGAGGCGTTTCGTGTCCCGAGAAGGGCGG

GAACAGGGCCTGTCCAGGAGGAAGTGGCCCTAAAACCAGTGCTGCTGAGACACCCAGTTCAGCCAGTGATAC

GGGTGAAGCTGCCCAGGATCTGCCTTTTAGAAGAAGCTGGTCAGTTAATTTGGATCAACTTCTAGTCTCAGC

GGGGGACCAGCAAAGATTACAGTCTCTTTTATCGTCAGTGGGATCGAAATCTACCATCCTAACTCTCATTCA

GGAAGCGAAAGCACAATCAGAGAATGAAGAAGATGTTTGCTTCATAGTCTTGAATAGAAAAGAAGGCTCAGG

TCTGGGATTCAGTGTGGCAGGAGGGACAGATGTGGAGCCAAAATGAATCACGGTCCACAGGGTGTTTTCTCA

GGGGGCGGCTTCTCAGGAAGGGACTATGAACCGAGGGGATTTCCTTCTGTCAGTCAACGGCGCCTCACTGGC

TGGCTTAGCCCACGGGAATGTCCTGAAGGTTCTGCACCAGGCACAGCTGCACAAAGATGCCCTCGTGGTCAT

CAAGAAAGGGATGGATCAGCCCAGGCCCTCTGCCCGGCAGGAGCCTCCCACAGCCAATGGGAAGGGTTTGCT

GTCCAGAAAGACCATCCCCCTGGAGCCTGGCATTGGGAGAAGTGTGGCTGTACACGATGCTCTGTGTGTTGA

AGTGCTGAAGACCTCGGCTGGGCTGGGACTGAGTCTGGATGGGGAAAATCATCGGTGACGGGAGATGGGCC

CTTGGTCATTAAAAGAGTGTACAAAGGTGGTGCGGCTGAACAAGCTGGAATAATAGAAGCTGGAGATGAAAT

TCTTGCTATTAATGGGAAACCTCTGGTTGGGCTCATGCACTTTGATGCCTGGAATATTATGAAGTCTGTCCC

AGAAGGACCTGTGCAGTTATTAATTAGAAAGCATAGGAATTCTTCATGAATTTTAACAAGAATCATTTTCTC

AGTTCTCTTCTTTCTTTAGCAAATCAGAGTGACTTCTTTAAACCACAGGTTGTTGAAATGGCCAACACTGGT

In a search of public sequence databases, the NOV8a nucleic acid sequence, located on chromsome 5 has 997 of 1128 bases (88%) identical to a Papin mRNA from *Rattus norvegicus* (GENBANK-ID: AF169411). Public nucleotide databases include all GenBank databases and the GeneSeq patent database.

SNP data for NOV1a can be found below in Example 3.

The disclosed NOV8a polypeptide (SEQ ID NO:25) encoded by SEQ ID NO:24 has 2814 amino acid residues and is presented in Table 8B using the one-letter amino acid code. Signal P, Psort and/or Hydropathy results predict that NOV8a has no signal peptide and is likely to be localized in the nucleus with a certainty of 0.7000. In other embodiments, NOV8a may also be localized to the microbody (peroxisome) with a certainty of 0.3000, the mitochondrial matrix space with a certainty of 0.1000, or the lysosome (lumen) with a certainty of 0.1000.

TABLE 8B

Encoded NOV8a protein sequence (SEQ ID NO:25).

MPITQDNAVLHLPLLYQWLQNSLQEGGDGPEQRLCQAAIQKLQEYIQLNFAVDESTVPPDHSPPEMEICTVY
LTKELGDTETVGLSFGNIPVFGDYGEKRRGGKKRKTHQGPVLDVGCIWVTELRKNSPAGKSGKVRLRDEILS
LNGQLMVGVDVSGASYLAEQCWNGGFIYLIMLRRFKHKAHSTYNGNSSNSSEPGETPTLELGDRTAKKGKRT
RKFGVISRPPANKAPEESKGSAGCEVSSDPSTELENGLDPELGNGHVFQLENGPDSLKEVAGPHLERSEVDR
GTEHRIPKTDAPLTTSNDKRRFSKGGKTDFQSSDCLARSKEEVGRIWKMELLKESDGLGIQVSGGRGSKRSP
HAIVVTQVKEGGAAHRLRDGRLSLGDELLVINGHLLVGLSHEEAVAILRSATGMVQLVVASKVGVLSAFQMP
GTDEPQDVCGAEESKGNLESPKQGSNKIKLKSRLSGRWGLYLMQPVGCVHRLESVEEYNELMVRNGDPRIRM
LEVSRDGRKHSLPQLLDSSSASQEYHIVKKSTRSLSTTQVESPWRLIRPSVISIIGLYKEKGKGLGFSIAGG
RDCIRGQMGIFVKTIFPNGSAAEDGRLKEGDEILDVNGIPIKGLTFQEAIHTFKQIRSGLFVLTVRTKLVSP
SLTPCSTPTHMSRSASPNFNTSGGASAGGSDEGSSSSLGRKTPGPKDRIVMEVTLNKEPRVGLGIGACCLAL
ENSPPGIYIHSLAPGSVAKMESNLSRGSILEVNSVNVNVRHAALSKVHAILSKCPPGPVRLVIGRHPNPKQV
SEQEMDEVIARSTYQESKEANSSPGLGTVISIGCFLLQQDSLISESELSQYFAHDVPGPLSDFMVAGSEDED
HPGSGCSTSEEGSLPPSTSTHKEPGKPRANSLVTLGSHRASGLFHKQVTVARQASLPGSPQALRNPLLRQRK
VGCYDANDASDEEEFDREGDCISLPGALPGPIRPLSEDDPRRVSISSSKGMDVBNQEERPRKTLVSKAISAP
LLGSSVDLEESIPEGMVDAASYAANLTDSAEAPKGSPGSWWKKELSGSSSAPKLEYTVRTDTQSPTNTGSPS
SPQQKSEGLGSRHRPVARVSPHCKRSEAEAKPSGSQTVNLTGRANDPCDLDSRVQATSVKVTVAGFQPGGAV
EKESLGKLTTGDACVSTSCELASALSHLDASHLTENLPKAASELGQQPMTELDSSSDLISSPGKKGAAHPDP
SKTSVDTGKVSRPENPSQPASPRVAKCKARSPVRLPHEGSPSPGEKAAAPPDYSKTRSASETSTPHNTRRVA
ALRGAGPGARGMTPAGAVLPGDPLTSQEQRQGAPGNHSKALEMTGIHAPESSQEPSLLEGADSVSSRAPQAS
LSMLPSTDNTKEACGHVSGHCCPGGSRESPVTDIDSFIKELDASAARSPSSQTGDSGSQEGSAQGHPPAGAG
GGSSCRAEPVPGGQTSSPRRAWAAGAPAYPQWASQPSVLDSINPDKHFTVNKNFLSNYSRNFSSFHEDSTSL
SGLGDSTEPSLSSMYGDAEDSSSDPESLTEAPRASARDGWSPPRSRVSLHKEDPSESEEEQIEICSTRGCPN
PPSSPAHLPTQAAICPASAKVLSLKYSTPRESVASPREKVACLPGSYTSGPDSSQPSSLLEMSSQEHETHAD
ISTSQNHRPSCAEETTEVTSASSAMENSPLSKVARHFHSPPIILSSPNMVNGLEHDLLDDETLNQYETSINA
AASLSSFSVDVPKNGESVLENLHISESQDLDDLLQKPKMIARRPIMAWFKEINKHNQGTHLRSKTEKEQPLM
PARSPDSKIQMVSSSQKKGVTVPHSPPQPKTNLENKDLSKKSPAEMLLTNGQKAKCGPKLKRLSLKGKAKVN
SEAPAANAVKAGGTDHRKPLISPQTSHKTLSKAVSQRLHVADHEDPDRNTTAAPRSPQCVLESKPPLATSGP
LKPSVSDTSIRTFVSPLTSPKPVPEQGMWSRFHMAVLSEPDRGCPTTPKSPKCRAEGRAPRADSGPVSPAAS
RNGMSVAGNRQSEPRLASHVAADTAQPRPTGEKGGNIMASDRLERTNQLKTIVEISEAVSETVCGNKPAESD
RRGGCLAQGNCQEKSEIRLYRQVAESSTSHPSSLPSHASQAEQEMSRSFSMAKLASSSSSLQTAIRKAEYSQ
GKSSLMSDSRGVPRNSIPGGPSGEDHLYFTPRPATRTYSMPAQFSSHFGREGHPPHSLGRSRDSQVPVTSSV
VPEAKASRGGLPSLANGQGIYSVKPLLDTSRNLPATDEGDIISVQETSCLVTDKIKVTRRHYCYEQNWPHES
TSFFSVKQRIKSFENLANADRPVAKSGASPFLSVSSKPPIGRRSSGSIVSGSLGHPGDAAARLLRRSLSSCS
ENQSEAGTLLPQMAKSPSIMTLTISRQNPPETSSKGSDSELKKSLGPLGIPTPTMTLASPVKRNKSSVRHTQ

TABLE 8B-continued

Encoded NOV8a protein sequence (SEQ ID NO:25).

PSPVSRSKLQELRALSMPDLDKLCSEDYSAGPSAVLFKTELEITPRRSPGPPAGGVSCPEKGGNRACPGGSG

PKTSAAETPSSASDTGEAAQDLPFRRSWSVNLDQLLVSAGDQQRLQSVLSSVGSKSTILTLIQEAKAQSENE

EDVCFIVLNRKEGSGLGFSVAGGTDVEPKSITVHRVFSQGAASQEGTMNRGDFLLSVNGASLAGLAHGNVLK

VLHQAQLHKDALVVIKKGMDQPRPSARQEPPTANGKGLLSRKTIPLEPGIGRSVAVHDALCVEVLKTSAGLG

LSLDGGKSSVTGDGPLVIKRVYKGGAAEQAGIIEAGDEILAINGKPLVGLMHFDANNIMKSVPEGPVQLLIR

KHRNSS

A search of sequence databases reveals that the NOV8a amino acid sequence has 937 of 1741 amino acid residues (53%) identical to, and 1133 of 1741 amino acid residues (65%) similar to, the 2766 amino acid residue Papin protein from *Rattus norvegicus* (Q9QZR8) (E=0.0), and 122 of 304 amino acid residues (40%) identical to, and 176 of 304 amino acid residues (57%) similar to, the 334 amino acid residue Human interleukin-16 monomer (patp:AAW19209) (E=1.0e$^{-46}$). Amino acid databases include the GenBank databases, SwissProt, PDB, PATP, and PIR. The global sequence homology (as defined by FASTA alignment with the full length sequence of this protein) is 72.943% amino acid homology and 69.689% amino acid identity. In addition, this protein contains the following protein domains (as defined by Interpro) at the indicated nucleotide positions: PDZdomains (IPR001478) at amino acid positions 336 to 422, 558 to 644, 700 to 784, 2597 to 2681, 2725 to 2810.

NOV8a is expressed in at least the following tissues: Nervous System. Brain. Prosencephalon/Forebrain. Diencephalon. Pituitary Gland; Hematopoietic and Lymphatic System. Hematopoietic Tissues. Lymphoid tissue. Lymph node; Whole Organism. In addition, the sequence is predicted to be expressed in the following tissues because of the expression pattern of (GENBANK-ID: AF 169411) a closely related Papin homolog in species *Rattus norvegicus*: brain. TaqMan data for NOV8 can be found below in Example 2.

NOV8b

A disclosed NOV8b nucleic acid of 8640 nucleotides (also referred to as CG57026-04) encoding a novel papin-like protein is shown in Table 8C. An open reading frame was identified beginning with an ATG initiation codon at nucleotides 101–103 and ending with a TGA codon at nucleotides 8534–8536. A putative untranslated region upstream from the initiation codon and downstream from the termination codon is underlined in Table 8C. The start and stop codons are in bold letters.

TABLE 8C

NGV8b nucleotide sequence (SEQ ID NO:26).

<u>AGCTGATGATGGCCAGGGACCCCAGGGGACGTGGGGCCCTGTGGGGTCTGGCCCCCAGGAGCAAGACCTCTG</u>

<u>ATGATGCTGGTGTCTGGGAGTGAGCACC</u>ATGCCCATCACCCAGGACAATGCCGTGCTGCACCTGCCCCTCCT

CTACCAGTGGCTGCAGAACAGCCTGCAGGAAGGTGGGGATGGGCCGGAGCAGCGGCTCTGCCAGGCGGCCAT

CCAGAAGCTGCAGGAGTACATCCAGCTGAACTTTGCTGTGGATGAGAGTACGGTCCCACCTGATCACAGCCC

CCCCGAAATGGAGATCTGTACTGTGTACCTCACCAAGGAGCTGGGGGACACAGAGACTGTGGGCCTGAGTTT

TGGGAACATCCCTGTTTTCGGGGACTATGGTGAAAAGCGCAGGGGGGGCAAGAAGAGGAAAACCCACCAGGG

TCCTGTGCTGGATGTGGGCTGCATCTGGGTGACAGAGCTGAGGAAGAACAGCCCAGCAGGGAAGAGTGGGAA

GGTCCGACTGCGGGATGAGATCCTCTCACTGAATGGGCAGCTGATGGTTGGAGTTGATGTCAGTGGGGCCAG

TTACCTGGCTGAGCAGTGCTGGAATGGCGGCTTTATCTACCTGATCATGCTGCGTCGCTTTAAGCACAAAGC

CCACTCCACTTATAATGGCAACAGTAGCAACAGCTCTGAACCAGGAGAAACACCTACCTTGGAGCTGGGTGA

CCGAACTGCGAAAAAGGGGAAACGAACCAGAAAGTTTGGGGTCATCTCCAGGCCTCCTGCCAACAAGGCCCC

TGAAGAATCCAAGGGCAGCGCTGGCTGTGAGGTGTCCAGTGACCCCAGCACTGAGCTGGAGAACGGCCTGGA

CCCTGAACTTGGAAACGGCCATGTCTTTCAGCTAGAAAATGGCCCAGATTCTCTCAAGGAGGTGGCTGGACC

CCATCTAGAGAGGTCAGAAGTGGACAGAGGGACAGAGCATAGAATTCCAAAGACAGATGCTCCTCTGACCAC

AAGCAATGACAAACGCCGCTTCTCAAAAGGTGGGAAGACGGACTTCCAATCGAGTGACTGCCTGGCACGGTC

CAAGGAGGAAGTTGGCCCGAATATGGAAGATGGAGCTGCTCAAAGAATCGGATGGGCTGGGAATTCAGGTTAG

TABLE 8C-continued

NGV8b nucleotide sequence (SEQ ID NO:26).

TGGAGGCCGAGGATCAAAGCGCTCACCTCACGCTATCGTTGTCACTCAAGTGAAGGAAGGAGGTGCCGCTCA
CAGGCTCAGGGATGGCAGGCTGTCCTTAGGAGATGAGCTGCTGGTAATCAATGGTCATTTACTGGTCGGGCT
CTCCCACGAGGAAGCAGTGGCCATTCTTCGCTCCGCCACGGGAATGGTGCAGCTTGTGGTGGCCAGCAAGGT
AGGTGTGCTTTCTGCATTTCAGATGCCTGGGACAGATGAACCCCAAGATGTGTGCGGTGCTGAGGAATCCAA
GGGGAACTTGGAAAGTCCCAAACAGGGCAGCAATAAAATCAAGCTCAAGAGTCGCCTTTCAGGTAGGTGGGG
GCTCTACCTGATGCAGCCTGTCGGGGGTGTACACCGCCTTGAGTCAGTTGAAGAATATAACGAGCTGATGGT
GCGGAATGGGGACCCCCGGATCCGGATGTTGGAGGTCTCCCGAGATGGCCGGAAACACTCCCTCCCGCAGCT
GCTGGACTCTTCCAGTGCCTCACAGGAATACCACATTGTGAAGAAGTCTACCCGCTCCTTAAGCACGACTCA
GGTGGAATCTCCTCGGAGGCTCATTCGGCCATCCGTCATCTCGATCATTGGGTTGTACAAAGAAAAAGGCAA
GGGCCTTGGCTTTAGTATTGCTGGAGGTCGAGACTGCATTCGTGGACAGATGGGGATTTTTGTCAAGACCAT
CTTCCCAAATGGATCAGCTGCAGAGGACGGAAGACTTAAAGAAGGGGATGAAATCCTAGATGTAAATGGAAT
ACCAATAAAGGGCTTGACATTTCAAGAAGCCATTCATACCTTTAAGCAAATCCGGAGTGGATTATTTGTTTT
AACGGTACGCACAAAGTTGGTGAGCCCCAGCCTCACACCCTGCTCGACACCCACACACATGAGCAGATCCGC
CTCCCCGAACTTCAATACCAGTGGGGGAGCCTCGGCGGGAGGTTCCGATGAAGGCAGTTCTTCATCCCTGGG
TCGGAAGACCCCTGGGCCCAAGGACAGGATCGTCATGGAAGTAACACTCAACAAAGAGCCAAGAGTTGGATT
AGGCATTGGTGCCTGCTGCTTGGCTCTGGAAAACAGTCCTCCTGGCATCTACATTCACAGCCTTGCTCCAGG
ATCAGTGGCCAAGATGGAGAGCAACCTGAGCCGCGGGGATCAAATCCTGGAAGTGAACTCCGTCAACGTCCG
CCATGCTGCTTTAAGCAAAGTCCACGCCATCTTGAGTAAATGCCCTCCAGGACCCGTTCGCCTTGTCATCGG
CCGGCACCCTAATCCAAAGGTTTCCGAGCAGGAAATGGATGAAGTCATAGCACGCAGCACTTATCAGGAGAG
CAAAGAGGCCAATTCCTCTCCTGGCTTAGGTACCCCCTTGAAGAGTCCCTCTCTTGCAAAAAAGGACTCCCT
TATTTCTGAATCTGAACTCTCCCAGTACTTTGCCCACGATGTCCCTGGCCCCTTGTCAGACTTCATGGTGGT
CGGTTCTGAGGACGAGGATCACCCGGGAAGTGGCTGCAGCACGTCGGAGGAGGGCAGCCTGCCTCCCAGCAC
CTCCACTCACAAGGAGCCTGGAAAACCCAGAGCCAACAGCCTCGTGACTCTTGGGAGCCATCGGGCTTCTGG
GCTCTTCCACAAGCAGGTGACAGTTGCCAGACAAGCCAGTCTCCCCGGAAGCCCACAGGCCCTCCGAAACCC
TCTCCTCCGCCAGAGGAAGGTAGGCTGCTACGATGCCAACGATGCCAGTGATGAGGAAGAGTTTGACAGAGA
AGGGGACTGCATTTCACTCCCAGGGGCCCTCCCGGGTCCCATCAGGCCTCTGTCAGAGGATGACCCGAGGCG
TGTCTCAATTTCCTCTTCCAAGGGCATGGACGTCCACAACCAAGAGGAACGACCCCGGAAAACACTGGTGAG
CAAGGCCATCTCGGCACCTCTTCTTGGTAGCTCAGTGGACTTAGAGGAGAGTATCCCAGAGGGCATGGTGGA
TGCTGCGTCCTATGCAGCCAACCTCACGGACTCTGCAGAGGCCCCCAAGGGGAGCCCTGGAAGCTGGTGGAA
GAAGGAACTGTCAGGATCAAGTAGCGCACCCAAATTGGAATACACAGTCCGTACAGACACCCAGAGTCCGAC
AAACACTGGGAGCCCCAGTTCCCCCCAGCAAAAAAGTGAAGGCCTGGGCTCCAGGCACAGACCAGTGGCCAG
GGTAAGCCCCCACTGCAAGAGATCCGAGGCTGAGGCCAAGCCCAGTGGCTCACAGACATGTAACCTGACTGG
CAGAGCCAATGATCCATGCGATCTGGACTCGAGAGTCCAGGCCACTTCTGTCAAAGTGACTGTCGCTGGCTT
TCAGCCAGGTGGAGCTGTGGAGAAGGAATCTCTGGGAAAGCTGACCACTGGAGATGCTTGTGTCTCTACCAG
CTGTGAACTAGCCAGTGCTCTGTCCCATCTGGATGCCAGCCACCTCACAGAGAACCTGCCCAAAGCTGCATC
AGAGCTGGGCAACAACCCATGACTGAACTGGACAGCTCCTCGGACCTCATCTCTTCCCCAGGGAAGAAGGG
GGCCGCTCATCCTGACCCCAGCAAGACCTCTGTAGACACAGGGAAAGTCAGTCGGCCAGAGAATCCCAGCCA
GCCTGCATCGCCCAGGGTCGCCAAGTGCAAGGCCAGGTCTCCAGTCAGGCTCCCCCATGAGGGCAGCCCCTC
CCCAGGGGAGAAAGCAGCGGCTCCCCCTGACTACAGCAAGACTCGATCAGCATCGGAAACCAGCACACCCCA

TABLE 8C-continued

NGV8b nucleotide sequence (SEQ ID NO:26).

CAATACCAGGAGGGTGGCTGCCCTCAGGGGAGCGGGACCTGGAGCAGAGGGAATGACACCAGCTGGTGCTGT

CCTGCCAGGAGACCCCCTCACATCCCAGGAGCAGAGACAGGGAGCTCCAGGTAACCACAGTAAGGCTCTGGA

AATGACAGGAATCCATGCACCTGAAAGCTCCCAGGAGCCTTCCCTGCTGGAGGGAGCAGATTCTGTGTCCTC

AAGGGCACCGCAGGCCAGCCTCTCCATGCTGCCATCCACTGACAACACCAAAGAAGCATGTGGCCATGTCTC

GGGGCACTGCTGCCCGGGGGGAGTAGAGAGAGCCCTGTGACGGACATTGACAGCTTCATCAAGGAGCTGGA

TGCTTCTGCAGCAAGGTCTCCGTCTTCCCAGACGGGGACAGTGGCTCTCAGGAGGGCAGTGCTCAGGGCCA

CCCACCAGCCGGGGCTGGAGGTGGGAGCTCCTGCCGTGCCGAACCAGTCCCGGGGGCCAGACCTCCTCCCC

GAGGAGGGCCTGGGCTGCTGGTGCCCCCGCCTACCCACAATGGGCCTCCCAGCCTTCGGTTTTAGATTCAAT

TAATCCCGACAAACATTTTACTGTGAACAAAAACTTTCTGAGCAACTACTCTAGAAATTTTAGCAGTTTTCA

TGAAGACAGCACCTCCCTATCAGGCCTGGGTGACAGCACGGAGCCGTCTCTGTCATCCATGTATGGCGATGC

TGAGGATTCTTCTTCTGACCCTGAGTCACTCACTGAAGCCCACGAGCTTCTGCCAGGGACGGCTGGTCCCC

TCCTCGTTCCCGTGTGTCTTTGCACAAGGAAGATCCTTCGGAGTCAGAAGAGGAACAGATTGAGATTTGTTC

CACACGTGGCTGCCCCAATCCACCCTCGAGTCCTGCTCATCTTCCCACCCAGGCTGCCATCTGTCCTGCCTC

AGCCAAAGTTCTGTCATTAAAATACAGCACTCCGAGAGAGTCGGTGGCCAGTCCCCGTGAGAAGGTCGCCTG

CTTGCCAGGCTCATACACTTCAGGCCCAGACTCTTCCCAGCCATCATCACTCTTGGAGATGAGCTCTCAGGA

GCATGAAACTCATGCGACATAAGCACTTCACAGAACCACAGGCCCTCGTGTGCAGAAGAAACCACAGAAGT

CACCAGCGCTAGCTCAGCCATGGAAAACAGTCCGCTGTCTAAAGTAGCCAGGCATTTTCACAGTCCGCCCAT

CATTCTCAGCTCCCCCAACATGGTAAATGGCTTGGAACATGACCTGCTAGATGACGAAACCCTGAATCAATA

CGAAACAAGCATTAATGCAGCTGCCAGTCTGTCCTCCTTCAGTGTGGATGTCCCTAAGAATGGAGAATCTGT

TTTGGAAAACCTCCACATCTCTGAAAGTCAAGACCTGGATGACTTGCTACAGAAACCAAAAATGATCGCTAG

GAGGCCCATCATGGCCTGGTTTAAAGAAATAAATAAACATAACCAAGGCACACATTTGAGGAGCAAAACCGA

GAAGGAACAACCTCTAATGCCTGCCAGAAGTCCCGACTCCAAGATTCAGATGGTGAGTTCAAGCCAAAAAAA

GGGCGTTACTGTGCCTCATAGCCCTCCTCAGCCGAAAACAAACCTGGAAAATAAGGACCTGTCTAAGAAGAG

TCCGGCAGAAATGCTTCTGACTAATGGTCAGAAGGCAAAGTGTGGTCCGAAGCTGAAGAGGCTCAGCCTCAA

GGGCAAGGCCAAAGTCAACTCTGAGGCCCCTGCTGCGAATGCTGTGAAGGCTGGGGGACGGACCACAGGAA

ACCCTTGATCTCACCCCAGACCTCCCACAAAACACTTTCTAAGGCAGTGTCACAGCGGCTCCATGTAGCCGA

CCACGAGGACCCTGACAGAAACACCACAGCTGCCCCCAGGTCCCCCCAGTGTGTGCTGGAAAGCAAGCCACC

TCTTGCCACCTCTGGGCCACTGAAACCCTCAGTGTCTGACACGAGCATCAGGACATTTGTCTCGCCCCTGAC

CTCTCCCAAGCCTGTTCCTGAGCAAGGCATGTGGAGCAGGTTCCACATGGCTGTCCTCTCTGAACCCGACAG

AGGTTGCCCAACCACCCCTAAATCTCCTAAGTGTAGAGCAGAGGGCAGGGCGCCCCGTGCTGACTCCGGGCC

GGTGAGTCCGGCAGCGTCTAGGAACGGCATGTCCGTGGCAGGGAACAGACAGAGTGAGCCGCGCCTGGCCAG

CCATGTGGCAGCAGACACAGCCCAACCCAGGCCGACTGGCGAAAAAGGAGGCAACATAATGGCCAGCGATCG

CCTCGAAAGAACAAACCAGCTGAAAATCGTGGAGATTTCTGCTGAAGCAGTGTCAGAGACTGTATGTGGTAA

CAAGCCAGCTGAAAGCGACAGACGGGGAGGGTGCTTGGCCCAGGGCAACTGTCAGGAGAAGAGTGAAATCAG

GCTCTATCGCCAGGTCGCAGAATCATCCACAAGTCATCCATCCTCACTCCCATCTCATGCCTCCCAGGCAGA

GCAGGAAATGTCACGATCATTCAGCATGGCAAAACTGGCGTCCTCCTCCTCCTCCCTTCAAACAGCCATTAG

AAAGGCAGAATACTCCCAGGGAAAATCAAGCCTGATGTCAGACTCCCGAGGGGTGCCCAGAAACAGCATTCC

AGGGGGCCCCTCGGGGGAGGACCATCTCTACTTCACCCCAAGGCCAGCGACCAGGACCTACTCCATGCCAGC

TABLE 8C-continued

NGV8b nucleotide sequence (SEQ ID NO:26).

CCAGTTCTCAAGCCATTTTGGACGGGAGGGTCACCCCCCACACAGCCTGGGTCGCTCTCGGGACAGCCAGGT

CCCTGTGACAAGCAGTGTTGTCCCCGAGGCAAAGGCATCCAGAGGTGGTCTTCCCAGCCTGGCTAATGGACA

GGGCATATATAGTGTAAAGCCGCTGCTGGACACATCGAGGAATCTTCCAGCCACAGATGAAGGGGATATCAT

TTCAGTCCAGGAGACGAGCTGCCTAGTCACAGACAAAATCAAAGTCACCAGACGACACTACTGCTATGAGCA

GAACTGGCCCCATGAATCTACCTCATTTTTCTCTGTGAAGCAGCGGATCAAGTCTTTTGAGAACCTGGCCAA

TGCTGACCGGCCTGTAGCCAAGTCCGGGGCTTCCCCATTTTTGTCGGTGAGCTCCAAGCCTCCCATTGGGAG

GCGGTCTTCCGGCAGCATTGTTTCCGGGAGCCTGGGCCACCCAGGTGACGCAGCAGCAAGGTTGTTGAGACG

AATCATGACACTGACCATCTCTCGGCAGAACCCACCAGAGACCAGTAGCAAGGGCTCTGATTCGGAACTAAA

GAAATCACTTGGTCCTTTGGGAATTCCCACCCCAACGATGACCCTGGCTTCTCCTGTTAAGAGGAACAAGTC

CTCGGTACGCCACACGCAGCCCTCGCCCGTGTCCCGCTCCAAGCTCCAGGAGCTGAGAGCCTTGAGCATGCC

TGACCTTGACAAGCTCTGCAGCGAGGATTACTCAGCAGGGCCGAGCGCCGTGCTCTTCAAAACTGAGCTGGA

GATCACCCCCAGGAGGTCACCTGGCCCTCCTGCTGGAGGCGTTTCGTGTCCCGAGAAGGGCGGGAACAGGGC

CTGTCCAGGAGGAAGTGGCCCTAAAACCAGTGCTGCTGAGACACCCAGTTCAGCCAGTGATACGGGTGAAGC

TGCCCAGGATCTGCCTTTTAGAAGAAGCTGGTCAGTTAATTTGGATCAACTTCTAGTCTCAGCGGGGGACCA

GCAAAGATTACAGTCTGTTTTATCGTCAGTGGGATCGAAATCTACCATCCTAACTCTCATTCAGGAAGCGAA

AGCACAATCAGAGAATGAAGAAGATGTTTGCTTCATAGTCTTGAATAGAAAAGAAGGCTCAGGTCTGGGATT

CAGTGTGGCAGGAGGGACAGATGTGGAGCCAAAATCAATCACGGTCCACAGGGTGTTTTCTCAGGGGCGGC

TTCTCAGGAAGGGACTATGAACCGAGGGGATTTCCTTCTGTCAGTCAACGGCGCCTCACTGGCTGGCTTAGC

CCACGGGAATGTCCTGAAGGTTCTGCACCAGGCACAGCTGCACAAAGATGCCCTCGTGGTCATCAAGAAAGG

GATGGATCAGCCCAGGCCCTCTGCCCGGCAGGAGCCTCCCACAGCCAATGGGAAGGGTTTGCTGTCCAGAAA

GACCATCCCCCTGGAGCCTGGCATTGGGAGAAGTGTGGCTGTACACGATGCTCTGTGTGTTGAAGTGCTGAA

GACCTCGGCTGGGCTGGGACTGAGTCTGGATGGGGAAAATCATCGGTGACGGGAGATGGGCCCTTGGTCAT

TAAAAGAGTGTACAAAGGTGGTGCGGCTGAACAAGCTGGAATAATAGAAGCTGGAGATGAAATTCTTGCTAT

TAATGGGAAACCTCTGGTTGGGCTCATGCACTTTGATGCCTGGAATATTATGAAGTCTGTCCCAGAAGGACC

TGTGCAGTTATTAATTAGAAAGCATAGGAATTCTTCATGAATTTTAACAAGAATCATTTTCTCAGTTCTCTT

CTTTCTTTAGCAAATCAGAGTGACTTCTTTAAACCACAGGTTGTTGAAATGGCCAACACTGGTACAGACACG

In a search of public sequence databases, the NOV8a nucleic acid sequence, located on chromsome 5 has 5828 of 5941 bases (98%) identical to a gb:GENBANK-ID:AF338650|acc:AF338650.1 mRNA from *Homo sapiens* (*Homo sapiens* PDZ domain-containing protein AIPC (AIPC) mRNA, complete cds) (E=0.0). Public nucleotide databases include all GenBank databases and the GeneSeq patent database.

The disclosed NOV8b polypeptide (SEQ ID NO:27) encoded by SEQ ID NO:26 has 2811 amino acid residues and is presented in Table 8D using the one-letter amino acid code. Signal P, Psort and/or Hydropathy results predict that NOV8b has no signal peptide and is likely to be localized in the nucleus with a certainty of 0.7000. In other embodiments, NOV8b is also likely to be localized to the microbody (peroxisome) with a certainty of 0.3000, the mitochondrial matrix space with a certainty of 0.1000, and to the lysosome (lumen) with a certainty of 0.1000.

TABLE 8D

Encoded NGV8b protein sequence (SEQ ID NO:27).

MPITQDNAVLHLPLLYQWLQNSLQEGGDGPEQRLCQAAIQKLQEYIQLNFAVDESTVPPDHSPPEMEICTVY

LTKELGDTETVGLSFGNIPVFGDYGEKRRGGKKRKTHQGPVLDVGCIWVTELRKNSPAGKSGKVRLRDEILS

TABLE 8D-continued

Encoded NGV8b protein sequence (SEQ ID NO:27).

LNGQLMVGVDVSGASYLAEQCWNGGFIYLIMLRRFKHKAHSTYNGNSSNSSEPGETPTLELGDRTAKKGKRT
RKFGVISRPPANKAPEESKGSAGCEVSSDPSTELENGLDPELGNGHVFQLENGPDSLKEVAGPHLERSEVDR
GTEHRIPKTDAPLTTSNDKRRFSKGGKTDFQSSDCLARSKEEVGRIWKMELLKESDGLGIQVSGGRGSKRSP
HAIVVTQVKEGGAAHRLRDGRLSLGDELLVINGHLLVGLSHEEAVAILRSATGMVQLVVASKVGVLSAFQMP
GTDEPQDVCGAEESKGNLESPKQGSNKIKLKSRLSGRWGLYLMQPVGCVHRLESVEEYNELMVRNGDPRIRM
LEVSRDGRKHSLPQLLDSSSASQEYHIVKKSTRSLSTTQVESPWRLIRPSVISIIGLYKEKGKGLGFSIAGG
RDCIRGQMGIFVKTIFPNGSAAEDGRLKEGDEILDVNGIPIKGLTFQEAIHTFKQIRSGLFVLTVRTKLVSP
SLTPCSTPTHMSRSASPNFNTSGGASAGGSDEGSSSSLGRKTPGPKDRIVMEVTLNKEPRVGLGIGACCLAL
ENSPPGIYIHSLAPGSVAKMESNLSRGDQILEVNSVNVRHAALSKVHAILSKCPPGPVRLVIGRHPNPKVSE
QEMDEVIARSTYQESKEANSSPGLGTPLKSPSLAKKDSLISESELSQYFAHDVPGPLSDFMVAGSEDEDHPG
SGCSTSEEGSLPPSTSTHKEPGKPRANSLVTLGSHRASGLFHKQVTVARQASLPGSPQALRNPLLRQRKVGC
YDANDASDEEEFDREGDCISLPGALPGPIRPLSEDDPRRVSISSSKGMDVBNQEERPRKTLVSKAISAPLLG
SSVDLEESIPEGMVDAASYAANLTDSAEAPKGSPGSWWKKELSGSSSAPKLEYTVRTDTQSPTNTGSPSSPQ
QKSEGLGSRHRPVARVSPHCKRSEAEAKPSGSQTVNLTGRANDPCDLDSRVQATSVKVTVAGFQPGGAVEKE
SLGKLTTGDACVSTSCELASALSHLDASHLTENLPKAASELGQQPMTELDSSSDLISSPGKKGAAHPDPSKT
SVDTGKVSRPENPSQPASPRVAKCKARSPVRLPHEGSPSPGEKAAAPPDYSKTRSASETSTPHNTRRVAALR
GAGPGARGMTPAGAVLPGDPLTSQEQRQGAPGNHSKALEMTGIHAPESSQEPSLLEGADSVSSRAPQASLSM
LPSTDNTKEACGHVSGHCCPGGSRESPVTDIDSFIKELDASAARSPSSQTGDSGSQEGSAQGHPPAGAGGGS
SCRAEPVPGGQTSSPRRAWAAGAPAYPQWASQPSVLDSINPDKHFTVNKNFLSNYSRNFSSFHEDSTSLSGL
GDSTEPSLSSMYGDAEDSSSDPESLTEAPRASARDGWSPPRSRVSLHKEDPSESEEEQIEICSTRGCPNPPS
SPAHLPTQAAICPASAKVLSLKYSTPRESVASPREKVACLPGSYTSGPDSSQPSSLLEMSSQEHETHADIST
SQNHRPSCAEETTEVTSASSAMENSPLSKVARHFHSPPIILSSPNMVNGLEHDLLDDETLNQYETSINAAAS
LSSFSVDVPKNGESVLENLHISESQDLDDLLQKPKMIARRPIMAWFKEINKHNQGTHLRSKTEKEQPLMPAR
SPDSKIQMVSSSQKKGVTVPHSPPQPKTNLENKDLSKKSPAEMLLTNGQKAKCGPKLKRLSLKGKAKVNSEA
PAANAVKAGGTDHRKPLISPQTSHKTLSKAVSQRLHVADHEDPDRNTTAAPRSPQCVLESKPPLATSGPLKP
SVSDTSIRTFVSPLTSPKPVPEQGMWSRFHMAVLSEPDRGCPTTPKSPKCRAEGRAPRADSGPVSPAASRNG
MSVAGNRQSEPRLASHVAADTAQPRPTGEKGGNIMASDRLERTNQLKTIVEISEAVSETVCGNKPAESDRRG
GCLAQGNCQEKSEIRLYRQVAESSTSHPSSLPSHASQAEQEMSRSFSMAKLASSSSSLQTAIRKAEYSQGKS
SLMSDSRGVPRNSIPGGPSGEDHLYFTPRPATRTYSMPAQFSSHFGREGHPPHSLGRSRDSQVPVTSSVVPE
AKASRGGLPSLANGQGIYSVKPLLDTSRNLPATDEGDIISVQETSCLVTDKIKVTRRHYCYEQNWPHESTSF
FSVKQRIKSFENLANADRPVAKSGASPFLSVSSKPPIGRRSSGSIVSGSLGHPGDAAARLLRRSLSSCSENQ
SEAGTLLPQMAKSPSIMTLTISRQNPPETSSKGSDSELKKSLGPLGIPTPTMTLASPVKRNKSSVRHTQPSP
VSRSKLQELRALSMPDLDKLCSEDYSAGPSAVLFKTELEITPRRSPGPPAGGVSCPEKGGNRACPGGSGPKT
SAAETPSSASDTGEAAQDLPFRRSWSVNLDQLLVSAGDQQRLQSVLSSVGSKSTILTLIQEAKAQSENEEDV
CFIVLNRKEGSGLGFSVAGGTDVEPKSITVHRVFSQGAASQEGTMNRGDFLLSVNGASLAGLAHGNVLKVLH
QAQLHKDALVVIKKGMDQPRPSARQEPPTANGKGLLSRKTIPLEPGIGRSVAVHDALCVEVLKTSAGLGLSL
DGGKSSVTGDGPLVIKRVYKGGAAEQAGIIEAGDEILAINGKPLVGLMHFDANNIMKSVPEGPVQLLIRKHR
NSS

A search of sequence databases reveals that the NOV8a amino acid sequence has 2017 of 2045 amino acid residues (98%) identical to, and 2022 of 2045 amino acid residues (98%) similar to, the 2641 amino acid residue ptnr:TREMBLNEW-ACC:AAK07661 protein from *Homo sapiens* (Human) (PDZ DOMAIN-CONTAINING PROTEIN AIPC) (E=0.0). Public amino acid databases include the GenBank databases, SwissProt, PDB and PIR.

NOV8b is expressed in at least the following tissues: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea and uterus. Expression information was derived from the tissue sources of the sequences that were included in the derivation of the sequence of CuraGen Acc. No. CG57026-04. The sequence is predicted to be expressed in the following tissues because of the expression pattern of (GENEBANK-ID:gb:GENBANK-ID:AF338650|acc:AF338650.1) a closely related Homo sapiens PDZ domain-containing protein AIPC (AIPC) mRNA, complete cds homolog in species *Homo sapiens*: prostate. TaqMan data for NOV8b can be found below in Example 2.

The NOV8a, and 8b proteins are very closely homologous as as shown in the alignment in Table 8E.

TABLE 8E

Alignment of NOV8a, and 8b.

```
              10        20        30        40        50        60
        ....|....|....|....|....|....|....|....|....|....|....|....|
NOV8a   MPITQDNAVLHLPLLYQWLQNSLQEGGDGPEQRLCQAAIQKLQEYIQLNFAVDESTVPPD
NOV8b   MPITQDNAVLHLPLLYQWLQNSLQEGGDGPEQRLCQAAIQKLQEYIQLNFAVDESTVPPD 70        80        90       100       110       120
        ....|....|....|....|....|....|....|....|....|....|....|....|
NOV8a   HSPPEMEICTVYLTKELGDTETVGLSFGNIPVFGDYGEKRRGGKKRKTHQGPVLDVGCIW
NOV8b   HSPPEMEICTVYLTKELGDTETVGLSFGNIPVFGDYGEKRRGGKKRKTHQGPVLDVGCIW 130       140       150       160       170       180
        ....|....|....|....|....|....|....|....|....|....|....|....|
NOV8a   VTELRKNSPAGKSGKVRLRDEILSLNGQLMVGVDVSGASYLAEQCWNGGFIYLIMLRRFK
NOV8b   VTELRKNSPAGKSGKVRLRDEILSLNGQLMVGVDVSGASYLAEQCWNGGFIYLIMLRRFK 190       200       210       220       230       240
        ....|....|....|....|....|....|....|....|....|....|....|....|
NOV8a   HKAHSTYNGNSSNSSEPGETPTLELGDRTAKKGKRTRKFGVISRPPANKAPEESKGSAGC
NOV8b   HKAHSTYNGNSSNSSEPGETPTLELGDRTAKKGKRTRKFGVISRPPANKAPEESKGSAGC 250       260       270       280       290       300
        ....|....|....|....|....|....|....|....|....|....|....|....|
NOV8a   EVSSDPSTELENGLDPELGNGHVFQLENGPDSLKEVAGPHLERSEVDRGTEHRIPKTDAP
NOV8b   EVSSDPSTELENGLDPELGNGHVFQLENGPDSLKEVAGPHLERSEVDRGTEHRIPKTDAP 310       320       330       340       350       360
        ....|....|....|....|....|....|....|....|....|....|....|....|
NOV8a   LTTSNDKRRFSKGGKTDFQSSDCLARSKEEVGRIWKMELLKESDGLGIQVSGGRGSKRSP
NOV8b   LTTSNDKRRFSKGGKTDFQSSDCLARSKEEVGRIWKMELLKESDGLGIQVSGGRGSKRSP 370       380       390       400       410       420
        ....|....|....|....|....|....|....|....|....|....|....|....|
NOV8a   HAIVVTQVKEGGAAHRLRDGRLSLGDELLVINGHLLVGLSHEEAVAILRSATGMVQLVVA
NOV8b   HAIVVTQVKEGGAAHRLRDGRLSLGDELLVINGHLLVGLSHEEAVAILRSATGMVQLVVA 430       440       450       460       470       480
        ....|....|....|....|....|....|....|....|....|....|....|....|
NOV8a   SKVGVLSAFQMPGTDEPQDVCGAEESKGNLESPKQGSNKIKLKSRLSGRWGLYLMQPVGG
NOV8b   SKVGVLSAFQMPGTDEPQDVCGAEESKGNLESPKQGSNKIKLKSRLSGRWGLYLMQPVGG 490       500       510       520       530       540
        ....|....|....|....|....|....|....|....|....|....|....|....|
NOV8a   VHRLESVEEYNELMVRNGDPRIRMLEVSRDGRKHSLPQLLDSSSASQEYHIVKKSTRSLS
NOV8b   VHRLESVEEYNELMVRNGDPRIRMLEVSRDGRKHSLPQLLDSSSASQEYHIVKKSTRSLS 550       560       570       580       590       600
        ....|....|....|....|....|....|....|....|....|....|....|....|
NOV8a   TTQVESPWRLIRPSVISIIGLYKEKGKGLGFSIAGGRDCIRGQMGIFVKTIFPNGSAAED
NOV8b   TTQVESPWRLIRPSVISIIGLYKEKGKGLGFSIAGGRDCIRGQMGIFVKTIFPNGSAAED 610       620       630       640       650       660
        ....|....|....|....|....|....|....|....|....|....|....|....|
NOV8a   GRLKEGDEILDVNGIPIKGLTFQEATHTFKQIRSGLFVLTVRTKLVSPSLTPCSTPTHMS
NOV8b   GRLKEGDEILDVNGIPIKGLTFQEATHTFKQIRSGLFVLTVRTKLVSPSLTPCSTPTHMS
```

TABLE 8E-continued

Alignment of NOV8a, and 8b.

```
              670        680        690        700        710        720
        ....|....|....|....|....|....|....|....|....|....|....|....|
NOV8a   RSASPNFNTSGGASAGGSDEGSSSSLGRKTPGPKDRIVMEVTLNKEPRVGLGIGACCLAL
NOV8b   RSASPNFNTSGGASAGGSDEGSSSSLGRKTPGPKDRIVMEVTLNKEPRVGLGIGACCLAL 730        740        750        760        770        780
        ....|....|....|....|....|....|....|....|....|....|....|....|
NOV8a   ENSPPGIYIHSLAPGSVAKMESNLSRGS-ILEVNSVNVRHAALSKVHAILSKCPPGPVRL
NOV8b   ENSPPGIYIHSLAPGSVAKMESNLSRGDQILEVNSVNVRHAALSKVHAILSKCPPGPVRL 790        800        810        820        830        840
        ....|....|....|....|....|....|....|....|....|....|....|....|
NOV8a   VIGRHPNPKVNQVSEQEMDEVIARSTYQESKEANSSPGLGTVESIGCFLLQDSLISESE
NOV8b   VIGRHPNP---VSEQEMDEVIARSTYQESKEANSSPGLGTPKS-PSLAQDSLISESE 850        860        870        880        890        900
        ....|....|....|....|....|....|....|....|....|....|....|....|
NOV8a   LSQYFAHDVPGPLSDFMVAGSEDEDHPGSGCSTSEEGSLPPSTSTHKEPGKPRANSLVTL
NOV8b   LSQYFAHDVPGPLSDFMVVGSEDEDHPGSGCSTSEEGSLPPSTSTHKEPGKPRANSLVTL 910        920        930        940        950        960
        ....|....|....|....|....|....|....|....|....|....|....|....|
NOV8a   GSHRASGLFHKQVTVARQASLPGSPQALRNPLLRQRKVGCYDANDASDEEEFDREGDCIS
NOV8b   GSHRASGLFHKQVTVARQASLPGSPQALRNPLLRQRKVGCYDANDASDEEEFDREGDCIS 970        980        990       1000       1010       1020
        ....|....|....|....|....|....|....|....|....|....|....|....|
NOV8a   LPGALPGPIRPLSEDDPRRVSISSSKGMDVHNQEERPRKTLVSKAISAPLLGSSVDLEES
NOV8b   LPGALPGPIRPLSEDDPRRVSISSSKGMDVHNQEERPRKTLVSKAISAPLLGSSVDLEES 1030       1040       1050       1060       1070       1080
        ....|....|....|....|....|....|....|....|....|....|....|....|
NOV8a   IPEGMVDAASYAANLTDSAEAPKGSPGSWWKKELSGSSSAPKLEYTVRTDTQSPTNTGSP
NOV8b   IPEGMVDAASYAANLTDSAEAPKGSPGSWWKKELSGSSSAPKLEYTVRTDTQSPTNTGSP 1090       1100       1110       1120       1130       1140
        ....|....|....|....|....|....|....|....|....|....|....|....|
NOV8a   SSPQQKSEGLGSRHRPVARVSPHCKRSEAEAKPSGSQTVNLTGRANDPCDLDSRVQATSV
NOV8b   SSPQQKSEGLGSRHRPVARVSPHCKRSEAEAKPSGSQTVNLTGRANDPCDLDSRVQATSV 1150       1160       1170       1180       1190       1200
        ....|....|....|....|....|....|....|....|....|....|....|....|
NOV8a   KVTVAGFQPGGAVEKESLGKLTTGDACVSTSCELASALSHLDASHLTENLPKAASELGQQ
NOV8b   KVTVAGFQPGGAVEKESLGKLTTGDACVSTSCELASALSHLDASHLTENLPKAASELGQQ 1210       1220       1230       1240       1250       1260
        ....|....|....|....|....|....|....|....|....|....|....|....|
NOV8a   PMTELDSSSDLISSPGKKGAAHPDPSKTSVDTGKVSRPENPSQPASPRVAKCKARSPVRL
NOV8b   PMTELDSSSDLISSPGKKGAAHPDPSKTSVDTGKVSRPENPSQPASPRVAKCKARSPVRL 1270       1280       1290       1300       1310       1320
        ....|....|....|....|....|....|....|....|....|....|....|....|
NOV8a   PHEGSPSPGEKAAAPPDYSKTRSASETSTPHNTRRVAALRGAGPGAEGMTPAGAVLPGDP
NOV8b   PHEGSPSPGEKAAAPPDYSKTRSASETSTPHNTRRVAALRGAGPGAEGMTPAGAVLPGDP 1330       1340       1350       1360       1370       1380
        ....|....|....|....|....|....|....|....|....|....|....|....|
NOV8a   LTSQEQRQGAPGNHSKALEMTGIHAPESSQEPSLLEGADSVSSRAPQASLSMLPSTDNTK
NOV8b   LTSQEQRQGAPGNHSKALEMTGIHAPESSQEPSLLEGADSVSSRAPQASLSMLPSTDNTK 1390       1400       1410       1420       1430       1440
        ....|....|....|....|....|....|....|....|....|....|....|....|
NOV8a   EACGHVSGHCCPGGSRESPVTDIDSFIKELDASAARSPSSQTGDSGSQEGSAQGHPPAGA
NOV8b   EACGHVSGHCCPGGSRESPVTDIDSFIKELDASAARSPSSQTGDSGSQEGSAQGHPPAGA 1450       1460       1470       1480       1490       1500
        ....|....|....|....|....|....|....|....|....|....|....|....|
NOV8a   GGGSSCRAEPVPGGQTSSPRRAWAAGAPAYPQWASQPSVLDSINPDKHFTVNKNFLSNYS
NOV8b   GGGSSCRAEPVPGGQTSSPRRAWAAGAPAYPQWASQPSVLDSINPDKHFTVNKNFLSNYS 1510       1520       1530       1540       1550       1560
        ....|....|....|....|....|....|....|....|....|....|....|....|
NOV8a   RNFSSFHEDSTSLSGLGDSTEPSLSSMYGDAEDSSSDPESLTEAPRASARDGWSPPRSRV
NOV8b   RNFSSFHEDSTSLSGLGDSTEPSLSSMYGDAEDSSSDPESLTEAPRASARDGWSPPRSRV
```

TABLE 8E-continued

Alignment of NOV8a, and 8b.

```
               1570      1580      1590      1600      1610      1620
           ....|....|....|....|....|....|....|....|....|....|....|....|
NOV8a      SLHKEDPSESEEEQIEICSTRGCPNPPSSPAHLPTQAAICPASAKVLSLKYSTPRESVAS
NOV8b      SLHKEDPSESEEEQIEICSTRGCPNPPSSPAHLPTQAAICPASAKVLSLKYSTPRESVAS 1630      1640      1650      1660      1670      1680
           ....|....|....|....|....|....|....|....|....|....|....|....|
NOV8a      PREKVACLPGSYTSGPDSSQPSSLLEMSSQEHETHADISTSQNHRPSCAEETTEVTSASS
NOV8b      PREKVACLPGSYTSGPDSSQPSSLLEMSSQEHETHADISTSQNHRPSCAEETTEVTSASS 1690      1700      1710      1720      1730      1740
           ....|....|....|....|....|....|....|....|....|....|....|....|
NOV8a      AMENSPLSKVARHFHSPPIILSSPNMVNGLEHDLLDDETLNQYETSINAAASLSSFSVDV
NOV8b      AMENSPLSKVARHFHSPPIILSSPNMVNGLEHDLLDDETLNQYETSINAAASLSSFSVDV 1750      1760      1770      1780      1790      1800
           ....|....|....|....|....|....|....|....|....|....|....|....|
NOV8a      PKNGESVLENLHISESQDLDDLLQKPKMIARRPIMAWFKEINKHNQGTHLRSKTEKEQPL
NOV8b      PKNGESVLENLHISESQDLDDLLQKPKMIARRPIMAWFKEINKHNQGTHLRSKTEKEQPL 1810      1820      1830      1840      1850      1860
           ....|....|....|....|....|....|....|....|....|....|....|....|
NOV8a      MPARSPDSKIQMVSSSQKKGVTVPHSPPQPKTNLENKDLSKKSPAEMLLTNGQKAKCGPK
NOV8b      MPARSPDSKIQMVSSSQKKGVTVPHSPPQPKTNLENKDLSKKSPAEMLLTNGQKAKCGPK 1870      1880      1890      1900      1910      1920
           ....|....|....|....|....|....|....|....|....|....|....|....|
NOV8a      LKRLSLKGKAKVNSEAPAANAVKAGGTDHRKPLISPQTSHKTLSKAVSQRLHVADHEDPD
NOV8b      LKRLSLKGKAKVNSEAPAANAVKAGGTDHRKPLISPQTSHKTLSKAVSQRLHVADHEDPD 1930      1940      1950      1960      1970      1980
           ....|....|....|....|....|....|....|....|....|....|....|....|
NOV8a      RNTTAAPRSPQCVLESKPPLATSGPLKPSVSDTSIRTFVSPLTSPKPVPEQGMWSRFHMA
NOV8b      RNTTAAPRSPQCVLESKPPLATSGPLKPSVSDTSIRTFVSPLTSPKPVPEQGMWSRFHMA 1990      2000      2010      2020      2030      2040
           ....|....|....|....|....|....|....|....|....|....|....|....|
NOV8a      VLSEPDRGCPTTPKSPKCRAEGRAPRADSGPVSPAASRNGMSVAGNRQSEPRLASHVAAD
NOV8b      VLSEPDRGCPTTPKSPKCRAEGRAPRADSGPVSPAASRNGMSVAGNRQSEPRLASHVAAD 2050      2060      2070      2080      2090      2100
           ....|....|....|....|....|....|....|....|....|....|....|....|
NOV8a      TAQPRPTGEKGGNIMASDRLERTNQLKIVEISAEAVSETVCGNKPAESDRRGGCLAQGNC
NOV8b      TAQPRPTGEKGGNIMASDRLERTNQLKIVEISAEAVSETVCGNKPAESDRRGGCLAQGNC 2110      2120      2130      2140      2150      2160
           ....|....|....|....|....|....|....|....|....|....|....|....|
NOV8a      QEKSEIRLYRQVAESSTSHPSSLPSHASQAEQEMSRSFSMAKLASSSSSLQTAIRKAEYS
NOV8b      QEKSEIRLYRQVAESSTSHPSSLPSHASQAEQEMSRSFSMAKLASSSSSLQTAIRKAEYS 2170      2180      2190      2200      2210      2220
           ....|....|....|....|....|....|....|....|....|....|....|....|
NOV8a      QGKSSLMSDSRGVPRNSIPGGPSGEDHLYFTRRPATRTYSMPAQFSSHFGREGHPPHSLG
NOV8b      QGKSSLMSDSRGVPRNSIPGGPSGEDHLYFTRRPATRTYSMPAQFSSHFGREGHPPHSLG 2230      2240      2250      2260      2270      2280
           ....|....|....|....|....|....|....|....|....|....|....|....|
NOV8a      RSRDSQVPVTSSVVPEAKASRGGLPSLANGQGIYSVKPLLDTSRNLPATDEGDIISVQET
NOV8b      RSRDSQVPVTSSVVPEAKASRGGLPSLANGQGIYSVKPLLDTSRNLPATDEGDIISVQET 2290      2300      2310      2320      2330      2340
           ....|....|....|....|....|....|....|....|....|....|....|....|
NOV8a      SCLVTDKIKVTRRHYCYEQNWPHESTSFFSVKQRIKSFENLANADRPVAKSGASPFLSVS
NOV8b      SCLVTDKIKVTRRHYCYEQNWPHESTSFFSVKQRIKSFENLANADRPVAKSGASPFLSVS 2350      2360      2370      2380      2390      2400
           ....|....|....|....|....|....|....|....|....|....|....|....|
NOV8a      SKPPIGRRSSGSIVSGSLGHPGDAAARLLRRSLSSCSENQSEAGTLLPQMAKSPSIMTLT
NOV8b      SKPPIGRRSSGSIVSGSLGHPGDAAARLLRRSLSSCSENQSEAGTLLPQMAKSPSIMTLT 2410      2420      2430      2440      2450      2460
           ....|....|....|....|....|....|....|....|....|....|....|....|
NOV8a      ISRQNPPETSSKGSDSELKKSLGPLGIPTPTMTLASPVKRNKSSVRHTQPSPVSRSKLQE
NOV8b      ISRQNPPETSSKGSDSELKKSLGPLGIPTPTMTLASPVKRNKSSVRHTQPSPVSRSKLQE
```

TABLE 8E-continued

Alignment of NOV8a, and 8b.

```
              2470       2480       2490       2500       2510       2520
         ....|....|....|....|....|....|....|....|....|....|....|....|
NOV8a    LRALSMPDLDKLCSEDYSAGPSAVLFKTELEITPRRSPGPPAGGVSCPEKGGNRACPGGS
NOV8b    LRALSMPDLDKLCSEDYSAGPSAVLFKTELEITPRRSPGPPAGGVSCPEKGGNRACPGGS 2530       2540       2550       2560       2570       2580
         ....|....|....|....|....|....|....|....|....|....|....|....|
NOV8a    GPKTSAAETPSSASDTGEAAQDLPFRRSESVNLDQLLVSAGDQQRLQSVLSSVGSKSTIL
NOV8b    GPKTSAAETPSSASDTGEAAQDLPFRRSESVNLDQLLVSAGDQQRLQSVLSSVGSKSTIL 2590       2600       2610       2620       2630       2640
         ....|....|....|....|....|....|....|....|....|....|....|....|
NOV8a    TLIQEAKAQSENEEDVCFIVLNRKEGSGLGFSVAGGTDVEPKSITVHRVFSQGAASQEGT
NOV8b    TLIQEAKAQSENEEDVCFIVLNRKEGSGLGFSVAGGTDVEPKSITVHRVFSQGAASQEGT 2650       2660       2670       2680       2690       2700
         ....|....|....|....|....|....|....|....|....|....|....|....|
NOV8a    MNRGDFLLSVNGASLAGLAHGNVLKVLHQAQLHKDALVVIKKGMDQPRPSARQEPPTANG
NOV8b    MNRGDFLLSVNGASLAGLAHGNVLKVLHQAQLHKDALVVIKKGMDQPRPSARQEPPTANG 2710       2720       2730       2740       2750       2760
         ....|....|....|....|....|....|....|....|....|....|....|....|
NOV8a    KGLLSRKTIPLEPGIGRSVAVHDALCVEVLKTSAGLGLSLDGGKSSVTGDGPLVIKRVYK
NOV8b    KGLLSRKTIPLEPGIGRSVAVHDALCVEVLKTSAGLGLSLDGGKSSVTGDGPLVIKRVYK 2770       2780       2790       2800       2810
         ....|....|....|....|....|....|....|....|....|....|
NOV8a    GGAAEQAGIIEAGDEILAINGKPLVGLMHFDAWNIMKSVPEGPVQLLIRKHRNSS   (SEQ ID NO:25)
NOV8b    GGAAEQAGIIEAGDEILAINGKPLVGLMHFDAWNIMKSVPEGPVQLLIRKHRNSS   (SEQ ID NO:27)
```

Homologies to either of the above NOV8 proteins will be shared by the other NOV8 protein insofar as they are homologous to each other as shown above. Any reference to NOV8 is assumed to refer to both of the NOV8 proteins in general, unless otherwise noted.

The disclosed NOV8 polypeptide has homology to the amino acid sequences shown in the BLASTP data listed in Table 8F.

TABLE 8F

BLAST results for NOV8

| Gene Index/ Identifier | Protein/Organism | Length (aa) | Identity (%) | Positives (%) | Expect |
|---|---|---|---|---|---|
| gi\|15295903\|ref\|XP_043060.2\| | similar to NONE_RETURNED (R. norvegicus) [Homo sapiens] | 1788 | 1712/1741 (98%) | 1716/1741 (98%) | 0.0 |
| gi\|2224541\|dbj\| BAA20760.1\|P | KIAA0300 [Homo sapiens] | 1608 | 1608/1608 (100%) | 1608/1608 (100%) | 0.0 |
| gi\|12621106\|ref\|NP_075229.1\| | PAPIN [Rattus norvegicus] | 2766 | 1906/2843 (67%) | 2147/2843 (75%) | 0.0 |
| gi\|12751452\|gb\|AAK07661.1\|AF338650_1 | PDZ domain-containing protein AIPC [Homo sapiens] | 2641 | 2256/2343 (96%) | 2275/2343 (96%) | 0.0 |
| gi\|12861607\|dbj\| BAB32241.1\| | putative [Mus musculus] | 364 | 314/387 (81%) | 337/387 (86%) | e-157 |

The homology between these and other sequences is shown graphically in the ClustalW analysis shown in Table 8G. In the ClustalW alignment of the NOV8 protein, as well as all other ClustalW analyses herein, the black outlined amino acid residues indicate regions of conserved sequence (i.e., regions that may be required to preserve structural or functional properties), whereas non-highlighted amino acid residues are less conserved and can potentially be altered to a much broader extent without altering protein structure or function.

TABLE 8G

ClustalW Analysis of NOV8

1) Novel NOV8a (SEQ ID NO:25)
2) Novel NOV8b (SEQ ID NO:27)
3) gi|15295903|ref|XP_043060.2| similar to NONE_RETURNED (R. norvegicus) [Homo sapiens] (SEQ ID NO:60)
4) gi|2224541|dbj|BAA20760.1|P KIAA0300 [Homo sapiens] (SEQ ID NO:61)
5) gi|12621106|ref|NP_075229.1| PAPIN [Rattus norvegicus] (SEQ ID NO:62)
6) gi|12751452|gb|AAK07661.1|AF338650_1 PDZ domain-containing protein AIPC [Homo sapiens] (SEQ ID NO:63)
7) gi|12861607|dbj|BAB32241.1| putative [Mus musculus] (SEQ ID NO:64)

```
                               10        20        30        40        50
                       ....|....|....|....|....|....|....|....|....|....|
NOV8a                  MPITQDNAVLHLPLLYQWLQNSLQEGGDGPEQRLCQAAIQKLQEYIQLNF
NOV8b                  MPITQDNAVLHLPLLYQWLQNSLQEGGDGPEQRLCQAAIQKLQEYIQLNF
gi|15295903|           --------------------------------------------------
gi|2224541|            --------------------------------------------------
gi|12621106|           --------------------------------------------------
gi|12751452|           MPITQDNAVLHLPLLYQWLQNSLQEGGDGPEQRLCQAAIQKLQEYIQLNF
gi|12861607|           --------------------------------------------------

60        70        80        90       100
                       ....|....|....|....|....|....|....|....|....|....|
NOV8a                  AVDESTVPPDHSPPEMEICTVYLTKELGDTETVGLSFGNIPVFGDYGEKR
NOV8b                  AVDESTVPPDHSPPEMEICTVYLTKELGDTETVGLSFGNIPVFGDYGEKR
gi|15295903|           --------------------------------------------------
gi|2224541|            --------------------------------------------------
gi|12621106|           --------------------------------------------------
gi|12751452|           AVDESTVPPDHSPPEMEICTVYLTKELGDTETVGLSFGNIPVFGDYGEKR
gi|12861607|           --------------------------------------------------

110       120       130       140       150
                       ....|....|....|....|....|....|....|....|....|....|
NOV8a                  RGGKKRKTHQGPVLDVGCIWVTELRKNSPAGKSGKVRLRDEILSLNGQLM
NOV8b                  RGGKKRKTHQGPVLDVGCIWVTELRKNSPAGKSGKVRLRDEILSLNGQLM
gi|15295903|           --------------------------------------------------
gi|2224541|            --------------------------------------------------
gi|12621106|           --------------------------------------------------
gi|12751452|           RGGKKRKTHQGPVLDVGCIWVTELRKNSPAGKSGKVRLRDEILSLNGQLM
gi|12861607|           --------------------------------------------------

160       170       180       190       200
                       ....|....|....|....|....|....|....|....|....|....|
NOV8a                  VGVDVSGASYLAEQCWNGGFIYLIMLRRFKHKAHSTYNGNSSNSSEPGET
NOV8b                  VGVDVSGASYLAEQCWNGGFIYLIMLRRFKHKAHSTYNGNSSNSSEPGET
gi|15295903|           --------------------------------------------------
gi|2224541|            --------------------------------------------------
gi|12621106|           --------------------------------------------------
gi|12751452|           VGVDVSGASYLAEQCWNGGFIYLIMLRRFKHKAHSTYNGNSSNSSEPGET
gi|12861607|           --------------------------------------------------

210       220       230       240       250
                       ....|....|....|....|....|....|....|....|....|....|
NOV8a                  PTLELGDRTAKKGKRTRKFGVISRPPANKAPEESKGSAGCEVSSDPSTEL
NOV8b                  PTLELGDRTAKKGKRTRKFGVISRPPANKAPEESKGSAGCEVSSDPSTEL
gi|15295903|           --------------------------------------------------
gi|2224541|            --------------------------------------------------
gi|12621106|           --------------------------------------------------
gi|12751452|           PTLELGDRTAKKGKRTRKFGVISRPPANKAPEESKGSAGCEVSSDPSTEL
gi|12861607|           --------------------------------------------------

260       270       280       290       300
                       ....|....|....|....|....|....|....|....|....|....|
NOV8a                  ENGLDPELGNGHVFQLENGPDSLKEVAGPHLERSEVDRGTEHRIPKTDAP
NOV8b                  ENGLDPELGNGHVFQLENGPDSLKEVAGPHLERSEVDRGTEHRIPKTDAP
gi|15295903|           --------------------------------------------------
gi|2224541|            --------------------------------------------------
gi|12621106|           --------------------------------------------------
gi|12751452|           ENGLDPELGNGHVFQLENGPDSLKEVAGPHLERSEVDRGTEHRIPKTDAP
gi|12861607|           --------------------------------------------------
```

TABLE 8G-continued

ClustalW Analysis of NOV8

```
                         310        320        330        340        350
                    ....|....|....|....|....|....|....|....|....|....|
NOV8a               LTTSNDKRRFSKGGKTDFQSSDCLARSKEEVGRIWKMELLKESDGLGIQV
NOV8b               LTTSNDKRRFSKGGKTDFQSSDCLARSKEEVGRIWKMELLKESDGLGIQV
gi|15295903|        --------------------------------------------------
gi|2224541|         --------------------------------------------------
gi|12621106|        --------------------------------------------------
gi|12751452|        LTTSNDKRRFSKGGKTDFQSSDCLA-RQEEVGRIWKMELLKESDGLGIQV
gi|12861607|        --------------------------------------------------

360        370        380        390        400
                    ....|....|....|....|....|....|....|....|....|....|
NOV8a               SGGRGSKRSPHAIVVTQVKEGGAAHRLRDGRLSLGDELLVINGHLLVGLS
NOV8b               SGGRGSKRSPHAIVVTQVKEGGAAHRLRDGRLSLGDELLVINGHLLVGLS
gi|15295903|        --------------------------------------------------
gi|2224541|         --------------------------------------------------
gi|12621106|        --------------------------------------------------
gi|12751452|        SGGRGSKRSPHAIVVTQVKEGGAAH-------------------------
gi|12861607|        --------------------------------------------------

410        420        430        440        450
                    ....|....|....|....|....|....|....|....|....|....|
NOV8a               HEEAVAILRSATGMVQLVVASKVGVLSAFQMPGTDEPQDVCGAEESKGNL
NOV8b               HEEAVAILRSATGMVQLVVASKVGVLSAFQMPGTDEPQDVCGAEESKGNL
gi|15295903|        --------------------------------------------------
gi|2224541|         --------------------------------------------------
gi|12621106|        --------------------------------------------------
gi|12751452|        --------------------------------------------------
gi|12861607|        --------------------------------------------------

460        470        480        490        500
                    ....|....|....|....|....|....|....|....|....|....|
NOV8a               ESPKQGSNKIKLKSRLSGRWGLYLMQPVGGVHRLESVEEYNELMVRNGDP
NOV8b               ESPKQGSNKIKLKSRLSGRWGLYLMQPVGGVHRLESVEEYNELMVRNGDP
gi|15295903|        --------------------------------------------------
gi|2224541|         --------------------------------------------------
gi|12621106|        --------------------------------------------------
gi|12751452|        --------------------------------------------------
gi|12861607|        --------------------------------------------------

510        520        530        540        550
                    ....|....|....|....|....|....|....|....|....|....|
NOV8a               RIRMLEVSRDGRKHSLPQLLDSSSASQEYHIVKKSTRSLSTTQVESPWRL
NOV8b               RIRMLEVSRDGRKHSLPQLLDSSSASQEYHIVKKSTRSLSTTQVESPRRL
gi|15295903|        --------------------------------------------------
gi|2224541|         --------------------------------------------------
gi|12621106|        --------------------------------------------------
gi|12751452|        -------------------------REYHIVKKSTRSLSTTQVESPWRL
gi|12861607|        --------------------------------------------------

560        570        580        590        600
                    ....|....|....|....|....|....|....|....|....|....|
NOV8a               IRPSVISIIGLYKEKGKGLGFSIAGGRDCIRGQMGIFVKTIFPNGSAAED
NOV8b               IRPSVISIIGLYKEKGKGLGFSIAGGRDCIRGQMGIFVKTIFPNGSAAED
gi|15295903|        --------------------------------------------------
gi|2224541|         --------------------------------------------------
gi|12621106|        --------------------------------------------------
gi|12751452|        IRPSVISIIGLYKEKGKGLGFSIAGGRDCIRGQMGIFVKTIFPNGSAAED
gi|12861607|        --------------------------------------------------

610        620        630        640        650
                    ....|....|....|....|....|....|....|....|....|....|
NOV8a               GRLKEGDEILDVNGIPIKGLTFQEAIHTFKQIRSGLFVLTVRTKLVSPSL
NOV8b               GRLKEGDEILDVNGIPIKGLTFQEAIHTFKQIRSGLFVLTVRTKLVSPSL
gi|15295903|        --------------------------------------------------
gi|2224541|         --------------------------------------------------
gi|12621106|        --------------------------------------------------
gi|12751452|        GRLKEGDEILDVNGIPIKGLTFQEAIHTFKQIRSGLFVLTVRTKLVSPSL
gi|12861607|        --------------------------------------------------

660        670        680        690        700
                    ....|....|....|....|....|....|....|....|....|....|
NOV8a               TPCSTPTHMSRSASPNFNTSGGASAGGSDEGSSSSLGRKTPGPKDRIVME
NOV8b               TPCSTPTHMSRSASPNFNTSGGASAGGSDEGSSSSLGRKTPGPKDRIVME
gi|15295903|        --------------------------------------------------
gi|2224541|         --------------------------------------------------
gi|12621106|        --------------------------------------------------
gi|12751452|        TPCSTPTHMSRSASPNFNTSGGASAGGSDEGSSSSLGRKTPGPKDRIVME
gi|12861607|        --------------------------------------------------
```

TABLE 8G-continued

ClustalW Analysis of NOV8

```
                        710        720        730        740        750
                   ....|....|....|....|....|....|....|....|....|....|
NOV8a              VTLNKEPRVGLGIGACCLALENSPPGIYIHSLAPGSVAKMESNLSRGS-I
NOV8b              VTLNKEPRVGLGIGACCLALENSPPGIYIHSLAPGSVAKMESNLSRGDQI
gi|15295903|       --------------------------------------------------
gi|2224541|        --------------------------------------------------
gi|12621106|       --------------------------------------------------
gi|12751452        VTLNKEPRVGLGIGACCLALENSPPGIYIHSLAPGSVAKMESNLSRGDQI
gi|12861607|       --------------------------------------------------

760        770        780        790        800
                   ....|....|....|....|....|....|....|....|....|....|
NOV8a              LEVNSVNVRHAALSKVHAILSKCPPGPVRLVIGRHPNPKVNQVSEQEMDE
NOV8b              LEVNSVNVRHAALSKVHAILSKCPPGPVRLVI---GRHPNPKVSEQEMDE
gi|15295903|       --------------------------------------------------
gi|2224541|        --------------------------------------------------
gi|12621106|       --------------------------------------------------
gi|12751452        LEVNSVNVRHAALSKVHAILSKCP-----------------VSEQEMDE
gi|12861607|       --------------------------------------------------

810        820        830        840        850
                   ....|....|....|....|....|....|....|....|....|....|
NOV8a              VIARSTYQESKEANSSPGLGTVISIGCFLLQQDSLISESELSQYFAHDVP
NOV8b              VIARSTYQESKEANSSPGLGTPLKS-PSLAKKDSLISESELSQYFAHDVP
gi|15295903|       --------------------------------------------------
gi|2224541|        --------------------------------------------------
gi|12621106|       --------------------------------------------------
gi|12751452        VIARSTYQESKEANSSPGLGTPLKS-PSLAKKDSLISESELSQYFAHDVP
gi|12861607|       --------------------------------------------------

860        870        880        890        900
                   ....|....|....|....|....|....|....|....|....|....|
NOV8a              GPLSDFMVAGSEDEDHPGSGCSTSEEGSLPPSTSTHKEPGKPRANSLVTL
NOV8b              GPLSDFMVAGSEDEDHPGSGCSTSEEGSLPPSTSTHKEPGKPRANSLVTL
gi|15295903|       --------------------------------------------------
gi|2224541|        --------------------------------------------------
gi|12621106|       --------------------------------------------------
gi|12751452        GPLSDFMVAGSEDEDHPGSGCSTSEEGSLPP--STSSEPGKPRANSLVTL
gi|12861607|       --------------------------------------------------

910        920        930        940        950
                   ....|....|....|....|....|....|....|....|....|....|
NOV8a              GSHRASGLFHKQVTVARQASLPGSPQALRNPLLRQRKVGCYDANDASDEE
NOV8b              GSHRASGLFHKQVTVARQASLPGSPQALRNPLLRQRKVGCYDANDASDEE
gi|15295903|       --------------------------------------------------
gi|2224541|        --------------------------------------------------
gi|12621106|       --------------------------------------------------
gi|12751452        GSHRASGLFHKQVTVARQASLPGSPQALRNPLLRQRKVGCYDANDASDEE
gi|12861607|       --------------------------------------------------

960        970        980        990       1000
                   ....|....|....|....|....|....|....|....|....|....|
NOV8a              EFDREGDCISLPGALPGERRPLEEDDPRRVSISSSKGMDVHNQEERPRKT
NOV8b              EFDREGDCISLPGALPGERRPLEEDDPRRVSISSSKGMDVHNQEERPRKT
gi|15295903|       ---------------MLREMQPTM--------------------------
gi|2224541|        --------------------------------------------------
gi|12621106|       ---------------MEMTQDM-------------------ALLHLP
gi|12751452        EFDREGDCISLPGALPGERRPLEEDDPRRVSISSSKGMDVHNQEERPRKT
gi|12861607|       --------------------------------------------------

1010       1020       1030       1040       1050
                   ....|....|....|....|....|....|....|....|....|....|
NOV8a              LVSKAMSAPLLGSSVDLEESIPEGMVDAASYAANLTDMAEAPKGSPGSWW
NOV8b              LVSKAMSAPLLGSSVDLEESIPEGMVDAASYAANLTDMAEAPKGSPGSWW
gi|15295903|       ---RTMQRPPRGA---LEAGGRRNCQDQVAHPNWNTQMVQTPR-------
gi|2224541|        --------------------------------------------------
gi|12621106|       LLYEWMQNSLREGGDSPEQRLCQAAIQKLQEYIQLNLMVDESTVPPDHSP
gi|12751452        LVSKAMSAPLLGSSVDLEESIPEGMVDAASYAANLTDMAEAPKGSPGSWW
gi|12861607|       --------------------------------------------------

1060       1070       1080       1090       1100
                   ....|....|....|....|....|....|....|....|....|....|
NOV8a              KKELSGSSSAPKLEYTVRTDTQSPTNTGSPSSPQQKSEGLGSRHRPVARV
NOV8b              KKELSGSSSAPKLEYTVRTDTQSPTNTGSPSSPQQKSEGLGSRHRPVARV
gi|15295903|       ---------------------VRRTLGAPVPPSRKVKAWAPGTDQWPGV
gi|2224541|        --------------------------------------------------
gi|12621106|       PEMEICTVYLTKQLGDTETVGLSFGNIPVFGDYGEKRRGGKKRKTHQGPV
gi|12751452        KKELSGSSSAPKLEYTVRTDTQSPTNTGSPSSPQQKSEGLGSRHRPVARV
gi|12861607|       --------------------------------------------------
```

TABLE 8G-continued

ClustalW Analysis of NOV8

```
                   1110       1120       1130       1140       1150
                ....|....|....|....|....|....|....|....|....|....|
NOV8a           SPHCKRSEADAKPSGSQTVKLTGRANDPCDLDSRVQATSVKVIVAGKQPG
NOV8b           SPHCKRSEADAKPSGSQTVKLTGRANDPCDLDSRVQATSVKVIVAGKQPG
gi|15295903|    SPHCKRSEADAKPSGSQTVKLTGRANDPCDLDSRVQATSVKVIVAGKQPG
gi|2224541|     --------------------------------------------------
gi|12621106|    LDVGCIWVTELKKMSPAGKSGKVRLRDEILSLNGQLMVGVDVIGASYLAE
gi|12751452     SPHCKRSEADAKPSGSQTVKLTGRANDPCDLDSRVQATSVKVIVAGKQPG
gi|12861607     --------------------------------------------------

1160       1170       1180       1190       1200
                ....|....|....|....|....|....|....|....|....|....|
NOV8a           GAVEK---ESLGKLTTGDACVSTSCELASALSHLDASHLTENLPKAASEL
NOV8b           GAVEK---ESLGKLTTGDACVSTSCELASALSHLDASHLTENLPKAASEL
gi|15295903|    GAVEKLCQESLGKLTTGDACVSTSCELASALSHLDASHLTENLPKAASEL
gi|2224541|     --------------------------------------------------
gi|12621106|    QCWNG-GFIYLIMLRRFKQKAHVYYNGNSGNSSEPGETPTLELGDQTSKK
gi|12751452     GAVEKLCQESLGKLTTGDACVSTSCELASALSHLDASHLTENLPKAASEL
gi|12861607     -----------MLRRFKQKAHVYYNGNSGNSSEPGETPTLELGDQTSKK 1210       1220       1230       1240       1250
                ....|....|....|....|....|....|....|....|....|....|
NOV8a           GKKPMTELDSSSDLISSPGKKGAAHPDPSKTSVDTGKVSRPENPSQPASP
NOV8b           GKKPMTELDSSSDLISSPGKKGAAHPDPSKTSVDTGKVSRPENPSQPASP
gi|15295903|    GKKPMT----SSDLISSPGKKGAAHPDPSKTSVDTGKVSRPENPSQPASP
gi|2224541|     ---------SSDLISSPGKKGAAHPDPSKTSVDTGKVSRPENPSQPASP
gi|12621106|    GKKTRK-----FGKISRPSISKTPEDSKSSSGCDTADDPNSELENG----
gi|12751452     GKKPMT----SSDLISSPGKKGAAHPDPSKTSVDTGKVSRPENPSQPASP
gi|12861607     GKKTRK-----FGKISRPAIIKAPEDSKSSSGCDTADDPNSELENG----

1260       1270       1280       1290       1300
                ....|....|....|....|....|....|....|....|....|....|
NOV8a           RVAKCKARSPVRLPHEGSPSPGEKAAAPPDYSKTRSASETSTPHNTRRVA
NOV8b           RVAKCKARSPVRLPHEGSPSPGEKAAAPPDYSKTRSASETSTPHNTRRVA
gi|15295903|    RVTKCKARSPVRLPHEGSPSPGEKAAAPPDYSKTRSASETSTPHNTRRVA
gi|2224541|     RVAKCKARSPVRLPHEGSPSPGEKAAAPPDYSKTRSASETSTPHNTRRVA
gi|12621106|    --ADPELGNGHAFELDNGPHSLKDVAGP---HLERSENREVELRVPKTE
gi|12751452     RVTKCKARSPVRLPHEGSPSPGEKAAAPPDYSKTRSASETSTPHNTRRVA
gi|12861607     --TDSELGNGHAFELENGENSLKDVAGP---HLERSENREAELRVPKTE 1310       1320       1330       1340       1350
                ....|....|....|....|....|....|....|....|....|....|
NOV8a           ALRGAGPGAEGMTPAGAVLPGDPLTSQEQRQGAPGNHSKALEMTGIHAPE
NOV8b           ALRGAGPGAEGMTPAGAVLPGDPLTSQEQRQGAPGNHSKALEMTGIHAPE
gi|15295903|    ALRGAGPGAEGMTPAGAVLPGDPLTSQEQRQGAPGNHSKALEMTGIHAPE
gi|2224541|     ALRGAGPGAEGMTPAGAVLPGDPLTSQEQRQGAPGNHSKALEMTGIHAPE
gi|12621106|    APLSDSNDKRRFSKTGKTDFQSSDCLARKEVGRIWKMELLKESDGKGIQV
gi|12751452     ALRGAGPGAEGMTPAGAVLPGDPLTSQEQRQGAPGNHSKALEMTGIHAPE
gi|12861607     APLSDSNDKRRFSKTGKTNFQSSDSLARKEVGRIWEMELLKESDGKGIQV 1360       1370       1380       1390       1400
                ....|....|....|....|....|....|....|....|....|....|
NOV8a           SSQEFSLLEGADSVSSRAPQASLSMLPSTDNTKEACGHVSGHCCPGGSRE
NOV8b           SSQEFSLLEGADSVSSRAPQASLSMLPSTDNTKEACGHVSGHCCPGGSRE
gi|15295903|    SSQEFSLLEGADSVSSRAPQASLSMLPSTDNTKEACGHVSGHCCPGGSRE
gi|2224541|     SSQEFSLLEGADSVSSRAPQASLSMLPSTDNTKEACGHVSGHCCPGGSRE
gi|12621106|    SGGRGSKRSPHAIVVKKVKSGGAKHRDGRLSLGKELLVKKGHLLVGLSHE
gi|12751452     SSQEFSLLEGADSVSSRAPQASLSMLPSTDNTKEACGHVSGHCCPGGSRE
gi|12861607     SGGRGSKRSPHAIVVKKVKKGGAKHRDGRLSLGKELLVKKGHLLVGLSHE 1410       1420       1430       1440       1450
                ....|....|....|....|....|....|....|....|....|....|
NOV8a           SPVTDIDSFIKELDASAARSP--SSQTGDSGSQEGSAQGHPPAGAGGGSS
NOV8b           SPVTDIDSFIKELDASAARSP--SSQTGDSGSQEGSAQGHPPAGAGGGSS
gi|15295903|    SPVTDIDSFIKELDASAARSP--SSQTGDSGSQEGSAQGHPPAGAGGGSS
gi|2224541|     SPVTDIDSFIKELDASAARSP--SSQTGDSGSQEGSAQGHPPAGAGGGSS
gi|12621106|    EAVAIERSATGMYQLVVASKMPGSEKKQDVGSSPESKGN-LESPKQGNCK
gi|12751452     SPVTDIDSFIKELDASAARSP--SSQTGDSGSQEGSAQGHPPAGAGGGSS
gi|12861607     EAVAIERSATGMYQLVVASKMPGSEKKQDVGSSPESKGNKLESPKQGNSK 1460       1470       1480       1490       1500
                ....|....|....|....|....|....|....|....|....|....|
NOV8a           CRAEPVPGGQTSSPRRAWAAGAPAYPQWASQPSVLDSINPDKHFTVNKNF
NOV8b           CRAEPVPGGQTSSPRRAWAAGAPAYPQWASQPSVLDSINPDKHFTVNKNF
gi|15295903|    CRAEPVPGGQTSSPRRAWAAGAPAYPQWASQPSVLDSINPDKHFTVNKNF
gi|2224541|     CRAEPVPGGQTSSPRRAWAAGAPAYPQWASQPSVLDSINPDKHFTVNKNF
gi|12621106|    TKLKSRLSCGVHRLESVEEYNELMVRNGDPKIRKLKVSRDGKKHSKPQLL
gi|12751452     CRAEPVPGGQTSSPRRAWAAGAPAYPQWASQPSVLDSINPDKHFTVNKNF
gi|12861607     MKLKSRLSCGVHRLESVEEYNELMVRNGDPKIRKLKVSRDGKKHSKPQLL
```

TABLE 8G-continued

ClustalW Analysis of NOV8

```
                      1510       1520       1530       1540       1550
                 ....|....|....|....|....|....|....|....|....|....|
NOV8a            LSN-YSRNFSSFHEDSTSLSGLGDST-----EPSLSSMYG----------
NOV8b            LSN-YSRNFSSFHEDSTSLSGLGDST-----EPSLSSMYG----------
gi|15295903|     LSN-YSRNFSSFHEDSTSLSGLGDST-----EPSLSSMYG----------
gi|2224541|      LSN-YSRNFSSFHEDSTSLSGLGDST-----EPSLSSMYG----------
gi|12621106      DSTGTSGEXHIVKXSXRSLSTTHVESPWRLIRPSXISXIGLYKEKGKGLG
gi|12751452      LSN-YSRNFSSFHEDSTSLSGLGDST-----EPSLSSMYG----------
gi|12861607|     DSTGTSGEXHIVKXSXRSLSTTHVESPWRLIRPSXISXIG----------

1560       1570       1580       1590       1600
                 ....|....|....|....|....|....|....|....|....|....|
NOV8a            --------------------------------------------------
NOV8b            --------------------------------------------------
gi|15295903|     --------------------------------------------------
gi|2224541|      --------------------------------------------------
gi|12621106      FSIAGGRDCIRGQMGIFVKTIFPNGSAAEDGRLKEGDEILDVNGIPIKGL
gi|12751452      --------------------------------------------------
gi|12861607|     --------------------------------------------------

1610       1620       1630       1640       1650
                 ....|....|....|....|....|....|....|....|....|....|
NOV8a            --------------------------------------------------
NOV8b            --------------------------------------------------
gi|15295903|     --------------------------------------------------
gi|2224541|      --------------------------------------------------
gi|12621106      TFQEAIHTPKQIRSGLFVLTVRTKLLSPSLTPCSTPTHMSRSSSPSFNTN
gi|12751452      --------------------------------------------------
gi|12861607|     --------------------------------------------------

1660       1670       1680       1690       1700
                 ....|....|....|....|....|....|....|....|....|....|
NOV8a            --------------------------------------------------
NOV8b            --------------------------------------------------
gi|15295903|     --------------------------------------------------
gi|2224541|      --------------------------------------------------
gi|12621106      SGGTPAGGGQEEGGSSSLGRKAPGPKDRIVMEVTLNKEPRVGLGIGACCL
gi|12751452      --------------------------------------------------
gi|12861607|     --------------------------------------------------

1710       1720       1730       1740       1750
                 ....|....|....|....|....|....|....|....|....|....|
NOV8a            --------------------------------------------------
NOV8b            --------------------------------------------------
gi|15295903|     --------------------------------------------------
gi|2224541|      --------------------------------------------------
gi|12621106      ALENSPPGIYIHSLAPGSVAKMESNLSRGDQILEVNSVNVRHAALSKVHA
gi|12751452      --------------------------------------------------
gi|12861607|     --------------------------------------------------

1760       1770       1780       1790       1800
                 ....|....|....|....|....|....|....|....|....|....|
NOV8a            --------------------------------------------------
NOV8b            --------------------------------------------------
gi|15295903|     --------------------------------------------------
gi|2224541|      --------------------------------------------------
gi|12621106      ILSKCPPGPVRLVIGRHPNPKVSEQEMDEVIARSTYQESREANSSPGLGT
gi|12751452      --------------------------------------------------
gi|12861607|     --------------------------------------------------

1810       1820       1830       1840       1850
                 ....|....|....|....|....|....|....|....|....|....|
NOV8a            --------------------------------------------------
NOV8b            --------------------------------------------------
gi|15295903|     --------------------------------------------------
gi|2224541|      --------------------------------------------------
gi|12621106      PLKSPSLAKKDSLLSESELSQYFVHDGQGSLSDFVVAGSEDEDHPGSGYE
gi|12751452      --------------------------------------------------
gi|12861607|     --------------------------------------------------

1860       1870       1880       1890       1900
                 ....|....|....|....|....|....|....|....|....|....|
NOV8a            --------------------------------------------------
NOV8b            --------------------------------------------------
gi|15295903|     --------------------------------------------------
gi|2224541|      --------------------------------------------------
gi|12621106      TSEDGSLLPVPSAHKARANSLVTLGSQRTSGLLHKQVTVARQASLPGSPQ
gi|12751452      --------------------------------------------------
gi|12861607|     --------------------------------------------------
```

TABLE 8G-continued

ClustalW Analysis of NOV8

```
                   1910      1920      1930      1940      1950
              ....|....|....|....|....|....|....|....|....|....|
NOV8a         --------------------------------------------------
NOV8b         --------------------------------------------------
gi|15295903|  --------------------------------------------------
gi|2224541|   --------------------------------------------------
gi|12621106|  VLRNPLLRQRRVRCYDSNGGSDDEDFDGEGDCISLPGVLPGPGKPLVEDD
gi|12751452|  --------------------------------------------------
gi|12861607|  --------------------------------------------------

1960      1970      1980      1990      2000
              ....|....|....|....|....|....|....|....|....|....|
NOV8a         --------------------------------------------------
NOV8b         --------------------------------------------------
gi|15295903|  --------------------------------------------------
gi|2224541|   --------------------------------------------------
gi|12621106|  TRPALTTSSKSIDVNKQEERLQKPLVSKACSVPLLGSSLDSEHSILNGAG
gi|12751452|  --------------------------------------------------
gi|12861607|  --------------------------------------------------

2010      2020      2030      2040      2050
              ....|....|....|....|....|....|....|....|....|....|
NOV8a         --------------------------------------------------
NOV8b         --------------------------------------------------
gi|15295903|  --------------------------------------------------
gi|2224541|   --------------------------------------------------
gi|12621106|  GTPPKVASLPGSGETPKNGPRGSGRKEMSGSRSSPKLEYRVPTDTQSPRS
gi|12751452|  --------------------------------------------------
gi|12861607|  --------------------------------------------------

2060      2070      2080      2090      2100
              ....|....|....|....|....|....|....|....|....|....|
NOV8a         --------------------------------------------------
NOV8b         --------------------------------------------------
gi|15295903|  --------------------------------------------------
gi|2224541|   --------------------------------------------------
gi|12621106|  PENHTSPPQKSENLVSRHKPVARISPHYKRSDAEEAPGGTANGPCAQDLK
gi|12751452|  --------------------------------------------------
gi|12861607|  --------------------------------------------------

2110      2120      2130      2140      2150
              ....|....|....|....|....|....|....|....|....|....|
NOV8a         --------------------------------------------------
NOV8b         --------------------------------------------------
gi|15295903|  --------------------------------------------------
gi|2224541|   --------------------------------------------------
gi|12621106|  VQASPVKDPVTSRQPGGTAEKELRGNPTPGDSSVPTNCGPASTPCHPNIG
gi|12751452|  --------------------------------------------------
gi|12861607|  --------------------------------------------------

2160      2170      2180      2190      2200
              ....|....|....|....|....|....|....|....|....|....|
NOV8a         --------------------------------------------------
NOV8b         --------------------------------------------------
gi|15295903|  --------------------------------------------------
gi|2224541|   --------------------------------------------------
gi|12621106|  LPTENPQGAAPECGPHPGTGWDGSSEHLCSPGKSREVHPDSSETPTVAEQ
gi|12751452|  --------------------------------------------------
gi|12861607|  --------------------------------------------------

2210      2220      2230      2240      2250
              ....|....|....|....|....|....|....|....|....|....|
NOV8a         --------------------------------------------------
NOV8b         --------------------------------------------------
gi|15295903|  --------------------------------------------------
gi|2224541|   --------------------------------------------------
gi|12621106|  VHQPESLSQPVSPRTSEPESQGISKMKPPSQRCVSPREKASTPPDSSRAW
gi|12751452|  --------------------------------------------------
gi|12861607|  --------------------------------------------------

2260      2270      2280      2290      2300
              ....|....|....|....|....|....|....|....|....|....|
NOV8a         --------------------------------------------------
NOV8b         --------------------------------------------------
gi|15295903|  --------------------------------------------------
gi|2224541|   --------------------------------------------------
gi|12621106|  AAPGDSSPSTRRIAVPMSTGAAPATAIPQASLVSQERSRGLSGPSKGLGT
gi|12751452|  --------------------------------------------------
gi|12861607|  --------------------------------------------------
```

TABLE 8G-continued

ClustalW Analysis of NOV8

```
                  2310       2320       2330       2340       2350
                  ....|....|....|....|....|....|....|....|....|....|
NOV8a             --------------------------------------------------
NOV8b             --------------------------------------------------
gi|15295903|      --------------------------------------------------
gi|2224541|       --------------------------------------------------
gi|12621106       KELCIPKSLKDGALLEDTAPASGKMSHASSPSGPVATERTLSGSPENPVT
gi|12751452       --------------------------------------------------
gi|12861607       --------------------------------------------------

2360       2370       2380       2390       2400
                  ....|....|....|....|....|....|....|....|....|....|
NOV8a             --------------------------------------------------
NOV8b             --------------------------------------------------
gi|15295903|      --------------------------------------------------
gi|2224541|       --------------------------------------------------
gi|12621106       DIDNFIEEASEARLSQSPQKADCRAHGDTFFSQPPGGAGSSSSHHAQMVR
gi|12751452       --------------------------------------------------
gi|12861607       --------------------------------------------------

2410       2420       2430       2440       2450
                  ....|....|....|....|....|....|....|....|....|....|
NOV8a             --------------------------------------------------
NOV8b             --------------------------------------------------
gi|15295903|      --------------------------------------------------
gi|2224541|       --------------------------------------------------
gi|12621106       SDQTSSPRKTGGTGSPPPQQWALQPSVLDSIHPDKHLAVNKTFLNNYSRN
gi|12751452       --------------------------------------------------
gi|12861607       --------------------------------------------------

2460       2470       2480       2490       2500
                  ....|....|....|....|....|....|....|....|....|....|
NOV8a             ------------------------DAEDSSSDPESLTEAPRASARDG
NOV8b             ------------------------DAEDSSSDPESLTEAPRASARDG
gi|15295903|      ------------------------DAEDSSSDPESLTEAPRASARDG
gi|2224541|       ------------------------DAEDSSSDPESLTEAPRASARDG
gi|12621106       FSNFHEDSISLSGPGGSSEPSPSSMYGAAEDSSSDPESLAEDPGAAARKN
gi|12751452       ------------------------DAEDSSSDPESLTEAPRASARDG
gi|12861607       --------------------------------------------------

2510       2520       2530       2540       2550
                  ....|....|....|....|....|....|....|....|....|....|
NOV8a             WSPPRSRVSLHKEDPSESEEEQIEICSTRGCPNPPSSPAHLPTQAAICPA
NOV8b             WSPPRSRVSLHKEDPSESEEEQIEICSTRGCPNPPSSPAHLPTQAAICPA
gi|15295903|      WSPPRSRVSLHKEDPSESEEEQIEICSTRGCPNPPSSPAHLPTQAAICPA
gi|2224541|       WSPPRSRVSLHKEDPSESEEEQIEICSTRGCPNPPSSPAHLPTQAAICPA
gi|12621106       WSPELSPESSPKEGSSESESEEIEICSTDGCPGTP-----TAPPPTQVA
gi|12751452       WSPPRSRVSLHKEDPSESEEEQIEICSTRGCPNPPSSPAHLPTQAAICPA
gi|12861607       --------------------------------------------------

2560       2570       2580       2590       2600
                  ....|....|....|....|....|....|....|....|....|....|
NOV8a             SAKVLSLKYSTPRESVASPREKVACLP-GSYTSGPDSSQPSSLLEMSSQE
NOV8b             SAKVLSLKYSTPRESVASPREKVACLP-GSYTSGPDSSQPSSLLEMSSQE
gi|15295903|      SAKVLSLKYSTPRESVASPREKVACLP-GSYTSGPDSSQPSSLLEMSSQE
gi|2224541|       SAKVLSLKYSTPRESVASPREKVACLP-GSYTSGPDSSQPSSLLEMSSQE
gi|12621106       LCPVLPKQRAVCKPVGDICEKACFVPGASRTSIPDSSQPFSFLKSSQE
gi|12751452       SAKVLSLKYSTPRESVASPREKVACLP-GSYTSGPDSSQPSSLLEMSSQE
gi|12861607       --------------------------------------------------

2610       2620       2630       2640       2650
                  ....|....|....|....|....|....|....|....|....|....|
NOV8a             HETHADISTSQNHRPSCAEETTEVTSASSAMENSPLSKVARHFHSPPIIL
NOV8b             HETHADISTSQNHRPSCAEETTEVTSASSAMENSPLSKVARHFHSPPIIL
gi|15295903|      HETHADISTSQNHRPSCAEETTEVTSASSAMENSPLSKVARHFHSPPIIL
gi|2224541|       HETHADISTSQNHRPSCAEETTEVTSASSAMENSPLSKVARHFHSPPIIL
gi|12621106       PETWASIKASQNHMPVCTEGIMKVTSTSSNMGKSQSSKTRHCRKAPFYL
gi|12751452       HETHADISTSQNHRPSCAEETTEVTSASSAMENSPLSKVARHFHSPPIIL
gi|12861607       --------------------------------------------------

2660       2670       2680       2690       2700
                  ....|....|....|....|....|....|....|....|....|....|
NOV8a             SSPNMVNGLEHDLLDDETLNQYETSINAAASLSSFSVDVPKNGESVLENL
NOV8b             SSPNMVNGLEHDLLDDETLNQYETSINAAASLSSFSVDVPKNGESVLENL
gi|15295903|      SSPNMVNGLEHDLLDDETLNQYETSINAAASLSSFSVDVPKNGESVLENL
gi|2224541|       SSPNMVNGLEHDLLDDETLNQYETSINAAASLSSFSVDVPKNGESVLENL
gi|12621106       GKPKMVNDLGRDLLDKGAPKKGAAKASVMRSKFKLGAKGPKNGEKVLAKL
gi|12751452       SSPNMVNGLEHDLLDDETLNQYETSINAAASLSSFSVDVPKNGESVLENL
gi|12861607       --------------------------------------------------
```

TABLE 8G-continued

ClustalW Analysis of NOV8

```
                      2710       2720       2730       2740       2750
                 ....|....|....|....|....|....|....|....|....|....|
NOV8a            HISESQDLDDLLQKPKMIARRPIMAWFKEINKHNQGTHLTSKTEKEQPLM
NOV8b            HISESQDLDDLLQKPKMIARRPIMAWFKEINKHNQGTHLTSKTEKEQPLM
gi|15295903|     HISESQDLDDLLQKPKMIARRPIMAWFKEINKHNQGTHLTSKTEKEQPLM
gi|2224541|      HISESQDLDDLLQKPKMIARRPIMAWFKEINKHNQGTHLTSKTEKEQPLM
gi|12621106|     HIRERGNLQDLLQKPKTISRRPISTWFKEINKDSQGSHLRSTSEKEQSSM
gi|12751452|     HISESQDLDDLLQKPKMIARRPIMAWFKEINKHNQGTHLTSKTEKEQPLM
gi|12861607|     -------------------------------------------------

2760       2770       2780       2790       2800
                 ....|....|....|....|....|....|....|....|....|....|
NOV8a            PARSPDSKIQMVSSSQKKGVTVPHSPPQPKINLENKDLSKKSPAEMLLTN
NOV8b            PARSPDSKIQMVSSSQKKGVTVPHSPPQPKINLENKDLSKKSPAEMLLTN
gi|15295903|     PARSPDSKIQMVSSSQKKGVTVPHSPPQPKINLENKDLSKKSPAEMLLTN
gi|2224541|      PARSPDSKIQMVSSSQKKGVTVPHSPPQPKINLENKDLSKKSPAEMLLTN
gi|12621106|     LALGPGSKANMVSSGHRKGVTVPKSPPSRSKSQENKDLPPKSVETLGN-
gi|12751452|     PARSPDSKIQMVSSSQKKGVTVPHSPPQPKINLENKDLSKKSPAEMLLTN
gi|12861607|     -------------------------------------------------

2810       2820       2830       2840       2850
                 ....|....|....|....|....|....|....|....|....|....|
NOV8a            GQKAKCGPKLKRLSLKGKAKVNSEAPAANAVKAGGTDHRKPLISPQTSHK
NOV8b            GQKAKCGPKLKRLSLKGKAKVNSEAPAANAVKAGGTDHRKPLISPQTSHK
gi|15295903|     GQKAKCGPKLKRLSLKGKAKVNSEAPAANAVKAGGTDHRKPLISPQTSHK
gi|2224541|      GQKAKCGPKLKRLSLKGKAKVNSEAPAANAVKAGGTDHRKPLISPQTSHK
gi|12621106|     CQKPKCSPKLKRLSSKGKASP--EVPVAISTKGSRNDHRKTLPSPQASHK
gi|12751452|     GQKAKCGPKLKRLSLKGKAKVNSEAPAANAVKAGGTDHRKPLISPQTSHK
gi|12861607|     -------------------------------------------------

2860       2870       2880       2890       2900
                 ....|....|....|....|....|....|....|....|....|....|
NOV8a            TLSKAVSQRLHVADHEDPDRNTTAAPRSPQCVLESKPPLATSGPLKPSVS
NOV8b            TLSKAVSQRLHVADHEDPDRNTTAAPRSPQCVLESKPPLATSGPLKPSVS
gi|15295903|     TLSKAVSQRLHVADHEDPDRNTTAAPRSPQCVLESKPPLATSGPLKPSVS
gi|2224541|      TLSKAVSQRLHVADHEDPDRNTTAAPRSPQCVLESKPPLATSGPLKPSVS
gi|12621106|     MFSKAVSHRLHSADQESPKNTAGDTPSPPQCVPESKPPQAALGSLSTSAS
gi|12751452|     TLSKAVSQRLHVADHEDPDRNTTAAPRSPQCVLESKPPLATSGPLKPSVS
gi|12861607|     -------------------------------------------------

2910       2920       2930       2940       2950
                 ....|....|....|....|....|....|....|....|....|....|
NOV8a            DTSIRTFVSPLTSPKPVPEQGMWSRFHMAVLSEPDRGCPTTPKSPKCRAE
NOV8b            DTSIRTFVSPLTSPKPVPEQGMWSRFHMAVLSEPDRGCPTTPKSPKCRAE
gi|15295903|     DTSIRTFVSPLTSPKPVPEQGMWSRFHMAVLSEPDRGCPTTPKSPKCRAE
gi|2224541|      DTSIRTFVSPLTSPKPVPEQGMWSRFHMAVLSEPDRGCPTTPKSPKCRAE
gi|12621106|     DTSIRTFTSPLTSPKLSPEQGANSRFHMAVYLESDTSCPTTSSSPRSGPE
gi|12751452|     DTSIRTFVSPLTSPKPVPEQGMWSRFHMAVLSEPDRGCPTTPKSPKCRAE
gi|12861607|     -------------------------------------------------

2960       2970       2980       2990       3000
                 ....|....|....|....|....|....|....|....|....|....|
NOV8a            GRAPRADSGPVSPAASRNGMSVAGNRQSE---PRLASHVAADTAQPRPTG
NOV8b            GRAPRADSGPVSPAASRNGMSVAGNRQSE---PRLASHVAADTAQPRPTG
gi|15295903|     GRAPRADSGPVSPAASRNGMSVAGNRQSE---PRLASHVAADTAQPRPTG
gi|2224541|      GRAPRADSGPVSPAASRNGMSVAGNRQSE---PRLASHVAADTAQPRPTG
gi|12621106|     GKAPHASSGSASPEASRASLALAGSIRQSKQFTPGRADLSVSSAIQPSGIC
gi|12751452|     GRAPRADSGPVSPAASRNGMSVAGNRQSE---PRLASHVAADTAQPRPTG
gi|12861607|     -------------------------------------------------

3010       3020       3030       3040       3050
                 ....|....|....|....|....|....|....|....|....|....|
NOV8a            EKGGNIMASDRLERTNQLKIVEISAEAVSETVCGNKPAESDRRGGCLAQG
NOV8b            EKGGNIMASDRLERTNQLKIVEISAEAVSETVCGNKPAESDRRGGCLAQG
gi|15295903|     EKGGNIMASDRLERTNQLKIVEISAEAVSETVCGNKPAESDRRGGCLAQG
gi|2224541|      EKGGNIMASDRLERTNQLKIVEISAEAVSETVCGNKPAESDRRGGCLAQG
gi|12621106|     EKGAEKKVSDPPSRTNQLKIVEISSERVPSNACCSPEESDRSGGFLTQN
gi|12751452|     EKGGNIMASDRLERTNQLKIVEISAEAVSETVCGNKPAESDRRGGCLAQG
gi|12861607|     -------------------------------------------------

3060       3070       3080       3090       3100
                 ....|....|....|....|....|....|....|....|....|....|
NOV8a            NCQEKSEIRLYRQVAESSTSHPSSLPSHASQAEQEMSRSFSMAKLASSSS
NOV8b            NCQEKSEIRLYRQVAESSTSHPSSLPSHASQAEQEMSRSFSMAKLASSSS
gi|15295903|     NCQEKSEIRLYRQVAESSTSHPSSLPSHASQAEQEMSRSFSMAKLASSSS
gi|2224541|      NCQEKSEIRLYRQVAESSTSHPSSLPSHASQAEQEMSRSFSMAKLASSSS
gi|12621106|     NCQEKSAIRLR-QSEESSPEHTPFEPSQASQVESERWSFSMAKEASSSS
gi|12751452|     NCQEKSEIRLYRQVAESSTSHPSSLPSHASQAEQEMSRSFSMAKLASSSS
gi|12861607|     -------------------------------------------------
```

TABLE 8G-continued

ClustalW Analysis of NOV8

```
                     3110       3120       3130       3140       3150
                 ....|....|....|....|....|....|....|....|....|....|
NOV8a            S-LQTAIRKAEYSQGKSSLMSDSRGVPRNSIPGGPSGEDHLYFTPRPATR
NOV8b            S-LQTAIRKAEYSQGKSSLMSDSRGVPRNSIPGGPSGEDHLYFTPRPATR
gi|15295903|     S-LQTAIRKAEYSQGKSSLMSDSRGVPRNSIPGGPSGEDHLYFTPRPATR
gi|2224541|      S-LQTAIRKAEYSQGKSSLMSDSRGVPRNSIPGGPSGEDHLYFTPRPATR
gi|12621106      SSLQLPAKLPESFQGKSSQMPASVGVPNGPIGLAGESPYFTPRPATR
gi|12751452      S-LQTAIRKAEYSQGKSSLMSDSRGVPRNSIPGGPSGEDHLYFTPRPATR
gi|12861607      --------------------------------------------------

3160       3170       3180       3190       3200
                 ....|....|....|....|....|....|....|....|....|....|
NOV8a            TYSMPAQFSSHFGREGHPPHSLGRSRDSQVPVTSSVVPEAKASRGGLPSL
NOV8b            TYSMPAQFSSHFGREGHPPHSLGRSRDSQVPVTSSVVPEAKASRGGLPSL
gi|15295903|     TYSMPAQFSSHFGREGHPPHSLGRSRDSQVPVTSSVVPEAKASRGGLPSL
gi|2224541|      TYSMPAQFSSHFGREGHPPHSLGRSRDSQVPVTSSVVPEAKASRGGLPSL
gi|12621106      TYSMPAQFSSHFGREGPSPHSPSHSPQDPQVPAMGGKLSEKTG----
gi|12751452      TYSMPAQFSSHFGREGHPPHSLGRSRDSQVPVTSSVVPEAKASRGGLPSL
gi|12861607      --------------------------------------------------

3210       3220       3230       3240       3250
                 ....|....|....|....|....|....|....|....|....|....|
NOV8a            ANGQGIYSVKPLLDTSRNLPATDEGDIISVQETSCLVTDKIKVTRRHYCY
NOV8b            ANGQGIYSVKPLLDTSRNLPATDEGDIISVQETSCLVTDKIKVTRRHYCY
gi|15295903|     ANGQGIYSVKPLLDTSRNLPATDEGDIISVQETSCLVTDKIKVTRRHYCY
gi|2224541|      ANGQGIYSVKPLLDTSRNLPATDEGDIISVQETSCLVTDKIKVTRRHYCY
gi|12621106      TNGQGYYSVKPLLTSNLSPVDGRDSDPETSCLPDKVKVTRRQYCC
gi|12751452      ANGQGIYSVKPLLDTSRNLPATDEGDIISVQETSCLVTDKIKVTRRHYCY
gi|12861607      --------------------------------------------------

3260       3270       3280       3290       3300
                 ....|....|....|....|....|....|....|....|....|....|
NOV8a            EQNWPHESTSFFSVKQRIKSFENLANADRPVAKSGASPFLSVSSKPPIGR
NOV8b            EQNWPHESTSFFSVKQRIKSFENLANADRPVAKSGASPFLSVSSKPPIGR
gi|15295903|     EQNWPHESTSFFSVKQRIKSFENLANADRPVAKSGASPFLSVSSKPPIGR
gi|2224541|      EQNWPHESTSFFSVKQRIKSFENLANADRPVAKSGASPFLSVSSKPPIGR
gi|12621106      EQWPHESTSFFSVKQRIKSFENLANDRPTAKCATSPFLSVSSKPPINR
gi|12751452      EQNWPHESTSFFSVKQRIKSFENLANADRPVAKSGASPFLSVSSKPPIGR
gi|12861607      --------------------------------------------------

3310       3320       3330       3340       3350
                 ....|....|....|....|....|....|....|....|....|....|
NOV8a            RSSGSIVSGSLGHPGDAAARLLRRSLSSCSENQSEAGTLLPQMAKSPSIM
NOV8b            RSSGSIVSGSLGHPGDAAARLLRRSLSSCSENQSEAGTLLPQMAKSPSIM
gi|15295903|     RSSGSIVSGSLGHPGDAAARLLRRSLSSCSENQSEAGTLLPQMAKSPSIM
gi|2224541|      RSSGSIVSGSLGHPGDAAARLLRRSLSSCSENQSEAGTLLPQMAKSPSIM
gi|12621106      RSSGSIPS---GSPSDMTRSLRRSLSSCSEQSEASLLPQMTKSPSSM
gi|12751452      RSSGSIVSGSLGHPGDAAARLLRRSLSSCSENQSEAGTLLPQMAKSPSIM
gi|12861607      --------------------------------------------------

3360       3370       3380       3390       3400
                 ....|....|....|....|....|....|....|....|....|....|
NOV8a            TLTISRQNPPETSSKGSDSELKKSLGPLGIPTPTMTLASPVKRNKSSVRH
NOV8b            TLTISRQNPPETSSKGSDSELKKSLGPLGIPTPTMTLASPVKRNKSSVRH
gi|15295903|     TLTISRQNPPETSSKGSDSELKKSLGPLGIPTPTMTLASPVKRNKSSVRH
gi|2224541|      TLTISRQNPPETSSKGSDSELKKSLGPLGIPTPTMTLASPVKRNKSSVRH
gi|12621106      TLTSRQNPPTSKGPSPPKKSLVPGIPTSTPASPSKRNKSSVRH
gi|12751452      TLTISRQNPPETSSKGSDSELKKSLGPLGIPTPTMTLASPVKRNKSSVRH
gi|12861607      --------------------------------------------------

3410       3420       3430       3440       3450
                 ....|....|....|....|....|....|....|....|....|....|
NOV8a            TQPSPVSRSKLQELRALSMPDLDKLCS-EDYSAGPSAVLFKTELEITPRR
NOV8b            TQPSPVSRSKLQELRALSMPDLDKLCS-EDYSAGPSAVLFKTELEITPRR
gi|15295903|     TQPSPVSRSKLQELRALSMPDLDKLCS-EDYSAGPSAVLFKTELEITPRR
gi|2224541|      TQPSPVSRSKLQELRALSMPDLDKLCS-EDYSAGPSAVLFKTELEITPRR
gi|12621106      AQPSPVSRSKLQERRTLSMPDLDKLCGEDDSASPGAVLFKTLEITPRR
gi|12751452      TQPSPVSRSKLQELRALSMPDLDKLCS-EDYSAGPSAVLFKTELEITPRR
gi|12861607      --------------------------------------------------

3460       3470       3480       3490       3500
                 ....|....|....|....|....|....|....|....|....|....|
NOV8a            SPGPPAGG-----------------VSCPEKGGNRACPGGSGPKTSAAET
NOV8b            SPGPPAGG-----------------VSCPEKGGNRACPGGSGPKTSAAET
gi|15295903|     SPGPPAGG-----------------VSCPEKGGNRACPGGSGPKTSAAET
gi|2224541|      SPGPPAGG-----------------VSCPEKGGNRACPGGSGPKTSAAET
gi|12621106      SKGSQATSPAGSPARGHADFNGSTFSCEMNGGIRAYTKGSPASEPAI
gi|12751452      SPGPPAGG-----------------VSCPEKGGNRACPGGSGPKTSAAET
gi|12861607      --------------------------------------------------
```

TABLE 8G-continued

ClustalW Analysis of NOV8

```
                3510       3520       3530       3540       3550
           ....|....|....|....|....|....|....|....|....|....|
NOV8a      PSSASDTGEAAQDLPFRRSWSVNLDQLLVSAGDQQRLQSVLSSVGSKSTI
NOV8b      PSSASDTGEAAQDLPFRRSWSVNLDQLLVSAGDQQRLQSVLSSVGSKSTI
gi|15295903|  PSSASDTGEAAQDLPFRRSWSVKLDQLLVSAGDQQRLQSVLSSVGSKSTI
gi|2224541|   PSSASDTGEAAQDLPFRRSWSVNLDQLLVSAGDQQRLQSVLSSVGSKSTI
gi|12621106|  AIGIRIEGEIVWATPSGISWSVSLDILLASVGIQQRLQGILSLVGSKSPI
gi|12751452|  PSSASDTGEAAQDLPFRRSWSVKLDQLLVSAGDQQRLQSVLSSVGSKSTI
gi|12861607|  -------------------------------------------------

3560       3570       3580       3590       3600
           ....|....|....|....|....|....|....|....|....|....|
NOV8a      LTLIQEAKAQSENEEDVCFIVLNRKEGSGLGFSVAGGTDVEPKSITVHRV
NOV8b      LTLIQEAKAQSENEEDVCFIVLNRKEGSGLGFSVAGGTDVEPKSITVHRV
gi|15295903|  LTLIQEAKAQSENEEDVCFIVLNRKEGSGLGFSVAGGTDVEPKSITVHRV
gi|2224541|   LTLIQEAKAQSENEEDVCFIVLNRKEGSGLGFSVAGGTDVEPKSITVHRV
gi|12621106|  LTLIQEAKAQSEITIEDICFIVLNKKEGSGLGFSVAGGADVEPKSIMVHRV
gi|12751452|  LTLIQEAKAQSENEEDVCFIVLNRKEGSGLGFSVAGGTDVEPKSITVHRV
gi|12861607|  -------------------------------------------------

3610       3620       3630       3640       3650
           ....|....|....|....|....|....|....|....|....|....|
NOV8a      FSQGAASQEGTMNRGDFLLSVNGASLAGLAHGNVLKVLHQAQLHKDALVV
NOV8b      FSQGAASQEGTMNRGDFLLSVNGASLAGLAHGNVLKVLHQAQLHKDALVV
gi|15295903|  FSQGAASQEGTMNRGDFLLSVNGASLAGLAHGNVLKVLHQAQLHKDALVV
gi|2224541|   FSQGAASQEGTMNRGDFLLSVNGASLAGLAHGNVLKVLHQAQLHKDALVV
gi|12621106|  FSQGVASQEGTISRGDFLLSVNGISLAGLAHSEVIKVLHQAILHKHAIII
gi|12751452|  FSQGAASQEGTMNRGDFLLSVNGASLAGLAHGNVLKVLHQAQLHKDALVV
gi|12861607|  -------------------------------------------------

3660       3670       3680       3690       3700
           ....|....|....|....|....|....|....|....|....|....|
NOV8a      IKKGMDQPRPSARQEPPTANGKGLLSRKTIFLEPGIGRSVAVHDALCVEV
NOV8b      IKKGMDQPRPSARQEPPTANGKGLLSRKTIFLEPGIGRSVAVHDALCVEV
gi|15295903|  IKKGMDQPRPSARQEPPTANGKGLLSRKTIFLEPGIGRSVAVHDALCVEV
gi|2224541|   IKKGMDQPRPSARQEPPTANGKGLLSRKTIFLEPGIGRSVAVHDALCVEV
gi|12621106|  IKKGNDQPGPSFIQEPPIANGKGPFPRITIFLEPGAGRICAAHDALCVEV
gi|12751452|  IKKGMDQPRPSARQEPPTANGKGLLSRKTIFLEPGIGRSVAVHDALCVEV
gi|12861607|  -------------------------------------------------

3710       3720       3730       3740       3750
           ....|....|....|....|....|....|....|....|....|....|
NOV8a      LKTSAGLGLSLDGGKSSVTGDGPLVIKRVTKGGAAEQAGIIEAGDEILAI
NOV8b      LKTSAGLGLSLDGGKSSVTGDGPLVIKRVTKGGAAEQAGIIEAGDEILAI
gi|15295903|  LKTSAGLGLSLDGGKSSVTGDGPLVIKRVTKGGAAEQAGIIEAGDEILAI
gi|2224541|   LKTSAGLGLSLDGGKSSVTGDGPLVIKRVTKGGAAEQAGIIEAGDEILAI
gi|12621106|  LKTSAGLGLSLDGGKSSVIGIGPLVIKRVTKGGAAEIAGTIEAGDEILAI
gi|12751452|  LKTSAGLGLSLDGGKSSVTGDGPLVIKRVTKGGAAEQAGIIEAGDEILAI
gi|12861607|  -------------------------------------------------

3760       3770       3780
           ....|....|....|....|....|....|....|.
NOV8a      MGKPLVGLMHFDAWNIMKSVPEGPVQLLIRKHRNSS
NOV8b      MGKPLVGLMHFDAWNIMKSVPEGPVQLLIRKHRNSS
gi|15295903|  MGKPLVGLMHFDAWNIMKSVPEGPVQLLIRKHRNSS
gi|2224541|   MGKPLVGLMHFDAWNIMKSVPEGPVQLLIRKHRNSS
gi|12621106|  MGKPLVGLIHFDAWNIMKSVPEGPVQIIIRKHRISS-
gi|12751452|  MGKPLVGLMHFDAWNIMKSVPEGPVQLLIRKHRNSS
gi|12861607|  ------------------------------------
```

Table 8H–J lists the domain description from DOMAIN analysis results against NOV8. This indicates that the NOV8 sequence has properties similar to those of other proteins known to contain this domain.

TABLE 8H

Domain Analysis of NOV8 gnl|Smart|smart00228, PDZ, Domain present in PSD-95, Dlg, and ZO-1/2.; Also called DHR (Dlg homologous region) or GLGF (relatively well conserved tetrapeptide in these domains). Some PDZs have been shown to bind C-terminal polypeptides; others appear to bind internal (non-C-terminal) polypeptides. Different PDZs possess different binding specificities. (SEQ ID NO:86)
CD-Length = 86 residues, 95.3% aligned
Score = 69.3 bits (168), Expect = 3e-12

TABLE 8H-continued

Domain Analysis of NOV8

```
Query:  333 RIWKMELLKESDGLGIQVSGGRGSKRSPHAIVVTQVKEGGAAHRLRDGRLSLGDELLVIN 392
            +||  |    |||  + ||+ |       +||+ |    | +   | |  || +| +|
Sbjct:    1 EPRLVELEKGGGGLGFSLVGGKDSGDGG--VVVSSVVPGSPAAK  AG LKPGDVILEVN  55

Query:  393 GHLLVGLSHEEAVAILRSATGMVQLVV 419
            |  + ||+|  ||| +|+ |  |  | |
Sbjct:   56 GTSVEGLTHLEAVDLLKEAGGKVTLTV  82
```

TABLE 8I

Domain Analysis of NOV8 gnl|Smart|smart00228, PDZ, Domain present in PSD-95, Dlg, and ZO-[11] [22].;
Also called DER (Dlg homologous region) or GLGF (relatively well
conserved tetrapeptide in these domains). Some PDZs have been shown to
bind C-terminal polypeptides; others appear to bind internal (non-C-
terminal) polypeptides. Different PDZs possess different binding
specificities. (SEQ ID NO:86)
CD-Length = 86 residues, 96.5% aligned
Score = 66.2 bits (160), Expect = 2e-11

```
Query:  556 ISIIGLYKEKGKGLGFSIAGGRDCIRGQMGIFVKTIFPNGSAAEDGRLKEGDEILDVNGI 615
            ++ |   |  ||||||+ ||+|      |  |+ | ++ |    ||+ |  || || ||+|||
Sbjct:    2 PRLVELEKGGG-GLGFSLVGGKD--SGDGGVVVSSVVPGSPAAKAG-LKPGDVILEVNGT  57

Query:  616 PIKGLTFQEAIHTFKQIRSGLFVLTVR 642
            ++|||   ||+   |+    + +  +|
Sbjct:   58 SVEGLTHLEAVDLLKEAGGKVTLTVLR  84
```

TABLE 8J

Domain Analysis of NOV8 gnl|Smart|smart00228, PDZ, Domain present in PSD-95, Dig, and ZO-[11] [22].;
Also called DER (Dlg homologous region) or GLGF (relatively well
conserved tetrapeptide in these domains). Some PDZs have been shown to
bind C-terminal polypeptides; others appear to bind internal (non-C-
terminal) polypeptides. Different PDZs possess different binding
specificities. (SEQ ID NO:86)
CD-Length = 86 residues, 97.7% aligned
Score = 60.1 bits (144), Expect = 2e-09

```
Query: 2597 FIVLNRKEGSGLGFSVAGGTDVEPKSITVHRVFSQGAASQEGTMNRGDFLLSVNGASLAG 2656
            +|    |  |||||+ ||  |    + |   |    |++ | + || +|| ||  |+ |
Sbjct:    3 RLVELEKGGGGLGFSLVGGKDSGDGGVVVSSVVPGSPAAKAG-LKPGDVILEVNGTSVEG  61

Query: 2697 LAHGNVLKVLHQAQLHKDALVVIKKG 2682
            | |   + +| +|    |   |++ |
Sbjct:   62 LTHLEAVDLLKEAG-GKVTLTVLRGG  86
```

Proteins belonging to the IGFBP-ALS family of proteins play an important role in regulating the levels of circulating hormones. The acid labile subunit of the complex plays an important role in regulating the stability of the complex and ensuring high levels of circulating hormones that are regulated by the IGFBP family of proteins. This protein also has a leucine rich repeat that is a common domain in many proteins that are important for the developing embryo. As a result this protein may play an important role in development and disease.

Insulin-like growth factors (IGFs) I and II are important regulators of cell proliferation and differentiation (Ueki I et al., Proc Natl Acad Sci USA 2000 Jun. 6;97(12):6868–73). After birth, plasma IGFs, representing mostlyliver-derived IGFs, circulate in ternary complexes of 150 kDa consisting of onemolecule each of IGF, IGF-binding protein (IGFBP) 3, and an acid labile subunit (ALS). Onset of ALS synthesis after birth is the primary factor driving the formation of ternary complexes. Capture of IGFs by ALS is thought to allow the development of a plasma reservoir without negative effects such as hypoglycemia and cell proliferation. To evaluate the importance of ALS and ternary complexes, mice have been created in which the ALS gene has been inactivated. The mutation was inherited in a Mendelian manner, without any effects on survival rates and birth weights. A growth deficit was observed in null mice after 3 weeks of life and reached 13% by 10 weeks. This modest phenotype was observed despite reductions of 62 and 88% in the concentrations of plasma IGF-I and IGFBP-3, respectively. Increased turnover accounted for these reductions because indices of synthesis in liver and kidney were not decreased. Surprisingly, absence of ALS did not affect glucose and insulin homeostasis. Therefore, ALS is required for postnatal accumulation of IGF-I and IGFBP-3 but, consistent with findings supporting a predominant role for locally produced IGF-I, is not critical for growth. This model should be useful to determine whether presence of ALS is needed for other actions of liver-derived IGF-I and for maintenance of homeostasis in presence of high circulating levels of IGF-II.

In the circulation, insulin-like growth factor-I (IGF-I) is bound in a trimeric complex of 150 kDa with IGF binding protein-3 (IGFBP-3) and the acid-labile subunit (ALS). (Moller S et al., J Hepatol 2000 March;32(3):441–6). Whereas circulating IGF-I and IGFBP-3 are reported to be low in patients with chronic liver failure, the level of ALS has not been described in relation to hepatic dysfunction. The aim of the present study was therefore to measure circulating and hepatic venous concentrations of ALS in relation to hepatic function and the IGF axis.

The insulin-like growth factor (IGF) binding proteins (IGFBPs) were initially identified as carrier proteins for IGF-I and IGF-II in a variety of biologic fluids (Rosenfeld R G et al., Pediatrics 1999 October;104(4 Pt 2):1018–21). Their presumed function was to protect IGF peptides from degradation and clearance, increase the half-life of the IGFs, and deliver them to appropriate tissue receptors. The concept of IGFBPs as simple carrier proteins has been complicated, however, by a number of observations: 1) the six IGFBPs vary in their tissue expression and their regulation by other hormones and growth factors; 2) the IGFBPs are subjected to proteolytic degradation, thereby altering their affinities for the IGFs; 3) IGFBP-3 and IGFBP-5, in addition to binding IGFs, also can associate with an acid-labile subunit, thereby increasing further the half-life of the IGFs; 4) in addition to modifying the access of IGF peptides to IGF and insulin receptors, several of the IGFBPs may be capable of increasing IGF action; 5) some of the IGFBPs may be capable of IGF-independent regulation of cell growth; 6) some of the IGFBPs are associated with cell membranes or possibly with membrane receptors; and 7) some of the IGFBPs have nuclear recognition sites and may be found within the nucleus. Additionally, a number of cDNAs identified recently have been found to encode proteins that bind IGFs, but with substantially lower affinities than is the case with IGFBPs. The N-terminal regions of the predicted proteins are structurally homologous to the classic IGFBPs, with conservation of the cysteine-rich region. These observations suggest that these low-affinity binders are members of an IGFBP superfamily, capable of regulating cell growth by both IGF-dependent and IGF-independent mechanisms.insulin-like growth factor, insulin-like growth factor binding proteins.

Total IGF-I level in serum is a sensitive index during growth hormone (GH) replacement therapy of adults, since GH stimulates the hepatic expressions of both insulin-like growth factor (IGF-I) and acid-labile subunit (ALS) and the major part of IGF-I in the circulation is found in a ternary complex together with ALS and IGFBP-3 (Hall K et al., J Endocrinol Invest 1999;22(5 Suppl):48–57). However, other regulators of the proteins constituting the ternary complex may influence IGF-I levels. In healthy subjects the serum IGF-I levels are low at birth, rise during childhood, with peak levels during puberty, and decline with increasing age. This pattern has been attributed to the age-dependent GH production, but it is unknown whether the wide range of IGF-I levels within each age interval is due to GH production or GH sensitivity. In elderly twins approximately 60% of IGF-I levels are genetically determined. The remaining environmental dependency of IGF-I is partly due to nutrition. Both caloric and protein content of the diet is of importance. Thus, low IGF-I levels are found in GH deficient patients as well as in patients with GH resistance due to malnutrition or GH receptor defects. It is essential that IGF-I determination is performed by assays in which IGFBPs do not interfere, and that IGF-I concentration is evaluated in relation to age, i.e. expressed in SD score, and the number of individuals constituting the reference intervals improves the sensitivity and specificity. Although determination of IGF-I is recommended in assessing GH deficiency in children, its diagnostic value in patients with adult onset of GH deficiency is not agreed upon. In the age group above 40–80 years many patients with pituitary/hypothalamic disorders and GH peaks below 3 microg/l during provocation tests have normal IGF-I levels. It is not clarified, whether the IGF-I levels within normal range for age is due to endogenous basal GH production being sufficient or other factors stimulating IGF-I, IGFBP-3 or ALS expressions.

Circulating insulin-like growth factors (IGFs) represent an important pool of potential hypoglycemic activity, which is largely inhibited by their sequestration in a heterotrimeric complex comprising growth factor, IGF-binding protein-3 (IGFBP-3), and acid-labile subunit (ALS) (Baxter R C Metabolism 1995 October;44(10 Suppl 4):12–7). Less than 1% of total IGFs circulate in the free form, yet even this amount might contribute significantly to circulating insulin-like activity. The ternary binding protein complex appears to inhibit insulin-like activity of bound IGFs by preventing their egress from the circulation. Although the integrity of this complex might be affected by limited proteolysis of IGFBP-3 in pregnancy and catabolic conditions, the evidence that this increases IGF bioavailability, and thus hypoglycemic potential, is as yet unclear. However, in patients with IGF-11-secreting tumors, hypoglycemia may result from a failure of the ternary complex to adequately sequester the IGFs. Improvement in complex formation, by treatment with corticosteroids or growth hormone, alleviates the hypoglycemia, even if (as seen with growth hormone treatment) IGF-II hypersecretion persists. In these patients, blood glucose levels are inversely correlated with IGFBP-2 levels, suggesting that this protein might play a part in transporting IGFs to their target tissues. Conversely, ALS levels correlate positively with blood glucose, emphasizing the importance of the ternary complex in preventing hypoglycemia. Unlike the other IGF-binding proteins, IGFBP-1 is acutely regulated in the circulation, in a manner consistent with its acting as a glucose counterregulator. It might act in this way by inhibiting the activity of free IGFs in the circulation.

Leucine-rich repeats (LRRs) are relatively short motifs (22–28 residues in length) found in a variety of cytoplasmic, membrane and extracellular proteins (InterPro). Although these proteins are associated with widely different functions, a common property involves protein-protein interaction. Little is known about the 3D structure of LRRs, although it is believed that they can form amphipathic structures with hydrophobic surfaces capable of interacting with membranes. In vitro studies of a synthetic LRR from Drosophila Toll protein have indicated that the peptides form gels by adopting beta-sheet structures that form extended filaments. These results are consistent with the idea that LRRs mediate protein-protein interactions and cellular adhesion. Other functions of LRR-containing proteins include, for example, binding to enzymes and vascular repair. The 3-D structure of ribonuclease inhibitor, a protein containing 15 LRRs, has been determined, revealing LRRs to be a new class of alpha/beta fold. LRRs form elongated non-globular structures and are often flanked by cysteine rich domains.

The disclosed NOV8 nucleic acid of the invention encoding a papin-like protein includes the nucleic acid whose sequence is provided in Table 8A and C, or a fragment thereof. The invention also includes a mutant or variant nucleic acid any of whose bases may be changed from the corresponding base shown in Table 8A and C while still encoding a protein that maintains its papin-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 12% percent of the bases may be so changed.

The disclosed NOV8 protein of the invention includes the papin-like protein whose sequence is provided in Table 8B and D. The invention also includes a mutant or variant protein any of whose residues may be changed from the corresponding residue shown in Table 2 while still encoding a protein that maintains its papin-like activities and physiological functions, or a functional fragment thereof. In the mutant or variant protein, up to about 43% percent of the residues may be so changed.

The invention further encompasses antibodies and antibody fragments, such as $F_{ab}$ or $(F_{ab})_2$, that bind immuno-specifically to any of the proteins of the invention.

The above defined information for this invention suggests that this papin-like protein (NOV8) may function as a member of a "papin family". Therefore, the NOV8 nucleic acids and proteins identified here may be useful in potential therapeutic applications implicated in (but not limited to) various pathologies and disorders as indicated below. The potential therapeutic applications for this invention include, but are not limited to: protein therapeutic, small molecule drug target, antibody target (therapeutic, diagnostic, drug targeting/cytotoxic antibody), diagnostic and/or prognostic marker, gene therapy (gene delivery/gene ablation), research tools, tissue regeneration in vivo and in vitro of all tissues and cell types composing (but not limited to) those defined here.

The NOV8 nucleic acids and proteins of the invention are useful in potential therapeutic applications implicated in cancer including but not limited to Inflamation, Autoimmune disorders, Aging and Cancer. For example, a cDNA encoding the papin-like protein (NOV8) may be useful in gene therapy, and the papin-like protein (NOV8) may be useful when administered to a subject in need thereof. By way of nonlimiting example, the compositions of the present invention will have efficacy for treatment of patients suffering from cancer, cystitis, incontinence, fertility, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation recovery. The NOV8 nucleic acid encoding papin-like protein, and the papin-like protein of the invention, or fragments thereof, may further be useful in diagnostic applications, wherein the presence or amount of the nucleic acid or the protein are to be assessed.

NOV8 nucleic acids and polypeptides are further useful in the generation of antibodies that bind immuno-specifically to the novel NOV8 substances for use in therapeutic or diagnostic methods. These antibodies may be generated according to methods known in the art, using prediction from hydrophobicity charts, as described in the "Anti-NOVX Antibodies" section below. The disclosed NOV8 protein has multiple hydrophilic regions, each of which can be used as an immunogen. In one embodiment, a contemplated NOV8 epitope is from about amino acids 10 to 50. In another embodiment, a NOV8 epitope is from about amino acids 80 to 120. In additional embodiments, NOV8 epitopes are from about amino acids 180 to 220, from about amino acids 230 to 300, from about amino acid 330 to 350, from about amino acid 370 to 400, from about amino acid 480 to 540, from about amino acid 550 to 560, and from about amino acids 620 to 840. These novel proteins can be used in assay systems for functional analysis of various human disorders, which will help in understanding of pathology of the disease and development of new drug targets for various disorders.

TABLE 9

Sequences and Corresponding SEQ ID Numbers

| NOVX Assignment | Internal Identification | SEQ ID NO (nucleic acid) | SEQ ID NO (polypeptide) | Homology |
| --- | --- | --- | --- | --- |
| 1a | 83420733_EXT | 1 | 2 | Insulin Like Growth Factor Binding Protein Complex-Acid Labile Subunit-like |
| 1b | AL356413.6 | 3 | 2 | Insulin Like Growth Factor Binding Protein Complex-Acid Labile Subunit-like |
| 1c | CG52997-02 | 4 | 5 | Insulin Like Growth Factor Binding Protein Complex-Acid Labile Subunit-like |
| 2 | 101599929_EXT1 | 6 | 7 | Attractin like |
| 3a | 124217931_EXT | 8 | 9 | Kinase-like |
| 3b | 124217931 | 10 | 11 | RHO/RAC-interacting citron kinase-like |

TABLE 9-continued

Sequences and Corresponding SEQ ID Numbers

| NOVX Assignment | Internal Identification | SEQ ID NO (nucleic acid) | SEQ ID NO (polypeptide) | Homology |
|---|---|---|---|---|
| 4 | 105827550_EXT | 12 | 13 | Plexin-like |
| 5 | GMAC027612_A | 14 | 15 | Dopamine receptor-like |
| 6 | GM523_e_1_A | 16 | 17 | Metabotropic Glutamate Receptor |
| 7a | sggc_draft_ba560a15_20000723_da1 | 18 | 19 | PV-1-like |
| 7b | 2847264.0.32 | 20 | 21 | PV-1-like |
| 7c | CG51878-03 | 22 | 23 | PV-1-like |
| 8a | SC134914330_A | 24 | 25 | Papin-like |
| 8b | CG57026-04 | 26 | 27 | Papin-like |

NOVX Nucleic Acids and Polypeptides

One aspect of the invention pertains to isolated nucleic acid molecules that encode NOVX polypeptides or biologically active portions thereof. Also included in the invention are nucleic acid fragments sufficient for use as hybridization probes to identify NOVX-encoding nucleic acids (e.g., NOVX mRNAs) and fragments for use as PCR primers for the amplification and/or mutation of NOVX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

An NOVX nucleic acid can encode a mature NOVX polypeptide. As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the full-length gene product, encoded by the corresponding gene. Alternatively, it may be defined as the polypeptide, precursor or proprotein encoded by an ORF described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an ORF, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "probes", as utilized herein, refers to nucleic acid sequences of variable length, preferably between at least about 10 nucleotides (nt), 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies.

The term "isolated" nucleic acid molecule, as utilized herein, is one, which is separated from other nucleic acid molecules which are present in the natural source of the nucleic acid. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated NOVX nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a nucleic acid molecule having the nucleotide sequence SEQ ID NOS:1, 3, 4, 6, 8, 10, 12, 14, 16, 18, 20, 22, 24, and 26, or a complement of this aforementioned nucleotide sequence, can be isolated using standard molecular biology techniques and the sequence information provided herein. Using all or a portion of the nucleic acid sequence of SEQ ID NOS:1, 3, 4, 6, 8, 10, 12, 14, 16, 18, 20, 22, 24, and 26 as a hybridization probe, NOVX molecules can be isolated using standard hybridization and cloning techniques (e.g., as described in Sambrook, et al., (eds.), MOLECULAR CLONING: A LABORATORY MANUAL $2^{nd}$ Ed., Cold Spring Harbor Laboratory Press, Cold Spring Harbor, N.Y., 1989; and Ausubel, et al., (eds.), CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to NOVX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides SEQ ID NOS:1, 3, 4, 6, 8, 10, 12, 14, 16, 18, 20, 22, 24, and 26, or a complement thereof Oligonucleotides may be chemically synthesized and may also be used as probes.

In another embodiment, an isolated nucleic acid molecule of the invention comprises a nucleic acid molecule that is a complement of the nucleotide sequence shown in SEQ ID NOS:1, 3, 4, 6, 8, 10, 12, 14, 16, 18, 20, 22, 24, and 26, or a portion of this nucleotide sequence (e.g., a fragment that can be used as a probe or primer or a fragment encoding a biologically-active portion of an NOVX polypeptide). A nucleic acid molecule that is complementary to the nucleotide sequence shown SEQ ID NOS:1, 3, 4, 6, 8, 10, 12, 14, 16, 18, 20, 22, 24, or 26 is one that is sufficiently complementary to the nucleotide sequence shown SEQ ID NOS:1, 3, 4, 6, 8, 10, 12, 14, 16, 18, 20, 22, 24, or 26 that it can hydrogen bond with little or no mismatches to the nucleotide sequence shown SEQ ID NOS:1, 3, 4, 6, 8, 10, 12, 14, 16, 18, 20, 22, 24, and 26, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of NOVX polypeptides. Isoforms can be expressed in different tissues of the same organism as a result of, for example, alternative splicing of RNA. Alternatively, isoforms can be encoded by different genes. In the invention, homologous nucleotide sequences include nucleotide sequences encoding for an NOVX polypeptide of species other than humans, including, but not limited to: vertebrates, and thus can include, e.g., frog, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence a does not, however, include the exact nucleotide sequence encoding human NOVX protein. Homologous nucleic acid sequences include those nucleic acid sequences that encode conservative amino acid substitutions (see below) in SEQ ID NOS:1, 3, 4, 6, 8, 10, 12, 14, 16, 18, 20, 22, 24, and 26, as well as a polypeptide possessing NOVX biological activity. Various biological activities of the NOVX proteins are described below.

An NOVX polypeptide is encoded by the open reading frame ("ORF") of an NOVX nucleic acid. An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bonafide cellular protein, a minimum size requirement is often set, e.g., a stretch of DNA that would encode a protein of 50 amino acids or more.

The nucleotide sequences determined from the cloning of the human NOVX genes allows for the generation of probes and primers designed for use in identifying and/or cloning NOVX homologues in other cell types, e.g. from other tissues, as well as NOVX homologues from other vertebrates. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence SEQ ID NOS:1, 3, 4, 6, 8, 10, 12, 14, 16, 18, 20, 22, 24, or 26; or an anti-sense strand nucleotide sequence of SEQ ID NOS:1, 3, 4, 6, 8, 10, 12, 14, 16, 18, 20, 22, 24, or 26; or of a naturally occurring mutant of SEQ ID NOS:1, 3, 4, 6, 8, 10, 12, 14, 16, 18, 20, 22, 24, and 26.

Probes based on the human NOVX nucleotide sequences can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissues which mis-express an NOVX protein, such as by measuring a level of an NOVX-encoding nucleic acid in a sample of cells from a subject e.g., detecting NOVX mRNA levels or determining whether a genomic NOVX gene has been mutated or deleted.

"A polypeptide having a biologically-active portion of an NOVX polypeptide" refers to polypeptides exhibiting activity similar, but not necessarily identical to, an activity of a polypeptide of the invention, including mature forms, as measured in a particular biological assay, with or without dose dependency. A nucleic acid fragment encoding a "biologically-active portion of NOVX" can be prepared by isolating a portion SEQ ID NOS:1, 3, 4, 6, 8, 10, 12, 14, 16, 18, 20, 22, 24, or 26, that encodes a polypeptide having an NOVX biological activity (the biological activities of the NOVX proteins are described below), expressing the encoded portion of NOVX protein (e.g., by recombinant expression in vitro) and assessing the activity of the encoded portion of NOVX.

NOVX Nucleic Acid and Polypeptide Variants

The invention further encompasses nucleic acid molecules that differ from the nucleotide sequences shown in SEQ ID NOS:1, 3, 4, 6, 8, 10, 12, 14, 16, 18, 20, 22, 24, and 26 due to degeneracy of the genetic code and thus encode the same NOVX proteins as that encoded by the nucleotide sequences shown in SEQ ID NOS:1, 3, 4, 6, 8, 10, 12, 14, 16, 18, 20, 22, 24, and 26. In another embodiment, an isolated nucleic acid molecule of the invention has a nucleotide sequence encoding a protein having an amino acid sequence shown in SEQ ID NOS:2, 5, 7, 9, 11, 13, 15, 17, 19, 21, 23, 25, or 27.

In addition to the human NOVX nucleotide sequences shown in SEQ ID NOS:1,3, 4, 6, 8, 10, 12, 14, 16, 18, 20, 22, 24, and 26, it will be appreciated by those skilled in the art that DNA sequence polymorphisms that lead to changes in the amino acid sequences of the NOVX polypeptides may exist within a population (e.g., the human population). Such genetic polymorphism in the NOVX genes may exist among individuals within a population due to natural allelic variation. As used herein, the terms "gene" and "recombinant gene" refer to nucleic acid molecules comprising an open reading frame (ORF) encoding an NOVX protein, preferably a vertebrate NOVX protein. Such natural allelic variations can typically result in 1–5% variance in the nucleotide sequence of the NOVX genes. Any and all such nucleotide variations and resulting amino acid polymorphisms in the NOVX polypeptides, which are the result of natural allelic variation and that do not alter the functional activity of the NOVX polypeptides, are intended to be within the scope of the invention.

Moreover, nucleic acid molecules encoding NOVX proteins from other species, and thus that have a nucleotide sequence that differs from the human SEQ ID NOS:1, 3, 4, 6, 8, 10, 12, 14, 16, 18, 20, 22, 24, and 26 are intended to be within the scope of the invention. Nucleic acid molecules corresponding to natural allelic variants and homologues of the NOVX cDNAs of the invention can be isolated based on their homology to the human NOVX nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NOS:1, 3, 4, 6, 8, 10, 12, 14, 16, 18, 20, 22, 24, and 26. In another embodiment, the nucleic acid is at least 10, 25, 50, 100, 250, 500, 750, 1000, 1500, or 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding NOVX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel, et al., (eds.), CURRENT POTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequences SEQ ID NOS:1, 3, 4, 6, 8, 10, 12, 14, 16, 18, 20, 22, 24, and 26, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NOS:1, 3, 4, 6, 8, 10, 12, 14, 16, 18, 20, 22, 24, and 26, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel, et al. (eds.), 1993, CURRENT PROTOCOLS IN MOLECULAR BIOLOGY, John Wiley & Sons, NY, and Kriegler, 1990; GENE TRANSFER AND EXPRESSION, A LABORATORY MANUAL, Stockton Press, NY.

In a third embodiment, a nucleic acid that is hybridizable to the nucleic acid molecule comprising the nucleotide sequences SEQ ID NOS:1, 3, 4, 6, 8, 10, 12, 14, 16, 18, 20, 22, 24, and 26, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel, et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981. *Proc Natl Acad Sci USA* 78: 6789–6792.

Conservative Mutations

In addition to naturally-occurring allelic variants of NOVX sequences that may exist in the population, the skilled artisan will further appreciate that changes can be introduced by mutation into the nucleotide sequences SEQ ID NOS:1, 3, 4, 6, 8, 10, 12, 14, 16, 18, 20, 22, 24, and 26, thereby leading to changes in the amino acid sequences of the encoded NOVX proteins, without altering the functional ability of said NOVX proteins. For example, nucleotide substitutions leading to amino acid substitutions at "non-essential" amino acid residues can be made in the sequence SEQ ID NOS:2, 5, 7, 9, 11, 13, 15, 17, 19, 21, 23, 25, or 27. A "non-essential" amino acid residue is a residue that can be altered from the wild-type sequences of the NOVX proteins without altering their biological activity, whereas an "essential" amino acid residue is required for such biological activity. For example, amino acid residues that are conserved among the NOVX proteins of the invention are predicted to be particularly non-amenable to alteration. Amino acids for which conservative substitutions can be made are well-known within the art.

Another aspect of the invention pertains to nucleic acid molecules encoding NOVX proteins that contain changes in amino acid residues that are not essential for activity. Such NOVX proteins differ in amino acid sequence from SEQ ID NOS:1, 3, 4, 6, 8, 10, 12, 14, 16, 18, 20, 22, 24, and 26 yet retain biological activity. In one embodiment, the isolated nucleic acid molecule comprises a nucleotide sequence encoding a protein, wherein the protein comprises an amino acid sequence at least about 45% homologous to the amino acid sequences SEQ ID NOS:2, 5, 7, 9, 11, 13, 15, 17, 19, 21, 23, 25, and 27. Preferably, the protein encoded by the nucleic acid molecule is at least about 60% homologous to SEQ ID NOS:2, 5, 7, 9, 11, 13, 15, 17, 19, 21, 23, 25, and 27; more preferably at least about 70% homologous SEQ ID NOS:2, 5, 7, 9, 11, 13, 15, 17, 19, 21, 23, 25, or 27; still more preferably at least about 80% homologous to SEQ ID NOS:2, 5, 7, 9, 11, 13, 15, 17, 19, 21, 23, 25, or 27; even more preferably at least about 90% homologous to SEQ ID NOS:2, 5, 7, 9, 11, 13, 15, 17, 19, 21, 23, 25, or 27; and most preferably at least about 95% homologous to SEQ ID NOS:2, 5, 7, 9, 11, 13, 15, 17, 19, 21, 23, 25, or 27.

An isolated nucleic acid molecule encoding an NOVX protein homologous to the protein of SEQ ID NOS:2, 5, 7, 9, 11, 13, 15, 17, 19, 21, 23, 25, or 27 can be created by introducing one or more nucleotide substitutions, additions or deletions into the nucleotide sequence of SEQ ID NOS:1, 3, 4, 6, 8, 10, 12, 14, 16, 18, 20, 22, 24, and 26, such that one or more amino acid substitutions, additions or deletions are introduced into the encoded protein.

Mutations can be introduced into SEQ ID NOS:1, 3, 4, 6, 8, 10, 12, 14, 16, 18, 20, 22, 24, and 26 by standard techniques, such as site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the NOVX protein is replaced with another amino acid residue from the same side chain family. Alternatively, in another embodiment, mutations can be introduced randomly along all or part of an NOVX coding sequence, such as by saturation mutagenesis, and the resultant mutants can be screened for NOVX biological activity to identify mutants that retain activity. Following mutagenesis SEQ ID NOS:1, 3, 4, 6, 8, 10, 12, 14, 16, 18, 20, 22, 24, and 26, the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, VLIM, HFY, wherein the letters within each group represent the single letter amino acid code.

In one embodiment, a mutant NOVX protein can be assayed for (i) the ability to form protein:protein interactions with other NOVX proteins, other cell-surface proteins, or biologically-active portions thereof, (ii) complex formation between a mutant NOVX protein and an NOVX ligand; or (iii) the ability of a mutant NOVX protein to bind to an intracellular target protein or biologically-active portion thereof, (e.g. avidin proteins).

In yet another embodiment, a mutant NOVX protein can be assayed for the ability to regulate a specific biological function (e.g., regulation of insulin release).

Antisense Nucleic Acids

Another aspect of the invention pertains to isolated antisense nucleic acid molecules that are hybridizable to or complementary to the nucleic acid molecule comprising the nucleotide sequence of SEQ ID NOS:1, 3, 4, 6, 8, 10, 12, 14, 16, 18, 20, 22, 24, and 26, or fragments, analogs or derivatives thereof. An "antisense" nucleic acid comprises a nucleotide sequence that is complementary to a 'sense' nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire NOVX coding strand, or to only a portion thereof. Nucleic acid molecules encoding fragments, homologs, derivatives and analogs of an NOVX protein of SEQ ID NOS:2, 5, 7, 9, 11, 13, 15, 17, 19, 21, 23, 25, or 27, or antisense nucleic acids complementary to an NOVX nucleic acid sequence of SEQ ID NOS:1, 3, 4, 6, 8, 10, 12, 14, 16, 18, 20, 22, 24, and 26, are additionally provided.

In one embodiment, an antisense nucleic acid molecule is antisense to a "coding region" of the coding strand of a nucleotide sequence encoding an NOVX protein. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding the NOVX protein. The term "noncoding region" refers to 5' and 3' sequences which flank the coding region that are not translated into amino acids (i.e., also referred to as 5' and 3' untranslated regions).

Given the coding strand sequences encoding the NOVX protein disclosed herein, antisense nucleic acids of the invention can be designed according to the rules of Watson and Crick or Hoogsteen base pairing. The antisense nucleic acid molecule can be complementary to the entire coding region of NOVX mRNA, but more preferably is an oligonucleotide that is antisense to only a portion of the coding or noncoding region of NOVX mRNA. For example, the antisense oligonucleotide can be complementary to the region surrounding the translation start site of NOVX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g. an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an NOVX protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. See, e.g., Gaultier, et al., 1987. *Nucl. Acids Res.* 15: 6625–6641. The antisense nucleic acid molecule can also comprise a 2'-o-methylribonucleotide (See, e.g., Inoue, et al. 1987. *Nucl. Acids Res.* 15: 6131–6148) or a chimeric RNA-DNA analogue (See, e.g., Inoue, et al., 1987. *FEBS Lett.* 215: 327–330.

Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585–591) can be used to catalytically cleave NOVX mRNA transcripts to thereby inhibit translation of NOVX mRNA. A ribozyme having specificity for an NOVX-encoding nucleic acid can be designed based upon the nucleotide sequence of an NOVX cDNA disclosed herein (i.e., SEQ ID NOS:1, 3, 4, 6, 8, 10, 12, 14, 16, 18, 20,22,24, and 26). For example, a derivative of a *Tetrahymena* L-19 IVS RNA can be constructed in which the nucleotide sequence of the active site is complementary to the nucleotide sequence to be cleaved in an NOVX-encoding mRNA. See, e.g., U.S. Pat. No. 4,987,071 to Cech, et al. and U.S. Pat. No. 5,116,742 to Cech, et al. NOVX mRNA can also be used to select a catalytic RNA having a specific ribonuclease activity from a pool of RNA molecules. See, e.g., Bartel et al., (1993) *Science* 261:1411–1418.

Alternatively, NOVX gene expression can be inhibited by targeting nucleotide sequences complementary to the regulatory region of the NOVX nucleic acid (e.g., the NOVX promoter and/or enhancers) to form triple helical structures that prevent transcription of the NOVX gene in target cells. See, e.g., Helene, 1991. *Anticancer Drug Des*. 6: 569–84; Helene, et al. 1992. *Ann. N. Y Acad. Sci*. 660: 27–36; Maher, 1992. *Bioassays* 14: 807–15.

In various embodiments, the NOVX nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. *Bioorg Med Chem* 4: 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. *Proc. Natl. Acad. Sci. USA* 93: 14670–14675.

PNAs of NOVX can be used in therapeutic and diagnostic applications. For example, PNAs can be used as antisense or antigene agents for sequence-specific modulation of gene expression by, e.g., inducing transcription or translation arrest or inhibiting replication. PNAs of NOVX can also be used, for example, in the analysis of single base pair mutations in a gene (e.g., PNA directed PCR clamping; as artificial restriction enzymes when used in combination with other enzymes, e.g., $S_1$ nucleases (See, Hyrup, et al, 1996. supra); or as probes or primers for DNA sequence and hybridization (See, Hyrup, et al., 1996, supra; Perry-O'Keefe, et al., 1996. supra).

In another embodiment, PNAs of NOVX can be modified, e.g. to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NOVX can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. *Nucl Acids Res* 24: 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. *Nucl Acid Res* 17: 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. *Bioorg. Med. Chem. Lett*. 5: 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. *Proc. Natl. Acad. Sci. U.S.A*. 86: 6553–6556; Lemaitre, et al., 1987. *Proc. Natl. Acad. Sci*. 84: 648–652; PCT Publication No. WO88/09810) or the blood-brain barrier (see, e.g., PCT Publication No. WO 89/10134). In addition, oligonucleotides can be modified with hybridization triggered cleavage agents (see, e.g., Krol, et al., 1988. *BioTechniques* 6:958–976) or intercalating agents (see, e.g. Zon, 1988. *Pharm. Res*. 5: 539–549). To this end, the oligonucleotide may be conjugated to another molecule, e.g., a peptide, a hybridization triggered cross-linking agent, a transport agent, a hybridization-triggered cleavage agent, and the like.

NOVX Polypeptides

A polypeptide according to the invention includes a polypeptide including the amino acid sequence of NOVX polypeptides whose sequences are provided in SEQ ID NOS:2, 5, 7, 9, 11, 13, 15, 17, 19, 21, 23, 25, or 27. The invention also includes a mutant or variant protein any of whose residues may be changed from the corresponding residues shown in SEQ ID NOS:2, 5, 7, 9, 11, 13, 15, 17, 19, 21, 23,25, or 27 while still encoding a protein that maintains its NOVX activities and physiological functions, or a functional fragment thereof.

In general, an NOVX variant that preserves NOVX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated NOVX proteins, and biologically-active portions thereof, or derivatives, fragments, analogs or homologs thereof. Also provided are polypeptide fragments suitable for use as immunogens to raise anti-NOVX antibodies. In one embodiment, native NOVX proteins can be isolated from cells or tissue sources by an appropriate purification scheme using standard protein purification techniques. In another embodiment, NOVX proteins are produced by recombinant DNA techniques. Alternative to recombinant expression, an NOVX protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the NOVX protein is derived, or substantially free from chemical precursors or other chemicals when chemically synthesized. The language "substantially free of cellular material" includes preparations of NOVX proteins in which the protein is separated from cellular components of the cells from which it is isolated or recombinantly-produced. In one embodiment, the language "substantially free of cellular material" includes preparations of NOVX proteins having less than about 30% (by dry weight) of non-NOVX proteins (also referred to herein as a "contaminating protein"), more preferably less than about 20% of non-NOVX proteins, still more preferably less than about 10% of non-NOVX proteins, and most preferably less than about 5% of non-NOVX proteins. When the NOVX protein or biologically-active portion thereof is recombinantly-produced, it is also preferably substantially free of culture medium, i.e., culture medium represents less than about 20%, more preferably less than about 10%, and most preferably less than about 5% of the volume of the NOVX protein preparation.

The language "substantially free of chemical precursors or other chemicals" includes preparations of NOVX proteins in which the protein is separated from chemical precursors or other chemicals that are involved in the synthesis of the protein. In one embodiment, the language "substantially free of chemical precursors or other chemicals" includes preparations of NOVX proteins having less than about 30% (by dry weight) of chemical precursors or non-NOVX chemicals, more preferably less than about 20% chemical precursors or non-NOVX chemicals, still more preferably less than about 10% chemical precursors or non-NOVX chemicals, and most preferably less than about 5% chemical precursors or non-NOVX chemicals.

Biologically-active portions of NOVX proteins include peptides comprising amino acid sequences sufficiently homologous to or derived from the amino acid sequences of the NOVX proteins (e.g., the amino acid sequence shown in SEQ ID NOS:2, 5, 7, 9, 11, 13, 15, 17, 19, 21, 23, 25, or 27) that include fewer amino acids than the full-length NOVX proteins, and exhibit at least one activity of an NOVX protein. Typically, biologically-active portions comprise a domain or motif with at least one activity of the NOVX protein. A biologically-active portion of an NOVX protein can be a polypeptide which is, for example, 10, 25, 50, 100 or more amino acid residues in length.

Moreover, other biologically-active portions, in which other regions of the protein are deleted, can be prepared by recombinant techniques and evaluated for one or more of the functional activities of a native NOVX protein.

In an embodiment, the NOVX protein has an amino acid sequence shown SEQ ID NOS:2, 5, 7, 9, 11, 13, 15, 17, 19, 21, 23, 25, or 27. In other embodiments, the NOVX protein is substantially homologous to SEQ ID NOS:2, 5, 7, 9, 11, 13, 15, 17, 19, 21, 23, 25, or 27, and retains the functional activity of the protein of SEQ ID NOS:2, 5, 7, 9, 11, 13, 15, 17, 19, 21, 23, 25, or 27, yet differs in amino acid sequence due to natural allelic variation or mutagenesis, as described in detail, below. Accordingly, in another embodiment, the NOVX protein is a protein that comprises an amino acid sequence at least about 45% homologous to the amino acid sequence SEQ ID NOS:2, 5, 7, 9, 11, 13, 15, 17, 19, 21, 23, 25, or 27, and retains the functional activity of the NOVX proteins of SEQ ID NOS:2, 5, 7, 9, 11, 13, 15, 17, 19, 21, 23, 25, or 27.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch, 1970. *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOS:1, 3, 4, 6, 8, 10, 12, 14, 16, 18, 20, 22, 24, and 26.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides NOVX chimeric or fusion proteins. As used herein, an NOVX "chimeric protein" or "fusion protein" comprises an NOVX polypeptide operatively-linked to a non-NOVX polypeptide. An "NOVX polypeptide" refers to a polypeptide having an amino acid sequence corresponding to an NOVX protein SEQ ID NOS:2, 5, 7, 9, 11, 13, 15, 17, 19, 21, 23, 25, or 27, whereas a "non-NOVX polypeptide" refers to a polypeptide having an amino acid sequence corresponding to a protein that is not substantially homologous to the NOVX protein, e.g., a protein that is different from the NOVX protein and that is derived from the same or a different organism. Within an NOVX fusion protein the NOVX polypeptide can correspond to all or a portion of an NOVX protein. In one embodiment, an NOVX fusion protein comprises at least one biologically-active portion of an NOVX protein. In another embodiment, an NOVX fusion protein comprises at least two biologically-active portions of an NOVX protein. In yet another embodiment, an NOVX fusion protein comprises at least three biologically-active portions of an NOVX protein. Within the fusion protein, the term "operatively-linked" is intended to indicate that the NOVX polypeptide and the non-NOVX polypeptide are fused in-frame with one another. The non-NOVX polypeptide can be fused to the N-terminus or C-terminus of the NOVX polypeptide.

In one embodiment, the fusion protein is a GST-NOVX fusion protein in which the NOVX sequences are fused to the C-terminus of the GST (glutathione S-transferase) sequences. Such fusion proteins can facilitate the purification of recombinant NOVX polypeptides.

In another embodiment, the fusion protein is an NOVX protein containing a heterologous signal sequence at its N-terminus. In certain host cells (e.g., mammalian host cells), expression and/or secretion of NOVX can be increased through use of a heterologous signal sequence.

In yet another embodiment, the fusion protein is an NOVX-immunoglobulin fusion protein in which the NOVX sequences are fused to sequences derived from a member of the immunoglobulin protein family. The NOVX-immunoglobulin fusion proteins of the invention can be incorporated into pharmaceutical compositions and administered to a subject to inhibit an interaction between an NOVX ligand and an NOVX protein on the surface of a cell, to thereby suppress NOVX-mediated signal transduction in vivo. The NOVX-immunoglobulin fusion proteins can be used to affect the bioavailability of an NOVX cognate ligand. Inhibition of the NOVX ligand/NOVX interaction may be useful therapeutically for both the treatment of proliferative and differentiative disorders, as well as modulating (e.g. promoting or inhibiting) cell survival. Moreover, the NOVX-immunoglobulin fusion proteins of the invention can be used as immunogens to produce anti-NOVX antibodies in a subject, to purify NOVX ligands, and in screening assays to identify molecules that inhibit the interaction of NOVX with an NOVX ligand.

An NOVX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). An NOVX-encoding nucleic acid can be cloned into such an expression vector such that the fusion moiety is linked in-frame to the NOVX protein.

NOVX Agonists and Antagonists

The invention also pertains to variants of the NOVX proteins that function as either NOVX agonists (i.e., mimetics) or as NOVX antagonists. Variants of the NOVX protein can be generated by mutagenesis (e.g., discrete point mutation or truncation of the NOVX protein). An agonist of the NOVX protein can retain substantially the same, or a subset of, the biological activities of the naturally occurring form of the NOVX protein. An antagonist of the NOVX protein can inhibit one or more of the activities of the naturally occurring form of the NOVX protein by, for example, competitively binding to a downstream or upstream member of a cellular signaling cascade which includes the NOVX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the NOVX proteins.

Variants of the NOVX proteins that function as either NOVX agonists (i.e., mimetics) or as NOVX antagonists can be identified by screening combinatorial libraries of mutants (e.g., truncation mutants) of the NOVX proteins for NOVX protein agonist or antagonist activity. In one embodiment, a variegated library of NOVX variants is generated by combinatorial mutagenesis at the nucleic acid level and is encoded by a variegated gene library. A variegated library of NOVX variants can be produced by, for example, enzymatically ligating a mixture of synthetic oligonucleotides into gene sequences such that a degenerate set of potential NOVX sequences is expressible as individual polypeptides, or alternatively, as a set of larger fusion proteins (e.g., for phage display) containing the set of NOVX sequences therein. There are a variety of methods which can be used to produce libraries of potential NOVX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NOVX sequences. Methods for synthesizing degenerate oligonucleotides are well-known within the art. See, e.g., Narang, 1983. *Tetrahedron* 39: 3; Itakura, et al., 1984. *Annu. Rev. Biochem.* 53: 323; Itakura, et al., 1984. *Science* 198: 1056; Ike, et al., 1983. *Nucl. Acids Res.* 11: 477.

Polypeptide Libraries

In addition, libraries of fragments of the NOVX protein coding sequences can be used to generate a variegated population of NOVX fragments for screening and subsequent selection of variants of an NOVX protein. In one embodiment, a library of coding sequence fragments can be generated by treating a double stranded PCR fragment of an NOVX coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encodes N-terminal and internal fragments of various sizes of the NOVX proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NOVX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify NOVX variants. See, e.g., Arkin and Yourvan, 1992. *Proc. Natl. Acad. Sci. USA* 89: 7811–7815; Delgrave, et al., 1993. *Protein Engineering* 6:327–331.

Anti-NOVX Antibodies

Also included in the invention are antibodies to NOVX proteins, or fragments of NOVX proteins. The term "antibody" as used herein refers to immunoglobulin molecules and a immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$, and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated NOVX-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of NOVX-related protein that is located on the surface of the protein, e.g., a hydrophilic region. A hydrophobicity analysis of the human NOVX-related protein sequence will indicate which regions of a NOVX-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without A Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow and Lane, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, MONOCLONAL ANTIBODIES: PRINCIPLES AND PRACTICE, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur et al., MONOCLONAL ANTIBODY PRODUCTION TECHNIQUES AND APPLICATIONS, Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al, (*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins.

The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991 *EMBO J.*, 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–11195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et al., Anti-Cancer Drug Design, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins,

*Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-dilsocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of an NOVX protein is facilitated by generation of hybridomas that bind to the fragment of an NOVX protein possessing such a domain. Thus, antibodies that are specific for a desired domain within an NOVX protein, or derivatives, fragments, analogs or homologs thereof, are also provided herein.

Anti-NOVX antibodies may be used in methods known within the art relating to the localization and/or quantitation of an NOVX protein (e.g., for use in measuring levels of the NOVX protein within appropriate physiological samples, for use in diagnostic methods, for use in imaging the protein, and the like). In a given embodiment, antibodies for NOVX proteins, or derivatives, fragments, analogs or homologs thereof, that contain the antibody derived binding domain, are utilized as pharmacologically-active compounds (hereinafter "Therapeutics").

An anti-NOVX antibody (e.g., monoclonal antibody) can be used to isolate an NOVX polypeptide by standard techniques, such as affinity chromatography or immunoprecipitation. An anti-NOVX antibody can facilitate the purification of natural NOVX polypeptide from cells and of recombinantly-produced NOVX polypeptide expressed in host cells. Moreover, an anti-NOVX antibody can be used to detect NOVX protein (e.g., in a cellular lysate or cell supernatant) in order to evaluate the abundance and pattern of expression of the NOVX protein. Anti-NOVX antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidinibiotin and avidinibiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

NOVX Recombinant Expression Vectors and Host Cells

Another aspect of the invention pertains to vectors, preferably expression vectors, containing a nucleic acid encoding an NOVX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g. NOVX proteins, mutant forms of NOVX proteins, fusion proteins, etc.).

The recombinant expression vectors of the invention can be designed for expression of NOVX proteins in prokaryotic or eukaryotic cells. For example, NOVX proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 3140), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the NOVX expression vector is a yeast expression vector. Examples of vectors for expression in yeast *Saccharomyces cerivisae* include pYepSec1 (Baldari, et al., 1987. *EMBO J.* 6: 229–234), pMFa (Kuijan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, NOVX can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Baneiji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to NOVX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NOVX protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding NOVX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NOVX protein. Accordingly, the invention further provides methods for producing NOVX protein using the host cells of the invention. In one embodiment, the method comprises culturing the host cell of invention (into which a recombinant expression vector encoding NOVX protein has been introduced) in a suitable medium such that NOVX protein is produced. In another embodiment, the method further comprises isolating NOVX protein from the medium or the host cell.

Transgenic NOVX Animals

The host cells of the invention can also be used to produce non-human transgenic animals. For example, in one embodiment, a host cell of the invention is a fertilized oocyte or an embryonic stem cell into which NOVX protein-coding sequences have been introduced. Such host cells can then be used to create non-human transgenic animals in which exogenous NOVX sequences have been introduced into their genome or homologous recombinant animals in which endogenous NOVX sequences have been altered. Such animals are useful for studying the function and/or activity of NOVX protein and for identifying and/or evaluating modulators of NOVX protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NOVX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NOVX-encoding nucleic acid into the male pronuclei of a fertilized oocyte (e.g., by microinjection, retroviral infection) and allowing the oocyte to develop in a pseudopregnant female foster animal. The human NOVX cDNA sequences SEQ ID NOS:1, 3, 4, 6, 8, 10, 12, 14, 16, 18, 20, 22, 24, and 26 can be introduced as a transgene into the genome of a non-human animal. Alternatively, a non-human homologue of the human NOVX gene, such as a mouse NOVX gene, can be isolated based on hybridization to the human NOVX cDNA (described further supra) and used as a transgene. Intronic sequences and polyadenylation signals can also be included in the transgene to increase the efficiency of expression of the transgene. A tissue-specific regulatory sequence(s) can be operably-linked to the NOVX transgene to direct expression of NOVX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the NOVX transgene in its genome and/or expression of NOVX mRNA in tissues or cells of the animals. A transgenic founder animal can then be used to breed additional animals carrying the transgene. Moreover, transgenic animals carrying a transgene-encoding NOVX protein can further be bred to other transgenic animals carrying other transgenes.

To create a homologous recombinant animal, a vector is prepared which contains at least a portion of an NOVX gene into which a deletion, addition or substitution has been introduced to thereby alter, e.g., functionally disrupt, the NOVX gene. The NOVX gene can be a human gene (e.g., the cDNA of SEQ ID NOS:1, 3, 4, 6, 8, 10, 12, 14, 16, 18, 20, 22, 24, and 26), but more preferably, is a non-human homologue of a human NOVX gene. For example, a mouse homologue of human NOVX gene of SEQ ID NOS:1, 3, 4, 6, 8, 10, 12, 14, 16, 18, 20, 22, 24, and 26 can be used to construct a homologous recombination vector suitable for altering an endogenous NOVX gene in the mouse genome. In one embodiment, the vector is designed such that, upon homologous recombination, the endogenous NOVX gene is functionally disrupted (i.e., no longer encodes a functional protein; also referred to as a "knock out" vector).

Alternatively, the vector can be designed such that, upon homologous recombination, the endogenous NOVX gene is mutated or otherwise altered but still encodes functional protein (e.g., the upstream regulatory region can be altered to thereby alter the expression of the endogenous NOVX protein). In the homologous recombination vector, the altered portion of the NOVX gene is flanked at its 5'- and 3'-termini by additional nucleic acid of the NOVX gene to allow for homologous recombination to occur between the exogenous NOVX gene carried by the vector and an endogenous NOVX gene in an embryonic stem cell. The additional flanking NOVX nucleic acid is of sufficient length for successful homologous recombination with the endogenous gene. Typically, several kilobases of flanking DNA (both at the 5'- and 3'-termini) are included in the vector. See, e.g. Thomas, et al., 1987. *Cell* 51: 503 for a description of homologous recombination vectors. The vector is ten introduced into an embryonic stem cell line (e.g., by electroporation) and cells in which the introduced NOVX gene has homologously-recombined with the endogenous NOVX gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/oxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g. by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The NOVX nucleic acid molecules, NOVX proteins, and anti-NOVX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an NOVX protein or anti-NOVX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The isolated nucleic acid molecules of the invention can be used to express NOVX protein (e.g., via a recombinant expression vector in a host cell in gene therapy applications), to detect NOVX mRNA (e.g., in a biological sample) or a genetic lesion in an NOVX gene, and to modulate NOVX activity, as described further, below. In addition, the NOVX proteins can be used to screen drugs or compounds that modulate the NOVX protein activity or expression as well as to treat disorders characterized by insufficient or excessive production of NOVX protein or production of NOVX protein forms that have decreased or aberrant activity compared to NOVX wild-type protein (e.g.; diabetes (regulates insulin release); obesity (binds and transport lipids); metabolic disturbances associated with obesity, the metabolic syndrome X as well as anorexia and wasting disorders associated with chronic diseases and various cancers, and infectious disease(possesses anti-microbial activity) and the various dyslipidemias. In addition, the anti-NOVX antibodies of the invention can be used to detect and isolate NOVX proteins and modulate NOVX activity. In yet a further aspect, the invention can be used in methods to influence appetite, absorption of nutrients and the disposition of metabolic substrates in both a positive and negative fashion.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to NOVX proteins or have a stimulatory or inhibitory effect on, e.g., NOVX protein expression or NOVX protein activity. The invention also includes compounds identified in the screening assays described herein.

In one embodiment, the invention provides assays for screening candidate or test compounds which bind to or modulate the activity of the membrane-bound form of an NOVX protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g. Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37:1233.

Libraries of compounds may be presented in solution (e.g., Houghten, 1992. *Biotechniques* 13: 412421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a membrane-bound form of NOVX protein, or a biologically-active portion thereof, on the cell surface is contacted with a test compound and the ability of the test compound to bind to an NOVX protein determined. The cell, for example, can of mammalian origin or a yeast cell. Determining the ability of the test compound to bind to the NOVX protein can be accomplished, for example, by coupling the test compound with a radioisotope or enzymatic label such that binding of the test compound to the NOVX protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of NOVX protein, or a biologically-active portion thereof, on the cell surface with a known compound which binds NOVX to form an assay mixture, contacting the assay mixture with a test compound, and determining the ability of the test compound to interact with an NOVX protein, wherein determining the ability of the test compound to interact with an NOVX protein comprises determining the ability of the test compound to preferentially bind to NOVX protein or a biologically-active portion thereof as compared to the known compound.

In another embodiment, an assay is a cell-based assay comprising contacting a cell expressing a membrane-bound form of NOVX protein, or a biologically-active portion thereof, on the cell surface with a test compound and determining the ability of the test compound to modulate (e.g., stimulate or inhibit) the activity of the NOVX protein or biologically-active portion thereof. Determining the ability of the test compound to modulate the activity of NOVX or a biologically-active portion thereof can be accomplished, for example, by determining the ability of the NOVX protein to bind to or interact with an NOVX target molecule. As used herein, a "target molecule" is a molecule with which an NOVX protein binds or interacts in nature, for example, a molecule on the surface of a cell which expresses an NOVX interacting protein, a molecule on the surface of a second cell, a molecule in the extracellular milieu, a molecule associated with the internal surface of a cell membrane or a cytoplasmic molecule. An NOVX target molecule can be a non-NOVX molecule or an NOVX protein or polypeptide of the invention. In one embodiment, an NOVX target molecule is a component of a signal transduction pathway that facilitates transduction of an extracellular signal (e.g. a signal generated by binding of a compound to a membrane-bound NOVX molecule) through the cell membrane and into the cell. The target, for example, can be a second intercellular protein that has catalytic activity or a protein that facilitates the association of downstream signaling molecules with NOVX.

Determining the ability of the NOVX protein to bind to or interact with an NOVX target molecule can be accomplished by one of the methods described above for determining direct binding. In one embodiment, determining the ability of the NOVX protein to bind to or interact with an NOVX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising an NOVX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting an NOVX protein or biologically-active portion thereof with a test compound and determining the ability of the test compound to bind to the NOVX protein or biologically-active portion thereof. Binding of the test compound to the NOVX protein can be determined either directly or indirectly as described above. In one such embodiment, the assay comprises contacting the NOVX protein or biologically-active portion thereof with a known compound which binds NOVX to form an assay mixture, contacting the assay mixture with a test compound, and determining the ability of the test compound to interact with an NOVX protein, wherein determining the ability of the test compound to interact with an NOVX protein comprises determining the ability of the test compound to preferentially bind to NOVX or biologically-active portion thereof as compared to the known compound.

In still another embodiment, an assay is a cell-free assay comprising contacting NOVX protein or biologically-active portion thereof with a test compound and determining the ability of the test compound to modulate (e.g. stimulate or inhibit) the activity of the NOVX protein or biologically-active portion thereof. Determining the ability of the test compound to modulate the activity of NOVX can be accomplished, for example, by determining the ability of the NOVX protein to bind to an NOVX target molecule by one of the methods described above for determining direct binding. In an alternative embodiment, determining the ability of the test compound to modulate the activity of NOVX protein can be accomplished by determining the ability of the NOVX protein further modulate an NOVX target molecule. For example, the catalytic/enzymatic activity of the target molecule on an appropriate substrate can be determined as described, supra.

In yet another embodiment, the cell-free assay comprises contacting the NOVX protein or biologically-active portion thereof with a known compound which binds NOVX protein to form an assay mixture, contacting the assay mixture with a test compound, and determining the ability of the test compound to interact with an NOVX protein, wherein determining the ability of the test compound to interact with an NOVX protein comprises determining the ability of the NOVX protein to preferentially bind to or modulate the activity of an NOVX target molecule.

The cell-free assays of the invention are amenable to use of both the soluble form or the membrane-bound form of NOVX protein. In the case of cell-free assays comprising the membrane-bound form of NOVX protein, it may be desirable to utilize a solubilizing agent such that the membrane-bound form of NOVX protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether), N-dodecyl—N,N-dimethyl-3-ammonio-1-propane sulfonate, 3-(3-cholamidopropyl)dimethylamminiol-1-propane sulfonate (CHAPS), or 3-(3-cholamidopropyl) dimethylamminiol-2-hydroxy-11-propane sulfonate (CHAPSO).

In more than one embodiment of the above assay methods of the invention, it may be desirable to immobilize either NOVX protein or its target molecule to facilitate separation of complexed from uncomplexed forms of one or both of the proteins, as well as to accommodate automation of the assay. Binding of a test compound to NOVX protein, or interaction of NOVX protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-NOVX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NOVX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of NOVX protein binding or activity determined using standard techniques.

Other techniques for immobilizing proteins on matrices can also be used in the screening assays of the invention. For example, either the NOVX protein or its target molecule can be immobilized utilizing conjugation of biotin and streptavidin. Biotinylated NOVX protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with NOVX protein or target molecules, but which do not interfere with binding of the NOVX protein to its target molecule, can be derivatized to the wells of the plate, and unbound target or NOVX protein trapped in the wells by antibody conjugation. Methods for detecting such complexes, in addition to those described above for the GST-immobilized complexes, include immunodetection of complexes using antibodies reactive with the NOVX protein or target molecule, as well as enzyme-linked assays that rely on detecting an enzymatic activity associated with the NOVX protein or target molecule.

In another embodiment, modulators of NOVX protein expression are identified in a method wherein a cell is contacted with a candidate compound and the expression of NOVX mRNA or protein in the cell is determined. The level of expression of NOVX mRNA or protein in the presence of the candidate compound is compared to the level of expression of NOVX mRNA or protein in the absence of the candidate compound. The candidate compound can then be identified as a modulator of NOVX mRNA or protein expression based upon this comparison. For example, when expression of NOVX mRNA or protein is greater (i.e., statistically significantly greater) in the presence of the candidate compound than in its absence, the candidate compound is identified as a stimulator of NOVX mRNA or protein expression. Alternatively, when expression of NOVX mRNA or protein is less (statistically significantly less) in the presence of the candidate compound than in its absence, the candidate compound is identified as an inhibitor of NOVX mRNA or protein expression. The level of NOVX mRNA or protein expression in the cells can be determined by methods described herein for detecting NOVX mRNA or protein.

In yet another aspect of the invention, the NOVX proteins can be used as "bait proteins" in a two-hybrid assay or three hybrid assay (see, e.g., U.S. Pat. No. 5,283,317; Zervos, et al., 1993. *Cell* 72: 223–232; Madura, et al., 1993. *J. Biol. Chem.* 268: 12046–12054; Bartel, et al., 1993. *Biotechniques* 14: 920–924; Iwabuchi, et al., 1993. *Oncogene* 8: 1693–1696; and Brent WO 94/10300), to identify other proteins that bind to or interact with NOVX ("NOVX-binding proteins" or "NOVX-bp") and modulate NOVX activity. Such NOVX-binding proteins are also likely to be involved in the propagation of signals by the NOVX proteins as, for example, upstream or downstream elements of the NOVX pathway.

The two-hybrid system is based on the modular nature of most transcription factors, which consist of separable DNA-binding and activation domains. Briefly, the assay utilizes two different DNA constructs. In one construct, the gene that codes for NOVX is fused to a gene encoding the DNA binding domain of a known transcription factor (e.g., GAL4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an NOVX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with NOVX.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the NOVX sequences, SEQ ID NOS:1, 3, 4, 6, 8, 10, 12, 14, 16, 18, 20, 22, 24, and 26, or fragments or derivatives thereof, can be used to map the location of the NOVX genes, respectively, on a chromosome. The mapping of the NOVX sequences to chromosomes is an important first step in correlating these sequences with genes associated with disease.

Briefly, NOVX genes can be mapped to chromosomes by preparing PCR primers (preferably 15–25 bp in length) from the NOVX sequences. Computer analysis of the NOVX, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the NOVX sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g. D'Eustachio, et al., 1983. *Science* 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NOVX sequences to design oligonucleotide primers, sub-localization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g. Egeland, et al., 1987. *Nature*, 325: 783–787.

Moreover, differences in the DNA sequences between individuals affected and unaffected with a disease associated with the NOVX gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The NOVX sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the NOVX sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The NOVX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NOS:1, 3,4, 6, 8, 10, 12, 14, 16, 18, 20, 22, 24, and 26 are used, amoreappropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining NOVX protein and/or nucleic acid expression as well as NOVX activity, in the context of a biological sample (e.g., blood, serum, cells, tissue) to thereby determine whether an individual is afflicted with a disease or disorder, or is at risk of developing a disorder, associated with aberrant NOVX expression or activity. The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers. The invention also provides for prognostic (or predictive) assays for determining whether an individual is at risk of developing a disorder associated with NOVX protein, nucleic acid expression or activity. For example, mutations in an NOVX gene can be assayed in a biological sample. Such assays can be used for prognostic or predictive purpose to thereby prophylactically treat an individual prior to the onset of a disorder characterized by or associated with NOVX protein, nucleic acid expression, or biological activity.

Another aspect of the invention provides methods for determining NOVX protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g. the genotype of the individual examined to determine the ability of the individual to respond to a particular agent.)

Yet another aspect of the invention pertains to monitoring the influence of agents (e.g., drugs, compounds) on the expression or activity of NOVX in clinical trials.

These and other agents are described in further detail in the following sections.

Diagnostic Assays

An exemplary method for detecting the presence or absence of NOVX in a biological sample involves obtaining a biological sample from a test subject and contacting the biological sample with a compound or an agent capable of detecting NOVX protein or nucleic acid (e.g., mRNA, genomic DNA) that encodes NOVX protein such that the presence of NOVX is detected in the biological sample. An agent for detecting NOVX mRNA or genomic DNA is a labeled nucleic acid probe capable of hybridizing to NOVX mRNA or genomic DNA. The nucleic acid probe can be, for example, a full-length NOVX nucleic acid, such as the nucleic acid of SEQ ID NOS:1, 3, 4, 6, 8, 10, 12, 14, 16, 18, 20, 22, 24, and 26, or a portion thereof, such as an oligonucleotide of at least 15, 30, 50, 100, 250 or 500 nucleotides in length and sufficient to specifically hybridize under stringent conditions to NOVX mRNA or genomic DNA. Other suitable probes for use in the diagnostic assays of the invention are described herein.

An agent for detecting NOVX protein is an antibody capable of binding to NOVX protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect NOVX mRNA, protein, or genomic DNA in a biological sample in vitro as well as in vivo. For example, in vitro techniques for detection of NOVX mRNA include Northern hybridizations and in situ hybridizations. In vitro techniques for detection of NOVX protein include enzyme linked immunosorbent assays (ELISAs), Western blots, immunoprecipitations, and immunofluorescence. In vitro techniques for detection of NOVX genomic DNA include Southern hybridizations. Furthermore, in vivo techniques for detection of NOVX protein include introducing into a subject a labeled anti-NOVX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting NOVX protein, mRNA, or genomic DNA, such that the presence of NOVX protein, mRNA or genomic DNA is detected in the biological sample, and comparing the presence of NOVX protein, mRNA or genomic DNA in the control sample with the presence of NOVX protein, mRNA or genomic DNA in the test sample.

The invention also encompasses kits for detecting the presence of NOVX in a biological sample. For example, the kit can comprise: a labeled compound or agent capable of detecting NOVX protein or mRNA in a biological sample; means for determining the amount of NOVX in the sample; and means for comparing the amount of NOVX in the sample with a standard. The compound or agent can be packaged in a suitable container. The kit can further comprise instructions for using the kit to detect NOVX protein or nucleic acid.

Prognostic Assays

The diagnostic methods described herein can furthermore be utilized to identify subjects having or at risk of developing a disease or disorder associated with aberrant NOVX expression or activity. For example, the assays described herein, such as the preceding diagnostic assays or the following assays, can be utilized to identify a subject having or at risk of developing a disorder associated with NOVX protein, nucleic acid expression or activity. Alternatively, the prognostic assays can be utilized to identify a subject having or at risk for developing a disease or disorder. Thus, the invention provides a method for identifying a disease or disorder associated with aberrant NOVX expression or activity in which a test sample is obtained from a subject and NOVX protein or nucleic acid (e.g., mRNA, genomic DNA) is detected, wherein the presence of NOVX protein or nucleic acid is diagnostic for a subject having or at risk of developing a disease or disorder associated with aberrant NOVX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NOVX expression or activity. For example, such methods can be used to determine whether a subject can be effectively treated with an agent for a disorder. Thus, the invention provides methods for determining whether a subject can be effectively treated with an agent for a disorder associated with aberrant NOVX expression or activity in which a test sample is obtained and NOVX protein or nucleic acid is detected (e.g., wherein the presence of NOVX protein or nucleic acid is diagnostic for a subject that can be administered the agent to treat a disorder associated with aberrant NOVX expression or activity).

The methods of the invention can also be used to detect genetic lesions in an NOVX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an NOVX-protein, or the misexpression of the NOVX gene. For example, such genetic lesions can be detected by ascertaining the existence of at least one of: (i) a deletion of one or more nucleotides from an NOVX gene; (ii) an addition of one or more nucleotides to an NOVX gene; (iii) a substitution of one or more nucleotides of an NOVX gene, (iv) a chromosomal rearrangement of an NOVX gene; (v) an alteration in the level of a messenger RNA transcript of an NOVX gene, (vi) aberrant modification of an NOVX gene, such as of the methylation pattern of the genomic DNA, (vii) the presence of a non-wild-type splicing pattern of a messenger RNA transcript of an NOVX gene, (viii) a non-wild-type level of an NOVX protein, (ix) allelic loss of an NOVX gene, and (x) inappropriate post-translational modification of an NOVX protein. As described herein, there are a large number of assay techniques known in the art which can be used for detecting lesions in an NOVX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the NOVX-gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to an NOVX gene under conditions such that hybridization and amplification of the NOVX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); QP Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an NOVX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in NOVX can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in NOVX can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NOVX gene and detect mutations by comparing the sequence of the sample NOVX with the corresponding wild-type (control) sequence. Examples of sequencing reactions include those based on techniques developed by Maxim and Gilbert, 1977. *Proc. Natl. Acad. Sci. USA* 74: 560 or Sanger, 1977. *Proc. Natl. Acad. Sci. USA* 74: 5463. It is also contemplated that any of a variety of automated sequencing procedures can be utilized when performing the diagnostic assays (see, e.g., Naeve, et al., 1995. *Biotechniques* 19: 448), including sequencing by mass spectrometry (see, e.g., PCT International Publication No. WO 94/16101; Cohen, et al., 1996. *Adv. Chromatography* 36: 127–162; and Griffin, et al., 1993. *Appl. Biochem. Biotechnol.* 38: 147–159).

Other methods for detecting mutations in the NOVX gene include methods in which protection from cleavage agents is used to detect mismatched bases in RNA/RNA or RNA/DNA heteroduplexes. See, e.g., Myers, et al., 1985. *Science* 230: 1242. In general, the art technique of "mismatch cleavage" starts by providing heteroduplexes of formed by hybridizing labeled) RNA or DNA containing the wild-type NOVX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NOVX cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis* 15: 1657–1662. According to an exemplary embodiment, a probe based on an NOVX sequence, e.g., a wild-type NOVX sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NOVX genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766; Cotton, 1993. *Mutat. Res.* 285: 125–144; Hayashi, 1992. *Genet. Anal. Tech. Appl.* 9: 73–79. Single-stranded DNA fragments of sample and control NOVX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al, 1985. *Nature* 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an NOVX gene.

Furthermore, any cell type or tissue, preferably peripheral blood leukocytes, in which NOVX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on NOVX activity (e.g., NOVX gene expression), as identified by a screening assay described herein can be administered to individuals to treat (prophylactically or therapeutically) disorders (The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers.) In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NOVX protein, expression of NOVX nucleic acid, or mutation content of NOVX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. PharmacoL Physiol.*, 23: 983–985; Linder, 1997. *Clin. Chem.*, 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of NOVX protein, expression of NOVX nucleic acid, or mutation content of NOVX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an NOVX modulator, such as a modulator identified by one of the exemplary screening assays described herein.

Monitoring of Effects During Clinical Trials

Monitoring the influence of agents (e.g., drugs, compounds) on the expression or activity of NOVX (e.g., the ability to modulate aberrant cell proliferation and/or differentiation) can be applied not only in basic drug screening, but also in clinical trials. For example, the effectiveness of an agent determined by a screening assay as described herein to increase NOVX gene expression, protein levels, or upregulate NOVX activity, can be monitored in clinical trails of subjects exhibiting decreased NOVX gene expression, protein levels, or downregulated NOVX activity. Alternatively, the effectiveness of an agent determined by a screening assay to decrease NOVX gene expression, protein levels, or downregulate NOVX activity, can be monitored in clinical trails of subjects exhibiting increased NOVX gene expression, protein levels, or upregulated NOVX activity. In such clinical trials, the expression or activity of NOVX and, preferably, other genes that have been implicated in, for example, a cellular proliferation or immune disorder can be used as a "read out" or markers of the immune responsiveness of a particular cell.

By way of example, and not of limitation, genes, including NOVX, that are modulated in cells by treatment with an agent (e.g., compound, drug or small molecule) that modulates NOVX activity (e.g., identified in a screening assay as described herein) can be identified. Thus, to study the effect of agents on cellular proliferation disorders, for example, in a clinical trial, cells can be isolated and RNA prepared and analyzed for the levels of expression of NOVX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NOVX or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an NOVX protein, mRNA, or genomic DNA in the preadministration sample; (iii) obtaining one or more post-administration samples from the subject; (iv) detecting the level of expression or activity of the NOVX protein, mRNA, or genomic DNA in the post-administration samples; (v) comparing the level of expression or activity of the NOVX protein, mRNA, or genomic DNA in the pre-administration sample with the NOVX protein, mRNA, or genomic DNA in the post administration sample or samples; and (vi) altering the administration of the agent to the subject accordingly. For example, increased administration of the agent may be desirable to increase the expression or activity of NOVX to higher levels than detected, i.e., to increase the effectiveness of the agent. Alternatively, decreased administration of the agent may be desirable to decrease expression or activity of NOVX to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant NOVX expression or activity. The disorders include cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation, adrenoleukodystrophy, congenital adrenal hyperplasia, prostate cancer, neoplasm; adenocarcinoma, lymphoma, uterus cancer, fertility, hemophilia, hypercoagulation, idiopathic thrombocytopenic purpura, immunodeficiencies, graft versus host disease, AIDS, bronchial asthma, Crohn's disease; multiple sclerosis, treatment of Albright Hereditary Ostoeodystrophy, and other diseases, disorders and conditions of the like.

These methods of treatment will be discussed more fully, below.

Disease and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g. from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant NOVX expression or activity, by administering to the subject an agent that modulates NOVX expression or at least one NOVX activity. Subjects at risk for a disease that is caused or contributed to by aberrant NOVX expression or activity can be identified by, for example, any or a combination of diagnostic or prognostic assays as described herein. Administration of a prophylactic agent can occur prior to the manifestation of symptoms characteristic of the NOVX aberrancy, such that a disease or disorder is prevented or, alternatively, delayed in its progression. Depending upon the type of NOVX aberrancy, for example, an NOVX agonist or NOVX antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating NOVX expression or activity for therapeutic purposes. The modulatory method of the invention involves contacting a cell with an agent that modulates one or more of the activities of NOVX protein activity associated with the cell. An agent that modulates NOVX protein activity can be an agent as described herein, such as a nucleic acid or a protein, a naturally-occurring cognate ligand of an NOVX protein, a peptide, an NOVX peptidomimetic, or other small molecule. In one embodiment, the agent stimulates one or more NOVX protein activity. Examples of such stimulatory agents include active NOVX protein and a nucleic acid molecule encoding NOVX that has been introduced into the cell. In another embodiment, the agent inhibits one or more NOVX protein activity. Examples of such inhibitory agents include antisense NOVX nucleic acid molecules and anti-NOVX antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of an NOVX protein or nucleic acid molecule. In one embodiment, the method involves administering an agent (e.g., an agent identified by a screening assay described herein), or combination of agents that modulates (e.g., up-regulates or down-regulates) NOVX expression or activity. In another embodiment, the method involves administering an NOVX protein or nucleic acid molecule as therapy to compensate for reduced or aberrant NOVX expression or activity.

Stimulation of NOVX activity is desirable in situations in which NOVX is abnormally downregulated and/or in which increased NOVX activity is likely to have a beneficial effect. One example of such a situation is where a subject has a disorder characterized by aberrant cell proliferation and/or differentiation (e.g., cancer or immune associated disorders). Another example of such a situation is where the subject has a gestational disease (e.g., preclampsia).

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Invention

The NOVX nucleic acids and proteins of the invention are useful in potential prophylactic and therapeutic applications implicated in a variety of disorders including, but not limited to: metabolic disorders, diabetes, obesity, infectious disease, anorexia, cancer-associated cancer, neurodegenerative disorders, Alzheimer's Disease, Parkinson's Disorder, immune disorders, hematopoietic disorders, and the various dyslipidemias, metabolic disturbances associated with obesity, the metabolic syndrome X and wasting disorders associated with chronic diseases and various cancers.

As an example, a cDNA encoding the NOVX protein of the invention may be useful in gene therapy, and the protein may be useful when administered to a subject in need thereof. By way of non-limiting example, the compositions of the invention will have efficacy for treatment of patients suffering from: metabolic disorders, diabetes, obesity, infectious disease, anorexia, cancer-associated cachexia, cancer, neurodegenerative disorders, Alzheimer's Disease, Parkinson's Disorder, immune disorders, hematopoietic disorders, and the various dyslipidemias.

Both the novel nucleic acid encoding the NOVX protein, and the NOVX protein of the invention, or fragments thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies, which immunospecifically-bind to the novel substances of the invention for use in therapeutic or diagnostic methods.

The invention will be further described in the following examples, which do not limit the scope of the invention described in the claims.

EXAMPLES

Example 1

Identification of NOVX Clones

The novel NOVX target sequences identified in the present invention were subjected to the exon linking process to confirm the sequence. PCR primers were designed by starting at the most upstream sequence available, for the forward primer, and at the most downstream sequence available for the reverse primer. Table 11A shows the sequences of the PCR primers used for obtaining different clones. In each case, the sequence was examined, walking inward from the respective termini toward the coding sequence, until a suitable sequence that is either unique or highly selective was encountered, or, in the case of the reverse primer, until the stop codon was reached. Such primers were designed based on in silico predictions for the full length cDNA, part (one or more exons) of the DNA or protein sequence of the target sequence, or by translated homology of the predicted exons to closely related human sequences from other species. These primers were then employed in PCR amplification based on the following pool of human cDNAs: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea, uterus. Usually the resulting amplicons were gel purified, cloned and sequenced to high redundancy. The PCR product derived from exon linking was cloned into the pCR2.1 vector from Invitrogen. The resulting bacterial clone has an insert covering the entire open reading frame cloned into the pCR2.1 vector. Table 17B shows a list of these bacterial clones. The resulting sequences from all clones were assembled with themselves, with other fragments in CuraGen Corporation's database and with public ESTs. Fragments and ESTs were included as components for an assembly when the extent of their identity with another component of the assembly was at least 95% over 50 bp. In addition, sequence traces were evaluated manually and edited for corrections if appropriate. These procedures provide the sequence reported herein.

TABLE 10

PCR Primers for Exon Linking

| NOVX Clone | Primer 1 (5'—3') | SEQ ID NO | Primer 2 (5'—3') | SEQ ID NO |
|---|---|---|---|---|
| NOV1c | TCATCACATGACAACATGAAGCTGT | 87 | GAAAGCCCTCAAACTCTCCATCTATG | 88 |
| NOV7a | CCAATCTCTGATGCCCTGCGAT | 89 | AGGTCAGTGCCGGAGCCTCC | 90 |

Physical Clone: Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein.

TABLE 11

Physical Clones for PCR products

| NOVX Clone | Bacterial Clone |
|---|---|
| NOV1 | Physical clone: 128940::83420733.698715.E24 |
| NOV2 | Physical clone: AL357059, AL022344, AL3555530, AL356100, AC016042 |
| NOV4 | Physical clone: AC009785 |
| NOV5 | Genomic clone: GMChromosome4 |
| NOV7a | Genomic file: gb_AC010319 HTG Homo sapiens\|chromosome 19 CTD-2521M24 |
| NOV8 | Physical clone: AC008803, AC010449, AC026718 |

Example 2

Quantitative Expression Analysis of Clones in Various Cells and Tissues

The quantitative expression of various clones was assessed using microtiter plates containing RNA samples from a variety of normal and pathology-derived cells, cell lines and tissues using real time quantitative PCR (RTQ PCR). RTQ PCR was performed on a Perkin-Elmer Biosystems ABI PRISM® 7700 Sequence Detection System. Various collections of samples are assembled on the plates, and referred to as Panel 1 (containing normal tissues and cancer cell lines), Panel 2 (containing samples derived from tissues from normal and cancer sources), Panel 3 (containing cancer cell lines), Panel 4 (containing cells and cell lines from normal tissues and cells related to inflammatory conditions), AI_comprehensive_panel (containing normal tissue and samples from autoinflammatory diseases), Panel CNSD.01 (containing samples from normal and diseased brains) and CNS_neurodegeneration_panel (containing samples from normal and diseased brains).

First, the RNA samples were normalized to reference nucleic acids such as constitutively expressed genes (for example, β-actin and GAPDH). Normalized RNA (5 ul) was converted to cDNA and analyzed by RTQ-PCR using One Step RT-PCR Master Mix Reagents (PE Biosystems; Catalog No. 4309169) and gene-specific primers according to the manufacturer's instructions. Probes and primers were designed for each assay according to Perkin Elmer Biosystem's Primer Express Software package (version I for Apple Computer's Macintosh Power PC) or a similar algorithm using the target sequence as input. Default settings were used for reaction conditions and the following parameters were set before selecting primers: primer concentration=250 nM, primer melting temperature ($T_m$) range=58°–60° C., primer optimal Tm=59° C., maximum primer difference=2° C., probe does not have 5' G, probe $T_m$ must be 10° C. greater than primer $T_m$, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 DM each, and probe, 200 nM.

PCR Conditions: Normalized RNA from each tissue and each cell line was spotted in each well of a 96 well PCR plate (Perkin Elmer Biosystems). PCR cocktails including two probes (a probe specific for the target clone and another gene-specific probe multiplexed with the target probe) were set up using 1×TaqMan™ PCR Master Mix for the PE Biosystems 7700, with 5 mM MgCl2, dNTPs (dA, G, C, U at 1:1:1:2 ratios), 0.25 U/ml AmpliTaq Gold™ (PE Biosystems), and 0.4 U/μl RNase inhibitor, and 0.25 U/μl reverse transcriptase. Reverse transcription was performed at 48° C. for 30 minutes followed by amplification/PCR cycles as follows: 95° C. 10 min, then 40 cycles of 950 C for 15 seconds, 60° C. for 1 minute. Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100.

Panel 1

In the results for Panel 1, the following abbreviations are used:
ca.=carcinoma,
*=established from metastasis,
met=metastasis,
s cell var=small cell variant,
non-s=non-sm=non-small,
squam=squamous,
pl. eff=pl effusion=pleural effusion,
glio=glioma,
astro=astrocytoma, and
neuro=neuroblastoma.

Panel 2

The plates for Panel 2 generally include 2 control wells and 94 test samples composed of RNA or cDNA isolated from human tissue procured by surgeons working in close cooperation with the National Cancer Institute's Cooperative Human Tissue Network (CHTN) or the National Disease Research Initiative (NDR1). The tissues are derived from human malignancies and in cases where indicated many malignant tissues have "matched margins" obtained from noncancerous tissue just adjacent to the tumor. These are termed normal adjacent tissues and are denoted "NAT" in the results below. The tumor tissue and the "matched margins" are evaluated by two independent pathologists (the surgical pathologists and again by a pathologists at NDRI or CHTN). This analysis provides a gross histopathological assessment of tumor differentiation grade. Moreover, most samples include the original surgical pathology report that provides information regarding the clinical stage of the patient. These matched margins are taken from the tissue surrounding (i.e. immediately proximal) to the zone of surgery (designated "NAT", for normal adjacent tissue, in Table RR). In addition, RNA and cDNA samples were obtained from various human tissues derived from autopsies performed on elderly people or sudden death victims (accidents, etc.). These tissues were ascertained to be free of disease and were purchased from various commercial sources such as Clontech (Palo Alto, Calif.), Research Genetics, and Invitrogen.

RNA integrity from all samples is controlled for quality by visual assessment of agarose gel electropherograms using 28S and 18S ribosomal RNA staining intensity ratio as a guide (2:1 to 2.5:1 28s: 18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

Panel 3D

The plates of Panel 3D are comprised of 94 cDNA samples and two control samples. Specifically, 92 of these samples are derived from cultured human cancer cell lines, 2 samples of human primary cerebellar tissue and 2 controls. The human cell lines are generally obtained from ATCC (American Type Culture Collection), NCI or the German tumor cell bank and fall into the following tissue groups: Squamous cell carcinoma of the tongue, breast cancer, prostate cancer, melanoma, epidermoid carcinoma, sarcomas, bladder carcinomas, pancreatic cancers, kidney cancers, leukemias/lymphomas, ovarian/uterine/cervical, gastric, colon, lung and CNS cancer cell lines. In addition, there are two independent samples of cerebellum. These cells are all cultured under standard recommended conditions and RNA extracted using the standard procedures. The cell lines in panel 3D and 1.3D are of the most common cell lines used in the scientific literature.

RNA integrity from all samples is controlled for quality by visual assessment of agarose gel electropherograms using 28S and 18S ribosomal RNA staining intensity ratio as a guide (2:1 to 2.5:1 28s:18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

Panel 4

Panel 4 includes samples on a 96 well plate (2 control wells, 94 test samples) composed of RNA (Panel 4r) or cDNA (Panel 4d) isolated from various human cell lines or tissues related to inflammatory conditions. Total RNA from control normal tissues such as colon and lung (Stratagene, La Jolla, Calif.) and thymus and kidney (Clontech) were employed. Total RNA from liver tissue from cirrhosis patients and kidney from lupus patients was obtained from BioChain (Biochain Institute, Inc., Hayward, Calif.). Intestinal tissue for RNA preparation from patients diagnosed as having Crohn's disease and ulcerative colitis was obtained from the National Disease Research Interchange (NDRI) (Philadelphia, Pa.).

Astrocytes, lung fibroblasts, dermal fibroblasts, coronary artery smooth muscle cells, small airway epithelium, bronchial epithelium, microvascular dermal endothelial cells, microvascular lung endothelial cells, human pulmonary aortic endothelial cells, human umbilical vein endothelial cells were all purchased from Clonetics (Walkersville, Md.) and grown in the media supplied for these cell types by Clonetics. These primary cell types were activated with various cytokines or combinations of cytokines for 6 and/or 12–14 hours, as indicated. The following cytokines were used; IL-1 beta at approximately 1–5 ng/ml, TNF alpha at approximately 5–10 ng/ml, IFN gamma at approximately 20–50 ng/ml, IL-4 at approximately 5–10 ng/ml, IL-9 at approximately 5–10 ng/ml, IL-13 at approximately 5–10 ng/ml. Endothelial cells were sometimes starved for various times by culture in the basal media from Clonetics with 0.1% serum.

Mononuclear cells were prepared from blood of employees at CuraGen Corporation, using Ficoll. LAK cells were prepared from these cells by culture in DMEM 5% FCS (Hyclone), 100 $\mu$M non essential amino acids (Gibco/Life Technologies, Rockville, Md.), 1 mM sodium pyruvate (Gibco), mercaptoethanol $5.5 \times 10^{-5}$ M (Gibco), and 10 mM Hepes (Gibco) and Interleukin 2 for 4–6 days. Cells were then either activated with 10–20 ng/ml PMA and 1–2 $\mu$g/ml ionomycin, IL-12 at 5–10 ng/ml, IFN gamma at 20–50 ng/ml and IL-18 at 5–10 ng/ml for 6 hours. In some cases, mononuclear cells were cultured for 4–5 days in DMEM 5% FCS (Hyclone), 100 $\mu$M non essential amino acids (Gibco), 1 mM sodium pyruvate (Gibco), mercaptoethanol $5.5 \times 10^{-5}$ M (Gibco), and 10 mM Hepes (Gibco) with PHA (phytohemagglutinin) or PWM (pokeweed mitogen) at approximately 5 $\mu$g/ml. Samples were taken at 24, 48 and 72 hours for RNA preparation. MLR (mixed lymphocyte reaction) samples were obtained by taking blood from two donors, isolating the mononuclear cells using Ficoll and mixing the isolated mononuclear cells 1:1 at a final concentration of approximately $2 \times 10^6$ cells/m in DMEM 5% FCS (Hyclone), 100 $\mu$M non essential amino acids (Gibco), 1 mM sodium pyruvate (Gibco), mercaptoethanol ($5.5 \times 10^{-5}$ M) (Gibco), and 10 mM Hepes (Gibco). The MLR was cultured and samples taken at various time points ranging from 1–7 days for RNA preparation.

Monocytes were isolated from mononuclear cells using CD14 Miltenyi Beads, +ve VS selection columns and a Vario Magnet according to the manufacturer's instructions. Monocytes were differentiated into dendritic cells by culture in DMEM 5% fetal calf serum (FCS) (Hyclone, Logan, Utah), 100 $\mu$M non essential amino acids (Gibco), 1 mM sodium pyruvate (Gibco), mercaptoethanol $5.5 \times 10^{-5}$ M (Gibco), and 10 mM Hepes (Gibco), 50 ng/ml GMCSF and 5 ng/ml IL-4 for 5–7 days. Macrophages were prepared by culture of monocytes for 5–7 days in DMEM 5% FCS (Hyclone), 100 $\mu$M non essential amino acids (Gibco), 1 mM sodium pyruvate (Gibco), mercaptoethanol $5.5 \times 10^{-5}$ M (Gibco), 10 mM Hepes (Gibco) and 10% AB Human Serum or MCSF at approximately 50 ng/ml. Monocytes, macrophages and dendritic cells were stimulated for 6 and 12–14 hours with lipopolysaccharide (LPS) at 100 ng/ml. Dendritic cells were also stimulated with anti-CD40 monoclonal antibody (Pharmingen) at 10 $\mu$g/ml for 6 and 12–14 hours.

CD4 lymphocytes, CD8 lymphocytes and NK cells were also isolated from mononuclear cells using CD4, CD8 and CD56 Miltenyi beads, positive VS selection columns and a Vario Magnet according to the manufacturer's instructions. CD45RA and CD45RO CD4 lymphocytes were isolated by depleting mononuclear cells of CD8, CD56, CD14 and CD19 cells using CD8, CD56, CD14 and CD19 Miltenyi beads and positive selection. Then CD45RO beads were used to isolate the CD45RO CD4 lymphocytes with the remaining cells being CD45RA CD4 lymphocytes. CD45RA CD4, CD45RO CD4 and CD8 lymphocytes were placed in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco) and plated at $10^6$ cels/ml onto Falcon 6 well tissue culture plates that had been coated overnight with 0.5 µg/ml anti-CD28 (Pharmingen) and 3 ug/ml anti-CD3 (OKT3, ATCC) in PBS. After 6 and 24 hours, the cells were harvested for RNA preparation. To prepare chronically activated CD8 lymphocytes, we activated the isolated CD8 lymphocytes for 4 days on anti-CD28 and anti-CD3 coated plates and then harvested the cells and expanded them in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco) and IL-2. The expanded CD8 cells were then activated again with plate bound anti-CD3 and anti-CD28 for 4 days and expanded as before. RNA was isolated 6 and 24 hours after the second activation and after 4 days of the second expansion culture. The isolated NK cells were cultured in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco) and IL-2 for 4–6 days before RNA was prepared.

To obtain B cells, tonsils were procured from NDRI. The tonsil was cut up with sterile dissecting scissors and then passed through a sieve. Tonsil cells were then spun down and resupended at 106 cells/ml in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco). To activate the cells, we used PWM at 5 µg/ml or anti-CD40 (Pharmingen) at approximately 10 µg/ml and IL-4 at 5–10 ng/ml. Cells were harvested for RNA preparation at 24,48 and 72 hours.

To prepare the primary and secondary Th1/Th2 and Tr1 cells, six-well Falcon plates were coated overnight with 10 µg/ml anti-CD28 (Pharmingen) and 2 µg/ml OKT3 (ATCC), and then washed twice with PBS. Umbilical cord blood CD4 lymphocytes (Poietic Systems, German Town, Md.) were cultured at $10^5$–$10^6$ cells/m in DMEM 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco) and IL-2 (4 ng/ml). IL-12 (5 ng/ml) and anti-IL4 (1 □g/ml) were used to direct to Th1, while IL-4 (5 ng/ml) and anti-IFN gamma (1 □g/ml) were used to direct to Th2 and IL-10 at 5 ng/ml was used to direct to Tr1. After 4–5 days, the activated Th1, Th2 and Tr1 lymphocytes were washed once in DMEM and expanded for 4–7 days in DMEM 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco) and IL-2 (1 ng/ml). Following this, the activated Th1, Th2 and Tr1 lymphocytes were re-stimulated for 5 days with anti-CD28/OKT3 and cytokines as described above, but with the addition of anti-CD95L (1 □g/ml) to prevent apoptosis. After 4–5 days, the Th1, Th2 and Tr1 lymphocytes were washed and then expanded again with IL-2 for 4–7 days. Activated Th1 and Th2 lymphocytes were maintained in this way for a maximum of three cycles. RNA was prepared from primary and secondary Th1, Th2 and Tr1 after 6 and 24 hours following the second and third activations with plate bound anti-CD3 and anti-CD28 mAbs and 4 days into the second and third expansion cultures in Interleukin 2.

The following leukocyte cells lines were obtained from the ATCC: Ramos, EOL-1, KU-812. EOL cells were further differenfiated by culture in 0.1 mM dbcAMP at $5 \times 10^5$ cells/ml for 8 days, changing the media every 3 days and adjusting the cell concentration to $5 \times 10^5$ cells/ml. For the culture of these cells, we used DMEM or RPMI (as recommended by the ATCC), with the addition of 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco). RNA was either prepared from resting cells or cells activated with PMA at 10 ng/ml and ionomycin at 1 µg/ml for 6 and 14 hours. Keratinocyte line CCD106 and an airway epithelial tumor line NCI-H292 were also obtained from the ATCC. Both were cultured in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco). CCD1106 cells were activated for 6 and 14 hours with approximately 5 ng/ml TNF alpha and 1 ng/ml IL-1 beta, while NCI-H292 cells were activated for 6 and 14 hours with the following cytokines: 5 ng/ml IL-4, 5 ng/ml IL-9, 5 ng/ml IL-13 and 25 ng/ml IFN gamma.

For these cell lines and blood cells, RNA was prepared by lysing approximately $10^7$ cells/ml using Trizol (Gibco BRL). Briefly, 1/10 volume of bromochloropropane (Molecular Research Corporation) was added to the RNA sample, vortexed and after 10 minutes at room temperature, the tubes were spun at 14,000 rpm in a Sorvall SS34 rotor. The aqueous phase was removed and placed in a 15 ml Falcon Tube. An equal volume of isopropanol was added and left at −20 degrees C. overnight. The precipitated RNA was spun down at 9,000 rpm for 15 min in a Sorvall SS34 rotor and washed in 70% ethanol. The pellet was redissolved in 300 µl of RNAse-free water and 35 µl buffer (Promega) 5 µl DTT, 7 µl RNAsin and 8 µl DNAse were added. The tube was incubated at 37 degrees C. for 30 minutes to remove contaminating genomic DNA, extracted once with phenol chloroform and re-precipitated with 1/10 volume of 3 M sodium acetate and 2 volumes of 100% ethanol. The RNA was spun down and placed in RNAse free water. RNA was stored at −80 degrees C.

Panel CNSD.01

The plates for Panel CNSD.01 include two control wells and 94 test samples comprised of cDNA isolated from postmortem human brain tissue obtained from the Harvard Brain Tissue Resource Center. Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains two brains from each of the following diagnoses: Alzheimer's disease, Parkinson's disease, Huntington's disease, Progressive Supernuclear Palsy, Depression, and "Normal controls". Within each of these brains, the following regions are represented: cingulate gyrus, temporal pole, globus palladus, substantia nigra, Brodman Area 4 (primary motor strip), Brodman Area 7 (parietal cortex), Brodman Area 9 (prefrontal cortex), and Brodman area 17 (occipital cortex). Not all brain regions are represented in all cases; e.g., Huntington's disease is characterized in part by neurodegeneration in the globus palladus, thus this region is impossible to obtain from confirmed Huntington's cases.

Likewise Parkinson's disease is characterized by degeneration of the substantia nigra making this region more difficult to obtain. Normal control brains were examined for neuropathology and found to be free of any pathology consistent with neurodegeneration.

RNA integrity from all samples is controlled for quality by visual assessment of agarose gel electropherograms using 28S and 18S ribosomal RNA staining intensity ratio as a guide (2:1 to 2.5:1 28s: 18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

In the labels employed to identify tissues in the CNS panel, the following abbreviations are used:

PSP=Progressive supranuclear palsy
Sub Nigra=Substantia nigra
Glob Palladus=Globus palladus
Temp Pole=Temporal pole
Cing Gyr=Cingulate gyrus
BA 4=Brodman Area 4

Panel CNS_Neurodegeneration_V1.0

The plates for Panel CNS_Neurodegeneration_V1.0 include two control wells and 47 test samples comprised of cDNA isolated from postmortem human brain tissue obtained from the Harvard Brain Tissue Resource Center (McLean Hospital) and the Human Brain and Spinal Fluid Resource Center (VA Greater Los Angeles Healthcare System). Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains six brains from Alzheimer's disease (AD) pateins, and eight brains from "Normal controls" who showed no evidence of dementia prior to death. The eight normal control brains are divided into two categories: Controls with no dementia and no Alzheimer's like pathology (Controls) and controls with no dementia but evidence of severe Alzheimer's like pathology, (specifically senile plaque load rated as level 3 on a scale of 0–3; 0=no evidence of plaques, 3=severe AD senile plaque load). Within each of these brains, the following regions are represented: Hippocampus, Temporal cortex (Broddmann Area 21), Somatosensory cortex (Broddmann area 7), and Occipital cortex (Brodmann area 17). These regions were chosen to encompass all levels of neurodegeneration in AD. The hippocampus is a region of early and severe neuronal loss in AD; the temporal cortex is known to show neurodegeneration in AD after the hippocampus; the somatosensory cortex shows moderate neuronal death in the late stages of the disease; the occipital cortex is spared in AD and therefore acts as a "control" region within AD patients. Not all brain regions are represented in all cases.

RNA integrity from all samples is controlled for quality by visual assessment of agarose gel electropherograms using 28S and 18S ribosomal RNA staining intensity ratio as a guide (2:1 to 2.5:1 28s: 18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

In the labels employed to identify tissues in the CNS_Neurodegeneration_V1.0 panel, the following abbreviations are used:

AD=Alzheimer's disease brain; patient was demented and showed AD-like pathology upon autopsy
Control=Control brains; patient not demented, showing no neuropathology
Control (Path)=Control brains; pateint not demented but showing sever AD-like pathology
SupTemporal Ctx=Superior Temporal Cortex
Inf Temporal Ctx=Inferior Temporal Cortex NOV1a Expression of gene NOV1a was assessed using the primer-probe sets Ag273b and Ag1094, described in Tables 12 and 13. Results from RTQ-PCR runs are shown in Tables 14, 15, 16, 17, and 18.

TABLE 12

Probe Name Ag273b

| Primers | Sequences | TM | Length | Start Position | SEQ ID NO: |
|---|---|---|---|---|---|
| Forward | 5'-CGGCTTGACGATGCTTCAC-3' | | 19 | 13 | 91 |
| Probe | FAM-5'-TGACTTTTCTGGGCTTACCAATGCTATTTCAA-3'-TAMRA | | 32 | 37 | 92 |
| Reverse | 5'-GCACCTATCTCAATATCTGCAATATTG-3' | | 27 | 85 | 93 |

TABLE 13

Probe Name Ag1094

| Primers | Sequences | TM | Length | Start Position | SEQ ID NO: |
|---|---|---|---|---|---|
| Forward | 5'-ATGGACTGGAAAACCTGGAA-3' | 59.4 | 20 | 192 | 94 |
| Probe | FAM-5'- | 66.5 | 29 | 213 | 95 |

TABLE 13-continued

Probe Name Ag1094

| Primers | Sequences | TM | Length | Start Position | SEQ ID NO: |
|---|---|---|---|---|---|
| | TCCTGCAAGCAGATAACAATTTTATCACA-3'-TAMRA | | | | |
| Reverse | 5'-TGCTAAAGGCACTTGGTTCA-3' | 59.5 | 20 | 247 | 96 |

TABLE 14

Panel 1

| Tissue Name | Relative Expression (%) tm566f_ag273b |
|---|---|
| Endothelial cells | 0.0 |
| Endothelial cells (treated) | 0.0 |
| Pancreas | 0.0 |
| Pancreatic Ca. CAPAN 2 | 0.0 |
| Adrenal gland | 0.0 |
| Thyroid | 0.0 |
| Salavary gland | 12.9 |
| Pituitary gland | 0.0 |
| Brain (fetal) | 0.0 |
| Brain (whole) | 0.2 |
| Brain (amygdala) | 0.0 |
| Brain (cerebellum) | 1.6 |
| Brain (hippocampus) | 0.0 |
| Brain (substantia nigra) | 0.0 |
| Brain (thalamus) | 2.9 |
| Brain (hypothalamus) | 0.0 |
| Spinal cord | 0.0 |
| CNS ca. (glio/astro) U87-MG | 0.0 |
| CNS ca. (glio/astro) U-118-MG | 0.0 |
| CNS ca. (astro) SW1783 | 0.0 |
| CNS ca.* (neuro; met) SK-N-AS | 6.6 |
| CNS Ca. (astro) SF-539 | 0.0 |
| CNS ca. (astro) SNB-75 | 10.2 |
| CNS ca. (glio) SNB-19 | 24.3 |
| CNS ca. (glio) U251 | 4.2 |
| CNS ca. (glio) SF-295 | 37.6 |
| Heart | 1.5 |
| Skeletal muscle | 0.0 |
| Bone marrow | 0.0 |
| Thymus | 0.4 |
| Spleen | 0.0 |
| Lymph node | 0.0 |
| Colon (ascending) | 9.9 |
| Stomach | 0.4 |
| Small intestine | 4.2 |
| Colon ca. SW480 | 0.0 |
| Colon ca.* (SW480 met) SW620 | 0.0 |
| Colon ca. HT29 | 34.4 |
| Colon ca. HCT-116 | 0.0 |
| Colon ca. CaCo-2 | 0.0 |
| Colon ca. HCT-15 | 0.0 |
| Colon ca. HCC-2998 | 0.0 |
| Gastric ca.* (liver met) NCI-N87 | 1.3 |
| Bladder | 0.1 |
| Trachea | 8.9 |
| Kidney | 0.2 |
| Kidney (fetal) | 1.3 |
| Renal Ca. 786-0 | 0.0 |
| Renal ca. A498 | 0.0 |
| Renal Ca. RXF 393 | 0.0 |
| Renal Ca. ACHN | 0.0 |
| Renal Ca. UO-31 | 0.0 |
| Renal Ca. TK-10 | 0.0 |
| Liver | 0.0 |
| Liver (fetal) | 0.0 |
| Liver ca. (hepatoblast) HepG2 | 0.0 |
| Lung | 0.5 |
| Lung (fetal) | 2.2 |
| Lung Ca. (small cell) LX-1 | 0.0 |
| Lung Ca. (small cell) NCI-H69 | 2.7 |
| Lung ca. (s. cell var.) SHP-77 | 44.1 |
| Lung Ca. (large cell) NCI-H460 | 0.0 |
| Lung ca. (non-sm. cell) A549 | 0.0 |
| Lung ca. (non-s. cell) NCI-H23 | 14.7 |
| Lung ca (non-s. cell) HOP-62 | 12.2 |
| Lung ca. (non-s. cl) NCI-H522 | 0.2 |
| Lung Ca. (squam.) SW 900 | 11.9 |
| Lung Ca. (squam.) NCI-H596 | 2.5 |
| Mammary gland | 4.8 |
| Breast ca.* (pl. effusion) MCF-7 | 0.4 |
| Breast ca.* (pl. ef) MCA-MB-231 | 0.0 |
| Breast ca.* (pl. effusion) T47D | 7.2 |
| Breast ca. BT-549 | 0.0 |
| Breast ca. MDA-N | 0.0 |
| Ovary | 0.0 |
| Ovarian ca. OVCAR-3 | 0.0 |
| Ovarian ca. OVCAR-4 | 0.0 |
| Ovarian ca. OVCAR-5 | 6.2 |
| Ovarian ca. OVCAR-8 | 0.0 |
| Ovarian ca. IGROV-1 | 0.0 |
| Ovarian ca.* (ascites) SK-OV-3 | 0.0 |
| Uterus | 0.0 |
| Placenta | 0.8 |
| Prostate | 3.6 |
| Prostate ca.* (bone met) PC-3 | 100.0 |
| Testis | 0.0 |
| Melanoma Hs688(A).T | 0.0 |
| Melanoma* (met) Hs688(B).T | 0.0 |
| Melanoma UACC-62 | 0.3 |
| Melanoma M14 | 0.0 |
| Melanoma LOX IMVI | 0.0 |
| Melanoma* (met) SK-MEL-5 | 0.0 |
| Melanoma SK-MEL-28 | 0.2 |

TABLE 15

Panel 1.3D

| Tissue Name | Relative Expression (%) 1.3Dtm2741f_ag1094 | 1.3Dtm2838f_ag1094 |
|---|---|---|
| Liver adenocarcinoma | 10.0 | 9.1 |
| Pancreas | 0.2 | 0.1 |
| Pancreatic ca. CAPAN 2 | 0.0 | 0.0 |
| Adrenal gland | 0.0 | 0.0 |
| Thyroid | 0.2 | 0.2 |
| Salivary gland | 8.9 | 4.3 |
| Pituitary gland | 0.0 | 0.2 |
| Brain (fetal) | 0.1 | 0.0 |
| Brain (whole) | 0.8 | 0.6 |
| Brain (amygdala) | 0.2 | 0.1 |
| Brain (cerebellum) | 0.5 | 0.7 |

TABLE 15-continued

Panel 1.3D

| Tissue Name | Relative Expression (%) | |
|---|---|---|
| | 1.3Dtm2741f_ag1094 | 1.3Dtm2838f_ag1094 |
| Brain (hippocampus) | 0.4 | 0.2 |
| Brain (substantia nigra) | 0.0 | 0.0 |
| Brain (thalamus) | 1.1 | 1.0 |
| Cerebral Cortex | 0.2 | 0.1 |
| Spinal cord | 0.2 | 0.0 |
| CNS ca. (glio/astro) U87-MG | 0.0 | 0.2 |
| CNS ca. (glio/astro) U-118-MG | 1.0 | 0.8 |
| CNS ca. (astro) SW1783 | 1.1 | 0.9 |
| CNS ca.* (neuro; met) SK-N-AS | 26.4 | 26.8 |
| CNS ca. (astro) SF-539 | 0.0 | 0.0 |
| CNS ca. (astro) SNB-75 | 15.1 | 12.9 |
| CNS ca. (glio) SNB-19 | 38.2 | 21.0 |
| CNS ca. (glio) U251 | 3.3 | 3.7 |
| CNS ca. (glio) SF-295 | 38.4 | 36.9 |
| Heart (fetal) | 0.2 | 0.5 |
| Heart | 0.6 | 0.3 |
| Fetal Skeletal | 2.9 | 2.2 |
| Skeletal muscle | 0.0 | 0.0 |
| Bone marrow | 0.0 | 0.2 |
| Thymus | 0.4 | 0.1 |
| Spleen | 0.0 | 0.0 |
| Lymph node | 0.0 | 0.0 |
| Colorectal | 1.6 | 0.6 |
| Stomach | 1.6 | 1.6 |
| Small intestine | 4.2 | 3.7 |
| Colon ca. SW480 | 0.0 | 0.0 |
| Colon ca.* (SW480 met) SW620 | 0.4 | 0.1 |
| Colon ca. HT29 | 21.0 | 25.5 |
| Colon ca. HCT-116 | 0.0 | 0.0 |
| Colon ca. CaCo-2 | 0.0 | 0.0 |
| 83219 CC Well to Mod Diff (ODO3866) | 0.0 | 0.0 |
| Colon ca. HCC-2998 | 0.0 | 0.0 |
| Gastric ca.* (liver met) NCI-N87 | 21.3 | 20.7 |
| Bladder | 0.1 | 0.0 |
| Trachea | 12.5 | 12.9 |
| Kidney | 0.0 | 0.0 |
| Kidney (fetal) | 0.9 | 0.6 |
| Renal ca. 786-0 | 0.0 | 0.0 |
| Renal ca. A498 | 2.0 | 1.5 |
| Renal ca. RXF 393 | 0.0 | 0.0 |
| Renal ca. ACHN | 0.0 | 0.0 |
| Renal ca. UO-31 | 0.0 | 0.0 |
| Renal ca. TK-10 | 0.0 | 0.0 |
| Liver | 0.4 | 0.6 |
| Liver (fetal) | 1.6 | 1.0 |
| Liver ca. (hepatoblast) HepG2 | 0.0 | 0.0 |
| Lung | 1.8 | 1.4 |
| Lung (fetal) | 11.7 | 7.5 |
| Lung ca. (small cell) LX-1 | 0.2 | 0.0 |
| Lung ca. (small cell) NCI-H69 | 2.4 | 3.1 |
| Lung ca. (s. cell var.) SHP-77 | 100.0 | 100.0 |
| Lung ca. (large cell) NCI-H460 | 0.0 | 0.0 |
| Lung ca. (non-sm. cell) A549 | 0.3 | 0.8 |
| Lung ca. (non-s. cell) NCI-H23 | 12.8 | 12.8 |
| Lung ca (non-s. cell) HOP-62 | 3.9 | 3.7 |
| Lung ca. (non-s. cl) NCI-H522 | 0.1 | 0.0 |
| Lung ca. (squam.) SW 900 | 4.8 | 6.4 |
| Lung ca (squam.) NCI-H596 | 1.3 | 0.9 |
| Mammary gland | 3.4 | 3.3 |
| Breast ca.* (pl. effusion) MCF-7 | 1.2 | 0.7 |
| Breast ca.* (pl. ef) MDA-MB-231 | 0.0 | 0.0 |
| Breast ca.* (pl. effusion) T47D | 3.2 | 3.0 |
| Breast ca. BT-549 | 2.1 | 1.7 |
| Breast ca. MDA-N | 0.0 | 0.0 |
| Ovary | 0.7 | 0.3 |
| Ovarian ca. OVCAR-3 | 0.4 | 0.3 |
| Ovarian ca. OVCAR-4 | 0.1 | 0.0 |
| Ovarian ca. OVCAR-5 | 8.5 | 6.2 |
| Ovarian ca. OVCAR-8 | 0.0 | 0.0 |
| Ovarian ca. IGROV-1 | 0.0 | 0.0 |
| Ovarian ca.* (ascites) SK-OV-3 | 0.3 | 0.2 |
| Uterus | 0.4 | 0.2 |
| Placenta | 1.0 | 1.3 |
| Prostate | 1.1 | 1.1 |
| Prostate ca.* (bone met) PC-3 | 13.2 | 13.9 |
| Testis | 0.3 | 0.4 |
| Melanoma Hs688(A).T | 0.0 | 0.0 |
| Melanoma* (met) Hs688(B).T | 0.0 | 0.0 |
| Melanoma UACC-62 | 0.0 | 0.0 |
| Melanoma M14 | 0.0 | 0.0 |
| Melanoma LOX IMVI | 0.0 | 0.0 |
| Melanoma* (met) SK-MEL-5 | 0.1 | 0.5 |
| Adipose | 0.5 | 0.4 |

TABLE 16

Panel 2D

| Tissue Name | Relative Expression (%) | |
|---|---|---|
| | 2Dtm2837f_ag1094 | 2dtm2940f_ag1094 |
| Normal Colon GENPAK 061003 | 12.4 | 11.4 |
| 83219 CC Well to Mod Diff (ODO3866) | 0.0 | 0.0 |
| 83220 CC NAT (ODO3866) | 1.0 | 1.5 |
| 83221 CC Gr.2 rectosigmoid (ODO3868) | 0.3 | 0.0 |
| 83222 CC NAT (ODO3868) | 0.4 | 0.2 |
| 83235 CC Mod Diff (ODO3920) | 0.0 | 0.0 |
| 83236 CC NAT (ODO3920) | 0.8 | 0.8 |
| 83237 CC Gr.2 ascend colon (ODO3921) | 2.4 | 2.2 |
| 83238 CC NAT (ODO3921) | 2.0 | 1.9 |
| 83241 CC from Partial Hepatectomy (ODO4309) | 0.0 | 0.0 |
| 83242 Liver NAT (ODO4309) | 0.2 | 0.3 |
| 87472 Colon mets to lung (OD04451-01) | 0.0 | 0.0 |
| 87473 Lung NAT (OD04451-02) | 0.9 | 0.6 |
| Normal Prostate Clontech A+ 6546-1 | 2.7 | 3.0 |
| 84140 Prostate Cancer (OD04410) | 1.5 | 1.4 |
| 84141 Prostate NAT (OD04410) | 6.5 | 8.0 |
| 87073 Prostate Cancer (OD04720-01) | 5.9 | 6.1 |
| 87074 Prostate NAT (OD04720-02) | 14.1 | 12.6 |
| Normal Lung GENPAK 061010 | 3.3 | 3.5 |
| 83239 Lung Met to Muscle (ODO4286) | 0.2 | 0.2 |
| 83240 Muscle NAT (ODO4286) | 0.0 | 0.0 |
| 84136 Lung Malignant Cancer (OD03126) | 7.9 | 6.0 |
| 84137 Lung NAT (OD03126) | 1.8 | 2.5 |
| 84871 Lung Cancer (OD04404) | 24.8 | 21.6 |
| 84872 Lung NAT (OD04404) | 1.8 | 1.7 |
| 84875 Lung Cancer (OD04565) | 0.7 | 1.2 |
| 84876 Lung NAT (OD04565) | 0.5 | 0.7 |
| 85950 Lung Cancer (OD04237-01) | 13.5 | 12.5 |
| 85970 Lung NAT (OD04237-02) | 1.4 | 1.0 |
| 83255 Ocular Mel Met to Liver (OD04310) | 0.0 | 0.0 |
| 83256 Liver NAT (ODO4310) | 0.2 | 0.4 |
| 84139 Melanoma Mets to Lung (OD04321) | 0.4 | 0.2 |
| 84138 Lung NAT (OD04321) | 2.5 | 1.2 |
| Normal Kidney GENPAK 061008 | 0.2 | 0.0 |
| 83786 Kidney Ca, Nuclear grade 2 (OD04338) | 0.0 | 0.0 |
| 83787 Kidney NAT (OD04338) | 0.2 | 0.2 |
| 83788 Kidney Ca Nuclear grade 1/2 (OD04339) | 0.0 | 0.0 |
| 83789 Kidney NAT (OD04339) | 0.0 | 0.0 |
| 83790 Kidney Ca, Clear cell type (OD04340) | 0.1 | 0.2 |
| 83791 Kidney NAT (OD04340) | 0.0 | 0.2 |
| 83792 Kidney Ca, Nuclear grade 3 (OD04348) | 0.0 | 0.0 |
| 83793 Kidney NAT (OD04348) | 0.0 | 0.1 |

TABLE 16-continued

Panel 2D

| Tissue Name | Relative Expression (%) 2Dtm2837f_ag1094 | 2dtm2940f_ag1094 |
|---|---|---|
| 87474 Kidney Cancer (OD04622-01) | 0.4 | 0.4 |
| 87475 Kidney NAT (OD04622-03) | 0.0 | 0.0 |
| 85973 Kidney Cancer (OD04450-01) | 0.0 | 0.0 |
| 85974 Kidney NAT (OD04450-03) | 0.0 | 0.0 |
| Kidney Cancer Clontech 8120607 | 0.4 | 0.3 |
| Kidney NAT Clontech 8120608 | 0.0 | 0.0 |
| Kidney Cancer Clontech 8120613 | 0.0 | 0.0 |
| Kidney NAT Clontech 8120614 | 0.0 | 0.0 |
| Kidney Cancer Clontech 9010320 | 0.0 | 0.0 |
| Kidney NAT Clontech 9010321 | 0.0 | 0.0 |
| Normal Uterus GENPAK 061018 | 0.1 | 0.0 |
| Uterus Cancer GENPAK 064011 | 0.5 | 0.6 |
| Normal Thyroid Clontech A+ 6570-1 | 0.5 | 0.4 |
| Thyroid Cancer GENPAK 064010 | 0.0 | 0.0 |
| Thyroid Cancer INVITROGEN A302152 | 0.0 | 0.0 |
| Thyroid NAT INVITROGEN A302153 | 0.2 | 0.1 |
| Normal Breast GENPAK 061019 | 5.5 | 5.6 |
| 84877 Breast Cancer (OD04566) | 0.5 | 0.7 |
| 85975 Breast Cancer (OD04590-01) | 3.0 | 3.9 |
| 85976 Breast Cancer Mets (OD04590-03) | 1.4 | 1.7 |
| 87070 Breast Cancer Metastasis (OD04655-05) | 100.0 | 100.0 |
| GENPAK Breast Cancer 064006 | 1.7 | 2.0 |
| Breast Cancer Res. Gen. 1024 | 0.8 | 0.8 |
| Breast Cancer Clontech 9100266 | 3.5 | 4.1 |
| Breast NAT Clontech 9100265 | 3.5 | 4.2 |
| Breast Cancer INVITROGEN A209073 | 0.7 | 0.7 |
| Breast NAT INVITROGEN A2090734 | 1.1 | 1.3 |
| Normal Liver GENPAK 061009 | 2.0 | 1.7 |
| Liver Cancer GENPAK 064003 | 0.0 | 0.0 |
| Liver Cancer Research Genetics RNA 1025 | 0.3 | 0.3 |
| Liver Cancer Research Genetics RNA 1026 | 0.0 | 0.0 |
| Paired Liver Cancer Tissue Research Genetics RNA 6004-T | 0.2 | 0.1 |
| Paired Liver Tissue Research Genetics RNA 6004-N | 0.0 | 0.1 |
| Paired Liver Cancer Tissue Research Genetics RNA 6005-T | 0.0 | 0.0 |
| Paired Liver Tissue Research Genetics RNA 6005-N | 0.1 | 0.1 |
| Normal Bladder GENPAK 061001 | 0.2 | 0.1 |
| Bladder Cancer Research Genetics RNA 1023 | 3.0 | 3.1 |
| Bladder Cancer INVITROGEN A302173 | 1.0 | 0.8 |
| 87071 Bladder Cancer (OD04718-01) | 0.0 | 0.0 |
| 87072 Bladder Normal Adjacent (OD04718-03) | 4.1 | 3.4 |
| Normal Ovary Res. Gen. | 0.0 | 0.0 |
| Ovarian Cancer GENPAK 064008 | 1.6 | 1.4 |
| 87492 Ovary Cancer (OD04768-07) | 0.0 | 0.0 |
| 87493 Ovary NAT (OD04768-08) | 0.0 | 0.0 |
| Normal Stomach GENPAK 061017 | 1.0 | 1.7 |
| Gastric Cancer Clontech 9060358 | 0.2 | 0.2 |
| NAT Stomach Clontech 9060359 | 0.1 | 0.2 |
| Gastric Cancer Clontech 9060395 | 0.4 | 0.7 |
| NAT Stomach Clontech 9060394 | 0.4 | 0.4 |
| Gastric Cancer Clontech 9060397 | 0.1 | 0.3 |
| NAT Stomach Clontech 9060396 | 0.1 | 0.2 |
| Gastric Cancer GENPAK 064005 | 1.0 | 1.3 |

TABLE 17

Panel 3D

| Tissue Name | Relative Expression (%) 3dtm5226f_ag1094 |
|---|---|
| 94905_Daoy_Medulloblastoma/Cerebellum_sscDNA | 0.0 |
| 94906_TE671_Medulloblastoma/Cerebellum_sscDNA | 0.2 |
| 94907_D283 Med_Medulloblastoma/Cerebellum_sscDNA | 0.2 |
| 94908_PFSK-1_Primitive Neuroectodermal/Cerebellum_sscDNA | 1.6 |
| 94909_XF-498_CNS_sscDNA | 30.4 |
| 94910_SNB-78_CNS/glioma_sscDNA | 0.7 |
| 94911_SF-268_CNS/gliobastoma_sscDNA | 0.0 |
| 94912_T98G_Glioblastoma_sscDNA | 3.3 |
| 96776_SK-N-SH_Neuroblastoma (metastasis)_sscDNA | 22.4 |
| 94913_SF-295_CNS/glioblastoma_sscDNA | 27.2 |
| 94914_Cerebellum_sscDNA | 6.7 |
| 96777_Cerebellum_sscDNA | 0.0 |
| 94916_NCI-H292_Mucoepidermoid lung carcinoma_sscDNA | 21.9 |
| 94917_DMS-114_Small cell lung cancer_sscDNA | 2.4 |
| 94918_DMS-79_Small cell lung cancer/neuroendocrine_sscDNA | 0.0 |
| 94919_NCI-H146_Small cell lung cancer/neuroendocrine_sscDNA | 100.0 |
| 94920_NCI-H526_Small cell lung cancer/neuroendocrine_sscDNA | 0.0 |
| 94921_NCI-N417_Small cell lung cancer/neuroendocrine_sscDNA | 0.0 |
| 94923_NCI-H82_Small cell lung cancer/neuroendocrine_sscDNA | 0.3 |
| 94924_NCI-H157_Squamous cell lung cancer (metastasis)_sscDNA | 0.0 |
| 94925_NCI-H1155_Large cell lung cancer/neuroendocrine_sscDNA | 65.1 |
| 94926_NCI-H1299_Large cell lung cancer/neuroendocrine_sscDNA | 0.0 |
| 94927_NCI-H727_Lung carcinoid_sscDNA | 13.8 |
| 94928_NCI-UMC-11_Lung carcinoid_sscDNA | 28.7 |
| 94929_LX-1_Small cell lung cancer_sscDNA | 0.7 |
| 94930_Colo-205_Colon cancer_sscDNA | 0.0 |
| 94931_KM12_Colon cancer_sscDNA | 0.1 |
| 94932_KM20L2_Colon cancer_sscDNA | 7.3 |
| 94933_NCI-H716_Colon cancer_sscDNA | 80.1 |
| 94935_SW-48_Colon adenocarcinoma_sscDNA | 0.3 |
| 94936_SW1116_Colon adenocarcinoma_sscDNA | 0.0 |
| 94937_LS 174T_Colon adenocarcinoma_sscDNA | 0.0 |
| 94938_SW-948_Colon adenocarcinoma_sscDNA | 0.6 |
| 94939_SW-480_Colon adenocarcinoma_sscDNA | 0.0 |
| 94940_NCI-SNU-5_Gastric carcinoma_sscDNA | 0.0 |
| 94941_KATO III_Gastric carcinoma_sscDNA | 0.0 |
| 94943_NCI-SNU-16_Gastric carcinoma_sscDNA | 1.7 |
| 94944_NCI-SNU-1_Gastric arcinoma_sscDNA | 0.0 |
| 94946_RF-1_Gastric adenocarcinoma_sscDNA | 0.0 |
| 94947_RF-48_Gastric | 0.0 |

TABLE 17-continued

Panel 3D

| Tissue Name | Relative Expression (%) 3dtm5226f_ag1094 |
|---|---|
| adenocarcinoma_sscDNA | |
| 96778_MKN-45_Gastric carcinoma_sscDNA | 0.1 |
| 94949_NCI-N87_Gastric carcinoma_sscDNA | 2.4 |
| 94951_OVCAR-5_Ovarian carcinoma_sscDNA | 0.0 |
| 94952_RL95-2_Uterine carcinoma_sscDNA | 2.8 |
| 94953_HelaS3_Cervical adenocarcinoma_sscDNA | 0.2 |
| 94954_Ca Ski_Cervical epidermoid carcinoma (metastasis)_sscDNA | 0.1 |
| 94955_ES-2_Ovarian clear cell carcinoma_sscDNA | 0.0 |
| 94957_Ramos/6h stim_Stimulated with PMA/ionomycin 6h_sscDNA | 0.1 |
| 94958_Ramos/14h stim_Stimulated with PMA/ionomycin 14h_sscDNA | 0.0 |
| 94962_MEG-01_Chronic myelogenous leukemia (megokaryoblast)_sscDNA | 1.7 |
| 94963_Raji_Burkitt's lymphoma_sscDNA | 0.0 |
| 94964_Daudi_Burkitt's lymphoma_sscDNA | 0.0 |
| 94965_U266_B-cell plasmocytoma/myeloma_sscDNA | 0.2 |
| 94968_CA46_Burkitt's lymphoma_sscDNA | 0.0 |
| 94970_RL_non-Hodgkin's B-cell lymphoma_sscDNA | 0.1 |
| 94972_JM1_pre-B-cell lymphoma/leukemia_sscDNA | 0.0 |
| 94973_Jurkat_T cell leukemia_sscDNA | 0.0 |
| 94974_TF-1_Erythroleukemia_sscDNA | 2.1 |
| 94975_HUT 78_T-cell lymphoma_sscDNA | 0.0 |
| 94977_U937_Histiocytic lymphoma_sscDNA | 0.0 |
| 94980_KU-812_Myelogenous leukemia_sscDNA | 8.2 |
| 94981_769-P_Clear cell renal carcinoma_sscDNA | 0.0 |
| 94983_Caki-2_Clear cell renal carcinoma_sscDNA | 0.3 |
| 94984_SW 839_Clear cell renal carcinoma_sscDNA | 0.0 |
| 94986_G401_Wilms' tumor_sscDNA | 0.0 |
| 94987_Hs766T_Pancreatic carcinoma (LN metastasis)_sscDNA | 4.9 |
| 94988_CAPAN-1_Pancreatic adenocarcinoma (liver metastasis)_sscDNA | 0.3 |
| 94989_SU86.86_Pancreatic carcinoma (liver metastasis)_sscDNA | 1.5 |
| 94990_BxPC-3_Pancreatic adenocarcinoma_sscDNA | 23.7 |
| 94991_HPAC_Pancreatic adenocarcinoma_sscDNA | 76.8 |
| 94992_MIA PaCa-2_Pancreatic carcinoma_sscDNA | 0.5 |
| 94993_CFPAC-1_Pancreatic ductal adenocarcinoma_sscDNA | 0.5 |
| 94994_PANC-1_Pancreatic epithelioid ductal carcinoma_sscDNA | 6.9 |
| 94996_T24_Bladder carcinma (transitional cell)_sscDNA | 4.1 |
| 94997_5637_Bladder carcinoma_sscDNA | 1.0 |
| 94998_HT-1197_Bladder carcinoma_sscDNA | 2.4 |
| 94999_UM-UC-3_Bladder carcinma (transitional cell)_sscDNA | 0.0 |
| 95000_A204_Rhabdomyosarcoma_sscDNA | 0.3 |
| 95001_HT-1080_Fibrosarcoma_sscDNA | 0.2 |
| 95002_MG-63_Osteosarcoma (bone)_sscDNA | 0.2 |
| 95003_SK-LMS-1_Leiomyosarcoma (vulva)_sscDNA | 0.0 |
| 95004_SJRH30_Rhabdomyosarcoma (met to bone marrow)_sscDNA | 0.2 |
| 95005_A431_Epidermoid carcinoma_sscDNA | 0.0 |
| 95007_WM266-4_Melanoma_sscDNA | 0.4 |
| 95010_DU 145_Prostate carcinoma (brain metastasis)_sscDNA | 0.0 |
| 95012_MDA-MB-468_Breast adenocarcinoma_sscDNA | 1.3 |
| 95013_SCC-4_Squamous cell carcinoma of tongue_sscDNA | 0.2 |
| 95014_SCC-9_Squamous cell carcinoma of tongue_sscDNA | 0.0 |
| 95015_SCC-15_Squamous cell carcinoma of tongue_sscDNA | 0.3 |
| 95017_CAL 27_Squamous cell carcinoma of tongue_sscDNA | 1.6 |

TABLE 18

Panel 4D

| Tissue Name | Relative Expression (%) 4Dtm2495f_ag1094 |
|---|---|
| 93768_Secondary Th1_anti-CD28/anti-CD3 | 0.0 |
| 93769_Secondary Th2_anti-CD28/anti-CD3 | 0.1 |
| 93770_Secondary Tr1_anti-CD28/anti-CD3 | 0.0 |
| 93573_Secondary Th1_resting day 4–6 in IL-2 | 0.0 |
| 93572_Secondary Th2_resting day 4–6 in IL-2 | 0.0 |
| 93571_Secondary Tr1_resting day 4–6 in IL-2 | 0.0 |
| 93568_primary Th1_anti-CD28/anti-CD3 | 0.0 |
| 93569_primary Th2_anti-CD28/anti-CD3 | 0.0 |
| 93570_primary Tr1_anti-CD28/anti-CD3 | 0.0 |
| 93565_primary Th1_resting dy 4–6 in IL-2 | 0.0 |
| 93566_primary Th2_resting dy 4–6 in IL-2 | 0.0 |
| 93567_primary Tr1_resting dy 4–6 in IL-2 | 0.0 |
| 93351_CD45RA CD4 lymphocyte_anti-CD28/anti-CD3 | 0.0 |
| 93352_CD45RO CD4 lymphocyte_anti-CD28/anti-CD3 | 0.0 |
| 93251_CD8 Lymphocytes_anti-CD28/anti-CD3 | 0.0 |
| 93353_chronic CD8 Lymphocytes 2ry_resting dy 4–6 in IL-2 | 0.0 |
| 93574_chronic CD8 Lymphocytes 2ry_activated CD3/CD28 | 0.3 |
| 93354_CD4_none | 0.0 |
| 93252_Secondary Th1/Th2/Tr1_anti-CD95 CH11 | 0.0 |
| 93103_LAK cells_resting | 0.0 |
| 93788_LAK cells_IL-2 | 0.0 |
| 93787_LAK cells_IL-2 + IL-12 | 4.2 |
| 93789_LAK cells_IL-2 + IFN gamma | 0.0 |
| 93790_LAK cells_IL-2 + IL-18 | 0.0 |
| 93104_LAK cells_PMA/ionomycin and IL-18 | 0.0 |
| 93578_NK Cells IL-2_resting | 0.0 |
| 93109_Mixed Lymphocyte Reaction_Two Way MLR | 0.0 |
| 93110_Mixed Lymphocyte Reaction_Two Way MLR | 0.0 |
| 93111_Mixed Lymphocyte Reaction_Two Way MLR | 0.0 |
| 93112_Mononuclear Cells (PBMCs)_resting | 0.0 |

TABLE 18-continued

Panel 4D

| Tissue Name | Relative Expression (%) 4Dtm2495f_ag1094 |
|---|---|
| 93113_Mononuclear Cells (PBMCs)_PWM | 0.0 |
| 93114_Mononuclear Cells (PBMCs)_PHA-L | 0.0 |
| 93249_Ramos (B cell)_none | 0.0 |
| 93250_Ramos (B cell)_ionomycin | 0.3 |
| 93349_B lymphocytes_PWM | 0.0 |
| 93350_B lymphocytes_CD40L and IL-4 | 0.0 |
| 92665_EOL-1 (Eosinophil)_dbcAMP differentiated | 0.0 |
| 93248_EOL-1 (Eosinophil)_dbcAMP/ PMAionomycin | 0.0 |
| 93356_Dendritic Cells_none | 0.0 |
| 93355_Dendritic Cells_LPS 100 ng/ml | 0.0 |
| 93775_Dendritic Cells_anti-CD40 | 0.0 |
| 93774_Monocytes_resting | 0.0 |
| 93776_Monocytes_LPS 50 ng/ml | 0.0 |
| 93581_Macrophages_resting | 41.8 |
| 93582_Macrophages_LPS 100 ng/ml | 0.1 |
| 93098_HUVEC (Endothelial)_none | 1.7 |
| 93099_HUVEC (Endothelial)_starved | 0.0 |
| 93100_HUVEC (Endothelial)_IL-1b | 0.0 |
| 93779_HUVEC (Endothelial)_IFN gamma | 0.0 |
| 93102_HUVEC (Endothelial)_TNF alpha + IFN gamma | 0.0 |
| 93101_HUVEC (Endothelial)_TNF alpha + IL4 | 0.3 |
| 93781_HUVEC (Endothelial)_IL-11 | 0.0 |
| 93583_Lung Microvascular Endothelial Cells_none | 0.0 |
| 93584_Lung Microvascular Endothelial Cells_TNFa (4 ng/ml) and IL1b (1 ng/ml) | 0.0 |
| 92662_Microvascular Dermal endothelium_none | 0.0 |
| 92663_Microsvasular Dermal endothelium_TNFa (4 ng/ml) and IL1b (1 ng/ml) | 0.0 |
| 93773_Bronchial epithelium_TNFa (4 ng/ml) and IL1b (1 ng/ml)** | 3.7 |
| 93347_Small Airway Epithelium_none | 4.5 |
| 93348_Small Airway Epithelium_TNFa (4 ng/ml) and IL1b (1 ng/ml) | 1.7 |
| 92668_Coronery Artery SMC_resting | 0.0 |
| 92669_Coronery Artery SMC_TNFa (4 ng/ml) and IL1b (1 ng/ml) | 0.0 |
| 93107_astrocytes resting | 8.5 |
| 93108_astrocytes_TNFa (4 ng/ml) and IL1b (1 ng/ml) | 0.2 |
| 92666_KU-812 (Basophil)_resting | 8.3 |
| 92667_KU-812 (Basophil)_PMA/ionoycin | 100.0 |
| 93579_CCD1106 (Keratinocytes)_none | 70.2 |
| 93580_CCD1106 (Keratinocytes)_TNFa and IFNg** | 3.0 |
| 93791_Liver Cirrhosis | 1.3 |
| 93792_Lupus Kidney | 0.0 |
| 93577_NCI-H292 | 16.6 |
| 93358_NCI-H292_IL-4 | 10.4 |
| 93360_NCI-H292_IL-9 | 20.2 |
| 93359_NCI-H292_IL-13 | 6.3 |
| 93357_NCI-H292_IFN gamma | 8.5 |
| 93777_HPAEC_- | 0.0 |
| 93778_HPAEC_IL-1 beta/TNA alpha | 0.0 |
| 93254_Normal Human Lung Fibroblast_none | 36.3 |
| 93253_Normal Human Lung Fibroblast_TNFa (4 ng/ml) and IL-1b (1 ng/ml) | 18.6 |
| 93257_Normal Human Lung Fibroblast_IL-4 | 16.0 |
| 93256_Normal Human Lung Fibroblast_IL-9 | 4.4 |
| 93255_Normal Human Lung Fibroblast_IL-13 | 11.4 |
| 93258_Normal Human Lung Fibroblast_IFN gamma | 36.9 |
| 93106_Dermal Fibroblasts CCD1070_resting | 0.1 |
| 93361_Dermal Fibroblasts CCD1070_TNF alpha 4 ng/ml | 0.0 |
| 93105_Dermal Fibroblasts CCD1070_IL-1 beta 1 ng/ml | 0.0 |
| 93772_dermal fibroblast_IFN gamma | 0.3 |
| 93771_dermal fibroblast_1L4 | 0.0 |
| 93260_IBD Colitis 2 | 0.3 |
| 93261_IBD Crohns | 0.3 |
| 735010_Colon_normal | 11.4 |
| 735019_Lung_none | 5.3 |
| 64028-1_Thymus_none | 1.2 |
| 64030-1_Kidney_none | 2.0 |

Panel 1 Summary: Ag273b Expression of the NOV1a gene is highest in a metastatic prostate cancer cell line PC-3 (CT=26.8). There is also substantial expression of this gene in a number of lung cancer cell lines and brain cancer cell lines. Thus, expression of the NOV1a gene could be used to distinguish lung, prostate or brain cancer cell lines from other samples. In addition, therapeutic inhibition of this gene product, through the use of small molecule drugs or antibodies, might have benefit in the treatment of lung, prostate or brain cancer. Among other normal tissues this gene is also low to moderately expressed in heart, colon, small intestine, trachea, salivary gland, fetal liver, and mammary gland.

The NOV1a gene encodes a novel insulin-like growth factor binding protein acid labile subunit. Among CNS tissues, this gene is expressed at moderate levels in cerebellum and thalamus. Insulin-like growth factor (IGF) has been shown to have neuroprotective effects, as is currently under investigation as a biopharmaceutical for the treatment of amyotropic lateral sclerosis. In serum, IGF is bound to both IGF-binding protein (IGFBP) and the acid labile subunit (IGFBP-ALS). In the brain, glia produce IGFBP; however the IGFBP-ALS has not been detected in the CNS. Therefore, the NOV1a gene may represent the CNS equivalent of IGFBP-ALS. Because of the neuroprotective effects of IGF, therapeutic modulation of this gene or its protein product may be useful in treating diseases in which neuronal death/degeneration occur such as amyotropic lateral sclerosis, multiple sclerosis, Alzheimer's disease, Parkinson's disease, Huntington's disease, spinocerebellar ataxia, or CNS injury such as stroke, head or spinal cord trauma.

Panel 1.3D Summary: Ag1094 Results from two experiments using the same probe/primer set are in excellent agreement and are consistent with what is observed in Panel 1. Expression of the NOV 1 a gene is highest in a lung cancer cell line (CT=28). There is also substantial expression of this gene in a number of additional lung cancer cell lines and brain cancer cell lines as well as in a metastatic prostate cancer cell line. Thus, NOV1a gene expression could be used to distinguish prostate, lung or brain cancer cell lines from other samples. In addition, therapeutic inhibition of this gene product, through the use of small molecule drugs or antibodies, might have benefit in the treatment of prostate, lung or brain cancer.

Among CNS tissues, there is low but significant expression in thalamus and cerebellum. Please see Panel 1 summary for description of potential utility of this gene in the CNS.

Panel 2D Summary: Ag1094 Results from two experiments using the same probe/primer set are in good agreement. Expression of the NOV1a gene is highest in a metastatic breast cancer sample (CT=26–27). In addition, several other breast cancer and lung cancer samples show increased expression when compared to their normal adjacent margin samples. This observation is consistent with the results in Panel 1.3D that show higher NOV1a gene expression in lung cancer cell lines. Thus, expression of this gene might be used to distinguish breast cancer or lung cancer tissue from their normal counterparts and might be of diagnostic value. Moreover, therapeutic modulation of the NOV1a gene or its gene product, through the use of small molecule drugs or antibodies, may be of benefit for treatment of breast or lung cancer.

Panel 3D Summary: Ag1094 Expression of the NOV1a gene is highest in a small cell lung cancer cell line (CT= 28.5). In addition, there is significant expression of this gene in other lung cancer cell lines as well as in several brain cancer and pancreatic cancer cell lines. These results are consistent with what is observed in the other panels. Thus, the expression of the NOV1a gene may be used to distinguish lung, breast or pancreas cancer cell line samples from other tissues. Moreover, therapeutic modulation of this gene or gene product, through the use of small molecule drugs or antibodies, may be of benefit for treatment of lung, breast or pancreatic cancer.

Panel 4D Summary: Ag1094 The NOV1a gene is expressed at high levels in basophils (CT 28.3) as well as in keratinocytes and normal lung fibroblasts (independently of their activation status). In addition, this gene is expressed at a lower level in a muco-epidermoid cell line (H292). Expression of the NOV1a gene is also found in normal lung which is consistent with the data from Panel 1.3D. The protein encoded by this transcript is a homolog of insulin-like growth factor binding protein acid labile subunit, a component of the systemic insulin-like growth factor-binding protein (IGFBP) complex. Therefore, this gene may play an important role in the biology of circulating IGFs. IGFs are involved in a wide array of cellular processes such as proliferation, prevention of apoptosis, and differentiation. Thus, the NOV1a gene may be a suitable target for protein therapeutic to modulate locally the mitogenic effect of IGF and could be useful in the treatment of emphysema, COPD, or skin related disease.

REFERENCES

1. Mewar R., McMorris F. A. (1997) Expression of insulin-like growth factor-binding protein messenger RNAs in developing rat oligodendrocytes and astrocytes. J. Neurosci. Res 50:721–728.

Insulin-like growth factors, IGF-I and IGF-II, are potent regulators of oligodendrocyte development. Most of the IGF present in vivo is bound to members of a family of six high-affinity IGF-binding proteins (IGFBPs), which can either potentiate or inhibit IGF action, depending on other conditions. Additionally, serum contains a structurally unrelated protein, acid-labile sub-unit (ALS), which forms a ternary complex with IGF and IGFBP3. In this study, reverse-transcriptase polymerase chain reaction (RT-PCR) was used to examine the expression of mRNAs for IGFBP 1–6 and ALS in purified populations of oligodendroglial cells and astrocytes. Astrocytes express all six IGFBPs. A2B5+/O4− oligodendrocyte precursors, O4+/O1− intermediate precursors, and O1+ oligodendrocytes express IGFBP3, 5, and 6, while IGFBP4 is expressed in oligodendrocyte precursors but not at more mature stages. They were unable to detect ALS mRNA in whole brain or in cultured oligodendroglial cells. The presence of differentially expressed IGFBPs in developing oligodendrocytes and astrocytes could significantly affect the biological activity of IGF-I and IGF-II in the central nervous system and the IGF-responsiveness of the IGFBP-expressing cells.

PMID: 9418960

2. Arnold P. M., Ma J. Y., Citron B. A., Zoubine M. N., Festoff B. W. (2000) Selective developmental regulation of gene expression for insulin-like growth factor-binding proteins in mouse spinal cord. Spine 25:1765–1770.

Study Design: Prospective, randomized experimental study in mice. STUDY OBJECTIVE: To determine whether insulin-like growth factor binding proteins (IGFBPs) are present in mouse spinal cord and, if so, what role they play in its development. SUMMARY OF BACKGROUND DATA: Insulin-like growth factors are well recognized hormonal effectors of growth hormone and are expressed in the mammalian spinal cord. The IGFBPs are a group of six genetically distinct proteins that bind IGFs and modulate their bioactivity. They appear in the brain during development, localize to the neuromuscular junction, and promote motor neuron survival. The benefit of IGF-I in amyotrophic lateral sclerosis ALS and its potential use in preventing motor neuron apoptosis in spinal cord injury dictates that studies of the presence and response of IGFBPs in that tissue be performed. METHODS: The IGFBPs in mouse spinal cord were analyzed by Western ligand blot, Western immunoblot, and reverse transcription-polymerase chain reaction at various time points from embryonic day 14 to postnatal day 30. RESULTS: Three IGFBPs with molecular masses of 24, 28, and 32 kDa were found, the latter two being the most prominent. The data indicate that these are IGFBP-4, -5, and -2. CONCLUSION: Both IGFBP-2 and BP-5 are developmentally regulated in mouse spinal cord, with higher levels of those at early embryonic stages indicating their potential role in development of the mouse spinal cord.

PMID: 10888943

3. Corse A. M., Bilak M. M., Bilak S. R., Lehar M., Rothstein J. D., Kuncl R. W. (1999) Preclinical testing of neuroprotective neurotrophic factors in a model of chronic motor neuron degeneration. Neurobiol. Dis. 6:335–346.

Many neurotrophic factors have been shown to enhance survival of embryonic motor neurons or affect their response to injury. Few studies have investigated the potential effects of neurotrophic factors on more mature motor neurons that might be relevant for neurodegenerative diseases. Using organotypic spinal cord cultures from postnatal rats, researchers have demonstrated that insulin-like growth factor-I (IGF-I) and glial-derived neurotrophic factor (GDNF) significantly increase choline acetyltransferase (ChAT) activity, but brain-derived neurotrophic factor (BDNF), neurotrophin-4 (NT-4/5), and neurotrophin-3 (NT-3) do not. Surprisingly, ciliary neurotrophic factor (CNTF) actually reduces CHAT activity compared to age-matched control cultures. Neurotrophic factors have also been shown to alter the sensitivity of some neurons to glutamate neurotoxicity, a postulated mechanism of injury in the neurodegenerative disease, amyotrophic lateral sclerosis (ALS). Incubation of organotypic spinal cord cultures in the presence of the glutamate transport inhibitor threo-hydroxyaspartate (THA) reproducibly causes death of motor neurons which is glutamate-mediated. In this model of motor neuron degeneration, IGF-I, GDNF, and NT-4/5 are potently neuroprotective, but BDNF, CNTF, and NT-3 are not. The organotypic glutamate toxicity model appears to be the best preclinical predictor to date of success in human clinical trials in ALS.

NOV3a

Expression of gene NOV3a was assessed using the primer-probe set Ag2100, described in Table 19. Results from RTQ-PCR runs are shown in Tables 20, 21, 22, 23, and 24.

TABLE 19

Probe Name Ag2100

| Primers | Sequences | TM | Length | Start Position | SEQ ID NO: |
|---|---|---|---|---|---|
| Forward | 5'-AGATCCCTGGAACAGAGGATT-3' | 59 | 21 | 2446 | 97 |
| Probe | TET-5'-TGTCTGAAGCCAATAAACTTGCAGCA-3'-TAMRA | 67.9 | 26 | 2474 | 98 |
| Reverse | 5'-CCTTCATGTTCCTTTGGGTAA-3' | 58.9 | 21 | 2513 | 99 |

TABLE 20

Panel 1.3D

| Tissue Name | Relative Expression % 1.3dtm3300t_ag2100 |
|---|---|
| Liver adenocarcinoma | 11.7 |
| Pancreas | 0.0 |
| Pancreatic ca. CAPAN 2 | 3.2 |
| Adrenal gland | 1.4 |
| Thyroid | 0.1 |
| Salivary gland | 0.1 |
| Pituitary gland | 2.1 |
| Brain (fetal) | 2.1 |
| Brain (whole) | 24.7 |
| Brain (amygdala) | 11.2 |
| Brain (cerebellum) | 2.7 |
| Brain (hippocampus) | 36.3 |
| Brain (substantia nigra) | 1.5 |
| Brain (thalamus) | 30.4 |
| Cerebral Cortex | 100.0 |
| Spinal cord | 2.5 |
| CNS ca. (glio/astro) U87-MG | 6.4 |
| CNS ca. (glio/astro) U-118-MG | 33.7 |
| CNS ca. (astro) SW1783 | 5.9 |
| CNS ca.* (neuro; met) SK-N-AS | 14.5 |
| CNS ca. (astro) SF-539 | 7.4 |
| CNS ca. (astro) SNB-75 | 5.8 |
| CNS ca. (glio) SNB-19 | 1.0 |
| CNS ca. (glio) U251 | 2.4 |
| CNS ca. (glio) SF-295 | 0.9 |
| Heart (fetal) | 0.4 |
| Heart | 0.1 |
| Fetal Skeletal | 3.4 |
| Skeletal muscle | 0.0 |
| Bone marrow | 5.4 |
| Thymus | 2.1 |
| Spleen | 0.6 |
| Lymph node | 0.4 |
| Colorectal | 1.8 |
| Stomach | 1.0 |
| Small intestine | 1.6 |
| Colon ca. SW480 | 13.1 |
| Colon ca.* (SW480 met) SW620 | 4.5 |
| Colon ca. HT29 | 4.1 |
| Colon ca. HCT-116 | 5.0 |
| Colon ca. CaCo-2 | 5.9 |
| 83219 CC Well to Mod Diff (ODO3866) | 2.8 |
| Colon ca. HCC-2998 | 3.7 |
| Gastric ca.* (liver met) NCI-N87 | 2.3 |
| Bladder | 0.9 |
| Trachea | 0.7 |
| Kidney | 0.7 |
| Kidney (fetal) | 1.8 |
| Renal ca. 786-0 | 7.1 |
| Renal ca. A498 | 3.7 |
| Renal ca. RXF 393 | 3.1 |
| Renal ca. ACHN | 4.4 |
| Renal ca. UO-31 | 6.3 |
| Renal ca. TK-10 | 3.2 |
| Liver | 0.0 |
| Liver (fetal) | 3.8 |
| Liver ca. (hepatoblast) HepG2 | 3.2 |
| Lung | 0.3 |
| Lung (fetal) | 0.9 |
| Lung ca. (small cell) LX-1 | 6.6 |
| Lung ca. (small cell) NCI-H69 | 8.5 |
| Lung ca. (s. cell var.) SHP-77 | 7.5 |
| Lung ca. (large cell) NCI-H460 | 0.0 |
| Lung ca. (non-sm. cell) A549 | 0.2 |
| Lung ca. (non-s. cell) NCI-H23 | 10.4 |
| Lung ca (non-s. cell) HOP-62 | 1.4 |
| Lung ca. (non-s. cl) NCI-H522 | 5.3 |
| Lung ca. (squam.) SW 900 | 3.2 |
| Lung ca. (squam.) NCI-H596 | 7.2 |
| Mammary gland | 0.2 |
| Breast ca.* (pl. effusion) MCF-7 | 5.6 |
| Breast ca.* (pl. ef) MDA-MB-231 | 14.5 |
| Breast ca.* (pl. effusion) T47D | 2.4 |
| Breast ca. BT-549 | 6.8 |
| Breast ca. MDA-N | 14.0 |
| Ovary | 2.2 |
| Ovarian ca. OVCAR-3 | 2.5 |
| Ovarian ca. OVCAR-4 | 0.8 |
| Ovarian ca. OVCAR-5 | 2.7 |
| Ovarian ca. OVCAR-8 | 3.2 |
| Ovarian ca. IGROV-1 | 2.0 |
| Ovarian ca* (ascites) SK-OV-3 | 7.4 |
| Uterus | 0.0 |
| Placenta | 0.2 |
| Prostate | 0.2 |
| Prostate ca.* (bone met) PC-3 | 2.0 |
| Testis | 4.0 |
| Melanoma Hs688(A).T | 0.7 |
| Melanoma* (met) Hs688(B).T | 0.3 |
| Melanoma UACC-62 | 0.5 |
| Melanoma M14 | 7.2 |
| Melanoma LOX IMVI | 2.8 |
| Melanoma* (met) SK-MEL-5 | 5.8 |
| Adipose | 0.2 |

TABLE 21

Panel 2.2

| Tissue Name | Relative Expression (%) 2.2x4tm6379t_ag2100_b2 |
|---|---|
| Normal Colon GENPAK 061003 | 6.2 |
| 97759 Colon cancer (OD06064) | 13.4 |
| 97760 Colon cancer NAT (OD06064) | 9.0 |
| 97778 Colon cancer (OD06159) | 4.5 |
| 97779 Colon cancer NAT (OD06159) | 5.9 |
| 98861 Colon cancer (OD06297-04 | 3.8 |

TABLE 21-continued

Panel 2.2

| Tissue Name | Relative Expression (%) 2.2x4tm6379t_ag2100_b2 |
|---|---|
| 98862 Colon cancer NAT (OD06297-015) | 10.0 |
| 83237 CC Gr.2 ascend colon (OD03921) | 4.3 |
| 83238 CC NAT (OD03921) | 2.8 |
| 97766 Colon cancer metastasis (OD06104) | 1.7 |
| 97767 Lung NAT (OD06104) | 3.1 |
| 87472 Colon mets to lung (OD04451-01) | 9.6 |
| 87473 Lung NAT (OD04451-02) | 3.2 |
| Normal Prostate Clontech A+ 6546-1 (8090438) | 1.2 |
| 84140 Prostate Cancer (OD04410) | 0.0 |
| 84141 Prostate NAT (OD04410) | 0.7 |
| Normal Ovary Res. Gen. | 2.8 |
| 98863 Ovarian cancer (OD06283-03) | 11.7 |
| 98865 Ovarian cancer NAT/fallopian tube (OD06283-07) | 3.0 |
| Ovarian Cancer GENPAK 064008 | 1.1 |
| 97773 Ovarian cancer (OD06145) | 0.9 |
| 97775 Ovarian cancer NAT (OD06145) | 0.0 |
| 98853 Ovarian cancer (OD06455-03) | 15.8 |
| 98854 Ovarian NAT (OD06455-07) Fallopian tube | 1.8 |
| Normal Lung GENPAK 061010 | 1.2 |
| 92337 Invasive poor diff. lung adeno (OD04945-01) | 8.4 |
| 92338 Lung NAT (OD04945-03) | 1.2 |
| 84136 Lung Malignant Cancer (OD03126) | 5.0 |
| 84137 Lung NAT (OD03126) | 0.6 |
| 90372 Lung Cancer (OD05014A) | 10.1 |
| 90373 Lung NAT (OD05014B) | 9.0 |
| 97761 Lung cancer (OD06081) | 10.1 |
| 97762 Lung cancer NAT (OD06081) | 4.0 |
| 85950 Lung Cancer (OD04237-01) | 4.1 |
| 85970 Lung NAT (OD04237-02) | 2.0 |
| 83255 Ocular Mel Met to Liver (OD04310) | 0.9 |
| 83256 Liver NAT (OD04310) | 0.4 |
| 84139 Melanoma Mets to Lung (OD04321) | 10.4 |
| 84138 Lung NAT (OD04321) | 2.0 |
| Normal Kidney GENPAK 061008 | 5.0 |
| 83786 Kidney Ca, Nuclear grade 2 (OD04338) | 15.3 |
| 83787 Kidney NAT (OD04338) | 5.1 |
| 83788 Kidney Ca Nuclear grade 1/2 (OD04339) | 100.0 |
| 83789 Kidney NAT (OD04339) | 9.3 |
| 83790 Kidney Ca, Clear cell type (OD04340) | 14.0 |
| 83791 Kidney NAT (OD04340) | 11.2 |
| 83792 Kidney Ca, Nuclear grade 3 (OD04348) | 9.0 |
| 83793 Kidney NAT (OD04348) | 30.3 |
| 98938 Kidney malignant cancer (OD06204B) | 3.6 |
| 98939 Kidney normal adjacent tissue (OD06204E) | 10.5 |
| 85973 Kidney Cancer (OD04450-01) | 2.4 |
| 85974 Kidney NAT (OD04450-03) | 13.3 |
| Kidney Cancer Clontech 8120613 | 6.6 |
| Kidney NAT Clontech 8120614 | 1.2 |
| Kidney Cancer Clontech 9010320 | 1.6 |
| Kidney NAT Clontech 9010321 | 4.5 |
| Kidney Cancer Clontech 8120607 | 0.5 |
| Kidney NAT Clontech 8120608 | 1.7 |
| Normal Uterus GENPAK 061018 | 1.1 |
| Uterus Cancer GENPAK 064011 | 1.5 |
| Normal Thyroid Clontech A+ 6570-1 (7080817) | 0.0 |
| Thyroid Cancer GENPAK 064010 | 0.6 |
| Thyroid Cancer INVITROGEN A302152 | 5.3 |
| Thyroid NAT INVITROGEN A302153 | 0.0 |
| Normal Breast GENPAK 061019 | 3.0 |
| 84877 Breast Cancer (OD04566) | 8.1 |
| Breast Cancer Res. Gen. 1024 | 2.9 |
| 85975 Breast Cancer (OD04590-01) | 14.7 |
| 85976 Breast Cancer Mets (OD04590-03) | 3.2 |
| 87070 Breast Cancer Metastasis (OD04655-05) | 5.4 |
| GENPAK Breast Cancer 064006 | 3.1 |
| Breast Cancer Clontech 9100266 | 2.6 |
| Breast NAT Clontech 9100265 | 2.3 |
| Breast Cancer INVITROGEN A209073 | 1.8 |
| Breast NAT INVITROGEN A2090734 | 2.5 |
| 97763 Breast cancer (OD06083) | 17.1 |
| 97764 Breast cancer node metastasis (OD06083) | 14.6 |
| Normal Liver GENPAK 061009 | 0.4 |
| Liver Cancer Research Genetics RNA 1026 | 0.0 |
| Liver Cancer Research Genetics RNA 1025 | 1.8 |
| Paired Liver Cancer Tissue Research Genetics RNA 6004-T | 1.1 |
| Paired Liver Tissue Research Genetics RNA 6004-N | 2.5 |
| Paired Liver Cancer Tissue Research Genetics RNA 6005-T | 1.6 |
| Paired Liver Tissue Research Genetics RNA 6005-N | 0.0 |
| Liver Cancer GENPAK 064003 | 0.7 |
| Normal Bladder GENPAK 061001 | 2.9 |
| Bladder Cancer Research Genetics RNA 1023 | 1.5 |
| Bladder Cancer INVITROGEN A302173 | 17.8 |
| Normal Stomach GENPAK 061017 | 10.4 |
| Gastric Cancer Clontech 9060397 | 1.1 |
| NAT Stomach Clontech 9060396 | 0.7 |
| Gastric Cancer Clontech 9060395 | 2.8 |
| NAT Stomach Clontech 9060394 | 2.8 |
| Gastric Cancer GENPAK 064005 | 6.0 |

TABLE 22

Panel 3D

| Tissue Name | Relative Expression (%) 3dx4tm5110t_ag2100_a2 |
|---|---|
| 94905_Daoy_Medulloblastoma/Cerebellum.sscDNA | 7.3 |
| 94906_TE671_Medulloblastom/Cerebellum_sscDNA | 3.8 |
| 94907_D283 Med_Medulloblastoma/Cerebellum_sscDNA | 15.7 |
| 94908_PFSK-1_Primitive Neuroectodermal/Cerebellum_sscDNA | 11.2 |
| 94909_XF-498 CNS_sscDNA | 21.2 |
| 94910_SNB-78_CNS/glioma_sscDNA | 11.3 |
| 94911_SF-268_CNS/glioblastoma_sscDNA | 7.6 |
| 94912_T98G_Glioblastoma_sscDNA | 12.0 |
| 96776_SK-N-SH_Neuroblastoma (metastasis)_sscDNA | 5.6 |
| 94913_SF-295_CNS/glioblastoma_sscDNA | 12.4 |
| 94914_Cerebellum_sscDNA | 16.1 |
| 96777_Cerebellum_sscDNA | 3.6 |
| 94916_NCI-H292_Mucoepidermoid lung carcinoma_sscDNA | 14.0 |
| 94917_DMS-114_Small cell lung cancer_sscDNA | 10.3 |
| 94918_DMS-79_Small cell lung cancer/neuroendocrine_sscDNA | 100.0 |
| 94919_NCI-H146_Small cell lung cancer/neuroendocrine_sscDNA | 14.2 |
| 94920_NCI-H526_Small cell lung cancer/neuroendocrine_sscDNA | 19.8 |
| 94921_NCI-N417_Small cell lung | 5.7 |

TABLE 22-continued

Panel 3D

| Tissue Name | Relative Expression (%) 3dx4tm5110t_ag2100_a2 |
|---|---|
| 94923_NCI-H82_Small cell lung cancer/neuroendocrine_sscDNA | 10.1 |
| 94924_NCI-H157_Squamous cell lung cancer (metastasis)_sscDNA | 13.8 |
| 94925_NCI-H1155_Large cell lung cancer/neuroendocrine_sscDNA | 36.0 |
| 94926_NCI-H1299_Large cell lung cancer/neuroendocrine_sscDNA | 22.7 |
| 94927_NCI-H727_Lung carcinoid_sscDNA | 14.3 |
| 94928_NCI-UMC-11_Lung carcinoid_sscDNA | 25.8 |
| 94929_LX-1_Small cell lung cancer_sscDNA | 11.0 |
| 94930_Colo-205_Colon cancer_sscDNA | 12.7 |
| 94931_KM12_Colon cancer_sscDNA | 17.1 |
| 94932_KM20L2_Colon cancer_sscDNA | 7.0 |
| 94933_NCI-H716_Colon cancer_sscDNA | 19.4 |
| 94935_SW-48_Colon adenocarcinoma_sscDNA | 10.6 |
| 94936_SW1116_Colon adenocarcinoma_sscDNA | 7.7 |
| 94937_LS 174T_Colon adenocarcinoma_sscDNA | 9.8 |
| 94938_SW-948_Colon adenocarcinoma_sscDNA | 1.4 |
| 94939_SW-480_Colon adenocarcinoma_sscDNA | 7.6 |
| 94940_NCI-SNU-5_Gastric carcinoma_sscDNA | 14.8 |
| 94941_KATO III_Gastric carcinoma_sscDNA | 18.8 |
| 94943_NCI-SNU-16_Gastric carcinoma_sscDNA | 12.5 |
| 94944_NCI-SNU-1_Gastric carcinoma_sscDNA | 12.3 |
| 94946_RF-1 Gastric adenocarcinoma_sscDNA | 5.3 |
| 94947_RF-48_Gastric adenocarcinoma_sscDNA | 7.7 |
| 96778_MKN-45_Gastric carcinoma_sscDNA | 11.7 |
| 94949_NCI-N87_Gastric carcinoma_sscDNA | 9.3 |
| 94951_OVCAR-5_Ovarian carcinoma_sscDNA | 3.0 |
| 94952_RL95-2_Uterine carcinoma_sscDNA | 4.5 |
| 94953_HelaS3_Cervical adenocarcinoma_sscDNA | 9.0 |
| 94954_Ca Ski_Cervical epidermoid carcinoma (metastasis)_sscDNA | 21.0 |
| 94955_ES-2_Ovarian clear cell carcinoma_sscDNA | 11.7 |
| 94957_Ramos/6h stim_Stimulated with PMA/ionomycin 6h_sscDNA | 10.8 |
| 94958_Ramos/14h stim_Stimulated with PMA/ionomycin 14h_sscDNA | 6.2 |
| 94962_MEG-01_Chronic myelogenous leukemia (megokaryoblast)_sscDNA | 5.8 |
| 94963_Raji_Burkitt's lymphoma_sscDNA | 6.8 |
| 94964_Daudi_Burkitt's lymphoma_sscDNA | 14.7 |
| 94965_U266_B-cell plasmacytoma/myeloma_sscDNA | 5.1 |
| 94968_CA46_Burkitt's lymphoma_sscDNA | 5.0 |
| 94970_RL_non-Hodgkin's B-cell lymphoma_sscDNA | 3.8 |
| 94972_JM1_pre-B-cell lymphoma/leukemia_sscDNA | 11.5 |
| 94973_Jurkat_T cell leukemia_sscDNA | 12.5 |
| 94974_TF-1_Erythroleukemia_sscDNA | 9.9 |
| 94975_HUT 78_T-cell lymphoma_sscDNA | 14.7 |
| 94977_U937_Histiocytic lymphoma_sscDNA | 8.1 |
| 94980_KU-812_Myelogenous leukemia_sscDNA | 17.7 |
| 94981_769-P_Clear cell renal carcinoma_sscDNA | 6.3 |
| 94983_Caki-2_Clear cell renal carcinoma_sscDNA | 9.5 |
| 94984_SW 839_Clear cell renal carcinoma_sscDNA | 5.2 |
| 94986_G401_Wilms' tumor_sscDNA | 6.3 |
| 94987_Hs766T_Pancreatic carcinoma (LN metastasis)_sscDNA | 15.7 |
| 94988_CAPAN-1_Pancreatic adenocarcinoma (liver metastasis)_sscDNA | 8.6 |
| 94989_SU86.86_Pancreatic carcinoma (liver metastasis)_sscDNA | 14.0 |
| 94990_BxPC-3_Pancreatic adenocarcinoma_sscDNA | 9.4 |
| 94991_HPAC_Pancreatic adenocarcinoma_sscDNA | 14.4 |
| 94992_MIA PaCa-2_Pancreatic carcinoma_sscDNA | 2.6 |
| 94993_CFPAC-1_Pancreatic ductal adenocarcinoma_sscDNA | 38.5 |
| 94994_PANC-1_Pancreatic epithelioid ductal carcinoma_sscDNA | 19.5 |
| 94996_T24_Bladder carcinma (transitional cell)_sscDNA | 9.0 |
| 94997_5637_Bladder carcinoma_sscDNA | 10.5 |
| 94998_HT-1197 Bladder carcinoma_sscDNA | 4.8 |
| 94999_UM-UC-3_Bladder carcinma (transitional cell)_sscDNA | 13.3 |
| 95000_A204_Rhabdomyosarcoma_sscDNA | 15.2 |
| 95001_HT-1080_Fibrosarcoma_sscDNA | 11.9 |
| 95002_MG-63_Osteosarcoma (bone)_sscDNA | 7.3 |
| 95003_SK-LMS-1_Leiomyosarcoma (vulva)_sscDNA | 47.8 |
| 95004_SJRH30_Rhabdomyosarcoma (met to bone marrow)_sscDNA | 10.2 |
| 95005_A431_Epidermoid carcinoma_sscDNA | 12.1 |
| 95007_WM266-4_Melanoma_sscDNA | 21.8 |
| 95010_DU 145_Prostate carcinoma (brain metastasis)_sscDNA | 0.2 |
| 95012_MDA-MB-468_Breast adenocarcinoma_sscDNA | 5.6 |
| 95013_SCC-4_Squamous cell carcinoma of tongue_sscDNA | 0.3 |
| 95014_SCC-9_Squamous cell carcinoma of tongue_sscDNA | 0.3 |
| 95015_SCG-15_Squamous cell carcinoma of tongue_sscDNA | 0.2 |
| 95017_CAL 27_Squamous cell carcinoma of tongue_sscDNA | 19.8 |

TABLE 23

Panel 4D

| Tissue Name | Relative Expression (%) 4dtm3359t—ag2100 |
|---|---|
| 93768_Secondary Th1_anti-CD28/anti-CD3 | 15.4 |
| 93769_Secondary Th2_anti-CD28/anti-CD3 | 11.9 |
| 93770_Secondary Tr1_anti-CD28/anti-CD3 | 15.6 |
| 93573_Secondary Th1_resting day 4–6 in IL-2 | 4.9 |
| 93572_Secondary Th2_resting day 4–6 in IL-2 | 3.3 |
| 93571_Secondary Tr1_resting day 4–6 in IL-2 | 6.0 |
| 93568_primary Th1_anti-CD28/anti-CD3 | 13.6 |
| 93569_primary Th2_anti-CD28/anti-CD3 | 12.0 |
| 93570_primary Tr1_anti-CD28/anti-CD3 | 22.2 |
| 93565_primary Th1_resting dy 4–6 in IL-2 | 100.0 |
| 93566_primary Th2_resting dy 4–6 in IL-2 | 37.9 |
| 93567_primary Tr1_resting dy 4–6 in IL-2 | 29.3 |
| 93351_CD45RA CD4 lymphocyte_anti-CD28/anti-CD3 | 13.6 |
| 93352_CD45RO CD4 lymphocyte_anti-CD28/anti-CD3 | 15.4 |
| 93251_CD8 Lymphocytes_anti-CD28/anti-CD3 | 10.6 |
| 93353_chronic CD8 Lymphocytes 2ry_resting dy 4–6 in IL-2 | 7.9 |
| 93574_chronic CD8 Lymphocytes 2ry_activated CD3/CD28 | 17.3 |
| 93354_CD4_none | 0.5 |
| 93252_Secondary Th1/Th2/Tr1_anti-CD95 CH11 | 17.1 |
| 93103_LAK cells_resting | 3.6 |
| 93788_LAK cells_IL-2 | 16.8 |
| 93787_LAK cells IL-2 + IL-12 | 8.4 |
| 93789_LAK cells_IL-2 + IFN gamma | 16.4 |
| 93790_LAK cells_IL-2 + IL-18 | 16.8 |
| 93104_LAK cells_PMA/ionomycin and IL-18 | 0.6 |
| 93578_NK Cells IL-2_resting | 15.3 |
| 93109_Mixed Lymphocyte Reaction_Two Way MLR | 1.8 |
| 93110_Mixed Lymphocyte Reaction_Two Way MLR | 6.1 |
| 93111_Mixed Lymphocyte Reaction_Two Way MLR | 10.1 |
| 93112_Mononuclear Cells (PBMCs)_resting | 0.1 |
| 93113_Mononuclear Cells (PBMCs)_PWM | 25.5 |
| 93114_Mononuclear Cells (PBMCs)_PHA-L | 24.0 |
| 93249_Ramos (B cell)_none | 17.7 |
| 93250_Ramos (B cell)_ionomycin | 92.0 |
| 93349_B lymphocytes_PWM | 48.6 |
| 93350_B lymphocytes_CD40L and IL-4 | 16.4 |
| 92665_EOL-1 (Eosinophil)_dbcAMP differentiated | 10.5 |
| 93248_EOL-1 (Eosinophil)_dbcAMP/PMAionomycin | 7.0 |
| 93356_Dendritic Cells_none | 0.5 |
| 93355_Dendritic Cells_LPS 100 ng/ml | 0.0 |
| 93775_Dendritic Cells_anti-CD40 | 0.0 |
| 93774_Monocytes_resting | 0.2 |
| 93776_Monocytes_LPS 50 ng/ml | 0.0 |
| 93581_Macrophages_resting | 4.4 |
| 93582_Macrophages_LPS 100 ng/ml | 0.6 |
| 93098_HUVEC (Endothelial)_none | 24.7 |
| 93099_HUVEC (Endothelial)_starved | 43.5 |
| 93100_HUVEC (Endothelial)_IL-1b | 12.2 |
| 93779_HUVEC (Endothelial)_IFN gamma | 16.6 |
| 93102_HUVEC (Endothelial)_TNF alpha + IFN gamma | 11.8 |
| 93101_HUVEC (Endothelial)_TNF alpha + IL4 | 11.4 |
| 93781_HUVEC (Endothelial)_IL-11 | 8.2 |
| 93583_Lung Microvascular Endothelial Cells_none | 7.3 |
| 93584_Lung Microvascular Endothelial Cells_TNFa (4 ng/ml) and IL1b (1 ng/ml) | 6.2 |
| 92662_Microvascular Dermal endothelium_none | 23.3 |
| 92663_Microvascular Dermal endothelium_TNFa (4 ng/ml) and IL1b (1 ng/ml) | 10.5 |
| 93773_Bronchial epithelium_TNFa (4 ng/ml) and IL1b (1 ng/ml)** | 0.6 |
| 93347_Small Airway Epithelium_none | 1.6 |
| 93348_Small Airway Epithelium_TNFa (4 ng/ml) and IL1b (1 ng/ml) | 7.4 |
| 92668_Coronery Artery SMC_resting | 4.4 |
| 92669_Coronery Artery SMC_TNFa (4 ng/ml) and IL1b (1 ng/ml) | 2.0 |
| 93107_astrocytes_resting | 1.3 |
| 93108_astrocytes_TNFa (4 ng/ml) and IL1b (1 ng/ml) | 0.5 |
| 92666_KU-812 (Basophil)_resting | 22.4 |
| 92667_KU-812 (Basophil)_PMA/ionomycin | 28.5 |
| 93579_CCD1106 (Keratinocytes)_none | 14.3 |
| 93580_CCD1106 (Keratinocytes)_TNFa and IFNg** | 18.4 |
| 93791_Liver Cirrhosis | 0.5 |
| 93792_Lupus Kidney | 3.3 |
| 93577_NCI-H292 | 29.5 |
| 93358_NCI-H292_IL-4 | 27.7 |
| 93360_NCI-H292_IL-9 | 32.3 |
| 93359_NCI-H292_IL-13 | 13.4 |
| 93357_NCI-H292_IFN gamma | 11.0 |
| 93777_HPAEC_- | 8.5 |
| 93778_HPAEC_IL-1 beta/TNA alpha | 7.7 |
| 93254_Normal Human Lung Fibroblast_none | 6.3 |
| 93253_Normal Human Lung Fibroblast_TNFa (4 ng/ml) and IL-1b (1 ng/ml) | 9.0 |
| 93257_Normal Human Lung Fibroblast_IL-4 | 3.7 |
| 93256_Normal Human Lung Fibroblast_IL-9 | 5.0 |
| 93255_Normal Human Lung Fibroblast_IL-13 | 1.7 |
| 93258_Normal Human Lung Fibroblast_IFN gamma | 3.4 |
| 93106_Dermal Fibroblasts CCD1070_resting | 57.4 |
| 93361_Dermal Fibroblasts CCD1070_TNF alpha 4 ng/ml | 79.0 |
| 93105_Dermal Fibroblasts CCD1070_IL-1 beta 1 ng/ml | 21.8 |
| 93772_dermal fibroblast_IFN gamma | 22.2 |
| 93771_dermal fibroblast_IL-4 | 45.7 |
| 93260_IBD Colitis 2 | 0.9 |
| 93261_IBD Crohns | 1.0 |
| 735010_Colon_normal | 3.7 |
| 735019_Lung_none | 1.5 |
| 64028-1_Thymus_none | 13.0 |
| 64030-1_Kidney_none | 31.2 |

TABLE 24

AI_comprehensive_panel_v1.0

| Tissue Name | Relative Expression (%) | |
|---|---|---|
| | tm7130t_ag2100_a2 | tm7159t_ag2100_b1 |
| 110967 COPD-F | 0.5 | 0.8 |
| 110980 COPD-F | 1.5 | 1.2 |
| 110968 COPD-M | 0.4 | 0.6 |
| 110977 COPD-M | 1.5 | 1.9 |
| 110989 Emphysema-F | 4.2 | 6.0 |
| 110992 Emphysema-F | 2.8 | 2.9 |
| 110993 Emphysema-F | 0.9 | 0.8 |
| 110994 Emphysema-F | 0.7 | 0.4 |
| 110995 Emphysema-F | 2.0 | 5.4 |
| 110996 Emphysema-F | 2.2 | 2.4 |
| 110997 Asthma-M | 1.9 | 3.1 |

TABLE 24-continued

AI_comprehensive_panel_v1.0

| Tissue Name | tm7130t_ ag2100_a2 | tm7159t_ ag2100_b1 |
|---|---|---|
| 111001 Asthma-F | 1.4 | 2.7 |
| 111002 Asthma-F | 1.0 | 1.0 |
| 111003 Atopic Asthma-F | 4.0 | 2.2 |
| 111004 Atopic Asthma-F | 16.6 | 17.0 |
| 111005 Atopic Asthma-F | 7.2 | 5.5 |
| 111006 Atopic Asthma-F | 0.9 | 0.7 |
| 111417 Allergy-M | 1.9 | 2.4 |
| 112347 Allergy-M | 0.0 | 0.0 |
| 112349 Normal Lung-F | 0.0 | 0.0 |
| 112357 Normal Lung-F | 6.1 | 6.0 |
| 112354 Normal Lung-M | 1.5 | 2.3 |
| 112374 Crohns-F | 2.9 | 5.2 |
| 112389 Match Control Crohns-F | 9.0 | 6.8 |
| 112375 Crohns-F | 2.5 | 3.8 |
| 112732 Match Control Crohns-F | 3.8 | 5.4 |
| 112725 Crohns-M | 0.1 | 0.7 |
| 112387 Match Control Crohns-M | 1.0 | 1.4 |
| 112378 Crohns-M | 0.0 | 0.0 |
| 112390 Match Control Crohns-M | 2.5 | 1.8 |
| 112726 Crohns-M | 3.8 | 5.9 |
| 112731 Match Control Crohns-M | 3.6 | 6.7 |
| 112380 Ulcer Col-F | 4.9 | 4.9 |
| 112734 Match Control Ulcer Col-F | 12.6 | 12.0 |
| 112384 Ulcer Col-F | 6.6 | 10.2 |
| 112737 Match Control Ulcer Col-F | 4.1 | 6.1 |
| 112386 Ulcer Col-F | 0.5 | 1.2 |
| 112738 Match Control Ulcer Col-F | 7.5 | 7.9 |
| 112381 Ulcer Col-M | 0.1 | 0.0 |
| 112735 Match Control Ulcer Col-M | 2.9 | 2.3 |
| 112382 Ulcer Col-M | 6.8 | 8.4 |
| 112394 Match Control Ulcer Col-M | 0.5 | 0.5 |
| 112383 Ulcer Col-M | 12.1 | 14.6 |
| 112736 Match Control Ulcer Col-M | 3.5 | 5.3 |
| 112423 Psoriasis-F | 1.4 | 1.1 |
| 112427 Match Control Psoriasis-F | 2.9 | 1.8 |
| 112418 Psoriasis-M | 0.8 | 0.8 |
| 112723 Match Control Psoriasis-M | 6.1 | 7.4 |
| 112419 Psoriasis-M | 1.0 | 1.3 |
| 112424 Match Control Psoriasis-M | 0.4 | 1.2 |
| 112420 Psoriasis-M | 1.8 | 2.4 |
| 112425 Match Control Psoriasis-M | 2.2 | 2.7 |
| 104689 (MF) OA Bone-Backus | 12.1 | 13.2 |
| 104690 (MF) Adj "Normal" Bone-Backus | 5.4 | 4.2 |
| 104691 (MF) OA Synovium-Backus | 43.3 | 35.7 |
| 104692 (BA) OA Cartilage-Backus | 0.9 | 0.4 |
| 104694 (BA) OA Bone-Backus | 16.8 | 16.7 |
| 104695 (BA) Adj "Normal" Bone-Backus | 6.5 | 6.1 |
| 104696 (BA) OA Synovium-Backus | 24.0 | 24.2 |
| 104700 (SS) OA Bone-Backus | 12.3 | 35.1 |
| 104701 (SS) Adj "Normal" Bone-Backus | 7.9 | 9.5 |
| 104702 (SS) OA Synovium-Backus | 8.3 | 7.9 |
| 117093 OA Cartilage Rep7 | 2.0 | 2.3 |
| 112672 OA Bone5 | 1.9 | 0.8 |
| 112673 OA Synovium5 | 0.3 | 1.2 |
| 112674 OA Synovial Fluid cells5 | 0.5 | 0.4 |
| 117100 OA Cartilage Rep14 | 0.4 | 0.3 |
| 112756 OA Bone9 | 100.0 | 100.0 |
| 112757 OA Synovium9 | 0.5 | 0.2 |
| 112758 OA Synovial Fluid Cells9 | 0.8 | 1.5 |
| 117125 RA Cartilage Rep2 | 1.0 | 0.6 |
| 113492 Bone2 RA | 2.8 | 3.6 |
| 113493 Synovium2 RA | 1.7 | 0.7 |
| 113494 Syn Fluid Cells RA | 0.9 | 2.1 |
| 113499 Cartilage4 RA | 2.1 | 1.8 |
| 113500 Bone4 RA | 1.8 | 2.5 |
| 113501 Synovium4RA | 2.1 | 2.3 |
| 113502 Syn Fluid Cells4 RA | 1.0 | 0.8 |
| 113495 Cartilage3 RA | 2.5 | 2.6 |
| 113496 Bone3 RA | 2.0 | 2.1 |
| 113497 Synovium3 RA | 1.3 | 1.4 |
| 113498 Syn Fluid Cells3 RA | 2.9 | 3.2 |
| 117106 Normal Cartilage Rep20 | 0.1 | 0.7 |
| 113663 Bone3 Normal | 0.3 | 0.1 |
| 113664 Synovium3 Normal | 0.0 | 0.0 |
| 113665 Syn Fluid Cells3 Normal | 0.1 | 0.2 |
| 117107 Normal Cartilage Rep22 | 0.9 | 0.3 |
| 113667 Bone4 Normal | 0.4 | 0.7 |
| 113668 Synovium4 Normal | 1.0 | 1.1 |
| 113669 Syn Fluid Cells4 Normal | 1.0 | 0.7 |

Panel 1.3D Summary: Ag2100 Expression of the NOV3a gene is highest in cerebral cortex (CT=26.3). This gene is expressed at more moderate levels in other parts of the CNS including amygdala, cerebellum, hippocampus, substantia nigra, thalamus, spinal cord, and fetal brain. Expression of the NOV3a gene in other normal tissues was lower than that in brain, suggesting a specific function for this protein in the CNS. Thus, this gene may be useful as a marker to distinguish brain from other tissues. The NOV3a gene encodes a protein with homology to citron-kinase. Citron-kinase (Citron-K) has been proposed by in vitro studies to be a crucial effector of Rho in regulation of cytokinesis. Citron-K is essential for cytokinesis in vivo in specific neuronal precursors and may play a fundamental role in specific human malformative syndromes of the CNS. General inhibitors of the RHO/RAC-INTERACTING CITRON KINASE family disrupt endothelial tight junctions, suggesting that specific modulators of this brain-preferential family member could be useful in delivery of therapeutics across the blood brain barrier. These general inhibitors also influence intracellular calcium flux, which is a central component of many important neuronal processes, such as apoptosis, neurotransmitter release and signal transduction. Thus, modulators of NOV3a protein function may prove useful in the treatment of neurodegenerative disorders involving apoptosis, such as spinal muscular atrophy, Alzheimer's disease, Huntington's disease, Parkinson's disease, and others. Diseases involving neurotransmitters or signal transduction, such as schizophrenia, mania, stroke, epilepsy and depression may also benefit from agents that modulate the function of the NOV3a gene product.

The NOV3a gene also shows low expression in several metabolic tissues including adrenal gland (CT=32), pituitary gland (CT=32) and fetal heart (CT=34). Interestingly, this gene is expressed at higher levels in adult skeletal muscle (CT=37) compared to fetal skeletal muscle (CT=31) as well as in adult liver (CT=40) compared to fetal liver (CT=31). Thus, the NOV3A gene may be used to differentiate between the fetal and adult skeletal muscle and liver. Moreover, the therapeutic modulation of this gene, specifically its use in replacement type therapy through the administration of purified protein, might be beneficial in the treatment of diseases involving the degeneration of liver or skeletal muscle, such as muscular dystrophy.

Panel 2.2 Summary: Ag2100 Expression of the NOV3a gene is highest in a kidney cancer sample (CT=28). In addition, there are a number of normal tissue/cancer tissue pairs in which this gene is expressed at higher levels in the tumor than the normal matched tissue. Thus, expression of the NOV3a gene could be used to distinguish between cancerous tissue and normal tissue. In addition, therapeutic modulation of this gene product, through the use of small molecule drugs or antibodies, might be of benefit in the treatment of cancer.

Panel 3D Summary: Ag2100 Expression of the NOV3a gene is highest in a lung cancer cell line (CT=26). However, low to moderate expression is also seen in the majority of cancer cell lines on this panel, suggesting that this gene may play an important role in many cell types.

Panel 4D Summary: Ag2100 The NOV3a gene is highly induced in Ramos B cells treated with PMA and ionomycin, in non-transformed B cells treated with PWM and in PBMC treated with PWM. All three of these observations are consistent with this transcript being induced in B cells after activation. Upon activation, T cells also produce this transcript, PBMC treated with PHA (T cell mitogen) express the transcript as well as primary activated Th1 cells. Primary Tr1 and Th2 express the transcript to a lesser extent. Fibroblost and endothelial cell lines on this panel also express NOV3a gene, although at lower levels as compared to the activated lymphocytes.

Role in Inflammation: The NOV3a gene product has homology to the RHO/RAC-interacting citron kinase. The citron kinase may play an important role in T cell activation, by regulating TCR-mediated T cell spreading, chemotaxis and other chemokine responses and in apoptosis. Since the protein encoded for by the NOV3a gene has high homology to this kinase, it too could contribute to T cell motility, activation and apoptosis. Likewise, this putative kinase may also be important in B cell motility, antigen receptor mediated activation and apoptosis.

Therapeutic Function: Small molecule therapeutics designed against the protein encoded for by the NOV3a gene could reduce or inhibit inflammation. Anti-sense therapeutics that would block the translation of the transcript and protein production could also inhibit inflammatory processes. These types of therapeutics could be important in the treatment of diseases such as osteoarthritis. Likewise, these therapeutics could be important in the treatment of asthma, psoriasis, diabetes, and IBD, which require activated T cells, as well as diseases that involve B cell activation such as systemic lupus erythematosus.

AI_comprehensive_panel_v1.0 Summary: Ag2100 The NOV3A gene is highly expressed in bone isolated from 5 different osteoarthritic (OA) patients, synovium in 3 out of 5 OA patients, but not in cartilege from OA patients nor in any tissues from rheumatoid arthritis (RA) patients or in control samples. Thus, small molecule therapeutics designed against the protein encoded for by the NOV3a gene could reduce or inhibit inflammation. Anti-sense therapeutics that would block the translation of the transcript and protein production could also inhibit inflammatory processes. These types of therapeutics could be important in the treatment of diseases such as osteoarthritis

REFERENCES

1. Di Cunto F., Imarisio S., Hirsch E., Broccoli V., Bulfone A., Migheli A., Atzori C., Turco E., Triolo R., Dotto G. P., Silengo L., Altruda F. (2000) Defective neurogenesis in citron kinase knockout mice by altered cytokinesis and massive apoptosis. Neuron 28:115–127.

Citron-kinase (Citron-K) has been proposed by in vitro studies as a crucial effector of Rho in regulation of cytokinesis. To further investigate in vivo its biologic functions, we have inactivated Citron-K gene in mice by homologous recombination. Citron-K−/− mice grow at slower rates, are severely ataxic, and die before adulthood as a consequence of fatal seizures. Their brains display defective neurogenesis, with depletion of specific neuronal populations. These abnormalities arise during development of the central nervous system due to altered cytokinesis and massive apoptosis. The results indicate that Citron-K is essential for cytokinesis in vivo but only in specific neuronal precursors. Moreover, they suggest a novel molecular mechanism for a subset of human malformative syndromes of the CNS.

PMID: 11086988

2. Jezior J. R., Brady J. D., Rosenstein D. I., McCammon K. A., Miner A. S., Ratz P. H. (2001) Dependency of detrusor contractions on calcium sensitization and calcium entry through LOE-908-sensitive channels. Br. J. Pharmacol. 134:78–87.

The subcellular mechanisms regulating stimulus-contraction coupling in detrusor remain to be determined. Ca(2+)-free solutions, Ca(2+) channel blockers, cyclopiazonic acid (CPA), and RhoA kinase (ROK) inhibitors were used to test the hypothesis that Ca(2+) influx and Ca(2+) sensitization play primary roles. In rabbit detrusor, peak bethanechol (BE)-induced force was inhibited 90% by incubation for 3 min in a Ca(2+)-free solution. By comparison, a 20 min incubation of rabbit femoral artery in a Ca(2+)-free solution reduced receptor-induced force by only 5%. In detrusor, inhibition of sarcoplasmic reticular (SR) Ca(2+) release by 2APB, or depletion of SR Ca(2+) by CPA, inhibited BE-induced force by only 27%. The CPA-insensitive force was abolished by LaCl(3). By comparison, 2APB inhibited receptor-induced force in rabbit femoral artery by 71%. In the presence of the non-selective cation channel (NSCC) inhibitor, LOE-908, BE did not produce an increase in [Ca(2+)](i) but did produce weak increases in myosin phosphorylation and force. Inhibitors of ROK-induced Ca(2+) sensitization, HA-1077 and Y-27632, inhibited BE-induced force by approximately 50%, and in combination with LOE-908, nearly abolished force. These data suggest that two principal muscarinic receptor-stimulated detrusor contractile mechanisms include NSCC activation, that elevates [Ca(2+)](i) and ROK activation, that sensitizes cross bridges to Ca(2+).

PMID: 11522599

3. Walsh S. V., Hopkins A. M., Chen J., Narumiya S., Parkos C. A., Nusrat A. (2001) Rho kinase regulates tight junction function and is necessary for tight junction assembly in polarized intestinal epithelia. Gastroenterology 121:566–579.

Background & Aims: Tight junctions are crucial determinants of barrier function in polarized intestinal epithelia and are regulated by Rho guanosine triphosphatase. Rho kinase (ROCK) is a downstream effector of Rho. Methods: A specific inhibitor of ROCK, Y-27632, was used to examine the role of ROCK in the regulation of tight junctions in model intestinal (T84) cells by electrophysiologic, biochemical, morphologic, and molecular biologic approaches. Results: ROCK inhibition induced reorganization of apical F-actin structures and enhanced paracellular permeability but did not alter the distribution or detergent solubility of tight junction proteins. Confocal microscopy showed colocalization of a subpool of ROCK with the tight junction protein zonula occludens 1. Inhibition of ROCK function by a dominant negative mutant of ROCK also produced reorganization of apical F-actin structures without disruption of tight junctions. ROCK inhibition in calcium switch assays showed that ROCK is necessary for the assembly of tight and adherens junctions. Upon calcium repletion, occludin, zonula occludens 1, and E-cadherin failed to redistribute to the intercellular junctions; assembly of the apical F-actin cytoskeleton was prevented; and barrier function failed to recover. Conclusions: It has been suggested that ROCK regulates intact tight junctions via its effects on the F-actin cytoskeleton. ROCK is also critical for assembly of the apical junctional proteins and the F-actin cytoskeleton organization during junctional formation.

PMID: 11522741

NOV4

Expression of gene NOV4 was assessed using the primer-probe sets Ag217, Ag850, and Ag1469, described in Tables 25, 26, and 27. Results from RTQ-PCR runs are shown in Tables 28, 29, 30, 31, 32, and 33.

TABLE 25

Probe Name Ag217

| Primers | Sequences | TM | Length | Start Position | SEQ ID NO: |
|---|---|---|---|---|---|
| Forward | 5'-ATCTGTGCTGAGGCATGTTCCT-3' | | 22 | 163 | 100 |
| Probe | FAM-5'-ATCCTCCTCCCTCCCCGGCTCTC-3'-TAMRA | | 23 | 192 | 101 |
| Reverse | 5'-CTGCATGGCTGGTGTGATG-3' | | 19 | 222 | 102 |

TABLE 26

Probe Name Ag850

| Primers | Sequences | TM | Length | Start Position | SEQ ID NO: |
|---|---|---|---|---|---|
| Forward | 5'-CCTTTCTTCTCTTCCTCCTCAA-3' | 59.1 | 22 | 25 | 103 |
| Probe | FAM-5'-CACCTGGCGAGTGCTCCTCTCTG-3'-TAMRA | 70 | 23 | 71 | 104 |
| Reverse | 5'-GGTGGATGGCGTTGTAGAG-3' | 59.1 | 19 | 96 | 105 |

(Please note that there is a single base mismatch within forward primer that is not predicted to affect binding)

TABLE 27

Probe Name Ag1469

| Primers | Sequences | TM | Length | Start Position | SEQ ID NO: |
|---|---|---|---|---|---|
| Forward | 5'-CGTACGTCTTCCATGATGAGTT-3' | 59.1 | 22 | 644 | 106 |
| Probe | TET-5'-CGTGGCCTCGATGATTAAGATCCCTT-3'-TAMRA | 69.8 | 26 | 666 | 107 |
| Reverse | 5'-AAGTCAGGGATGATGGTGAAG-3' | 59 | 21 | 699 | 108 |

TABLE 28

Panel 1

| Tissue Name | Relative Expression (%) tm303f |
|---|---|
| Endothelial cells | 0.0 |
| Endothelial cells (treated) | 0.0 |
| Pancreas | 0.0 |
| Pancreatic ca. CAPAN 2 | 5.4 |
| Adrenal gland | 0.0 |
| Thyroid | 0.0 |
| Salavary gland | 0.0 |
| Pituitary gland | 0.0 |
| Brain (fetal) | 0.0 |
| Brain (whole) | 0.0 |
| Brain (amygdala) | 0.0 |
| Brain (cerebellum) | 0.0 |
| Brain (hippocampus) | 0.0 |
| Brain (substantia nigra) | 0.0 |
| Brain (thalamus) | 0.0 |
| Brain (hypothalamus) | 0.0 |
| Spinal cord | 0.0 |
| CNS ca. (glio/astro) U87-MG | 0.0 |
| CNS ca. (glio/astro) U-118-MG | 0.0 |
| CNS ca. (astro) SW1783 | 0.3 |
| CNS ca.* (neuro; met) SK-N-AS | 6.7 |
| CNS ca. (astro) SF-539 | 0.0 |
| CNS ca. (astro) SNB-75 | 0.0 |
| CNS ca. (glio) SNB-19 | 0.0 |
| CNS ca. (glio) U251 | 0.6 |
| CNS ca. (glio) SF-295 | 15.3 |

TABLE 28-continued

Panel 1

| Tissue Name | Relative Expression (%) tm303f |
|---|---|
| Heart | 0.0 |
| Skeletal muscle | 0.0 |
| Bone marrow | 0.0 |
| Thymus | 0.0 |
| Spleen | 0.0 |
| Lymph node | 0.0 |
| Colon (ascending) | 0.0 |
| Stomach | 0.0 |
| Small intestine | 0.0 |
| Colon ca. SW480 | 2.4 |
| Colon ca.* (SW480 met) SW620 | 4.1 |
| Colon ca. HT29 | 0.0 |
| Colon ca. HCT-116 | 0.0 |
| Colon ca. CaCo-2 | 0.0 |
| Colon ca. HCT-15 | 0.0 |
| Colon ca. HCC-2998 | 0.0 |
| Gastric ca.* (liver met) NCI-N87 | 45.4 |
| Bladder | 0.0 |
| Trachea | 0.0 |
| Kidney | 4.1 |
| Kidney (fetal) | 0.0 |
| Renal ca. 786-0 | 0.0 |
| Renal ca. A498 | 0.0 |
| Renal ca. RXF 393 | 0.0 |
| Renal ca. ACHN | 0.0 |
| Renal ca. UO-31 | 0.0 |
| Renal ca. TK-10 | 0.0 |
| Liver | 0.0 |
| Liver (fetal) | 0.0 |
| Liver ca. (hepatoblast) HepG2 | 0.0 |
| Lung | 0.0 |
| Lung (fetal) | 0.0 |
| Lung ca. (small cell) LX-1 | 3.1 |
| Lung ca. (small cell) NCI-H69 | 0.2 |
| Lung ca. (s. cell var.) SHP-77 | 0.0 |
| Lung ca. (large cell) NCI-H460 | 0.0 |
| Lung ca. (non-sm. cell) A549 | 2.2 |
| Lung ca. (non-s. cell) NCI-H23 | 0.0 |
| Lung ca (non-s. cell) HOP-62 | 0.0 |
| Lung ca. (non-s. cl) NCI-H522 | 0.0 |
| Lung ca. (squam.) SW 900 | 0.6 |
| Lung ca. (squam.) NCI-H596 | 0.2 |
| Mammary gland | 0.0 |
| Breast ca.* (pl. effusion) MCF-7 | 0.0 |
| Breast ca.* (pl. ef) MDA-MB-231 | 0.0 |
| Breast ca.* (pl. effusion) T47D | 0.0 |
| Breast ca. BT-549 | 0.0 |
| Breast ca. MDA-N | 0.0 |
| Ovary | 0.0 |
| Ovarian ca. OVCAR-3 | 0.0 |
| Ovarian ca. OVCAR-4 | 0.0 |
| Ovarian ca. OVCAR-5 | 0.1 |
| Ovarian ca. OVCAR-8 | 0.0 |
| Ovarian ca. IGROV-1 | 0.0 |
| Ovarian ca.* (ascites) SK-OV-3 | 0.0 |
| Uterus | 7.4 |
| Placenta | 100.0 |
| Prostate | 0.0 |
| Prostate ca.* (bone met) PC-3 | 0.0 |
| Testis | 4.2 |
| Melanoma Hs688(A).T | 0.0 |
| Melanoma* (met) Hs6S8(B).T | 0.0 |
| Melanoma UACC-62 | 0.0 |
| Melanoma M14 | 0.0 |
| Melanoma LOX IMVI | 0.0 |
| Melanoma* (met) SK-MEL-5 | 0.0 |
| Melanoma SK-MEL-28 | 0.0 |

TABLE 29

Panel 1.3D

| Tissue Name | Relative Expression % 13Dtm2782t_ag1469 |
|---|---|
| Liver adenocarcinoma | 0.0 |
| Pancreas | 0.0 |
| Pancreatic ca. CAPAN 2 | 0.0 |
| Adrenal gland | 0.6 |
| Thyroid | 0.6 |
| Salivary gland | 0.0 |
| Pituitary gland | 0.9 |
| Brain (fetal) | 14.5 |
| Brain (whole) | 9.1 |
| Brain (amygdala) | 8.2 |
| Brain (cerebellum) | 0.9 |
| Brain (hippocampus) | 14.9 |
| Brain (substantia nigra) | 0.8 |
| Brain (thalamus) | 3.6 |
| Cerebral Cortex | 100.0 |
| Spinal cord | 0.6 |
| CNS ca. (glio/astro) U87-MG | 0.9 |
| CNS ca. (glio/astro) U-118-MG | 15.1 |
| CNS ca. (astro) SW1783 | 0.5 |
| CNS ca.* (neuro; met) SK-N-AS | 1.3 |
| CNS ca (astro) SF-539 | 0.0 |
| CNS ca. (astro) SNB-75 | 10.2 |
| CNS ca. (glio) SNB-19 | 16.3 |
| CNS ca (glio) U251 | 1.7 |
| CNS ca. (glio) SF-295 | 0.3 |
| Heart (fetal) | 81.2 |
| Heart | 2.3 |
| Fetal Skeletal | 16.3 |
| Skeletal muscle | 0.1 |
| Bone marrow | 0.3 |
| Thymus | 0.4 |
| Spleen | 0.6 |
| Lymph node | 1.9 |
| Colorectal | 4.4 |
| Stomach | 1.4 |
| Small intestine | 0.5 |
| Colon ca. SW480 | 0.0 |
| Colon ca.* (SW480 met) SW620 | 0.0 |
| Colon ca. HT29 | 0.0 |
| Colon ca. HCT-116 | 0.0 |
| Colon ca. CaCo-2 | 0.0 |
| 83219 CC Well to Mod Diff (ODO3866) | 6.5 |
| Colon ca. HCC-2998 | 0.0 |
| Gastric ca.* (liver met) NCI-N87 | 0.0 |
| Bladder | 0.4 |
| Trachea | 0.0 |
| Kidney | 0.1 |
| Kidney (fetal) | 1.2 |
| Renal ca. 786-0 | 0.0 |
| Renal ca. A498 | 4.1 |
| Renal ca. RXF 393 | 2.5 |
| Renal ca. ACHN | 0.0 |
| Renal ca. UO-31 | 0.4 |
| Renal ca. TK-10 | 0.2 |
| Liver | 0.0 |
| Liver (fetal) | 0.1 |
| Liver ca. (hepatoblast) HepG2 | 0.0 |
| Lung | 0.0 |
| Lung (fetal) | 1.1 |
| Lung ca. (small cell) LX-1 | 0.0 |
| Lung ca. (small cell) NCI-H69 | 0.0 |
| Lung ca. (s. cell var.) SHP-77 | 2.1 |
| Lung ca. (large cell) NCI-H460 | 0.0 |
| Lung ca. (non-sm. cell) A549 | 0.0 |
| Lung ca. (non-s. cell) NCI-H23 | 0.2 |
| Lung ca (non-s. cell) HOP-62 | 0.0 |
| Lung ca. (non-s. cl) NCI-H522 | 0.0 |
| Lung ca. (squam.) SW 900 | 0.0 |
| Lung ca. (squam.) NCI-H596 | 0.0 |
| Mammary gland | 8.9 |
| Breast ca.* (pl. effusion) MCF-7 | 12.9 |
| Breast ca.* (pl. ef) MDA-MB-231 | 0.6 |

TABLE 29-continued

Panel 1.3D

| Tissue Name | Relative Expression % 13Dtm2782t_ag1469 |
|---|---|
| Breast ca.* (pl. effusion) T47D | 0.0 |
| Breast ca. BT-549 | 1.1 |
| Breast ca. MDA-N | 0.0 |
| Ovary | 9.8 |
| Ovarian ca. OVCAR-3 | 0.1 |
| Ovarian ca. OVCAR-4 | 0.0 |
| Ovarian ca. OVCAR-5 | 0.0 |
| Ovarian ca. OVCAR-8 | 0.0 |
| Ovarian ca. IGROV-1 | 4.5 |
| Ovarian ca.* (ascites) SK-OV-3 | 0.6 |
| Uterus | 0.3 |
| Placenta | 2.4 |
| Prostate | 0.0 |
| Prostate ca.* (bone met) PC-3 | 0.4 |
| Testis | 1.7 |
| Melanoma Hs688(A).T | 2.5 |
| Melanoma* (met) Hs688(B).T | 6.8 |
| Melanoma UACC-62 | 0.0 |
| Melanoma M14 | 0.0 |
| Melanoma LOX IMVI | 0.0 |
| Melanoma* (met) SK-MEL-5 | 0.4 |
| Adipose | 10.6 |

TABLE 30

General_screening_panel_v1.4

| Tissue Name | Relative Expression (%) 1.4tm7173f_ag217_b2 | Relative Expression (%) 1.4tm7186f_ag850_b2 |
|---|---|---|
| D6005-01_Human adipose | 0.3 | 0.2 |
| 112193_Metastatic melanoma | 0.0 | 0.0 |
| 112192_Metastatic melanoma | 0.4 | 0.2 |
| 95280_Epidermis (metastatic melanoma) | 0.0 | 0.2 |
| 95279_Epidermis (metastatic melanoma) | 1.0 | 0.6 |
| Melanoma (met)_SK-MEL-5 | 0.0 | 0.0 |
| 112196_Tongue (oncology) | 0.8 | 0.4 |
| 113461_Testis Pool | 1.0 | 0.5 |
| Prostate ca. (bone met)_PC-3 | 0.0 | 0.0 |
| 113455_Prostate Pool | 1.0 | 0.7 |
| 103396_Placenta | 33.5 | 31.8 |
| 113463_Uterus Pool | 0.1 | 0.0 |
| Ovarian carcinoma_OVCAR-3 | 0.1 | 0.1 |
| Ovarian carcinoma (ascites)_SK-OV-3 | 0.1 | 0.1 |
| 95297_Adenocarcinoma (ovary) | 0.1 | 0.0 |
| Ovarian carcinoma_OVCAR-5 | 4.4 | 4.9 |
| Ovarian carcinoma_IGROV-1 | 0.8 | 0.2 |
| Ovarian carcinoma_OVCAR-8 | 7.2 | 3.0 |
| 103368_Ovary | 0.5 | 0.6 |
| MCF7_breast carcinoma (pleural effusion) | 0.0 | 0.0 |
| Breast ca. (pleural effusion)_MDA-MB-231 | 0.4 | 0.0 |
| 112189_ductal cell carcinoma (breast) | 9.2 | 11.4 |
| Breast ca. (pleural effusion)_T47D | 14.5 | 4.5 |
| Breast carcinoma_MDA-N | 0.0 | 0.0 |
| 113452_Breast Pool | 2.6 | 1.4 |
| 103398_Trachea | 0.5 | 0.4 |
| 112354_lung | 0.1 | 0.0 |
| 103374_Fetal Lung | 0.2 | 0.4 |
| 94921_Small cell carcinoma of the lung | 0.7 | 0.4 |
| Lung ca. (small cell)_LX-1 | 18.4 | 21.2 |
| 94919_Small cell carcinoma of the lung | 1.8 | 0.8 |
| Lung ca. (s. cell var.)_SHP-77 | 1.8 | 1.0 |

TABLE 30-continued

General_screening_panel_v1.4

| Tissue Name | Relative Expression (%) 1.4tm7173f_ag217_b2 | Relative Expression (%) 1.4tm7186f_ag850_b2 |
|---|---|---|
| 95268_Lung (Large cell carcinoma) | 22.3 | 24.7 |
| 94920_Small cell carcinoma of the lung | 0.0 | 0.1 |
| Lung ca. (non-s. cell)_NCI-H23 | 6.0 | 3.5 |
| Lung ca. (large cell)_NCI-H460 | 0.6 | 0.3 |
| Lung ca. (non-s. cell)_HOP-62 | 3.7 | 1.2 |
| Lung ca. (non-s. cl)_NCI-H522 | 0.0 | 0.0 |
| 103392_Liver | 0.0 | 0.0 |
| 103393_Fetal Liver | 1.0 | 1.1 |
| Liver ca. (hepatoblast)_HepG2 | 0.4 | 0.2 |
| 113465_Kidney Pool | 1.8 | 0.8 |
| 103373_Fetal Kidney | 2.9 | 2.5 |
| Renal ca._786-0 | 0.1 | 0.0 |
| 112188_renal cell carcinoma | 0.3 | 0.2 |
| Renal ca._ACHN | 1.2 | 1.9 |
| 112190_Renal cell carcinoma | 0.0 | 0.0 |
| Renal ca._TK-10 | 0.7 | 0.2 |
| Bladder | 1.0 | 0.5 |
| Gastric ca. (liver met)_NCI-N87 | 87.0 | 64.6 |
| 112197_Stomach | 0.0 | 0.0 |
| 94938_Colon Adenocarcinoma | 0.0 | 0.0 |
| Colon ca._SW480 | 69.8 | 58.3 |
| Colon ca. (SW480 met)_SW620 | 29.8 | 22.4 |
| Colon ca._HT29 | 1.7 | 1.0 |
| Colon ca._HCT-116 | 0.0 | 0.0 |
| Colon ca._CaCo-2 | 1.0 | 0.7 |
| 83219_CC Well to Mod Diff (ODO3866) | 0.6 | 0.2 |
| 94936_Colon Adenocarcinoma | 0.9 | 0.6 |
| 94930_Colon | 0.7 | 0.3 |
| 94935_Colon Adenocarcinoma | 0.0 | 0.0 |
| 113468_Colon Pool | 0.7 | 0.5 |
| 113457_Small Intestine Pool | 6.3 | 2.8 |
| 113460_Stomach Pool | 1.1 | 2.1 |
| 113467_Bone Marrow Pool | 1.3 | 0.9 |
| 103371_Fetal Heart | 0.0 | 0.0 |
| 113451_Heart Pool | 0.2 | 0.0 |
| 113466_Lymph Node Pool | 2.1 | 3.0 |
| 103372_Fetal Skeletal Muscle | 0.1 | 0.0 |
| 113456_Skeletal Muscle Pool | 0.0 | 0.1 |
| 113459_Spleen Pool | 0.0 | 0.0 |
| 113462_Thymus Pool | 6.7 | 3.3 |
| CNS ca. (glio/astro)_U87-MG | 0.7 | 0.6 |
| CNS ca. (glio/astro)_U-118-MG | 0.3 | 0.2 |
| CNS ca. (neuro; met)_SK-N-AS | 21.0 | 16.9 |
| 95264_Brain astrocytoma | 2.2 | 2.4 |
| CNS ca. (astro)_SNB-75 | 0.0 | 0.0 |
| CNS ca. (glio)_SNB-19 | 0.5 | 0.1 |
| CNS ca. (glio)_SF-295 | 100.0 | 100.0 |
| 113447_Brain (Amygdala) Pool | 0.0 | 0.0 |
| 103382_Brain (cerebellum) | 0.2 | 0.2 |
| 64019-1_brain (fetal) | 0.8 | 0.7 |
| 113448_Brain (Hippocampus) Pool | 0.0 | 0.1 |
| 113464_Cerebral Cortex Pool | 0.2 | 0.2 |
| 113449_Brain (Substantia nigra) Pool | 0.0 | 0.0 |
| 113450_Brain (Thalamus) Pool | 0.0 | 0.0 |
| 103384_Brain (whole) | 0.3 | 0.2 |
| 113458_Spinal Cord Pool | 0.4 | 0.2 |
| 103375_Adrenal Gland | 0.4 | 0.3 |
| 113454_Pituitary gland Pool | 0.8 | 0.5 |
| 103397_Salivary Gland | 0.0 | 0.0 |
| 103369_Thyroid (female) | 0.4 | 0.1 |
| Pancreatic ca._CAPAN2 | 34.6 | 25.5 |
| 113453_Pancreas Pool | 5.7 | 4.5 |

TABLE 31

Panel 2D

| Tissue Name | Relative Expression (%) | | |
|---|---|---|---|
| | 2Dtm2759t_ ag1469 | 2Dtm3205t_ ag1469 | 2Dtm3211t_ ag1469 |
| Normal Colon GENPAK 061003 | 21.2 | 24.0 | 25.7 |
| 83219 CC Well to Mod Diff (ODO3866) | 4.9 | 6.7 | 6.3 |
| 83220 CC NAT (ODO3866) | 2.4 | 7.6 | 5.7 |
| 83221 CC Gr.2 rectosigmoid (ODO3868) | 4.4 | 6.5 | 4.5 |
| 83222 CC NAT (ODO3868) | 13.1 | 14.5 | 11.2 |
| 83235 CC Mod Diff (ODO3920) | 2.2 | 2.4 | 2.6 |
| 83236 CC NAT (ODO3920) | 6.3 | 6.5 | 4.9 |
| 83237 CC Gr.2 ascend colon (ODO3921) | 5.7 | 9.3 | 6.4 |
| 83238 CC NAT (ODO3921) | 8.4 | 11.3 | 8.6 |
| 83241 CC from Partial Hepatectomy (ODO4309) | 5.2 | 4.5 | 3.2 |
| 83242 Liver NAT (ODO4309) | 2.0 | 3.4 | 2.7 |
| 87472 Colon mets to lung (OD04451-01) | 4.5 | 4.3 | 4.0 |
| 87473 Lung NAT (OD04451-02) | 3.0 | 3.0 | 3.1 |
| Normal Prostate Clontech A+ 6546-1 | 0.2 | 0.3 | 0.5 |
| 84140 Prostate Cancer (OD04410) | 2.9 | 5.4 | 2.8 |
| 84141 Prostate NAT (OD04410) | 9.9 | 13.5 | 10.2 |
| 87073 Prostate Cancer (OD04720-01) | 6.0 | 6.8 | 4.6 |
| 87074 Prostate NAT (OD04720-02) | 11.3 | 8.9 | 4.2 |
| Normal Lung GENPAK 061010 | 18.6 | 19.2 | 12.7 |
| 83239 Lung Met to Muscle (ODO4286) | 0.0 | 1.2 | 1.0 |
| 83240 Muscle NAT (ODO4286) | 4.7 | 6.0 | 4.4 |
| 84136 Lung Malignant Cancer (OD03126) | 4.8 | 8.5 | 5.8 |
| 84137 Lung NAT (OD03126) | 8.5 | 15.9 | 8.1 |
| 84871 Lung Cancer (OD04404) | 7.9 | 7.6 | 4.9 |
| 84872 Lung NAT (OD04404) | 16.5 | 23.0 | 14.5 |
| 84875 Lung Cancer (OD04565) | 4.9 | 3.1 | 3.4 |
| 84876 Lung NAT (OD04565) | 3.6 | 9.5 | 2.9 |
| 85950 Lung Cancer (OD04237-01) | 1.4 | 4.1 | 2.1 |
| 85970 Lung NAT (OD04237-02) | 8.4 | 9.3 | 7.5 |
| 83255 Ocular Mel Met to Liver (ODO4310) | 0.6 | 0.5 | 0.2 |
| 83256 Liver NAT ODO4310 | 1.0 | 1.0 | 0.7 |
| 84139 Melanoma Mets to Lung (OD04321) | 0.2 | 0.2 | 0.2 |
| 84138 Lung NAT (OD04321) | 6.7 | 9.4 | 5.4 |
| Normal Kidney GENPAK 061008 | 11.7 | 17.3 | 12.4 |
| 83786 Kidney Ca, Nuclear grade 2 (OD04338) | 3.0 | 3.8 | 4.1 |
| 83787 Kidney NAT (OD04338) | 13.8 | 19.5 | 14.3 |
| 83788 Kidney Ca Nuclear grade 1/2 (OD04339) | 16.8 | 19.1 | 15.0 |
| 83789 Kidney NAT (OD04339) | 4.9 | 4.6 | 4.6 |
| 83790 Kidney Ca, Clear cell type (OD04340) | 0.9 | 1.6 | 0.8 |
| 83791 Kidney NAT (OD04340) | 11.5 | 18.3 | 14.1 |
| 83792 Kidney Ca, Nuclear grade 3 (OD04348) | 0.6 | 1.2 | 0.4 |
| 83793 Kidney NAT (OD04348) | 8.5 | 15.4 | 10.9 |
| 87474 Kidney Cancer (OD04622-01) | 2.9 | 4.3 | 3.4 |
| 87475 Kidney NAT (OD04622-03) | 1.9 | 4.5 | 3.9 |
| 85973 Kidney Cancer (OD04450-01) | 0.3 | 0.0 | 0.4 |
| 85974 Kidney NAT (OD04450-03) | 5.4 | 7.8 | 4.8 |
| Kidney Cancer Clontech 8120607 | 1.4 | 2.3 | 1.7 |
| Kidney NAT Clontech 8120608 | 3.6 | 4.2 | 3.1 |
| Kidney Cancer Clontech 8120613 | 0.6 | 0.3 | 0.7 |
| Kidney NAT Clontech 8120614 | 59.9 | 5.4 | 4.9 |
| Kidney Cancer Clontech 9010320 | 10.7 | 9.2 | 11.7 |
| Kidney NAT Clontech 9010321 | 8.8 | 8.1 | 14.2 |
| Normal Uterus GENPAK 061018 | 15.0 | 15.3 | 14.2 |
| Uterus Cancer GENPAK 064011 | 9.3 | 10.2 | 13.1 |
| Normal Thyroid Clontech A+ 6570-1 | 3.1 | 3.6 | 2.6 |
| Thyroid Cancer GENPAK 064010 | 20.7 | 30.1 | 23.2 |
| Thyroid Cancer INVITROGEN A302152 | 9.4 | 20.9 | 7.3 |
| Thyroid NAT INVITROGEN A302153 | 1.6 | 4.0 | 4.0 |
| Normal Breast GENPAK 061019 | 45.4 | 62.4 | 41.8 |
| 84877 Breast Cancer (OD04566) | 4.5 | 5.7 | 3.0 |
| 85975 Breast Cancer (OD04590-01) | 10.5 | 17.8 | 14.9 |
| 85976 Breast Cancer Mets (OD04590-03) | 44.4 | 51.4 | 35.1 |
| 87070 Breast Cancer Metastasis (OD04655-05) | 11.0 | 14.2 | 12.2 |
| GENPAK Breast Cancer 064006 | 7.1 | 8.3 | 6.0 |
| Breast Cancer Res. Gen. 1024 | 38.2 | 37.1 | 43.8 |
| Breast Cancer Clontech 9100266 | 5.4 | 4.8 | 4.1 |
| Breast NAT Clontech 9100265 | 4.9 | 10.3 | 6.8 |
| Breast Cancer INVITROGEN A209073 | 11.7 | 24.7 | 13.5 |
| Breast NAT INVITROGEN A2090734 | 20.9 | 23.3 | 16.0 |
| Normal Liver GENPAK 061009 | 8.5 | 12.6 | 5.5 |
| Liver Cancer GENPAK 064003 | 0.4 | 0.9 | 0.5 |
| Liver Cancer Research Genetics RNA 1025 | 3.9 | 4.2 | 2.0 |
| Liver Cancer Research Genetics RNA 1026 | 1.7 | 4.2 | 3.7 |
| Paired Liver Cancer Tissue Research Genetics RNA 6004-T | 2.8 | 2.8 | 2.8 |
| Paired Liver Tissue Research Genetics RNA 6004-N | 0.8 | 1.3 | 0.8 |
| Paired Liver Cancer Tissue Research Genetics RNA | 3.7 | 3.0 | 1.1 |

TABLE 31-continued

Panel 2D

| | Relative Expression (%) | | |
|---|---|---|---|
| Tissue Name | 2Dtm2759t__ag1469 | 2Dtm3205t__ag1469 | 2Dtm3211t__ag1469 |
| 6005-T Paired Liver Tissue Research Genetics RNA 6005-N | 1.2 | 2.6 | 1.6 |
| Normal Bladder GENPAK 061001 | 5.8 | 9.7 | 11.0 |
| Bladder Cancer Research Genetics RNA 1023 | 2.6 | 4.3 | 3.6 |
| Bladder Cancer INVITROGEN A302173 | 2.3 | 1.2 | 1.8 |
| 87071 Bladder Cancer OD04718-01) | 0.7 | 3.6 | 1.8 |
| 87072 Bladder Normal Adjacent (OD04718-03) | 12.7 | 16.6 | 15.1 |
| Normal Ovary Res. Gen. | 13.2 | 15.9 | 12.2 |
| Ovarian Cancer GENPAK 064008 | 100.0 | 100.0 | 100.0 |
| 87492 Ovary Cancer (OD04768-07) | 0.6 | 0.7 | 0.6 |
| 87493 Ovary NAT (OD04768-08) | 18.8 | 26.4 | 23.7 |
| Normal Stomach GENPAK 061017 | 17.2 | 19.8 | 20.7 |
| Gastric Cancer Clontech 9060358 | 4.6 | 7.0 | 4.2 |
| NAT Stomach Clontech 9060359 | 2.7 | 3.3 | 3.8 |
| Gastric Cancer Clontech 9060395 | 17.0 | 17.3 | 14.7 |
| NAT Stomach Clontech 9060394 | 9.9 | 15.1 | 9.3 |
| Gastric Cancer Clontech 9060397 | 8.5 | 11.1 | 10.1 |
| NAT Stomach Clontech 9060396 | 2.1 | 2.8 | 2.8 |
| Gastric Cancer GENPAK 064005 | 8.2 | 13.0 | 9.2 |

TABLE 32

Panel 4D

| | Relative Expression (%) | | Relative Expression (%) |
|---|---|---|---|
| Tissue Name | 4dx4tm5043f__ag217_b1 | 4dx4tm5056f__ag217_b1 | 4Dtm2436t__ag1469 |
| 93768__Secondary Th1__anti-CD28/anti-CD3 | 0.0 | 1.2 | 0.0 |
| 93769__Secondary Th2__anti-CD28/anti-CD3 | 0.0 | 0.0 | 5.5 |
| 93770__Secondary Tr1__anti-CD28/anti-CD3 | 2.6 | 0.0 | 1.6 |
| 93573__Secondary Th1__resting day 4–6 in IL-2 | 1.8 | 0.0 | 3.3 |
| 93572__Secondary Th2__resting day 4–6 in IL-2 | 0.0 | 0.0 | 23.0 |
| 93571__Secondary Tr1__resting day 4–6 in IL-2 | 7.0 | 1.6 | 12.6 |
| 93568__primary Th1__anti-CD28/anti-CD3 | 0.0 | 0.0 | 4.3 |
| 93569__primary Th2__anti-CD28/anti-CD3 | 0.0 | 0.0 | 22.2 |
| 93570__primary Tr1__anti-CD28/anti-CD3 | 0.8 | 0.0 | 12.6 |
| 93565__primary Th1__resting dy 4–6 in IL-2 | 0.0 | 0.0 | 33.7 |
| 93560__primary Th2__resting dy 4–6 in IL-2 | 0.0 | 0.0 | 45.7 |
| 93567__primary Tr1__resting dy 4–6 in IL-2 | 0.0 | 1.3 | 74.7 |
| 93351__CD45RA CD4 lymphocyte__anti-CD28/anti-CD3 | 8.1 | 9.2 | 0.9 |
| 93352__CD45RO CD4 lymphocyte__anti-CD28/anti-CD3 | 0.0 | 0.0 | 0.0 |
| 93251__CD8 Lymphocytes__anti-CD28/anti-CD3 | 0.0 | 0.0 | 2.4 |
| 93353__chronic CD8 Lymphocytes 2ry__resting dy 4–6 in IL-2 | 0.0 | 0.0 | 0.7 |
| 93574__chronic CD8 Lymphocytes 2ry__activated CD3/CD28 | 2.1 | 2.5 | 0.3 |
| 93354__CD4__none | 0.0 | 0.0 | 3.0 |
| 93252__Secondary Th1/Th2/Tr1__anti-CD95 CH11 | 0.0 | 0.0 | 5.9 |
| 93103__LAK cells__resting | 0.0 | 0.0 | 6.0 |

TABLE 32-continued

Panel 4D

| Tissue Name | Relative Expression (%) | | Relative Expression (%) |
|---|---|---|---|
| | 4dx4tm5043f_ag217_b1 | 4dx4tm5056f_ag217_b1 | 4Dtm2436t_ag1469 |
| 93788_LAK cells_IL-2 | 0.0 | 0.0 | 1.8 |
| 93787_LAK cells_IL-2 + IL-12 | 0.0 | 0.0 | 11.0 |
| 93789_LAK cells_IL-2 + IFN gamma | 0.0 | 0.0 | 11.9 |
| 93790_LAK cells_IL-2 + IL-18 | 2.2 | 0.0 | 9.8 |
| 93104_LAK cells_PMA/ionomycin and IL-18 | 0.0 | 0.0 | 2.8 |
| 93578_NK Cells IL-2_resting | 0.0 | 0.0 | 13.7 |
| 93109_Mixed Lymphocyte Reaction_Two Way MLR | 0.0 | 0.0 | 6.0 |
| 93110_Mixed Lymphocyte Reaction_Two Way MLR | 0.0 | 0.0 | 1.3 |
| 93111_Mixed Lymphocyte Reaction_Two Way MLR | 0.0 | 1.5 | 0.6 |
| 93112_Mononuclear Cells (PBMCs)_resting | 0.0 | 0.0 | 1.6 |
| 93113_Mononuclear Cells (PBMCs)_PWM | 0.0 | 0.0 | 5.1 |
| 93114_Mononuclear Cells (PBMCs)_PHA-L | 0.0 | 0.0 | 6.2 |
| 93249_Ramos (B cell)_none | 0.0 | 0.0 | 0.0 |
| 93250_Ramos (B cell)_ionomycin | 0.0 | 1.5 | 0.0 |
| 93349_B lymphocytes_PWM | 0.0 | 3.4 | 0.0 |
| 93350_B lymphocytes_CD40L and IL-4 | 0.0 | 1.7 | 2.9 |
| 92665_EOL-1 (Eosinophil)_dbcAMP differentiated | 0.0 | 0.0 | 0.0 |
| 93248_EOL-1 (Eosinophil)_dbcAMP/PMAionomycin | 0.0 | 0.0 | 0.0 |
| 93356_Dendritic Cells_none | 0.0 | 0.0 | 0.7 |
| 93355_Dendritic Cells_LPS 100 ng/ml | 1.9 | 1.4 | 0.0 |
| 93775_Dendritic Cells_anti-CD40 | 0.0 | 0.0 | 0.0 |
| 93774_Monocytes_resting | 0.0 | 0.0 | 0.2 |
| 93776_Monocytes_LPS 50 ng/ml | 0.0 | 0.0 | 0.4 |
| 93581_Macrophages_resting | 0.0 | 1.5 | 0.0 |
| 93582_Macrophages_LPS 100 ng/ml | 6.4 | 0.0 | 0.0 |
| 93098_HUVEC (Endothelial)_none | 0.0 | 0.0 | 22.4 |
| 93099_HUVEC (Endothelial)_starved | 0.0 | 0.0 | 45.7 |
| 93100_HUVEC (Endothelial)_IL-1b | 0.0 | 0.0 | 4.1 |
| 93779_HUVEC (Endothelial)_IFN gamma | 0.0 | 0.0 | 38.7 |
| 93102_HUVEC (Endothelial)_TNF alpha + IFN gamma | 0.0 | 0.0 | 4.9 |
| 93101_HUVEC (Endothelial)_TNF alpha + IL4 | 0.0 | 0.0 | 6.4 |
| 93781_HUVEC (Endothelial)_IL-11 | 0.0 | 2.8 | 16.6 |
| 93583_Lung Microvascular Endothelial Cells_none | 0.0 | 1.1 | 92.7 |
| 93584_Lung Microvascular Endothelial Cells_TNFa (4 ng/ml) and IL1b (1 ng/ml) | 0.0 | 0.0 | 25.5 |
| 92662_Microvascular Dermal endothelium_none | 3.7 | 0.0 | 100.0 |
| 92663_Microvascular Dermal endothelium_TNFa (4 ng/ml) and IL1b (1 ng/ml) | 0.0 | 0.0 | 20.7 |
| 93773_Bronchial epithelium_TNFa (4 ng/ml) and IL1b (1 ng/ml)** | 3.9 | 3.2 | 0.0 |
| 93347_Small Airway Epithelium_none | 6.2 | 4.5 | 0.2 |
| 93348_Small Airway Epithelium_TNFa (4 ng/ml) and IL1b (1 ng/ml) | 11.2 | 9.7 | 1.6 |
| 92668_Coronery Artery SMC_resting | 5.8 | 5.9 | 3.3 |
| 92669_Coronery Artery SMC_TNFa (4 ng/ml) and IL1b (1 ng/ml) | 4.2 | 1.9 | 2.4 |
| 93107_astrocytes_resting | 61.1 | 41.5 | 27.2 |
| 93108_astrocytes_TNFa (4 ng/ml) and IL1b (1 ng/ml) | 78.6 | 69.9 | 10.4 |
| 92666_KU-812 (Basophil)_resting | 0.0 | 0.0 | 0.3 |
| 92667_KU-812 (Basophil)_PMA/ionomycin | 0.0 | 0.0 | 1.7 |
| 93579_CCD1106 (Keratinocytes)_none | 0.0 | 0.0 | 0.0 |
| 93580_CCD1106 (Keratinocytes)_TNFa and IFNg** | 0.0 | 0.0 | 0.0 |
| 93791_Liver Cirrhosis | 10.9 | 5.4 | 4.0 |
| 93792_Lupus Kidney | 0.0 | 2.3 | 10.4 |
| 93577_NCI-H292 | 11.6 | 2.8 | 0.0 |
| 93358_NCI-H292_IL4 | 2.9 | 3.3 | 0.0 |
| 93360_NCI-H292_IL-9 | 2.3 | 1.8 | 0.0 |
| 93359_NCI-H292_IL-13 | 2.8 | 0.0 | 0.0 |
| 93357_NCI-H292_IFN gamma | 3.8 | 0.0 | 0.3 |
| 93777_HPAEC_- | 0.0 | 0.0 | 57.8 |

TABLE 32-continued

Panel 4D

| Tissue Name | Relative Expression (%) 4dx4tm5043f__ag217_b1 | Relative Expression (%) 4dx4tm5056f__ag217_b1 | Relative Expression (%) 4Dtm2436t__ag1469 |
|---|---|---|---|
| 93778__HPAEC__IL-1 beta/TNA alpha | 0.0 | 0.0 | 8.8 |
| 93254__Normal Human Lung Fibroblast__none | 0.0 | 0.0 | 7.5 |
| 93253__Normal Human Lung Fibroblast__TNFa (4 ng/ml) and IL-1b (1 ng/ml) | 0.0 | 0.0 | 6.7 |
| 93257__Normal Human Lung Fibroblast__IL-4 | 0.0 | 0.0 | 13.8 |
| 93256__Normal Human Lung Fibroblast__IL-9 | 0.0 | 0.0 | 7.2 |
| 93255__Normal Human Lung Fibroblast__IL-13 | 0.0 | 0.0 | 20.6 |
| 93258__Normal Human Lung Fibroblast__IFN gamma | 0.0 | 1.3 | 34.6 |
| 93106__Dermal Fibroblasts CCD1070__resting | 40.7 | 30.0 | 1.5 |
| 93361__Dermal Fibroblasts CCD1070__TNF alpha 4 ng/ml | 13.1 | 17.9 | 8.2 |
| 93105__Dermal Fibroblasts CCD1070__IL-1 beta 1 ng/ml | 27.0 | 19.2 | 0.0 |
| 93772__dermal fibroblast__IFN gamma | 0.0 | 0.0 | 5.6 |
| 93771__dermal fibroblast__IL-4 | 2.3 | 2.6 | 7.0 |
| 93260__IBD Colitis 2 | 2.3 | 0.0 | 4.0 |
| 93261__IBD Crohns | 0.0 | 1.1 | 0.7 |
| 735010__Colon__normal | 18.6 | 5.9 | 2.3 |
| 735019__Lung__none | 13.2 | 8.1 | 10.6 |
| 64028-1__Thymus__none | 100.0 | 100.0 | 11.8 |
| 64030-1__Kidney__none | 3.9 | 1.6 | 2.8 |

TABLE 33

Panel 4.1D

| Tissue Name | Relative Expression (%) 4.1dx4tm6089f__ag850_b2 |
|---|---|
| 93768__Secondary Th1__anti-CD28/anti-CD3 | 0.0 |
| 93769__Secondary Th2__anti-CD28/anti-CD3 | 0.0 |
| 93770__Secondary Tr1__anti-CD28/anti-CD3 | 0.0 |
| 93573__Secondary Th1__resting day 4–6 in IL-2 | 0.0 |
| 93572__Secondary Th2__resting day 4–6 in IL-2 | 0.0 |
| 93571__Secondary Tr1__resting day 4–6 in IL-2 | 0.7 |
| 93568__primary Th1__anti-CD28/anti-CD3 | 0.2 |
| 93569__primary Th2__anti-CD28/anti-CD3 | 0.0 |
| 93570__primary Tr1__anti-CD28/anti-CD3 | 0.6 |
| 93565__primary Th1__resting dy 4–6 in IL-2 | 0.0 |
| 93566__primary Th2__resting dy 4–6 in IL-2 | 0.0 |
| 93567__primary Tr1__resting dy 4–6 in IL-2 | 0.0 |
| 93351__CD45RA CD4 lymphocyte__anti-CD28/anti-CD3 | 7.4 |
| 93352__CD45RO CD4 lymphocyte__anti-CD28/anti-CD3 | 0.2 |
| 93251__CD8 Lymphocytes__anti-CD28/anti-CD3 | 0.0 |
| 93353__chronic CD8 Lymphocytes 2ry__resting dy 4–6 in IL-2 | 0.2 |
| 93574__chronic CD8 Lymphocytes 2ry__activated CD3/CD28 | 0.3 |
| 93354__CD4__none | 0.0 |
| 93252__Secondary Th1/Th2/Tr1__anti-CD95 CH11 | 0.1 |
| 93103__LAK cells__resting | 0.0 |
| 93788__LAK cells__IL-2 | 0.0 |
| 93787__LAK cells __IL-2 + IL-12 | 0.0 |
| 93789__LAK cells__IL-2 + IFN gamma | 0.0 |
| 93790__LAK cells IL-2 + IL-18 | 0.0 |
| 93104__LAK cells__PMA/ionomycin and IL-18 | 0.6 |
| 93578__NK Cells IL-2__resting | 0.0 |
| 93109__Mixed Lymphocyte Reaction__Two Way MLR | 0.0 |
| 93110__Mixed Lymphocyte Reaction__Two Way MLR | 0.0 |
| 93111__Mixed Lymphocyte Reaction__Two Way MLR | 0.2 |
| 93112__Mononuclear Cells (PBMCs)__resting | 0.0 |
| 93113__Mononuclear Cells (PBMCs)__PWM | 0.0 |
| 93114__Mononuclear Cells (PBMCs)__PHA-L | 0.0 |
| 93249__Ramos (B cell) none | 0.0 |
| 93250__Ramos (B cell)__ionomycin | 0.0 |
| 93349__B lymphocytes__PWM | 0.0 |
| 93350__B lymphocytes__CD40L and IL-4 | 0.1 |
| 92665__EOL-1 (Eosinophil)__dbcAMP differentiated | 0.0 |
| 93248__EOL-1 (Eosinophil)__dbcAMP/PMAionomycin | 0.0 |
| 93356__Dendritic Cells__none | 0.0 |
| 93355__Dendritic Cells__LPS 100 ng/ml | 0.3 |
| 93775__Dendritic Cells__anti-CD40 | 0.0 |
| 93774__Monocytes__resting | 0.0 |
| 93776__Monocytes__LPS 50 ng/ml | 0.0 |
| 93581__Macrophages__resting | 0.0 |
| 93582__Macrophages__LPS 100 ng/ml | 0.8 |
| 93098__HUVEC (Endothelial)__none | 0.0 |
| 93099__HUVEC (Endothelial)__starved | 0.0 |
| 93100__HUVEC (Endothelial)__IL-1b | 0.0 |
| 93779__HUVEC (Endothelial)__IFN gamma | 0.8 |

TABLE 33-continued

Panel 4.1D

| Tissue Name | Relative Expression (%) 4.1dx4tm6089f_ag850_b2 |
|---|---|
| 93102_HUVEC (Endothelial)_TNF alpha + IFN gamma | 1.0 |
| 93101_HUVEC (Endothelial)_TNF alpha + IL4 | 0.0 |
| 93781_HUVEC (Endothelial)_IL-11 | 0.0 |
| 93583_Lung Microvascular Endothelial Cells_none | 0.0 |
| 93584_Lung Microvascular Endothelial Cells_TNFa (4 ng/ml) and IL1b (1 ng/ml) | 0.0 |
| 92662_Microvascular Dermal endothelium_none | 0.3 |
| 92663_Microvasular Dermal endothelium_TNFa (4 ng/ml) and IL1b (1 ng/ml) | 0.0 |
| 93773_Bronchial epithelium_TNFa (4 ng/ml) and IL1b (1 ng/ml)** | 0.9 |
| 93347_Small Airway Epithelium_none | 1.8 |
| 93348_Small Airway Epithelium_TNFa (4 ng/ml) and IL1b (1 ng/ml) | 4.0 |
| 92668_Coronery Artery SMC_resting | 1.8 |
| 92669_Coronery Artery SMC_TNFa (4 ng/ml) and IL1b (1 ng/ml) | 1.3 |
| 93107_astrocytes_resting | 31.9 |
| 93108_astrocytes_TNFa (4 ng/ml) and IL1b (1 ng/ml) | 33.4 |
| 92666_KU-812 (Basophil)_resting | 0.0 |
| 92667_KU-812 (Basophil)_PMA/ionomycin | 0.0 |
| 93579_CCD1106 (Keratinocytes)_none | 0.0 |
| 93580_CCD1106 (Keratinocytes)_TNFa and IFNg** | 0.0 |
| 93791_Liver Cirrhosis | 1.0 |
| 93577_NCI-H292 | 2.2 |
| 93358_NCI-H292_IL-4 | 1.1 |
| 93360_NCI-H292_IL-9 | 1.5 |
| 93359_NCI-H292_IL-13 | 0.9 |
| 93357_NCI-H292_IFN gamma | 0.3 |
| 93777_HPAEC_- | 0.0 |
| 93778_HPAEC_IL-i beta/TNA alpha | 0.0 |
| 93254_Normal Human Lung Fibroblast_none | 0.0 |
| 93253_Normal Human Lung Fibroblast_TNFa (4 ng/ml) and IL-1b (1 ng/ml) | 0.0 |
| 93257_Normal Human Lung Fibroblast_IL-4 | 0.1 |
| 93256_Normal Human Lung Fibroblast_IL-9 | 0.0 |
| 93255_Normal Human Lung Fibroblast_IL-13 | 0.1 |
| 93258_Normal Human Lung Fibroblast_IFN gamma | 0.8 |
| 93106_Dermal Fibroblasts CCD1070_resting | 14.5 |
| 93361_Dermal Fibroblasts CCD1070_TNF alpha 4 ng/ml | 15.2 |
| 93105_Dermal Fibroblasts CCD1070_IL-1 beta 1 ng/ml | 10.1 |
| 93772_dermal fibroblast_IFN gamma | 0.0 |
| 93771_dermal fibroblast_IL-4 | 0.0 |
| 93892_Dermal fibroblasts_none | 0.0 |
| 99202_Neutrophils_TNFa + LPS | 0.0 |
| 99203_Neutrophils_none | 0.0 |
| 735010_Colon_normal | 0.6 |
| 735019_Lung_none | 0.9 |
| 64028-1_Thymus_none | 6.0 |
| 64030-1_Kidney_none | 100.0 |

Panel 1 Summary: Ag217 Expression of the NOV4 gene is highest in placenta (CT=21.3). In addition, expression of this gene is also high in testis and uterus tissues. Thus, NOV4 gene expression could be used to distinguish placenta, and to a lesser degree testis and uterus tissue from other tissues. In addition, since these tissues are part of the reproductive system, this gene may play a role in reproduction. Therefore, therapeutic modulation of the NOV4 gene or its product might be of use in the treatment of diseases of reproduction, such as infertility. Furthermore, expression of the NOV4 is much higher in adult kidney (CT=26) than fetal kidney (CT=33) suggesting that this gene may be useful as a marker to distinguish the two.

Panel 1.3D Summary: Ag1469 Expression of the NOV4 gene on this panel is highest in cerebral cortex (CT=27.3). Thus, the expression of this gene might be used to distinguish cerebral cortex from other samples. Among CNS samples, this gene is more moderately expressed in fetal brain, amygdala, hippocampus and thalamus. NOV4 gene expression is also detected in hippocampal and cortical tissue on panel CNS_Neurodegeneration_V1.0, but does not show Alzheimer's disease-specific expression. The NOV4 gene encodes a protein with homology to plexin, a transmembrane cell adhesion molecule that interacts with the semaphorins in axon guidance and CNS development. Semaphorins can act as axon guidance proteins, specifically as chemorepellents that inhibit CNS regenerative capacity. Decreasing levels of this protein may be of use in inducing a compensatory synaptogenic response, as semaphorins are one of the major obstacles to CNS regeneration. Therefore, reducing the level of the NOV4 transcript or its protein product to may be beneficial in the treatment of Alzheimer's disease, Parkinson's disease, Huntington's disease, spinocerebellar ataxia, progressive supranuclear palsy, multiple sclerosis, ALS, head trauma, stroke, or any other disease/condition associated with neuronal loss.

The NOV4 gene is also moderately expressed in adipose and ovary. Interestingly, this gene is more highly expressed in fetal heart (CT=28) when compared to adult heart (CT=33) as well as in fetal skeletal muscle (CT=30) when compared to adult skeletal muscle (CT=37). Thus, the expression of the NOV4 gene might be used to distinguish fetal heart or muscle from adult tissue. Moreover, the therapeutic modulation of this gene, specifically its use in replacement type therapy through the administration of purified protein, might be beneficial in the treatment of diseases involving the degeneration of heart or skeletal muscle, such as the consequence of myocardial infarction or in muscular dystrophy.

General_Screening_Panel_v1.4 Summary: Ag217/Ag850 Results from two experiments using different probe/primer sets are in good agreement. Expression of the NOV4 gene on this panel is highest in a sample derived from a brain cancer cell line. In addition, there is substantial expression of this gene in pancreatic, colon, gastric and lung cancer cell lines. Thus, the expression of this gene could be used to distinguish the above mentioned sample types from other tissues. In addition, the therapeutic modulation of the NOV4 gene product, through the use of small molecule drugs or antibodies could be of benefit in the treatment of brain, pancreatic, gastric, colon or lung cancers.

This gene is also expressed at low to moderate levels in a number of other samples on this panel, including kidney, placenta, testis, cerebral cortex and cerebellum.

Panel 2D Summary: Ag1469 Results from three experiments using the same probe/primer set are in good agreement. Expression of the NOV4 gene is highest in an ovarian cancer sample (CT=28). Interestingly, expression of this gene is lower in kidney tumors relative to matched normal kidney margins. This pattern of expression is observed in 6/9 of the normal adjacent kidney/kidney cancer pairs on this panel. Thus, expression of the NOV4 gene could be used as a marker to distinguish normal kidney tissue from kidney tumors and may also have diagnostic benefit. Finally, therapeutic modulation of this gene product might have benefit in the treatment of kidney cancer.

Panel 2.2 Summary: Ag217/Ag850 Results from two experiments using different probe/primer sets are in reasonable agreement. Expression of the NOV4 gene is highest in a sample derived from normal kidney tissue adjacent to a kidney cancer, among the samples on this panel. Furthermore, in the majority of cases this gene is expressed more highly in normal kidney tissues adjacent to kidney cancers. These results are consistent with what is seen in Panel 2D. Thus, expression of the NOV4 gene could be used to distinguish normal kidney tissue from kidney cancer. In addition, therapeutic modulation of the protein encoded by this gene may be of use in the treatment of kidney cancer.

Panel 4D Summary: AR217/Ag1469 Results from two experiments using different probe/primer sets show some differences. Using the Ag1469 probe/primer set, the NOV4 gene is moderately expressed in the microvascular dermal and lung endothelium (CT 29.2) as well as in primary Tr1 and Th2 T cells. With the Ag217 probe/primer set, the NOV4 gene is expressed at moderate levels in thymus and astrocytes independent of treatment. In addition, lower expression of this gene is seen in dermal fibroblasts. The protein encoded by the NOV4 gene is homologous to murine plexin 2, a transmembrane cell-adhesion molecule. Plexins are receptors for multiple (and perhaps all) classes of semaphorins. Semaphorins influence neural regeneration. Therefore, the expression of this gene in astrocytes suggests that the use of small molecule drugs could be favorable for the treatment of CNS injury. Expression of the NOV4 gene in thymus and some T cells (with Ag1469) suggests a potential role for this plexin in development or differentiation. Therefore, antibodies raised against this protein might be useful as a marker or to modulate T cell differentiation for the treatment of T cell-mediated diseases.

Panel 4.1D Summary: Ag850 The NOV4 gene is expressed in normal kidney, thymus, a dermal fibroblast cell line (CCD1070) and in astrocytes, among the samples on this panel. Expression of this gene is highest in kidney (CT=28.1), consistent with what is observed in Panel 2.2. The NOV4 gene encodes a protein that has homology to retinoic acid-responsive protein, which is known to be expressed at blood organ barriers and may function in transport (ref. 3). Astrocytes contribute to the blood brain barrier (ref. 4), so based on the homology of this gene to Stra6 and its expression in astrocytes, the NOV4 gene product may be important in maintaining the blood brain barrier and perhaps in the transport of small molecules across this barrier. Therefore, regulation of NOV4 gene product with small molecule therapeutics could allow the passage of specific therapeutic molecules into the brain usually blocked by tight junctions. Furthermore, modulation of the function of this protein may also be important in the treatment of autism, since it has been recently shown that autism may be linked to pathology associated with infection and this particular gene is found within a chromosomal locus associated with autism (ref. 5).

REFERENCES

1. Murakami Y., Suto F., Shimizu M., Shinoda T., Kameyama T., Fujisawa H. (2001) Differential expression of plexin-A subfamily members in the mouse nervous system. Dev. Dyn. 220:246–258.

Plexins comprise a family of transmembrane proteins (the plexin family) which are expressed in nervous tissues. Some plexins have been shown to interact directly with secreted or transmembrane semaphorins, while plexins belonging to the A subfamily are suggested to make complexes with other membrane proteins, neuropilins, and propagate chemorepulsive signals of secreted semaphorins of class 3 into cells or neurons. Despite that much information has been gathered on the plexin-semaphorin interaction, the role of plexins in the nervous system is not well understood. To gain insight into the functions of plexins in the nervous system, spatial and temporal expression patterns of three members of the plexin-A subfamily (plexin-A1, -A2, and -A3) were analyzed in the developing mouse nervous system by in situ hybridization analysis in combination with immunohistochemistry. The three plexins are differentially expressed in sensory receptors or neurons in a developmentally regulated manner, suggesting that a particular plexin or set of plexins is shared by neuronal elements and functions as the receptor for semaphorins to regulate neuronal development.

PMID: 11241833

2. Ohta K., Mizutani A., Kawakami A., Murakami Y., Kasuya Y., Takagi S., Tanaka H., Fujisawa H. (1995) Plexin: a novel neuronal cell surface molecule that mediates cell adhesion via a homophilic binding mechanism in the presence of calcium ions. Neuron 14:1189–1199.

Plexin (previously referred to as B2) is a neuronal cell surface molecule that has been identified in *Xenopus*. cDNA cloning reveals that plexin has no homology to known neuronal cell surface molecules but possesses, in its extracellular segment, three internal repeats of cysteine clusters that are homologous to the cysteine-rich domain of the c-met proto-oncogene protein product. The exogenous plexin proteins expressed on the surfaces of L cells by cDNA transfection mediate cell adhesion via a homophilic binding mechanism, under the presence of calcium ions. Plexin is expressed in the receptors and neurons of particular sensory systems. These findings indicate that plexin is a novel calcium-dependent cell adhesion molecule and suggest its involvement in specific neuronal cell interaction and/or contact.

3. Bouillet P., Sapin V, Chazaud C., Messaddeq N., Decimo D., Dolle P., Chambon P. (1997) Developmental expression pattern of Stra6, a retinoic acid-responsive gene encoding a new type of membrane protein. Mech. Dev. 63: 173–186.

Retinoic acid plays important roles in development, growth and differentiation by regulating the expression of target genes. A new retinoic acid-inducible gene, Stra6, has been identified in P19 embryonal carcinoma cells using a subtractive hybridization cDNA cloning technique. Stra6 codes for a very hydrophobic membrane protein of a new type, which does not display similarities with previously characterized integral membrane proteins. Stra6, which exhibits a specific pattern of expression during development and in the adult, is strongly expressed at the level of blood-organ barriers. Interestingly, in testis Sertoli cells, Stra6 has a spermatogenic cycle-dependent expression which is lost in testes of RAR alpha null mutants where Stra6 is expressed in all tubules. The Stra6 protein may be a component of an as yet unidentified transport machinery.

PMID: 9203140

4. Pardridge W. M. (1999) Blood-brain barrier biology and methodology. J. Neurovirol. 5: 556–69.

The blood-brain barrier (BBB) is formed by epithelial-like high resistance tight junctions within the endothelium of capillaries perfusing the vertebrate brain. Because of the presence of the BBB, circulating molecules gain access to brain cells only via one of two processes: (i) lipid-mediated transport of small molecules through the BBB by free diffusion, or (ii) catalyzed transport. The latter includes carrier-mediated transport processes for low molecular weight nutrients and water soluble vitamins or receptor-mediated transport for circulating peptides (e.g., insulin), plasma proteins (e.g., transferrin), or viruses. While BBB permeability, per se, is controlled by the biochemical properties of the plasma membranes of the capillary endothelial cells, overall brain microvascular biology is a function of the paracrine interactions between the capillary endothelium and the other two major cells comprising the microcirculation of brain, i.e., the capillary pericyte, which shares the basement membrane with the endothelial cell, and the astrocyte foot process, which invests 99% of the abluminal surface of the capillary basement membrane in brain. Microvascular functions frequently ascribed to the capillary endothelium are actually executed by either the capillary pericyte or the capillary astrocyte foot process. With respect to BBB methodology, there are a variety of in vivo methods for studying biological transport across this important membrane. The classical physiologic techniques may now be correlated with modem biochemical and molecular biological approaches using freshly isolated animal or human brain capillaries. Isolated brain capillary endothelial cells can also be grown in tissue culture to form an 'in vitro BBB' model. However, BBB research cannot be performed using only the in vitro BBB model, but rather it is necessary to correlate observations made with the in vitro BBB model with in vivo studies.

PMID: 10602397

5. Homig M., Weissenbock H., Horscroft N., Lipkin W. I. (1999) An infection-based model of neurodevelopmental damage. Proc. Natl. Acad. Sci. USA 96: 12102–12107.

Perinatal exposure to infectious agents and toxins is linked to the pathogenesis of neuropsychiatric disorders, but the mechanisms by which environmental triggers interact with developing immune and neural elements to create neurodevelopmental disturbances are poorly understood. Hornig et al. describe a model for investigating disorders of central nervous system development based on neonatal rat infection with Borna disease virus, a neurotropic noncytolytic RNA virus. Infection results in abnormal righting reflexes, hyperactivity, inhibition of open-field exploration, and stereotypic behaviors. Architecture is markedly disrupted in hippocampus and cerebellum, with reduction in granule and Purkinje cell numbers. Neurons are lost predominantly by apoptosis, as supported by increased mRNA levels for pro-apoptotic products (Fas, caspase-1), decreased mRNA levels for the anti-apoptotic bcl-x, and in situ labeling of fragmented DNA. Although inflammatory infiltrates are observed transiently in frontal cortex, glial activation (microgliosis >astrocytosis) is prominent throughout the brain and persists for several weeks in concert with increased levels of proinflammatory cytokine mRNAs (interleukins 1alpha, 1beta, and 6 and tumor necrosis factor alpha) and progressive hippocampal and cerebellar damage. The resemblance of these functional and neuropathologic abnormalities to human neurodevelopmental disorders suggests the utility of this model for defining cellular, biochemical, histologic, and functional outcomes of interactions of environmental influences with the developing central nervous system.

PMID: 10518583

NOV5

Expression of gene NOV5 was assessed using the primer-probe set Ag2976, described in Table 34. Results from RTQ-PCR runs are shown in Tables 35, 36, 37, 38, and 39.

TABLE 34

Probe Name Ag2976

| Primers | Sequences | TM | Length | Start Position | SEQ ID NO: |
|---|---|---|---|---|---|
| Forward | 5'-ACCCCAAATGGATTCCATTA-3' | 59 | 20 | 1428 | 109 |
| Probe | FAM-5'-CCCTCATGGATCTGCATAACCACACA-3'-TAMRA | 69.9 | 26 | 1465 | 110 |
| Reverse | 5'-CTTGTGTGTGCATGCTTGTC-3' | 58.9 | 20 | 1516 | 111 |

TABLE 35

Panel 1.3D

| | Relative Expression (%) | |
|---|---|---|
| Tissue Name | 1.3dtm3946f_ag2976 | 1.3dx4tm5499f_ag2976_b2 |
| Liver adenocarcinoma | 0.0 | 0.0 |
| Pancreas | 0.0 | 0.0 |
| Pancreatic ca CAPAN 2 | 0.0 | 0.0 |
| Adrenal gland | 0.0 | 0.7 |
| Thyroid | 0.0 | 0.0 |
| Salivary gland | 0.0 | 0.0 |
| Pituitary gland | 0.4 | 0.0 |
| Brain (fetal) | 0.7 | 1.0 |
| Brain (whole) | 1.1 | 6.5 |
| Brain (amygdala) | 6.9 | 4.4 |
| Brain (cerebellum) | 0.0 | 0.9 |
| Brain (hippocampus) | 18.9 | 3.3 |
| Brain (substantia nigra) | 1.9 | 7.5 |
| Brain (thalamus) | 2.0 | 5.5 |
| Cerebral Cortex | 5.0 | 5.3 |
| Spinal cord | 0.2 | 0.3 |
| CNS ca. (glio/astro) U87-MG | 1.5 | 0.7 |
| CNS ca. (glio/astro) U-118-MG | 0.6 | 0.4 |
| CNS ca (astro) SW1783 | 0.3 | 0.0 |
| CNS ca.* (neuro; met) SK-N-AS | 0.0 | 0.0 |
| CNS ca. (astro) SF-539 | 0.0 | 0.0 |
| CNS ca.. (astro) SNB-75 | 0.0 | 0.0 |
| CNS ca. (glio) SNB-19 | 0.0 | 0.0 |
| CNS ca. (glio) U251 | 0.0 | 0.5 |
| CNS ca (glio) SF-295 | 0.0 | 0.0 |
| Heart (fetal) | 0.2 | 0.0 |
| Heart | 0.0 | 0.0 |
| Fetal Skeletal | 6.8 | 3.5 |
| Skeletal muscle | 0.1 | 0.8 |
| Bone marrow | 0.0 | 0.0 |
| Thymus | 0.0 | 0.5 |

TABLE 35-continued

Panel 1.3D

| Tissue Name | Relative Expression (%) 1.3dtm3946f_ag2976 | 1.3dx4tm5499f_ag2976_b2 |
| --- | --- | --- |
| Spleen | 0.0 | 1.8 |
| Lymph node | 100.0 | 0.2 |
| Colorectal | 0.8 | 1.3 |
| Stomach | 54.0 | 100.0 |
| Small intestine | 0.4 | 0.5 |
| Colon ca. SW480 | 0.0 | 0.0 |
| Colon ca.* (SW480 met) SW620 | 1.0 | 1.8 |
| Colon ca. HT29 | 0.2 | 0.0 |
| Colon ca. HCT-116 | 0.0 | 0.0 |
| Colon ca. CaCo-2 | 0.0 | 0.0 |
| 83219 CC Well to Mod Diff (ODO3866) | 0.6 | 0.0 |
| Colon ca. HCC-2998 | 0.2 | 0.0 |
| Gastric ca.* (liver met) NCI-N87 | 0.4 | 0.3 |
| Bladder | 0.4 | 0.4 |
| Trachea | 0.0 | 0.0 |
| Kidney | 0.0 | 0.0 |
| Kidney (fetal) | 0.0 | 0.0 |
| Renal ca. 786-0 | 0.3 | 0.0 |
| Renal ca. A498 | 0.2 | 0.5 |
| Renal ca. RXF 393 | 0.0 | 0.0 |
| Renal ca. ACHN | 0.0 | 0.0 |
| Renal ca. UO-31 | 0.0 | 0.0 |
| Renal ca. TK-10 | 0.0 | 0.0 |
| Liver | 0.2 | 0.0 |
| Liver (fetal) | 0.0 | 0.0 |
| Liver ca (hepatoblast) HepG2 | 0.0 | 0.0 |
| Lung | 0.3 | 0.2 |
| Lung (fetal) | 0.6 | 0.0 |
| Lung ca. (small Cell) LX-1 | 0.9 | 3.6 |
| Lung ca. (small Cell) NCI-H69 | 3.6 | 2.4 |
| Lung ca. (s. cell var.) SHP-77 | 2.9 | 1.4 |
| Lung ca. (large cell) NCI-H460 | 0.0 | 19.9 |
| Lung ca. (non-sm. cell) A549 | 0.0 | 0.0 |
| Lung ca. (non-s. cell) NCI-H23 | 0.6 | 0.2 |
| Lung ca (non-s. cell) HOP-62 | 0.0 | 0.7 |
| Lung ca. (non-s. cl) NCI-H522 | 0.0 | 0.0 |
| Lung ca. (squam.) SW 900 | 0.0 | 0.0 |
| Lung ca. (squam.) NCI-H596 | 0.2 | 0.2 |
| Mammary gland | 0.2 | 0.0 |
| Breast ca. * (pl. effusion) MCF-7 | 0.3 | 0.4 |
| Breast ca.* (pl. ef) MDA-MB-231 | 0.1 | 0.0 |
| Breast ca.* (pl. effusion) T47D | 0.0 | 0.0 |
| Breast ca. BT-549 | 0.2 | 0.2 |
| Breast ca. MDA-N | 0.3 | 0.0 |
| Ovary | 0.1 | 0.0 |
| Ovarian ca. OVCAR-3 | 0.6 | 0.0 |
| Ovarian ca. OVCAR-4 | 0.0 | 0.0 |
| Ovarian ca. OVCAR-5 | 0.0 | 0.0 |
| Ovarian ca. OVCAR-8 | 2.0 | 0.0 |
| Ovarian ca. IGROV-1 | 0.0 | 0.0 |
| Ovarian ca.* (ascites) SK-OV-3 | 0.0 | 0.0 |
| Uterus | 0.0 | 0.0 |
| Placenta | 0.3 | 0.0 |
| Prostate | 0.0 | 0.0 |
| Prostate ca.* (bone met) PC-3 | 0.1 | 0.0 |
| Testis | 8.8 | 13.6 |
| Melanoma Hs688(A).T | 0.0 | 0.0 |
| Melanoma* (met) Hs688(B).T | 0.0 | 0.0 |
| Melanoma UACC-62 | 0.1 | 0.0 |
| Melanoma M14 | 0.2 | 0.0 |
| Melanoma LOX IMVI | 0.0 | 0.0 |
| Melanoma* (met) SK-MEL-5 | 0.2 | 0.5 |
| Adipose | 0.3 | 0.3 |

TABLE 36

Panel 2D

| Tissue Name | Relative Expression (%) 2dtm3947f_ag2976 |
| --- | --- |
| Normal Colon GENPAK 061003 | 12.9 |
| 83219 CC Well to Mod Diff (ODO3866) | 20.2 |
| 83220 CC NAT (ODO3866) | 12.9 |
| 83221 CC Gr. 2 rectosigmoid (ODO3868) | 0.0 |
| 83222 CC NAT (ODO3868) | 0.0 |
| 83235 CC Mod Diff (ODO3920) | 0.0 |
| 83236 CC NAT (ODO3920) | 0.0 |
| 83237 CC Gr. 2 ascend colon (ODO3921) | 10.6 |
| 83238 CC NAT (ODO3921) | 17.0 |
| 83241 CC from Partial Hepatectomy (ODO4309) | 0.0 |
| 83242 Liver NAT (ODO4309) | 0.7 |
| 87472 Colon mets to lung (OD04451-01) | 0.3 |
| 87473 Lung NAT (OD04451-02) | 0.0 |
| Normal Prostate Clontech A+ 6546-1 | 0.0 |
| 84140 Prostate Cancer (OD04410) | 0.5 |
| 84141 Prostate NAT (OD04410) | 1.6 |
| 87073 Prostate Cancer (OD04720-01) | 0.8 |
| 87074 Prostate NAT (OD04720-02) | 1.4 |
| Normal Lung GENPAK 061010 | 5.2 |
| 83239 Lung Met to Muscle (ODO4286) | 9.8 |
| 83240 Muscle NAT (ODO4286) | 0.0 |
| 84136 Lung Malignant Cancer (OD03126) | 0.0 |
| 84137 Lung NAT (OD03126) | 0.0 |
| 84871 Lung Cancer (OD04404) | 0.3 |
| 84872 Lung NAT (OD04404) | 0.5 |
| 84875 Lung Cancer (OD04565) | 0.8 |
| 84876 Lung NAT (OD04565) | 0.0 |
| 85950 Lung Cancer (OD04237-01) | 1.7 |
| 85970 Lung NAT (OD04237-02) | 0.7 |
| 83255 Ocular Mel Met to Liver (ODO4310) | 0.0 |
| 83256 Liver NAT (ODO4310) | 0.0 |
| 84139 Melanoma Mets to Lung (OD04321) | 0.0 |
| 84138 Lung NAT (OD04321) | 0.0 |
| Normal Kidney GENPAK 061008 | 0.8 |
| 83786 Kidney Ca, Nuclear grade 2 (OD04338) | 0.7 |
| 83787 Kidney NAT (OD04338) | 0.3 |
| 83788 Kidney Ca Nuclear grade 1/2 (OD04339) | 0.3 |
| 83789 Kidney NAT (OD04339) | 2.0 |
| 83790 Kidney Ca, Clear cell type (OD04340) | 0.2 |
| 83791 Kidney NAT (OD04340) | 1.5 |
| 83792 Kidney Ca, Nuclear grade 3 (OD04348) | 0.0 |
| 83793 Kidney NAT (OD04348) | 0.9 |
| 87474 Kidney Cancer (OD04622-01) | 0.0 |
| 87475 Kidney NAT (OD04622-03) | 0.0 |
| 85973 Kidney Cancer (OD04450-01) | 0.3 |
| 85974 Kidney NAT (OD04450-03) | 0.1 |
| Kidney Cancer Clontech 8120607 | 0.0 |
| Kidney NAT Clontech 8120608 | 0.0 |
| Kidney Cancer Clontech 8120613 | 0.0 |
| Kideny NAT Clontech 8120614 | 0.0 |
| Kidney Cancer Clontech 9010320 | 0.0 |
| Kidney NAT Clontech 9010321 | 0.3 |
| Normal Uterus GENPAK 061018 | 0.0 |
| Uterus Cancer GENPAK 064011 | 5.2 |
| Normal Thyroid Clontech A+ 6570-1 | 0.0 |
| Thyroid Cancer GENPAK 064010 | 0.0 |
| Thyroid Cancer INVITROGEN A302152 | 0.0 |
| Thyroid NAT INVITROGEN A302153 | 0.0 |
| Normal Break GENPAK 061019 | 0.0 |
| 84877 Breast Cancer (OD04566) | 0.0 |
| 85975 Breast Cancer (OD04590-01) | 0.0 |
| 85976 Breast Cancer Mets (OD04590-03) | 1.1 |
| 87070 Breast Cancer Metastasis (OD04655-05) | 0.0 |
| GENPAK Breast Cancer 064006 | 0.0 |
| Breast Cancer Res. Gen. 1024 | 6.2 |
| Breast Cancer Clontech 9100266 | 0.9 |
| Breast NAT Clontech 9100265 | 0.0 |
| Breast Cancer INVITROGEN A209073 | 1.4 |

TABLE 36-continued

Panel 2D

| Tissue Name | Relative Expression (%) 2dtm3947f_ag2976 |
|---|---|
| Breat NAT INVITROGEN A2090734 | 0.2 |
| Normal Liver GENPAK 061009 | 0.0 |
| Liver Cancer GENPAK 064003 | 5.7 |
| Liver Cancer Research Genetics RNA 1025 | 0.0 |
| Liver Cancer Research Genetics RNA 1026 | 0.0 |
| Paired Liver Cancer Tissue Research Genetics RNA 6004-T | 1.3 |
| Paired Liver Tissue Research Genetics RNA 6004-N | 2.5 |
| Paired Liver Cancer Tissue Research Genetics RNA 6005-T | 0.0 |
| Paired Liver Tissue Research Genetics RNA 6005-N | 3.1 |
| Normal Bladder GENPAK 061001 | 4.8 |
| Bladder Cancer Research Genetics RNA 1023 | 2.1 |
| Bladder Cancer INVITROGEN A302173 | 15.2 |
| 87071 Bladder Cancer (OD04718-01) | 2.0 |
| 87072 Bladder Normal Adjacent (OD04718-03) | 0.0 |
| Normal Ovary Res. Gen. | 4.6 |
| Ovarian Cancer GENPAK 064008 | 0.4 |
| 87492 Ovary Cancer (OD04768-07) | 0.9 |
| 87493 Ovary NAT (OD04768-08) | 0.0 |
| Normal Stomach GENPAK 061017 | 100.0 |
| Gastric Cancer Clontech 9060358 | 0.0 |
| NAT Stomach Clontech 9060359 | 70.2 |
| Gastric Cancer Clontech 9060395 | 0.0 |
| NAT Stomach Clontech 9060394 | 26.4 |
| Gastric Cancer Clontech 9060397 | 0.0 |
| NAT Stomach Clontech 9060396 | 33.0 |
| Gastric Cancer GENPAK 064005 | 2.5 |

TABLE 37

Panel 3D

| Tissue Name | Relative Expression (%) 3dx4tm5126f_ag2976_a1 | Tissue Name | Relative Expression (%) 3dx4tm5126f_ag2976_a1 |
|---|---|---|---|
| 94905_Daoy_Medulloblastoma/Cerebellum_sscDNA | 7.9 | 94954_Ca Ski_Cervical epidermoid carcinoma (metastasis)_sscDNA | 0.0 |
| 94906_TE671_Medulloblastom/Cerebellum_sscDNA | 0.0 | 94955_ES-2_Ovarian clear cell carcinoma_sscDNA | 0.0 |
| 94907_D283 Med_Medulloblastoma/Cerebellum_sscDNA | 0.0 | 94957_Ramos/6h stim_Stimulated with PMA/ionomycin 6h_sscDNA | 0.0 |
| 94908_PFSK-1_Primitive Neuroectodermal/Cerebellum_sscDNA | 0.0 | 94958_Ramos/14h stim_Stimulated with PMA/ionomycin 14h_sscDNA | 5.1 |
| 94909_XF-498_CNS_sscDNA | 0.0 | 94962_MEG-01_Chronic myelogenous leukemia (megakaryoblast)_sscDNA | 0.0 |
| 94910_SNB-78_CNS/glioma_sscDNA | 0.0 | 94963_Raji_Burkitt's lymphoma_sscDNA | 0.0 |
| 94911_SF-268_CNS/glioblastoma_sscDNA | 0.0 | 94964_Daudi_Burkitt's lymphoma_sscDNA | 0.0 |
| 94912_T98G_Glioblastoma_sscDNA | 0.0 | 94965_U266_B-cell plasmacytoma/myeloma_sscDNA | 0.0 |
| 96776_SK-N-SH_Neuroblastoma (metastasis)_sscDNA | 0.0 | 94968_CA46_Burkitt's lymphoma_sscDNA | 6.0 |
| 94913_SF-295_CNS/glioblastoma_sscDNA | 0.0 | 94970_RL_non-Hodgkin's B-cell lymphoma_sscDNA | 0.0 |
| 94914_Cerebellum_sscDNA | 19.4 | 94972_JM1_pre-B-cell lymphoma/leukemia_sscDNA | 0.0 |
| 96777_Cerebellum_sscDNA | 0.0 | 94973_Jurkat_T cell leukemia_sscDNA | 0.0 |
| 94916_NCI- | 0.0 | 94974_TF- | 0.0 |

TABLE 37-continued

Panel 3D

| Tissue Name | Relative Expression (%) 3dx4tm5126f_ag2976_a1 | Tissue Name | Relative Expression (%) 3dx4tm5126f_ag2976_a1 |
|---|---|---|---|
| H292__Mucoepidermoid lung carcinoma__sscDNA | | 1__Erythroleukemia__sscDNA | |
| 94917__DMS-114__Small cell lung cancer__sscDNA | 15.0 | 94975__HUT 78__T-cell lymphoma__sscDNA | 2.8 |
| 94918__DMS-79__Small cell lung cancer/neuroendocrine__sscDNA | 69.5 | 94977__U937__Histiocytic lymphoma__sscDNA | 0.0 |
| 94919__NCI-H146__Small cell lung cancer/neuroendocrine__sscDNA | 0.0 | 94980__KU-812__Myelogenous leukemia__sscDNA | 0.0 |
| 94920__NCI-H526__Small cell lung cancer/neuroendocrine__sscDNA | 75.8 | 94981__769-P__'Clear cell renal carcinoma__sscDNA | 0.0 |
| 94921__NCI-N417__Small cell lung cancer/neuroendocrine__sscDNA | 0.0 | 94983__Caki-2__Clear cell renal carcinoma__sscDNA | 0.0 |
| 94923__NCI-H82__Small cell lung cancer/neuroendocrine__sscDNA | 0.0 | 94984__SW 839__Clear cell renal carcinoma__sscDNA | 0.0 |
| 94924__NCI-H157__Squamous cell lung cancer (metastasis)__sscDNA | 19.4 | 94986__G401__Wilms' tumor__sscDNA | 0.0 |
| 94925__NCI-H1155__Large cell lung cancer/neuroendocrine__sscDNA | 100.0 | 94987__Hs766T__Pancreatic carcinoma (LN metastasis)__sscDNA | 4.5 |
| 94926__NCI-H1299__Large cell lung cancer/neuroendocrine__sscDNA | 5.8 | 94988__CAPAN-1__Pancreatic adenocarcinoma (liver metastasis)__sscDNA | 0.0 |
| 94927__NCI-H727__Lung carcinoid__sscDNA | 17.1 | 94989__SU86.86__Pancreatic carcinoma (liver metastasis)__sscDNA | 4.5 |
| 94928__NCI-UMC-11__Lung carcinoid__sscDNA | 0.0 | 94990__BxPC-3__Pancreatic adenocarcinoma__sscDNA | 0.0 |
| 94929__LX-1__Small cell lung cancer__sscDNA | 0.0 | 94991__HPAC__Pancreatic adenocarcinoma__sscDNA | 0.0 |
| 94930__Colo-205__Colon cancer__sscDNA | 0.0 | 94992__MIA PaCa-2__Pancreatic carcinoma__sscDNA | 0.0 |
| 94931__KM12__Colon cancer__sscDNA | 0.0 | 94993__CFPAC-1__Pancreatic ductal adenocarcinoma__sscDNA | 0.0 |
| 94932__KM20L2__Colon cancer__sscDNA | 0.0 | 94994__PANC-1__Pancreatic epithelioid ductal carcinoma__sscDNA | 5.0 |
| 94933__NCI-H716__Colon cancer__sscDNA | 0.0 | 94996__T24__Bladder carcinma (transitional cell)__sscDNA | 0.0 |
| 94935__SW-48__Colon adenocarcinoma__sscDNA | 0.0 | 94997__5637__Bladder carcinoma__sscDNA | 0.0 |
| 94936__SW1116__Colon adenocarcinoma__sscDNA | 0.0 | 94998__HT-1197__Bladder carcinoma__sscDNA | 32.2 |
| 94937__LS 174T__Colon adenocarcinoma__sscDNA | 0.0 | 94999__UM-UC-3__Bladder carcinma (transitional cell)__sscDNA | 0.0 |
| 94938__SW-948__Colon adenocarcinoma__sscDNA | 0.0 | 95000__A204__Rhabdomyosarcoma__sscDNA | 0.0 |
| 94939__SW-480__Colon adenocarcinoma__sscDNA | 19.4 | 95001__HT-1080__Fibrosarcoma__sscDNA | 0.0 |
| 94940__NCI-SNU-5__Gastric carcinoma__sscDNA | 0.0 | 95002__MG-63__Osteosarcoma (bone)__sscDNA | 0.0 |
| 94941__KATO III__Gastric carcinoma__sscDNA | 0.0 | 95003__SK-LMS-1__Leiomyosarcoma (vulva)__sscDNA | 0.0 |
| 94943__NCI-SNU-16__Gastric carcinoma__sscDNA | 5.2 | 95004__SJRH30__Rhabdomyosarcoma (met to bone marrow)__sscDNA | 0.0 |
| 94944__NCI-SNU-1__Gastric carcinoma__sscDNA | 0.0 | 95005__A431__Epidermoid-carcinoma__sscDNA | 13.9 |
| 94946__RF-1__Gastric adenocarcinoma__sscDNA | 0.0 | 95007__WM266-4__Melanoma__sscDNA | 0.0 |
| 94947__RF-48__Gastric adenocarcinoma__sscDNA | 5.1 | 95010__DU 145__Prostate carcinoma (brain metastasis)__sscDNA | 0.0 |
| 96778__MKN-45__Gastric | 0.0 | 95012__MDA-MB-468__Breast | 0.0 |

TABLE 37-continued

Panel 3D

| Tissue Name | Relative Expression (%) 3dx4tm5126f_ag2976_a1 | Tissue Name | Relative Expression (%) 3dx4tm5126f_ag2976_a1 |
|---|---|---|---|
| carcinoma_sscDNA | | adenocarcinoma_sscDNA | |
| 94949_NCI-N87_Gastric carcinoma_sscDNA | 0.0 | 95013_SCC-4_Squamous cell carcinoma of tongue_sscDNA | 0.0 |
| 94951_OVCAR-5_Ovarian carcinoma_sscDNA | 11.4 | 95014_SCC-9_Squamous cell carcinoma of tongue_sscDNA | 0.0 |
| 94952_RL95-2_Uterine carcinoma_sscDNA | 0.0 | 95015_SCC-15_Squamous cell carcinoma of tongue_sscDNA | 0.0 |
| 94953_HelaS3_Cervical adenocarcinoma_sscDNA | 0.0 | 95017_CAL 27_Squamous cell carcinoma of tongue_sscDNA | 0.0 |

TABLE 38

Panel 4D

| Tissue Name | Relative Expression (%) 4dtm3948f_ag2976 | Tissue Name | Relative Expression (%) 4dtm3948f_ag2976 |
|---|---|---|---|
| 93768_Secondary Th1_anti-CD28/anti-CD3 | 1.5 | 93100_HUVEC (Endothelial)_IL-1b | 0.0 |
| 93769_Secondary Th2_anti-CD28/anti-CD3 | 0.0 | 93779_HUVEC (Endothelial)_IFN gamma | 0.0 |
| 93770_Secondary Tr1_anti-CD28/anti-CD3 | 0.0 | 93102_HUVEC (Endothelial)_TNF alpha + IFN gamma | 0.0 |
| 93573_Secondary Th1_resting day 4–6 in IL-2 | 1.3 | 93101_HUVEC (Endothelial)_TNF alpha + IL4 | 0.0 |
| 93572_Secondary Th2_resting day 4–6 in IL-2 | 1.5 | 93781_HUVEC (Endothelial)_IL-11 | 0.0 |
| 93571_Secondary Tr1_resting day 4–6 in IL-2 | 0.0 | 93583_Lung Microvascular Endothelial Cells_none | 0.0 |
| 93568_primary Th1_anti-CD28/anti-CD3 | 0.0 | 93584_Lung Microvascular Endothelial Cells_TNFa (4 ng/ml) and IL1b (1 ng/ml) | 0.0 |
| 93569_primary Th2_anti-CD28/anti-CD3 | 0.0 | 92662_Microvascular Dermal endothelium_none | 0.0 |
| 93570_primary Tr1_anti-CD28/anti-CD3 | 0.0 | 92663_Microsvascular Dermal endothelium_TNFa (4 ng/ml) and IL1b (1 ng/ml) | 0.0 |
| 93565_primary Th1_resting dy 4–6 in IL-2 | 0.0 | 93773_Bronchial epithelium_TNFa (4 ng/ml) and IL1b (1 ng/ml)** | 0.0 |
| 93566_primary Th2_resting dy 4–6 in IL-2 | 0.0 | 93347_Small Airway Epithelium_none | 0.0 |
| 93567_primary Tr1_resting dy 4–6 in IL-2 | 0.0 | 93348_Small Airway Epithelium_TNFa (4 ng/ml) and IL1b (1 ng/ml) | 0.0 |
| 93351_CD45RA CD4 lymphocyte_anti-CD28/anti-CD3 | 0.0 | 92668_Coronery Artery SMC_resting | 3.0 |
| 93352_CD45RO CD4 lymphocyte_anti-CD28/anti-CD3 | 0.0 | 92669_Coronery Artery SMC_TNFa (4 ng/ml) and IL1b (1 ng/ml) | 0.0 |
| 93251_CD8 Lymphocytes_anti-CD28/anti-CD3 | 0.0 | 93107_astrocytes resting | 1.5 |
| 93353_chronic CD8 Lymphocytes 2ry_resting dy 4–6 in IL-2 | 0.0 | 93108_astrocytes_TNFa (4 ng/ml) and IL1b (1 ng/ml) | 0.0 |
| 93574_chronic CD8 Lymphocytes 2ry_activated CD3/CD28 | 0.0 | 92666_KU-812 (Basophil)_resting | 2.6 |
| 93354_CD4_none | 3.0 | 92667_KU-812 (Basophil)_PMA/ionoycin | 0.0 |
| 93252_Secondary Th1/Th2/Tr1_anti-CD95 CH11 | 0.0 | 93579_CCD1106 (Keratinocytes)_none | 0.0 |
| 93103_LAK cells resting | 0.0 | 93580_CCD1106 (Keratinocytes)_TNFa and | 3.3 |

TABLE 38-continued

Panel 4D

| Tissue Name | Relative Expression (%) 4dtm3948f_ag2976 | Tissue Name | Relative Expression (%) 4dtm3948f_ag2976 |
|---|---|---|---|
| | | IFNg** | |
| 93788_LAK cells_IL-2 | 0.0 | 93791_Liver Cirrhosis | 40.6 |
| 93787_LAK cells_IL-2 + IL-12 | 0.0 | 93792_Lupus Kidney | 1.0 |
| 93789_LAK cells_IL-2 + IFN gamma | 0.0 | 93577_NCI-H292 | 0.2 |
| 93790_LAK cells_IL-2 + IL-18 | 0.0 | 93358_NCI-H292_IL-4 | 0.0 |
| 93104_LAK cells_PMA/ionomycin and IL-18 | 2.8 | 93360_NCI-H292_IL-9 | 2.6 |
| 93578_NK Cells IL-2_resting | 0.0 | 93359_NCI-H292_IL-13 | 0.0 |
| 93109_Mixed Lymphocyte Reaction_Two Way MLR | 0.0 | 93357_NCI-H292_IFN gamma | 0.2 |
| 93110_Mixed Lymphocyte Reaction_Two Way MLR | 0.0 | 93777_HPAEC_- | 1.7 |
| 93111_Mixed Lymphocyte Reaction_Two Way MLR | 0.0 | 93778_HPAEC_IL-1 beta/TNA alpha | 0.0 |
| 93112_Mononuclear Cells (PBMCs)_resting | 0.0 | 93254_Normal Human Lung Fibroblast_none | 1.3 |
| 93113_Mononuclear Cells (PBMCs)_PWM | 1.6 | 93253_Normal Human Lung Fibroblast_TNFa (4 ng/ml) and IL-1b (1 ng/ml) | 0.0 |
| 93114_Mononuclear Cells (PBMCs)_PHA-L | 0.0 | 93257_Normal Human Lung Fibroblast_IL-4 | 1.7 |
| 93249_Ramos (B cell)_none | 6.2 | 93256_Normal Human Lung Fibroblast_IL-9 | 0.0 |
| 93250_Ramos (B cell)_ionomycin | 10.7 | 93255_Normal Human Lung Fibroblast_IL-13 | 2.8 |
| 93349_B lymphocytes_PWM | 0.0 | 93258_Normal Human Lung Fibroblast_IFN gamma | 0.0 |
| 93350_B lymphoytes_CD40L and IL-4 | 0.0 | 93106_Dermal Fibroblasts CCD1070_resting | 0.0 |
| 92665_EOL-1 (Eosinophil)_dbcAMP differentiated | 0.0 | 93361_Dermal Fibroblasts CCD1070_TNF alpha 4 ng/ml | 0.0 |
| 93248_EOL-1 (Eosinophil)_dbcAMP/PMA ionomycin | 0.0 | 93105_Dermal Fibroblasts CCD1070_IL-1 beta 1 ng/ml | 0.0 |
| 93356_Dendritic Cells_none | 0.0 | 93772_dermal fibroblast_IFN gamma | 1.4 |
| 93355_Dendritic Cells_LPS 100 ng/ml | 5.0 | 93771_dermal fibroblast_IL-4 | 12.5 |
| 93775_Dendritic Cells_anti-CD40 | 1.1 | 93260_IBD Colitis 2 | 4.9 |
| 93774_Monocytes_resting | 0.6 | 93261_IBD Crohns | 1.6 |
| 93776_Monocytes_LPS 50 ng/ml | 2.6 | 735010_Colon_normal | 100.0 |
| 93581_Macrophages_resting | 0.4 | 735019_Lung_none | 40.6 |
| 93582_Macrophages_LPS 100 ng/ml | 0.0 | 64028-1_Thymus_none | 2.1 |
| 93098_HUVEC (Endothelial)_none | 1.5 | 64030-1_Kidney_none | 1.6 |
| 93099_HIUVEC (Endothelial)_starved | 0.0 | | |

TABLE 39

Panel CNSD.01

| Tissue Name | Relative Expression (%) cns1x4tm6194f_ag2976_a2 | Tissue Name | Relative Expression (%) cns1x4tm6194f_ag2976_a2 |
|---|---|---|---|
| 102633_BA4 Control | 12.0 | 102605_BA17 PSP | 0.0 |
| 102641_BA4 Control2 | 51.2 | 102612_BA17 PSP2 | 5.3 |
| 102625_BA4 Alzheimer's2 | 2.6 | 102637_Sub Nigra Control | 13.9 |
| 102649_BA4 Parkinson's | 23.8 | 102645_Sub Nigra Control2 | 50.3 |
| 102656_BA4 Parkinson's2 | 51.6 | 102629_Sub Nigra | 13.9 |

TABLE 39-continued

Panel CNSD.01

| Tissue Name | Relative Expression (%) cns1x4tm6194f__ ag2976_a2 | Tissue Name | Relative Expression (%) cns1x4tm6194f__ ag2976_a2 |
|---|---|---|---|
| 102664_BA4 Huntington's | 25.2 | Alzheimer's2 | |
| 102671_BA4 Huntington's2 | 0.0 | 102660_Sub Nigra Parkinson's2 | 72.5 |
| 102603_BA4 PSP | 0.0 | 102667_Sub Nigra Huntington's | 87.2 |
| 102610_BA4 PSP2 | 10.2 | 102674_Sub Nigra Huntington's2 | 47.6 |
| 102588_BA4 Depression | 6.3 | 102614_SubNigraPSP2 | 6.1 |
| 102596_BA4 Depression2 | 0.0 | 102592_Sub Nigra Depression | 1.0 |
| 102634_BA7 Control | 14.2 | 102599_Sub Nigra Depression2 | 0.0 |
| 102642_BA7 Control2 | 55.8 | 102636_Glob Palladus Control | 6.3 |
| 102626_BA7 Alzheimer's2 | 9.4 | 102644_Glob Palladus Control2 | 24.9 |
| 102650_BA7 Parkinson's | 3.6 | 102620_Glob Palladus Alzheimer's | 15.8 |
| 102657_BA7 Parkinson's2 | 28.3 | 102628_Glob Palladus Alzheimer's2 | 1.0 |
| 102665_BA7 Huntington's | 34.7 | 102652_Glob Palladus Parkinson's | 17.6 |
| 102672_BA7 Huntington's2 | 13.6 | 102659_Glob Palladus Parkinson's2 | 4.8 |
| 102604_BA7 PSP | 6.6 | 102606_Glob Palladus PSP | 0.0 |
| 102611_BA7 PSP2 | 0.0 | 102613_Glob Palladus PSP2 | 0.0 |
| 102589_BA7 Depression | 0.0 | 102591_Glob Palladus Depression | 5.0 |
| 102632_BA9 Control | 16.1 | 102638_Temp Pole Control | 9.7 |
| 102640_BA9 Control2 | 100.0 | 102646_Temp Pole Control2 | 55.7 |
| 102617_BA9 Alzheimer's | 1.9 | 102622_Temp Pole Alzheimer's | 6.3 |
| 102624_BA9 Alzheimer's2 | 11.9 | 102630_Temp Pole Alzheimer's2 | 0.0 |
| 102648_BA9 Parkinson's | 9.3 | 102653_Temp Pole Parkinson's | 2.9 |
| 102655_BA9 Parkinson's2 | 29.7 | 102661_Temp Pole Parkinson's2 | 17.3 |
| 102663_BA9 Huntington's | 41.4 | 102668_Temp Pole Huntington's | 58.1 |
| 102670_BA9 Huntington's2 | 0.0 | 102607_Temp Pole PSP | 9.8 |
| 102602_BA9 PSP | 5.3 | 102615_Temp Pole PSP2 | 0.0 |
| 102609_BA9 PSP2 | 0.0 | 102600_Temp Pole Depression2 | 12.4 |
| 102587_BA9 Depression | 5.9 | 102639_Cing Gyr Control | 37.1 |
| 102595_BA9 Depression2 | 0.0 | 102647_Cing Gyr Control2 | 20.2 |
| 102635_BA17 Control | 13.4 | 102623_Cing Gyr Alzheimer's | 7.2 |
| 102643_BA17 Control2 | 30.9 | 102631_Cing Gyr Alzheiiner's2 | 12.4 |
| 102627_BA17 Alzheimer's2 | 6.2 | 102654_Cing Gyr Parkinson's | 5.4 |
| 102651_BA17 Parkinson's | 24.8 | 102662_Cing Gyr Parkinson's2 | 32.8 |
| 102658_BA17 Parkinson's2 | 26.0 | 102669_Cing Gyr Huntington's | 49.7 |
| 102666_BA17 Huntington's | 51.1 | 102676_Cing Gyr Huntington's2 | 14.1 |
| 102673_BA17 Huntington's2 | 11.8 | 102608_Cing Gyr PSP | 9.0 |
| 102590_BA17 Depression | 0.0 | 102616_Cing Gyr PSP2 | 5.3 |
| 102597_BA17 Depression2 | 4.8 | 102594_Cing Gyr Depression | 0.0 |
| | | 102601_Cing Gyr Depression2 | 0.0 |

Panel 1.3D Summary: Ag2976 Results from two experiments using the same probe/primer set show some discrepancies; therefore, only those results that are common between the two experiments will be considered here. The NOV5 gene is expressed at moderate levels in stomach (CT=28–29) and testis (CT=30–31). In addition, low but significant expression of this gene is seen in several parts of the CNS, including amygdala, hippocampus, substantia nigra, thalamus, and cerebral cortex. The NOV5 gene encodes a protein with homology to the dopamine receptor of the D1/D5 class. The dopamine (D2) receptor is the most well-established site of action of all known antipsychotics, suggesting a central role for the dopaminergic system in neuropsychiatric disease. The homology of this receptor with the dopamine D5 receptor makes it an excellent candidate drug target for psychiatric diseases, especially depression, bipolar disorder, schizophrenia, and schizoaffective disorder. In addition, NOV5 gene expression appears to be down regulated in a number of brain cancer cell lines.

Panel 2D Summary: Ag2976 Expression of the NOV5 gene is highest in stomach (CT=30), among the samples on this panel; this result is consistent with what is observed in Panel 1.3D. Interestingly, expression of this gene is lower in 3/3 gastric tumors when compared to the normal margins. Thus, expression of the NOV5 gene could be used to distinguish normal stomach tissue from gastric cancer tissue. In addition, therapeutic modulation of the NOV5 gene product might be of benefit for the treatment of gastric cancers.

Panel 3D Summary: Ag2976 Low but significant expression of the NOV5 gene is limited to three lung cancer cell lines. Thus, expression of this gene might be of use in the distinction of lung cancer cell lines from other cell lines.

Panel 4D Summary: Ag2976 Expression of the NOV5 gene is highest in colon (CT 30.2). Expression of this gene is decreased expression in IBD colitis and IBD Crohn's, suggesting a potential role in these diseases. In addition, the NOV5 gene is expressed at low levels in lung, dermal fibroblasts treated with IL-4, liver cirrhosis and Ramos B cells.

Panel CNSD.01 Summary: Ag2976 The NOV5 gene is expressed at low to moderate levels in the brain, and is present in at least hippocampus, cerebral cortex, subtantia nigra, thalamus, globus palladus and amygdala. In Panel CNS-1, this gene shows decreased expression in several regions of the brain of depressed patients. The dopamine (D2) receptor is the most well-established site of action of all known antipsychotics, suggesting a central role for the dopaminergic system in neuropsychiatric disease. The homology of this receptor with the dopamine D5 receptor, in addition to its downregulation in depression, makes it an excellent candidate drug target for psychiatric diseases, especially depression, bipolar disorder, schizophrenia, and schizoaffective disorder.

NOV7a and NOV7b

Expression of gene NOV7a and NOV7b was assessed using the primer-probe sets Ag760 and Ag1537, described in Tables 40 and 41. Results from RTQ-PCR runs are shown in Tables 42, 43, 44, and 45.

TABLE 42-continued

Panel 1.2

| Tissue Name | Relative Expression (%) 1.2tm880t__ ag760 | Relative Expression (%) 1.2tm2211f__ ag1537 |
|---|---|---|
| Pancreatic ca. CAPAN 2 | 0.0 | 0.0 |
| Adrenal Gland (new lot*) | 19.1 | 37.4 |
| Thyroid | 100.0 | 14.9 |
| Salavary gland | 15.8 | 34.6 |
| Pituitary gland | 27.4 | 2.1 |
| Brain (fetal) | 0.7 | 0.0 |
| Brain (whole) | 0.5 | 0.2 |
| Brain (amygdala) | 0.3 | 0.3 |
| Brain (cerebellum) | 0.1 | 0.0 |
| Brain (hippocampus) | 0.7 | 0.8 |
| Brain (thalamus) | 0.4 | 0.6 |
| Cerebral Cortex | 0.3 | 0.8 |
| Spinal cord | 0.6 | 0.1 |
| CNS ca. (glio/astro) U87-MG | 0.0 | 0.0 |
| CNS ca. (glio/astro) U-118-MG | 0.0 | 0.0 |
| CNS ca. (astro) SW1783 | 0.0 | 0.0 |
| CNS ca.* (neuro; met) SK-N-AS | 0.0 | 0.0 |
| CNS ca. (astro) SF-539 | 0.0 | 0.0 |

TABLE 40

Probe Name Ag760

| Primers | Sequences | TM | Length | Start Position | SEQ ID NO: |
|---|---|---|---|---|---|
| Forward | 5'-CACCATGACAACGACACCTATA-3' | 58.4 | 22 | 1924 | 112 |
| Probe | TET-5'-ATATGGCACCAACATCACATGCACG-3'-TAMRA | 69.7 | 25 | 1947 | 113 |
| Reverse | 5'-TGGGTAGAAAGTGTGTGTGAAA-3' | 58.2 | 22 | 1979 | 114 |

TABLE 41

Probe Name Ag1537

| Primers | Sequences | TM | Length | Start Position | SEQ ID NO: |
|---|---|---|---|---|---|
| Forward | 5'-AAGGAGCTGGAAGAGAAGAAGA-3' | 58.9 | 22 | 38 | 115 |
| Probe | FAM-5'-ATCAGAAACTCAGCCCTGGACACCTG-3'-TAMRA | 69.6 | 26 | 92 | 116 |
| Reverse | 5'-GCTGCGACTTGGTCTTGAT-3' | 59 | 19 | 119 | 117 |

TABLE 42

Panel 1.2

| Tissue Name | Relative Expression (%) 1.2tm880t__ ag760 | Relative Expression (%) 1.2tm2211f__ ag1537 |
|---|---|---|
| Endothelial cells | 1.3 | 2.5 |
| Heart (fetal) | 2.3 | 17.6 |
| Pancreas | 74.2 | 35.4 |

TABLE 42-continued

Panel 1.2

| Tissue Name | Relative Expression (%) 1.2tm880t__ ag760 | Relative Expression (%) 1.2tm2211f__ ag1537 |
|---|---|---|
| CNS ca. (astro) SNB-75 | 0.0 | 0.0 |
| CNS ca. (glio) SNB-19 | 0.0 | 0.0 |
| CNS ca. (glio) U251 | 0.2 | 0.1 |

TABLE 42-continued

Panel 1.2

| Tissue Name | Relative Expression (%) 1.2tm880t_ag760 | Relative Expression (%) 1.2tm2211f_ag1537 |
|---|---|---|
| CNS ca. (glio) SF-295 | 0.0 | 0.1 |
| Heart | 17.0 | 50.3 |
| Skeletal Muscle (new lot*) | 16.0 | 18.2 |
| Bone marrow | 1.4 | 2.7 |
| Thymus | 2.8 | 0.9 |
| Spleen | 30.8 | 29.1 |
| Lymph node | 14.4 | 2.7 |
| Colorectal | 1.1 | 2.3 |
| Stomach | 33.2 | 11.5 |
| Small intestine | 41.5 | 52.5 |
| Colon ca. SW480 | 0.0 | 0.0 |
| Colon ca.* (SW480 met)SW620 | 0.0 | 0.0 |
| Colon ca. HT29 | 0.0 | 0.0 |
| Colon ca. HCT-116 | 0.0 | 0.0 |
| Colon ca. CaCo-2 | 0.0 | 0.0 |
| 83219 CC Well to Mod Diff (ODO3866) | 1.4 | 1.7 |
| Colon ca. HCC-2998 | 0.0 | 0.0 |
| Gastric ca.* (liver met) NCI-N87 | 0.7 | 0.9 |
| Bladder | 13.1 | 52.5 |
| Trachea | 9.6 | 2.1 |
| Kidney | 22.4 | 100.0 |
| Kidney (fetal) | 31.9 | 23.8 |
| Renal ca. 786-0 | 0.0 | 0.0 |
| Renal ca. A498 | 0.1 | 0.0 |
| Renal ca. RXF 393 | 0.0 | 0.0 |
| Renal ca. ACHN | 0.0 | 0.0 |
| Renal ca UO-31 | 0.0 | 0.0 |
| Renal ca. TK-10 | 0.0 | 0.0 |
| Liver | 1.6 | 2.1 |
| Liver (fetal) | 4.0 | 4.4 |
| Liver ca. (hepatoblast) HepG2 | 0.0 | 0.0 |
| Lung | 4.1 | 1.0 |
| Lung (fetal) | 2.1 | 0.3 |
| Lung ca. (small cell) LX-1 | 0.0 | 0.0 |
| Lung ca. (small cell) NCI-H69 | 0.0 | 0.0 |
| Lung ca. (s.cell var.) SHP-77 | 0.0 | 0.0 |
| Lung ca. (large cell) NCI-H460 | 0.0 | 0.0 |
| Lung ca. (non-sm. cell) A549 | 0.0 | 0.0 |
| Lung ca. (non-s.cell) NCI-H23 | 0.0 | 0.0 |
| Lung ca (non-s.cell) HOP-62 | 0.0 | 0.0 |
| Lung ca. (non-s.cl) NCI-H522 | 0.0 | 0.0 |
| Lung ca. (squam.) SW 900 | 0.0 | 0.0 |
| Lung ca. (squam.) NCI-H596 | 0.0 | 0.0 |
| Mammary gland | 19.3 | 14.8 |
| Breast ca.* (pl. effusion) MCF-7 | 0.0 | 0.0 |
| Breast ca.* (pl.ef) MDA-MB-231 | 0.0 | 0.0 |
| Breast ca.* (pl. effusion) T47D | 0.0 | 0.0 |
| Breast ca. BT-549 | 0.0 | 0.0 |
| Breast ca. MDA-N | 1.2 | 2.2 |
| Ovary | 0.8 | 3.0 |
| Ovarian ca. OVCAR-3 | 0.0 | 0.0 |
| Ovarian ca. OVCAR-4 | 0.0 | 0.0 |
| Ovarian ca. OVCAR-5 | 0.1 | 0.1 |
| Ovarian ca. OVCAR-8 | 0.0 | 0.2 |
| Ovarian ca. IGROV-1 | 0.0 | 0.0 |
| Ovarian ca.* (ascites) SK-OV-3 | 0.0 | 0.0 |
| Uterus | 12.8 | 9.2 |
| Placenta | 7.3 | 3.1 |
| Prostate | 12.3 | 19.5 |
| Prostate ca.* (bone met)PC-3 | 0.0 | 0.0 |
| Testis | 1.4 | 0.2 |
| Melanoma Hs688(A).T | 0.0 | 0.0 |
| Melanoma* (met) Hs688(B).T | 0.0 | 0.0 |
| Melanoma UACC-62 | 0.0 | 0.0 |
| Melanoma M14 | 0.0 | 0.0 |
| Melanoma LOX IMVI | 0.0 | 0.0 |
| Melanoma* (met) SK-MEL-5 | 0.0 | 0.0 |

TABLE 43

Panel 1.3D

| Tissue Name | Relative Expression (%) 1.3dx4tm5483t_ag760_b2 | Tissue Name | Relative Expression (%) 1.3dx4tm5483t_ag760_b2 |
|---|---|---|---|
| Liver adenocarcinoma | 0.0 | Kidney (fetal) | 33.4 |
| Pancreas | 43.7 | Renal ca. 786-0 | 0.0 |
| Pancreatic ca. CAPAN 2 | 0.0 | Renal ca. A498 | 0.2 |
| Adrenal gland | 21.5 | Renal ca. RXF 393 | 0.0 |
| Thyroid | 79.7 | Renal ca. ACHN | 0.0 |
| Salivary gland | 13.9 | Renal ca. UO-31 | 0.0 |
| Pituitary gland | 13.4 | Renal ca. TK-10 | 0.0 |
| Brain (fetal) | 0.7 | Liver | 1.9 |
| Brain (whole) | 0.9 | Liver (fetal) | 12.4 |
| Brain (amygdala) | 1.6 | Liver ca. (hepatoblast) HepG2 | 0.0 |
| Brain (cerebellum) | 0.4 | Lung | 15.3 |
| Brain (hippocampus) | 1.8 | Lung (fetal) | 6.1 |
| Brain (substantia nigra) | 2.3 | Lung ca. (small cell) LX-1 | 0.0 |
| Brain (thalamus) | 2.7 | Lung ca. (small cell) NCI-H69 | 0.0 |
| Cerebral Cortex | 0.7 | Lung ca. (s.cell var.) SHP-77 | 0.0 |
| Spinal cord | 1.7 | Lung ca. (large cell) NCI-H460 | 0.4 |
| CNS ca. (glio/astro) U87-MG | 0.0 | Lung ca. (non-sm. cell) A549 | 0.0 |
| CNS ca. (glio/astro) U-118-MG | 0.0 | Lung ca. (non-s.cell) NCI-H23 | 0.0 |
| CNS ca. (astro) SW1783 | 0.0 | Lung ca (non-s.cell) HOP-62 | 0.0 |
| CNS ca.* (neuro; met) SK-N-AS | 0.0 | Lung ca. (non-s.cl) NCI-H522 | 0.0 |
| CNS ca. (astro) SF-539 | 0.0 | Lung ca. (squam.) SW 900 | 0.0 |
| CNS ca. (astro) SNB-75 | 0.0 | Lung ca. (squam.) NCI-H596 | 0.0 |
| CNS ca. (glio) SNB-19 | 0.0 | Mammary gland | 26.7 |

TABLE 43-continued

Panel 1.3D

| Tissue Name | Relative Expression (%) 1.3dx4tm5483t_ag760_b2 | Tissue Name | Relative Expression (%) 1.3dx4tm5483t_ag760_b2 |
|---|---|---|---|
| CNS ca. (glio) U251 | 0.7 | Breast ca.* (pl. effusion) MCF-7 | 0.0 |
| CNS ca. (glio) SF-295 | 0.0 | Breast ca.* (pl.ef) MDA-MB-231 | 0.0 |
| Heart (fetal) | 6.9 | Breast ca.* (pl. effusion) T47D | 0.0 |
| Heart | 10.9 | Breast ca. BT-549 | 0.0 |
| Fetal Skeletal | 19.4 | Breast ca. MDA-N | 0.2 |
| Skeletal muscle | 9.9 | Ovary | 1.8 |
| Bone marrow | 7.8 | Ovarian ca. OVCAR-3 | 0.0 |
| Thymus | 6.9 | Ovarian ca. OVCAR-4 | 0.0 |
| Spleen | 90.4 | Ovarian ca. OVCAR-5 | 0.0 |
| Lymph node | 73.5 | Ovarian ca. OVCAR-8 | 0.0 |
| Colorectal | 7.9 | Ovarian ca. IGROV-1 | 0.0 |
| Stomach | 65.6 | Ovarian ca.* (ascites) SK-OV-3 | 0.0 |
| Small intestine | 100.0 | Uterus | 87.5 |
| Colon ca. SW480 | 0.0 | Placenta | 6.4 |
| Colon ca.* (SW480 met)SW620 | 0.0 | Prostate | 11.3 |
| Colon ca. HT29 | 0.0 | Prostate ca.* (bone met)PC-3 | 0.0 |
| Colon ca. HCT-116 | 0.0 | Testis | 2.1 |
| Colon ca. CaCo-2 | 0.0 | Melanoma Hs688(A).T | 0.0 |
| 83219 CC Well to Mod Diff (ODO3866) | 24.0 | Melanoma* (met) Hs688(B).T | 0.0 |
| Colon Ca. HCC-2998 | 0.0 | Melanoma UACC-62 | 0.0 |
| Gastric ca.* (liver met) NCI-N87 | 1.7 | Melanoma M14 | 0.0 |
| Bladder | 17.0 | Melanoma LOX IMVI | 0.0 |
| Trachea | 26.9 | Melanoma* (met) SK-MEL-5 | 0.0 |
| Kidney | 18.2 | Adipose | 26.6 |

TABLE 44

Panel 2D

| Tissue Name | Relative Expression (%) 2dtm2348f_ag1537 | Tissue Name | Relative Expression (%) 2dtm2348f_ag1537 |
|---|---|---|---|
| Normal Colon GENPAK 061003 | 12.3 | Kidney NAT Clontech 8120608 | 23.5 |
| 83219 CC Well to Mod Diff (ODO3866) | 10.7 | Kidney Cancer Clontech 8120613 | 21.5 |
| 83220 CC NAT (ODO3866) | 12.2 | Kidney NAT Clontech 8120614 | 12.3 |
| 83221 CC Gr.2 rectosigmoid (ODO3868) | 3.2 | Kidney Cancer Clontech 9010320 | 34.4 |
| 83222 CC NAT (ODO3868) | 0.8 | Kidney NAT Clontech 9010321 | 27.7 |
| 83235 CC Mod Duff (ODO3920) | 3.4 | Normal Uterus GENPAK 061018 | 9.3 |
| 83236 CC NAT (ODO3920) | 2.2 | Uterus Cancer GENPAK 064011 | 6.4 |
| 83237 CC Gr.2 ascend colon (ODO3921) | 13.4 | Normal Thyroid Clontech A+ 6570-1 | 84.1 |
| 83238 CC NAT (ODO3921) | 5.8 | Thyroid Cancer GENPAK 064010 | 20.6 |
| 83241 CC from Partial Hepatectomy (ODO4309) | 9.6 | Thyroid Cancer INVITROGEN A302152 | 15.2 |
| 83242 Liver NAT (ODO4309) | 0.6 | Thyroid NAT INVITROGEN A302153 | 21.3 |
| 87472 Colon mets to lung (ODO4451-01) | 5.5 | Normal Breast GENPAK 061019 | 22.1 |
| 87473 Lung NAT (ODO4451-02) | 0.8 | 84877 Breast Cancer (ODO4566) | 8.4 |
| Normal Prostate Clontech A+ 6546-1 | 14.1 | 85975 Breast Cancer (ODO4590-01) | 21.0 |
| 84140 Prostate Cancer (ODO4410) | 8.8 | 85976 Breast Cancer Mets (ODO4590-03) | 27.7 |
| 84141 Prostate NAT (ODO4410) | 6.9 | 87070 Breast Cancer Metastasis (ODO4655-05) | 9.1 |
| 87073 Prostate Cancer (OD04720-01) | 3.1 | GENPAK Breast Cancer 064006 | 10.1 |

TABLE 44-continued

Panel 2D

| Tissue Name | Relative Expression (%) 2dtm2348f_ag1537 | Tissue Name | Relative Expression (%) 2dtm2348f_ag1537 |
|---|---|---|---|
| 87074 Prostate NAT (OD04720-02) | 10.3 | Breast Cancer Res. Gen. 1024 | 7.1 |
| Normal Lung GENPAK 061010 | 11.8 | Breast Cancer Clontech 9100266 | 10.4 |
| 83239 Lung Met to Muscle (OD04286) | 6.4 | Breast NAT Clontech 9100265 | 7.4 |
| 83240 Muscle NAT (OD04286) | 9.9 | Breast Cancer INVITROGEN A209073 | 27.4 |
| 84136 Lung Malignant Cancer (OD03126) | 19.3 | Breast NAT INVITROGEN A2090734 | 8.7 |
| 84137 Lung NAT (OD03126) | 3.3 | Normal Liver GENPAK 061009 | 1.1 |
| 84871 Lung Cancer (OD04404) | 5.2 | Liver Cancer GENPAK 064003 | 6.5 |
| 84872 Lung NAT (OD04404) | 25.3 | Liver Cancer Research Genetics RNA 1025 | 0.7 |
| 84875 Lung Cancer (OD04565) | 3.4 | Liver Cancer Research Genetics RNA 1026 | 8.1 |
| 84876 Lung NAT (OD04565) | 3.1 | Paired Liver Cancer Tissue Research Genetics RNA 6004-T | 1.9 |
| 85950 Lung Cancer (OD04237-01) | 11.0 | Paired Liver Tissue Research Genetics RNA 6004-N | 3.6 |
| 85970 Lung NAT (OD04237-02) | 18.2 | Paired Liver Cancer Tissue Research Genetics KNA 6005-T | 9.3 |
| 83255 Ocular Mel Met to Liver (OD04310) | 0.7 | Paired Liver Tissue Research Genetics RNA 6005-N | 0.6 |
| 83256 Liver NAT (OD04310) | 1.7 | Normal Bladder GENPAK 061001 | 14.1 |
| 84139 Melanoma Mets to Lung (OD04321) | 3.9 | Bladder Cancer Research Genetics RNA 1023 | 4.4 |
| 84138 Lung NAT (OD04321) | 3.7 | Bladder Cancer INVITROGEN A302173 | 3.6 |
| Normal Kidney GENPAK 061008 | 40.6 | 87071 Bladder Cancer (OD04718-01) | 7.4 |
| 83786 Kidney Ca, Nuclear grade 2 (OD04338) | 5.7 | 87072 Bladder Normal Adjacent (OD04718-03) | 15.2 |
| 83787 Kidney NAT (OD04338) | 11.1 | Normal Ovary Res. Gen. | 1.4 |
| 83788 Kidney Ca Nuclear grade 1/2 (OD04339) | 2.5 | Ovarian Cancer GENPAK 064008 | 6.5 |
| 83789 Kidney NAT (OD04339) | 17.6 | 87492 Ovary Cancer (OD04768-07) | 1.6 |
| 83790 Kidney Ca, Clear cell type (OD04340) | 100.0 | 87493 Ovary NAT (OD04768-08) | 9.2 |
| 83791 Kidney NAT (OD04340) | 22.7 | Normal Stomach GENPAK 061017 | 13.5 |
| 83792 Kidney Ca, Nuclear grade 3 (OD04348) | 55.1 | Gastric Cancer Clontech 9060358 | 2.8 |
| 83793 Kidney NAT (OD04348) | 19.9 | NAT Stomach Clontech 9060359 | 12.6 |
| 87474 Kidney Cancer (OD04622-01) | 25.0 | Gastric Cancer Clontech 9060395 | 20.6 |
| 87475 Kidney NAT (OD04622-03) | 7.4 | NAT Stomach Clontech 9060394 | 7.5 |
| 85973 Kidney Cancer (OD04450-01) | 1.3 | Gastric Cancer Clontech 9060397 | 10.0 |
| 85974 Kidney NAT (OD04450-03) | 9.2 | NAT Stomach Clontech 9060396 | 3.2 |
| Kidney Cancer Clontech 8120607 | 9.2 | Gastric Cancer GENPAK 064005 | 6.7 |

TABLE 45

Panel 4D

| Tissue Name | Relative Expression (%) 4Dtm2478t_ag760 | Tissue Name | Relative Expression (%) 4Dtm2478t_ag760 |
|---|---|---|---|
| 93768_Secondary Th1_anti-CD28/anti-CD3 | 0.0 | 93100_HUVEC (Endothelial)_IL-1b | 3.4 |
| 93769_Secondary Th2_anti-CD28/anti-CD3 | 0.1 | 93779_HUVEC (Endothelial)_IFN gamma | 36.6 |
| 93770_Secondary Tr1_anti-CD28/anti-CD3 | 0.0 | 93102_HUVEC (Endothelial)_TNF alpha + IFN gamma | 4.0 |
| 93573_Secondary Th1_resting day 4–6 in IL-2 | 0.1 | 93101_HUVEC (Endothelial)_TNF alpha + IL4 | 3.4 |
| 93572_Secondary Th2_resting day 4–6 in IL-2 | 0.0 | 93781_HUVEC (Endothelial)_IL-11 | 5.5 |
| 93571_Secondary Tr1_resting day 4–6 in IL-2 | 0.0 | 93583_Lung Microvascular Endothelial Cells_none | 47.0 |
| 93568_primary Th1_anti-CD28/anti-CD3 | 0.0 | 93584_Lung Microvascular Endothelial Cells_TNFa (4 ng/ml) and IL1b (1 ng/ml) | 22.8 |
| 93569_primary Th_2 anti-CD28/anti-CD3 | 0.0 | 92662_Microvascular Dermal endothelium_none | 40.1 |
| 93570_primary Tr1_anti-CD28/anti-CD3 | 0.1 | 92663_Microvasular Dermal endothelium_TNFa (4 ng/ml) and IL1b (1 ng/ml) | 17.9 |
| 93565_primary Th1_resting dy 4–6 in IL-2 | 0.0 | 93773_Bronchial epithelium_TNFa (4 ng/ml) and IL1b (1 ng/ml)** | 0.0 |
| 93566_primary Th2_resting dy 4–6 in IL-2 | 0.0 | 93347_Small Airway Epithelium_none | 0.0 |
| 93567_primary Tr1_resting dy 4–6 in IL-2 | 0.0 | 93348_Small Airway Epithelium_TNFa (4 ng/ml) and IL1b (1 ng/ml) | 0.0 |
| 93351_CD45RA CD4 lymphocyte_anti-CD28/anti-CD3 | 0.6 | 92668_Coronery Artery SMC_resting | 0.0 |
| 93352_CD45RO CD4 lymphocyte_anti-CD28/anti-CD3 | 0..2 | 92669_Coronery Artery SMC_TNFa (4 ng/ml) and IL1b (1 ng/ml) | 0.0 |
| 93251_CD8 Lymphocytes_anti-CD28/anti-CD3 | 0.0 | 93107_astrocytes resting | 0.0 |
| 93353_chronic CD8 Lymphocytes 2ry_resting dy 4-6 in IL-2 | 0.0 | 93108_astrocytes_TNFa (4 ng/ml) and IL1b (1 ng/ml) | 0.0 |
| 93574_chronic CD8 Lymphocytes 2ry_activated CD3/CD28 | 0.0 | 92666_KU-812 (Basophil)_resting | 24.3 |
| 93354_CD4_none | 0.3 | 92667_KU-812 (Basophil)_PMA/ionoycin | 29.7 |
| 93252_Secondary Th1/Th2/Tr1_anti-CD95 CH11 | 0.0 | 93579_CCD1106 (Keratinocytes)_none | 0.0 |
| 93103_LAK cells_resting | 0.1 | 93580_CCD1106 (Keratinocytes)_TNFa and IFNg** | 0.0 |
| 93788_LAK cells_IL-2 | 0.1 | 93791_Liver Cirrhosis | 19.5 |
| 93787_LAK cells_IL-2 + IL-12 | 0.0 | 93792_Lupus Kidney | 34.4 |
| 93789_LAK cells_IL-2 + IFN gamma | 1.0 | 93577_NCI-H292 | 0.0 |
| 93790_LAK cells_IL-2 + IL-18 | 0.7 | 93358_NCI-H292_IL-4 | 0.0 |
| 93104_LAK cells_PMA/ionomycin and IL-18 | 0.0 | 93360_NCI-H292_IL-9 | 0.0 |
| 93578_NK Cells IL-2_resting | 0.4 | 93359_NCI-H292_IL-13 | 0.0 |
| 93109_Mixed Lymphocyte Reaction_Two Way MLR | 3.5 | 93357_NCI-H292_IFN gamma | 0.0 |
| 93110_Mixed Lymphocyte Reaction_Two Way MLR | 1.3 | 93777_HPAEC_- | 0.9 |
| 93111_Mixed Lymphocyte Reaction_Two Way MLR | 0.0 | 93778_HPAEC_IL-1 beta/TNA alpha | 0.7 |
| 93112_Mononuclear Cells (PBMCs)_resting | 0.1 | 93254_Normal Human Lung Fibroblast_none | 0.0 |
| 93113_Mononuclear Cells (PBMCs)_PWM | 0.0 | 93253_Normal Human Lung Fibroblast_TNFa (4 ng/ml) and IL-1b (1 ng/ml) | 0.0 |
| 93114_Mononuclear Cells (PBMCs)_PHA-L | 0.1 | 93257_Normal Human Lung Fibroblast_IL-4 | 0.0 |
| 93249_Ramos (B cell)_none | 0.0 | 93256_Normal Human Lung | 0.0 |

TABLE 45-continued

Panel 4D

| Tissue Name | Relative Expression (%) 4Dtm2478t_ag760 | Tissue Name | Relative Expression (%) 4Dtm2478t_ag760 |
|---|---|---|---|
| 93250_Ramos (B cell)_ionomycin | 0.1 | Fibroblast_IL-9 93255_Normal Human Lung Fibroblast_IL-13 | 0.0 |
| 93349_B lymphocytes_PWM | 0.0 | 93258_Normal Human Lung Fibroblast_IFN gamma | 0.0 |
| 93350_B lymphoytes_CD40L and IL-4 | 0.3 | 93106_Dermal Fibroblasts CCD1070_resting | 0.0 |
| 92665_EOL-1 (Eosinophil)_dbcAMP differentiated | 0.0 | 93361_Dermal Fibroblasts CCD1070_TNF alpha 4 ng/ml | 0.0 |
| 93248_EOL-1 (Eosinopbil)_dbcAMP/PMA ionomycin | 0.0 | 93105_Dermal Fibroblasts CCD1070_IL-1 beta 1 ng/ml | 0.1 |
| 93356_Dendritic Cells_none | 0.0 | 93772_dermal fibroblast_IFN gamma | 0.0 |
| 93355_Dendritic Cells_LPS 100 ng/ml | 2.3 | 93771_dermal fibroblast_IL-4 | 0.1 |
| 93775_Dendritic Cells_anti-CD40 | 0.0 | 93260_IBD Colitis 2 | 1.5 |
| 93774_Monocytes_resting | 0.8 | 93261_IBD Crohns | 9.0 |
| 93776_Monocytes LPS 50 ng/ml | 0.0 | 735010_Colon_normal | 40.3 |
| 93581_Macrophages_resting | 0.0 | 735019_Lung_none | 100.0 |
| 93582_Macrophages_LPS 100 ng/ml | 0.6 | 64028-1_Thymus_none | 95.3 |
| 93098_HUVEC (Endothelial)_none | 3.8 | 64030-1_Kidney_none | 59.9 |
| 93099_HUVEC (Endothelial)_starved | 16.8 | | |

Panel 1.2 Summary: Ag760/Ag1537 Results from two experiments using different probe/primer sets show some differences. Using Ag760, expression of the NOV7a gene is high to moderate across many of the normal tissue samples on this panel with highest expression in thyroid (CT=20.1). Using Ag1537, expression of the NOV7a gene is high to moderate across many of the normal tissue samples on this panel with highest expression in kidney (CT=21.6). Although the level of expression in some of the samples varies between the experiments, it is clear that that this gene is exclusively expressed in samples derived from normal tissues and not in cancer cell lines. Thus, expression of this gene could be used to distinguish between normal tissues and cultured cells.

The PV-1-like protein is a plasma membrane protein with an extracellular domain. Expression of this gene is high (CT values less than or equal to 27) in a wide array of metabolic tissues including pancreas, adrenal gland, thyroid, pituitary, adult and fetal heart, skeletal muscle and adult and fetal liver. The extracellular domain of this protein makes it a potential antibody target for the treatment of diseases in any or all of these tissues.

Panel 1.3D Summary: Ag760 Expression of the NOV7a gene is highest in small intestine (CT=26). This gene is exclusively expressed in samples derived from normal tissues and not cancer cell lines, consistent with what is observed in Panel 1.2. Thus, the expression of this gene could be used to distinguish between normal tissues and cultured cells.

Among metabolic tissues expression is high in pancreas, adipose, adrenal gland, thyroid, pituitary gland, heart, skeletal muscle, and liver.

This gene is expressed at low to moderate levels throughout the CNS and is specifically found in amygdala, cerebellum, hippocampus, substantia nigra, thalamus, cerebral cortex and spinal cord.

Panel 2D Summary: Ag1537 Expression of the NOV7a gene is highest in a kidney cancer sample (CT=25). Overall, this gene is widely expressed widely across Panel 2D in both normal and adjacent cancer tissue. However, in a couple of instances, it appears that the NOV7a gene is more highly expressed in kidney cancer tissue than in adjacent normal tissue. Therefore, this gene could be used to distinguish kidney cancers from normal kidney tissue. In addition, therapeutic modulation of this gene, through the use of small molecule drugs or antibodies, might be of benefit in the treatment of kidney cancer.

Panel 4D Summary: Ag760 Expression of the NOV7a gene is highest in lung and thymus (CT=26). High expression of this gene is also seen in normal kidney and colon with more moderate expression in endothelial cells and basophils. Expression of the NOV7a gene in lung and lung microvascular endothelial cells is consistent with the expression pattern observed for the PV-1 protein (1). Antibodies raised against the protein encoded by the NOV7a gene could prevent transendothelial trafficking of inflammatory cells to different tissues sites and therefore have a potential use for treatment of inflammatory diseases including delayed type hypersensitivity, asthma, emphysema, rheumatoid arthritis and IBD.

REFERENCES

1. Stan R. V., Kubitza M., and Palade G. E. (1999) PV-1 is a component of the fenestral and stomatal diaphragms in fenestrated endothelia. Proc. Natl. Acad. Sci. USA 96:13203–13207.

PV-1 is a novel endothelial protein shown by immunocytochemical tests to be specifically associated with the stomatal diaphragms of caveolae in lung endothelium. Although the highest expression levels of both mRNA and protein are in the lung, PV-1 also has been found to be expressed in other organs. Using a specific antibody to the extracellular domain of PV-1, Stan et al. have extended the survey on the presence of this protein at light and electron microscope level in several rat organs. Stan et al. show that by immunofluorescence the antibody recognizes with high specificity the endothelium of the fenestrated peritubular capillaries of the kidney and those of the intestinal villi, pancreas, and adrenals. By immunolocalization at electron microscope level, the antibody recognizes specifically the diaphragms of the fenestrae and the stomatal diaphragms of caveolae and transendothelial channels in the endothelia of these vascular beds. No signal was detected in the continuous endothelium of the heart, skeletal muscle, intestinal muscularis, or brain capillaries or the nondiaphragmed fenestrated endothelium of kidney glomeruli. Taken together, these findings define the only antigen to be localized thus far in fenestral diaphragms. They also show that the stomatal diaphragms of caveolae and transendothelial channels and the fenestral diaphragms might be biochemically related, in addition to being morphologically similar structures.

PMID: 10557298

NOV8a and NOV8b

Expression of gene NOV8a and its variant was assessed using the primer-probe sets Ag147, Ag718, Ag3681, and Ag4085, described in Tables 46, 47, and 48. Results from RTQ-PCR runs are shown in Tables 49, 50, 51, 52, and 53.

TABLE 46

Probe Name Ag147

| Primers | Sequences | TM | Length | Start Position | SEQ ID NO: |
|---|---|---|---|---|---|
| Forward | 5'-TGAAGACAGCACCTCCCTATCA-3' | | 22 | 1411 | 118 |
| Probe | FAM-5'-CGGCTCCGTGCTGTCACCCAG-3'-TAMRA | | 21 | 1436 | 119 |
| Reverse | 5'-AAGAATCCTCAGCATCGCCATA-3' | | 22 | 1472 | 120 |

TABLE 47

Probe Name Ag718

| Primers | Sequences | TM | Length | Start Position | SEQ ID NO: |
|---|---|---|---|---|---|
| Forward | 5'-AGAAGGAATCTCTGGGAAAGCT-3' | 59.9 | 22 | 949 | 121 |
| Probe | FAM-5'-CCACTGGAGATGCTTGTGTCTCTACCA-3'-TAMRA | 68.6 | 27 | 973 | 122 |
| Reverse | 5'-GACAGAGCACTGGCTAGTTCAC-3' | 59.2 | 22 | 1003 | 123 |

TABLE 48

Probe Name Ag3681/Ag4085 (identical sequences)

| Primers | Sequences | TM | Length | Start Position | SEQ ID NO: |
|---|---|---|---|---|---|
| Forward | 5'-GAATCATCCACAAGTCATCCAT-3' | 58.7 | 22 | 5818 | 124 |
| Probe | FAM-5'-CTCACTCCCATCTCATGCCTCCCAG-3'-TAMRA | 71.2 | 25 | 5841 | 125 |

TABLE 48-continued

Probe Name Ag3681/Ag4085 (identical sequences)

| Primers | Sequences | TM | Length | Start Position | SEQ ID NO: |
|---|---|---|---|---|---|
| Reverse | 5'-CATGCTGAATGATCGTGACA-3' | 59.2 | 20 | 5879 | 126 |

TABLE 49

Panel 1

| Tissue Name | Relative Expression (%) tm289f | Tissue Name | Relative Expression (%) tm289f |
|---|---|---|---|
| Endothelial cells | 0.0 | Renal ca. 786-0 | 1.3 |
| Endothelial cells (treated) | 1.2 | Renal ca. A498 | 0.4 |
| Pancreas | 1.6 | Renal ca. RXF 393 | 0.4 |
| Pancreatic ca. CAPAN 2 | 0.5 | Renal ca. ACHN | 1.1 |
| Adrenal gland | 3.0 | Renal ca. UO-31 | 1.4 |
| Thyroid | 0.4 | Renal ca. TK-b | 0.8 |
| Salavary gland | 0.9 | Liver | 0.5 |
| Pituitary gland | 2.0 | Liver (fetal) | 0.2 |
| Brain (fetal) | 7.7 | Liver ca. (hepatoblast) HepG2 | 0.2 |
| Brain (whole) | 45.1 | Lung | 7.6 |
| Brain (amygdala) | 8.0 | Lung (fetal) | 3.2 |
| Brain (cerebellum) | 49.0 | Lung ca. (small cell) LX-1 | 0.2 |
| Brain (hippocampus) | 8.4 | Lung Ca. (small cell) NCI-H69 | 0.6 |
| Brain (substantia nigra) | 11.7 | Lung Ca. (s.cell var.) SHP-77 | 0.0 |
| Brain (thalamus) | 5.3 | Lung Ca. (large cell) NCI-H460 | 0.0 |
| Brain (hypothalamus) | 1.5 | Lung Ca. (non-sm. cell) A549 | 0.4 |
| Spinal cord | 5.6 | Lung Ca. (non-s.cell) NCI-H23 | 0.4 |
| CNS ca. (glio/astro) U87-MG | 0.2 | Lung ca (non-s.cell) HOP-62 | 2.4 |
| CNS ca. (glio/astro) U-118-MG | 0.0 | Lung ca. (non-s.d) NCI-H522 | 0.9 |
| CNS ca. (astro) SW1783 | 0.0 | Lung Ca. (squam.) SW 900 | 2.4 |
| CNS ca.* (neuro; met) SK-N-AS | 0.2 | Lung Ca. (squam.) NCI-H596 | 0.1 |
| CNS ca. (astro) SF-539 | 0.8 | Mammary gland | 15.6 |
| CNS ca. (astro) SNB-75 | 0.8 | Breast ca.* (pl. effusion) MCF-7 | 0.8 |
| CNS ca (glio) SNB-19 | 8.6 | Breast ca.* (pl.ef) MDA-MB-231 | 0.4 |
| CNS ca (glio) U251 | 0.7 | Breast ca.* (pl. effusion) T47D | 10.7 |
| CNS ca. (glio) SF-295 | 3.6 | Breast ca. BT-549 | 0.0 |
| Heart | 11.3 | Breast ca. MDA-N | 0.3 |
| Skeletal muscle | 1.6 | Ovary | 8.1 |
| Bone marrow | 0.3 | Ovarian Ca. OVCAR-3 | 0.7 |
| Thymus | 6.4 | Ovarian ca OVCAR-4 | 4.7 |
| Spleen | 0.5 | Ovarian ca. OVCAR-5 | 1.3 |
| Lymph node | 1.2 | Ovarian ca. OVCAR-8 | 1.3 |
| Colon (ascending) | 1.6 | Ovarian ca. IGROV-1 | 0.5 |
| Stomach | 5.9 | Ovarian ca.* (ascites) SK-OV-3 | 1.3 |
| Small intestine | 1.7 | Uterus | 9.0 |
| Colon ca. SW480 | 2.4 | Placenta | 32.1 |
| Colon ca.* (SW480 met) SW620 | 0.2 | Prostate | 1.9 |
| Colon ca. HT29 | 0.2 | Prostate ca* (bone met) PC-3 | 0.0 |
| Colon ca. HCT-116 | 0.0 | Testis | 100.0 |
| Colon ca. CaCo-2 | 1.1 | Melanoma Hs688(A).T | 0.2 |
| Colon ca. HCT-15 | 0.7 | Melanoma* (met) Hs688(B).T | 0.2 |
| Colon ca. HCC-2998 | 1.5 | Melanoma UACC-62 | 0.0 |
| Gastric ca* (liver met) NCI-87 | 11.4 | Melanoma M14 | 0.1 |
| Bladder | 2.3 | Melanoma LOX IMVI | 0.2 |
| Trachea | 3.2 | Melanoma* (met) SK-MEL-5 | 0.0 |
| Kidney | 6.7 | Melanoma SK-MEL-28 | 0.1 |
| Kidney (fetal) | 6.1 | | |

TABLE 50

Panel 1.2

| | Relative Expression (%) | | |
|---|---|---|---|
| Tissue Name | 1.2tm888f_ag718 | 1.2tm1997f_ag718 | 1.2tm2041f_ag718 |
| Endothelial cells | 0.6 | 0.4 | 0.2 |
| Heart (fetal) | 7.4 | 10.2 | 8.1 |
| Pancreas | 14.8 | 0.1 | 0.0 |

TABLE 50-continued

Panel 1.2

| | Relative Expression (%) | | |
|---|---|---|---|
| Tissue Name | 1.2tm888f_ ag718 | 1.2tm1997f_ ag718 | 1.2tm2041f_ ag718 |
| Pancreatic ca. CAPAN 2 | 0.0 | 0.0 | 0.0 |
| Adrenal Gland (new lot*) | 5.4 | 4.0 | 4.3 |
| Thyroid | 3.8 | 0.0 | 0.0 |
| Salavary gland | 4.0 | 1.9 | 1.4 |
| Pituitary gland | 19.2 | 0.4 | 0.2 |
| Brain (fetal) | 41.8 | 1.3 | 1.5 |
| Brain (whole) | 37.6 | 1.6 | 3.5 |
| Brain (amygdala) | 16.3 | 7.1 | 5.5 |
| Brain (cerebellum) | 17.3 | 1.8 | 1.6 |
| Brain (hippocampus) | 26.6 | 16.6 | 16.2 |
| Brain (thalamus) | 14.5 | 6.7 | 9.3 |
| Cerebral Cortex | 79.6 | 81.8 | 100.0 |
| Spinal cord | 15.0 | 0.7 | 0.9 |
| CNS ca. (glio/astro) U87-MG | 0.0 | 0.0 | 0.0 |
| CNS ca. (glio/astro) U-118-MG | 0.0 | 0.0 | 0.0 |
| CNS ca. (astro) SW1783 | 0.0 | 0.0 | 0.0 |
| CNS ca.* (neuro; met) SK-N-AS | 2.9 | 0.4 | 0.4 |
| CNS ca. (astro) SF-539 | 2.4 | 1.2 | 1.0 |
| CNS ca. (astro) SNB-75 | 0.7 | 0.4 | 0.2 |
| CNS ca. (glio) SNB-19 | 27.2 | 7.2 | 5.8 |
| CNS ca. (glio) U251 | 4.6 | 0.6 | 0.9 |
| CNS ca. (glio) SF-295 | 7.2 | 7.4 | 5.0 |
| Heart | 73.7 | 100.0 | 79.0 |
| Skeletal Muscle (new lot*) | 36.9 | 17.3 | 15.3 |
| Bone marrow | 0.6 | 0.2 | 0.2 |
| Thymus | 1.7 | 0.1 | 0.0 |
| Spleen | 0.6 | 0.2 | 0.1 |
| Lymph node | 1.9 | 0.0 | 0.0 |
| Colorectal | 0.7 | 0.8 | 0.9 |
| Stomach | 8.4 | 0.3 | 0.6 |
| Small intestine | 4.3 | 1.9 | 1.8 |
| Colon ca. SW480 | 10.2 | 4.3 | 4.1 |
| Colon ca.* (SW480 met) SW620 | 0.3 | 0.0 | 0.0 |
| Colon ca. HT29 | 0.0 | 0.0 | 0.0 |
| Colon ca. HCT-116 | 0.1 | 0.1 | 0.0 |
| Colon ca. CaCo-2 | 1.4 | 0.5 | 0.4 |
| 83219 CC Well to Mod Diff (ODO3866) | 0.3 | 0.3 | 0.3 |
| Colon ca. HCC-2998 | 1.4 | 1.4 | 1.2 |
| Gastric ca.* (liver met) NCI-N87 | 35.4 | 15.8 | 8.7 |
| Bladder | 6.2 | 4.6 | 3.7 |
| Trachea | 4.2 | 0.3 | 0.2 |
| Kidney | 16.7 | 46.7 | 48.0 |
| Kidney (fetal) | 20.2 | 2.8 | 2.9 |
| Renal ca. 786-0 | 1.7 | 0.9 | 0.9 |
| Renal ca. A498 | 0.2 | 0.1 | 0.1 |
| Renal ca. RXF 393 | 0.4 | 0.1 | 0.2 |
| Renal ca. ACHN | 2.9 | 3.1 | 1.9 |
| Renal ca. UO-31 | 1.5 | 1.4 | 1.2 |
| Renal ca. TK-10 | 0.5 | 0.4 | 0.2 |
| Liver | 1.6 | 0.6 | 0.5 |
| Liver (fetal) | 1.1 | 0.4 | 0.5 |
| Liver ca. (hepatoblast) HepG2 | 0.1 | 0.3 | 0.0 |
| Lung | 12.8 | 0.4 | 0.6 |
| Lung (fetal) | 9.6 | 0.5 | 0.6 |
| Lung ca. (small cell) LX-1 | 0.3 | 0.2 | 0.2 |
| Lung ca. (small cell) NCI-H69 | 0.9 | 0.6 | 0.4 |
| Lung ca. (s.cell var.) SHP-77 | 0.3 | 0.0 | 0.0 |
| Lung ca. (large cell) NCI-H460 | 0.2 | 0.2 | 2.7 |
| Lung ca. (non-sm. cell) A549 | 0.3 | 0.2 | 0.2 |
| Lung ca. (non-s.cell) NCI-H23 | 0.6 | 0.7 | 0.4 |
| Lung ca (non-s.cell) HOP-62 | 5.0 | 4.6 | 0.6 |
| Lung ca (non-s.cl) NCI-H522 | 1.0 | 1.2 | 0.5 |
| Lung ca. (squam.) SW 900 | 2.4 | 2.6 | 2.0 |
| Lung ca. (squam.) NCI-H596 | 0.3 | 0.1 | 0.0 |
| Mammary gland | 13.4 | 2.1 | 3.0 |
| Breast ca.* (pl. effusion) MCF-7 | 0.2 | 0.0 | 0.0 |
| Breast ca.* (pl.ef) MDA-MB-231 | 2.1 | 0.9 | 0.4 |
| Breast ca.* (pl. effusion) T47D | 14.5 | 9.5 | 8.7 |
| Breast ca. BT-549 | 1.4 | 0.5 | 0.5 |
| Breast ca. MDA-N | 0.2 | 0.1 | 0.0 |
| Ovary | 19.1 | 18.9 | 13.6 |
| Ovarian ca. OVCAR-3 | 6.7 | 3.0 | 2.9 |

TABLE 50-continued

Panel 1.2

| Tissue Name | Relative Expression (%) | | |
|---|---|---|---|
| | 1.2tm888f_ag718 | 1.2tm1997f_ag718 | 1.2tm2041f_ag718 |
| Ovarian ca. OVCAR-4 | 17.8 | 19.6 | 17.2 |
| Ovarian ca. OVCAR-5 | 3.3 | 2.8 | 2.1 |
| Ovarian ca. OVCAR-8 | 1.4 | 1.5 | 1.0 |
| Ovarian ca. IGROV-1 | 1.8 | 1.3 | 0.8 |
| Ovarian ca.* (ascites) SK-OV-31 | 0.3 | 5.1 | 6.4 |
| Uterus | 7.0 | 1.8 | 1.4 |
| Placenta | 100.0 | 3.1 | 3.9 |
| Prostate | 4.0 | 2.8 | 1.4 |
| Prostate ca.* (bone met) PC-3 | 7.7 | 5.4 | 4.4 |
| Testis | 45.7 | 1.5 | 1.3 |
| Melanoma Hs688(A).T | 0.0 | 0.0 | 0.0 |
| Melanoma* (met) Hs688(B).T | 0.1 | 0.0 | 0.0 |
| Melanoma UACC-62 | 0.5 | 0.2 | 0.2 |
| Melanoma M14 | 0.1 | 0.2 | 0.0 |
| Melanoma LOX IMVI | 0.0 | 0.0 | 0.0 |
| Melanoma* (met) SK-MEL-5 | 0.2 | 0.1 | 0.2 |

TABLE 51

Panel 2D

| Tissue Name | Relative Expression (%) | |
|---|---|---|
| | 2dtm2721f_ag718 | 2Dtm2831f_ag718 |
| Normal Colon GENPAK 061003 | 13.6 | 15.9 |
| 83219 CC Well to Mod Diff (ODO3866) | 0.9 | 2.0 |
| 83220 CC NAT (ODO3866) | 1.7 | 1.5 |
| 83221 CC Gr.2 rectosigmoid (ODO3868) | 3.4 | 3.2 |
| 83222 CC NAT (ODO3868) | 2.6 | 2.6 |
| 83235 CC Mod Diff (ODO3920) | 2.4 | 3.0 |
| 83236 CC NAT (ODO3920) | 2.9 | 3.1 |
| 83237 CC Gr.2 ascend colon (ODO3921) | 6.5 | 9.1 |
| 83238 CC NAT (ODO3921) | 1.3 | 1.2 |
| 83241 CC from Partial Hepatectomy (ODO4309) | 1.3 | 0.7 |
| 83242 Liver NAT (ODO4309) | 1.3 | 1.5 |
| 87472 Colon mets to lung (OD04451-01) | 4.5 | 4.9 |
| 87473 Lung NAT (OD04451-02) | 26.8 | 29.7 |
| Normal Prostate Clontech A+ 6546-1 | 5.2 | 5.6 |
| 84140 Prostate Cancer (OD04410) | 12.6 | 11.3 |
| 84141 Prostate NAT (OD04410) | 10.6 | 16.4 |
| 87073 Prostate Cancer (OD04720-01) | 19.6 | 19.3 |
| 87074 Prostate NAT (OD04720-02) | 14.7 | 16.4 |
| Normal Lung GENPAK 061010 | 53.6 | 56.6 |
| 83239 Lung Met to Muscle (ODO4286) | 0.5 | 0.5 |
| 83240 Muscle NAT (ODO4286) | 3.6 | 5.5 |
| 84136 Lung Malignant Cancer (OD03126) | 22.5 | 18.9 |
| 84137 LungNAT (OD03126) | 73.2 | 79.6 |
| 84871 Lung Cancer (OD04404) | 9.9 | 10.9 |
| 84872 Lung NAT (OD04404) | 29.9 | 31.2 |
| 84875 Lung Cancer (OD04565) | 3.3 | 5.8 |
| 84876 Lung NAT (OD04565) | 50.0 | 47.0 |
| 85950 Lung Cancer (OD04237-01) | 4.6 | 3.0 |
| 85970 Lung NAT (OD04237-02) | 28.3 | 39.2 |
| 83255 Ocular Mel Met to Liver (ODO4310) | 1.6 | 0.6 |
| 83256 Liver NAT (ODO4310) | 0.3 | 0.7 |
| 84139 Melanoma Mets to Lung (OD04321) | 0.6 | 1.3 |
| 84138 Lung NAT (OD04321) | 48.6 | 57.0 |
| Normal Kidney GENPAK 061008 | 59.9 | 63.7 |
| 83786 Kidney Ca, Nuclear grade 2 (OD04338) | 2.4 | 4.2 |
| 83787 Kidney NAT (OD04338) | 21.6 | 23.3 |
| 83788 Kidney Ca Nuclear grade 1/2 (OD04339) | 2.0 | 2.4 |
| 83789 Kidney NAT (OD04339) | 68.8 | 70.7 |
| 83790 Kidney Ca, Clear cell type (OD04340) | 100.0 | 100.0 |
| 83791 Kidney NAT (OD04340) | 59.0 | 65.1 |
| 83792 Kidney Ca, Nuclear grade 3 (OD04348) | 3.9 | 4.0 |
| 83793 Kidney NAT (OD04348) | 34.9 | 29.9 |
| 87474 Kidney Cancer (OD04622-01) | 6.0 | 12.0 |
| 87475 Kidney NAT (OD04622-03) | 8.1 | 8.7 |
| 85973 Kidney Cancer (OD04450-01) | 0.8 | 1.4 |
| 85974 Kidney NAT (OD04450-03) | 26.2 | 25.5 |
| Kidney Cancer Clontech 8120607 | 1.1 | 0.4 |
| Kidney NAT Clontech 8120608 | 18.6 | 20.6 |
| Kidney Cancer Clontech 8120613 | 3.5 | 3.4 |
| Kidney NAT Clontech 8120614 | 52.8 | 54.0 |
| Kidney Cancer Clontech 9010320 | 10.3 | 9.9 |
| Kidney NAT Clontech 9010321 | 34.2 | 31.0 |
| Normal Uterus GENPAK 061018 | 7.1 | 4.5 |
| Uterus Cancer GENPAK 064011 | 12.9 | 11.8 |
| Normal Thyroid Clontech A+ 6570-1 | 2.5 | 1.8 |
| Thyroid Cancer GENPAK 064010 | LS | 1.8 |
| Thyroid Cancer INVITROGEN A302152 | 3.5 | 3.4 |
| Thyroid NAT INVITROGEN A302153 | 2.3 | 2.7 |
| Normal Breast GENPAK 061019 | 27.5 | 26.6 |
| 84877 Breast Cancer (OD04566) | 6.2 | 11.7 |
| 85975 Breast Cancer (OD04590-01) | 7.5 | 6.2 |
| 85976 Breast Cancer Mets (OD04590-03) | 21.2 | 24.5 |
| 87070 Breast Cancer Metastasis (OD04655-05) | 4.6 | 5.8 |
| GENPAK Breast Cancer 064006 | 15.8 | 18.6 |
| Breast Cancer Res. Gen. 1024 | 29.7 | 26.4 |
| Breast Cancer Clontech 9100266 | 2.4 | 3.6 |
| Breast NAT Clontech 9100265 | 6.5 | 6.2 |
| Breast Cancer INVITROGEN A209073 | 22.5 | 24.7 |
| Breast NAT INVITROGEN A2090734 | 15.1 | 18.4 |
| Normal Liver GENPAK 061009 | 0.7 | 0.7 |
| Liver Cancer GENPAK 064003 | 1.6 | 1.3 |
| Liver Cancer Research Genetics RNA 1025 | 1.6 | 1.9 |
| Liver Cancer Research Genetics RNA 1026 | 1.8 | 1.2 |
| Paired Liver Cancer Tissue Research Genetics RNA 6004-T | 0.8 | 1.6 |
| Paired Liver Tissue Research Genetics RNA 6004-N | 0.8 | 1.4 |
| Paired Liver Cancer Tissue Research | 1.3 | 1.0 |

TABLE 51-continued

Panel 2D

| Tissue Name | Relative Expression (%) 2dtm2721f_ag718 | 2Dtm2831f_ag718 |
|---|---|---|
| Genetics RNA 6005-T | | |
| Paired Liver Tissue Research Genetics RNA 6005-N | 0.0 | 0.0 |
| Normal Bladder GENPAK 061001 | 7.0 | 3.9 |
| Bladder Cancer Research Genetics RNA 1023 | 1.0 | 1.6 |
| Bladder Cancer INVITROGEN A302173 | 12.9 | 16.8 |
| 87071 Bladder Cancer (OD04718-01) | 16.7 | 21.8 |
| 87072 Bladder Normal Adjacent (OD04718-03) | 4.7 | 4.8 |
| Normal Ovary Res. Gen. | 13.7 | 15.3 |
| Ovarian Cancer GENPAK 064008 | 37.6 | 46.3 |
| 87492 Ovary Cancer (OD04768-07) | 24.5 | 22.8 |
| 87493 Ovary NAT (OD04768-08) | 3.6 | 4.4 |
| Normal Stomach GENPAK 061017 | 14.2 | 16.2 |
| Gastric Cancer Clontech 9060358 | 4.6 | 5.5 |
| NAT Stomach Clontech 9060359 | 2.2 | 3.3 |
| Gastric Cancer Clontech 9060395 | 3.2 | 3.0 |
| NAT Stomach Clontech 9060394 | 2.8 | 2.0 |
| Gastric Cancer Clontech 9060397 | 4.6 | 4.7 |
| NAT Stomach Clontech 9060396 | 1.0 | 2.3 |
| Gastric Cancer GENPAK 064005 | 5.3 | 5.3 |

TABLE 52

Panel 4D/4R

| Tissue Name | Relative Expression(%) 4Dtm1839f_ag718 | 4Dtm1909f_ag718 | 4rtm2719f_ag718 |
|---|---|---|---|
| 93768_Secondary Th1_anti-CD28/anti-CD3 | 0.0 | 0.3 | 0.0 |
| 93769_Secondary Th2_anti-CD28/anti-CD3 | 0.1 | 0.1 | 0.5 |
| 93770_Secondary Tr1_anti-CD28/anti-CD3 | 0.6 | 0.0 | 0.9 |
| 93573_Secondary Th1_resting day 4–6 in IL-2 | 0.0 | 0.2 | 0.3 |
| 93572_Secondary Th2_resting day 4–6 in IL-2 | 0.2 | 0.3 | 0.1 |
| 93571_Secondary Tr1_resting day 4–6 in IL-2 | 0.1 | 0.2 | 0.8 |
| 93568_primary Th1_anti-CD28/anti-CD3 | 0.5 | 0.2 | 0.3 |
| 93569_primary Th2_anti-CD28/anti-CD3 | 0.3 | 0.3 | 0.3 |
| 93570_primary Tr1_anti-CD28/anti-CD3 | 0.6 | 0.5 | 0.0 |
| 93565_primary Th1_resting dy 4–6 in IL-2 | 1.0 | 0.3 | 2.3 |
| 93566_primary Th2_resting dy 4–6 in IL-2 | 0.2 | 0.4 | 0.0 |
| 93567_primary Tr1_resting dy 4–6 in IL-2 | 0.2 | 0.0 | 0.0 |
| 93351_CD45RA CD4 lymphocyte_anti-CD28/anti-CD3 | 0.2 | 0.4 | 0.4 |
| 93352_CD45RO CD4 lymphocyte_anti-CD28/anti-CD3 | 0.2 | 0.0 | 1.2 |
| 93251_CD8 Lymphocytes_anti-CD28/anti-CD3 | 0.4 | 0.3 | 0.6 |
| 93353_chronic CD8 Lymphocytes 2ry_resting dy 4–6 in IL-2 | 0.4 | 0.7 | 0.8 |
| 93574_chronic CD8 Lymphocytes 2ry_activated CD3/CD28 | 0.2 | 0.1 | 0.0 |
| 93354_CD4_none | 0.9 | 0.5 | 0.9 |
| 93252_Secondary Th1/Th2/Tr1_anti-CD95 CH11 | 0.4 | 0.3 | 0.0 |
| 93103_LAK cells_resting | 0.2 | 0.3 | 0.5 |
| 93788_LAK cells_IL-2 | 0.4 | 0.3 | 0.7 |
| 93787_LAK cells_IL-2 + IL-12 | 0.0 | 0.2 | 0.0 |
| 93789_LAK cells_IL-2 + IFN gamma | 0.3 | 0.6 | 1.0 |
| 93790_LAK cells_IL-2 + IL-18 | 0.3 | 0.3 | 0.6 |
| 93104_LAK cells_PMA/ionomycin and IL-18 | 0.2 | 0.1 | 0.0 |
| 93578_NK Cells IL-2_resting | 0.0 | 0.7 | 0.8 |
| 93109_Mixed Lymphocyte Reaction_Two Way MLR | 0.1 | 0.5 | 0.0 |
| 93110_Mixed Lymphocyte Reaction_Two Way MLR | 0.2 | 0.2 | 0.0 |

TABLE 52-continued

Panel 4D/4R

| Tissue Name | Relative Expression(%) | | |
|---|---|---|---|
| | 4Dtm1839f__ag718 | 4Dtm1909f__ag718 | 4rtm2719f__ag718 |
| 93111__Mixed Lymphocyte Reaction__Two Way MLR | 0.0 | 0.2 | 0.0 |
| 93112__Mononuclear Cells (PBMCs)__resting | 0.2 | 0.2 | 0.0 |
| 93113__Mononuclear Cells (PBMCs)__PWM | 0.9 | 0.9 | 1.5 |
| 93114__Mononuclear Cells (PBMCs)__PHA-L | 0.5 | 0.3 | 0.4 |
| 93249__Ramos (B cell)__none | 0.3 | 0.2 | 0.9 |
| 93250__Ramos (B cell)__ionomycin | 0.3 | 0.0 | 0.8 |
| 93349__B lymphocytes__PWM | 0.5 | 0.3 | 1.5 |
| 93350__B lymphoytes__CD40L and IL-4 | 1.2 | 0.9 | 1.2 |
| 92665__EOL-1 (Eosinophil)__dbcAMP differentiated | 0.1 | 0.0 | 0.0 |
| 93248__EOL-1 (Eosinophil)__dbcAMP/PMAionoycin | 0.4 | 1.0 | 1.5 |
| 93356__Dendritic Cells__none | 0.5 | 0.3 | 0.3 |
| 93355__Dendritic Cells__LPS 100 ng/ml | 0.0 | 0.3 | 0.0 |
| 93775__Dendritic Cells__anti-CD40 | 0.1 | 0.2 | 0.0 |
| 93774__Monocytes__resting | 0.3 | 0.0 | 0.4 |
| 93776__Monocytes__LPS 50 ng/ml | 0.6 | 0.5 | 0.0 |
| 93581__Macrophages__resting | 0.2 | 0.4 | 0.0 |
| 93582__Macrophages__LPS 100 ng/ml | 0.2 | 0.2 | 0.0 |
| 93098__HUVEC (Endothelial)__none | 1.4 | 1.5 | 2.1 |
| 93099__HUVEC (Endothelial)__starved | 5.0 | 3.7 | 10.3 |
| 93100__HUVEC (Endothelial)__IL-1b | 3.9 | 3.4 | 21.6 |
| 93779__HUVEC (Endothelial)__IFN gamma | 0.6 | 0.7 | 1.7 |
| 93102__HUVEC (Endothelial)__TNF alpha + IFN gamma | 4.5 | 5.5 | 8.1 |
| 93101__HUVEC (Endothelial)__TNF alpha + IL4 | 4.4 | 4.4 | 6.4 |
| 93781__HUVEC (Endothelial)__IL-11 | 0.8 | 0.6 | 1.3 |
| 93583__Lung Microvascular Endothelial Cells__none | 6.2 | 5.4 | 8.8 |
| 93584__Lung Microvascular Endothelial Cells__TNFa (4 ng/ml) and Il1b (1 ng/ml) | 10.2 | 7.4 | 40.3 |
| 92662__Microvascular Dermal endothelium__none | 17.0 | 17.1 | 9.0 |
| 92663__Microsvasular Dermal endothelium__TNFa (4 ng/ml) and Il1b (1 ng/ml) | 27.9 | 22.2 | 53.6 |
| 93773__Bronchial epithelium__TNFa (4 ng/ml) and Il1b (1 ng/ml)** | 12.1 | 15.4 | 17.6 |
| 93347__Small Airway Epithelium__none | 2.2 | 3.8 | 6.9 |
| 93348__Small Airway Epithelium__TNFa (4 ng/ml) and Il1b (1 ng/ml) | 36.9 | 28.9 | 63.7 |
| 92668__Coronery Artery SMC__resting | 0.4 | 0.2 | 0.9 |
| 92669__Coronery Artery SMC__TNFa (4 ng/ml) and Il1b(1 ng/ml) | 0.2 | 0.0 | 0.3 |
| 93107__astrocytes__resting | 0.3 | 0.5 | 0.8 |
| 93108__astrocytes__TNFa (4 ng/ml) and Il1b (1 ng/ml) | 4.0 | 2.3 | 6.5 |
| 92666__KU-812 (Basophil)__resting | 0.2 | 0.4 | 0.3 |
| 92667__KU-812 (Basophil)__PMA/ionoycin | 0.2 | 0.3 | 0.0 |
| 93579__CCD1106 (Keratinocytes)__none | 6.2 | 5.7 | 10.4 |
| 93580__CCD1106 (Keratinocytes) TNFa and IFNg** | 100.0 | 100.0 | 30.6 |
| 93791__Liver Cirrhosis | 1.3 | 0.7 | 6.2 |
| 93792__Lupus Kidney | 14.9 | 11.5 | 25.2 |
| 93577__NCI-H292 | 13.7 | 12.2 | 25.0 |
| 93358__NCI-H292__IL-4 | 24.7 | 23.8 | 100.0 |
| 93360__NCI-H292__IL-9 | 13.8 | 10.7 | 28.9 |
| 93359__NCI-H292__IL-13 | 9.5 | 12.0 | 12.7 |
| 93357__NCI-H292__IFN gamma | 8.5 | 10.0 | 15.7 |
| 93777__HPAEC__- | 0.8 | 1.3 | 2.3 |
| 93778__HPAEC__IL-1 beta/TNA alpha | 8.7 | 11.0 | 11.7 |
| 93254__Normal Human Lung Fibroblast__none | 0.3 | 0.2 | 0.0 |
| 93253__Normal Human Lung Fibroblast__TNFa (4 ng/ml) and IL-1b (1 ng/ml) | 0.2 | 0.5 | 0.3 |
| 93257__Normal Human Lung Fibroblast__IL-4 | 0.2 | 0.0 | 1.8 |
| 93256__Normal Human Lung Fibroblast__IL-9 | 0.0 | 0.2 | 0.7 |
| 93255__Normal Human Lung Fibroblast__IL-13 | 0.2 | 0.1 | 0.0 |
| 93258__Normal Human Lung Fibroblast__IFN gamma | 0.4 | 0.0 | 0.5 |
| 93106__Dermal Fibroblasts CCD1070__resting | 0.4 | 0.8 | 0.3 |

TABLE 52-continued

Panel 4D/4R

| Tissue Name | Relative Expression(%) | | |
|---|---|---|---|
| | 4Dtm1839f_ag718 | 4Dtm1909f_ag718 | 4rtm2719f_ag718 |
| 93361_Dermal Fibroblasts CCD1070_TNF alpha 4 ng/ml | 0.9 | 0.5 | 0.8 |
| 93105_Dermal Fibroblasts CCD1070_IL-1 beta 1 ng/ml | 0.3 | 0.7 | 0.3 |
| 93772_dermal fibroblast_IFN gamma | 0.2 | 0.0 | 0.0 |
| 93771_dermal fibroblast_IL-4 | 0.1 | 0.2 | 0.0 |
| 93260_IBD Colitis 2 | 0.1 | 0.3 | 0.3 |
| 93261_IBD Crohns | 0.3 | 0.5 | 1.7 |
| 735010_Colon_normal | 1.6 | 2.8 | 5.6 |
| 735019_Lung_none | 18.9 | 21.8 | 51.0 |
| 64028-1_Thymus_none | 88.3 | 88.9 | 96.6 |
| 64030-1_Kidney_none | 6.8 | 8.0 | 15.7 |

TABLE 53

Panel 4.1D

| Tissue Name | Relative Expression(%) 4.1dx4tm5977f_ag3681_b1 | Relative Expression(%) 4.1dtm6217f_ag4085 |
|---|---|---|
| 93768_Secondary Th1_anti-CD28/anti-CD3 | 1.9 | 3.0 |
| 93769_Secondary Th2_anti-CD28/anti-CD3 | 4.0 | 2.2 |
| 93770_Secondary Tr1_anti-CD28/anti-CD3 | 3.5 | 2.5 |
| 93573_Secondary Th1_resting day 4–6 in IL-2 | 1.9 | 2.0 |
| 93572_Secondary Th2_resting day 4–6 in IL-2 | 4.1 | 0.0 |
| 93571_Secondary Tr1_resting day 4–6 in IL-2 | 2.5 | 2.2 |
| 93568_primary Th1_anti-CD28/anti-CD3 | 2.0 | 5.1 |
| 93569_primary Th2_anti-CD28/anti-CD3 | 3.5 | 1.8 |
| 93570_primary Tr1_anti-CD28/anti-CD3 | 2.4 | 5.4 |
| 93565_primary Th1_resting dy 4–6 in IL-2 | 0.5 | 1.6 |
| 93566_primary Th2_resting dy 4–6 in IL-2 | 1.9 | 0.0 |
| 93567_primary Tr1_resting dy 4–6 in IL-2 | 4.1 | 0.0 |
| 93351_CD45RA CD4 lymphocyte_anti-CD28/anti-CD3 | 3.5 | 1.7 |
| 93352_CD45RO CD4 lymphocyte_anti-CD28/anti-CD3 | 3.3 | 1.9 |
| 93251_CD8 Lymphocytes_anti-CD28/anti-CD3 | 2.6 | 1.4 |
| 93353_chronic CD8 Lymphocytes 2ry_resting dy 4–6 in IL-2 | 3.6 | 0.9 |
| 93574_chronic CD8 Lymphocytes 2ry_activated CD3/CD28 | 1.1 | 1.3 |
| 93354_CD4_none | 2.6 | 2.7 |
| 93252_Secondary Th1/Th2/Tr1_anti-CD95 CH11 | 2.0 | 0.9 |
| 93103_LAK cells_resting | 2.0 | 1.4 |
| 93788_LAK cells_IL-2 | 1.6 | 1.3 |
| 93787_LAK cells_IL-2 + IL-12 | 1.9 | 1.1 |
| 93789_LAK cells IL-2 + IFN gamma | 2.8 | 0.0 |
| 93790_LAK cells IL-2 + IL-18 | 2.4 | 0.0 |
| 93104_LAK cells_PMA/ionomycin and IL-18 | 1.7 | 1.1 |
| 93578_NK Cells IL-2_resting | 3.1 | 2.5 |
| 93109_Mixed Lymphocyte Reaction_Two Way MLR | 2.6 | 3.3 |
| 93110_Mixed Lymphocyte Reaction_Two Way MLR | 0.8 | 0.0 |
| 93111_Mixed Lymphocyte Reaction_Two Way MLR | 1.4 | 1.8 |
| 93112_Mononuclear Cells (PBMCs)_resting | 1.8 | 1.2 |
| 93113_Mononuclear Cells (PBMCs)_PWM | 1.2 | 1.4 |
| 93114_Mononuclear Cells (PBMCs)_PHA-L | 1.7 | 0.0 |
| 93249_Ramos (B cell)_none | 1.0 | 0.9 |
| 93250_Ramos (B cell)_ionomycin | 0.0 | 0.0 |
| 93349_B lymphocytes_PWM | 0.3 | 0.8 |
| 93350_B lymphoytes_CD40L and IL-4 | 4.1 | 4.3 |
| 92665_EOL-1 (Eosinophil)_dbcAMP differentiated | 5.6 | 2.6 |
| 93248_EOL-1 (Eosinophil)_dbcAMP/PMAionomycin | 7.1 | 4.3 |
| 93356_Dendritic Cells_none | 1.8 | 3.4 |
| 93355_Dendritic Cells_LPS 100 ng/ml | 0.6 | 0.0 |
| 93775_Dendritic Cells_anti-CD40 | 2.8 | 0.0 |
| 93774_Monocytes_resting | 2.4 | 2.2 |
| 93776_Monocytes_LPS 50 ng/ml | 3.7 | 5.5 |
| 93581_Macrophages_resting | 2.1 | 0.0 |
| 93582_Macrophages_LPS 100 ng/ml | 1.3 | 2.1 |
| 93098_HUVEC (Endothelial)_none | 4.7 | 6.1 |
| 93099_HUVEC (Endothelial)_starved | 6.8 | 5.5 |

TABLE 53-continued

Panel 4.1D

| Tissue Name | Relative Expression(%) 4.1dx4tm5977f_ ag3681_b1 | Relative Expression(%) 4.1dtm6217f_ ag4085 |
|---|---|---|
| 93100_HUVEC (Endothelial)_IL-1b | 19.5 | 14.9 |
| 93779_HUVEC (Endothelial)_IFN gamma | 4.6 | 8.7 |
| 93102_HUVEC (Endothelial)_TNF alpha + IFN gamma | 24.8 | 32.1 |
| 93101_HUVEC (Endothelial)_TNF alpha + IL4 | 14.4 | 13.3 |
| 93781_HUVEC (Endothelial)_IL-11 | 2.9 | 5.0 |
| 93583_Lung Microvascular Endothelial Cells_none | 27.4 | 29.1 |
| 93584_Lung Microvascular Endothelial Cells_TNFa (4 ng/ml) and Il1b (1 ng/ml) | 60.1 | 44.4 |
| 92662_Microvascular Dermal endothelium_none | 20.6 | 18.8 |
| 92663_Microvasular Dermal endothelium_TNFa (4 ng/ml) and Il1b (1 ng/ml) | 48.3 | 47.6 |
| 93773_Bronchial epithelium_TNFa (4 ng/ml) and Il1b (1 ng/ml)** | 22.7 | 22.8 |
| 93347_Small Airway Epithelium_none | 6.4 | 6.9 |
| 93348_Small Airway Epithelium_TNFa (4 ng/ml) and Il1b (1 ng/ml) | 36.3 | 27.4 |
| 92668_Coronery Artery SMC_resting | 1.3 | 2.5 |
| 92669_Coronery Artery SMC_TNFa (4 ng/ml) and Il1b (1 ng/ml) | 0.9 | 4.6 |
| 93108_astrocytes_TNFa (4 ng/ml) and Il1b (1 ng/ml) | 7.5 | 13.3 |
| 92666_KU-812 (Basophil)_resting | 0.4 | 2.5 |
| 92667_KU-812 (Basophil)_PMA/ionoycin | 2.3 | 4.7 |
| 93579_CCD1106 (Keratinocytes)_none | 20.2 | 44.8 |
| 93580_CCD1106 (Keratinocytes)_TNFa and IFNg** | 53.385.9 | |
| 93791_Liver Cirrhosis | 6.7 | 2.8 |
| 93577_NCI-H292 | 19.9 | 18.3 |
| 93358_NCI-H292_IL-4 | 30.3 | 39.0 |
| 93360_NCI-H292_IL-9 | 15.2 | 18.8 |
| 93359_NCI-H292_IL-13 | 35.9 | 52.5 |
| 93357_NCI-H292_IFN gamma | 32.2 | 33.7 |
| 93777_HPAEC_- | 6.7 | 12.9 |
| 93778_HPAEC_IL-1 beta/TNA alpha | 36.8 | 28.7 |
| 93254_Normal Human Lung Fibroblast_none | 1.2 | 4.0 |
| 93253_Normal Human Lung Fibroblast_TNFa (4 ng/ml) and IL-1b (1 ng/ml) | 1.1 | 2.4 |
| 93257_Normal Human Lung Fibroblast_IL-4 | 2.4 | 0.0 |
| 93256_Normal Human Lung Fibroblast_IL-9 | 1.2 | 1.5 |
| 93255_Normal Human Lung Fibroblast_IL-13 | 0.4 | 2.4 |
| 93258_Normal Human Lung Fibroblast_IFN gamma | 0.7 | 1.5 |
| 93106_Dermal Fibroblasts CCD1070_resting | 3.2 | 5.4 |
| 93361_Dermal Fibroblasts CCD1070_TNF alpha 4 ng/ml | 1.9 | 14.9 |
| 93105_Dermal Fibroblasts CCD1070_IL-1 beta 1 ng/ml | 5.7 | 1.4 |
| 93772_dermal fibroblast_IFN gamma | 1.0 | 0.0 |
| 93771_dermal fibroblast_IL-4 | 0.4 | 2.6 |
| 93892_Dermal fibroblasts_none | 0.0 | 1.8 |
| 99202_Neutrophils_TNFa + LPS | 0.0 | 0.9 |
| 99203_Neutrophils_none | 2.9 | 2.4 |
| 735010_Colon_normal | 3.2 | 9.7 |
| 735019_Lung_none | 63.2 | 63.7 |
| 64028-1_Thymus_none | 23.0 | 40.1 |
| 64030-1_Kidney_none | 100.0 | 100.0 |

Panel 1 Summary: Ag147 Expression of the NOV8a gene is highest in testis (CT=25.1). This gene is also highly to moderately expressed throughout the CNS, including in amygdala, cerebellum, hippocampus, substantia nigra, thalamus, hypothalamus and spinal cord, suggesting an important functional role in CNS processes. The NOV8a gene encodes a protein with homology to PAPIN, plakophilin-related armadillo repeat protein-interacting PSD-95/D1g-A/ZO-1 (PDZ) protein. Ligands of PAPIN are thought to form a complex with p0071/NPRAP/S-catenin and presenilin 1 and may play roles in Notch or Wnt/Wingless pathways. Because presenilin is known to play a role in Alzheimer's disease, inhibitors of interactions between the NOV8A gene product and its biological interactors may be useful in the treatment of Alzheimer's disease or other diseases linked to the Wnt pathway, such as cancer or autism.

Lower levels of expression of the NOV8a gene are also seen in some metabolic tissues including pancreas, adrenal gland, pituitary gland, thyroid, heart, skeletal muscle and liver. Therefore, this gene may play a role in the development of diseases in any or all of these tissues.

Panel 1.2 Summary: Ag718 Results from three experiments using the same probe/primer set show only modest agreement. This discussion pertains to results seen in the majority of the experiments. Expression of the NOV8a gene is highest in heart and cerebral cortex. Thus, this gene could potentially be used to distinguish heart and cerebral cortex from other tissues. This gene is also highly to moderately expressed in other regions of the CNS, including spinal cord, hippocampus, amygdala, cerebellum, and thalamus. Please see Panel 1 summary for description of potential utility of this gene in the CNS.

Panel 2D Summary: Ag718 Results from three experiments using the same probe/primer set are in excellent agreement. Expression of the NOV8a gene in Panel 2D is highest in a sample derived from a kidney cancer. However, the predominant expression pattern in this panel is higher expression in normal tissues when compared to adjacent cancer tissues. This gene is expressed at lower levels 7 of 9 kidney cancers and 5 of 5 lung cancers relative to the normal controls. Thus, expression of the NOV8a gene could be used to distinguish normal kidney or lung tissue from cancerous kidney or lung tissue and may have utility as a diagnostic marker. Finally, therapeutic modulation of this gene product might have benefit in the treatment of lung or kidney cancer.

Panel 4D/4R Summary: Ag718 Results from three experiments using the same probe/primer set are in reasonable agreement. The NOV8a gene is expressed highly in keratinocytes treated with TNFa and IFNg. Significant expression of this gene is also seen in thymus, small airway epithelium and microvascular dermal endothelium treated with TNF-a and IL-1b. Therefore, antibodies against the protein encoded by the NOV8a gene might be useful in down modulating inflammatory responses observed in asthma, emphysema, skin diseases such as psoriasis, and contact hypersensitivity.

Panel 4.1D Summary: Ag3681/Ag4085 The NOV8a gene is expressed highly in keratinocytes treated with TNFa and IFNg, consistent with what is seen in Panels 4D/4R. Significant expression of this gene is also seen in lung microvascular endothelial cells treated with TNFa and IL-1b. Therefore, antibodies against the protein encoded by the NOV8a gene might be useful in down modulating inflammatory responses observed in asthma, emphysema, skin diseases such as psoriasis, and contact hypersensitivity.

REFERENCES

1. Deguchi M., Iizuka T., Hata Y., Nishimura W., Hirao K., Yao I., Kawabe H., Takai Y. (2000) PAPIN. A novel multiple PSD-95/D1g-A/ZO-1 protein interacting with neural plakophilin-related armadillo repeat protein/delta-catenin and p0071. J. Biol. Chem. 275:29875–29880.

A neural plakophilin-related armadillo repeat protein (NPRAP)/delta-catenin interacts with one of Alzheimer disease-related gene products, presenilin 1. Deguchi et al. have previously reported the interaction of NPRAP/delta-catenin with synaptic scaffolding molecule, which is involved in the assembly of synaptic components. NPRAP/delta-catenin also interacts with E-cadherin and beta-catenin and is implicated in the organization of cell-cell junctions. p0071, a ubiquitous isoform of NPRAP/delta-catenin, is localized at desmosomes in HeLa and A431 cells and at adherens junctions in Madin-Darby bovine kidney cells. Deguchi et al. have identified here a novel protein interacting with NPRAP/delta-catenin and p0071 and named this protein plakophilin-related armadillo repeat protein-interacting PSD-95/D1g-A/ZO-1 (PDZ) protein (PAPIN). PAPIN has six PDZ domains and binds to NPRAP/delta-catenin and p0071 via the second PDZ domain. PAPIN and p0071 are ubiquitously expressed in various tissues and are localized at cell-cell junctions in normal rat kidney cells and bronchial epithelial cells. PAPIN may be a scaffolding protein connecting components of epithelial junctions with p0071.

PMID: 10896674

2. Fraser P. E., Yu G., Levesque L., Nishimura M., Yang D. S., Mount H. T., Westaway D., St George-Hyslop P. H. (2001) Presenilin function: connections to Alzheimer's disease and signal transduction. Biochem. Soc. Symp. 67:89–100.

Missense mutations in presenilin 1 (PS1) and presenilin 2 (PS2) are associated with early-onset familial Alzheimer's disease which displays an accelerated deposition of amyloid plaques and neurofibrillary tangles. Presenilins are multi-spanning transmembrane proteins which localize primarily to the endoplasmic reticulum and the Golgi compartments. Fraser et al. have previously demonstrated that PS1 exists as a high-molecular-mass complex that is likely to contain several functional ligands. Potential binding proteins were screened by the yeast two-hybrid system using the cytoplasmically orientated PS1 loop domain which was shown to interact strongly with members of the armadillo family of proteins, including beta-catenin, p0071 and a novel neuron-specific plakophilin-related armadillo protein (NPRAP). Armadillo proteins can have dual functions that encompass the stabilization of cellular junctions/synapses and the mediation of signal transduction pathways. These observations suggest that PS1 may contribute to both aspects of armadillo-related pathways involving neurite outgrowth and nuclear translocation of beta-catenin upon activation of the wingless (Wnt) pathway. Alzheimer's disease (AD)-related presenilin mutations exhibit a dominant gain of aberrant function resulting in the prevention of beta-catenin translocation following Wnt signalling. These findings indicate a functional role for PS1 in signalling and suggest that mis-trafficking of selected presenilin ligands may be a potential mechanism in the genesis of AD.

PMID: 11447843

3. Wassink T. H., Piven J., Vieland V. J., Huang J., Swiderski R. E., Pietila J., Braun T., Beck G., Folstein S. E., Haines J. L., Sheffield V. C. (2001) Evidence supporting WNT2 as an autism susceptibility gene. Am. J. Med. Genet. 105:406–413.

Wassink et al. examined WNT2 as a candidate disease gene for autism for the following reasons. First, the WNT family of genes influences the development of numerous organs and systems, including the central nervous system. Second, WNT2 is located in the region of chromosome 7q31–33 linked to autism and is adjacent to a chromosomal breakpoint in an individual with autism. Third, a mouse knockout of Dvl1, a member of a gene family essential for the function of the WNT pathway, exhibits a behavioral phenotype characterized primarily by diminished social interaction. Wassink et al. screened the WNT2 coding sequence for mutations in a large number of autistic probands and found two families containing nonconservative coding sequence variants that segregated with autism in those families. Wassink et al. also identified linkage disequilibrium (LD) between a WNT2 3'UTR SNP and a sample of autism-affected sibling pair (ASP) families and trios. The LD arose almost exclusively from a subgroup of ASP families defined by the presence of severe language abnormalities and was also found to be associated with the evidence for linkage to 7q from our previously published genomewide linkage screen. Furthermore, expression analysis demonstrated WNT2 expression in the human thalamus. Based on these findings, Wassink et al. hypothesize that rare mutations occur in the WNT2 gene that significantly increase susceptibility to autism even when present in single copies, while a more common WNT2 allele (or alleles) not yet identified may exist that contributes to the disorder to a lesser degree.

PMID: 11449391

4. De Ferrari G. V., Inestrosa N. C. (2000) Wnt signaling function in Alzheimer's disease. Brain Res Brain Res Rev 33:1–12.

Alzheimer's disease (AD) is a neurodegenerative disease with progressive dementia accompanied by three main structural changes in the brain: diffuse loss of neurons; intracellular protein deposits termed neurofibrillary tangles (NFT) and extracellular protein deposits termed amyloid or senile plaques, surrounded by dystrophic neurites. Two major hypotheses have been proposed in order to explain the molecular hallmarks of the disease: The 'amyloid cascade' hypothesis and the 'neuronal cytoskeletal degeneration' hypothesis. While the former is supported by genetic studies of the early-onset familial forms of AD (FAD), the latter revolves around the observation in vivo that cytoskeletal changes—including the abnormal phosphorylation state of the microtubule associated protein tau—may precede the deposition of senile plaques. Recent studies have suggested that the trafficking process of membrane associated proteins is modulated by the FAD-linked presenilin (PS) proteins, and that amyloid beta-peptide deposition may be initiated intracellularly, through the secretory pathway. Current hypotheses concerning presenilin function are based upon its cellular localization and its putative interaction as macromolecular complexes with the cell-adhesion/signaling beta-catenin molecule and the glycogen synthase kinase 3beta (GSK-3beta) enzyme. Developmental studies have shown that PS proteins function as components in the Notch signal transduction cascade and that beta-catenin and GSK-3beta are transducers of the Wnt signaling pathway. Both pathways are thought to have an important role in brain development, and they have been connected through Dishevelled (Dvl) protein, a known transducer of the Wnt pathway. In addition to a review of the current state of research on the subject, DeFerrari et al. present a cell signaling model in which a sustained loss of function of Wnt signaling components would trigger a series of misrecognition events, determining the onset and development of AD.

PMID: 10967351

Example 3

SNP Analysis of NOVX Clones

SeqCalling™ Technology: cDNA was derived from various human samples representing multiple tissue types, normal and diseased states, physiological states, and developmental states from different donors. Samples were obtained as whole tissue, cell lines, primary cells or tissue cultured primary cells and cell lines. Cells and cell lines may have been treated with biological or chemical agents that regulate gene expression for example, growth factors, chemokines, steroids. The cDNA thus derived was then sequenced using CuraGen's proprietary SeqCalling technology. Sequence traces were evaluated manually and edited for corrections if appropriate. cDNA sequences from all samples were assembled with themselves and with public ESTs using bioinformatics programs to generate CuraGen's human SeqCalling database of SeqCalling assemblies. Each assembly contains one or more overlapping cDNA sequences derived from one or more human samples. Fragments and ESTs were included as components for an assembly when the extent of identity with another component of the assembly was at least 95% over 50 bp. Each assembly can represent a gene and/or its variants such as splice forms and/or single nucleotide polymorphisms (SNPs) and their combinations.

Variant sequences are included in this application. A variant sequence can include a single nucleotide polymorphism (SNP). A SNP can, in some instances, be referred to as a "cSNP" to denote that the nucleotide sequence containing the SNP originates as a cDNA. A SNP can arise in several ways. For example, a SNP may be due to a substitution of one nucleotide for another at the polymorphic site. Such a substitution can be either a transition or a transversion. A SNP can also arise from a deletion of a nucleotide or an insertion of a nucleotide, relative to a reference allele. In this case, the polymorphic site is a site at which one allele bears a gap with respect to a particular nucleotide in another allele. SNPs occurring within genes may result in an alteration of the amino acid encoded by the gene at the position of the SNP. Intragenic SNPs may also be silent, however, in the case that a codon including a SNP encodes the same amino acid as a result of the redundancy of the genetic code. SNPs occurring outside the region of a gene, or in an intron within a gene, do not result in changes in any amino acid sequence of a protein but may result in altered regulation of the expression pattern for example, alteration in temporal expression, physiological response regulation, cell type expression regulation, intensity of expression, stability of transcribed message.

Method of Novel SNP Identification: SNPs are identified by analyzing sequence assemblies using CuraGen's proprietary SNPTool algorithm. SNPTool identifies variation in assemblies with the following criteria: SNPs are not analyzed within 10 base pairs on both ends of an alignment; Window size (number of bases in a view) is 10; The allowed number of mismatches in a window is 2; Minimum SNP base quality (PHRED score) is 23; Minimum number of changes to score an SNP is 2/assembly position. SNPTool analyzes the assembly and displays SNP positions, associated individual variant sequences in the assembly, the depth of the assembly at that given position, the putative assembly allele frequency, and the SNP sequence variation. Sequence traces are then selected and brought into view for manual validation. The consensus assembly sequence is imported into CuraTools along with variant sequence changes to identify potential amino acid changes resulting from the SNP sequence variation. Comprehensive SNP data analysis is then exported into the SNPCalling database.

Method of Novel SNP Confirmation: SNPs are confirmed employing a validated method know as Pyrosequencing (Pyrosequencing, Westborough, Mass.). Detailed protocols for Pyrosequencing can be found in: Alderbom et al. Determination of Single Nucleotide Polymorphisms by Real-time Pyrophosphate DNA Sequencing. (2000). Genome Research. 10, Issue 8, August. 1249–1265. In brief, Pyrosequencing is a real time primer extension process of genotyping. This protocol takes double-stranded, biotinylated PCR products from genomic DNA samples and binds them to streptavidin beads. These beads are then denatured producing single stranded bound DNA. SNPs are characterized utilizing a technique based on an indirect bioluminometric assay of pyrophosphate (PPi) that is released from each dNTP upon DNA chain elongation. Following Klenow polymerase-mediated base incorporation, PPi is released and used as a substrate, together with adenosine 5'-phospbosulfate (APS), for ATP sulfurylase, which results in the formation of ATP. Subsequently, the ATP accomplishes the conversion of luciferin to its oxi-derivative by the action of luciferase. The ensuing light output becomes proportional to the number of added bases, up to about four bases. To allow processivity of the method dNTP excess is degraded by apyrase, which is also present in the starting reaction mixture, so that only dNTPs are added to the template during the sequencing. The process has been fully automated and adapted to a 96-well format, which allows rapid screening of large SNP panels. The DNA and protein sequences for the novel single nucleotide polymorphic variants are reported. Variants are reported individually but any combination of all or a select subset of variants are also included. In addition, the positions of the variant bases and the variant amino acid residues are underlined.

Results

Variants are reported individually but any combination of all or a select subset of variants are also included as contemplated NOVX embodiments of the invention.

NOV1a SNP Data:

NOV1a has two SNP variants, whose variant positions for its nucleotide and amino acid sequences is numbered according to SEQ ID NOs:1 and 2, respectively. The nucleotide sequence of the NOV1a variant differs as shown in Table 54.

TABLE 54 cSNP and Coding Variants for NOV1a

| NT Position of cSNP | Wild Type NT | Variant NT | Amino Acid position | Amino Acid Change |
|---|---|---|---|---|
| 994 | C | T | 271 | P -> S |
| 1707 | A | G | 508 | No change |

NOV7a SNP Data:

NOV7a has four SNP variants, whose variant positions for its nucleotide and amino acid sequences is numbered according to SEQ ID NOs:X and Y, respectively. The nucleotide sequence of the NOV7a variant differs as shown in Table 55.

TABLE 55 cSNP and Coding Variants for NOV7a

| NT Position of cSNP | Wild Type NT | Variant NT | Amino Acid position | Amino Acid Change |
|---|---|---|---|---|
| 1023 | C | G | 341 | No change |
| 1247 | C | T | 416 | A -> V |

NOV8a SNP Data:

NOV8a has one SNP variant, whose variant position for its nucleotide and amino acid sequences is numbered according to SEQ ID NOs:X and Y, respectively. The nucleotide sequence of the NOV8a variant differs as shown in Table 56.

TABLE 57 cSNP and Coding Variants for NOV8a

| NT Position of cSNP | Wild Type NT | Variant NT | Amino Acid position | Amino Acid Change |
|---|---|---|---|---|
| 703 | G | A | 201 | No change |
| 4244 | G | A | 1381 | No change |

Example 4

SAGE Analysis for NOV1

Serial Analysis of Gene Expression, or SAGE, is an experimental technique designed to gain a quantitative measure of gene expression. The SAGE technique itself includes several steps utilizing molecular biological, DNA sequencing and bioinformatics techniques. These steps (reviewed in Adams M D, "Serial analysis of gene expression: ESTs get smaller."Bioessays. 18(4):261–2 (1996)) have been used to produce 9 or 10 base "tags", which are then, in some manner, assigned gene descriptions. For experimental reasons, these tags are immediately adjacent to the 3' end of the 3'-most NlaIII restriction site in cDNA sequences. The Cancer Genome Anatomy Project, or CGAP, is an NCI-initiated and sponsored project, which hopes to delineate the molecular fingerprint of the cancer cell. It has created a database of those cancer-related projects that used SAGE analysis in order to gain insight into the initiation and development of cancer in the human body. The SAGE expression profiles reported in this invention are generated by first identifying the Unigene accession ID associated with the given MTC gene by querying the Unigene database at http://www.ncbi.nlm.nih.gov/UniGene/. This page has then a link to the SAGE: Gene to Tag mapping (http://www.ncbi.nlm.nih.gov/SAGE/SAGEcid.cgi?cid="unigeneID").

This generated the reports that are included in this application, which list the number of tags found for the given gene in a given sample along with the relative expression. This information is then used to understand whether the gene has a more general role in tumorogenesis and/or tumor progression. A list of the SAGE libraries generated by CGAP and used in the analysis can be found at http://www.ncbi.nlm.nih.gov/SAGE/sagelb.cgi.

SAGE data

UniGene cluster: Hs.255372

Hs.255372 : hypothetical protein DKFZp564O1278

SAGE library data and reliable tag summary.

Reliable tags found in SAGE libraries:

| Library name | Tags per million | Tag counts | Total tags |
|---|---|---|---|
| SAGE HCT116 | 16 | 1 | 60322 |
| SAGE Caco 2 | 16 | 1 | 61601 |
| SAGE Chen Tumor Pr | 14 | 1 | 68384 |
| SAGE HX | 93 | 3 | 32157 |
| SAGE H126 | 185 | 6 | 32420 |
| SAGE Duke H392 | 17 | 1 | 57529 |
| SAGE SW837 | 16 | 1 | 60986 |
| SAGE RKO | 96 | 5 | 52084 |
| SAGE PR317 normal prostate | 16 | 1 | 59419 |
| SAGE NC1 | 19 | 1 | 50115 |
| SAGE Tu98 | 61 | 3 | 49005 |
| SAGE SciencePark MCF7 Control 0h | 16 | 1 | 61079 |
| SAGE LNCaP | 44 | 1 | 22637 |
| SAGE OVT-7 | 18 | 1 | 54914 |
| SAGE MDA453 | 52 | 1 | 18924 |
| SAGE mammary epithelium | 20 | 1 | 49167 |
| SAGE OVT-8 | 29 | 1 | 33575 |
| SAGE Duke-H988 | 35 | 1 | 28015 |

Reliable tags NOT found in SAGE libraries:

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims.

What is claimed is:

1. An isolated nucleic acid molecule comprising a nucleic acid sequence encoding a polypeptide comprising an amino acid sequence of SEQ ID NO:13.

2. The nucleic acid molecule of claim 1, wherein said nucleic acid molecule comprises a nucleotide sequence SEQ ID NO:12.

3. The nucleic acid molecule of claim 1, wherein said nucleic acid molecule hybridizes under stringent conditions to a nucleotide sequence consisting of SEQ ID NO:12, or a complement of said nucleotide sequence.

4. A vector comprising the nucleic acid molecule of claim 1.

5. The vector of claim 4, further comprising a promoter operably-linked to said nucleic acid molecule.

6. A cell comprising the vector of claim 4.

7. A method for determining the presence or amount of the nucleic acid molecule of claim 1 in a sample, the method comprising:

(a) providing the sample;

(b) contacting the sample with a probe that binds to said nucleic acid molecule; and (c) determining the presence or amount of the probe bound to said nucleic acid molecule, thereby determining the presence or amount of the nucleic acid molecule in said sample.

8. A method of claim 7 wherein presence or amount of the nucleic acid molecule is used as a marker for cell or tissue type.

9. The method of claim 8 wherein the cell or tissue type is cancerous.

10. A composition comprising the nucleic acid molecule of claim 1 and a pharmaceutically-acceptable carrier.

11. An isolated nucleic acid molecule comprising a nucleic acid sequence, wherein said nucleic acid sequence is a complement of SEQ ID NO:13.

* * * * *

SEQUENCE LISTING

<160> NUMBER OF SEQ ID NOS: 127

<210> SEQ ID NO 1
<211> LENGTH: 2838
<212> TYPE: DNA
<213> ORGANISM: Homo sapiens

<400> SEQUENCE: 1

| | | | | | |
|---|---|---|---|---|---|
| aactttatga | agctatggga | cttgacaaaa | agtgatattt | gagaagaaag | tacgcagtgg | 60 |
| ttggtgtttt | ctttttttta | ataaaggaat | tgaattactt | tgaacacctc | ttccagctgt | 120 |
| gcattacaga | taacgtcagg | aagagtctct | gctttacaga | atcggatttc | atcacatgac | 180 |
| aacatgaagc | tgtggattca | tctcttttat | tcatctctcc | ttgcctgtat | atctttacac | 240 |
| tcccaaactc | cagtgctctc | atccagaggc | tcttgtgatt | ctctttgcaa | ttgtgaggaa | 300 |
| aaagatggca | caatgctaat | aaattgtgaa | gcaaaggta | tcaagatggt | atctgaaata | 360 |
| agtgtgccac | catcacgacc | tttccaacta | agcttattaa | ataacggctt | gacgatgctt | 420 |
| cacacaaatg | acttttctgg | gcttaccaat | gctatttcaa | tacaccttgg | atttaacaat | 480 |
| attgcagata | ttgagatagg | tgcatttaat | ggccttggcc | tcctgaaaca | acttcatatc | 540 |
| aatcacaatt | ctttagaaat | tcttaaagag | gatactttcc | atggactgga | aaacctggaa | 600 |
| ttcctgcaag | cagataacaa | ttttatcaca | gtgattgaac | caagtgcctt | tagcaagctc | 660 |
| aacagactca | aagtgttaat | tttaaatgac | aatgctattg | agagtcttcc | tccaaacatc | 720 |
| ttccgatttg | ttccttttaac | ccatctagat | cttcgtggaa | atcaattaca | aacattgcct | 780 |
| tatgttggtt | ttctcgaaca | cattggccga | atattggatc | ttcagttgga | ggacaacaaa | 840 |
| tgggcctgca | attgtgactt | attgcagtta | aaaacttggt | tggagaacat | gcctccacag | 900 |
| tctataattg | gtgatgttgt | ctgcaacagc | cctccatttt | ttaaaggaag | tatactcagt | 960 |
| agactaaaga | aggaatctat | ttgccctact | ccaccagtgt | atgaagaaca | tgaggatcct | 1020 |
| tcaggatcat | tacatctggc | agcaacatct | tcaataaatg | atagtcgcat | gtcaactaag | 1080 |
| accacgtcca | ttctaaaact | acccaccaaa | gcaccaggtt | tgatacctta | tattacaaag | 1140 |
| ccatccactc | aacttccagg | accttactgc | cctattcctt | gtaactgcaa | agtcctatcc | 1200 |
| ccatcaggac | ttctaataca | ttgtcaggag | cgcaacattg | aaagcttatc | agatctgaga | 1260 |
| cctcctccgc | aaaatcctag | aaagctcatt | ctagcgggaa | atattattca | cagtttaatg | 1320 |
| aagtctgatc | tagtggaata | tttcactttg | gaaatgcttc | acttgggaaa | caatcgtatt | 1380 |
| gaagttcttg | aagaaggatc | gtttatgaac | ctaacgagat | tacaaaaact | ctatctaaat | 1440 |
| ggtaaccacc | tgaccaaatt | aagtaaaggc | atgttccttg | gtctccataa | tcttgaatac | 1500 |
| ttatatcttg | aatacaatgc | cattaaggaa | atactgccag | gaacctttaa | tccaatgcct | 1560 |
| aaacttaaag | tcctgtattt | aaataacaac | ctcctccaag | ttttaccacc | acatattttt | 1620 |
| tcagggggttc | ctctaactaa | ggtaaatctt | aaaacaaacc | agtttaccca | tctacctgta | 1680 |

-continued

```
agtaatattt tggatgatct tgatttacta acccagattg accttgagga taacccctgg   1740
gactgctcct gtgacctggt tggactgcag caatggatac aaaagttaag caagaacaca   1800
gtgacagatg acatcctctg cacttccccc gggcatctcg acaaaaagga attgaaagcc   1860
ctaaatagtg aaattctctg tccaggttta gtaaataacc catccatgcc aacacagact   1920
agttacctta tggtcaccac tcctgcaaca acaacaaata cggctgatac tattttacga   1980
tctcttacgg acgctgtgcc actgtctgtt ctaatattgg gacttctgat tatgttcatc   2040
actattgttt tctgtgctgc agggatagtg gttcttgttc ttcaccgcag gagaagatac   2100 aaaagaaac aagtagatga gcaaatgaga gacaacagtc ctgtgcatct tcagtacagc    2160
atgtatggcc ataaaaccac tcatcacact actgaaagac cctctgcctc actctatgaa   2220
cagcacatgt tgagccccat ggttcatgtc tatagaagtc catcctttgg tccaaagcat   2280
ctggaagagg aagaagagag gaatgagaaa gaaggaagtg atgcaaaaca tctccaaaga   2340
agtcttttgg aacaggaaaa tcattcacca ctcacagggt caaatatgaa atacaaaacc   2400
acgaaccaat caacagaatt tttatccttc caagatgcca gctcattgta cagaaacatt   2460
ttagaaaaag aaagggaact tcagcaactg ggaatcacag aatacctaag gaaaaacatt   2520
gctcagctcc agcctgatat ggaggcacat tatcctggag cccacgaaga gctgaagtta   2580
atggaaacat taatgtactc acgtccaagg aaggtattag tggaacagac aaaaaatgag   2640
tattttgaac ttaaagctaa tttacatgct gaacctgact atttagaagt cctggagcag   2700
caaacataga tggagagttt gagggctttc gcagaaatgc tgtgattctg ttttaagtcc   2760
ataccttgta aattagtgcc ttacgtgagt gtgtcatcca tcagaaccta agcacagcag   2820
taaactatgg agaaaaaa                                                 2838
```

<210> SEQ ID NO 2
<211> LENGTH: 841
<212> TYPE: PRT
<213> ORGANISM: Homo sapiens

<400> SEQUENCE: 2

```
Met Lys Leu Trp Ile His Leu Phe Tyr Ser Ser Leu Leu Ala Cys Ile
  1               5                  10                  15

Ser Leu His Ser Gln Thr Pro Val Leu Ser Ser Arg Gly Ser Cys Asp
             20                  25                  30

Ser Leu Cys Asn Cys Glu Glu Lys Asp Gly Thr Met Leu Ile Asn Cys
         35                  40                  45

Glu Ala Lys Gly Ile Lys Met Val Ser Glu Ile Ser Val Pro Pro Ser
     50                  55                  60

Arg Pro Phe Gln Leu Ser Leu Leu Asn Asn Gly Leu Thr Met Leu His
 65                  70                  75                  80

Thr Asn Asp Phe Ser Gly Leu Thr Asn Ala Ile Ser Ile His Leu Gly
                 85                  90                  95

Phe Asn Asn Ile Ala Asp Ile Glu Ile Gly Ala Phe Asn Gly Leu Gly
            100                 105                 110

Leu Leu Lys Gln Leu His Ile Asn His Asn Ser Leu Glu Ile Leu Lys
        115                 120                 125

Glu Asp Thr Phe His Gly Leu Glu Asn Leu Glu Phe Leu Gln Ala Asp
    130                 135                 140

Asn Asn Phe Ile Thr Val Ile Glu Pro Ser Ala Phe Ser Lys Leu Asn
145                 150                 155                 160

Arg Leu Lys Val Leu Ile Leu Asn Asp Asn Ala Ile Glu Ser Leu Pro
```

-continued

```
                165                 170                 175
Pro Asn Ile Phe Arg Phe Val Pro Leu Thr His Leu Asp Leu Arg Gly
                180                 185                 190

Asn Gln Leu Gln Thr Leu Pro Tyr Val Gly Phe Leu Glu His Ile Gly
            195                 200                 205

Arg Ile Leu Asp Leu Gln Leu Glu Asp Asn Lys Trp Ala Cys Asn Cys
        210                 215                 220

Asp Leu Leu Gln Leu Lys Thr Trp Leu Glu Asn Met Pro Pro Gln Ser
225                 230                 235                 240

Ile Ile Gly Asp Val Val Cys Asn Ser Pro Pro Phe Phe Lys Gly Ser
                245                 250                 255

Ile Leu Ser Arg Leu Lys Lys Glu Ser Ile Cys Pro Thr Pro Pro Val
                260                 265                 270

Tyr Glu Glu His Glu Asp Pro Ser Gly Ser Leu His Leu Ala Ala Thr
            275                 280                 285

Ser Ser Ile Asn Asp Ser Arg Met Ser Thr Lys Thr Thr Ser Ile Leu
        290                 295                 300

Lys Leu Pro Thr Lys Ala Pro Gly Leu Ile Pro Tyr Ile Thr Lys Pro
305                 310                 315                 320

Ser Thr Gln Leu Pro Gly Pro Tyr Cys Pro Ile Pro Cys Asn Cys Lys
                325                 330                 335

Val Leu Ser Pro Ser Gly Leu Leu Ile His Cys Gln Glu Arg Asn Ile
                340                 345                 350

Glu Ser Leu Ser Asp Leu Arg Pro Pro Gln Asn Pro Arg Lys Leu
            355                 360                 365

Ile Leu Ala Gly Asn Ile Ile His Ser Leu Met Lys Ser Asp Leu Val
        370                 375                 380

Glu Tyr Phe Thr Leu Glu Met Leu His Leu Gly Asn Asn Arg Ile Glu
385                 390                 395                 400

Val Leu Glu Glu Gly Ser Phe Met Asn Leu Thr Arg Leu Gln Lys Leu
                405                 410                 415

Tyr Leu Asn Gly Asn His Leu Thr Lys Leu Ser Lys Gly Met Phe Leu
                420                 425                 430

Gly Leu His Asn Leu Glu Tyr Leu Tyr Leu Glu Tyr Asn Ala Ile Lys
            435                 440                 445

Glu Ile Leu Pro Gly Thr Phe Asn Pro Met Pro Lys Leu Lys Val Leu
        450                 455                 460

Tyr Leu Asn Asn Asn Leu Leu Gln Val Leu Pro Pro His Ile Phe Ser
465                 470                 475                 480

Gly Val Pro Leu Thr Lys Val Asn Leu Lys Thr Asn Gln Phe Thr His
                485                 490                 495

Leu Pro Val Ser Asn Ile Leu Asp Asp Leu Asp Leu Leu Thr Gln Ile
                500                 505                 510

Asp Leu Glu Asp Asn Pro Trp Asp Cys Ser Cys Asp Leu Val Gly Leu
            515                 520                 525

Gln Gln Trp Ile Gln Lys Leu Ser Lys Asn Thr Val Thr Asp Asp Ile
530                 535                 540

Leu Cys Thr Ser Pro Gly His Leu Asp Lys Lys Glu Leu Lys Ala Leu
545                 550                 555                 560

Asn Ser Glu Ile Leu Cys Pro Gly Leu Val Asn Asn Pro Ser Met Pro
                565                 570                 575

Thr Gln Thr Ser Tyr Leu Met Val Thr Thr Pro Ala Thr Thr Thr Asn
            580                 585                 590
```

```
Thr Ala Asp Thr Ile Leu Arg Ser Leu Thr Asp Ala Val Pro Leu Ser
            595                 600                 605
Val Leu Ile Leu Gly Leu Leu Ile Met Phe Ile Thr Ile Val Phe Cys
        610                 615                 620
Ala Ala Gly Ile Val Val Leu Val Leu His Arg Arg Arg Tyr Lys
625                 630                 635                 640
Lys Lys Gln Val Asp Glu Gln Met Arg Asp Asn Ser Pro Val His Leu
                645                 650                 655
Gln Tyr Ser Met Tyr Gly His Lys Thr Thr His Thr Thr Glu Arg
            660                 665                 670
Pro Ser Ala Ser Leu Tyr Glu Gln His Met Val Ser Pro Met Val His
            675                 680                 685
Val Tyr Arg Ser Pro Ser Phe Gly Pro Lys His Leu Glu Glu Glu Glu
            690                 695                 700
Glu Arg Asn Glu Lys Glu Gly Ser Asp Ala Lys His Leu Gln Arg Ser
705                 710                 715                 720
Leu Leu Glu Gln Glu Asn His Ser Pro Leu Thr Gly Ser Asn Met Lys
                725                 730                 735
Tyr Lys Thr Thr Asn Gln Ser Thr Glu Phe Leu Ser Phe Gln Asp Ala
            740                 745                 750
Ser Ser Leu Tyr Arg Asn Ile Leu Glu Lys Glu Arg Glu Leu Gln Gln
            755                 760                 765
Leu Gly Ile Thr Glu Tyr Leu Arg Lys Asn Ile Ala Gln Leu Gln Pro
        770                 775                 780
Asp Met Glu Ala His Tyr Pro Gly Ala His Glu Glu Leu Lys Leu Met
785                 790                 795                 800
Glu Thr Leu Met Tyr Ser Arg Pro Arg Lys Val Leu Val Glu Gln Thr
                805                 810                 815
Lys Asn Glu Tyr Phe Glu Leu Lys Ala Asn Leu His Ala Glu Pro Asp
            820                 825                 830
Tyr Leu Glu Val Leu Glu Gln Gln Thr
            835                 840

<210> SEQ ID NO 3
<211> LENGTH: 2526
<212> TYPE: DNA
<213> ORGANISM: Homo sapiens

<400> SEQUENCE: 3
atgaagctgt ggattcatct cttttattca tctctccttg cctgtatatc tttacactcc    60
caaactccag tgctctcatc cagaggctct tgtgattctc tttgcaattg tgaggaaaaa   120
gatggcacaa tgctaataaa ttgtgaagca aaaggtatca agatggtatc tgaaataagt   180
gtgccaccat cacgaccttt ccaactaagc ttattaaata acggcttgac gatgcttcac   240
acaaatgact tttctgggct taccaatgct atttcaatac accttggatt taacaatatt   300
gcagatattg agataggtgc atttaatggc cttggcctcc tgaaacaact tcatatcaat   360
cacaattctt tagaaattct taagaggat actttccatg gactggaaaa cctggaattc   420
ctgcaagcag ataacaattt tatcacagtg attgaaccaa gtgcctttag caagctcaac   480
agactcaaag tgttaatttt aaatgacaat gctattgaga gtcttcctcc aaacatcttc   540
cgatttgttc ctttaaccca tctagatctt cgtggaaatc aattacaaac attgccttat   600
gttggttttc tcgaacacat tggccgaata ttggatctta gttggaggaa caacaaatgg   660
```

-continued

```
gcctgcaatt gtgacttatt gcagttaaaa acttggttgg agaacatgcc tccacagtct    720
ataattggtg atgttgtctg caacagccct ccatttttta aaggaagtat actcagtaga    780
ctaaagaagg aatctatttg ccctactcca ccagtgtatg aagaacatga ggatccttca    840
ggatcattac atctggcagc aacatcttca ataaatgata gtcgcatgtc aactaagacc    900
acgtccattc taaaactacc caccaaagca ccaggtttga taccttatat tacaaagcca    960
tccactcaac ttccaggacc ttactgccct attccttgta actgcaaagt cctatcccca   1020
tcaggacttc taatacattg tcaggagcgc aacattgaaa gcttatcaga tctgagacct   1080
cctccgcaaa atcctagaaa gctcattcta gcgggaaata ttattcacag tttaatgaag   1140
tctgatctag tggaatattt cactttggaa atgcttcact tgggaaacaa tcgtattgaa   1200
gttcttgaag aaggatcgtt tatgaaccta acgagattac aaaaactcta tctaaatggt   1260
aaccacctga ccaaattaag taaaggcatg ttccttggtc tccataatct tgaatactta   1320
tatcttgaat acaatgccat taaggaaata ctgccaggaa cctttaatcc aatgcctaaa   1380
cttaaagtcc tgtatttaaa taacaacctc ctccaagttt taccaccaca tatttttca    1440 ggggttcctc taactaaggt aaatcttaaa acaaaccagt ttacccatct acctgtaagt   1500
aatattttgg atgatcttga tttgctaacc cagattgacc ttgaggataa ccctgggac    1560 tgctcctgtg acctggttgg actgcagcaa tggatacaaa agttaagcaa gaacacagtg   1620
acagatgaca tcctctgcac ttcccccggg catctcgaca aaaaggaatt gaaagcccta   1680
aatagtgaaa ttctctgtcc aggtttagta aataacccat ccatgccaac acagactagt   1740
taccttatgg tcaccactcc tgcaacaaca acaaatacgg ctgatactat tttacgatct   1800
cttacggacg ctgtgccact gtctgttcta atattgggac ttctgattat gttcatcact   1860
attgttttct gtgctgcagg gatagtggtt cttgttcttc accgcaggag aagatacaaa   1920
aagaaacaag tagatgagca aatgagagac aacagtcctg tgcatcttca gtacagcatg   1980
tatggccata aaaccactca tcacactact gaaagaccct ctgcctcact ctatgaacag   2040
cacatggtga gccccatggt tcatgtctat agaagtccat cctttggtcc aaagcatctg   2100
gaagaggaag aagagaggaa tgagaaagaa ggaagtgatg caaaacatct ccaagaagt    2160 cttttggaac aggaaaatca ttccaccactc acagggtcaa atatgaaata caaaaccacg   2220
aaccaatcaa cagaattttt atccttccaa gatgccagct cattgtacag aaacatttta   2280
gaaaaagaaa gggaacttca gcaactggga atcacagaat acctaaggaa aaacattgct   2340
cagctccagc ctgatatgga ggcacattat cctggagccc acgaagagct gaagttaatg   2400
gaaacattaa tgtactcacg tccaaggaag gtattagtgg aacagacaaa aaatgagtat   2460
tttgaactta aagctaattt acatgctgaa cctgactatt agaagtcct  ggagcagcaa   2520 acatag                                                              2526
```

<210> SEQ ID NO 4
<211> LENGTH: 2531
<212> TYPE: DNA
<213> ORGANISM: Homo sapiens

<400> SEQUENCE: 4

```
ggattctctc ttttattcat ctctccttgc ctgtatatct ttacactccc aaactccagt     60
gctctcatcc agaggctctt gtgattctct ttgcaattgt gaggaaaaag atggcacaat    120
gctaataaat tgtgaagcaa aaggtatcaa gatggtatct gaaataagtg tgctaccatc    180
acgacctttc caactaagct tattaaataa cggcttgacg atgcttcaca caaatgactt    240
```

-continued

```
ttctgggctt accaatgcta tttcaataca ccttggattt aacaatattg cagatattga      300
gataggtgca tttaatggcc ttggcctcct gaaacaactt catatcaatc acaattcttt      360
agaaattctt aaagaggata ctttccatgg actggaaaac ctggaattcc tgcaagcaga      420
taacaatttt atcacagtga ttgaaccaag tgcctttagc aagctcaaca gactcaaagt      480
gttaatttta aatgacaatg ctattgagag tcttcctcca aacatcttcc gatttgttcc      540
tttaacccat ctagatcttc gtggaaatca attacaaaca ttgccttatg ttggttttct      600
cgaacacatt ggccgaatat tggatcttca gttggaggac aacaaatggg cctgcaattg      660
tgacttattg cagttaaaaa cttggttgga gaacatgcct ccacagtcta taattggtga      720
tgttgtctgc aacagccctc cattttttaa aggaagtata ctcagtagac taaagaagga      780
atctatttgc cctactccac cagtgtatga agaacatgag gatccttcag gatcattaca      840
tctggcagca acatcttcaa taaatgatag tcgcatgtca actaagacca cgtccattct      900
aaaactaccc accaaagcac caggtttgat accttatatt acaaagccat ccactcaact      960
tccaggacct tactgcccta ttccttgtaa ctgcaaagtc ctatccccat caggacttct     1020
aatacattgt caggagcgca acattgaaag cttatcagat ctgagacctc ctccgcaaaa     1080
tcctagaaag ctcattctag cgggaaatat tattcacagt ttaatgaagt ctgatctagt     1140
ggaatatttc actttggaaa tgcttcactt gggaaacaat cgtattgaag ttcttgaaga     1200
aggatcgttt atgaacctaa cgagattaca aaaactctat ctaaatggta accacctgac     1260
caaattaagt aaaggcatgt tccttggtct ccataatctt gaatacttat atcttgaata     1320
caatgccatt aaggaaatac tgccaggaac ctttaatcca atgcctaaac ttaaagtcct     1380
gtatttaaat aacaacctcc tccaagtttt accaccacat attttttcag gggttcctct     1440
aactaaggta aatcttaaaa caaaccagtt tacccatcta cctgtaagta atattttgga     1500
tgatcttgat ttgctaaccc agattgacct tgaggataac ccctgggact gctcctgtga     1560
cctggttgga ctgcagcaat ggatacaaaa gttaagcaag aacacagtga cagatgacat     1620
cctctgcact tcccccgggc atctcgacaa aaaggaattg aaagccctaa atagtgaaat     1680
tctctgtcca ggtttagtaa ataacccatc catgccaaca cagactagtt accttatggt     1740
caccactcct gcaacaacaa caaatacggc tgatactatt ttacgatctc ttacggacgc     1800
tgtgccactg tctgttctaa tattgggact tctgattatg ttcatcacta ttgttttctg     1860
tgctgcaggg atagtggttc ttgttcttca ccgcaggaga agatacaaaa agaaacaagt     1920
agatgagcaa atgagagaca acagtcctgt gcatcttcag tacagcatgt atggccataa     1980
aaccactcat cacactactg aaagaccctc tgcctcactc tatgaacagc acatggtgag     2040
ccccatggtt catgtctata gaagtccatc ctttggtcca aagcatctgg aagaggaaga     2100
agagaggaat gagaaagaag gaagtgatgc aaaacatctc caaagaagtc ttttggaaca     2160
ggaaaatcat tcaccactca cagggtcaaa tatgaaatac aaaaccacga accaatcaac     2220
agaatttta tccttccaag atgccagctc attgtacaga acatttag aaaaagaaag     2280
ggaacttcag caactgggaa tcacagaata cctaaggaaa acattgctc agctccagcc     2340
tgatatggag gcacattatc ctggagccca cgaagagctg aagttaatgg aaacattaat     2400
gtactcacgt ccaaggaagg tattagtgga acagacaaaa aatgagtatt ttgaacttaa     2460
agctaattta catgctgaac ctgactattt agaagtcctg gagcagcaaa cataagggcg     2520
aattctgctg t                                                          2531
```

<210> SEQ ID NO 5
<211> LENGTH: 837
<212> TYPE: PRT
<213> ORGANISM: Homo sapiens

<400> SEQUENCE: 5

```
Asp Ser Leu Phe Tyr Ser Ser Leu Leu Ala Cys Ile Ser Leu His Ser
  1               5                  10                  15

Gln Thr Pro Val Leu Ser Arg Gly Ser Cys Asp Ser Leu Cys Asn
             20                  25                  30

Cys Glu Glu Lys Asp Gly Thr Met Leu Ile Asn Cys Glu Ala Lys Gly
         35                  40                  45

Ile Lys Met Val Ser Glu Ile Ser Val Leu Pro Ser Arg Pro Phe Gln
     50                  55                  60

Leu Ser Leu Leu Asn Asn Gly Leu Thr Met Leu His Thr Asn Asp Phe
 65                  70                  75                  80

Ser Gly Leu Thr Asn Ala Ile Ser Ile His Leu Gly Phe Asn Asn Ile
                 85                  90                  95

Ala Asp Ile Glu Ile Gly Ala Phe Asn Gly Leu Gly Leu Leu Lys Gln
            100                 105                 110

Leu His Ile Asn His Asn Ser Leu Glu Ile Leu Lys Glu Asp Thr Phe
        115                 120                 125

His Gly Leu Glu Asn Leu Glu Phe Leu Gln Ala Asp Asn Asn Phe Ile
    130                 135                 140

Thr Val Ile Glu Pro Ser Ala Phe Ser Lys Leu Asn Arg Leu Lys Val
145                 150                 155                 160

Leu Ile Leu Asn Asp Asn Ala Ile Glu Ser Leu Pro Pro Asn Ile Phe
                165                 170                 175

Arg Phe Val Pro Leu Thr His Leu Asp Leu Arg Gly Asn Gln Leu Gln
            180                 185                 190

Thr Leu Pro Tyr Val Gly Phe Leu Glu His Ile Gly Arg Ile Leu Asp
        195                 200                 205

Leu Gln Leu Glu Asp Asn Lys Trp Ala Cys Asn Cys Asp Leu Leu Gln
    210                 215                 220

Leu Lys Thr Trp Leu Glu Asn Met Pro Pro Gln Ser Ile Ile Gly Asp
225                 230                 235                 240

Val Val Cys Asn Ser Pro Pro Phe Phe Lys Gly Ser Ile Leu Ser Arg
                245                 250                 255

Leu Lys Lys Glu Ser Ile Cys Pro Thr Pro Val Tyr Glu Glu His
            260                 265                 270

Glu Asp Pro Ser Gly Ser Leu His Leu Ala Ala Thr Ser Ser Ile Asn
        275                 280                 285

Asp Ser Arg Met Ser Thr Lys Thr Thr Ser Ile Leu Lys Leu Pro Thr
    290                 295                 300

Lys Ala Pro Gly Leu Ile Pro Tyr Ile Thr Lys Pro Ser Thr Gln Leu
305                 310                 315                 320

Pro Gly Pro Tyr Cys Pro Ile Pro Cys Asn Cys Lys Val Leu Ser Pro
                325                 330                 335

Ser Gly Leu Leu Ile His Cys Gln Glu Arg Asn Ile Glu Ser Leu Ser
            340                 345                 350

Asp Leu Arg Pro Pro Gln Asn Pro Arg Lys Leu Ile Leu Ala Gly
        355                 360                 365

Asn Ile Ile His Ser Leu Met Lys Ser Asp Leu Val Glu Tyr Phe Thr
    370                 375                 380
```

-continued

```
Leu Glu Met Leu His Leu Gly Asn Asn Arg Ile Glu Val Leu Glu Glu
385                 390                 395                 400

Gly Ser Phe Met Asn Leu Thr Arg Leu Gln Lys Leu Tyr Leu Asn Gly
                405                 410                 415

Asn His Leu Thr Lys Leu Ser Lys Gly Met Phe Leu Gly Leu His Asn
                420                 425                 430

Leu Glu Tyr Leu Tyr Leu Glu Tyr Asn Ala Ile Lys Glu Ile Leu Pro
                435                 440                 445

Gly Thr Phe Asn Pro Met Pro Lys Leu Lys Val Leu Tyr Leu Asn Asn
                450                 455                 460

Asn Leu Leu Gln Val Leu Pro Pro His Ile Phe Ser Gly Val Pro Leu
465                 470                 475                 480

Thr Lys Val Asn Leu Lys Thr Asn Gln Phe Thr His Leu Pro Val Ser
                485                 490                 495

Asn Ile Leu Asp Asp Leu Asp Leu Leu Thr Gln Ile Asp Leu Glu Asp
                500                 505                 510

Asn Pro Trp Asp Cys Ser Cys Asp Leu Val Gly Leu Gln Gln Trp Ile
                515                 520                 525

Gln Lys Leu Ser Lys Asn Thr Val Thr Asp Asp Ile Leu Cys Thr Ser
530                 535                 540

Pro Gly His Leu Asp Lys Lys Glu Leu Lys Ala Leu Asn Ser Glu Ile
545                 550                 555                 560

Leu Cys Pro Gly Leu Val Asn Asn Pro Ser Met Pro Thr Gln Thr Ser
                565                 570                 575

Tyr Leu Met Val Thr Pro Ala Thr Thr Asn Thr Ala Asp Thr
                580                 585                 590    Thr

Ile Leu Arg Ser Leu Thr Asp Ala Val Pro Leu Ser Val Leu Ile Leu
                595                 600                 605

Gly Leu Leu Ile Met Phe Ile Thr Ile Val Phe Cys Ala Ala Gly Ile
610                 615                 620

Val Val Leu Val Leu His Arg Arg Arg Tyr Lys Lys Gln Val
625                 630                 635                 640

Asp Glu Gln Met Arg Asp Asn Ser Pro Val His Leu Gln Tyr Ser Met
                645                 650                 655

Tyr Gly His Lys Thr Thr His His Thr Thr Glu Arg Pro Ser Ala Ser
                660                 665                 670

Leu Tyr Glu Gln His Met Val Ser Pro Met Val His Val Tyr Arg Ser
                675                 680                 685

Pro Ser Phe Gly Pro Lys His Leu Glu Glu Glu Glu Arg Asn Glu
                690                 695                 700

Lys Glu Gly Ser Asp Ala Lys His Leu Gln Arg Ser Leu Leu Glu Gln
705                 710                 715                 720

Glu Asn His Ser Pro Leu Thr Gly Ser Asn Met Lys Tyr Lys Thr Thr
                725                 730                 735

Asn Gln Ser Thr Glu Phe Leu Ser Phe Gln Asp Ala Ser Ser Leu Tyr
                740                 745                 750

Arg Asn Ile Leu Glu Lys Glu Arg Glu Leu Gln Gln Leu Gly Ile Thr
                755                 760                 765

Glu Tyr Leu Arg Lys Asn Ile Ala Gln Leu Gln Pro Asp Met Glu Ala
                770                 775                 780

His Tyr Pro Gly Ala His Glu Glu Leu Lys Leu Met Glu Thr Leu Met
785                 790                 795                 800
```

| | | | |
|---|---|---|---|
| Tyr Ser Arg Pro Arg Lys Val Leu Val Glu Gln Thr Lys Asn Glu Tyr | | | |
| 805 | | 810 | 815 |
| Phe Glu Leu Lys Ala Asn Leu His Ala Glu Pro Asp Tyr Leu Glu Val | | | |
| 820 | | 825 | 830 |
| Leu Glu Gln Gln Thr | | | |
| 835 | | | |

<210> SEQ ID NO 6
<211> LENGTH: 3609
<212> TYPE: DNA
<213> ORGANISM: Homo sapiens

<400> SEQUENCE: 6

| | | | | | |
|---|---|---|---|---|---|
| cagtggatgc | agaaggcaga | cagcagcacc | gagacgatga | aggagaagag | gacagcggct | 60 |
| gcgatcaccg | tgcggcacag | gaccggctcc | tgcttctcgg | gccgctgtgt | caactccacc | 120 |
| tgcctctgcg | acccgggctg | ggtgggggac | cagtgccagc | actgccaggg | caggttcagg | 180 |
| ttaacagaac | cttctggata | tttaacagat | ggcccaatta | actataaata | taaaactaaa | 240 |
| tgtacttggc | tcattgaagg | cccaaatgca | gtgttaagat | taagattcaa | tcattttgct | 300 |
| acagaatgta | gctgggatca | tatgtatgtt | tatgatggag | attcaatata | tgcacctta | 360 |
| atagcttctt | ttagtggttt | gatagtccct | gaaataaggg | gcaatgaaac | tgtgcctgaa | 420 |
| gttgttacta | catctggcta | tgcactgtta | cattttttta | gtgatgctgc | gtataatcta | 480 |
| actggtttca | acattttcta | ttcgatcaat | tcttgtccta | caattgctc | tggtcatggg | 540 |
| aagtgtacaa | ctagtgtctc | tgttccaagt | caagtatatt | gtgaatgtga | taaatactgg | 600 |
| aagggtgaag | cttgtgatat | tccttactgt | aaagccaatt | gcggcagtcc | agatcacggt | 660 |
| tactgtgacc | tgactggaga | aaaattatgt | gtctgcaatg | atagttggca | aggtataggt | 720 |
| cctgattgtt | ctttgaatgt | tccctctact | gagtcttact | ggattctgcc | aaacgttaaa | 780 |
| cccttcagtc | cttctgtagg | tcgggcttca | cataaagcag | ttttacacgg | gaaattatg | 840 |
| tgggtgattg | gtggatatac | ttttaactac | agttcttttc | aaatggtcct | aagttacaat | 900 |
| ttagaaagca | gtatatggaa | tgtaggaact | ccatcaaggg | gacctctcca | gagatatgga | 960 |
| cactctcttg | ctttatatca | ggaaaacatc | tttatgtatg | gaggcagaat | tgaaacaaat | 1020 |
| gatggcaatg | tcacagatga | attatgggtt | tttaacatac | atagtcagtc | atggagtaca | 1080 |
| aaaactccta | ctgttcttgg | acatggtcag | cagtatgctg | tggagggaca | ttcagcacat | 1140 |
| attatggagt | tggatagtag | agatgttgtc | atgatcataa | tatttggata | ttctgcaata | 1200 |
| tatggttata | caagcagcat | acaggaatac | catatctgtt | caaacacttg | gcttgttcca | 1260 |
| gaaactaaag | gagctattgt | acaaggtgga | tatggccata | ctagtgtgta | tgatgaaata | 1320 |
| acaaagtcca | tttatgttca | tggagggtat | aaagcattgc | cagggaacaa | atatggattg | 1380 |
| gttgatgatc | tttataaata | tgaagttaac | actaagactt | ggactatttt | gaaagaaagt | 1440 |
| gggtttgcca | gataccttca | ttcagctgtt | cttatcaatg | gagctatgct | tatttttgga | 1500 |
| ggaaatacc | ataatgacac | ttccttgagt | aacggtgcaa | aatgttttc | tgccgatttc | 1560 |
| ctggcatatg | acatatgccc | aggctggagt | gcagtggcac | gatctcagct | cactgccacc | 1620 |
| tccacctccc | acgttcaagc | gattctcaat | aggtccatgt | atatatttgg | gggattttct | 1680 |
| agtgtactcc | ttaatgatat | ccttgtatac | aagcctccaa | attgcaaggc | tttcagagat | 1740 |
| gaagaacttt | gtaaaaatgc | tggtccaggg | ataaaatgtg | tttggaataa | aaatcactgt | 1800 |
| gaatcttggg | aatctgggaa | tactaataat | attcttagag | caaagtgctt | ttctaaaaga | 1860 |

```
aatctctgca gtgacagatg ttacagatat gcagattgtg ccagctgtac tgccaataca   1920
aatgggtgcc aatggtgtga tgacaagaaa tgcatttcgg caaatagtaa ctgcagtatg   1980
gttagtattt ttgggtatat aaccttgcct tcacagttcc cattctatta ttgctacaga   2040
tatgcagatt gtgccagctg tactgccaat acaaatgggt gccaatggtg tgatgacaag   2100
aaatgcattg ctttaccagc tcatctttgt ggagaaggat ggagtcatat tggggatgct   2160
tgtcttagag tcaattccag tagagaaaac tatgacaatg caaaacttta ttgctataat   2220
cttagtggaa atcttgcttc attaacaacc tcaaaagaag tagaatttgt tctggatgaa   2280
atacagaagt atacacaaca gaaagtatca ccttgggtag gcttgcgcaa gatcaatata   2340
tcctattggg gatgggaaga catgtctcct tttacaaaca caacactaca gtggcttcct   2400
ggcgaaccca atgattctgg gttttgtgca tatctgaaaa gggctgcagt ggcaggctta   2460
aaagctaatc cttgtacatc tatggcaaat ggccttgtct gtgaaaaacc tgttaatcaa   2520
aatgcgaggc cgtgcaaaaa gccatgctct ctgaggacta catgttccaa ctgtacaagc   2580
aatggcatgg agtgtatgtg gtgcagcagt acgaaacgat gtgttgactc taatgcctat   2640
atcatctctt ttccatatgg acaatgtcta gagtggcaaa ctgccacctg ctcccgtgct   2700
caaaattgtt ctggattgag aacctgtgga cagtgtttgg aacagcctga atgtggctgg   2760
tgcaatgatc ctagtaatac aggaagagga cattgcattg aaggttcttc acggggacca   2820
atgaagctta ttggaatgca ccacagtgag atggttcttg acaccaatct ttgccccaaa   2880
gaaaagaact atgagtggtc ctttatccag tgtccagctt gccagtgtaa tggacatagc   2940
acttgcatca ataataatgt gtgcgaacag tgtaaaaatc tcaccacagg aaagcagtgt   3000
caagattgta tgccaggtta ttatggagat ccaaccaatg gtggacagtg cacagcttgt   3060
acatgcagtg gccatgcaaa tatctgtcat ctgcacacag gaaaatgttt ctgcacaact   3120
aaaggaataa aggtgaccaa atgccaattg tgtgactctg aaaatcgcta tgttggtaat   3180
ccacttagag gaacatgtta ttgtaagtat agccttttga ttgattatca atttaccttc   3240
agcttattac aggaagatga tcgccaccat actgccataa actttatagc aaacccagaa   3300
caggtgagga aaaatctgga tatatcaatt aatgcatcaa caactttaa tctcaacatt   3360
acgtggtctg tcggttcagc tggaacaata tctggggaag agacttctat agtttccaag   3420
aataatataa aggaatacag agatagtttt tcctatgaaa aatttaactt tagaagcaat   3480
cctaacatta cattctatgt gtacgtcagc aacttttcct ggcctattaa aatacaggta   3540
agtgttaaga gtatttactt ctaatgacca taatatcatt aagaaaagaa tggtgctttt   3600
gtccaaagt                                                          3609
```

<210> SEQ ID NO 7
<211> LENGTH: 1185
<212> TYPE: PRT
<213> ORGANISM: Homo sapiens

<400> SEQUENCE: 7

Met Gln Lys Ala Asp Ser Ser Thr Glu Thr Met Lys Glu Lys Arg Thr
 1               5                  10                  15

Ala Ala Ala Ile Thr Val Arg His Arg Thr Gly Ser Cys Phe Ser Gly
             20                  25                  30

Arg Cys Val Asn Ser Thr Cys Leu Cys Asp Pro Gly Trp Val Gly Asp
         35                  40                  45

Gln Cys Gln His Cys Gln Gly Arg Phe Arg Leu Thr Glu Pro Ser Gly
     50                  55                  60

-continued

```
Tyr Leu Thr Asp Gly Pro Ile Asn Tyr Lys Tyr Lys Thr Lys Cys Thr
 65                  70                  75                  80

Trp Leu Ile Glu Gly Pro Asn Ala Val Leu Arg Leu Arg Phe Asn His
             85                  90                  95

Phe Ala Thr Glu Cys Ser Trp Asp His Met Tyr Val Tyr Asp Gly Asp
            100                 105                 110

Ser Ile Tyr Ala Pro Leu Ile Ala Ser Phe Ser Gly Leu Ile Val Pro
        115                 120                 125

Glu Ile Arg Gly Asn Glu Thr Val Pro Glu Val Thr Thr Ser Gly
130                 135                 140

Tyr Ala Leu Leu His Phe Phe Ser Asp Ala Ala Tyr Asn Leu Thr Gly
145                 150                 155                 160

Phe Asn Ile Phe Tyr Ser Ile Asn Ser Cys Pro Asn Asn Cys Ser Gly
                165                 170                 175

His Gly Lys Cys Thr Thr Ser Val Ser Val Pro Ser Gln Val Tyr Cys
            180                 185                 190

Glu Cys Asp Lys Tyr Trp Lys Gly Glu Ala Cys Asp Ile Pro Tyr Cys
            195                 200                 205

Lys Ala Asn Cys Gly Ser Pro Asp His Gly Tyr Cys Asp Leu Thr Gly
        210                 215                 220

Glu Lys Leu Cys Val Cys Asn Asp Ser Trp Gln Gly Ile Gly Pro Asp
225                 230                 235                 240

Cys Ser Leu Asn Val Pro Ser Thr Glu Ser Tyr Trp Ile Leu Pro Asn
                245                 250                 255

Val Lys Pro Phe Ser Pro Ser Val Gly Arg Ala Ser His Lys Ala Val
            260                 265                 270

Leu His Gly Lys Phe Met Trp Val Ile Gly Tyr Thr Phe Asn Tyr
        275                 280                 285

Ser Ser Phe Gln Met Val Leu Ser Tyr Asn Leu Glu Ser Ser Ile Trp
290                 295                 300

Asn Val Gly Thr Pro Ser Arg Gly Pro Leu Gln Arg Tyr Gly His Ser
305                 310                 315                 320

Leu Ala Leu Tyr Gln Glu Asn Ile Phe Met Tyr Gly Gly Arg Ile Glu
            325                 330                 335

Thr Asn Asp Gly Asn Val Thr Asp Glu Leu Trp Val Phe Asn Ile His
            340                 345                 350

Ser Gln Ser Trp Ser Thr Lys Thr Pro Thr Val Leu Gly His Gly Gln
        355                 360                 365

Gln Tyr Ala Val Glu Gly His Ser Ala His Ile Met Glu Leu Asp Ser
370                 375                 380

Arg Asp Val Val Met Ile Ile Phe Gly Tyr Ser Ala Ile Tyr Gly
385                 390                 395                 400

Tyr Thr Ser Ser Ile Gln Glu Tyr His Ile Cys Ser Asn Thr Trp Leu
                405                 410                 415

Val Pro Glu Thr Lys Gly Ala Ile Val Gln Gly Gly Tyr Gly His Thr
            420                 425                 430

Ser Val Tyr Asp Glu Ile Thr Lys Ser Ile Tyr Val His Gly Gly Tyr
        435                 440                 445

Lys Ala Leu Pro Gly Asn Lys Tyr Gly Leu Val Asp Asp Leu Tyr Lys
450                 455                 460

Tyr Glu Val Asn Thr Lys Thr Trp Thr Ile Leu Lys Glu Ser Gly Phe
465                 470                 475                 480
```

-continued

```
Ala Arg Tyr Leu His Ser Ala Val Leu Ile Asn Gly Ala Met Leu Ile
            485                 490                 495

Phe Gly Gly Asn Thr His Asn Asp Thr Ser Leu Ser Asn Gly Ala Lys
            500                 505                 510

Cys Phe Ser Ala Asp Phe Leu Ala Tyr Asp Ile Cys Pro Gly Trp Ser
            515                 520                 525

Ala Val Ala Arg Ser Gln Leu Thr Ala Thr Ser Thr Ser His Val Gln
            530                 535                 540

Ala Ile Leu Asn Arg Ser Met Tyr Ile Phe Gly Gly Phe Ser Ser Val
545                 550                 555                 560

Leu Leu Asn Asp Ile Leu Val Tyr Lys Pro Pro Asn Cys Lys Ala Phe
            565                 570                 575

Arg Asp Glu Glu Leu Cys Lys Asn Ala Gly Pro Gly Ile Lys Cys Val
            580                 585                 590

Trp Asn Lys Asn His Cys Glu Ser Trp Glu Ser Gly Asn Thr Asn Asn
            595                 600                 605

Ile Leu Arg Ala Lys Cys Phe Ser Lys Arg Asn Leu Cys Ser Asp Arg
            610                 615                 620

Cys Tyr Arg Tyr Ala Asp Cys Ala Ser Cys Thr Ala Asn Thr Asn Gly
625                 630                 635                 640

Cys Gln Trp Cys Asp Asp Lys Lys Cys Ile Ser Ala Asn Ser Asn Cys
            645                 650                 655

Ser Met Val Ser Ile Phe Gly Tyr Ile Thr Leu Pro Ser Gln Phe Pro
            660                 665                 670

Phe Tyr Tyr Cys Tyr Arg Tyr Ala Asp Cys Ala Ser Cys Thr Ala Asn
            675                 680                 685

Thr Asn Gly Cys Gln Trp Cys Asp Asp Lys Lys Cys Ile Ala Leu Pro
            690                 695                 700

Ala His Leu Cys Gly Glu Gly Trp Ser His Ile Gly Asp Ala Cys Leu
705                 710                 715                 720

Arg Val Asn Ser Ser Arg Glu Asn Tyr Asp Asn Ala Lys Leu Tyr Cys
            725                 730                 735

Tyr Asn Leu Ser Gly Asn Leu Ala Ser Leu Thr Thr Ser Lys Glu Val
            740                 745                 750

Glu Phe Val Leu Asp Glu Ile Gln Lys Tyr Thr Gln Gln Lys Val Ser
            755                 760                 765

Pro Trp Val Gly Leu Arg Lys Ile Asn Ile Ser Tyr Trp Gly Trp Glu
770                 775                 780

Asp Met Ser Pro Phe Thr Asn Thr Thr Leu Gln Trp Leu Pro Gly Glu
785                 790                 795                 800

Pro Asn Asp Ser Gly Phe Cys Ala Tyr Leu Glu Arg Ala Ala Val Ala
            805                 810                 815

Gly Leu Lys Ala Asn Pro Cys Thr Ser Met Ala Asn Gly Leu Val Cys
            820                 825                 830

Glu Lys Pro Val Asn Gln Asn Ala Arg Pro Cys Lys Lys Pro Cys Ser
            835                 840                 845

Leu Arg Thr Ser Cys Ser Asn Cys Thr Ser Asn Gly Met Glu Cys Met
            850                 855                 860

Trp Cys Ser Ser Thr Lys Arg Cys Val Asp Ser Asn Ala Tyr Ile Ile
865                 870                 875                 880

Ser Phe Pro Tyr Gly Gln Cys Leu Glu Trp Gln Thr Ala Thr Cys Ser
            885                 890                 895

Arg Ala Gln Asn Cys Ser Gly Leu Arg Thr Cys Gly Gln Cys Leu Glu
```

```
                    900           905            910
Gln Pro Glu Cys Gly Trp Cys Asn Asp Pro Ser Asn Thr Gly Arg Gly
        915                 920                 925
His Cys Ile Glu Gly Ser Ser Arg Gly Pro Met Lys Leu Ile Gly Met
    930                 935                 940
His His Ser Glu Met Val Leu Asp Thr Asn Leu Cys Pro Lys Glu Lys
945                 950                 955                 960
Asn Tyr Glu Trp Ser Phe Ile Gln Cys Pro Ala Cys Gln Cys Asn Gly
                965                 970                 975
His Ser Thr Cys Ile Asn Asn Val Cys Glu Gln Cys Lys Asn Leu
            980                 985                 990
Thr Thr Gly Lys Gln Cys Gln Asp Cys Met Pro Gly Tyr Tyr Gly Asp
        995                 1000                1005
Pro Thr Asn Gly Gly Gln Cys Thr Ala Cys Thr Cys Ser Gly His Ala
    1010                1015                1020
Asn Ile Cys His Leu His Thr Gly Lys Cys Phe Cys Thr Thr Lys Gly
1025                1030                1035                1040
Ile Lys Gly Asp Gln Cys Gln Leu Cys Asp Ser Glu Asn Arg Tyr Val
                1045                1050                1055
Gly Asn Pro Leu Arg Gly Thr Cys Tyr Cys Lys Tyr Ser Leu Leu Ile
            1060                1065                1070
Asp Tyr Gln Phe Thr Phe Ser Leu Leu Gln Glu Asp Arg His His
        1075                1080                1085
Thr Ala Ile Asn Phe Ile Ala Asn Pro Glu Gln Val Arg Lys Asn Leu
    1090                1095                1100
Asp Ile Ser Ile Asn Ala Ser Asn Asn Phe Asn Leu Asn Ile Thr Trp
1105                1110                1115                1120
Ser Val Gly Ser Ala Gly Thr Ile Ser Gly Glu Glu Thr Ser Ile Val
                1125                1130                1135
Ser Lys Asn Asn Ile Lys Glu Tyr Arg Asp Ser Phe Ser Tyr Glu Lys
            1140                1145                1150
Phe Asn Phe Arg Ser Asn Pro Asn Ile Thr Phe Tyr Val Tyr Val Ser
        1155                1160                1165
Asn Phe Ser Trp Pro Ile Lys Ile Gln Val Ser Val Lys Ser Ile Tyr
    1170                1175                1180
Phe
1185

<210> SEQ ID NO 8
<211> LENGTH: 6201
<212> TYPE: DNA
<213> ORGANISM: Homo sapiens

<400> SEQUENCE: 8
atgttgaagt tcaaatatgg agcgcggaat cctttggatg ctggtgctgc tgaacccatt      60
gccagccggg cctccaggct gaatctgttc ttccagggga aaccaccctt tatgactcaa     120
cagcagatgt ctcctctttc ccgagaaggg atattagatg ccctctttgt tctctttgaa     180
gaatgcagtc agcctgctct gatgaagatt aagcacgtga gcaactttgt ccggaagtgt     240
tccgacacca tagctgagtt acaggagctc cagccttcgg caaaggactt cgaagtcaga     300
agtcttgtag ttgtggtca ctttgctgaa gtgcaggtgg taagagagaa agcaaccggg     360
gacatctatg ctatgaaagt gatgaagaag aaggctttat tggcccagga gcaggtttca     420
ttttttgagg aagagcggaa catattatct cgaagcacaa gcccgtggat ccccaattta     480
```

-continued

```
cagtatgcct ttcaggacaa aaatcacctt tatctggtga tggaatatca gcctggaggg   540
gacttgctgt cacttttgaa tagatatgag gaccagttag atgaaaacct gatacagttt   600
tacctagctg agctgatttt ggctgttcac agcgttcatc tgatgggata cgtgcatcgg   660
gacatcaagc ctgagaacat tctcgttgac cgcacaggac acatcaagct ggtggatttt   720
ggatctgccg cgaaaatgaa ttcaaacaag gtgaatgcca actcccgat tgggaccccca    780 gattacatgg ctcctgaagt gctgactgtg atgaacgggg atggaaaagg cacctacggc   840
ctggactgtg actggtggtc agtgggcgtg attgcctatg atatgattta tgggagatcc   900
cccttcgcag agggaacctc tgccagaacc ttcaataaca ttatgaattt ccagcggttt   960
ttgaaatttc cagatgaccc caaagtgagc agtgactttc ttgatctgat tcaaagcttg  1020
ttgtgcggcc agaaagagag actgaagttt gaaggtcttt gctgccatcc tttcttctct  1080
aaaattgact ggaacaacat tcgtaacgct cctcccccct tcgttcccac cctcaagtct  1140
gacgatgaca cctccaattt tgatgaacca gagaagaatt cgtgggtttc atcctctccg  1200
tgccagctga gccctcagg cttctcgggt gaagaactgc cgtttgtggg gttttcgtac   1260
agcaaggcac tggggattct tggtagatct gagtctgttg tgtcgggtct ggactcccct  1320
gccaagacta gctccatgga aagaaactt ctcatcaaaa gcaaagagct acaagactct   1380
caggacaagt gtcacaagat ggagcaggaa atgacccggt tacatcggag agtgtcagag  1440
gtggaggctg tgcttagtca gaaggaggtg gagctgaagg cctctgagac tcagagatcc   1500
ctcctggagc aggaccttgc tacctacatc acagaatgca gtagcttaaa gcgaagtttg  1560
gagcaagcac ggatggaggt gtcccaggag gatgacaaag cactgcagct tctccatgat  1620
atcagagagc agagccggaa gctccaagaa atcaaagagc aggagtacca ggctcaagtg  1680
gaagaaatga ggttgatgat gaatcagttg gaagaggatc ttgtctcagc aagaagacgg  1740
agtgatctct acgaatctga gctgagagag tctcggcttg ctgctgaaga attcaagcgg  1800
aaagcgacag aatgtcagca taaactgttg aaggctaagg atcagggaa gcctgaagtg  1860 ggagaatatg cgaaactgga gaagatcaat gctgagcagc agctcaaaat tcaggagctc  1920
caagagaaac tggagaaggc tgtaaaagcc agcacggagg ccaccgagct gctgcagaat  1980
atccgccagg caaggagcg agccgagagg gagctggaga gctgcagaa ccgagaggat   2040 tcttctgaag gcatcagaaa gaagctggtg gaagctgagg aacgccgcca ttctctggag  2100
aacaaggtaa agagactaga gaccatggag cgtagagaaa acagactgaa ggatgacatc  2160
cagacaaaat cccaacagat ccagcagatg gctgataaaa ttctggagct cgaagagaaa  2220
catcgggagg cccaagtctc agcccagcac ctagaagtgc acctgaaaca gaaagagcag  2280
cactatgagg aaaagattaa agtattggac aatcagataa gaaagacct ggctgacaag  2340 gagacactgg agaacatgat gcagagacac gaggaggagg cccatgagaa gggcaaaatt  2400
ctcagcgaac agaaggcgat gatcaatgct atggattcca agatcagatc cctgaacag    2460 aggattgtgg aactgtctga agccaataaa cttgcagcaa atagcagtct tttttacccaa  2520 aggaacatga aggcccaaga agagatgatt tctgaactca ggcaacagaa attttacctg  2580
gagacacagg ctgggaagtt ggaggcccag aaccgaaaac tggaggagca gctggagaag  2640
atcagccacc aagaccacag tgacaagaat cggctgctgg aactggagac aagattgcgg  2700
gaggtgagtc tagagcacga ggagcagaaa ctggagctca gcgccagct cacagagcta  2760 cagctctccc tgcaggagcg cgagtcacag ttgacagccc tgcaggctgc acgggcggcc  2820
```

```
ctggagagcc agcttcgcca ggcgaagaca gagctggaag agaccacagc agaagctgaa      2880
gaggagatcc aggcactcac ggcacataga gatgaaatcc agcgcaaatt tgatgctctt      2940
cgtaacagct gtactgtgat cacagacctg gaggagcagc taaaccagct gaccgaggac      3000
aacgctgaac tcaacaacca aaacttctac ttgtccaaac aactcgatga ggcttctggc      3060
gccaacgacg agattgtaca actgcgaagt gaagtggacc atctccgccg ggagatcacg      3120
gaacgagaga tgcagcttac cagccagaag caaacgatgg aggctctgaa gaccacgtgc      3180
accatgctgg aggaacaggt catggatttg gaggccctaa cgatgagct gctagaaaaa       3240 gagcggcagt gggaggcctg gaggagcgtc ctgggtgatg agaaatccca gtttgagtgt      3300
cgggttcgag agctgcagag gatgctggac accgagaaac agagcagggc gagagccgat      3360
cagcggatca ccgagtctcg ccaggtggtg gagctggcag tgaaggagca caggctgag       3420 attctcgctc tgcagcaggc tctcaaagag cagaagctga aggccgagag cctctctgac      3480
aagctcaatg acctggagaa gaagcatgct atgcttgaaa tgaatgcccg aagcttacag      3540
cagaagctgg agactgaacg agagctcaaa cagaggcttc tggaagagca agccaaatta      3600
cagcagcaga tggacctgca gaaaaatcac attttccgtc tgactcaagg actgcaagaa      3660
gctctagatc gggctgatct actgaagaca gaaagaagtg acttggagta tcagctggaa      3720
aacattcagg tgctctattc tcatgaaaag gtgaaaatgg aaggcactat ttctcaacaa      3780
accaaactca ttgattttct gcaagccaaa atggaccaac tgctaaaaaa gaaaaaggtg      3840
cctctgcagt acaatgagct gaagctggcc ctggagaagg agaaagctcg ctgtgcagag      3900
ctagaggaag cccttcagaa gacccgcatc gagctccggt ccgcccggga ggaagctgcc      3960
caccgcaaag caacggacca cccacaccca tccacgccag ccaccgcgag gcagcagatc      4020
gccatgtctg ccatcgtgcg gtcgccagag caccagccca gtgccatgag cctgctggcc      4080
ccgccatcca gccgcagaaa ggagtcttca actccagagg aatttagtcg gcgtcttaag      4140
gaacgcatgc accacaatat tcctcaccga ttcaacgtag gactgaacat gcgagccaca      4200
aagtgtgctg tgtgtctgga taccgtgcac tttggacgcc aggcatccaa atgtctagaa      4260
tgtcaggtga tgtgtcaccc caagtgctcc acgtgcttgc cagccacctg cggcttgcct      4320
gctgaatatg ccacacactt caccgaggcc ttctgccgtg acaaaatgaa ctccccaggt      4380
ctccagacca aggagcccag cagcagcttg cacctggaag ggtggatgaa ggtgcccagg      4440
aataacaaac gaggacagca aggctgggac aggaagtaca ttgtcctgga gggatcaaaa      4500
gtcctcattt atgacaatga agccagagaa gctggacaga ggccggtgga agaatttgag      4560
ctgtgccttc ccgacgggga tgtatctatt catggtgccg ttggtgcttc cgaactcgca      4620
aatacagcca aagcagatgt cccatacata ctgaagatgg aatctcaccc gcacaccacc      4680
tgctggcccg ggagaaccct ctacttgcta gctcccagct tccctgacaa acagcgctgg      4740
gtcaccgcct tagaatcagt tgtcgcaggt gggagagttt ctagggaaaa agcagaagct      4800
gatgctaaac tgcttggaaa ctccctgctg aaactggaag gtgatgaccg tctagacatg      4860
aactgcacgc tgcccttcag tgaccaggta gtgttggtgg caccgaggga agggctctac      4920
gccctgaatg tcttgaaaaa ctccctaacc catgtcccag gaattggagc agtcttccaa      4980
atttatatta tcaaggacct ggagaagcta ctcatgatag caggtgaaga gcgggcactg      5040
tgtcttgtgg acgtgaagaa agtgaaacag tccctggccc agtcccacct gcctgcccag      5100
cccgacatct cacccaacat ttttgaagct gtcaagggct gccacttgtt ggggcaggc       5160 aagattgaga acgggctctg catctgtgca gccatgccca gcaaagtcgt cattctccgc      5220
```

```
tacaacgaaa acctcagcaa atactgcatc cggaaagaga tagagacctc agagccctgc    5280
agctgtatcc acttcaccaa ttacagtatc ctcattggaa ccaataaatt ctacgaaatc    5340
gacatgaagc agtacacgct cgaggaattc ctggataaga atgaccattc cttggcacct    5400
gctgtgtttg ccgcctcttc aacagcttcc ctgtctcaa tcgtgcaggt gaacagcgca     5460
gggcagcgag aggagtactt gctgtgtttc acgaatttg gagtgttcgt ggattcttac     5520
ggaagacgta gccgcacaga cgatctcaag tggagtcgct taccttttggc ctttgcctac   5580 agagaaccct atctgtttgt gacccacttc aactcactcg aagtaattga gatccaggca   5640
cgctcctcag cagggacccc tgcccgagcg tacctggaca tcccgaaccc gcgctacctg   5700
ggccctgcca tttcctcagg agcgatttac ttggcgtcct cataccagga taaattaagg   5760
gtcatttgct gcaagggaaa cctcgtgaag gagtccggca ctgaacacca ccggggcccg   5820
tccacctccc gcagcagccc caacaagcga ggcccaccca cgtacaacga gcacatcacc   5880
aagcgcgtgg cctccagccc agcgccgccc gaaggcccca gccaccgcg agagccaagc    5940 acacccacc gctaccgcga ggggcggacc gagctgcgca gggacaagtc tcctggccgc    6000
cccctggagc gagagaagtc ccccggccgg atgctcagca cgcggagaga gcggtccccc   6060
gggaggctgt ttgaagacag cagcagggc cggctgcctg cgggagccgt gaggaccccg    6120
ctgtcccagg tgaacaaggt gaggcagcat tccgaggcct gtgtgtctgt tgcggaggcc    6180
aggagtgact tggggaactg a                                              6201
```

<210> SEQ ID NO 9
<211> LENGTH: 2066
<212> TYPE: PRT
<213> ORGANISM: Homo sapiens

<400> SEQUENCE: 9

```
Met Leu Lys Phe Lys Tyr Gly Ala Arg Asn Pro Leu Asp Ala Gly Ala
 1               5                  10                  15

Ala Glu Pro Ile Ala Ser Arg Ala Ser Arg Leu Asn Leu Phe Phe Gln
            20                  25                  30

Gly Lys Pro Pro Phe Met Thr Gln Gln Gln Met Ser Pro Leu Ser Arg
        35                  40                  45

Glu Gly Ile Leu Asp Ala Leu Phe Val Leu Phe Glu Glu Cys Ser Gln
    50                  55                  60

Pro Ala Leu Met Lys Ile Lys His Val Ser Asn Phe Val Arg Lys Cys
65                  70                  75                  80

Ser Asp Thr Ile Ala Glu Leu Gln Glu Leu Gln Pro Ser Ala Lys Asp
                85                  90                  95

Phe Glu Val Arg Ser Leu Val Gly Cys Gly His Phe Ala Glu Val Gln
            100                 105                 110

Val Val Arg Glu Lys Ala Thr Gly Asp Ile Tyr Ala Met Lys Val Met
        115                 120                 125

Lys Lys Lys Ala Leu Leu Ala Gln Glu Gln Val Ser Phe Phe Glu Glu
    130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn His Leu Tyr Leu Val Met Glu Tyr
                165                 170                 175

Gln Pro Gly Gly Asp Leu Leu Ser Leu Leu Asn Arg Tyr Glu Asp Gln
            180                 185                 190
```

-continued

```
Leu Asp Glu Asn Leu Ile Gln Phe Tyr Leu Ala Glu Leu Ile Leu Ala
        195                 200                 205

Val His Ser Val His Leu Met Gly Tyr Val His Arg Asp Ile Lys Pro
    210                 215                 220

Glu Asn Ile Leu Val Asp Arg Thr Gly His Ile Lys Leu Val Asp Phe
225                 230                 235                 240

Gly Ser Ala Ala Lys Met Asn Ser Asn Lys Val Asn Ala Lys Leu Pro
                245                 250                 255

Ile Gly Thr Pro Asp Tyr Met Ala Pro Glu Val Leu Thr Val Met Asn
            260                 265                 270

Gly Asp Gly Lys Gly Thr Tyr Gly Leu Asp Cys Asp Trp Trp Ser Val
        275                 280                 285

Gly Val Ile Ala Tyr Glu Met Ile Tyr Gly Arg Ser Pro Phe Ala Glu
    290                 295                 300

Gly Thr Ser Ala Arg Thr Phe Asn Asn Ile Met Asn Phe Gln Arg Phe
305                 310                 315                 320

Leu Lys Phe Pro Asp Asp Pro Lys Val Ser Ser Asp Phe Leu Asp Leu
                325                 330                 335

Ile Gln Ser Leu Leu Cys Gly Gln Lys Glu Arg Leu Lys Phe Glu Gly
            340                 345                 350

Leu Cys Cys His Pro Phe Phe Ser Lys Ile Asp Trp Asn Asn Ile Arg
        355                 360                 365

Asn Ala Pro Pro Pro Phe Val Pro Thr Leu Lys Ser Asp Asp Asp Thr
    370                 375                 380

Ser Asn Phe Asp Glu Pro Glu Lys Asn Ser Trp Val Ser Ser Ser Pro
385                 390                 395                 400

Cys Gln Leu Ser Pro Ser Gly Phe Ser Gly Glu Glu Leu Pro Phe Val
                405                 410                 415

Gly Phe Ser Tyr Ser Lys Ala Leu Gly Ile Leu Gly Arg Ser Glu Ser
            420                 425                 430

Val Val Ser Gly Leu Asp Ser Pro Ala Lys Thr Ser Ser Met Glu Lys
        435                 440                 445

Lys Leu Leu Ile Lys Ser Lys Glu Leu Gln Asp Ser Gln Asp Lys Cys
    450                 455                 460

His Lys Met Glu Gln Glu Met Thr Arg Leu His Arg Arg Val Ser Glu
465                 470                 475                 480

Val Glu Ala Val Leu Ser Gln Lys Glu Val Glu Leu Lys Ala Ser Glu
                485                 490                 495

Thr Gln Arg Ser Leu Leu Glu Gln Asp Leu Ala Thr Tyr Ile Thr Glu
            500                 505                 510

Cys Ser Ser Leu Lys Arg Ser Leu Glu Gln Ala Arg Met Glu Val Ser
        515                 520                 525

Gln Glu Asp Asp Lys Ala Leu Gln Leu Leu His Asp Ile Arg Glu Gln
    530                 535                 540

Ser Arg Lys Leu Gln Glu Ile Lys Glu Gln Glu Tyr Gln Ala Gln Val
545                 550                 555                 560

Glu Glu Met Arg Leu Met Met Asn Gln Leu Glu Glu Asp Leu Val Ser
                565                 570                 575

Ala Arg Arg Arg Ser Asp Leu Tyr Glu Ser Glu Leu Arg Glu Ser Arg
            580                 585                 590

Leu Ala Ala Glu Glu Phe Lys Arg Lys Ala Thr Glu Cys Gln His Lys
        595                 600                 605

Leu Leu Lys Ala Lys Asp Gln Gly Lys Pro Glu Val Gly Glu Tyr Ala
```

-continued

```
                610                 615                 620
Lys Leu Glu Lys Ile Asn Ala Glu Gln Gln Leu Lys Ile Gln Glu Leu
625                 630                 635                 640

Gln Glu Lys Leu Glu Lys Ala Val Lys Ala Ser Thr Glu Ala Thr Glu
                645                 650                 655

Leu Leu Gln Asn Ile Arg Gln Ala Lys Glu Arg Ala Glu Arg Glu Leu
                660                 665                 670

Glu Lys Leu Gln Asn Arg Glu Asp Ser Ser Glu Gly Ile Arg Lys Lys
                675                 680                 685

Leu Val Glu Ala Glu Arg Arg His Ser Leu Glu Asn Lys Val Lys
690                 695                 700

Arg Leu Glu Thr Met Glu Arg Arg Glu Asn Arg Leu Lys Asp Asp Ile
705                 710                 715                 720

Gln Thr Lys Ser Gln Gln Ile Gln Gln Met Ala Asp Lys Ile Leu Glu
                725                 730                 735

Leu Glu Glu Lys His Arg Glu Ala Gln Val Ser Ala Gln His Leu Glu
                740                 745                 750

Val His Leu Lys Gln Lys Glu Gln His Tyr Glu Glu Lys Ile Lys Val
                755                 760                 765

Leu Asp Asn Gln Ile Lys Lys Asp Leu Ala Asp Lys Glu Thr Leu Glu
770                 775                 780

Asn Met Met Gln Arg His Glu Glu Ala His Glu Lys Gly Lys Ile
785                 790                 795                 800

Leu Ser Glu Gln Lys Ala Met Ile Asn Ala Met Asp Ser Lys Ile Arg
                805                 810                 815

Ser Leu Glu Gln Arg Ile Val Glu Leu Ser Glu Ala Asn Lys Leu Ala
                820                 825                 830

Ala Asn Ser Ser Leu Phe Thr Gln Arg Asn Met Lys Ala Gln Glu Glu
                835                 840                 845

Met Ile Ser Glu Leu Arg Gln Gln Lys Phe Tyr Leu Glu Thr Gln Ala
850                 855                 860

Gly Lys Leu Glu Ala Gln Asn Arg Lys Leu Glu Glu Gln Leu Glu Lys
865                 870                 875                 880

Ile Ser His Gln Asp His Ser Asp Lys Asn Arg Leu Leu Glu Leu Glu
                885                 890                 895

Thr Arg Leu Arg Glu Val Ser Leu Glu His Glu Glu Gln Lys Leu Glu
                900                 905                 910

Leu Lys Arg Gln Leu Thr Glu Leu Gln Leu Ser Leu Gln Glu Arg Glu
                915                 920                 925

Ser Gln Leu Thr Ala Leu Gln Ala Ala Arg Ala Ala Leu Glu Ser Gln
930                 935                 940

Leu Arg Gln Ala Lys Thr Glu Leu Glu Glu Thr Thr Ala Glu Ala Glu
945                 950                 955                 960

Glu Glu Ile Gln Ala Leu Thr Ala His Arg Asp Glu Ile Gln Arg Lys
                965                 970                 975

Phe Asp Ala Leu Arg Asn Ser Cys Thr Val Ile Thr Asp Leu Glu Glu
                980                 985                 990

Gln Leu Asn Gln Leu Thr Glu Asp Asn Ala Glu Leu Asn Asn Gln Asn
                995                 1000                1005

Phe Tyr Leu Ser Lys Gln Leu Asp Glu Ala Ser Gly Ala Asn Asp Glu
    1010                1015                1020

Ile Val Gln Leu Arg Ser Glu Val Asp His Leu Arg Arg Glu Ile Thr
1025                1030                1035                1040
```

-continued

```
Glu Arg Glu Met Gln Leu Thr Ser Gln Lys Gln Thr Met Glu Ala Leu
            1045                1050                1055

Lys Thr Thr Cys Thr Met Leu Glu Glu Gln Val Met Asp Leu Glu Ala
        1060                1065                1070

Leu Asn Asp Glu Leu Leu Glu Lys Glu Arg Gln Trp Glu Ala Trp Arg
        1075                1080                1085

Ser Val Leu Gly Asp Glu Lys Ser Gln Phe Glu Cys Arg Val Arg Glu
    1090                1095                1100

Leu Gln Arg Met Leu Asp Thr Glu Lys Gln Ser Arg Ala Arg Ala Asp
1105                1110                1115                1120

Gln Arg Ile Thr Glu Ser Arg Gln Val Val Glu Leu Ala Val Lys Glu
            1125                1130                1135

His Lys Ala Glu Ile Leu Ala Leu Gln Gln Ala Leu Lys Glu Gln Lys
        1140                1145                1150

Leu Lys Ala Glu Ser Leu Ser Asp Lys Leu Asn Asp Leu Glu Lys Lys
    1155                1160                1165

His Ala Met Leu Glu Met Asn Ala Arg Ser Leu Gln Gln Lys Leu Glu
1170                1175                1180

Thr Glu Arg Glu Leu Lys Gln Arg Leu Leu Glu Gln Ala Lys Leu
1185                1190                1195                1200

Gln Gln Gln Met Asp Leu Gln Lys Asn His Ile Phe Arg Leu Thr Gln
            1205                1210                1215

Gly Leu Gln Glu Ala Leu Asp Arg Ala Asp Leu Leu Lys Thr Glu Arg
        1220                1225                1230

Ser Asp Leu Glu Tyr Gln Leu Glu Asn Ile Gln Val Leu Tyr Ser His
    1235                1240                1245

Glu Lys Val Lys Met Glu Gly Thr Ile Ser Gln Gln Thr Lys Leu Ile
1250                1255                1260

Asp Phe Leu Gln Ala Lys Met Asp Gln Pro Ala Lys Lys Lys Val
1265                1270                1275                1280

Pro Leu Gln Tyr Asn Glu Leu Lys Leu Ala Leu Glu Lys Glu Lys Ala
            1285                1290                1295

Arg Cys Ala Glu Leu Glu Glu Ala Leu Gln Lys Thr Arg Ile Glu Leu
        1300                1305                1310

Arg Ser Ala Arg Glu Glu Ala Ala His Arg Lys Ala Thr Asp His Pro
    1315                1320                1325

His Pro Ser Thr Pro Ala Thr Ala Arg Gln Gln Ile Ala Met Ser Ala
        1330                1335                1340

Ile Val Arg Ser Pro Glu His Gln Pro Ser Ala Met Ser Leu Leu Ala
1345                1350                1355                1360

Pro Pro Ser Ser Arg Arg Lys Glu Ser Ser Thr Pro Glu Glu Phe Ser
            1365                1370                1375

Arg Arg Leu Lys Glu Arg Met His His Asn Ile Pro His Arg Phe Asn
        1380                1385                1390

Val Gly Leu Asn Met Arg Ala Thr Lys Cys Ala Val Cys Leu Asp Thr
    1395                1400                1405

Val His Phe Gly Arg Gln Ala Ser Lys Cys Leu Glu Cys Gln Val Met
    1410                1415                1420

Cys His Pro Lys Cys Ser Thr Cys Leu Pro Ala Thr Cys Gly Leu Pro
1425                1430                1435                1440

Ala Glu Tyr Ala Thr His Phe Thr Glu Ala Phe Cys Arg Asp Lys Met
            1445                1450                1455
```

-continued

```
Asn Ser Pro Gly Leu Gln Thr Lys Glu Pro Ser Ser Leu His Leu
        1460                1465                1470

Glu Gly Trp Met Lys Val Pro Arg Asn Asn Lys Arg Gly Gln Gln Gly
    1475                1480                1485

Trp Asp Arg Lys Tyr Ile Val Leu Glu Gly Ser Lys Val Leu Ile Tyr
1490                1495                1500

Asp Asn Glu Ala Arg Glu Ala Gly Gln Arg Pro Val Glu Glu Phe Glu
1505                1510                1515                1520

Leu Cys Leu Pro Asp Gly Asp Val Ser Ile His Gly Ala Val Gly Ala
            1525                1530                1535

Ser Glu Leu Ala Asn Thr Ala Lys Ala Asp Val Pro Tyr Ile Leu Lys
        1540                1545                1550

Met Glu Ser His Pro His Thr Thr Cys Trp Pro Gly Arg Thr Leu Tyr
    1555                1560                1565

Leu Leu Ala Pro Ser Phe Pro Asp Lys Gln Arg Trp Val Thr Ala Leu
1570                1575                1580

Glu Ser Val Val Ala Gly Gly Arg Val Ser Arg Glu Lys Ala Glu Ala
1585                1590                1595                1600

Asp Ala Lys Leu Leu Gly Asn Ser Leu Leu Lys Leu Glu Gly Asp Asp
            1605                1610                1615

Arg Leu Asp Met Asn Cys Thr Leu Pro Phe Ser Asp Gln Val Val Leu
        1620                1625                1630

Val Gly Thr Glu Glu Gly Leu Tyr Ala Leu Asn Val Leu Lys Asn Ser
    1635                1640                1645

Leu Thr His Val Pro Gly Ile Gly Ala Val Phe Gln Ile Tyr Ile Ile
1650                1655                1660

Lys Asp Leu Glu Lys Leu Leu Met Ile Ala Gly Glu Glu Arg Ala Leu
1665                1670                1675                1680

Cys Leu Val Asp Val Lys Lys Val Lys Gln Ser Leu Ala Gln Ser His
            1685                1690                1695

Leu Pro Ala Gln Pro Asp Ile Ser Pro Asn Ile Phe Glu Ala Val Lys
        1700                1705                1710

Gly Cys His Leu Phe Gly Ala Gly Lys Ile Glu Asn Gly Leu Cys Ile
    1715                1720                1725

Cys Ala Ala Met Pro Ser Lys Val Val Ile Leu Arg Tyr Asn Glu Asn
    1730                1735                1740

Leu Ser Lys Tyr Cys Ile Arg Lys Glu Ile Glu Thr Ser Glu Pro Cys
1745                1750                1755                1760

Ser Cys Ile His Phe Thr Asn Tyr Ser Ile Leu Ile Gly Thr Asn Lys
            1765                1770                1775

Phe Tyr Glu Ile Asp Met Lys Gln Tyr Thr Leu Glu Glu Phe Leu Asp
        1780                1785                1790

Lys Asn Asp His Ser Leu Ala Pro Ala Val Phe Ala Ala Ser Ser Asn
    1795                1800                1805

Ser Phe Pro Val Ser Ile Val Gln Val Asn Ser Ala Gly Gln Arg Glu
    1810                1815                1820

Glu Tyr Leu Leu Cys Phe His Glu Phe Gly Val Phe Val Asp Ser Tyr
1825                1830                1835                1840

Gly Arg Arg Ser Arg Thr Asp Asp Leu Lys Trp Ser Arg Leu Pro Leu
            1845                1850                1855

Ala Phe Ala Tyr Arg Glu Pro Tyr Leu Phe Val Thr His Phe Asn Ser
        1860                1865                1870

Leu Glu Val Ile Glu Ile Gln Ala Arg Ser Ser Ala Gly Thr Pro Ala
```

-continued

```
            1875                1880                1885
Arg Ala Tyr Leu Asp Ile Pro Asn Pro Arg Tyr Leu Gly Pro Ala Ile
     1890                1895                1900
Ser Ser Gly Ala Ile Tyr Leu Ala Ser Ser Tyr Gln Asp Lys Leu Arg
1905                1910                1915                1920
Val Ile Cys Cys Lys Gly Asn Leu Val Lys Glu Ser Gly Thr Glu His
             1925                1930                1935
His Arg Gly Pro Ser Thr Ser Arg Ser Ser Pro Asn Lys Arg Gly Pro
         1940                1945                1950
Pro Thr Tyr Asn Glu His Ile Thr Lys Arg Val Ala Ser Ser Pro Ala
         1955                1960                1965
Pro Pro Glu Gly Pro Ser His Pro Arg Glu Pro Ser Thr Pro His Arg
     1970                1975                1980
Tyr Arg Glu Gly Arg Thr Glu Leu Arg Arg Asp Lys Ser Pro Gly Arg
1985                1990                1995                2000
Pro Leu Glu Arg Glu Lys Ser Pro Gly Arg Met Leu Ser Thr Arg Arg
             2005                2010                2015
Glu Arg Ser Pro Gly Arg Leu Phe Glu Asp Ser Ser Arg Gly Arg Leu
         2020                2025                2030
Pro Ala Gly Ala Val Arg Thr Pro Leu Ser Gln Val Asn Lys Val Arg
         2035                2040                2045
Gln His Ser Glu Ala Cys Val Ser Val Ala Glu Ala Arg Ser Asp Leu
     2050                2055                2060
Gly Asn
2065
```

```
<210> SEQ ID NO 10
<211> LENGTH: 6189
<212> TYPE: DNA
<213> ORGANISM: Homo sapiens

<400> SEQUENCE: 10
atgttgaagt tcaaatatgg agcgcggaat cctttggatg ctggtgctgc tgaacccatt      60
gccagccggg cctccaggct gaatctgttc ttccagggga accaccctt tatgactcaa     120 cagcagatgt ctcctctttc ccgagaaggg atattagatg ccctctttgt tctctttgaa     180
gaatgcagtc agcctgctct gatgaagatt aagcacgtga gcaactttgt ccggaagtgt     240
tccgacacca tagctgagtt acaggagctc cagccttcgg caaaggactt cgaagtcaga     300
agtcttgtag gttgtggtca ctttgctgaa gtgcaggtgg taagagagaa agcaaccggg     360
gacatctatg ctatgaaagt gatgaagaag aaggctttat tggcccagga gcaggtttca     420
ttttttgagg aagagcggaa catattatct cgaagcacaa gcccgtggat cccccaatta     480
cagtatgcct ttcaggacaa aaatcacctt tatctggtga tggaatatca gcctggaggg     540
gacttgctgt cacttttgaa tagatatgag gaccagttag atgaaaacct gatacagttt     600
tacctagctg agctgatttt ggctgttcac agcgttcatc tgatgggata cgtgcatcgg     660
gacatcaagc tgagaacat tctcgttgac cgcacaggac acatcaagct ggtggatttt     720
ggatctgccg cgaaaatgaa ttcaaacaag gtgaatgcca actcccgat gggaccccca     780 gattacatgc tcctgaagt gctgactgtg atgaacgggg atggaaaagg cacctacggc     840
ctggactgtg actggtggtc agtgggcgtg attgcctatg agatgattta tggagatccc     900
cccttcgcag agggaaccct ctgccagaac ttcaataaca ttatgaattt ccagcggttt     960
ttgaaatttc cagatgaccc caaagtgagc agtgactttc ttgatctgat tcaaagcttg    1020
```

-continued

```
ttgtgcggcc agaaagagag actgaagttt gaaggtcttt gctgccatcc tttcttctct    1080
aaaattgact ggaacaacat tcgtaacgct cctccccct tcgttcccac cctcaagtct    1140
gacgatgaca cctccaattt tgatgaacca gagaagaatt cgtgggtttc atcctctccg    1200
tgccagctga gccctcagg cttctcgggt gaagaactgc cgtttgtggg gttttcgtac    1260
agcaaggcac tgggattct tggtagatct gagtctgttg tgtcgggtct ggactcccct    1320
gccaagacta gctccatgga aagaaactt ctcatcaaa gcaaagagct acaagactct    1380
caggacaagt gtcacaagat ggagcaggaa atgacccggt tacatcggag agtgtcagag    1440
gtggaggctg tgcttagtca gaaggaggtg gagctgaagg cctctgagac tcagagatcc    1500
ctcctggagc aggaccttgc tacctacatc acagaatgca gtagcttaaa gcgaagtttg    1560
gagcaagcac ggatggaggt gtcccaggag gatgacaaag cactgcagct tctccatgat    1620
atcagagagc agagccggaa gctccaagaa atcaaagagc aggagtacca ggctcaagtg    1680
gaagaaatga ggttgatgat gaatcagttg gaagaggatc ttgtctcagc aagaagacgg    1740
agtgatctct acgaatctga gctgagagag tctcggcttg ctgctgaaga attcaagcgg    1800
aaagcgacag aatgtcagca taaactgttg aaggctaagg atcagggaa gcctgaagtg    1860 ggagaatatg cgaaactgga gaagatcaat gctgagcagc agctcaaaat tcaggagctc    1920
caagagaaac tggagaaggc tgtaaaagcc agcacggagg ccaccgagct gctgcagaat    1980
atccgccagg caaggagcg agccgagagg gagctggaga agctgcagaa ccgagaggat    2040
tcttctgaag gcatcagaaa gaagctggtg gaagctgagg aacgccgcca ttctctggag    2100
aacaaggtaa agagactaga gaccatggag cgtagagaaa acagactgaa ggatgacatc    2160
cagacaaaat cccaacagat ccagcagatg gctgataaaa ttctggagct cgaagagaaa    2220
catcgggagg cccaagtctc agcccagcac ctagaagtgc acctgaaaca gaaagagcag    2280
cactatgagg aaaagattaa agtattggac aatcagataa agaaagacct ggctgacaag    2340
gagacactgg agaacatgat gcagagacac gaggaggagg cccatgagaa gggcaaaatt    2400
ctcagcgaac agaaggcgat gatcaatgct atggattcca agatcagatc cctggaacag    2460
aggattgtgg aactgtctga agccaataaa cttgcagcaa atagcagtct ttttacccaa    2520
aggaacatga aggcccaaga agagatgatt tctgaactca gcaacagaa attttacctg    2580 gagacacagg ctgggaagtt ggaggcccag aaccgaaaac tggaggagca gctggagaag    2640
atcagccacc aagaccacag tgacaagaat cggctgctgg aactggagac aagattgcgg    2700
gaggtgagtc tagagcacga ggagcagaaa ctggagctca gcgccagct cacagagcta    2760 cagctctccc tgcaggagcg cgagtcacag ttgacagccc tgcaggctgc acgggcggcc    2820
ctggagagcc agcttcgcca ggcgaagaca gagctggaag agaccacagc agaagctgaa    2880
gaggagatcc aggcactcac ggcacataga gatgaaatcc agcgcaaatt tgatgctctt    2940
cgtaacagct gtactgtgat cacagacctg gaggagcagc taaaccagct gaccgaggac    3000
aacgctgaac tcaacaacca aaacttctac ttgtccaaac aactcgatga ggcttctggc    3060
gccaacgacg agattgtaca actgcgaagt gaagtggacc atctccgccg ggagatcacg    3120
gaacgagaga tgcagcttac cagccagaag caaacgatgg aggctctgaa gaccacgtgc    3180
accatgctgg aggaacaggt catggatttg gaggccctaa acgatgagct gctagaaaaa    3240
gagcggcagt gggaggcctg gaggagcgtc ctgggtgatg agaaatccca gtttgagtgt    3300
cgggttcgag agctgcagag gatgctggac accgagaaac agagcagggc gagagccgat    3360
```

```
cagcggatca ccgagtctcg ccaggtggtg gagctggcag tgaaggagca caaggctgag      3420
attctcgctc tgcagcaggc tctcaaagag cagaagctga aggccgagag cctctctgac      3480
aagctcaatg acctggagaa gaagcatgct atgcttgaaa tgaatgcccg aagcttacag      3540
cagaagctgg agactgaacg agagctcaaa cagaggcttc tggaagagca agccaaatta      3600
cagcagcaga tggacctgca gaaaaatcac attttccgtc tgactcaagg actgcaagaa      3660
gctctagatc gggctgatct actgaagaca gaaagaagtg acttggagta tcagctggaa      3720
aacattcagg tgctctattc tcatgaaaag gtgaaaatgg aaggcactat ttctcaacaa      3780
accaaactca ttgattttct gcaagccaaa atggaccaac tgctaaaaa gaaaaaggtg      3840 cctctgcagt acaatgagct gaagctggcc ctggagaagg agaaagctcg ctgtgcagag      3900
ctagaggaag cccttcagaa gacccgcatc gagctccggt ccgcccggga ggaagctgcc      3960
caccgcaaag caacggacca cccacaccca tccacgccag ccaccgcgag gcagcagatc      4020
gccatgtctg ccatcgtgcg gtcgccagag caccagccca gtgccatgag cctgctggcc      4080
ccgccatcca gccgcagaaa ggagtcttca actccagagg aatttagtcg gcgtcttaag      4140
gaacgcatgc accacaatat tcctcaccga ttcaacgtag gactgaacat gcgagccaca      4200
aagtgtgctg tgtgtctgga taccgtgcac tttggacgcc aggcatccaa atgtctagaa      4260
tgtcaggtga tgtgtcaccc caagtgctcc acgtgcttgc cagccacctg cggcttgcct      4320
gctgaatatg ccacacactt caccgaggcc ttctgccgtg acaaaatgaa ctccccaggt      4380
ctccagacca aggagcccag cagcagcttg cacctggaag ggtggatgaa ggtgcccagg      4440
aataacaaac gaggacagca aggctgggac aggaagtaca ttgtcctgga gggatcaaaa      4500 gtcctcatt atgacaatga agccagaga gctggacaga ggccggtgga agaatttgag       4560
ctgtgccttc ccgacgggga tgtatctatt catggtgccg ttggtgcttc cgaactcgca      4620
aatacagcca aagcagatgt cccatacata ctgaagatgg aatctcaccc gcacaccacc      4680
tgctggcccg ggagaaccct ctacttgcta gctcccagct tccctgacaa acagcgctgg      4740
gtcaccgcct tagaatcagt tgtcgcaggt gggagagttt ctagggaaaa agcagaagct      4800
gatgctaaac tgcttggaaa ctccctgctg aaactggaag gtgatgaccg tctagacatg      4860
aactgcacgc tgcccttcag tgaccaggta gtgttggtgg gcaccgagga agggctctac      4920
gccctgaatg tcttgaaaaa ctccctaacc catgtcccag gaattggagc agtcttccaa      4980
atttatatta tcaaggacct ggagaagcta ctcatgatag caggtgaaga gcgggcactg      5040
tgtcttgtgg acgtgaagaa agtgaaacag tccctggccc agtcccacct gcctgcccag      5100
cccgacatct cacccaacat ttttgaagct gtcaagggct gccacttgtt tgggcaggc      5160 aagattgaga acgggctctg catctgtgca gccatgccca gcaaagtcgt cattctccgc      5220
tacaacgaaa acctcagcaa atactgcatc cggaaagaga tagagacctc agagccctgc      5280
agctgtatcc acttccaccaa ttacagtatc ctcattggaa ccaataaatt ctacgaaatc      5340
gacatgaagc agtacacgct cgaggaattc ctggataaga atgaccattc cttggcacct      5400
gctgtgtttg ccgcctcttc caacagcttc cctgtctcaa tcgtgcaggt gaacagcgca      5460
gggcagcgag aggagtactt gctgtgtttc cacgaatttg gagtgttcgt ggattcttac      5520
ggaagacgta gccgcacaga cgatctcaag tggagtcgct tacctttggc ctttgcctac      5580
agagaaccct atctgtttgt gacccacttc aactcactcg aagtaattga gatccaggca      5640
cgctcctcag cagggacccc tgcccgagcg tacctgaca tcccgaaccc gcgctacctg       5700
ggccctgcca tttcctcagg agcgatttac ttggcgtcct cataccagga taaattaagg      5760
```

-continued

```
gtcatttgct gcaagggaaa cctcgtgaag gagtccggca ctgaacacca ccggggcccg    5820
tccacctccc gcagcagccc caacaagcga ggcccaccca cgtacaacga gcacatcacc    5880
aagcgcgtgg cctccagccc agcgccgccc gaaggcccca gccacccgcg agagccaagc    5940 acacccacc gctaccgcga ggggcggacc gagctgcgca gggacaagtc tcctggccgc    6000
cccctggagc gagagaagtc ccccggccgg atgctcagca cgcggagaga gcggtccccc    6060
gggaggctgt ttgaagacag cagcagggc cggctgcctg cgggagccgt gaggaccccg    6120
ctgtcccagg tgaacaaggt gtgggaccag tcttcagtat aaatctcagc cagaaaaacc    6180
aactcctca                                                            6189
```

<210> SEQ ID NO 11
<211> LENGTH: 2053
<212> TYPE: PRT
<213> ORGANISM: Homo sapiens

<400> SEQUENCE: 11

```
Met Leu Lys Phe Lys Tyr Gly Ala Arg Asn Pro Leu Asp Ala Gly Ala
 1               5                  10                  15

Ala Glu Pro Ile Ala Ser Arg Ala Ser Arg Leu Asn Leu Phe Phe Gln
             20                  25                  30

Gly Lys Pro Pro Phe Met Thr Gln Gln Met Ser Pro Leu Ser Arg
         35                  40                  45

Glu Gly Ile Leu Asp Ala Leu Phe Val Leu Phe Glu Glu Cys Ser Gln
     50                  55                  60

Pro Ala Leu Met Lys Ile Lys His Val Ser Asn Phe Val Arg Lys Cys
 65                  70                  75                  80

Ser Asp Thr Ile Ala Glu Leu Gln Glu Leu Gln Pro Ser Ala Lys Asp
                 85                  90                  95

Phe Glu Val Arg Ser Leu Val Gly Cys Gly His Phe Ala Glu Val Gln
            100                 105                 110

Val Val Arg Glu Lys Ala Thr Gly Asp Ile Tyr Ala Met Lys Val Met
        115                 120                 125

Lys Lys Lys Ala Leu Leu Ala Gln Glu Gln Val Ser Phe Phe Glu Glu
130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn His Leu Tyr Leu Val Met Glu Tyr
                165                 170                 175

Gln Pro Gly Gly Asp Leu Leu Ser Leu Leu Asn Arg Tyr Glu Asp Gln
            180                 185                 190

Leu Asp Glu Asn Leu Ile Gln Phe Tyr Leu Ala Glu Leu Ile Leu Ala
        195                 200                 205

Val His Ser Val His Leu Met Gly Tyr Val His Arg Asp Ile Lys Pro
    210                 215                 220

Glu Asn Ile Leu Val Asp Arg Thr Gly His Ile Lys Leu Val Asp Phe
225                 230                 235                 240

Gly Ser Ala Ala Lys Met Asn Ser Asn Lys Val Asn Ala Lys Leu Pro
                245                 250                 255

Ile Gly Thr Pro Asp Tyr Met Ala Pro Glu Val Leu Thr Val Met Asn
            260                 265                 270

Gly Asp Gly Lys Gly Thr Tyr Gly Leu Asp Cys Asp Trp Trp Ser Val
        275                 280                 285
```

-continued

```
Gly Val Ile Ala Tyr Glu Met Ile Tyr Gly Arg Ser Pro Phe Ala Glu
    290                 295                 300
Gly Thr Ser Ala Arg Thr Phe Asn Asn Ile Met Asn Phe Gln Arg Phe
305                 310                 315                 320
Leu Lys Phe Pro Asp Asp Pro Lys Val Ser Ser Asp Phe Leu Asp Leu
                325                 330                 335
Ile Gln Ser Leu Leu Cys Gly Gln Lys Glu Arg Leu Lys Phe Glu Gly
            340                 345                 350
Leu Cys Cys His Pro Phe Phe Ser Lys Ile Asp Trp Asn Asn Ile Arg
        355                 360                 365
Asn Ala Pro Pro Pro Phe Val Pro Thr Leu Lys Ser Asp Asp Asp Thr
    370                 375                 380
Ser Asn Phe Asp Glu Pro Glu Lys Asn Ser Trp Val Ser Ser Ser Pro
385                 390                 395                 400
Cys Gln Leu Ser Pro Ser Gly Phe Ser Gly Glu Leu Pro Phe Val
                405                 410                 415
Gly Phe Ser Tyr Ser Lys Ala Leu Gly Ile Leu Gly Arg Ser Glu Ser
                420                 425                 430
Val Val Ser Gly Leu Asp Ser Pro Ala Lys Thr Ser Ser Met Glu Lys
            435                 440                 445
Lys Leu Leu Ile Lys Ser Lys Glu Leu Gln Asp Ser Gln Asp Lys Cys
    450                 455                 460
His Lys Met Glu Gln Glu Met Thr Arg Leu His Arg Arg Val Ser Glu
465                 470                 475                 480
Val Glu Ala Val Leu Ser Gln Lys Glu Val Glu Leu Lys Ala Ser Glu
                485                 490                 495
Thr Gln Arg Ser Leu Leu Glu Gln Asp Leu Ala Thr Tyr Ile Thr Glu
                500                 505                 510
Cys Ser Ser Leu Lys Arg Ser Leu Glu Gln Ala Arg Met Glu Val Ser
            515                 520                 525
Gln Glu Asp Asp Lys Ala Leu Gln Leu Leu His Asp Ile Arg Glu Gln
    530                 535                 540
Ser Arg Lys Leu Gln Glu Ile Lys Glu Gln Glu Tyr Gln Ala Gln Val
545                 550                 555                 560
Glu Glu Met Arg Leu Met Met Asn Gln Leu Glu Glu Asp Leu Val Ser
                565                 570                 575
Ala Arg Arg Arg Ser Asp Leu Tyr Glu Ser Glu Leu Arg Glu Ser Arg
                580                 585                 590
Leu Ala Ala Glu Glu Phe Lys Arg Lys Ala Thr Glu Cys Gln His Lys
            595                 600                 605
Leu Leu Lys Ala Lys Asp Gln Gly Lys Pro Glu Val Gly Glu Tyr Ala
    610                 615                 620
Lys Leu Glu Lys Ile Asn Ala Glu Gln Gln Leu Lys Ile Gln Glu Leu
625                 630                 635                 640
Gln Glu Lys Leu Glu Lys Ala Val Lys Ala Ser Thr Glu Ala Thr Glu
                645                 650                 655
Leu Leu Gln Asn Ile Arg Gln Ala Lys Glu Arg Ala Glu Arg Glu Leu
                660                 665                 670
Glu Lys Leu Gln Asn Arg Glu Asp Ser Ser Glu Gly Ile Arg Lys Lys
            675                 680                 685
Leu Val Glu Ala Glu Glu Arg Arg His Ser Leu Glu Asn Lys Val Lys
    690                 695                 700
Arg Leu Glu Thr Met Glu Arg Arg Glu Asn Arg Leu Lys Asp Asp Ile
```

-continued

```
            705                 710                 715                 720
Gln Thr Lys Ser Gln Gln Ile Gln Gln Met Ala Asp Lys Ile Leu Glu
                725                 730                 735
Leu Glu Glu Lys His Arg Glu Ala Gln Val Ser Ala Gln His Leu Glu
                740                 745                 750
Val His Leu Lys Gln Lys Glu Gln His Tyr Glu Glu Lys Ile Lys Val
                755                 760                 765
Leu Asp Asn Gln Ile Lys Lys Asp Leu Ala Asp Lys Glu Thr Leu Glu
            770                 775                 780
Asn Met Met Gln Arg His Glu Glu Ala His Glu Lys Gly Lys Ile
785                 790                 795                 800
Leu Ser Glu Gln Lys Ala Met Ile Asn Ala Met Asp Ser Lys Ile Arg
                805                 810                 815
Ser Leu Glu Gln Arg Ile Val Glu Leu Ser Glu Ala Asn Lys Leu Ala
                820                 825                 830
Ala Asn Ser Ser Leu Phe Thr Gln Arg Asn Met Lys Ala Gln Glu Glu
                835                 840                 845
Met Ile Ser Glu Leu Arg Gln Gln Lys Phe Tyr Leu Glu Thr Gln Ala
850                 855                 860
Gly Lys Leu Glu Ala Gln Asn Arg Lys Leu Glu Glu Gln Leu Glu Lys
865                 870                 875                 880
Ile Ser His Gln Asp His Ser Asp Lys Asn Arg Leu Leu Glu Leu Glu
                885                 890                 895
Thr Arg Leu Arg Glu Val Ser Leu Glu His Glu Glu Gln Lys Leu Glu
                900                 905                 910
Leu Lys Arg Gln Leu Thr Glu Leu Gln Leu Ser Leu Gln Glu Arg Glu
            915                 920                 925
Ser Gln Leu Thr Ala Leu Gln Ala Ala Arg Ala Ala Leu Glu Ser Gln
            930                 935                 940
Leu Arg Gln Ala Lys Thr Glu Leu Glu Glu Thr Ala Glu Ala Glu
945                 950                 955                 960
Glu Glu Ile Gln Ala Leu Thr Ala His Arg Asp Glu Ile Gln Arg Lys
                965                 970                 975
Phe Asp Ala Leu Arg Asn Ser Cys Thr Val Ile Thr Asp Leu Glu Glu
                980                 985                 990
Gln Leu Asn Gln Leu Thr Glu Asp Asn Ala Glu Leu Asn Asn Gln Asn
            995                 1000                1005
Phe Tyr Leu Ser Lys Gln Leu Asp Glu Ala Ser Gly Ala Asn Asp Glu
            1010                1015                1020
Ile Val Gln Leu Arg Ser Glu Val Asp His Leu Arg Arg Glu Ile Thr
1025                1030                1035                1040
Glu Arg Glu Met Gln Leu Thr Ser Gln Lys Gln Thr Met Glu Ala Leu
                1045                1050                1055
Lys Thr Thr Cys Thr Met Leu Glu Glu Gln Val Met Asp Leu Glu Ala
                1060                1065                1070
Leu Asn Asp Glu Leu Leu Glu Lys Glu Arg Gln Trp Glu Ala Trp Arg
            1075                1080                1085
Ser Val Leu Gly Asp Glu Lys Ser Gln Phe Glu Cys Arg Val Arg Glu
            1090                1095                1100
Leu Gln Arg Met Leu Asp Thr Glu Lys Gln Ser Arg Ala Arg Ala Asp
1105                1110                1115                1120
Gln Arg Ile Thr Glu Ser Arg Gln Val Val Glu Leu Ala Val Lys Glu
                1125                1130                1135
```

-continued

```
His Lys Ala Glu Ile Leu Ala Leu Gln Gln Ala Leu Lys Glu Gln Lys
        1140                1145                1150
Leu Lys Ala Glu Ser Leu Ser Asp Lys Leu Asn Asp Leu Glu Lys Lys
    1155                1160                1165
His Ala Met Leu Glu Met Asn Ala Arg Ser Leu Gln Gln Lys Leu Glu
1170                1175                1180
Thr Glu Arg Glu Leu Lys Gln Arg Leu Glu Glu Gln Ala Lys Leu
1185                1190                1195                1200
Gln Gln Gln Met Asp Leu Gln Lys Asn His Ile Phe Arg Leu Thr Gln
                1205                1210                1215
Gly Leu Gln Glu Ala Leu Asp Arg Ala Asp Leu Leu Lys Thr Glu Arg
            1220                1225                1230
Ser Asp Leu Glu Tyr Gln Leu Glu Asn Ile Gln Val Leu Tyr Ser His
        1235                1240                1245
Glu Lys Val Lys Met Glu Gly Thr Ile Ser Gln Gln Thr Lys Leu Ile
    1250                1255                1260
Asp Phe Leu Gln Ala Lys Met Asp Gln Pro Ala Lys Lys Lys Lys Val
1265                1270                1275                1280
Pro Leu Gln Tyr Asn Glu Leu Lys Leu Ala Leu Glu Lys Glu Lys Ala
                1285                1290                1295
Arg Cys Ala Glu Leu Glu Glu Ala Leu Gln Lys Thr Arg Ile Glu Leu
            1300                1305                1310
Arg Ser Ala Arg Glu Glu Ala Ala His Arg Lys Ala Thr Asp His Pro
        1315                1320                1325
His Pro Ser Thr Pro Ala Thr Ala Arg Gln Gln Ile Ala Met Ser Ala
    1330                1335                1340
Ile Val Arg Ser Pro Glu His Gln Pro Ser Ala Met Ser Leu Leu Ala
1345                1350                1355                1360
Pro Pro Ser Ser Arg Arg Lys Glu Ser Ser Thr Pro Glu Glu Phe Ser
                1365                1370                1375
Arg Arg Leu Lys Glu Arg Met His His Asn Ile Pro His Arg Phe Asn
            1380                1385                1390
Val Gly Leu Asn Met Arg Ala Thr Lys Cys Ala Val Cys Leu Asp Thr
        1395                1400                1405
Val His Phe Gly Arg Gln Ala Ser Lys Cys Leu Glu Cys Gln Val Met
    1410                1415                1420
Cys His Pro Lys Cys Ser Thr Cys Leu Pro Ala Thr Cys Gly Leu Pro
1425                1430                1435                1440
Ala Glu Tyr Ala Thr His Phe Thr Glu Ala Phe Cys Arg Asp Lys Met
                1445                1450                1455
Asn Ser Pro Gly Leu Gln Thr Lys Glu Pro Ser Ser Ser Leu His Leu
            1460                1465                1470
Glu Gly Trp Met Lys Val Pro Arg Asn Lys Arg Gly Gln Gln Gly
        1475                1480                1485
Trp Asp Arg Lys Tyr Ile Val Leu Glu Gly Ser Lys Val Leu Ile Tyr
    1490                1495                1500
Asp Asn Glu Ala Arg Glu Ala Gly Gln Arg Pro Val Glu Glu Phe Glu
1505                1510                1515                1520
Leu Cys Leu Pro Asp Gly Asp Val Ser Ile His Gly Ala Val Gly Ala
                1525                1530                1535
Ser Glu Leu Ala Asn Thr Ala Lys Ala Asp Val Pro Tyr Ile Leu Lys
            1540                1545                1550
```

-continued

```
Met Glu Ser His Pro His Thr Thr Cys Trp Pro Gly Arg Thr Leu Tyr
    1555                1560                1565

Leu Leu Ala Pro Ser Phe Pro Asp Lys Gln Arg Trp Val Thr Ala Leu
    1570                1575                1580

Glu Ser Val Val Ala Gly Gly Arg Val Ser Arg Glu Lys Ala Glu Ala
1585                1590                1595                1600

Asp Ala Lys Leu Leu Gly Asn Ser Leu Leu Lys Leu Glu Gly Asp Asp
                1605                1610                1615

Arg Leu Asp Met Asn Cys Thr Leu Pro Phe Ser Asp Gln Val Val Leu
            1620                1625                1630

Val Gly Thr Glu Glu Gly Leu Tyr Ala Leu Asn Val Leu Lys Asn Ser
        1635                1640                1645

Leu Thr His Val Pro Gly Ile Gly Ala Val Phe Gln Ile Tyr Ile Ile
    1650                1655                1660

Lys Asp Leu Glu Lys Leu Leu Met Ile Ala Gly Glu Glu Arg Ala Leu
1665                1670                1675                1680

Cys Leu Val Asp Val Lys Lys Val Lys Gln Ser Leu Ala Gln Ser His
                1685                1690                1695

Leu Pro Ala Gln Pro Asp Ile Ser Pro Asn Ile Phe Glu Ala Val Lys
            1700                1705                1710

Gly Cys His Leu Phe Gly Ala Gly Lys Ile Glu Asn Gly Leu Cys Ile
        1715                1720                1725

Cys Ala Ala Met Pro Ser Lys Val Val Ile Leu Arg Tyr Asn Glu Asn
    1730                1735                1740

Leu Ser Lys Tyr Cys Ile Arg Lys Glu Ile Glu Thr Ser Glu Pro Cys
1745                1750                1755                1760

Ser Cys Ile His Phe Thr Asn Tyr Ser Ile Leu Ile Gly Thr Asn Lys
                1765                1770                1775

Phe Tyr Glu Ile Asp Met Lys Gln Tyr Thr Leu Glu Glu Phe Leu Asp
            1780                1785                1790

Lys Asn Asp His Ser Leu Ala Pro Ala Val Phe Ala Ala Ser Ser Asn
        1795                1800                1805

Ser Phe Pro Val Ser Ile Val Gln Val Asn Ser Ala Gly Gln Arg Glu
    1810                1815                1820

Glu Tyr Leu Leu Cys Phe His Glu Phe Gly Val Phe Val Asp Ser Tyr
1825                1830                1835                1840

Gly Arg Arg Ser Arg Thr Asp Asp Leu Lys Trp Ser Arg Leu Pro Leu
                1845                1850                1855

Ala Phe Ala Tyr Arg Glu Pro Tyr Leu Phe Val Thr His Phe Asn Ser
            1860                1865                1870

Leu Glu Val Ile Glu Ile Gln Ala Arg Ser Ser Ala Gly Thr Pro Ala
        1875                1880                1885

Arg Ala Tyr Leu Asp Ile Pro Asn Pro Arg Tyr Leu Gly Pro Ala Ile
    1890                1895                1900

Ser Ser Gly Ala Ile Tyr Leu Ala Ser Ser Tyr Gln Asp Lys Leu Arg
1905                1910                1915                1920

Val Ile Cys Cys Lys Gly Asn Leu Val Lys Glu Ser Gly Thr Glu His
                1925                1930                1935

His Arg Gly Pro Ser Thr Ser Arg Ser Ser Pro Asn Lys Arg Gly Pro
            1940                1945                1950

Pro Thr Tyr Asn Glu His Ile Thr Lys Arg Val Ala Ser Ser Pro Ala
        1955                1960                1965

Pro Pro Glu Gly Pro Ser His Pro Arg Glu Pro Ser Thr Pro His Arg
```

```
                      1970                1975                1980
Tyr Arg Glu Gly Arg Thr Glu Leu Arg Arg Asp Lys Ser Pro Gly Arg
     1985                1990                1995                2000

Pro Leu Glu Arg Glu Lys Ser Pro Gly Arg Met Leu Ser Thr Arg Arg
            2005                2010                2015

Glu Arg Ser Pro Gly Arg Leu Phe Glu Asp Ser Ser Arg Gly Arg Leu
          2020                2025                2030

Pro Ala Gly Ala Val Arg Thr Pro Leu Ser Gln Val Asn Lys Val Trp
     2035                2040                2045

Asp Gln Ser Ser Val
     2050

<210> SEQ ID NO 12
<211> LENGTH: 5691
<212> TYPE: DNA
<213> ORGANISM: Homo sapiens

<400> SEQUENCE: 12
atgaaagcca tgccctggaa ctggacctgc cttctctccc acctcctcat ggtgggcatg     60
ggctcctcca ctttgctcac ccggcagcca gccccgctgt cccagaagca gcggtcattt    120
gtcacattcc gaggagagcc cgccgagggt tcaatcacc tggtggtgga tgagaggaca     180
ggacacattt acttggggc cgtcaatcgg atttacaagc tctccagcga cctgaaggtc     240
ttggtgacgc atgagacagg gccggacgag acaaccccca gtgttaccc accccgcatc     300 gtccagacct gcaatgagcc cctgaccacc accaacaatg tcaacaagat gctcctcata    360
gactacaagg agaacaggct gattgcctgt gggagcctgt accaaggcat ctgcaagctg    420
ctgaggctgg aggacctctt caagctgggg gagccttatc ataagaagga gcactatctg    480
tcaggtgtca cgagagcgg ctcagtcttt ggagtgatcg tctcctacag caacctggat    540
gacaagctgt tcattgccac ggcagtggat gggaagcccg agtattttcc caccatctcc    600
agccggaaac tgaccaagaa ctctgaggcg gatggcatgt cgcgtacgt cttccatgat    660 gagttcgtgg cctcgatgat taagatccct tcggacacct tcaccatcat ccctgacttt    720
gatatctact atgtctatgg ttttagcagt ggcaactttg tctacttttt gaccctccaa    780
cctgagatgg tgtctccacc aggctccacc accaaggagc aggtgtatac atccaagctc    840
gtgaggcttt gcaaggagga cacagccttc aactcctatg tagaggtgcc cattggctgt    900
gagcgcagtg gggtggagta ccgcctgctg caggctgcct acctgtccaa gcgggggcc    960 gtgcttggca ggacccttgg agtccatcca tgatgatgacc tgctcttcac cgtcttctcc   1020
aagggccaga gcggaaaat gaaatccctg atgagtcgg ccctgtgcat cttcatcttg   1080
aagcagataa atgaccgcat taaggagcgg ctgcagtctt gttaccgggg cgagggcacg   1140
ctggacctgg cctggctcaa ggtgaaggac atcccctgca gcagtgcgct cttaaccatt   1200
gacgataact tctgtggcct ggacatgaat gctcccctgg agtgtccga catggtgcgt   1260 ggaattcccg tcttcacgga ggacagggac cgcatgacgt ctgtcatcgc atatgtctac   1320
aagaaccact ctctggcctt tgtgggcacc aaaagtggca agctgaagaa gatccgggtg   1380
gatggaccca gggcaacgc cctccagtat gagacggtgc aggtggtgga ccccggccca   1440
gtcctccggg atatggcctt ctccaaggac cacgagcaac tctacatcat gtcagagagg   1500
cagctcacca gagtccctgt ggagtcctgt ggtcagtatc agagctgcgg cgagtgcctt   1560
ggctcaggcg acccccactg tggctggtgt gtgctgcaca acacgtgcac ccggaaggag   1620
```

```
cggtgtgagc ggtccaagga gccccgcagg tttgcctcgg agatgaagca gtgtgtccgg    1680
ctgacggtcc atcccaacaa tatctccgtc tctcagtaca acgtgctgct ggtcctggag    1740
acgtacaatg tcccggagct gtcagctggc gtcaactgca cctttgagga cctgtcagag    1800
atggatgggc tggtcgtggg caatcagatc cagtgctact cccctgcagc caaggaggtg    1860
ccccggatca tcacagagaa tggggaccac catgtcgtac agcttcagct caaatcaaag    1920
gagaccggca tgaccttcgc cagcaccagc tttgtcttct acaattgcag cgtccacaat    1980
tcgtgcctgt cctgcgtgga gagtccatac cgctgccact ggtgtaaata ccggcatgtc    2040
tgcacccatg accccaagac ctgctccttc caggaaggcc gagtgaagct gcccgaggac    2100
tgcccccagc tgctgcgagt ggacaagatc ctggtgcccg tggaggtgat caagcctatc    2160
acgctgaagg ccaagaacct cccccagccc cagtctgggc agcgtggcta cgaatgcatc    2220
ctcaacattc agggcagcga gcagcgagtg cccgccctgc gcttcaacag ctccagcgta    2280
cagtgccaga acacctctta ttcctatgaa gggatggaga tcaacaacct gcccgtggag    2340
ttgacagtcg tgtggaatgg gcacttcaac attgacaacc cagctcagaa taaagttcac    2400
ctctacaagt gtgagccat gcgtgagagc tgcgggctgt gcctcaaggc tgacccagac    2460
ttcgcatgtg ctggtgcca gggcccaggc cagtgcaccc tgcgccagca ctgccctgcc    2520
caggagagcc agtggctgga gctgtctggt gccaaaagca agtgcacaaa cccccgcatc    2580
acagagataa tcccggtgac aggcccccgg gaaggggca ccaaggtcac tatccgaggg    2640
gagaacctgg gcctggaatt cgcgacatc gcctcccatg tcaaggttgc tggcgtggag    2700
tgcagcccct tagtggatgg ttacatccct gcagaacaga tcgtgtgtga gatggggag    2760 gccaagccca ccagcatgc aggcttcgtg gagatctgcg tggctgtgtg tcggcctgaa    2820
ttcatggccc ggtcctcaca gctctattac ttcatgacac tgactctctc agatctgaag    2880
cccagccggg ggcccatgtc cggagggacc caagtgacca tcacaggcac caacctgaat    2940
gccggaagca acgtggtggt gatgtttgga aagcagccct gtctcttcca caggcgatct    3000
ccatcctaca ttgtctgcaa caccacatcc tcagatgagg tgctagagat gaaggtgtcg    3060
gtgcaggtgg acagggccaa gatccaccag gacctggtct ttcagtatgt ggaagacccc    3120
accatcgtgc ggattgagcc agaatggagc attgtcagtg aaacacacc catcgccgta    3180 tgggggaccc acctggacct catacagaac ccccagatcc gtgccaagca tggagggaag    3240
gagcacatca atatctgtga ggttctgaac gctactgaga tgacctgtca ggcgcccgcc    3300
ctcgctctgg gtcctgacca ccagtcagac ctgaccgaga ggcccgagga gtttggcttc    3360
atcctggaca cgtccagtc cctgctcatc ctcaacaaga ccaacttcac ctactatccc    3420
aacccggtgt ttgaggcctt tggtccctca ggaatcctgg agctcaagcc tggcacgccc    3480
atcatcctaa agggcaagaa cctgatcccg cctgtggctg ggggcaacgt gaagctgaac    3540
tacactgtgc tggttgggga aagccgtgc accgtgaccg tgtcagatgt ccagctgctc    3600
tgcgagtccc ccaacctcat cggcaggcac aaagtgatgg cccgtgtcgg tggcatggag    3660 tactcccgg ggatggtgta cattgccccg gacagcccgc tcagcctgcc cgccatcgtc    3720
agcatcgcag tggctggcgg cctcctcatc attttcatcg tggccgtgct cattgcctat    3780
aaacgcaagt cccgcgaaag tgacctcacg ctgaagcggc tgcagatgca gatggacaac    3840
ctggagtccc gtgtggccct ggagtgcaag gaagcctttg ccgagctgca gacggacatc    3900
catgagctga ccagtgacct ggatggagcc gggattccgt tcctggacta tagaacttac    3960
accatgcggg tgctgttccc aggaattgaa gaccaccctg tcctccggga ccttgaggtc    4020
```

-continued

```
ccgggctacc ggcaggagcg tgtggagaaa ggcctgaagc tcttcgccca gctcatcaac    4080
aacaaggtgt tcctgctgtc cttcatccgc acgcttgagt cccagcgtag cttctccatg    4140
cgcgaccgtg gcaacgtggc ctcactcatc atgaccgtgc tgcagagcaa gctggagtac    4200
gccactgatg tgctgaagca gctgctggcc gacctcattg acaagaacct ggagagcaag    4260
aaccaccecta agctgctgct caggaggact gagtcagtgg ctgagaagat gctgaccaat    4320
tggtttactt tcctcctcta caagttcctc aaggagtgtg ctggggagcc cctcttctcc    4380
ctgttctgtg ccatcaagca gcagatggag aagggcccca ttgacgccat cacgggcgag    4440
gcccgctact ccttgagcga ggacaagctc atccgccagc agattgacta caaaaccctg    4500
gtcctgagct gtgtcagccc agacaatgcc aacagccccg aggtcccagt aaagatcctc    4560
aactgtgaca ccatcactca ggtcaaggag aagattctgg atgccatctt caagaatgtg    4620
ccttgctccc accggcccaa agctgcagat atggatctgg agtggcgaca aggaagtggg    4680
gcaaggatga tcttgcagga tgaagacatc accaccaaga ttgagaatga ttggaagcga    4740
ctgaacacac tggcccacta ccaggtgcca gatggttccg tggtggcatt agtgtccaag    4800
caggtgacag cctataacgc agtgaacaac tccaccgtct ccaggacctc agcaagtaaa    4860
tatgaaaaca tgatccggta cacgggcagc cccgacagcc tccgctcacg gacacctatg    4920
atcactcctg acctggagag tggagtcaag atgtggcacc tagtgaagaa ccacgagcac    4980
ggagaccaga aggaggggga ccgggggagc aagatggtgt ctgaaatcta cctgaccccga    5040
ctcctggcca ctaagggcac actgcagaag tttgtggatg acctctttga gaccatcttc    5100
agcacggcac accgtggctc tgccctgccc ctggccatca agtacatgtt tgacttcctg    5160
gatgagcagg ctgataaaca tggcattcat gacccgcacg tccgccatac ctggaagagc    5220
aattgcctgc ccctgaggtt ttgggtcaac atgatcaaga cccgcagtt tgtgtttgac    5280
atccataaga acagcatcac agacgcctgc ctctctgtgg tggctcagac cttcatggac    5340
tcttgctcca cgtcagagca ccggctgggc aaggactcgc cctccaacaa gctgctgtat    5400
gccaaggaca tccccagcta caagaattgg gtggagaggt attactcaga catagggaag    5460
atgccagcca tcagcgacca agacatgaac gcatacctgg ctgagcagtc ccggatgcac    5520
atgaatgagt tcaacaccat gagtgcactc tcagagatct tctcctatgt gggcaaatac    5580
agcgaggaga tccttggacc tctggaccac gatgaccagt gtgggaagca gaaactggcc    5640
tacaaactag aacaagtcat aaccctcatg agcttagaca gctgaaataa a              5691
```

<210> SEQ ID NO 13
<211> LENGTH: 1896
<212> TYPE: PRT
<213> ORGANISM: Homo sapiens

<400> SEQUENCE: 13

```
Met Lys Ala Met Pro Trp Asn Trp Thr Cys Leu Leu Ser His Leu Leu
 1               5                  10                  15

Met Val Gly Met Gly Ser Ser Thr Leu Leu Thr Arg Gln Pro Ala Pro
                20                  25                  30

Leu Ser Gln Lys Gln Arg Ser Phe Val Thr Phe Arg Gly Glu Pro Ala
            35                  40                  45

Glu Gly Phe Asn His Leu Val Val Asp Glu Arg Thr Gly His Ile Tyr
        50                  55                  60

Leu Gly Ala Val Asn Arg Ile Tyr Lys Leu Ser Ser Asp Leu Lys Val
 65                  70                  75                  80
```

-continued

```
Leu Val Thr His Glu Thr Gly Pro Asp Glu Asp Asn Pro Lys Cys Tyr
                 85                  90                  95

Pro Pro Arg Ile Val Gln Thr Cys Asn Glu Pro Leu Thr Thr Thr Asn
            100                 105                 110

Asn Val Asn Lys Met Leu Leu Ile Asp Tyr Lys Glu Asn Arg Leu Ile
        115                 120                 125

Ala Cys Gly Ser Leu Tyr Gln Gly Ile Cys Lys Leu Leu Arg Leu Glu
    130                 135                 140

Asp Leu Phe Lys Leu Gly Glu Pro Tyr His Lys Lys Glu His Tyr Leu
145                 150                 155                 160

Ser Gly Val Asn Glu Ser Gly Ser Val Phe Gly Val Ile Val Ser Tyr
                165                 170                 175

Ser Asn Leu Asp Asp Lys Leu Phe Ile Ala Thr Ala Val Asp Gly Lys
                180                 185                 190

Pro Glu Tyr Phe Pro Thr Ile Ser Ser Arg Lys Leu Thr Lys Asn Ser
            195                 200                 205

Glu Ala Asp Gly Met Phe Ala Tyr Val Phe His Asp Glu Phe Val Ala
        210                 215                 220

Ser Met Ile Lys Ile Pro Ser Asp Thr Phe Thr Ile Ile Pro Asp Phe
225                 230                 235                 240

Asp Ile Tyr Tyr Val Tyr Gly Phe Ser Ser Gly Asn Phe Val Tyr Phe
                245                 250                 255

Leu Thr Leu Gln Pro Glu Met Val Ser Pro Pro Gly Ser Thr Thr Lys
            260                 265                 270

Glu Gln Val Tyr Thr Ser Lys Leu Val Arg Leu Cys Lys Glu Asp Thr
        275                 280                 285

Ala Phe Asn Ser Tyr Val Glu Val Pro Ile Gly Cys Glu Arg Ser Gly
    290                 295                 300

Val Glu Tyr Arg Leu Leu Gln Ala Ala Tyr Leu Ser Lys Ala Gly Ala
305                 310                 315                 320

Val Leu Gly Arg Thr Leu Gly Val His Pro Asp Asp Leu Leu Phe
                325                 330                 335

Thr Val Phe Ser Lys Gly Gln Lys Arg Lys Met Lys Ser Leu Asp Glu
            340                 345                 350

Ser Ala Leu Cys Ile Phe Ile Leu Lys Gln Ile Asn Asp Arg Ile Lys
        355                 360                 365

Glu Arg Leu Gln Ser Cys Tyr Arg Gly Glu Gly Thr Leu Asp Leu Ala
    370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
                405                 410                 415

Asp Met Val Arg Gly Ile Pro Val Phe Thr Glu Asp Arg Asp Arg Met
            420                 425                 430

Thr Ser Val Ile Ala Tyr Val Tyr Lys Asn His Ser Leu Ala Phe Val
        435                 440                 445

Gly Thr Lys Ser Gly Lys Leu Lys Ile Arg Val Asp Gly Pro Arg
    450                 455                 460

Gly Asn Ala Leu Gln Tyr Glu Thr Val Gln Val Asp Pro Gly Pro
465                 470                 475                 480

Val Leu Arg Asp Met Ala Phe Ser Lys Asp His Glu Gln Leu Tyr Ile
                485                 490                 495
```

-continued

```
Met Ser Glu Arg Gln Leu Thr Arg Val Pro Val Ser Cys Gly Gln
            500                 505                 510

Tyr Gln Ser Cys Gly Glu Cys Leu Gly Ser Gly Asp Pro His Cys Gly
            515                 520                 525

Trp Cys Val Leu His Asn Thr Cys Thr Arg Lys Glu Arg Cys Glu Arg
            530                 535                 540

Ser Lys Glu Pro Arg Arg Phe Ala Ser Glu Met Lys Gln Cys Val Arg
545                 550                 555                 560

Leu Thr Val His Pro Asn Asn Ile Ser Val Ser Gln Tyr Asn Val Leu
                565                 570                 575

Leu Val Leu Glu Thr Tyr Asn Val Pro Glu Leu Ser Ala Gly Val Asn
            580                 585                 590

Cys Thr Phe Glu Asp Leu Ser Glu Met Asp Gly Leu Val Val Gly Asn
            595                 600                 605

Gln Ile Gln Cys Tyr Ser Pro Ala Ala Lys Glu Val Pro Arg Ile Ile
            610                 615                 620

Thr Glu Asn Gly Asp His His Val Val Gln Leu Gln Leu Lys Ser Lys
625                 630                 635                 640

Glu Thr Gly Met Thr Phe Ala Ser Thr Ser Phe Val Phe Tyr Asn Cys
                645                 650                 655

Ser Val His Asn Ser Cys Leu Ser Cys Val Glu Ser Pro Tyr Arg Cys
                660                 665                 670

His Trp Cys Lys Tyr Arg His Val Cys Thr His Asp Pro Lys Thr Cys
            675                 680                 685

Ser Phe Gln Glu Gly Arg Val Lys Leu Pro Glu Asp Cys Pro Gln Leu
            690                 695                 700

Leu Arg Val Asp Lys Ile Leu Val Pro Val Glu Val Ile Lys Pro Ile
705                 710                 715                 720

Thr Leu Lys Ala Lys Asn Leu Pro Gln Pro Gln Ser Gly Gln Arg Gly
                725                 730                 735

Tyr Glu Cys Ile Leu Asn Ile Gln Gly Ser Glu Gln Arg Val Pro Ala
            740                 745                 750

Leu Arg Phe Asn Ser Ser Ser Val Gln Cys Gln Asn Thr Ser Tyr Ser
            755                 760                 765

Tyr Glu Gly Met Glu Ile Asn Asn Leu Pro Val Glu Leu Thr Val Val
            770                 775                 780

Trp Asn Gly His Phe Asn Ile Asp Asn Pro Ala Gln Asn Lys Val His
785                 790                 795                 800

Leu Tyr Lys Cys Gly Ala Met Arg Glu Ser Cys Gly Leu Cys Leu Lys
                805                 810                 815

Ala Asp Pro Asp Phe Ala Cys Gly Trp Cys Gln Gly Pro Gly Gln Cys
            820                 825                 830

Thr Leu Arg Gln His Cys Pro Ala Gln Glu Ser Gln Trp Leu Glu Leu
            835                 840                 845

Ser Gly Ala Lys Ser Lys Cys Thr Asn Pro Arg Ile Thr Glu Ile Ile
850                 855                 860

Pro Val Thr Gly Pro Arg Glu Gly Gly Thr Lys Val Thr Ile Arg Gly
865                 870                 875                 880

Glu Asn Leu Gly Leu Glu Phe Arg Asp Ile Ala Ser His Val Lys Val
                885                 890                 895

Ala Gly Val Glu Cys Ser Pro Leu Val Asp Gly Tyr Ile Pro Ala Glu
            900                 905                 910

Gln Ile Val Cys Glu Met Gly Glu Ala Lys Pro Ser Gln His Ala Gly
```

-continued

```
                915                 920                 925
Phe Val Glu Ile Cys Val Ala Val Cys Arg Pro Glu Phe Met Ala Arg
    930                 935                 940
Ser Ser Gln Leu Tyr Tyr Phe Met Thr Leu Thr Leu Ser Asp Leu Lys
945                 950                 955                 960
Pro Ser Arg Gly Pro Met Ser Gly Thr Gln Val Thr Ile Thr Gly
                965                 970                 975
Thr Asn Leu Asn Ala Gly Ser Asn Val Val Met Phe Gly Lys Gln
            980                 985                 990
Pro Cys Leu Phe His Arg Arg Ser Pro Ser Tyr Ile Val Cys Asn Thr
        995                 1000                1005
Thr Ser Ser Asp Glu Val Leu Glu Met Lys Val Ser Val Gln Val Asp
    1010                1015                1020
Arg Ala Lys Ile His Gln Asp Leu Val Phe Gln Tyr Val Glu Asp Pro
1025                1030                1035                1040
Thr Ile Val Arg Ile Glu Pro Glu Trp Ser Ile Val Ser Gly Asn Thr
                1045                1050                1055
Pro Ile Ala Val Trp Gly Thr His Leu Asp Leu Ile Gln Asn Pro Gln
            1060                1065                1070
Ile Arg Ala Lys His Gly Gly Lys Glu His Ile Asn Ile Cys Glu Val
        1075                1080                1085
Leu Asn Ala Thr Glu Met Thr Cys Gln Ala Pro Ala Leu Ala Leu Gly
    1090                1095                1100
Pro Asp His Gln Ser Asp Leu Thr Glu Arg Pro Glu Glu Phe Gly Phe
1105                1110                1115                1120
Ile Leu Asp Asn Val Gln Ser Leu Leu Ile Leu Asn Lys Thr Asn Phe
                1125                1130                1135
Thr Tyr Tyr Pro Asn Pro Val Phe Glu Ala Phe Gly Pro Ser Gly Ile
            1140                1145                1150
Leu Glu Leu Lys Pro Gly Thr Pro Ile Ile Leu Lys Gly Lys Asn Leu
        1155                1160                1165
Ile Pro Pro Val Ala Gly Gly Asn Val Lys Leu Asn Tyr Thr Val Leu
    1170                1175                1180
Val Gly Glu Lys Pro Cys Thr Val Thr Val Ser Asp Val Gln Leu Leu
1185                1190                1195                1200
Cys Glu Ser Pro Asn Leu Ile Gly Arg His Lys Val Met Ala Arg Val
                1205                1210                1215
Gly Gly Met Glu Tyr Ser Pro Gly Met Val Tyr Ile Ala Pro Asp Ser
            1220                1225                1230
Pro Leu Ser Leu Pro Ala Ile Val Ser Ile Ala Val Ala Gly Gly Leu
        1235                1240                1245
Leu Ile Ile Phe Ile Val Ala Val Leu Ile Ala Tyr Lys Arg Lys Ser
    1250                1255                1260
Arg Glu Ser Asp Leu Thr Leu Lys Arg Leu Gln Met Gln Met Asp Asn
1265                1270                1275                1280
Leu Glu Ser Arg Val Ala Leu Glu Cys Lys Glu Ala Phe Ala Glu Leu
                1285                1290                1295
Gln Thr Asp Ile His Glu Leu Thr Ser Asp Leu Asp Gly Ala Gly Ile
            1300                1305                1310
Pro Phe Leu Asp Tyr Arg Thr Tyr Thr Met Arg Val Leu Phe Pro Gly
        1315                1320                1325
Ile Glu Asp His Pro Val Leu Arg Asp Leu Glu Val Pro Gly Tyr Arg
    1330                1335                1340
```

-continued

```
Gln Glu Arg Val Glu Lys Gly Leu Lys Leu Phe Ala Gln Leu Ile Asn
1345                1350                1355                1360

Asn Lys Val Phe Leu Leu Ser Phe Ile Arg Thr Leu Glu Ser Gln Arg
            1365                1370                1375

Ser Phe Ser Met Arg Asp Arg Gly Asn Val Ala Ser Leu Ile Met Thr
        1380                1385                1390

Val Leu Gln Ser Lys Leu Glu Tyr Ala Thr Asp Val Leu Lys Gln Leu
    1395                1400                1405

Leu Ala Asp Leu Ile Asp Lys Asn Leu Glu Ser Lys Asn His Pro Lys
1410                1415                1420

Leu Leu Leu Arg Arg Thr Glu Ser Val Ala Glu Lys Met Leu Thr Asn
1425                1430                1435                1440

Trp Phe Thr Phe Leu Leu Tyr Lys Phe Leu Lys Glu Cys Ala Gly Glu
            1445                1450                1455

Pro Leu Phe Ser Leu Phe Cys Ala Ile Lys Gln Gln Met Glu Lys Gly
        1460                1465                1470

Pro Ile Asp Ala Ile Thr Gly Glu Ala Arg Tyr Ser Leu Ser Glu Asp
    1475                1480                1485

Lys Leu Ile Arg Gln Gln Ile Asp Tyr Lys Thr Leu Val Leu Ser Cys
1490                1495                1500

Val Ser Pro Asp Asn Ala Asn Ser Pro Glu Val Pro Val Lys Ile Leu
1505                1510                1515                1520

Asn Cys Asp Thr Ile Thr Gln Val Lys Glu Lys Ile Leu Asp Ala Ile
            1525                1530                1535

Phe Lys Asn Val Pro Cys Ser His Arg Pro Lys Ala Ala Asp Met Asp
        1540                1545                1550

Leu Glu Trp Arg Gln Gly Ser Gly Ala Arg Met Ile Leu Gln Asp Glu
    1555                1560                1565

Asp Ile Thr Thr Lys Ile Glu Asn Asp Trp Lys Arg Leu Asn Thr Leu
1570                1575                1580

Ala His Tyr Gln Val Pro Asp Gly Ser Val Val Ala Leu Val Ser Lys
1585                1590                1595                1600

Gln Val Thr Ala Tyr Asn Ala Val Asn Asn Ser Thr Val Ser Arg Thr
            1605                1610                1615

Ser Ala Ser Lys Tyr Glu Asn Met Ile Arg Tyr Thr Gly Ser Pro Asp
        1620                1625                1630

Ser Leu Arg Ser Arg Thr Pro Met Ile Thr Pro Asp Leu Glu Ser Gly
    1635                1640                1645

Val Lys Met Trp His Leu Val Lys Asn His Glu His Gly Asp Gln Lys
1650                1655                1660

Glu Gly Asp Arg Gly Ser Lys Met Val Ser Glu Ile Tyr Leu Thr Arg
1665                1670                1675                1680

Leu Leu Ala Thr Lys Gly Thr Leu Gln Lys Phe Val Asp Asp Leu Phe
            1685                1690                1695

Glu Thr Ile Phe Ser Thr Ala His Arg Gly Ser Ala Leu Pro Leu Ala
        1700                1705                1710

Ile Lys Tyr Met Phe Asp Phe Leu Asp Glu Gln Ala Asp Lys His Gly
    1715                1720                1725

Ile His Asp Pro His Val Arg His Thr Trp Lys Ser Asn Cys Leu Pro
1730                1735                1740

Leu Arg Phe Trp Val Asn Met Ile Lys Asn Pro Gln Phe Val Phe Asp
1745                1750                1755                1760
```

```
Ile His Lys Asn Ser Ile Thr Asp Ala Cys Leu Ser Val Val Ala Gln
            1765                1770                1775

Thr Phe Met Asp Ser Cys Ser Thr Ser Glu His Arg Leu Gly Lys Asp
        1780                1785                1790

Ser Pro Ser Asn Lys Leu Leu Tyr Ala Lys Asp Ile Pro Ser Tyr Lys
    1795                1800                1805

Asn Trp Val Glu Arg Tyr Tyr Ser Asp Ile Gly Lys Met Pro Ala Ile
1810                1815                1820

Ser Asp Gln Asp Met Asn Ala Tyr Leu Ala Glu Gln Ser Arg Met His
1825                1830                1835                1840

Met Asn Glu Phe Asn Thr Met Ser Ala Leu Ser Glu Ile Phe Ser Tyr
            1845                1850                1855

Val Gly Lys Tyr Ser Glu Glu Ile Leu Gly Pro Leu Asp His Asp Asp
        1860                1865                1870

Gln Cys Gly Lys Gln Lys Leu Ala Tyr Lys Leu Glu Gln Val Ile Thr
    1875                1880                1885

Leu Met Ser Leu Asp Ser Asn Lys
    1890                1895

<210> SEQ ID NO 14
<211> LENGTH: 1535
<212> TYPE: DNA
<213> ORGANISM: Homo sapiens

<400> SEQUENCE: 14
cccgaaatgc tgccgccaag gagcaacgac accgcgtacc cggggcagtt agcgctatac      60
cagcagctgg cgcaggggaa tgccgtgggg ggctcggcgg gggcaccgcc actggggccc     120
gtgcaggtgg tcaccgcctg cctgctgacc ctactcgtca tctggacctt gctgggcaac     180
gtgctggtgt ccgcagccat cgtgtggagc cgccacctgc gcgccaagat gaccaacgtc     240
ttcatcgtgt ctctacctgt gtcagacctc ttcgtggcgc tgctggtcat gtcctggaag     300
gcagtcgccg aggtggccgg ttactggccc tttgaagcgt tctgcgacgt ctgggtggcc     360 tcgacatca tgtgctccac cgcctccatc ctgaacctgt gcgtcatcag cgtggcccgc     420
tactgggcca tctccaggcc cttccgctac gagcgcaaga tgacccagcg catggccttg     480
gtcatggtcc gcccggcctg gaccttgtcc agcctcatct ccttcattcc ggtccagctc     540
aactggcaca gggaccaggc ggtctcttgg ggtgggctgg acctgccaaa caacctggcc     600
aactggacgc cctgggagga ggccgtttgg gagcccgacg tgagggcaga gaactgtgac     660
tccagcctga atcgaaccta cgccatccct cctcgctca tcagcttcta catccccatg     720
gccatcatga tcgtgaccta cacgcgcatc taccgcatcg cccaggtgca gatccgcagg     780
atttcctccc tggagagggc cgcagagcac gtgcagagct gccggagcag cgcaggctgc     840
acgcccgaca ccagcctgcg gttttccatc aagaaggaga ccgaggttct caagaccctg     900
tcggtgatca tgggggtctt cgtgtgttgc tggctgccct tcttcatcct taactgcatg     960 gttccttct gcagtggaca ccccaaaggc cctccggccg gcttcccctg cgtcagtgag    1020
accacattcg atgtcttcat ctggttctgc tgggccaact cctcactcaa cccagtcccc    1080
agtcactatg ccttcaacgc cgacttccgg aaggtgtttg cccagctgct ggggtgcagc    1140
cacgtctgct cccgcacgcc ggtggagacg gtgaacatca gcaatgagct catctcctac    1200
aaccaagaca cggtcttcca caaggaaatg cagctgcct acatccacat gatgcccaac    1260
gccattcccc ccggggaccg ggaggtggac aacgatgagg aggaggagag tccttcgat    1320
```

```
cgcatgtccc agatctatca gacatcccca gatggtgacc atgttgcaga gtctgtctgg    1380
gagctggact gcgaggggga gatttcttta gacaaaataa cacctttcac cccaaatgga    1440
ttccattaaa ctgcattaag aaacccctc atggatctgc ataaccacac agacattgac      1500
aagcatgcac acacaagcaa atacatggct ttcca                                1535
```

<210> SEQ ID NO 15
<211> LENGTH: 480
<212> TYPE: PRT
<213> ORGANISM: Homo sapiens

<400> SEQUENCE: 15

```
Met Leu Pro Pro Arg Ser Asn Asp Thr Ala Tyr Pro Gly Gln Leu Ala
 1               5                  10                  15

Leu Tyr Gln Gln Leu Ala Gln Gly Asn Ala Val Gly Gly Ser Ala Gly
             20                  25                  30

Ala Pro Pro Leu Gly Pro Val Gln Val Val Thr Ala Cys Leu Leu Thr
         35                  40                  45

Leu Leu Val Ile Trp Thr Leu Leu Gly Asn Val Leu Val Ser Ala Ala
     50                  55                  60

Ile Val Trp Ser Arg His Leu Arg Ala Lys Met Thr Asn Val Phe Ile
 65                  70                  75                  80

Val Ser Leu Pro Val Ser Asp Leu Phe Val Ala Leu Leu Val Met Ser
                 85                  90                  95

Trp Lys Ala Val Ala Glu Val Ala Gly Tyr Trp Pro Phe Glu Ala Phe
            100                 105                 110

Cys Asp Val Trp Val Ala Phe Asp Ile Met Cys Ser Thr Ala Ser Ile
        115                 120                 125

Leu Asn Leu Cys Val Ile Ser Val Ala Arg Tyr Trp Ala Ile Ser Arg
    130                 135                 140

Pro Phe Arg Tyr Glu Arg Lys Met Thr Gln Arg Met Ala Leu Val Met
145                 150                 155                 160

Val Arg Pro Ala Trp Thr Leu Ser Ser Leu Ile Ser Phe Ile Pro Val
                165                 170                 175

Gln Leu Asn Trp His Arg Asp Gln Ala Val Ser Trp Gly Gly Leu Asp
            180                 185                 190

Leu Pro Asn Asn Leu Ala Asn Trp Thr Pro Trp Glu Glu Ala Val Trp
        195                 200                 205

Glu Pro Asp Val Arg Ala Glu Asn Cys Asp Ser Ser Leu Asn Arg Thr
    210                 215                 220

Tyr Ala Ile Pro Ser Ser Leu Ile Ser Phe Tyr Ile Pro Met Ala Ile
225                 230                 235                 240

Met Ile Val Thr Tyr Thr Arg Ile Tyr Arg Ile Ala Gln Val Gln Ile
                245                 250                 255

Arg Arg Ile Ser Ser Leu Glu Arg Ala Ala Glu His Val Gln Ser Cys
            260                 265                 270

Arg Ser Ser Ala Gly Cys Thr Pro Asp Thr Ser Leu Arg Phe Ser Ile
        275                 280                 285

Lys Lys Glu Thr Glu Val Leu Lys Thr Leu Ser Val Ile Met Gly Val
    290                 295                 300

Phe Val Cys Cys Trp Leu Pro Phe Phe Ile Leu Asn Cys Met Val Pro
305                 310                 315                 320

Phe Cys Ser Gly His Pro Lys Gly Pro Pro Ala Gly Phe Pro Cys Val
                325                 330                 335
```

```
Ser Glu Thr Thr Phe Asp Val Phe Ile Trp Phe Cys Trp Ala Asn Ser
            340                 345                 350

Ser Leu Asn Pro Val Pro Ser His Tyr Ala Phe Asn Ala Asp Phe Arg
        355                 360                 365

Lys Val Phe Ala Gln Leu Leu Gly Cys Ser His Val Cys Ser Arg Thr
    370                 375                 380

Pro Val Glu Thr Val Asn Ile Ser Asn Glu Leu Ile Ser Tyr Asn Gln
385                 390                 395                 400

Asp Thr Val Phe His Lys Glu Ile Ala Ala Tyr Ile His Met Met
                405                 410                 415

Pro Asn Ala Ile Pro Pro Gly Asp Arg Glu Val Asp Asn Asp Glu Glu
                420                 425                 430

Glu Glu Ser Pro Phe Asp Arg Met Ser Gln Ile Tyr Gln Thr Ser Pro
            435                 440                 445

Asp Gly Asp His Val Ala Glu Ser Val Trp Glu Leu Asp Cys Glu Gly
        450                 455                 460

Glu Ile Ser Leu Asp Lys Ile Thr Pro Phe Thr Pro Asn Gly Phe His
465                 470                 475                 480

<210> SEQ ID NO 16
<211> LENGTH: 2657
<212> TYPE: DNA
<213> ORGANISM: Homo sapiens

<400> SEQUENCE: 16
gattcatgaa gatgttgaca agactacaag ttcttatgtt agctttgttt tcaaagggat      60
ttttagtctc tttaggagat cacaacttta tgaggagaga aattaaaata gaaggagacc     120
ttgttttagg gggcttattt cctattaatg aaaaaggcac tggaactgaa gagtgtggac     180
gaatcaatga agacagaggt atccaacgcc tggaggccat gttgtttgcc attgatgaaa     240
tcaacaaaga caattacttg cttccaggag tgaagctggg ggttcacatt ttggatacat     300
gttcaagaga cacctatgca ttagagcagt cactggagtt tgtcagagca tcgttgacta     360
aagtggatga agctgaatat atgtgtcctg atggatcata tgctattcaa gaaaacatcc     420
cactactcat tgcaggagtc attggcggtt cgtacagcag tgtttccata caggtagcaa     480
acctgctgag gctcttccag atccctcaga taagctacgc ctccaccagt gccaaactca     540
gcgacaaatc gcgctatgat tattttgcca ggaccgtgcc ccctgacttc taccaggcca     600
aagccatggc cgagatcttg cgctacttta ctggaccta tgtgtccact gttgcctctg     660
aaggtgacta tggggagaca gggattgagg ccttcgagca ggaagcaagg ctacgcaaca     720
tctgcatcgc cactgctgaa aaggtggggc gctccaacat ccgcaagtcc tacgacagcg     780
tgatccgtga gctcctgcag aaacctaacg cgcgagttgt ggtcctgttc atgcgcagtg     840
atgactcacg agagttgatc gctgcagcca gccgcgtgaa tgcttccttc acctgggtgg     900
ccagcgatgg ctgggtgca caggagagca ttgtcaaggg cagtgagcac gtcgcctatg     960
gagccatcac cctggagctg gcgtcccacc ctgttcgtca gtttgatcgc tacttccaga    1020
gcctcaaccc ctacaacaat catcgtaacc cctggttccg agacttctgg gagcagaagt    1080
tccagtgcag cctccagaac aagagaaacc acagacagat ttgtgacaag cacctggcca    1140
ttgacagcag caactatgaa caagaatcca gatcatgtt tgtggtgaat gcagtgtatg    1200
ccatggcgca tgcgctgcac aaaatgcaac gcaccctctg tcccaacacc accaagctct    1260
gtgatgcaat gaagatcctg gatggaaaga agttgtacaa agattattg ctgaaaatca    1320
```

-continued

```
acttccttgc tccattcaac ccaaataaag gagcagacag cattgtgaag tttgacactt    1380
acggagacgg gatgggaaga tacaacgtgt tcaacttcca gcatataggt ggaaagtatt    1440
cctacttaaa agttggccac tgggcagaaa ctttatatct agatgtggac tctattcatt    1500
ggtcccggaa ctcagtcccc acttcccagt gcagtgatcc ctgtgccccc aatgaaatga    1560
aaaacatgca gccaggagat gttgctgct ggatctgcat cccatgtgag ccctatgaat    1620
acctggttga tgagttcacc tgcatggatt gtggccctgg ccagtggccc actgcagacc    1680
tatctggatg ctacaacctt ccagaggatt acatcaggtg ggaagatgcc tgggcaatag    1740
gcccagtcac tattgcctgc ctgggttta tgtgtacatg catagtcata actgttttta    1800
tcaagcacaa caacacaccc ttggtcaaag catcaggccg agaactctgc tacatcttgt    1860
tatttggagt tagcctgtcc tattgcatga cattcttctt cattgctaag ccatcgcctg    1920
tcatctgtgc attgcgccga cttgggcttg ggacctcctt tgccatctgt tattcagctc    1980
tcctgaccaa gacaaactgc atcgctcgca tctttgatgg ggtcaagaat ggcgctcaga    2040
ggccaaaatt catcagcccc agttctcagg tttttatctg cctgggtttg atactggtgc    2100
aaattgtgat ggtgtctgtg tggcttatct tggagactcc aggtactaga agatacaccc    2160
tgccagagaa gcgggaaaca gtcatcctaa aatgcaatgt caaagattcc agcatgttga    2220
tctctctgac ctatgacgtg gttctggtga ttctatgcac tgtgtatgcc ttcaaaacaa    2280
ggaagtgtcc tgaaaacttc aatgaagcca agttcatagg cttcaccatg tacaccacct    2340
gcatcatctg gttggcattc ctccctatat tttatgtgac atcaagtgac tacagagtac    2400
agacgacaac aatgtgcatc tccgttagct tgagtggttt cgtggtcttg ggctgtttgt    2460
ttgcccccaa ggtgcacatt gtcctgttcc aacccagaa gaatgtggtc acacacagac    2520
ttcacctcaa caggttcagt gtcagtggaa ctgcgaccac atattctcag gcctctgcaa    2580
gcacgtatgt gccaacggtg tgcaatgggc gggaagtcct cgactccacc acctcatctc    2640
tgtgattgtg aattgca                                                   2657
```

<210> SEQ ID NO 17
<211> LENGTH: 879
<212> TYPE: PRT
<213> ORGANISM: Homo sapiens
<400> SEQUENCE: 17

```
Met Lys Met Leu Thr Arg Leu Gln Val Leu Met Leu Ala Leu Phe Ser
  1               5                  10                  15

Lys Gly Phe Leu Val Ser Leu Gly Asp His Asn Phe Met Arg Arg Glu
                 20                  25                  30

Ile Lys Ile Glu Gly Asp Leu Val Leu Gly Gly Leu Phe Pro Ile Asn
             35                  40                  45

Glu Lys Gly Thr Gly Thr Glu Glu Cys Gly Arg Ile Asn Glu Asp Arg
         50                  55                  60

Gly Ile Gln Arg Leu Glu Ala Met Leu Phe Ala Ile Asp Glu Ile Asn
 65                  70                  75                  80

Lys Asp Asn Tyr Leu Leu Pro Gly Val Lys Leu Gly Val His Ile Leu
                 85                  90                  95

Asp Thr Cys Ser Arg Asp Thr Tyr Ala Leu Glu Gln Ser Leu Glu Phe
                100                 105                 110

Val Arg Ala Ser Leu Thr Lys Val Asp Glu Ala Glu Tyr Met Cys Pro
            115                 120                 125

Asp Gly Ser Tyr Ala Ile Gln Glu Asn Ile Pro Leu Leu Ile Ala Gly
```

-continued

```
            130                 135                 140
Val Ile Gly Gly Ser Tyr Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
                180                 185                 190

Pro Asp Phe Tyr Gln Ala Lys Ala Met Ala Glu Ile Leu Arg Tyr Phe
            195                 200                 205

Asn Trp Thr Tyr Val Ser Thr Val Ala Ser Glu Gly Asp Tyr Gly Glu
210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
                260                 265                 270

Val Leu Phe Met Arg Ser Asp Asp Ser Arg Glu Leu Ile Ala Ala Ala
            275                 280                 285

Ser Arg Val Asn Ala Ser Phe Thr Trp Val Ala Ser Asp Gly Trp Gly
290                 295                 300

Ala Gln Glu Ser Ile Val Lys Gly Ser Glu His Val Ala Tyr Gly Ala
305                 310                 315                 320

Ile Thr Leu Glu Leu Ala Ser His Pro Val Arg Gln Phe Asp Arg Tyr
                325                 330                 335

Phe Gln Ser Leu Asn Pro Tyr Asn Asn His Arg Asn Pro Trp Phe Arg
            340                 345                 350

Asp Phe Trp Glu Gln Lys Phe Gln Cys Ser Leu Gln Asn Lys Arg Asn
            355                 360                 365

His Arg Gln Ile Cys Asp Lys His Leu Ala Ile Asp Ser Ser Asn Tyr
            370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                405                 410                 415

Lys Leu Cys Asp Ala Met Lys Ile Leu Asp Gly Lys Lys Leu Tyr Lys
            420                 425                 430

Asp Tyr Leu Leu Lys Ile Asn Phe Leu Ala Pro Phe Asn Pro Asn Lys
            435                 440                 445

Gly Ala Asp Ser Ile Val Lys Phe Asp Thr Tyr Gly Asp Gly Met Gly
450                 455                 460

Arg Tyr Asn Val Phe Asn Phe Gln His Ile Gly Gly Lys Tyr Ser Tyr
465                 470                 475                 480

Leu Lys Val Gly His Trp Ala Glu Thr Leu Tyr Leu Asp Val Asp Ser
                485                 490                 495

Ile His Trp Ser Arg Asn Ser Val Pro Thr Ser Gln Cys Ser Asp Pro
                500                 505                 510

Cys Ala Pro Asn Glu Met Lys Asn Met Gln Pro Gly Asp Val Cys Cys
            515                 520                 525

Trp Ile Cys Ile Pro Cys Glu Pro Tyr Glu Tyr Leu Val Asp Glu Phe
            530                 535                 540

Thr Cys Met Asp Cys Gly Pro Gly Gln Trp Pro Thr Ala Asp Leu Ser
545                 550                 555                 560
```

-continued

```
Gly Cys Tyr Asn Leu Pro Glu Asp Tyr Ile Arg Trp Glu Asp Ala Trp
                565                 570                 575
Ala Ile Gly Pro Val Thr Ile Ala Cys Leu Gly Phe Met Cys Thr Cys
            580                 585                 590
Ile Val Ile Thr Val Phe Ile Lys His Asn Asn Thr Pro Leu Val Lys
        595                 600                 605
Ala Ser Gly Arg Glu Leu Cys Tyr Ile Leu Phe Gly Val Ser Leu
    610                 615                 620
Ser Tyr Cys Met Thr Phe Phe Ile Ala Lys Pro Ser Pro Val Ile
625                 630                 635                 640
Cys Ala Leu Arg Arg Leu Gly Leu Gly Thr Ser Phe Ala Ile Cys Tyr
                645                 650                 655
Ser Ala Leu Leu Thr Lys Thr Asn Cys Ile Ala Arg Ile Phe Asp Gly
            660                 665                 670
Val Lys Asn Gly Ala Gln Arg Pro Lys Phe Ile Ser Pro Ser Ser Gln
        675                 680                 685
Val Phe Ile Cys Leu Gly Leu Ile Leu Val Gln Ile Val Met Val Ser
    690                 695                 700
Val Trp Leu Ile Leu Glu Thr Pro Gly Thr Arg Arg Tyr Thr Leu Pro
705                 710                 715                 720
Glu Lys Arg Glu Thr Val Ile Leu Lys Cys Asn Val Lys Asp Ser Ser
                725                 730                 735
Met Leu Ile Ser Leu Thr Tyr Asp Val Val Leu Val Ile Leu Cys Thr
            740                 745                 750
Val Tyr Ala Phe Lys Thr Arg Lys Cys Pro Glu Asn Phe Asn Glu Ala
        755                 760                 765
Lys Phe Ile Gly Phe Thr Met Tyr Thr Thr Cys Ile Ile Trp Leu Ala
    770                 775                 780
Phe Leu Pro Ile Phe Tyr Val Thr Ser Ser Asp Tyr Arg Val Gln Thr
785                 790                 795                 800
Thr Thr Met Cys Ile Ser Val Ser Leu Ser Gly Phe Val Val Leu Gly
                805                 810                 815
Cys Leu Phe Ala Pro Lys Val His Ile Val Leu Phe Gln Pro Gln Lys
            820                 825                 830
Asn Val Val Thr His Arg Leu His Leu Asn Arg Phe Ser Val Ser Gly
        835                 840                 845
Thr Ala Thr Thr Tyr Ser Gln Ala Ser Ala Ser Thr Tyr Val Pro Thr
    850                 855                 860
Val Cys Asn Gly Arg Glu Val Leu Asp Ser Thr Thr Ser Ser Leu
865                 870                 875

<210> SEQ ID NO 18
<211> LENGTH: 1366
<212> TYPE: DNA
<213> ORGANISM: Homo sapiens

<400> SEQUENCE: 18
atgggtctgg ccatggagca cggagggtcc tacgctcggg cggggggcag ctctcggggc      60
tgctggtatt acctgcgcta cttcttcctc ttcgtctccc tcatccaatt cctcatcatc     120
ctggggctcg tgctcttcat ggtctatggc aacgtgcacg tgagcacaga gtccaacctg     180
caggccaccg agcgccgagc cgagggccta cagtcagc tcctagggct cacggcctcc     240
cagtccaact tgaccaagga gctcaacttc accacccgcg ccaaggatgc catcatgcag     300
```

-continued

```
atgtggctga atgctcgccg cgacctggac cgcatcaatg ccagcttccg ccagtgccag    360
ggtgaccggg taatctacac gaacaatcag aggtacatgg ctgccatcat cttgagtgag    420
aagcaatgca gagatcaatt caaggacatg aacaagagct gcgatgcctt gctcttcatg    480
ctgaatcaga aggtgaagac gctggaggtg agatagcca aggagaagac catttgcact     540
aaggataagg aaagcgtgct gctgaacaaa cgcgtggcgg aggaacagct ggttgaatgc    600
gtgaaaaccc gggagctgca gcaccaagag cgccagctgg ccaaggagca actgcaaaag    660
gtgcaagccc tctgcctgcc cctggacaag gacaagtttg agatggacct tcgtaacctg    720
tggagggact ccattatccc acgcagcctg acaacctggg ttacaacct ctaccatccc    780 ctgggctcgg aattggcctc catccgcaga gcctgcgacc acatgcccag cctcatgagc    840
tccaaggtgg aaggtcagtg ccggagcctc cgggcggata tcgaacgcgt ggcccgcgag    900
aactcagacc tccaacgcca gaagctggaa gcccagcagg gcctgcgggc cagtcaggag    960
gcgaaacaga aggtggagaa ggaggctcag gcccgggagg ccaagctcca agctgaatgc   1020
tcccggcaga cccagctagc gctggaggag aaggcggtgc tgcggaagga acgagacaac   1080
ctggccaagg agctggaaga agaagagg gaggcggagc agctcaggat ggagctggcc     1140
atcagaaact cagccctgga cacctgcatc aagaccaagt cgcagccgat gatgccagtg   1200
tcaaggccca tgggccctgt ccccaacccc cagcccatcg acccagctag cctggaggag   1260
ttcaagagga agatcctgga gtcccagagg cccctgcag gcatccctgt agccccatcc   1320
agtggctgag gaggctccgg cactgaccta agggcgaatc ccagca                  1366
```

<210> SEQ ID NO 19
<211> LENGTH: 442
<212> TYPE: PRT
<213> ORGANISM: Homo sapiens

<400> SEQUENCE: 19

```
Met Gly Leu Ala Met Glu His Gly Gly Ser Tyr Ala Arg Ala Gly Gly
 1               5                  10                  15

Ser Ser Arg Gly Cys Trp Tyr Tyr Leu Arg Tyr Phe Phe Leu Phe Val
                20                  25                  30

Ser Leu Ile Gln Phe Leu Ile Ile Leu Gly Leu Val Leu Phe Met Val
            35                  40                  45

Tyr Gly Asn Val His Val Ser Thr Glu Ser Asn Leu Gln Ala Thr Glu
     50                  55                  60

Arg Arg Ala Glu Gly Leu Tyr Ser Gln Leu Leu Gly Leu Thr Ala Ser
 65                  70                  75                  80

Gln Ser Asn Leu Thr Lys Glu Leu Asn Phe Thr Thr Arg Ala Lys Asp
                 85                  90                  95

Ala Ile Met Gln Met Trp Leu Asn Ala Arg Arg Asp Leu Asp Arg Ile
            100                 105                 110

Asn Ala Ser Phe Arg Gln Cys Gln Gly Asp Arg Val Ile Tyr Thr Asn
        115                 120                 125

Asn Gln Arg Tyr Met Ala Ala Ile Ile Leu Ser Glu Lys Gln Cys Arg
    130                 135                 140

Asp Gln Phe Lys Asp Met Asn Lys Ser Cys Asp Ala Leu Leu Phe Met
145                 150                 155                 160

Leu Asn Gln Lys Val Lys Thr Leu Glu Val Glu Ile Ala Lys Glu Lys
                165                 170                 175

Thr Ile Cys Thr Lys Asp Lys Glu Ser Val Leu Leu Asn Lys Arg Val
            180                 185                 190
```

```
Ala Glu Glu Gln Leu Val Glu Cys Val Lys Thr Arg Glu Leu Gln His
            195                 200                 205

Gln Glu Arg Gln Leu Ala Lys Glu Gln Leu Gln Lys Val Gln Ala Leu
        210                 215                 220

Cys Leu Pro Leu Asp Lys Asp Lys Phe Glu Met Asp Leu Arg Asn Leu
225                 230                 235                 240

Trp Arg Asp Ser Ile Ile Pro Arg Ser Leu Asp Asn Leu Gly Tyr Asn
                245                 250                 255

Leu Tyr His Pro Leu Gly Ser Glu Leu Ala Ser Ile Arg Arg Ala Cys
            260                 265                 270

Asp His Met Pro Ser Leu Met Ser Ser Lys Val Glu Gly Gln Cys Arg
        275                 280                 285

Ser Leu Arg Ala Asp Ile Glu Arg Val Ala Arg Glu Asn Ser Asp Leu
        290                 295                 300

Gln Arg Gln Lys Leu Glu Ala Gln Gln Gly Leu Arg Ala Ser Gln Glu
305                 310                 315                 320

Ala Lys Gln Lys Val Glu Lys Glu Ala Gln Ala Arg Glu Ala Lys Leu
                325                 330                 335

Gln Ala Glu Cys Ser Arg Gln Thr Gln Leu Ala Leu Glu Glu Lys Ala
            340                 345                 350

Val Leu Arg Lys Glu Arg Asp Asn Leu Ala Lys Glu Leu Glu Glu Lys
        355                 360                 365

Lys Arg Glu Ala Glu Gln Leu Arg Met Glu Leu Ala Ile Arg Asn Ser
370                 375                 380

Ala Leu Asp Thr Cys Ile Lys Thr Lys Ser Gln Pro Met Met Pro Val
385                 390                 395                 400

Ser Arg Pro Met Gly Pro Val Pro Asn Pro Gln Pro Ile Asp Pro Ala
                405                 410                 415

Ser Leu Glu Glu Phe Lys Arg Lys Ile Leu Glu Ser Gln Arg Pro Pro
            420                 425                 430

Ala Gly Ile Pro Val Ala Pro Ser Ser Gly
        435                 440

<210> SEQ ID NO 20
<211> LENGTH: 1421
<212> TYPE: DNA
<213> ORGANISM: Homo sapiens

<400> SEQUENCE: 20
gaattctagg tggtggtgag cagggacggt gcaccggacg gcgggatcga gcaaatgggt      60
ctggccatgg agtacggagg gtcctacgct cgggcggggg gcagctctcg gggctgctgg     120
tattacctgc gctacttctt cctcttcgtc tccctcatcc aattcctcat catcctgggg     180
ctcgtgctct tcatggtcta tggcgacgtg cacgtgagca cagagtccaa cctgcaggcc     240
accgagcgcc gagccgaggg cctatacagt cagctcctag ggctcacggc ctcccagtcc     300
aacttgacca aggagctcaa cttcaccacc cgcgccaagg atgccatcat gcagatgtgg     360
ctgaatgctc gccgcgacct ggaccgcatc aatgccagct ccgccagtg ccagggtgac     420
cgggtcatct acacgaacaa tcagaggtac atggctgcca tcatcttgag tgagaagcaa     480
tgcagagatc aattcaagga catgaacaag agctgcgatg ccttgctctt catgctgaat     540
cagaaggtga agacgctgga ggtggagata gccaaggaga agaccatttg cactaaggat     600
aaggaaagcg tgctgctgaa caaacgcgtg gcggaggaac agctggttga atgcgtgaaa     660
```

-continued

```
acccgggagc tgcagcacca agagcgccag ctggccaagg agcaactgca aaaggtgcaa    720
gccctctgcc tgcccctgga caaggacaag tttgagatgg accttcgtaa cctgtggagg    780
gactccatta tcccacgcag cctggacaac ctgggttaca acctctacca tcccctgggc    840
tcggaattgg cctccatccg cagagcctgc gaccacatgc ccagcctcat gagctccaag    900
gtggaggagc tggcccggag cctccgggcg gatatcgaac gcgtggcccg cgagaactca    960
gacctccaac gccagaagct ggaagcccag cagggcctgc gggccagtca ggaggcgaaa   1020
cagaaggtgg agaaggaggc tcaggcccgg gaggccaagc tccaagctga atgctcccgg   1080
cagacccagc tagcgctgga ggagaaggcg gtgctgcgga aggaacgaga caacctggcc   1140
aaggagctgg aagagaagaa gagggaggcg gagcagctca ggatggagct ggccatcaga   1200
aactcagccc tggacacctg catcaagacc aagtcgcagc cgatgatgcc agtgtcaagg   1260
cccatgggcc tgtccccaa cccccagccc atcgacccag ctagcctgga ggagttcaag   1320
aggaagatcc tggagtccca gaggccccct gcaggcatcc tgtagccccc atccagtggc   1380
tgaggaggct ccaggcctga ggaccaaggg atggcccgac t                       1421
```

<210> SEQ ID NO 21
<211> LENGTH: 442
<212> TYPE: PRT
<213> ORGANISM: Homo sapiens

<400> SEQUENCE: 21

```
Met Gly Leu Ala Met Glu Tyr Gly Gly Ser Tyr Ala Arg Ala Gly Gly
  1               5                  10                  15

Ser Ser Arg Gly Cys Trp Tyr Tyr Leu Arg Tyr Phe Phe Leu Phe Val
             20                  25                  30

Ser Leu Ile Gln Phe Leu Ile Ile Leu Gly Leu Val Leu Phe Met Val
         35                  40                  45

Tyr Gly Asp Val His Val Ser Thr Glu Ser Asn Leu Gln Ala Thr Glu
     50                  55                  60

Arg Arg Ala Glu Gly Leu Tyr Ser Gln Leu Leu Gly Leu Thr Ala Ser
 65                  70                  75                  80

Gln Ser Asn Leu Thr Lys Glu Leu Asn Phe Thr Thr Arg Ala Lys Asp
                 85                  90                  95

Ala Ile Met Gln Met Trp Leu Asn Ala Arg Arg Asp Leu Asp Arg Ile
            100                 105                 110

Asn Ala Ser Phe Arg Gln Cys Gln Gly Asp Arg Val Ile Tyr Thr Asn
        115                 120                 125

Asn Gln Arg Tyr Met Ala Ala Ile Ile Leu Ser Glu Lys Gln Cys Arg
    130                 135                 140

Asp Gln Phe Lys Asp Met Asn Lys Ser Cys Asp Ala Leu Leu Phe Met
145                 150                 155                 160

Leu Asn Gln Lys Val Lys Thr Leu Glu Val Glu Ile Ala Lys Glu Lys
                165                 170                 175

Thr Ile Cys Thr Lys Asp Lys Glu Ser Val Leu Leu Asn Lys Arg Val
            180                 185                 190

Ala Glu Glu Gln Leu Val Glu Cys Val Lys Thr Arg Glu Leu Gln His
        195                 200                 205

Gln Glu Arg Gln Leu Ala Lys Glu Gln Leu Gln Lys Val Gln Ala Leu
    210                 215                 220

Cys Leu Pro Leu Asp Lys Asp Lys Phe Glu Met Asp Leu Arg Asn Leu
225                 230                 235                 240
```

-continued

```
Trp Arg Asp Ser Ile Ile Pro Arg Ser Leu Asp Asn Leu Gly Tyr Asn
            245                 250                 255
Leu Tyr His Pro Leu Gly Ser Glu Leu Ala Ser Ile Arg Arg Ala Cys
        260                 265                 270
Asp His Met Pro Ser Leu Met Ser Ser Lys Val Glu Glu Leu Ala Arg
    275                 280                 285
Ser Leu Arg Ala Asp Ile Glu Arg Val Ala Arg Glu Asn Ser Asp Leu
290                 295                 300
Gln Arg Gln Lys Leu Glu Ala Gln Gly Leu Arg Ala Ser Gln Glu
305                 310                 315                 320
Ala Lys Gln Lys Val Glu Lys Glu Ala Gln Ala Arg Glu Ala Lys Leu
                325                 330                 335
Gln Ala Glu Cys Ser Arg Gln Thr Gln Leu Ala Leu Glu Glu Lys Ala
            340                 345                 350
Val Leu Arg Lys Glu Arg Asp Asn Leu Ala Lys Glu Leu Glu Glu Lys
        355                 360                 365
Lys Arg Glu Ala Glu Gln Leu Arg Met Glu Leu Ala Ile Arg Asn Ser
    370                 375                 380
Ala Leu Asp Thr Cys Ile Lys Thr Lys Ser Gln Pro Met Met Pro Val
385                 390                 395                 400
Ser Arg Pro Met Gly Pro Val Pro Asn Pro Gln Pro Ile Asp Pro Ala
                405                 410                 415
Ser Leu Glu Glu Phe Lys Arg Lys Ile Leu Glu Ser Gln Arg Pro Pro
            420                 425                 430
Ala Gly Ile Pro Val Ala Pro Ser Ser Gly
        435                 440

<210> SEQ ID NO 22
<211> LENGTH: 2024
<212> TYPE: DNA
<213> ORGANISM: Homo sapiens

<400> SEQUENCE: 22
```

| | | | | | |
|---|---|---|---|---|---|
| atgggtctgg | ccatggagca | cggagggtcc | tacgctcggg | cgggggggcag | ctctcggggc | 60 |
| tgctggtatt | acctgcgcta | cttcttcctc | ttcgtctccc | tcatccaatt | cctcatcatc | 120 |
| ctggggctcg | tgctcttcat | ggtctatggc | aacgtgcacg | tgagcacaga | gtccaacctg | 180 |
| caggccaccg | agcgccgagc | cgagggccta | tacagtcagc | tcctagggct | cacggcctcc | 240 |
| cagtccaact | tgaccaagga | gctcaacttc | accacccgcg | ccaaggatgc | catcatgcag | 300 |
| atgtggctga | atgctcgtcg | cgacctggac | cgcatcaatg | ccagcttccg | ccagtgccag | 360 |
| ggtgaccggg | tcatctacac | gaacaatcag | aggtacatgg | ctgccatcat | cttgagtgag | 420 |
| aagcaatgca | gagatcaatt | caaggacatg | aacaagagct | gcgatgcctt | gctcttcatg | 480 |
| ctgaatcaga | aggtgaagac | gctggaggtg | gagatagcca | aggagaagac | catttgcact | 540 |
| aaggataagg | aaagcgtgct | gctgaacaaa | cgcgtggcgg | aggaacagct | ggttgaatgc | 600 |
| gtgaaaaccc | gggagctgca | gcaccaagag | cgccagctgg | ccaaggagca | actgcaaagg | 660 |
| gtgcaagccc | tctgcctgcc | cctggacaag | gacaagtttg | agatggacct | tcgtaacctg | 720 |
| tggagggact | ccattatccc | acgcagcctg | gacaacctgg | gttacaacct | ctaccatccc | 780 |
| ctgggctcgg | aattggcctc | catccgcaga | gcctgcgacc | acatgccag | cctcgtgagc | 840 |
| tccaaggtgg | aggagctggc | ccggagcctc | cgggcggata | tcgaacgcgt | ggcccgcgag | 900 |
| aactcagacc | tccaacgcca | gaagctggaa | gcccagcagg | gcctgcgggc | cagtcaggag | 960 |

-continued

```
gcgaaacaga aggtggagaa ggaggctcag gcccgggagg ccaagctcca agctgaatgc    1020
tcccggcaga cccagctagc gctggaggag aaggcggtgc tgcggaagga acgagacaac    1080
ctggccaagg agctggaaga gaagaagagg gaggcggagc agctcaggat ggagctggcc    1140
atcagaaact cagccctgga cacctgcatc aagaccaagt cgcagccgat gatgccagtg    1200
tcaaggccca tgggccctgt ccccaacccc cagcccatcg acccagctag cctggaggag    1260
ttcaagagga agatcctgga gtcccagagg ccccctgcag gcatccctgt agccccatcc    1320
agtggctgag gaggctccag gcctgaggac caagggatgg cccgactcgg cggtttgcgg    1380
aggatgcagg agatgctcca cagcgcccga cacaacccccc tcccgccgcc ccaaccacc    1440 cagggccacc atcagacaac tccctgcatg caaaccccta gtaccctctc acacccgcac    1500
ccgcgcctca tgatccctca cccagagcac acggccgcgg agatgacgtc acgcaagcaa    1560
cggcgctgac gtcacatatc accgtggtga tggcgtcacg tggccatgta gacgtcacga    1620
agagatatag cgatggcgtc gtgcagatgc agcacgtcgc acacagacat ggggaacttg    1680
gcatgacgtc acaccgagat gcagcaacga cgtcacgggc catgtcgacg tcacacatat    1740
taatgtcaca cagacgcggc gatggcatca cacagacggt gatgatgtca cacacagaca    1800
cagtgacaac acacaccatg acaacgacac ctatagatat ggcaccaaca tcacatgcac    1860
gcatgccctt tcacacacac tttctaccca attctcacct agtgtcacgt tcccccgacc    1920
ctggcacacg ggccaaggta cccacaggat cccatcccct cccgcacagc cctgggcccc    1980
agcacctccc ctcctccagc ctcctggcct cccggtagta cacg                    2024
```

<210> SEQ ID NO 23
<211> LENGTH: 442
<212> TYPE: PRT
<213> ORGANISM: Homo sapiens

<400> SEQUENCE: 23

```
Met Gly Leu Ala Met Glu His Gly Gly Ser Tyr Ala Arg Ala Gly Gly
 1               5                  10                  15

Ser Ser Arg Gly Cys Trp Tyr Tyr Leu Arg Tyr Phe Phe Leu Phe Val
            20                  25                  30

Ser Leu Ile Gln Phe Leu Ile Ile Leu Gly Leu Val Leu Phe Met Val
        35                  40                  45

Tyr Gly Asn Val His Val Ser Thr Glu Ser Asn Leu Gln Ala Thr Glu
    50                  55                  60

Arg Arg Ala Glu Gly Leu Tyr Ser Gln Leu Leu Gly Leu Thr Ala Ser
65                  70                  75                  80

Gln Ser Asn Leu Thr Lys Glu Leu Asn Phe Thr Thr Arg Ala Lys Asp
                85                  90                  95

Ala Ile Met Gln Met Trp Leu Asn Ala Arg Arg Asp Leu Asp Arg Ile
            100                 105                 110

Asn Ala Ser Phe Arg Gln Cys Gln Gly Asp Arg Val Ile Tyr Thr Asn
        115                 120                 125

Asn Gln Arg Tyr Met Ala Ala Ile Ile Leu Ser Glu Lys Gln Cys Arg
    130                 135                 140

Asp Gln Phe Lys Asp Met Asn Lys Ser Cys Asp Ala Leu Leu Phe Met
145                 150                 155                 160

Leu Asn Gln Lys Val Lys Thr Leu Glu Val Glu Ile Ala Lys Glu Lys
                165                 170                 175

Thr Ile Cys Thr Lys Asp Lys Glu Ser Val Leu Leu Asn Lys Arg Val
            180                 185                 190
```

-continued

```
Ala Glu Glu Gln Leu Val Glu Cys Val Lys Thr Arg Glu Leu Gln His
            195                 200                 205

Gln Glu Arg Gln Leu Ala Lys Glu Gln Leu Gln Arg Val Gln Ala Leu
        210                 215                 220

Cys Leu Pro Leu Asp Lys Asp Lys Phe Glu Met Asp Leu Arg Asn Leu
225                 230                 235                 240

Trp Arg Asp Ser Ile Ile Pro Arg Ser Leu Asp Asn Leu Gly Tyr Asn
                245                 250                 255

Leu Tyr His Pro Leu Gly Ser Glu Leu Ala Ser Ile Arg Arg Ala Cys
            260                 265                 270

Asp His Met Pro Ser Leu Val Ser Ser Lys Val Glu Glu Leu Ala Arg
        275                 280                 285

Ser Leu Arg Ala Asp Ile Glu Arg Val Ala Arg Glu Asn Ser Asp Leu
        290                 295                 300

Gln Arg Gln Lys Leu Glu Ala Gln Gln Gly Leu Arg Ala Ser Gln Glu
305                 310                 315                 320

Ala Lys Gln Lys Val Glu Lys Glu Ala Gln Ala Arg Glu Ala Lys Leu
                325                 330                 335

Gln Ala Glu Cys Ser Arg Gln Thr Gln Leu Ala Leu Glu Glu Lys Ala
            340                 345                 350

Val Leu Arg Lys Glu Arg Asp Asn Leu Ala Lys Glu Leu Glu Glu Lys
        355                 360                 365

Lys Arg Glu Ala Glu Gln Leu Arg Met Glu Leu Ala Ile Arg Asn Ser
        370                 375                 380

Ala Leu Asp Thr Cys Ile Lys Thr Lys Ser Gln Pro Met Met Pro Val
385                 390                 395                 400

Ser Arg Pro Met Gly Pro Val Pro Asn Pro Gln Pro Ile Asp Pro Ala
                405                 410                 415

Ser Leu Glu Glu Phe Lys Arg Lys Ile Leu Glu Ser Gln Arg Pro Pro
            420                 425                 430

Ala Gly Ile Pro Val Ala Pro Ser Ser Gly
        435                 440

<210> SEQ ID NO 24
<211> LENGTH: 8640
<212> TYPE: DNA
<213> ORGANISM: Homo sapiens

<400> SEQUENCE: 24
agctgatgat ggccagggac cccaggggac gtggggccct gtggggtctg gcccccagga      60
gcaagacctc tgatgatgct ggtgtctggg agtgagcacc atgcccatca cccaggacaa     120
tgccgtgctg cacctgcccc tcctctacca gtggctgcag aacagcctgc aggaaggtgg     180
ggatgggccg gagcagcggc tctgccaggc ggccatccag aagctgcagg agtacatcca     240
gctgaacttt gctgtggatg agagtacggt cccacctgat cacagccccc ccgaaatgga     300
gatctgtact gtgtacctca ccaaggagct gggggacaca gagactgtgg gcctgagttt     360
tgggaacatc cctgttttcg gggactatgg tgaaaagcgc agggggggca agaagaggaa     420 aaccccaccag ggtcctgtgc tggatgtggg ctgcatctgg gtgacagagc tgaggaagaa     480
cagcccagca gggaagagtg ggaaggtccg actgcgggat gagatcctct cactgaatgg     540
gcagctgatg gttggagttg atgtcagtgg ggccagttac ctggctgagc agtgctggaa     600
tggcggcttt atctacctga tcatgctgcg tcgctttaag cacaaagccc actccactta     660
```

-continued

```
taatggcaac agtagcaaca gctctgaacc aggagaaaca cctaccttgg agctgggtga      720
ccgaactgcg aaaaggggga aacgaaccag aaagtttggg gtcatctcca ggcctcctgc      780
caacaaggcc cctgaagaat ccaagggcag cgctggctgt gaggtgtcca gtgaccccag      840
cactgagctg gagaacggcc tggaccctga acttggaaac ggccatgtct ttcagctaga      900
aaatggccca gattctctca aggaggtggc tggaccccat ctagagaggt cagaagtgga      960
cagagggaca gagcatagaa ttccaaagac agatgctcct ctgaccacaa gcaatgacaa     1020
acgccgcttc tcaaaaggtg gaagacgga cttccaatcg agtgactgcc tggcacggtc      1080
caaggaggaa gttggccgaa tatggaagat ggagctgctc aaagaatcgg atgggctggg     1140
aattcaggtt agtggaggcc gaggatcaaa gcgctcacct cacgctatcg ttgtcactca     1200
agtgaaggaa ggaggtgccg ctcacaggct cagggatggc aggctgtcct taggagatga     1260
gctgctggta atcaatggtc atttactggt cgggctctcc cacgaggaag cagtggccat     1320
tcttcgctcc gccacgggaa tggtgcagct tgtggtggcc agcaaggtag gtgtgctttc     1380
tgcatttcag atgcctggga cagatgaacc ccaagatgtg tgcggtgctg aggaatccaa     1440
ggggaacttg gaaagtccca acagggcag caataaaatc aagctcaaga gtcgcctttc      1500
aggtaggtgg gggctctacc tgatgcagcc tgtcgggggt gtacaccgcc ttgagtcagt     1560
tgaagaatat aacagctga tggtgcgaa tggggacccc cggatccgga tgttggaggt      1620
ctcccgagat ggccggaaac actccctccc gcagctgctg gactcttcca gtgcctcaca     1680
ggaataccac attgtgaaga gtctacccg ctccttaagc acgactcagg tggaatctcc      1740
ttggaggctc attcggccat ccgtcatctc gatcattggg ttgtacaaag aaaaaggcaa     1800
gggccttggc tttagtattg ctggaggtcg agactgcatt cgtggacaga tgggatttt     1860 tgtcaagacc atcttcccaa atggatcagc tgcagaggac ggaagactta agaaggtga     1920 tgaaatccta gatgtaaatg gaataccaat aaagggcttg acatttcaag aagccattca     1980
tacctttaag caaatccgga gtggattatt tgttttaacg gtacgcacaa agttggtgag     2040
ccccagcctc acaccctgct cgacacccac acacatgagc agatccgcct ccccgaactt     2100
caataccagt gggggagcct cggcgggagg ttccgatgaa ggcagttctt catccctggg     2160
tcggaagacc cctgggccca aggacaggat cgtcatggaa gtaacactca acaaagagcc     2220
aagagttgga ttaggcattg gtgcctgctg cttggctctg gaaaacagtc ctcctggcat     2280
ctacattcac agccttgctc caggatcagt ggccaagatg gagagcaacc tgtcgcgggg     2340
atcaatcctg gaagtgaact ccgtcaacgt ccgccatgct gctttaagca agtccacgc      2400 catcttgagt aaatgccctc caggaccgt tcgccttgtc atcggccggc accctaatcc      2460
aaaggtgaat caggtttccg agcaggaaat ggatgaagtc atagcacgca gcacttatca     2520
ggagagcaaa gaggccaatt cctctcctgg cttaggtact gtaatctcaa tcggatgttt     2580
tcttcttcaa caggactccc ttatttctga atctgaactc tcccagtact ttgcccacga     2640
tgtccctggc cccttgtcag acttcatggt ggccggttct gaggacgagg atcacccggg     2700
aagtggctgc agcacgtcgg aggagggcag cctgcctccc agcacctcca ctcacaagga     2760
gcctggaaaa cccagagcca acagcctcgt gactcttggg agccatcggg cttctgggct     2820
cttccacaag caggtgacag ttgccagaca agccagtctc cccggaagcc acaggcccct     2880
ccgaaaccct ctcctccgcc agaggaaggt aggctgctac gatgccaacg atgccagtga     2940 tgaggaaagag tttgacagag aagggggactg catttcactc ccaggggccc tcccgggtcc     3000
catcaggcct ctgtcagagg atgacccgag gcgtgtctca atttcctctt ccaagggcat     3060
```

```
ggacgtccac aaccaagagg aacgaccccg gaaaacactg gtgagcaagg ccatctcggc    3120
acctcttctt ggtagctcag tggacttaga ggagagtatc ccagagggca tggtggatgc    3180
tgcgtcctat gcagccaacc tcacggactc tgcagaggcc cccaagggga gccctggaag    3240
ctggtggaag aaggaactgt caggatcaag tagcgcaccc aaattggaat acacagtccg    3300
tacagacacc cagagtccga caaacactgg gagcccagt tccccccagc aaaaagtga     3360 aggcctgggc tccaggcaca gaccagtggc cagggtaagc ccccactgca agagatccga    3420
ggctgaggcc aagcccagtg gctcacagac agtgaacctg actggcagag ccaatgatcc    3480
atgcgatctg gactcgagag tccaggccac ttctgtcaaa gtgactgtcg ctggctttca    3540
gccaggtgga gctgtggaga aggaatctct gggaaagctg accactggag atgcttgtgt    3600
ctctaccagc tgtgaactag ccagtgctct gtcccatctg gatgccagcc acctcacaga    3660
gaacctgccc aaagctgcat cagagctggg gcaacaaccc atgactgaac tggacagctc    3720
ctcggacctc atctcttccc cagggaagaa gggggccgct catcctgacc ccagcaagac    3780
ctctgtagac acaggaaag tcagtcggcc agagaatccc agccagcctg catcgcccag    3840
ggtcgccaag tgcaaggcca ggtctccagt caggctcccc catgagggca gcccctcccc    3900
aggggagaaa gcagcggctc cccctgacta cagcaagact cgatcagcat cggaaaccag    3960 cacacccac aataccagga gggtggctgc cctcagggga gcgggacctg gagcagaggg    4020
aatgacacca gctggtgctg tcctgccagg agacccctc acatcccagg agcagagaca     4080
gggagctcca ggtaaccaca gtaaggctct ggaaatgaca ggaatccatg cacctgaaag    4140
ctcccaggag ccttcctgc tggagggagc agattctgtg tcctcaaggg caccgcaggc     4200
cagcctctcc atgctgccat ccactgacaa caccaaagaa gcatgtggcc atgtctcggg    4260
gcactgctgc ccggggggga gtagagagag ccctgtgacg gacattgaca gcttcatcaa    4320
ggagctggat gcttctgcag caaggtctcc gtcttcccag acgggggaca gtggctctca    4380
ggagggcagt gctcagggcc acccaccagc cggggctgga ggtgggagct cctgccgtgc    4440
cgaaccagtc ccgggggggcc agacctcctc cccgaggagg gctgggctg ctggtgcccc      4500 cgcctaccca caatgggcct cccagccttc ggttttagat tcaattaatc ccgacaaaca    4560
ttttactgtg aacaaaaact ttctgagcaa ctactctaga aattttagca gttttcatga    4620
agacagcacc tccctatcag gcctgggtga cagcacggag ccgtctctgt catccatgta    4680
tggcgatgct gaggattctt cttctgaccc tgagtcactc actgaagccc cacgagcttc    4740
tgccagggac ggctggtccc ctcctcgttc ccgtgtgtct ttgcacaagg aagatccttc    4800
ggagtcagaa gaggaacaga ttgagatttg ttccacacgt ggctgcccca atccacccct    4860
gagtcctgct catcttccca cccaggctgc catctgtcct gcctcagcca agttctgtc     4920 attaaaatac agcactccga gagagtcggt ggccagtccc cgtgagaagg tcgcctgctt    4980
gccaggctca tacttcag gcccagactc ttcccagcca tcatcactct ggagatgag      5040 ctctcaggag catgaaactc atgcggacat aagcacttca cagaaccaca ggccctcgtg    5100
tgcagaagaa accacagaag tcaccagcgc tagctcagcc atggaaaaca gtccgctgtc    5160
taaagtagcc aggcattttc acagtccgcc catcattctc agctccccca acatggtaaa    5220
tggcttggaa catgacctgc tagatgacga aaccctgaat caatacgaaa caagcattaa    5280
tgcagctgcc agtctgtcct ccttcagtgt ggatgtccct aagaatggag aatctgtttt    5340
ggaaaacctc cacatctctg aaagtcaaga cctggatgac ttgctacaga aaccaaaaat    5400
```

```
gatcgctagg aggcccatca tggcctggtt taaagaaata aataaacata accaaggcac  5460
acatttgagg agcaaaaccg agaaggaaca acctctaatg cctgccagaa gtcccgactc  5520
caagattcag atggtgagtt caagccaaaa aaagggcgtt actgtgcctc atagccctcc  5580
tcagccgaaa acaaacctgg aaaataagga cctgtctaag aagagtccgg cagaaatgct  5640
tctgactaat ggtcagaagg caaagtgtgg tccgaagctg aagaggctca gcctcaaggg  5700
caaggccaaa gtcaactctg aggcccctgc tgcgaatgct gtgaaggctg ggggacgga  5760 ccacaggaaa cccttgatct caccccagac ctcccacaaa acactttcta aggcagtgtc  5820
acagcggctc catgtagccg accacgagga ccctgacaga acaccacag ctgccccag  5880 gtcccccag tgtgtgctgg aaagcaagcc acctcttgcc acctctgggc cactgaaacc  5940
ctcagtgtct gacacgagca tcaggacatt tgtctcgccc ctgacctctc caagcctgt  6000 tcctgagcaa ggcatgtgga gcaggttcca catggctgtc ctctctgaac cgacagagg  6060 ttgcccaacc accctaaat tcctaagtg tagagcagag ggcagggcgc cccgtgctga  6120
ctccgggccg gtgagtccgg cagcgtctag aacggcatg tccgtggcag ggaacagaca  6180
gagtgagccg cgcctggcca gccatgtggc agcagacaca gcccaaccca ggccgactgg  6240 cgaaaagga ggcaacataa tggccagcga tcgcctcgaa agaacaaacc agctgaaaat  6300
cgtggagatt tctgctgaag cagtgtcaga gactgtatgt ggtaacaagc cagctgaaag  6360
cgacagacgg ggagggtgct tggcccaggg caactgtcag gagaagagtg aaatcaggct  6420
ctatcgccag gtcgcagaat catccacaag tcatccatcc tcactcccat tcatgcctc  6480 ccaggcagag caggaaatgt cacgatcatt cagcatggca aaactggcgt cctcctcctc  6540
ctcccttcaa acagccatta gaaaggcaga atactcccag ggaaaatcaa gcctgatgtc  6600
agactcccga ggggtgccca gaaacagcat tccaggggc cctcggggg aggaccatct  6660 ctacttcacc ccaaggccag cgaccaggac ctactccatg ccagcccagt tctcaagcca  6720
ttttggacgg gagggtcacc ccccacacag cctgggtcgc tctcgggaca gccaggtccc  6780
tgtgacaagc agtgttgtcc ccgaggcaaa ggcatccaga ggtggtcttc ccagcctggc  6840
taatggacag ggcatatata gtgtaaagcc gctgctggac acatcgagga atcttccagc  6900
cacagatgaa ggggatatca tttcagtcca ggagacgagc tgcctagtca cagacaaaat  6960
caaagtcacc agacgacact actgctatga gcagaactgg ccccatgaat ctacctcatt  7020
tttctctgtg aagcagcgga tcaagtcttt tgagaacctg gccaatgctg accggcctgt  7080
agccaagtcc ggggcttccc catttttgtc ggtgagctcc aagcctccca ttgggaggcg  7140
gtcttccggc agcattgttt ccgggagcct gggccaccca ggtgacgcag cagcaaggtt  7200
gttgagacgc agcttgagtt cctgcagcga aaaccaaagc gaagccggca ccctcctgcc  7260
ccagatggcc aagtctccct caatcatgac actgaccatc tctcggcaga acccaccaga  7320
gaccagtagc aagggctctg attcggaact aaagaaatca cttggtcctt tgggaattcc  7380
caccccaacg atgaccctgg cttctcctgt taagaggaac aagtcctcgg tacgccacac  7440
gcagccctcg cccgtgtccc gctccaagct ccaggagctg agagcttga gcatgcctga  7500 ccttgacaag ctctgcagcg aggattactc agcagggccg agcgccgtgc tcttcaaaac  7560
tgagctggga atcaccccca ggaggtcacc tggccctcct gctggaggcg tttcgtgtcc  7620
cgagaagggc gggaacaggg cctgtccagg aggaagtggc cctaaaacca gtgctgctga  7680
gacacccagt tcagccagtg atacgggtga agctgcccag gatctgcctt ttagaagaag  7740
ctggtcagtt aatttggatc aacttctagt ctcagcgggg gaccagcaaa gattacagtc  7800
```

-continued

```
tgttttatcg tcagtgggat cgaaatctac catcctaact ctcattcagg aagcgaaagc    7860
acaatcagag aatgaagaag atgtttgctt catagtcttg aatagaaaag aaggctcagg    7920 tctggattc agtgtggcag gagggacaga tgtggagcca aaatcaatca cggtccacag     7980
ggtgttttct caggggggcgg cttctcagga agggactatg aaccgagggg atttccttct   8040
gtcagtcaac ggcgcctcac tggctggctt agcccacggg aatgtcctga aggttctgca    8100
ccaggcacag ctgcacaaag atgccctcgt ggtcatcaag aaagggatgg atcagcccag    8160
gccctctgcc cggcaggagc ctcccacagc caatgggaag gtttgctgt ccagaaagac     8220 catcccctg gagcctggca ttgggagaag tgtggctgta cacgatgctc tgtgtgttga     8280
agtgctgaag acctcggctg ggctgggact gagtctggat gggggaaaat catcggtgac    8340
gggagatggg cccttggtca ttaaaagagt gtacaaaggt ggtgcggctg aacaagctgg    8400
aataatagaa gctggagatg aaattcttgc tattaatggg aaacctctgg ttgggctcat    8460
gcactttgat gcctggaata ttatgaagtc tgtcccagaa ggacctgtgc agttattaat    8520
tagaaagcat aggaattctt catgaatttt aacaagaatc attttctcag ttctcttctt    8580
tctttagcaa atcagagtga cttctttaaa ccacaggttg ttgaaatggc caacactggt    8640
```

<210> SEQ ID NO 25
<211> LENGTH: 2814
<212> TYPE: PRT
<213> ORGANISM: Homo sapiens

<400> SEQUENCE: 25

```
Met Pro Ile Thr Gln Asp Asn Ala Val Leu His Leu Pro Leu Leu Tyr
 1               5                  10                  15

Gln Trp Leu Gln Asn Ser Leu Gln Glu Gly Gly Asp Gly Pro Glu Gln
            20                  25                  30

Arg Leu Cys Gln Ala Ala Ile Gln Lys Leu Gln Glu Tyr Ile Gln Leu
        35                  40                  45

Asn Phe Ala Val Asp Glu Ser Thr Val Pro Pro Asp His Ser Pro Pro
    50                  55                  60

Glu Met Glu Ile Cys Thr Val Tyr Leu Thr Lys Glu Leu Gly Asp Thr
65                  70                  75                  80

Glu Thr Val Gly Leu Ser Phe Gly Asn Ile Pro Val Phe Gly Asp Tyr
                85                  90                  95

Gly Glu Lys Arg Arg Gly Gly Lys Lys Arg Lys Thr His Gln Gly Pro
            100                 105                 110

Val Leu Asp Val Gly Cys Ile Trp Val Thr Glu Leu Arg Lys Asn Ser
        115                 120                 125

Pro Ala Gly Lys Ser Gly Lys Val Arg Leu Arg Asp Glu Ile Leu Ser
    130                 135                 140

Leu Asn Gly Gln Leu Met Val Gly Val Asp Val Ser Gly Ala Ser Tyr
145                 150                 155                 160

Leu Ala Glu Gln Cys Trp Asn Gly Gly Phe Ile Tyr Leu Ile Met Leu
                165                 170                 175

Arg Arg Phe Lys His Lys Ala His Ser Thr Tyr Asn Gly Asn Ser Ser
            180                 185                 190

Asn Ser Ser Glu Pro Gly Glu Thr Pro Thr Leu Glu Leu Gly Asp Arg
        195                 200                 205

Thr Ala Lys Lys Gly Lys Arg Thr Arg Lys Phe Gly Val Ile Ser Arg
    210                 215                 220
```

-continued

```
Pro Pro Ala Asn Lys Ala Pro Glu Glu Ser Lys Gly Ser Ala Gly Cys
225                 230                 235                 240

Glu Val Ser Ser Asp Pro Ser Thr Glu Leu Glu Asn Gly Leu Asp Pro
                245                 250                 255

Glu Leu Gly Asn Gly His Val Phe Gln Leu Glu Asn Gly Pro Asp Ser
            260                 265                 270

Leu Lys Glu Val Ala Gly Pro His Leu Glu Arg Ser Glu Val Asp Arg
        275                 280                 285

Gly Thr Glu His Arg Ile Pro Lys Thr Asp Ala Pro Leu Thr Thr Ser
    290                 295                 300

Asn Asp Lys Arg Arg Phe Ser Lys Gly Gly Lys Thr Asp Phe Gln Ser
305                 310                 315                 320

Ser Asp Cys Leu Ala Arg Ser Lys Glu Glu Val Gly Arg Ile Trp Lys
                325                 330                 335

Met Glu Leu Leu Lys Glu Ser Asp Gly Leu Gly Ile Gln Val Ser Gly
                340                 345                 350

Gly Arg Gly Ser Lys Arg Ser Pro His Ala Ile Val Val Thr Gln Val
            355                 360                 365

Lys Glu Gly Gly Ala Ala His Arg Leu Arg Asp Gly Arg Leu Ser Leu
        370                 375                 380

Gly Asp Glu Leu Leu Val Ile Asn Gly His Leu Leu Val Gly Leu Ser
385                 390                 395                 400

His Glu Glu Ala Val Ala Ile Leu Arg Ser Ala Thr Gly Met Val Gln
                405                 410                 415

Leu Val Val Ala Ser Lys Val Gly Val Leu Ser Ala Phe Gln Met Pro
                420                 425                 430

Gly Thr Asp Glu Pro Gln Asp Val Cys Gly Ala Glu Glu Ser Lys Gly
            435                 440                 445

Asn Leu Glu Ser Pro Lys Gln Gly Ser Asn Lys Ile Lys Leu Lys Ser
450                 455                 460

Arg Leu Ser Gly Arg Trp Gly Leu Tyr Leu Met Gln Pro Val Gly Gly
465                 470                 475                 480

Val His Arg Leu Glu Ser Val Glu Glu Tyr Asn Glu Leu Met Val Arg
                485                 490                 495

Asn Gly Asp Pro Arg Ile Arg Met Leu Glu Val Ser Arg Asp Gly Arg
                500                 505                 510

Lys His Ser Leu Pro Gln Leu Leu Asp Ser Ser Ala Ser Gln Glu
            515                 520                 525

Tyr His Ile Val Lys Lys Ser Thr Arg Ser Leu Ser Thr Thr Gln Val
        530                 535                 540

Glu Ser Pro Trp Arg Leu Ile Arg Pro Ser Val Ile Ser Ile Ile Gly
545                 550                 555                 560

Leu Tyr Lys Glu Lys Gly Lys Gly Leu Gly Phe Ser Ile Ala Gly Gly
                565                 570                 575

Arg Asp Cys Ile Arg Gly Gln Met Gly Ile Phe Val Lys Thr Ile Phe
                580                 585                 590

Pro Asn Gly Ser Ala Ala Glu Asp Gly Arg Leu Lys Glu Gly Asp Glu
            595                 600                 605

Ile Leu Asp Val Asn Gly Ile Pro Ile Lys Gly Leu Thr Phe Gln Glu
        610                 615                 620

Ala Ile His Thr Phe Lys Gln Ile Arg Ser Gly Leu Phe Val Leu Thr
625                 630                 635                 640

Val Arg Thr Lys Leu Val Ser Pro Ser Leu Thr Pro Cys Ser Thr Pro
```

```
                    645                 650                 655
Thr His Met Ser Arg Ser Ala Ser Pro Asn Phe Asn Thr Ser Gly Gly
            660                 665                 670

Ala Ser Ala Gly Gly Ser Asp Glu Gly Ser Ser Ser Leu Gly Arg
        675                 680                 685

Lys Thr Pro Gly Pro Lys Asp Arg Ile Val Met Glu Val Thr Leu Asn
    690                 695                 700

Lys Glu Pro Arg Val Gly Leu Gly Ile Gly Ala Cys Cys Leu Ala Leu
705                 710                 715                 720

Glu Asn Ser Pro Pro Gly Ile Tyr Ile His Ser Leu Ala Pro Gly Ser
            725                 730                 735

Val Ala Lys Met Glu Ser Asn Leu Ser Arg Gly Ser Ile Leu Glu Val
            740                 745                 750

Asn Ser Val Asn Val Arg His Ala Ala Leu Ser Lys Val His Ala Ile
            755                 760                 765

Leu Ser Lys Cys Pro Pro Gly Pro Val Arg Leu Val Ile Gly Arg His
        770                 775                 780

Pro Asn Pro Lys Val Asn Gln Val Ser Glu Gln Glu Met Asp Glu Val
785                 790                 795                 800

Ile Ala Arg Ser Thr Tyr Gln Glu Ser Lys Glu Ala Asn Ser Ser Pro
            805                 810                 815

Gly Leu Gly Thr Val Ile Ser Ile Gly Cys Phe Leu Leu Gln Gln Asp
            820                 825                 830

Ser Leu Ile Ser Glu Ser Glu Leu Ser Gln Tyr Phe Ala His Asp Val
        835                 840                 845

Pro Gly Pro Leu Ser Asp Phe Met Val Ala Gly Ser Glu Asp Glu Asp
    850                 855                 860

His Pro Gly Ser Gly Cys Ser Thr Ser Glu Glu Gly Ser Leu Pro Pro
865                 870                 875                 880

Ser Thr Ser Thr His Lys Glu Pro Gly Lys Pro Arg Ala Asn Ser Leu
            885                 890                 895

Val Thr Leu Gly Ser His Arg Ala Ser Gly Leu Phe His Lys Gln Val
            900                 905                 910

Thr Val Ala Arg Gln Ala Ser Leu Pro Gly Ser Pro Gln Ala Leu Arg
        915                 920                 925

Asn Pro Leu Leu Arg Gln Arg Lys Val Gly Cys Tyr Asp Ala Asn Asp
    930                 935                 940

Ala Ser Asp Glu Glu Phe Asp Arg Glu Gly Asp Cys Ile Ser Leu
945                 950                 955                 960

Pro Gly Ala Leu Pro Gly Pro Ile Arg Pro Leu Ser Glu Asp Pro
            965                 970                 975

Arg Arg Val Ser Ile Ser Ser Lys Gly Met Asp Val His Asn Gln
            980                 985                 990

Glu Glu Arg Pro Arg Lys Thr Leu Val Ser Lys Ala Ile Ser Ala Pro
            995                1000                1005

Leu Leu Gly Ser Ser Val Asp Leu Glu Glu Ser Ile Pro Glu Gly Met
    1010                1015                1020

Val Asp Ala Ala Ser Tyr Ala Ala Asn Leu Thr Asp Ser Ala Glu Ala
1025                1030                1035                1040

Pro Lys Gly Ser Pro Gly Ser Trp Trp Lys Lys Glu Leu Ser Gly Ser
            1045                1050                1055

Ser Ser Ala Pro Lys Leu Glu Tyr Thr Val Arg Thr Asp Thr Gln Ser
            1060                1065                1070
```

-continued

```
Pro Thr Asn Thr Gly Ser Pro Ser Pro Gln Gln Lys Ser Glu Gly
        1075                1080                1085

Leu Gly Ser Arg His Arg Pro Val Ala Arg Val Ser Pro His Cys Lys
    1090                1095                1100

Arg Ser Glu Ala Glu Ala Lys Pro Ser Gly Ser Gln Thr Val Asn Leu
1105                1110                1115                1120

Thr Gly Arg Ala Asn Asp Pro Cys Asp Leu Asp Ser Arg Val Gln Ala
        1125                1130                1135

Thr Ser Val Lys Val Thr Val Ala Gly Phe Gln Pro Gly Gly Ala Val
            1140                1145                1150

Glu Lys Glu Ser Leu Gly Lys Leu Thr Thr Gly Asp Ala Cys Val Ser
        1155                1160                1165

Thr Ser Cys Glu Leu Ala Ser Ala Leu Ser His Leu Asp Ala Ser His
    1170                1175                1180

Leu Thr Glu Asn Leu Pro Lys Ala Ala Ser Glu Leu Gly Gln Gln Pro
1185                1190                1195                1200

Met Thr Glu Leu Asp Ser Ser Ser Asp Leu Ile Ser Ser Pro Gly Lys
        1205                1210                1215

Lys Gly Ala Ala His Pro Asp Pro Ser Lys Thr Ser Val Asp Thr Gly
        1220                1225                1230

Lys Val Ser Arg Pro Glu Asn Pro Ser Gln Pro Ala Ser Pro Arg Val
            1235                1240                1245

Ala Lys Cys Lys Ala Arg Ser Pro Val Arg Leu Pro His Glu Gly Ser
        1250                1255                1260

Pro Ser Pro Gly Glu Lys Ala Ala Pro Pro Asp Tyr Ser Lys Thr
1265                1270                1275                1280

Arg Ser Ala Ser Glu Thr Ser Thr Pro His Asn Thr Arg Arg Val Ala
            1285                1290                1295

Ala Leu Arg Gly Ala Gly Pro Gly Ala Glu Gly Met Thr Pro Ala Gly
        1300                1305                1310

Ala Val Leu Pro Gly Asp Pro Leu Thr Ser Gln Glu Gln Arg Gln Gly
        1315                1320                1325

Ala Pro Gly Asn His Ser Lys Ala Leu Glu Met Thr Gly Ile His Ala
        1330                1335                1340

Pro Glu Ser Ser Gln Glu Pro Ser Leu Leu Glu Gly Ala Asp Ser Val
1345                1350                1355                1360

Ser Ser Arg Ala Pro Gln Ala Ser Leu Ser Met Leu Pro Ser Thr Asp
        1365                1370                1375

Asn Thr Lys Glu Ala Cys Gly His Val Ser Gly His Cys Cys Pro Gly
        1380                1385                1390

Gly Ser Arg Glu Ser Pro Val Thr Asp Ile Asp Ser Phe Ile Lys Glu
        1395                1400                1405

Leu Asp Ala Ser Ala Ala Arg Ser Pro Ser Ser Gln Thr Gly Asp Ser
    1410                1415                1420

Gly Ser Gln Glu Gly Ser Ala Gln Gly His Pro Pro Ala Gly Ala Gly
1425                1430                1435                1440

Gly Gly Ser Ser Cys Arg Ala Glu Pro Val Pro Gly Gly Gln Thr Ser
            1445                1450                1455

Ser Pro Arg Arg Ala Trp Ala Ala Gly Ala Pro Ala Tyr Pro Gln Trp
        1460                1465                1470

Ala Ser Gln Pro Ser Val Leu Asp Ser Ile Asn Pro Asp Lys His Phe
    1475                1480                1485
```

```
Thr Val Asn Lys Asn Phe Leu Ser Asn Tyr Ser Arg Asn Phe Ser Ser
    1490                1495                1500

Phe His Glu Asp Ser Thr Ser Leu Ser Gly Leu Gly Asp Ser Thr Glu
1505                1510                1515                1520

Pro Ser Leu Ser Ser Met Tyr Gly Asp Ala Glu Asp Ser Ser Ser Asp
            1525                1530                1535

Pro Glu Ser Leu Thr Glu Ala Pro Arg Ala Ser Ala Arg Asp Gly Trp
        1540                1545                1550

Ser Pro Pro Arg Ser Arg Val Ser Leu His Lys Glu Asp Pro Ser Glu
    1555                1560                1565

Ser Glu Glu Glu Gln Ile Glu Ile Cys Ser Thr Arg Gly Cys Pro Asn
1570                1575                1580

Pro Pro Ser Ser Pro Ala His Leu Pro Thr Gln Ala Ala Ile Cys Pro
1585                1590                1595                1600

Ala Ser Ala Lys Val Leu Ser Leu Lys Tyr Ser Thr Pro Arg Glu Ser
            1605                1610                1615

Val Ala Ser Pro Arg Glu Lys Val Ala Cys Leu Pro Gly Ser Tyr Thr
        1620                1625                1630

Ser Gly Pro Asp Ser Ser Gln Pro Ser Ser Leu Leu Glu Met Ser Ser
    1635                1640                1645

Gln Glu His Glu Thr His Ala Asp Ile Ser Thr Ser Gln Asn His Arg
1650                1655                1660

Pro Ser Cys Ala Glu Glu Thr Thr Glu Val Thr Ser Ala Ser Ser Ala
1665                1670                1675                1680

Met Glu Asn Ser Pro Leu Ser Lys Val Ala Arg His Phe His Ser Pro
            1685                1690                1695

Pro Ile Ile Leu Ser Ser Pro Asn Met Val Asn Gly Leu Glu His Asp
        1700                1705                1710

Leu Leu Asp Asp Glu Thr Leu Asn Gln Tyr Glu Thr Ser Ile Asn Ala
    1715                1720                1725

Ala Ala Ser Leu Ser Ser Phe Ser Val Asp Val Pro Lys Asn Gly Glu
1730                1735                1740

Ser Val Leu Glu Asn Leu His Ile Ser Glu Ser Gln Asp Leu Asp Asp
1745                1750                1755                1760

Leu Leu Gln Lys Pro Lys Met Ile Ala Arg Arg Pro Ile Met Ala Trp
            1765                1770                1775

Phe Lys Glu Ile Asn Lys His Asn Gln Gly Thr His Leu Arg Ser Lys
        1780                1785                1790

Thr Glu Lys Glu Gln Pro Leu Met Pro Ala Arg Ser Pro Asp Ser Lys
    1795                1800                1805

Ile Gln Met Val Ser Ser Ser Gln Lys Lys Gly Val Thr Val Pro His
1810                1815                1820

Ser Pro Pro Gln Pro Lys Thr Asn Leu Glu Asn Lys Asp Leu Ser Lys
1825                1830                1835                1840

Lys Ser Pro Ala Glu Met Leu Leu Thr Asn Gly Gln Lys Ala Lys Cys
            1845                1850                1855

Gly Pro Lys Leu Lys Arg Leu Ser Leu Lys Gly Lys Ala Lys Val Asn
        1860                1865                1870

Ser Glu Ala Pro Ala Ala Asn Ala Val Lys Ala Gly Gly Thr Asp His
    1875                1880                1885

Arg Lys Pro Leu Ile Ser Pro Gln Thr Ser His Lys Thr Leu Ser Lys
1890                1895                1900

Ala Val Ser Gln Arg Leu His Val Ala Asp His Glu Asp Pro Asp Arg
```

-continued

```
            1905                1910                1915                1920
Asn Thr Thr Ala Ala Pro Arg Ser Pro Gln Cys Val Leu Glu Ser Lys
                1925                1930                1935
Pro Pro Leu Ala Thr Ser Gly Pro Leu Lys Pro Ser Val Ser Asp Thr
            1940                1945                1950
Ser Ile Arg Thr Phe Val Ser Pro Leu Thr Ser Pro Lys Pro Val Pro
        1955                1960                1965
Glu Gln Gly Met Trp Ser Arg Phe His Met Ala Val Leu Ser Glu Pro
    1970                1975                1980
Asp Arg Gly Cys Pro Thr Thr Pro Lys Ser Pro Lys Cys Arg Ala Glu
1985                1990                1995                2000
Gly Arg Ala Pro Arg Ala Asp Ser Gly Pro Val Ser Pro Ala Ala Ser
                2005                2010                2015
Arg Asn Gly Met Ser Val Ala Gly Asn Arg Gln Ser Glu Pro Arg Leu
            2020                2025                2030
Ala Ser His Val Ala Ala Asp Thr Ala Gln Pro Arg Pro Thr Gly Glu
        2035                2040                2045
Lys Gly Gly Asn Ile Met Ala Ser Asp Arg Leu Glu Arg Thr Asn Gln
    2050                2055                2060
Leu Lys Ile Val Glu Ile Ser Ala Glu Ala Val Ser Glu Thr Val Cys
2065                2070                2075                2080
Gly Asn Lys Pro Ala Glu Ser Asp Arg Arg Gly Gly Cys Leu Ala Gln
                2085                2090                2095
Gly Asn Cys Gln Glu Lys Ser Glu Ile Arg Leu Tyr Arg Gln Val Ala
            2100                2105                2110
Glu Ser Ser Thr Ser His Pro Ser Ser Leu Pro Ser His Ala Ser Gln
        2115                2120                2125
Ala Glu Gln Glu Met Ser Arg Ser Phe Ser Met Ala Lys Leu Ala Ser
    2130                2135                2140
Ser Ser Ser Ser Leu Gln Thr Ala Ile Arg Lys Ala Glu Tyr Ser Gln
2145                2150                2155                2160
Gly Lys Ser Ser Leu Met Ser Asp Ser Arg Gly Val Pro Arg Asn Ser
                2165                2170                2175
Ile Pro Gly Gly Pro Ser Gly Glu Asp His Leu Tyr Phe Thr Pro Arg
            2180                2185                2190
Pro Ala Thr Arg Thr Tyr Ser Met Pro Ala Gln Phe Ser Ser His Phe
        2195                2200                2205
Gly Arg Glu Gly His Pro Pro His Ser Leu Gly Arg Ser Arg Asp Ser
    2210                2215                2220
Gln Val Pro Val Thr Ser Ser Val Val Pro Glu Ala Lys Ala Ser Arg
2225                2230                2235                2240
Gly Gly Leu Pro Ser Leu Ala Asn Gly Gln Gly Ile Tyr Ser Val Lys
                2245                2250                2255
Pro Leu Leu Asp Thr Ser Arg Asn Leu Pro Ala Thr Asp Glu Gly Asp
            2260                2265                2270
Ile Ile Ser Val Gln Glu Thr Ser Cys Leu Val Thr Asp Lys Ile Lys
        2275                2280                2285
Val Thr Arg Arg His Tyr Cys Tyr Glu Gln Asn Trp Pro His Glu Ser
    2290                2295                2300
Thr Ser Phe Phe Ser Val Lys Gln Arg Ile Lys Ser Phe Glu Asn Leu
2305                2310                2315                2320
Ala Asn Ala Asp Arg Pro Val Ala Lys Ser Gly Ala Ser Pro Phe Leu
                2325                2330                2335
```

-continued

```
Ser Val Ser Ser Lys Pro Pro Ile Gly Arg Arg Ser Ser Gly Ser Ile
        2340                2345                2350
Val Ser Gly Ser Leu Gly His Pro Gly Asp Ala Ala Ala Arg Leu Leu
        2355                2360            2365
Arg Arg Ser Leu Ser Ser Cys Ser Glu Asn Gln Ser Glu Ala Gly Thr
    2370                2375                2380
Leu Leu Pro Gln Met Ala Lys Ser Pro Ser Ile Met Thr Leu Thr Ile
2385                2390                2395                2400
Ser Arg Gln Asn Pro Pro Glu Thr Ser Ser Lys Gly Ser Asp Ser Glu
            2405                2410                2415
Leu Lys Lys Ser Leu Gly Pro Leu Gly Ile Pro Thr Pro Thr Met Thr
        2420                2425                2430
Leu Ala Ser Pro Val Lys Arg Asn Lys Ser Ser Val Arg His Thr Gln
        2435                2440                2445
Pro Ser Pro Val Ser Arg Ser Lys Leu Gln Glu Leu Arg Ala Leu Ser
    2450                2455                2460
Met Pro Asp Leu Asp Lys Leu Cys Ser Glu Asp Tyr Ser Ala Gly Pro
2465                2470                2475                2480
Ser Ala Val Leu Phe Lys Thr Glu Leu Glu Ile Thr Pro Arg Arg Ser
            2485                2490                2495
Pro Gly Pro Pro Ala Gly Gly Val Ser Cys Pro Glu Lys Gly Gly Asn
        2500                2505                2510
Arg Ala Cys Pro Gly Gly Ser Gly Pro Lys Thr Ser Ala Ala Glu Thr
        2515                2520                2525
Pro Ser Ser Ala Ser Asp Thr Gly Glu Ala Ala Gln Asp Leu Pro Phe
    2530                2535                2540
Arg Arg Ser Trp Ser Val Asn Leu Asp Gln Leu Leu Val Ser Ala Gly
2545                2550                2555                2560
Asp Gln Gln Arg Leu Gln Ser Val Leu Ser Ser Val Gly Ser Lys Ser
            2565                2570                2575
Thr Ile Leu Thr Leu Ile Gln Glu Ala Lys Ala Gln Ser Glu Asn Glu
        2580                2585                2590
Glu Asp Val Cys Phe Ile Val Leu Asn Arg Lys Glu Gly Ser Gly Leu
        2595                2600                2605
Gly Phe Ser Val Ala Gly Gly Thr Asp Val Glu Pro Lys Ser Ile Thr
    2610                2615                2620
Val His Arg Val Phe Ser Gln Gly Ala Ala Ser Gln Glu Gly Thr Met
2625                2630                2635                2640
Asn Arg Gly Asp Phe Leu Leu Ser Val Asn Gly Ala Ser Leu Ala Gly
            2645                2650                2655
Leu Ala His Gly Asn Val Leu Lys Val Leu His Gln Ala Gln Leu His
        2660                2665                2670
Lys Asp Ala Leu Val Val Ile Lys Lys Gly Met Asp Gln Pro Arg Pro
        2675                2680                2685
Ser Ala Arg Gln Glu Pro Pro Thr Ala Asn Gly Lys Gly Leu Leu Ser
    2690                2695                2700
Arg Lys Thr Ile Pro Leu Glu Pro Gly Ile Gly Arg Ser Val Ala Val
2705                2710                2715                2720
His Asp Ala Leu Cys Val Glu Val Leu Lys Thr Ser Ala Gly Leu Gly
            2725                2730                2735
Leu Ser Leu Asp Gly Gly Lys Ser Ser Val Thr Gly Asp Gly Pro Leu
        2740                2745                2750
```

-continued

```
Val Ile Lys Arg Val Tyr Lys Gly Gly Ala Ala Glu Gln Ala Gly Ile
     2755                2760                2765

Ile Glu Ala Gly Asp Glu Ile Leu Ala Ile Asn Gly Lys Pro Leu Val
  2770                2775                2780

Gly Leu Met His Phe Asp Ala Trp Asn Ile Met Lys Ser Val Pro Glu
2785                2790                2795                2800

Gly Pro Val Gln Leu Leu Ile Arg Lys His Arg Asn Ser Ser
              2805                2810

<210> SEQ ID NO 26
<211> LENGTH: 8640
<212> TYPE: DNA
<213> ORGANISM: Homo sapiens

<400> SEQUENCE: 26
agctgatgat ggccagggac cccaggggac gtggggccct gtggggtctg gcccccagga      60
gcaagacctc tgatgatgct ggtgtctggg agtgagcacc atgcccatca cccaggacaa     120
tgccgtgctg cacctgcccc tcctctacca gtggctgcag aacagcctgc aggaaggtgg     180
ggatgggccg gagcagcggc tctgccaggc ggccatccag aagctgcagg agtacatcca     240
gctgaacttt gctgtggatg agagtacggt cccacctgat cacagccccc cgaaatgga      300 gatctgtact gtgtacctca ccaaggagct ggggacaca gagactgtgg gcctgagttt      360
tgggaacatc cctgttttcg gggactatgg tgaaaagcgc agggggggca agaagaggaa     420 aaccccaccag gtcctgtgc tggatgtggg ctgcatctgg gtgacagagc tgaggaagaa     480
cagcccagca gggaagagtg ggaaggtccg actgcgggat gagatcctct cactgaatgg     540
gcagctgatg gttggagttg atgtcagtgg ggccagttac ctggctgagc agtgctggaa     600
tgcggctttt atctacctga tcatgctgcg tcgctttaag cacaaagccc actccactta     660
taatggcaac agtagcaaca gctctgaacc aggagaaaca cctaccttgg agctgggtga     720
ccgaactgcg aaaaagggga acgaaccag aaagtttggg gtcatctcca ggcctcctgc     780
caacaaggcc cctgaagaat ccaagggcag cgctggctgt gaggtgtcca gtgaccccag     840
cactgagctg gagaacggcc tggaccctga acttggaaac ggccatgtct ttcagctaga     900
aaatggccca gattctctca ggaggtggc tggaccccat ctagagaggt cagaagtgga     960
cagagggaca gagcatagaa ttccaaagac agatgctcct ctgaccacaa gcaatgacaa    1020
acgccgcttc tcaaaaggtg ggaagacgga cttccaatcg agtgactgcc tggcacggtc    1080
caaggaggaa gttggccgaa tatggaagat ggagctgctc aaagaatcgg atgggctggg    1140
aattcaggtt agtggaggcc gaggatcaaa gcgctcacct cacgctatcg ttgtcactca    1200
agtgaaggaa ggaggtgccg ctcacaggct cagggatggc aggctgtcct taggagatga    1260
gctgctggta atcaatggtc atttactggt cgggctctcc cacgaggaag cagtggccat    1320
tcttcgctcc gccacgggaa tggtgcagct tgtggtggcc agcaaggtag gtgtgctttc    1380
tgcatttcag atgcctggga cagatgaacc ccaagatgtg tgcggtgctg aggaatccaa    1440
ggggaacttg gaaagtccca acagggcag caataaaatc aagctcaaga gtcgcctttc    1500
aggtaggtgg gggctctacc tgatgcagcc tgtcggggt gtacaccgcc ttgagtcagt    1560
tgaagaatat aacgagctga tggtgcgaa tgggacccc cggatccgga gttggaggt    1620 ctcccgagat ggccggaaac actccctccc gcagctgctg gactcttcca gtgcctcaca    1680
ggaataccac attgtgaaga gtctacccg ctccttaagc acgactcagg tggaatctcc    1740
tcggaggctc attcggccat ccgtcatctc gatcattggg ttgtacaaag aaaaaggcaa    1800
```

```
gggccttggc tttagtattg ctggaggtcg agactgcatt cgtggacaga tggggatttt    1860
tgtcaagacc atcttcccaa atggatcagc tgcagaggac ggaagactta agaagggga    1920 tgaaatccta gatgtaaatg gaataccaat aaagggcttg acatttcaag aagccattca    1980
tacctttaag caaatccgga gtggattatt tgttttaacg gtacgcacaa agttggtgag    2040
ccccagcctc acaccctgct cgacacccac acacatgagc agatccgcct ccccgaactt    2100
caataccagt gggggagcct cggcgggagg ttccgatgaa ggcagttctt catccctggg    2160
tcggaagacc cctgggccca aggacaggat cgtcatggaa gtaacactca acaaagagcc    2220
aagagttgga ttaggcattg gtgcctgctg cttggctctg aaaacagtc ctcctggcat    2280 ctacattcac agccttgctc caggatcagt ggccaagatg gagagcaacc tgagccgcgg    2340
ggatcaaatc ctggaagtga actccgtcaa cgtccgccat gctgctttaa gcaaagtcca    2400
cgccatcttg agtaaatgcc ctccaggacc cgttcgcctt gtcatcggcc ggcaccctaa    2460
tccaaaggtt tccgagcagg aaatggatga agtcatagca cgcagcactt atcaggagag    2520
caaagaggcc aattcctctc ctggcttagg taccccttg aagagtccct ctcttgcaaa    2580
aaaggactcc cttatttctg aatctgaact ctcccagtac tttgcccacg atgtccctgg    2640 cccttgtca gacttcatgg tggtcggttc tgaggacgag gatcacccgg gaagtggctg    2700
cagcacgtcg gaggagggca gcctgcctcc cagcacctcc actcacaagg agcctggaaa    2760
acccagagcc aacagcctcg tgactcttgg gagccatcgg gcttctgggc tcttccacaa    2820
gcaggtgaca gttgccagac aagccagtct ccccggaagc ccacaggccc tccgaaaccc    2880
tctcctccgc cagaggaagg taggctgcta cgatgccaac gatgccagtg atgaggaaga    2940
gtttgacaga gaagggggact gcatttcact cccaggggcc ctcccgggtc ccatcaggcc    3000
tctgtcagag gatgacccga ggcgtgtctc aatttcctct tccaagggca tggacgtcca    3060
caaccaagag gaacgacccc ggaaaacact ggtgagcaag gccatctcgg cacctcttct    3120
tggtagctca gtggacttag aggagagtat cccagagggc atggtggatg ctgcgtccta    3180
tgcagccaac ctcacggact ctgcagaggc ccccaagggg agccctggaa gctggtggaa    3240
gaaggaactg tcaggatcaa gtagcgcacc caaattggaa tacacagtcc gtacagacac    3300
ccagagtccg acaaacactg ggagcccag ttccccccag caaaaaagtg aaggcctggg    3360
ctccaggcac agaccagtgg ccagggtaag cccccactgc aagagatccg aggctgaggc    3420
caagcccagt ggctcacaga cagtgaacct gactggcaga gccaatgatc catgcgatct    3480
ggactcgaga gtccaggcca cttctgtcaa agtgactgtc gctggctttc agccaggtgg    3540
agctgtggag aaggaatctc tgggaaagct gaccactgga gatgcttgtg tctctaccag    3600
ctgtgaacta gccagtgctc tgtcccatct ggatgccagc cacctcacag agaacctgcc    3660
caaagctgca tcagagctgg ggcaacaacc catgactgaa ctggacagct cctcggacct    3720
catctcttcc ccagggaaga aggggccgc tcatcctgac cccagcaaga cctctgtaga    3780
cacagggaaa gtcagtcggc cagagaatcc cagccagcct gcatcgccca gggtcgccaa    3840
gtgcaaggcc aggtctccag tcaggctccc ccatgagggc agccctcc cagggagaa    3900 agcagcggct ccccctgact acagcaagac tcgatcagca tcggaaacca gcacacccca    3960
caataccagg agggtggctg ccctcagggg agcgggacct ggagcagagg gaatgacacc    4020
agctggtgct gtcctgccag gagacccct cacatcccag gagcagagac agggagctcc    4080
aggtaaccac agtaaggctc tggaaatgac aggaatccat gcacctgaaa gctcccagga    4140
```

```
gccttccctg ctggagggag cagattctgt gtcctcaagg gcaccgcagg ccagcctctc    4200
catgctgcca tccactgaca acaccaaaga agcatgtggc catgtctcgg ggcactgctg    4260 cccgggggggg agtagagaga gccctgtgac ggacattgac agcttcatca aggagctgga   4320
tgcttctgca gcaaggtctc cgtcttccca gacggggac agtggctctc aggagggcag     4380
tgctcagggc cacccaccag ccggggctgg aggtgggagc tcctgccgtg ccgaaccagt    4440 cccgggggc cagacctcct ccccgaggag ggcctgggct gctggtgccc ccgcctaccc    4500
acaatgggcc tcccagcctt cggttttaga ttcaattaat cccgacaaac atttactgt     4560 gaacaaaaac tttctgagca actactctag aaattttagc agttttcatg aagacagcac   4620
ctccctatca ggcctgggtg acagcacgga gccgtctctg tcatccatgt atggcgatgc    4680
tgaggattct tcttctgacc ctgagtcact cactgaagcc ccacgagctt ctgccaggga    4740
cggctggtcc cctcctcgtt cccgtgtgtc tttgcacaag gaagatcctt cggagtcaga    4800
agaggaacag attgagattt gttccacacg tggctgcccc aatccaccct cgagtcctgc    4860
tcatcttccc acccaggctg ccatctgtcc tgcctcagcc aaagttctgt cattaaaata    4920
cagcactccg agagagtcgg tggccagtcc ccgtgagaag gtcgcctgct tgccaggctc    4980
atacacttca ggcccagact cttcccagcc atcatcactc ttggagatga gctctcagga    5040
gcatgaaact catgcggaca taagcacttc acagaaccac aggccctcgt gtgcagaaga    5100
aaccacagaa gtcaccagcg ctagctcagc catggaaaac agtccgctgt ctaaagtagc    5160
caggcatttt cacagtccgc ccatcattct cagctccccc aacatggtaa atggcttgga    5220
acatgacctg ctagatgacg aaaccctgaa tcaatacgaa acaagcatta atgcagctgc    5280
cagtctgtcc tccttcagtg tggatgtccc taagaatgga gaatctgttt tggaaaacct    5340
ccacatctct gaaagtcaag acctggatga cttgctacag aaaccaaaaa tgatcgctag    5400
gaggcccatc atggcctggt ttaaagaaat aaataaacat aaccaaggca cacatttgag    5460
gagcaaaacc gagaaggaac aacctctaat gcctgccaga agtcccgact ccaagattca    5520
gatggtgagt tcaagccaaa aaagggcgt tactgtgcct catagccctc ctcagccgaa    5580
aacaaacctg gaaaataagg acctgtctaa gaagagtccg gcagaaatgc ttctgactaa    5640
tggtcagaag gcaaagtgtg gtccgaagct gaagaggctc agcctcaagg gcaaggccaa    5700
agtcaactct gaggcccctg ctgcgaatgc tgtgaaggct gggggacgg accacaggaa     5760 acccttgatc tcaccccaga cctcccacaa aacactttct aaggcagtgt cacagcggct    5820
ccatgtagcc gaccacgagg accctgacag aaacaccaca gctgccccca ggtccccca    5880 gtgtgtgctg gaaagcaagc cacctcttgc cacctctggg ccactgaaac cctcagtgtc    5940
tgacacgagc atcaggacat ttgtctcgcc cctgacctct cccaagcctg ttcctgagca    6000
aggcatgtgg agcaggttcc acatggctgt cctctctgaa cccgacagag gttgcccaac    6060
cacccctaaa tctcctaagt gtagagcaga gggcagggcg cccgtgctg actccgggcc     6120 ggtgagtccg gcagcgtcta ggaacggcat gtccgtggca gggaacagac agagtgagcc    6180
gcgcctggcc agccatgtgg cagcagacac agcccaaccc aggccgactg gcgaaaaagg    6240
aggcaacata atggccagcg atcgcctcga agaacaaac cagctgaaaa tcgtggagat     6300
ttctgctgaa gcagtgtcag agactgtatg tggtaacaag ccagctgaaa gcgacagacg    6360
gggagggtgc ttggcccagg gcaactgtca ggagaagagt gaaatcaggc tctatcgcca    6420
ggtcgcagaa tcatccacaa gtcatccatc ctcactccca tctcatgcct cccaggcaga    6480
gcaggaaatg tcacgatcat tcagcatggc aaaactggcg tcctcctcct cctcccttca    6540
```

-continued

```
aacagccatt agaaaggcag aatactccca gggaaaatca agcctgatgt cagactcccg    6600
aggggtgccc agaaacagca ttccagggggg cccctcgggg gaggaccatc tctacttcac    6660
cccaaggcca gcgaccagga cctactccat gccagcccag ttctcaagcc attttggacg    6720
ggagggtcac cccccacaca gcctgggtcg ctctcgggac agccaggtcc ctgtgacaag    6780
cagtgttgtc cccgaggcaa aggcatccag aggtggtctt cccagcctgg ctaatggaca    6840
gggcatatat agtgtaaagc cgctgctgga cacatcgagg aatcttccag ccacagatga    6900 agggatatc atttcagtcc aggagacgag ctgcctagtc acagacaaaa tcaaagtcac     6960
cagacgacac tactgctatg agcagaactg gccccatgaa tctacctcat ttttctctgt    7020
gaagcagcgg atcaagtctt ttgagaacct ggccaatgct gaccggcctg tagccaagtc    7080
cggggcttcc ccattttgt cggtgagctc caagcctccc attgggaggc ggtcttccgg     7140
cagcattgtt tccgggagcc tgggccaccc aggtgacgca gcagcaaggt tgttgagacg    7200
cagcttgagt tcctgcagcg aaaaccaaag cgaagccggc accctcctgc cccagatggc    7260
caagtctccc tcaatcatga cactgaccat ctctcggcag aacccaccag agaccagtag    7320
caagggctct gattcggaac taaagaaatc acttggtcct ttgggaattc ccaccccaac    7380
gatgaccctg gcttctcctg ttaagaggaa caagtcctcg gtacgccaca cgcagccctc    7440
gcccgtgtcc cgctccaagc tccaggagct gagagccttg agcatgcctg accttgacaa    7500
gctctgcagc gaggattact cagcagggcc gagcgccgtg ctcttcaaaa ctgagctgga    7560
gatcaccccc aggaggtcac ctggcccctcc tgctggaggc gtttcgtgtc ccgagaaggg    7620
cgggaacagg gcctgtccag gaggaagtgg ccctaaaacc agtgctgctg agacacccag    7680
ttcagccagt gatacgggtg aagctgccca ggatctgcct tttagaagaa gctggtcagt    7740
taatttggat caacttctag tctcagcggg ggaccagcaa agattacagt ctgttttatc    7800
gtcagtggga tcgaaatcta ccatcctaac tctcattcag gaagcgaaag cacaatcaga    7860
gaatgaagaa gatgtttgct tcatagtctt gaatagaaaa aaggctcag gtctgggatt     7920 cagtgtggca ggagggacag atgtggagcc aaaatcaatc acggtccaca gggtgttttc    7980
tcagggggcg gcttctcagg aagggactat gaaccgaggg gatttccttc tgtcagtcaa    8040
cggcgcctca ctggctggct tagcccacgg gaatgtcctg aaggttctgc accaggcaca    8100
gctgcacaaa gatgccctcg tggtcatcaa gaaagggatg gatcagccca ggccctctgc    8160
ccggcaggag cctcccacag ccaatgggaa gggtttgctg tccagaaaga ccatcccccct  8220 ggagcctggc attgggagaa gtgtggctgt acacgatgct ctgtgtgttg aagtgctgaa    8280 gacctcgget gggctgggac tgagtctgga tgggggaaaa tcatcggtga cgggagatgg    8340
gcccttggtc attaaaagag tgtacaaagg tggtgcggct gaacaagctg gaataataga    8400
agctggagat gaaattcttg ctattaatgg gaaacctctg gttgggctca tgcactttga    8460
tgcctggaat attatgaagt ctgtcccaga aggacctgtg cagttattaa ttagaaagca    8520
taggaattct tcatgaattt taacaagaat catttctca gttctcttct ttctttagca     8580
aatcagagtg acttctttaa accacaggtt gttgaaatgg ccaacactgg tacagacacg    8640
```

<210> SEQ ID NO 27
<211> LENGTH: 2811
<212> TYPE: PRT
<213> ORGANISM: Homo sapiens

<400> SEQUENCE: 27

-continued

```
Met Pro Ile Thr Gln Asp Asn Ala Val Leu His Leu Pro Leu Leu Tyr
 1               5                  10                  15

Gln Trp Leu Gln Asn Ser Leu Gln Glu Gly Gly Asp Gly Pro Glu Gln
                 20                  25                  30

Arg Leu Cys Gln Ala Ala Ile Gln Lys Leu Gln Glu Tyr Ile Gln Leu
             35                  40                  45

Asn Phe Ala Val Asp Glu Ser Thr Val Pro Pro Asp His Ser Pro Pro
         50                  55                  60

Glu Met Glu Ile Cys Thr Val Tyr Leu Thr Lys Glu Leu Gly Asp Thr
 65                  70                  75                  80

Glu Thr Val Gly Leu Ser Phe Gly Asn Ile Pro Val Phe Gly Asp Tyr
                 85                  90                  95

Gly Glu Lys Arg Arg Gly Gly Lys Lys Arg Lys Thr His Gln Gly Pro
                100                 105                 110

Val Leu Asp Val Gly Cys Ile Trp Val Thr Glu Leu Arg Lys Asn Ser
            115                 120                 125

Pro Ala Gly Lys Ser Gly Lys Val Arg Leu Arg Asp Glu Ile Leu Ser
        130                 135                 140

Leu Asn Gly Gln Leu Met Val Gly Val Asp Val Ser Gly Ala Ser Tyr
145                 150                 155                 160

Leu Ala Glu Gln Cys Trp Asn Gly Gly Phe Ile Tyr Leu Ile Met Leu
                165                 170                 175

Arg Arg Phe Lys His Lys Ala His Ser Thr Tyr Asn Gly Asn Ser Ser
            180                 185                 190

Asn Ser Ser Glu Pro Gly Glu Thr Pro Thr Leu Glu Leu Gly Asp Arg
        195                 200                 205

Thr Ala Lys Lys Gly Lys Arg Thr Arg Lys Phe Gly Val Ile Ser Arg
210                 215                 220

Pro Pro Ala Asn Lys Ala Pro Glu Glu Ser Lys Gly Ser Ala Gly Cys
225                 230                 235                 240

Glu Val Ser Ser Asp Pro Ser Thr Glu Leu Glu Asn Gly Leu Asp Pro
                245                 250                 255

Glu Leu Gly Asn Gly His Val Phe Gln Leu Glu Asn Gly Pro Asp Ser
            260                 265                 270

Leu Lys Glu Val Ala Gly Pro His Leu Glu Arg Ser Glu Val Asp Arg
        275                 280                 285

Gly Thr Glu His Arg Ile Pro Lys Thr Asp Ala Pro Leu Thr Thr Ser
290                 295                 300

Asn Asp Lys Arg Arg Phe Ser Lys Gly Gly Lys Thr Asp Phe Gln Ser
305                 310                 315                 320

Ser Asp Cys Leu Ala Arg Ser Lys Glu Glu Val Gly Arg Ile Trp Lys
                325                 330                 335

Met Glu Leu Leu Lys Glu Ser Asp Gly Leu Gly Ile Gln Val Ser Gly
            340                 345                 350

Gly Arg Gly Ser Lys Arg Ser Pro His Ala Ile Val Val Thr Gln Val
        355                 360                 365

Lys Glu Gly Gly Ala Ala His Arg Leu Arg Asp Gly Arg Leu Ser Leu
370                 375                 380

Gly Asp Glu Leu Leu Val Ile Asn Gly His Leu Leu Val Gly Leu Ser
385                 390                 395                 400

His Glu Glu Ala Val Ala Ile Leu Arg Ser Ala Thr Gly Met Val Gln
                405                 410                 415

Leu Val Val Ala Ser Lys Val Gly Val Leu Ser Ala Phe Gln Met Pro
```

-continued

```
            420             425             430
Gly Thr Asp Glu Pro Gln Asp Val Cys Gly Ala Glu Glu Ser Lys Gly
            435             440             445
Asn Leu Glu Ser Pro Lys Gln Gly Ser Asn Lys Ile Lys Leu Lys Ser
            450             455             460
Arg Leu Ser Gly Arg Trp Gly Leu Tyr Leu Met Gln Pro Val Gly Gly
465             470             475             480
Val His Arg Leu Glu Ser Val Glu Glu Tyr Asn Glu Leu Met Val Arg
            485             490             495
Asn Gly Asp Pro Arg Ile Arg Met Leu Glu Val Ser Arg Asp Gly Arg
            500             505             510
Lys His Ser Leu Pro Gln Leu Leu Asp Ser Ser Ala Ser Gln Glu
            515             520             525
Tyr His Ile Val Lys Lys Ser Thr Arg Ser Leu Ser Thr Thr Gln Val
            530             535             540
Glu Ser Pro Arg Arg Leu Ile Arg Pro Ser Val Ile Ser Ile Ile Gly
545             550             555             560
Leu Tyr Lys Glu Lys Gly Lys Gly Leu Gly Phe Ser Ile Ala Gly Gly
            565             570             575
Arg Asp Cys Ile Arg Gly Gln Met Gly Ile Phe Val Lys Thr Ile Phe
            580             585             590
Pro Asn Gly Ser Ala Ala Glu Asp Gly Arg Leu Lys Glu Gly Asp Glu
            595             600             605
Ile Leu Asp Val Asn Gly Ile Pro Ile Lys Gly Leu Thr Phe Gln Glu
            610             615             620
Ala Ile His Thr Phe Lys Gln Ile Arg Ser Gly Leu Phe Val Leu Thr
625             630             635             640
Val Arg Thr Lys Leu Val Ser Pro Ser Leu Thr Pro Cys Ser Thr Pro
            645             650             655
Thr His Met Ser Arg Ser Ala Ser Pro Asn Phe Asn Thr Ser Gly Gly
            660             665             670
Ala Ser Ala Gly Gly Ser Asp Glu Gly Ser Ser Ser Leu Gly Arg
            675             680             685
Lys Thr Pro Gly Pro Lys Asp Arg Ile Val Met Glu Val Thr Leu Asn
690             695             700
Lys Glu Pro Arg Val Gly Leu Gly Ile Gly Ala Cys Cys Leu Ala Leu
705             710             715             720
Glu Asn Ser Pro Pro Gly Ile Tyr Ile His Ser Leu Ala Pro Gly Ser
            725             730             735
Val Ala Lys Met Glu Ser Asn Leu Ser Arg Gly Asp Gln Ile Leu Glu
            740             745             750
Val Asn Ser Val Asn Val Arg His Ala Ala Leu Ser Lys Val His Ala
            755             760             765
Ile Leu Ser Lys Cys Pro Pro Gly Pro Val Arg Leu Val Ile Gly Arg
            770             775             780
His Pro Asn Pro Lys Val Ser Glu Gln Glu Met Asp Glu Val Ile Ala
785             790             795             800
Arg Ser Thr Tyr Gln Glu Ser Lys Glu Ala Asn Ser Ser Pro Gly Leu
            805             810             815
Gly Thr Pro Leu Lys Ser Pro Ser Leu Ala Lys Lys Asp Ser Leu Ile
            820             825             830
Ser Glu Ser Glu Leu Ser Gln Tyr Phe Ala His Asp Val Pro Gly Pro
            835             840             845
```

-continued

```
Leu Ser Asp Phe Met Val Val Gly Ser Glu Asp Glu Asp His Pro Gly
    850                 855                 860
Ser Gly Cys Ser Thr Ser Glu Glu Gly Ser Leu Pro Pro Ser Thr Ser
865                 870                 875                 880
Thr His Lys Glu Pro Gly Lys Pro Arg Ala Asn Ser Leu Val Thr Leu
                885                 890                 895
Gly Ser His Arg Ala Ser Gly Leu Phe His Lys Gln Val Thr Val Ala
                900                 905                 910
Arg Gln Ala Ser Leu Pro Gly Ser Pro Gln Ala Leu Arg Asn Pro Leu
                915                 920                 925
Leu Arg Gln Arg Lys Val Gly Cys Tyr Asp Ala Asn Asp Ala Ser Asp
    930                 935                 940
Glu Glu Glu Phe Asp Arg Gly Asp Cys Ile Ser Leu Pro Gly Ala
945                 950                 955                 960
Leu Pro Gly Pro Ile Arg Pro Leu Ser Glu Asp Asp Pro Arg Arg Val
                965                 970                 975
Ser Ile Ser Ser Ser Lys Gly Met Asp Val His Asn Gln Glu Glu Arg
                980                 985                 990
Pro Arg Lys Thr Leu Val Ser Lys Ala Ile Ser Ala Pro Leu Leu Gly
    995                 1000                1005
Ser Ser Val Asp Leu Glu Glu Ser Ile Pro Glu Gly Met Val Asp Ala
    1010                1015                1020
Ala Ser Tyr Ala Ala Asn Leu Thr Asp Ser Ala Glu Ala Pro Lys Gly
1025                1030                1035                1040
Ser Pro Gly Ser Trp Trp Lys Lys Glu Leu Ser Gly Ser Ser Ser Ala
                1045                1050                1055
Pro Lys Leu Glu Tyr Thr Val Arg Thr Asp Thr Gln Ser Pro Thr Asn
                1060                1065                1070
Thr Gly Ser Pro Ser Ser Pro Gln Gln Lys Ser Glu Gly Leu Gly Ser
    1075                1080                1085
Arg His Arg Pro Val Ala Arg Val Ser Pro His Cys Lys Arg Ser Glu
    1090                1095                1100
Ala Glu Ala Lys Pro Ser Gly Ser Gln Thr Val Asn Leu Thr Gly Arg
1105                1110                1115                1120
Ala Asn Asp Pro Cys Asp Leu Asp Ser Arg Val Gln Ala Thr Ser Val
                1125                1130                1135
Lys Val Thr Val Ala Gly Phe Gln Pro Gly Gly Ala Val Glu Lys Glu
                1140                1145                1150
Ser Leu Gly Lys Leu Thr Thr Gly Asp Ala Cys Val Ser Thr Ser Cys
    1155                1160                1165
Glu Leu Ala Ser Ala Leu Ser His Leu Asp Ala Ser His Leu Thr Glu
    1170                1175                1180
Asn Leu Pro Lys Ala Ala Ser Glu Leu Gly Gln Gln Pro Met Thr Glu
1185                1190                1195                1200
Leu Asp Ser Ser Asp Leu Ile Ser Ser Pro Gly Lys Lys Gly Ala
                1205                1210                1215
Ala His Pro Asp Pro Ser Lys Thr Ser Val Asp Thr Gly Lys Val Ser
            1220                1225                1230
Arg Pro Glu Asn Pro Ser Gln Pro Ala Ser Pro Arg Val Ala Lys Cys
            1235                1240                1245
Lys Ala Arg Ser Pro Val Arg Leu Pro His Glu Gly Ser Pro Ser Pro
    1250                1255                1260
```

-continued

```
Gly Glu Lys Ala Ala Pro Pro Asp Tyr Ser Lys Thr Arg Ser Ala
1265                1270                1275                1280

Ser Glu Thr Ser Thr Pro His Asn Thr Arg Arg Val Ala Ala Leu Arg
                1285                1290                1295

Gly Ala Gly Pro Gly Ala Glu Gly Met Thr Pro Ala Gly Ala Val Leu
            1300                1305                1310

Pro Gly Asp Pro Leu Thr Ser Gln Glu Gln Arg Gln Gly Ala Pro Gly
        1315                1320                1325

Asn His Ser Lys Ala Leu Glu Met Thr Gly Ile His Ala Pro Glu Ser
    1330                1335                1340

Ser Gln Glu Pro Ser Leu Leu Glu Gly Ala Asp Ser Val Ser Ser Arg
1345                1350                1355                1360

Ala Pro Gln Ala Ser Leu Ser Met Leu Pro Ser Thr Asp Asn Thr Lys
                1365                1370                1375

Glu Ala Cys Gly His Val Ser Gly His Cys Cys Pro Gly Gly Ser Arg
            1380                1385                1390

Glu Ser Pro Val Thr Asp Ile Asp Ser Phe Ile Lys Glu Leu Asp Ala
        1395                1400                1405

Ser Ala Ala Arg Ser Pro Ser Ser Gln Thr Gly Asp Ser Gly Ser Gln
    1410                1415                1420

Glu Gly Ser Ala Gln Gly His Pro Ala Gly Ala Gly Gly Ser
1425                1430                1435                1440

Ser Cys Arg Ala Glu Pro Val Pro Gly Gly Gln Thr Ser Ser Pro Arg
                1445                1450                1455

Arg Ala Trp Ala Ala Gly Ala Pro Ala Tyr Pro Gln Trp Ala Ser Gln
            1460                1465                1470

Pro Ser Val Leu Asp Ser Ile Asn Pro Asp Lys His Phe Thr Val Asn
        1475                1480                1485

Lys Asn Phe Leu Ser Asn Tyr Ser Arg Asn Phe Ser Ser Phe His Glu
    1490                1495                1500

Asp Ser Thr Ser Leu Ser Gly Leu Gly Asp Ser Thr Glu Pro Ser Leu
1505                1510                1515                1520

Ser Ser Met Tyr Gly Asp Ala Glu Asp Ser Ser Asp Pro Glu Ser
                1525                1530                1535

Leu Thr Glu Ala Pro Arg Ala Ser Ala Arg Asp Gly Trp Ser Pro Pro
            1540                1545                1550

Arg Ser Arg Val Ser Leu His Lys Glu Asp Pro Ser Glu Ser Glu Glu
        1555                1560                1565

Glu Gln Ile Glu Ile Cys Ser Thr Arg Gly Cys Pro Asn Pro Pro Ser
    1570                1575                1580

Ser Pro Ala His Leu Pro Thr Gln Ala Ala Ile Cys Pro Ala Ser Ala
1585                1590                1595                1600

Lys Val Leu Ser Leu Lys Tyr Ser Thr Pro Arg Glu Ser Val Ala Ser
                1605                1610                1615

Pro Arg Glu Lys Val Ala Cys Leu Pro Gly Ser Tyr Thr Ser Gly Pro
            1620                1625                1630

Asp Ser Ser Gln Pro Ser Ser Leu Leu Glu Met Ser Ser Gln Glu His
        1635                1640                1645

Glu Thr His Ala Asp Ile Ser Thr Ser Gln Asn His Arg Pro Ser Cys
    1650                1655                1660

Ala Glu Glu Thr Thr Glu Val Thr Ser Ala Ser Ser Ala Met Glu Asn
1665                1670                1675                1680

Ser Pro Leu Ser Lys Val Ala Arg His Phe His Ser Pro Pro Ile Ile
```

-continued

```
                1685                1690                1695
Leu Ser Ser Pro Asn Met Val Asn Gly Leu Glu His Asp Leu Leu Asp
        1700                1705                1710
Asp Glu Thr Leu Asn Gln Tyr Glu Thr Ser Ile Asn Ala Ala Ala Ser
        1715                1720                1725
Leu Ser Ser Phe Ser Val Asp Val Pro Lys Asn Gly Glu Ser Val Leu
        1730                1735                1740
Glu Asn Leu His Ile Ser Glu Ser Gln Asp Leu Asp Asp Leu Leu Gln
1745                1750                1755                1760
Lys Pro Lys Met Ile Ala Arg Arg Pro Ile Met Ala Trp Phe Lys Glu
        1765                1770                1775
Ile Asn Lys His Asn Gln Gly Thr His Leu Arg Ser Lys Thr Glu Lys
        1780                1785                1790
Glu Gln Pro Leu Met Pro Ala Arg Ser Pro Asp Ser Lys Ile Gln Met
        1795                1800                1805
Val Ser Ser Gln Lys Lys Gly Val Thr Val Pro His Ser Pro Pro
    1810                1815                1820
Gln Pro Lys Thr Asn Leu Glu Asn Lys Asp Leu Ser Lys Lys Ser Pro
1825                1830                1835                1840
Ala Glu Met Leu Leu Thr Asn Gly Gln Lys Ala Lys Cys Gly Pro Lys
        1845                1850                1855
Leu Lys Arg Leu Ser Leu Lys Gly Lys Ala Lys Val Asn Ser Glu Ala
        1860                1865                1870
Pro Ala Ala Asn Ala Val Lys Ala Gly Gly Thr Asp His Arg Lys Pro
        1875                1880                1885
Leu Ile Ser Pro Gln Thr Ser His Lys Thr Leu Ser Lys Ala Val Ser
    1890                1895                1900
Gln Arg Leu His Val Ala Asp His Glu Asp Pro Asp Arg Asn Thr Thr
1905                1910                1915                1920
Ala Ala Pro Arg Ser Pro Gln Cys Val Leu Glu Ser Lys Pro Pro Leu
        1925                1930                1935
Ala Thr Ser Gly Pro Leu Lys Pro Ser Val Ser Asp Thr Ser Ile Arg
        1940                1945                1950
Thr Phe Val Ser Pro Leu Thr Ser Pro Lys Pro Val Pro Glu Gln Gly
        1955                1960                1965
Met Trp Ser Arg Phe His Met Ala Val Leu Ser Glu Pro Asp Arg Gly
        1970                1975                1980
Cys Pro Thr Thr Pro Lys Ser Pro Lys Cys Arg Ala Glu Gly Arg Ala
1985                1990                1995                2000
Pro Arg Ala Asp Ser Gly Pro Val Ser Pro Ala Ala Ser Arg Asn Gly
                2005                2010                2015
Met Ser Val Ala Gly Asn Arg Gln Ser Glu Pro Arg Leu Ala Ser His
                2020                2025                2030
Val Ala Ala Asp Thr Ala Gln Pro Arg Pro Thr Gly Glu Lys Gly Gly
        2035                2040                2045
Asn Ile Met Ala Ser Asp Arg Leu Glu Arg Thr Asn Gln Leu Lys Ile
    2050                2055                2060
Val Glu Ile Ser Ala Glu Ala Val Ser Glu Thr Val Cys Gly Asn Lys
2065                2070                2075                2080
Pro Ala Glu Ser Asp Arg Arg Gly Gly Cys Leu Ala Gln Gly Asn Cys
                2085                2090                2095
Gln Glu Lys Ser Glu Ile Arg Leu Tyr Arg Gln Val Ala Glu Ser Ser
            2100                2105                2110
```

-continued

Thr Ser His Pro Ser Ser Leu Pro Ser His Ala Ser Gln Ala Glu Gln
        2115                2120                2125

Glu Met Ser Arg Ser Phe Ser Met Ala Lys Leu Ala Ser Ser Ser Ser
    2130                2135                2140

Ser Leu Gln Thr Ala Ile Arg Lys Ala Glu Tyr Ser Gln Gly Lys Ser
2145                2150                2155                2160

Ser Leu Met Ser Asp Ser Arg Gly Val Pro Arg Asn Ser Ile Pro Gly
            2165                2170                2175

Gly Pro Ser Gly Glu Asp His Leu Tyr Phe Thr Pro Arg Pro Ala Thr
        2180                2185                2190

Arg Thr Tyr Ser Met Pro Ala Gln Phe Ser Ser His Phe Gly Arg Glu
        2195                2200                2205

Gly His Pro Pro His Ser Leu Gly Arg Ser Arg Asp Ser Gln Val Pro
    2210                2215                2220

Val Thr Ser Ser Val Val Pro Glu Ala Lys Ala Ser Arg Gly Gly Leu
2225                2230                2235                2240

Pro Ser Leu Ala Asn Gly Gln Gly Ile Tyr Ser Val Lys Pro Leu Leu
            2245                2250                2255

Asp Thr Ser Arg Asn Leu Pro Ala Thr Asp Glu Gly Asp Ile Ile Ser
        2260                2265                2270

Val Gln Glu Thr Ser Cys Leu Val Thr Asp Lys Ile Lys Val Thr Arg
        2275                2280                2285

Arg His Tyr Cys Tyr Glu Gln Asn Trp Pro His Glu Ser Thr Ser Phe
    2290                2295                2300

Phe Ser Val Lys Gln Arg Ile Lys Ser Phe Glu Asn Leu Ala Asn Ala
2305                2310                2315                2320

Asp Arg Pro Val Ala Lys Ser Gly Ala Ser Pro Phe Leu Ser Val Ser
            2325                2330                2335

Ser Lys Pro Pro Ile Gly Arg Arg Ser Ser Gly Ser Ile Val Ser Gly
            2340                2345                2350

Ser Leu Gly His Pro Gly Asp Ala Ala Ala Arg Leu Leu Arg Arg Ser
        2355                2360                2365

Leu Ser Ser Cys Ser Glu Asn Gln Ser Glu Ala Gly Thr Leu Leu Pro
    2370                2375                2380

Gln Met Ala Lys Ser Pro Ser Ile Met Thr Leu Thr Ile Ser Arg Gln
2385                2390                2395                2400

Asn Pro Pro Glu Thr Ser Ser Lys Gly Ser Asp Ser Glu Leu Lys Lys
            2405                2410                2415

Ser Leu Gly Pro Leu Gly Ile Pro Thr Pro Thr Met Thr Leu Ala Ser
            2420                2425                2430

Pro Val Lys Arg Asn Lys Ser Ser Val Arg His Thr Gln Pro Ser Pro
        2435                2440                2445

Val Ser Arg Ser Lys Leu Gln Glu Leu Arg Ala Leu Ser Met Pro Asp
    2450                2455                2460

Leu Asp Lys Leu Cys Ser Glu Asp Tyr Ser Ala Gly Pro Ser Ala Val
2465                2470                2475                2480

Leu Phe Lys Thr Glu Leu Glu Ile Thr Pro Arg Arg Ser Pro Gly Pro
            2485                2490                2495

Pro Ala Gly Gly Val Ser Cys Pro Glu Lys Gly Gly Asn Arg Ala Cys
            2500                2505                2510

Pro Gly Gly Ser Gly Pro Lys Thr Ser Ala Ala Glu Thr Pro Ser Ser
        2515                2520                2525

-continued

```
Ala Ser Asp Thr Gly Glu Ala Ala Gln Asp Leu Pro Phe Arg Arg Ser
    2530                2535                2540

Trp Ser Val Asn Leu Asp Gln Leu Leu Val Ser Ala Gly Asp Gln Gln
2545                2550                2555                2560

Arg Leu Gln Ser Val Leu Ser Ser Val Gly Ser Lys Ser Thr Ile Leu
        2565                2570                2575

Thr Leu Ile Gln Glu Ala Lys Ala Gln Ser Glu Asn Glu Glu Asp Val
    2580                2585                2590

Cys Phe Ile Val Leu Asn Arg Lys Glu Gly Ser Gly Leu Gly Phe Ser
        2595                2600                2605

Val Ala Gly Gly Thr Asp Val Glu Pro Lys Ser Ile Thr Val His Arg
    2610                2615                2620

Val Phe Ser Gln Gly Ala Ala Ser Gln Glu Gly Thr Met Asn Arg Gly
2625                2630                2635                2640

Asp Phe Leu Leu Ser Val Asn Gly Ala Ser Leu Ala Gly Leu Ala His
        2645                2650                2655

Gly Asn Val Leu Lys Val Leu His Gln Ala Gln Leu His Lys Asp Ala
        2660                2665                2670

Leu Val Val Ile Lys Lys Gly Met Asp Gln Pro Arg Pro Ser Ala Arg
        2675                2680                2685

Gln Glu Pro Pro Thr Ala Asn Gly Lys Gly Leu Leu Ser Arg Lys Thr
    2690                2695                2700

Ile Pro Leu Glu Pro Gly Ile Gly Arg Ser Val Ala Val His Asp Ala
2705                2710                2715                2720

Leu Cys Val Glu Val Leu Lys Thr Ser Ala Gly Leu Gly Leu Ser Leu
        2725                2730                2735

Asp Gly Gly Lys Ser Ser Val Thr Gly Asp Gly Pro Leu Val Ile Lys
        2740                2745                2750

Arg Val Tyr Lys Gly Gly Ala Ala Glu Gln Ala Gly Ile Ile Glu Ala
        2755                2760                2765

Gly Asp Glu Ile Leu Ala Ile Asn Gly Lys Pro Leu Val Gly Leu Met
    2770                2775                2780

His Phe Asp Ala Trp Asn Ile Met Lys Ser Val Pro Glu Gly Pro Val
2785                2790                2795                2800

Gln Leu Leu Ile Arg Lys His Arg Asn Ser Ser
        2805                2810

<210> SEQ ID NO 28
<211> LENGTH: 798
<212> TYPE: PRT
<213> ORGANISM: Homo sapiens

<400> SEQUENCE: 28

Met Leu Ile Asn Cys Glu Ala Lys Gly Ile Lys Met Val Ser Glu Ile
1               5                   10                  15

Ser Val Pro Pro Ser Arg Pro Phe Gln Leu Ser Leu Leu Asn Asn Gly
                20                  25                  30

Leu Thr Met Leu His Thr Asn Asp Phe Ser Gly Leu Thr Asn Ala Ile
        35                  40                  45

Ser Ile His Leu Gly Phe Asn Asn Ile Ala Asp Ile Glu Ile Gly Ala
    50                  55                  60

Phe Asn Gly Leu Gly Leu Leu Lys Gln Leu His Ile Asn His Asn Ser
65                  70                  75                  80

Leu Glu Ile Leu Lys Glu Asp Thr Phe His Gly Leu Glu Asn Leu Glu
                85                  90                  95
```

-continued

```
Phe Leu Gln Ala Asp Asn Asn Phe Ile Thr Val Ile Glu Pro Ser Ala
                100                 105                 110
Phe Ser Lys Leu Asn Arg Leu Lys Val Leu Ile Leu Asn Asp Asn Ala
            115                 120                 125
Ile Glu Ser Leu Pro Pro Asn Ile Phe Arg Phe Val Pro Leu Thr His
        130                 135                 140
Leu Asp Leu Arg Gly Asn Gln Leu Gln Thr Leu Pro Tyr Val Gly Phe
145                 150                 155                 160
Leu Glu His Ile Gly Arg Ile Leu Asp Leu Gln Leu Glu Asp Asn Lys
                165                 170                 175
Trp Ala Cys Asn Cys Asp Leu Leu Gln Leu Lys Thr Trp Leu Glu Asn
            180                 185                 190
Met Pro Pro Gln Ser Ile Ile Gly Asp Val Val Cys Asn Ser Pro Pro
        195                 200                 205
Phe Phe Lys Gly Ser Ile Leu Ser Arg Leu Lys Lys Glu Ser Ile Cys
    210                 215                 220
Pro Thr Pro Pro Val Tyr Glu Glu His Glu Asp Pro Ser Gly Ser Leu
225                 230                 235                 240
His Leu Ala Ala Thr Ser Ser Ile Asn Asp Ser Arg Met Ser Thr Lys
                245                 250                 255
Thr Thr Ser Ile Leu Lys Leu Pro Thr Lys Ala Pro Gly Leu Ile Pro
            260                 265                 270
Tyr Ile Thr Lys Pro Ser Thr Gln Leu Pro Gly Pro Tyr Cys Pro Ile
        275                 280                 285
Pro Cys Asn Cys Lys Val Leu Ser Pro Ser Gly Leu Leu Ile His Cys
    290                 295                 300
Gln Glu Arg Asn Ile Glu Ser Leu Ser Asp Leu Arg Pro Pro Pro Gln
305                 310                 315                 320
Asn Pro Arg Lys Leu Ile Leu Ala Gly Asn Ile Ile His Ser Leu Met
                325                 330                 335
Lys Ser Asp Leu Val Glu Tyr Phe Thr Leu Glu Met Leu His Leu Gly
            340                 345                 350
Asn Asn Arg Ile Glu Val Leu Glu Glu Gly Ser Phe Met Asn Leu Thr
        355                 360                 365
Arg Leu Gln Lys Leu Tyr Leu Asn Gly Asn His Leu Thr Lys Leu Ser
    370                 375                 380
Lys Gly Met Phe Leu Gly Leu His Asn Leu Glu Tyr Leu Tyr Leu Glu
385                 390                 395                 400
Tyr Asn Ala Ile Lys Glu Ile Leu Pro Gly Thr Phe Asn Pro Met Pro
                405                 410                 415
Lys Leu Lys Val Leu Tyr Leu Asn Asn Asn Leu Leu Gln Val Leu Pro
            420                 425                 430
Pro His Ile Phe Ser Gly Val Pro Leu Thr Lys Val Asn Leu Lys Thr
        435                 440                 445
Asn Gln Phe Thr His Leu Pro Val Ser Asn Ile Leu Asp Asp Leu Asp
    450                 455                 460
Leu Leu Thr Gln Ile Asp Leu Glu Asp Asn Pro Trp Asp Cys Ser Cys
465                 470                 475                 480
Asp Leu Val Gly Leu Gln Gln Trp Ile Gln Lys Leu Ser Lys Asn Thr
                485                 490                 495
Val Thr Asp Asp Ile Leu Cys Thr Ser Pro Gly His Leu Asp Lys Lys
            500                 505                 510
```

```
Glu Leu Lys Ala Leu Asn Ser Glu Ile Leu Cys Pro Gly Leu Val Asn
            515                 520                 525

Asn Pro Ser Met Pro Thr Gln Thr Ser Tyr Leu Met Val Thr Thr Pro
        530                 535                 540

Ala Thr Thr Thr Asn Thr Ala Asp Thr Ile Leu Arg Ser Leu Thr Asp
545                 550                 555                 560

Ala Val Pro Leu Ser Val Leu Ile Leu Gly Leu Leu Ile Met Phe Ile
                565                 570                 575

Thr Ile Val Phe Cys Ala Ala Gly Ile Val Leu Val Leu His Arg
            580                 585                 590

Arg Arg Arg Tyr Lys Lys Gln Val Asp Glu Gln Met Arg Asp Asn
            595                 600                 605

Ser Pro Val His Leu Gln Tyr Ser Met Tyr Gly His Lys Thr Thr His
610                 615                 620

His Thr Thr Glu Arg Pro Ser Ala Ser Leu Tyr Glu Gln His Met Val
625                 630                 635                 640

Ser Pro Met Val His Val Tyr Arg Ser Pro Ser Phe Gly Pro Lys His
                645                 650                 655

Leu Glu Glu Glu Glu Arg Asn Glu Lys Gly Ser Asp Ala Lys
            660                 665                 670

His Leu Gln Arg Ser Leu Leu Glu Gln Glu Asn His Ser Pro Leu Thr
            675                 680                 685

Gly Ser Asn Met Lys Tyr Lys Thr Thr Asn Gln Ser Thr Glu Phe Leu
            690                 695                 700

Ser Phe Gln Asp Ala Ser Ser Leu Tyr Arg Asn Ile Leu Glu Lys Glu
705                 710                 715                 720

Arg Glu Leu Gln Gln Leu Gly Ile Thr Glu Tyr Leu Arg Lys Asn Ile
                725                 730                 735

Ala Gln Leu Gln Pro Asp Met Glu Ala His Tyr Pro Gly Ala His Glu
            740                 745                 750

Glu Leu Lys Leu Met Glu Thr Leu Met Tyr Ser Arg Pro Arg Lys Val
            755                 760                 765

Leu Val Glu Gln Thr Lys Asn Glu Tyr Phe Glu Leu Lys Ala Asn Leu
            770                 775                 780

His Ala Glu Pro Asp Tyr Leu Glu Val Leu Glu Gln Gln Thr
785                 790                 795

<210> SEQ ID NO 29
<211> LENGTH: 440
<212> TYPE: PRT
<213> ORGANISM: Homo sapiens

<400> SEQUENCE: 29

Met Leu Ile Asn Cys Glu Ala Lys Gly Ile Lys Met Val Ser Glu Ile
  1               5                  10                  15

Ser Val Pro Pro Ser Arg Pro Phe Gln Leu Ser Leu Leu Asn Asn Gly
                 20                  25                  30

Leu Thr Met Leu His Thr Asn Asp Phe Ser Gly Leu Thr Asn Ala Ile
             35                  40                  45

Ser Ile His Leu Gly Phe Asn Asn Ile Ala Asp Ile Glu Ile Gly Ala
         50                  55                  60

Phe Asn Gly Leu Gly Leu Leu Lys Gln Leu His Ile Asn His Asn Ser
 65                  70                  75                  80

Leu Glu Ile Leu Lys Glu Asp Thr Phe His Gly Leu Glu Asn Leu Glu
                 85                  90                  95
```

```
Phe Leu Gln Ala Asp Asn Asn Phe Ile Thr Val Ile Glu Pro Ser Ala
                100                 105                 110
Phe Ser Lys Leu Asn Arg Leu Lys Val Leu Ile Leu Asn Asp Asn Ala
            115                 120                 125
Ile Glu Ser Leu Pro Pro Asn Ile Phe Arg Phe Val Pro Leu Thr His
        130                 135                 140
Leu Asp Leu Arg Gly Asn Gln Leu Gln Thr Leu Pro Tyr Val Gly Phe
145                 150                 155                 160
Leu Glu His Ile Gly Arg Ile Leu Asp Leu Gln Leu Glu Asp Asn Lys
                165                 170                 175
Trp Ala Cys Asn Cys Asp Leu Leu Gln Leu Lys Thr Trp Leu Glu Asn
            180                 185                 190
Met Pro Pro Gln Ser Ile Ile Gly Asp Val Val Cys Asn Ser Pro Pro
        195                 200                 205
Phe Phe Lys Gly Ser Ile Leu Ser Arg Leu Lys Lys Glu Ser Ile Cys
210                 215                 220
Pro Thr Pro Pro Val Tyr Glu Glu His Glu Asp Pro Ser Gly Ser Leu
225                 230                 235                 240
His Leu Ala Ala Thr Ser Ser Ile Asn Asp Ser Arg Met Ser Thr Lys
                245                 250                 255
Thr Thr Ser Ile Leu Lys Leu Pro Thr Lys Ala Pro Gly Leu Ile Pro
            260                 265                 270
Tyr Ile Thr Lys Pro Ser Thr Gln Leu Pro Gly Pro Tyr Cys Pro Ile
        275                 280                 285
Pro Cys Asn Cys Lys Val Leu Ser Pro Ser Gly Leu Leu Ile His Cys
290                 295                 300
Gln Glu Arg Asn Ile Glu Ser Leu Ser Asp Leu Arg Pro Pro Pro Gln
305                 310                 315                 320
Asn Pro Arg Lys Leu Ile Leu Ala Gly Asn Ile Ile His Ser Leu Met
                325                 330                 335
Lys Ser Asp Leu Val Glu Tyr Phe Thr Leu Glu Met Leu His Leu Gly
            340                 345                 350
Asn Asn Arg Ile Glu Val Leu Glu Glu Gly Ser Phe Met Asn Leu Thr
        355                 360                 365
Arg Leu Gln Lys Leu Tyr Leu Asn Gly Asn His Leu Thr Lys Leu Ser
370                 375                 380
Lys Gly Met Phe Leu Gly Leu His Asn Leu Glu Tyr Leu Tyr Leu Glu
385                 390                 395                 400
Tyr Asn Ala Ile Lys Glu Ile Leu Pro Gly Thr Phe Asn Pro Met Pro
                405                 410                 415
Lys Leu Lys Val Leu Tyr Leu Asn Asn Thr Ser Ser Lys Phe Tyr His
            420                 425                 430
His Ile Phe Phe Gln Gly Phe Leu
        435                 440

<210> SEQ ID NO 30
<211> LENGTH: 853
<212> TYPE: PRT
<213> ORGANISM: Homo sapiens

<400> SEQUENCE: 30

Tyr Phe Ser Leu Phe Arg Ser Ile Gln Leu Phe Ala Asp Cys Lys Lys
 1               5                  10                  15
Met Phe Leu Trp Leu Phe Leu Ile Leu Ser Ala Leu Ile Ser Ser Thr
```

-continued

```
                  20                  25                  30
Asn Ala Asp Ser Asp Ile Ser Val Glu Ile Cys Asn Val Cys Ser Cys
         35                  40                  45
Val Ser Val Glu Asn Val Leu Tyr Val Asn Cys Glu Lys Val Ser Val
 50                  55                  60
Tyr Arg Pro Asn Gln Leu Lys Pro Pro Trp Ser Asn Phe Tyr His Leu
 65                  70                  75                  80
Asn Phe Gln Asn Asn Phe Leu Asn Ile Leu Tyr Pro Asn Thr Phe Leu
             85                  90                  95
Asn Phe Ser His Ala Val Ser Leu His Leu Gly Asn Asn Lys Leu Gln
            100                 105                 110
Asn Ile Glu Gly Gly Ala Phe Leu Gly Leu Ser Ala Leu Lys Gln Leu
            115                 120                 125
His Leu Asn Asn Glu Leu Lys Ile Leu Arg Ala Asp Thr Phe Leu
            130                 135                 140
Gly Ile Glu Asn Leu Glu Tyr Leu Gln Ala Asp Tyr Asn Leu Ile Lys
145                 150                 155                 160
Tyr Ile Glu Arg Gly Ala Phe Asn Lys Leu His Lys Leu Lys Val Leu
                165                 170                 175
Ile Leu Asn Asp Asn Leu Ile Ser Phe Leu Pro Asp Asn Ile Phe Arg
            180                 185                 190
Phe Ala Ser Leu Thr His Leu Asp Ile Arg Gly Asn Arg Ile Gln Lys
            195                 200                 205
Leu Pro Tyr Ile Gly Val Leu Glu His Ile Gly Arg Val Val Glu Leu
        210                 215                 220
Gln Leu Glu Asp Asn Pro Trp Asn Cys Ser Cys Asp Leu Leu Pro Leu
225                 230                 235                 240
Lys Ala Trp Leu Glu Asn Met Pro Tyr Asn Ile Tyr Ile Gly Glu Ala
                245                 250                 255
Ile Cys Glu Thr Pro Ser Asp Leu Tyr Gly Arg Leu Leu Lys Glu Thr
            260                 265                 270
Asn Lys Gln Glu Leu Cys Pro Met Gly Thr Gly Ser Asp Phe Asp Val
            275                 280                 285
Arg Ile Leu Pro Pro Ser Gln Leu Glu Asn Gly Tyr Thr Thr Pro Asn
290                 295                 300
Gly His Thr Thr Gln Thr Ser Leu His Arg Leu Val Thr Lys Pro Pro
305                 310                 315                 320
Lys Thr Thr Asn Pro Ser Lys Ile Ser Gly Ile Val Ala Gly Lys Ala
                325                 330                 335
Leu Ser Asn Arg Asn Leu Ser Gln Ile Val Ser Tyr Gln Thr Arg Val
            340                 345                 350
Pro Pro Leu Thr Pro Cys Pro Ala Pro Cys Phe Cys Lys Thr His Pro
            355                 360                 365
Ser Asp Leu Gly Leu Ser Val Asn Cys Gln Glu Lys Asn Ile Gln Ser
        370                 375                 380
Met Ser Glu Leu Ile Pro Lys Pro Leu Asn Ala Lys Lys Leu His Val
385                 390                 395                 400
Asn Gly Asn Ser Ile Lys Asp Val Asp Val Ser Asp Phe Thr Asp Phe
                405                 410                 415
Glu Gly Leu Asp Leu Leu His Leu Gly Ser Asn Gln Ile Thr Val Ile
            420                 425                 430
Lys Gly Asp Val Phe His Asn Leu Thr Asn Leu Arg Arg Leu Tyr Leu
            435                 440                 445
```

-continued

```
Asn Gly Asn Gln Ile Glu Arg Leu Tyr Pro Glu Ile Phe Ser Gly Leu
    450                 455                 460
His Asn Leu Gln Tyr Leu Tyr Leu Glu Tyr Asn Leu Ile Lys Glu Ile
465                 470                 475                 480
Ser Ala Gly Thr Phe Asp Ser Met Pro Asn Leu Gln Leu Leu Tyr Leu
                485                 490                 495
Asn Asn Asn Leu Leu Lys Ser Leu Pro Val Tyr Ile Phe Ser Gly Ala
            500                 505                 510
Pro Leu Ala Arg Leu Asn Leu Arg Asn Asn Lys Phe Met Tyr Leu Pro
        515                 520                 525
Val Ser Gly Val Leu Asp Gln Leu Gln Ser Leu Thr Gln Ile Asp Leu
    530                 535                 540
Glu Gly Asn Pro Trp Asp Cys Thr Cys Asp Leu Val Ala Leu Lys Leu
545                 550                 555                 560
Trp Val Glu Lys Leu Ser Asp Gly Ile Val Lys Glu Leu Lys Cys
                565                 570                 575
Glu Thr Pro Val Gln Phe Ala Asn Ile Glu Leu Lys Ser Leu Lys Asn
                580                 585                 590
Glu Ile Leu Cys Pro Lys Leu Leu Asn Lys Pro Ser Ala Pro Phe Thr
            595                 600                 605
Ser Pro Ala Pro Ala Ile Thr Phe Thr Thr Pro Leu Gly Pro Ile Arg
    610                 615                 620
Ser Pro Pro Gly Gly Pro Val Pro Leu Ser Ile Leu Ile Leu Ser Ile
625                 630                 635                 640
Leu Val Val Leu Ile Leu Thr Val Phe Val Ala Phe Cys Leu Leu Val
                645                 650                 655
Phe Val Leu Arg Arg Asn Lys Lys Pro Thr Val Lys His Glu Gly Leu
                660                 665                 670
Gly Asn Pro Asp Cys Gly Ser Met Gln Leu Gln Leu Arg Lys His Asp
            675                 680                 685
His Lys Thr Asn Lys Lys Asp Gly Leu Ser Thr Glu Ala Phe Ile Pro
690                 695                 700
Gln Thr Ile Glu Gln Met Ser Lys Ser His Thr Cys Gly Leu Lys Glu
705                 710                 715                 720
Ser Glu Thr Gly Phe Met Phe Ser Asp Pro Pro Gly Gln Lys Val Val
                725                 730                 735
Met Arg Asn Val Ala Asp Lys Glu Lys Asp Leu Leu His Val Asp Thr
            740                 745                 750
Arg Lys Arg Leu Ser Thr Ile Asp Glu Leu Asp Glu Leu Phe Pro Ser
        755                 760                 765
Arg Asp Ser Asn Val Phe Ile Gln Asn Phe Leu Glu Ser Lys Lys Glu
        770                 775                 780
Tyr Asn Ser Ile Gly Val Ser Gly Phe Glu Ile Arg Tyr Pro Glu Lys
785                 790                 795                 800
Gln Pro Asp Lys Lys Ser Lys Lys Ser Leu Ile Gly Gly Asn His Ser
                805                 810                 815
Lys Ile Val Val Glu Gln Arg Lys Ser Glu Tyr Phe Glu Leu Lys Ala
            820                 825                 830
Lys Leu Gln Ser Ser Pro Asp Tyr Leu Gln Val Leu Glu Glu Gln Thr
        835                 840                 845
Ala Leu Asn Lys Ile
    850
```

<210> SEQ ID NO 31
<211> LENGTH: 314
<212> TYPE: PRT
<213> ORGANISM: Homo sapiens

<400> SEQUENCE: 31

```
Leu Gln Gln Trp Ile Gln Lys Leu Ser Lys Asn Thr Val Thr Asp Asp
  1               5                  10                  15

Ile Leu Cys Thr Ser Pro Gly His Leu Asp Lys Lys Glu Leu Lys Ala
                 20                  25                  30

Leu Asn Ser Glu Ile Leu Cys Pro Gly Leu Val Asn Asn Pro Ser Met
             35                  40                  45

Pro Thr Gln Thr Ser Tyr Leu Met Val Thr Pro Ala Thr Thr Thr
         50                  55                  60

Asn Thr Ala Asp Thr Ile Leu Arg Ser Leu Thr Asp Ala Val Pro Leu
 65                  70                  75                  80

Ser Val Leu Ile Leu Gly Leu Leu Ile Met Phe Ile Thr Ile Val Phe
                 85                  90                  95

Cys Ala Ala Gly Ile Val Val Leu Val Leu His Arg Arg Arg Arg Tyr
                100                 105                 110

Lys Lys Lys Gln Val Asp Glu Gln Met Arg Asp Asn Ser Pro Val His
            115                 120                 125

Leu Gln Tyr Ser Met Tyr Gly His Lys Thr Thr His His Thr Thr Glu
        130                 135                 140

Arg Pro Ser Ala Ser Leu Tyr Glu Gln His Met Val Ser Pro Met Val
145                 150                 155                 160

His Val Tyr Arg Ser Pro Ser Phe Gly Pro Lys His Leu Glu Glu Glu
                165                 170                 175

Glu Glu Arg Asn Glu Lys Glu Gly Ser Asp Ala Lys His Leu Gln Arg
            180                 185                 190

Ser Leu Leu Glu Gln Glu Asn Ser Pro Leu Thr Gly Ser Asn Met
        195                 200                 205

Lys Tyr Lys Thr Thr Asn Gln Ser Thr Glu Phe Leu Ser Phe Gln Asp
    210                 215                 220

Ala Ser Ser Leu Tyr Arg Asn Ile Leu Glu Lys Glu Arg Glu Leu Gln
225                 230                 235                 240

Gln Leu Gly Ile Thr Glu Tyr Leu Arg Lys Asn Ile Ala Gln Leu Gln
                245                 250                 255

Pro Asp Met Glu Ala His Tyr Pro Gly Ala His Glu Glu Leu Lys Leu
            260                 265                 270

Met Glu Thr Leu Met Tyr Ser Arg Pro Arg Lys Val Leu Val Glu Gln
        275                 280                 285

Thr Lys Asn Glu Tyr Phe Glu Leu Lys Ala Asn Leu His Ala Glu Pro
    290                 295                 300

Asp Tyr Leu Glu Val Leu Glu Gln Gln Thr
305                 310
```

<210> SEQ ID NO 32
<211> LENGTH: 966
<212> TYPE: PRT
<213> ORGANISM: Homo sapiens

<400> SEQUENCE: 32

```
Arg Arg Gly Ala Gln Gly Gly Lys Met His Thr Cys Cys Pro Pro Val
  1               5                  10                  15
```

-continued

```
Thr Leu Glu Gln Asp Leu His Arg Lys Met His Ser Trp Met Leu Gln
            20                  25                  30

Thr Leu Ala Phe Ala Val Thr Ser Leu Val Leu Ser Cys Ala Glu Thr
        35                  40                  45

Ile Asp Tyr Tyr Gly Glu Ile Cys Asp Asn Ala Cys Pro Cys Glu Glu
 50                  55                  60

Lys Asp Gly Ile Leu Thr Val Ser Cys Glu Asn Arg Gly Ile Ile Ser
 65                  70                  75                  80

Leu Ser Glu Ile Ser Pro Arg Phe Pro Ile Tyr His Leu Leu Leu
                 85                  90                  95

Ser Gly Asn Leu Leu Asn Arg Leu Tyr Pro Asn Glu Phe Val Asn Tyr
            100                 105                 110

Thr Gly Ala Ser Ile Leu His Leu Gly Ser Asn Val Ile Gln Asp Ile
        115                 120                 125

Glu Thr Gly Ala Phe His Gly Leu Arg Gly Leu Arg Arg Leu His Leu
130                 135                 140

Asn Asn Asn Lys Leu Glu Leu Leu Arg Asp Asp Thr Phe Leu Gly Leu
145                 150                 155                 160

Glu Asn Leu Glu Tyr Leu Gln Val Asp Tyr Asn Tyr Ile Ser Val Ile
                165                 170                 175

Glu Pro Asn Ala Phe Gly Lys Leu His Leu Leu Gln Val Leu Ile Leu
            180                 185                 190

Asn Asp Asn Leu Leu Ser Ser Leu Pro Asn Asn Leu Phe Arg Phe Val
        195                 200                 205

Pro Leu Thr His Leu Asp Leu Arg Gly Asn Arg Leu Lys Leu Leu Pro
    210                 215                 220

Tyr Val Gly Leu Leu Gln His Met Asp Lys Val Val Glu Leu Gln Leu
225                 230                 235                 240

Glu Glu Asn Pro Trp Asn Cys Ser Cys Glu Leu Ile Ser Leu Lys Asp
                245                 250                 255

Trp Leu Asp Ser Ile Ser Tyr Ser Ala Leu Val Gly Asp Val Val Cys
            260                 265                 270

Glu Thr Pro Phe Arg Leu His Gly Arg Asp Leu Asp Glu Val Ser Lys
        275                 280                 285

Gln Glu Leu Cys Pro Arg Arg Leu Ile Ser Asp Tyr Glu Met Arg Pro
290                 295                 300

Gln Thr Pro Leu Ser Thr Thr Gly Tyr Leu His Thr Thr Pro Ala Ser
305                 310                 315                 320

Val Asn Ser Val Ala Thr Ser Ser Ala Val Tyr Lys Pro Pro Leu
                325                 330                 335

Lys Pro Pro Lys Gly Thr Arg Gln Pro Asn Lys Pro Arg Val Arg Pro
            340                 345                 350

Thr Ser Arg Gln Pro Ser Lys Asp Leu Gly Tyr Ser Asn Tyr Gly Pro
        355                 360                 365

Ser Ile Ala Tyr Gln Thr Lys Ser Pro Val Pro Leu Glu Cys Pro Thr
    370                 375                 380

Ala Cys Ser Cys Asn Leu Gln Ile Ser Asp Leu Gly Leu Asn Val Asn
385                 390                 395                 400

Cys Gln Glu Arg Lys Ile Glu Ser Ile Ala Glu Leu Gln Pro Lys Pro
                405                 410                 415

Tyr Asn Pro Lys Lys Met Tyr Leu Thr Glu Asn Tyr Ile Ala Val Val
            420                 425                 430

Arg Arg Thr Asp Phe Leu Glu Ala Thr Gly Leu Asp Leu Leu His Leu
```

-continued

```
                435                 440                 445
Gly Asn Asn Arg Ile Ser Met Ile Gln Asp Arg Ala Phe Gly Asp Leu
            450                 455                 460
Thr Asn Leu Arg Arg Leu Tyr Leu Asn Gly Asn Arg Ile Glu Arg Leu
465                 470                 475                 480
Ser Pro Glu Leu Phe Tyr Gly Leu Gln Ser Leu Gln Tyr Leu Phe Leu
                485                 490                 495
Gln Tyr Asn Leu Ile Arg Glu Ile Gln Ser Gly Thr Phe Asp Pro Val
            500                 505                 510
Pro Asn Leu Gln Leu Leu Phe Leu Asn Asn Asn Leu Leu Gln Ala Met
            515                 520                 525
Pro Ser Gly Val Phe Ser Gly Leu Thr Leu Leu Arg Leu Asn Leu Arg
530                 535                 540
Ser Asn His Phe Thr Ser Leu Pro Val Ser Gly Val Leu Asp Gln Leu
545                 550                 555                 560
Lys Ser Leu Ile Gln Ile Asp Leu His Asp Asn Pro Trp Asp Cys Thr
                565                 570                 575
Cys Asp Ile Val Gly Met Lys Leu Trp Val Glu Gln Leu Lys Val Gly
            580                 585                 590
Val Leu Val Asp Glu Val Ile Cys Lys Ala Pro Lys Lys Phe Ala Glu
            595                 600                 605
Thr Asp Met Arg Ser Ile Lys Ser Glu Leu Leu Cys Pro Asp Tyr Ser
610                 615                 620
Asp Val Val Ser Thr Pro Thr Pro Ser Ser Ile Gln Val Pro Ala
625                 630                 635                 640
Arg Thr Ser Ala Val Thr Pro Ala Val Arg Leu Asn Ser Thr Gly Ala
                645                 650                 655
Pro Ala Ser Leu Gly Ala Gly Gly Ala Ser Ser Val Pro Leu Ser
            660                 665                 670
Val Leu Ile Leu Ser Leu Leu Leu Val Phe Ile Met Ser Val Phe Val
            675                 680                 685
Ala Ala Gly Leu Phe Val Leu Val Met Lys Arg Arg Lys Lys Asn Gln
690                 695                 700
Ser Asp His Thr Ser Thr Asn Asn Ser Asp Val Ser Ser Phe Asn Met
705                 710                 715                 720
Gln Tyr Ser Val Tyr Gly Gly Gly Gly Thr Gly His Pro His
                725                 730                 735
Ala His Val His His Arg Gly Pro Ala Leu Pro Lys Val Lys Thr Pro
            740                 745                 750
Ala Gly His Val Tyr Glu Tyr Ile Pro His Pro Leu Gly His Met Cys
            755                 760                 765
Lys Asn Pro Ile Tyr Arg Ser Arg Glu Gly Asn Ser Val Glu Asp Tyr
770                 775                 780
Lys Asp Leu His Glu Leu Lys Val Thr Tyr Ser Ser Asn His His Leu
785                 790                 795                 800
Gln Gln Gln Gln Gln Pro Pro Pro Pro Gln Gln Pro Gln Gln Gln
                805                 810                 815
Pro Pro Pro Gln Leu Gln Leu Gln Pro Gly Glu Glu Arg Arg Glu
            820                 825                 830
Ser His His Leu Arg Ser Pro Ala Tyr Ser Val Ser Thr Ile Glu Pro
            835                 840                 845
Arg Glu Asp Leu Leu Ser Pro Val Gln Asp Ala Asp Arg Phe Tyr Arg
850                 855                 860
```

-continued

```
Gly Ile Leu Glu Pro Asp Lys His Cys Ser Thr Thr Pro Ala Gly Asn
865                 870                 875                 880

Ser Leu Pro Glu Tyr Pro Lys Phe Pro Cys Ser Pro Ala Ala Tyr Thr
                885                 890                 895

Phe Ser Pro Asn Tyr Asp Leu Arg Arg Pro His Gln Tyr Leu His Pro
                900                 905                 910

Gly Ala Gly Asp Ser Arg Leu Arg Glu Pro Val Leu Tyr Ser Pro Pro
                915                 920                 925

Ser Ala Val Phe Val Glu Pro Asn Arg Asn Glu Tyr Leu Glu Leu Lys
        930                 935                 940

Ala Lys Leu Asn Val Glu Pro Asp Tyr Leu Glu Val Leu Glu Lys Gln
945                 950                 955                 960

Thr Thr Phe Ser Gln Phe
                965

<210> SEQ ID NO 33
<211> LENGTH: 1428
<212> TYPE: PRT
<213> ORGANISM: Mus musculus

<400> SEQUENCE: 33

Met Val Ala Val Ala Val Ala Ser Thr Glu Ala Arg Leu Arg Gly
1               5                   10                  15

Ser Thr Thr Ala Thr Ala Pro Ala Gly Arg Lys Gly Arg Gln His
                20                  25                  30

Arg Pro Cys Thr Ala Thr Gly Ala Trp Arg Pro Gly Pro Arg Ala Arg
            35                  40                  45

Leu Cys Leu Pro Arg Val Leu Ser Arg Ala Leu Pro Pro Pro Leu
    50                  55                  60

Leu Pro Leu Leu Phe Ser Leu Leu Leu Pro Leu Pro Arg Glu Ala
65                  70                  75                  80

Glu Ala Ala Ala Val Ala Ala Val Ser Gly Ser Ala Ala Ala Glu
                85                  90                  95

Ala Lys Glu Cys Asp Arg Pro Cys Val Asn Gly Gly Arg Cys Asn Pro
            100                 105                 110

Gly Thr Gly Gln Cys Val Cys Pro Thr Gly Trp Val Gly Glu Gln Cys
        115                 120                 125

Gln His Cys Gly Gly Arg Phe Arg Leu Thr Gly Ser Ser Gly Phe Val
    130                 135                 140

Thr Asp Gly Pro Gly Asn Tyr Lys Tyr Lys Thr Lys Cys Thr Trp Leu
145                 150                 155                 160

Ile Glu Gly Tyr Pro Asn Ala Val Leu Arg Leu Arg Phe Asn His Phe
                165                 170                 175

Ala Thr Glu Cys Ser Trp Asp His Leu Tyr Val Tyr Asp Gly Asp Ser
            180                 185                 190

Ile Tyr Ala Pro Leu Ile Ala Ala Phe Ser Gly Leu Ile Val Pro Glu
        195                 200                 205

Arg Asp Gly Asn Glu Thr Ala Pro Glu Val Thr Val Thr Ser Gly Tyr
    210                 215                 220

Ala Leu Leu His Phe Phe Ser Asp Ala Ala Tyr Asn Leu Thr Gly Phe
225                 230                 235                 240

Asn Ile Thr Tyr Asn Phe Asp Met Cys Pro Asn Asn Cys Ser Ala Arg
                245                 250                 255

Gly Glu Cys Lys Ser Ser Asn Ser Ser Ser Ala Val Glu Cys Glu Cys
```

-continued

```
                260                 265                 270
Ser Glu Asn Trp Lys Gly Glu Ser Cys Asp Ile Pro His Cys Thr Asp
            275                 280                 285

Asn Cys Gly Phe Pro His Arg Gly Ile Cys Asn Ala Ser Asp Thr Arg
        290                 295                 300

Gly Cys Ser Cys Phe Pro His Trp Gln Gly Pro Gly Cys Ser Ile Pro
305                 310                 315                 320

Val Pro Ala Asn Gln Ser Phe Trp Thr Arg Glu Tyr Ser Asp Leu
                325                 330                 335

Lys Leu Pro Arg Ala Ser His Lys Ala Val Asn Gly Asn Ile Met
            340                 345                 350

Trp Val Val Gly Gly Tyr Met Phe Asn His Ser Asp Tyr Ser Met Val
                355                 360                 365

Leu Ala Tyr Asp Leu Thr Ser Arg Glu Trp Leu Pro Leu Asn His Ser
        370                 375                 380

Val Asn Ser Val Val Arg Tyr Gly His Ser Leu Ala Leu His Lys
385                 390                 395                 400

Asp Lys Ile Tyr Met Tyr Gly Lys Ile Asp Ser Thr Gly Asn Val
                405                 410                 415

Thr Asn Glu Leu Arg Val Phe His Ile His Asn Glu Ser Trp Val Leu
            420                 425                 430

Leu Thr Pro Lys Ala Lys Asp Gln Tyr Ala Val Val Gly His Ser Ala
435                 440                 445

His Ile Val Thr Leu Ala Ser Gly Arg Val Val Met Leu Val Ile Phe
    450                 455                 460

Gly His Cys Pro Leu Tyr Gly Tyr Ile Ser Val Val Gln Glu Tyr Asp
465                 470                 475                 480

Leu Glu Lys Asn Thr Trp Ser Ile Leu His Thr Gln Gly Ala Leu Val
                485                 490                 495

Gln Gly Gly Tyr Gly His Ser Ser Ala Tyr Asp Asp Arg Thr Lys Ala
            500                 505                 510

Leu Tyr Val His Gly Gly Tyr Lys Ala Phe Ser Ala Asn Lys Tyr Arg
        515                 520                 525

Leu Ala Asp Asp Leu Tyr Arg Tyr Asp Val Asp Thr Gln Met Trp Thr
530                 535                 540

Ile Leu Lys Asp Ser Arg Phe Phe Arg Tyr Leu His Thr Ala Val Ile
545                 550                 555                 560

Val Ser Gly Thr Met Leu Val Phe Gly Gly Asn Thr His Asn Asp Thr
                565                 570                 575

Ser Met Ser His Gly Ala Lys Cys Phe Ser Ser Asp Phe Met Ala Tyr
            580                 585                 590

Asp Ile Ala Cys Asp Arg Trp Ser Val Leu Pro Arg Pro Glu Leu His
        595                 600                 605

His Asp Val Asn Arg Phe Gly His Ser Ala Val Leu Tyr Asn Ser Thr
    610                 615                 620

Met Tyr Val Phe Gly Gly Phe Asn Ser Leu Leu Leu Ser Asp Val Leu
625                 630                 635                 640

Val Phe Thr Ser Glu Gln Cys Asp Ala His Arg Ser Glu Ala Ala Cys
                645                 650                 655

Val Ala Ala Gly Pro Gly Ile Arg Cys Leu Trp Asp Thr Gln Ser Ser
            660                 665                 670

Arg Cys Thr Ser Trp Glu Leu Ala Thr Glu Glu Gln Ala Glu Lys Leu
        675                 680                 685
```

-continued

```
Lys Ser Glu Cys Phe Ser Lys Arg Thr Leu Asp His Asp Arg Cys Asp
    690                 695                 700
Gln His Thr Asp Cys Tyr Ser Cys Thr Ala Asn Thr Asn Asp Cys His
705                 710                 715                 720
Trp Cys Asn Asp His Cys Val Pro Val Asn His Ser Cys Thr Glu Gly
                725                 730                 735
Gln Ile Ser Ile Ala Lys Tyr Glu Ser Cys Pro Lys Asp Asn Pro Met
            740                 745                 750
Tyr Tyr Cys Asn Lys Lys Thr Ser Cys Arg Ser Cys Ala Leu Asp Gln
        755                 760                 765
Asn Cys Gln Trp Glu Pro Arg Asn Gln Glu Cys Ile Ala Leu Pro Glu
    770                 775                 780
Asn Ile Cys Gly Asn Gly Trp His Leu Val Gly Asn Ser Cys Leu Lys
785                 790                 795                 800
Ile Thr Thr Ala Lys Glu Asn Tyr Asp Asn Ala Lys Leu Ser Cys Arg
                805                 810                 815
Asn His Asn Ala Phe Leu Ala Ser Leu Thr Ser Gln Lys Lys Val Glu
            820                 825                 830
Leu Val Leu Lys Gln Leu Arg Leu Met Gln Ser Ser Gln Ser Met Ser
        835                 840                 845
Lys Leu Thr Leu Thr Pro Trp Val Gly Leu Arg Lys Ile Asn Val Ser
    850                 855                 860
Tyr Trp Cys Trp Glu Asp Met Ser Pro Phe Thr Asn Ser Leu Leu Gln
865                 870                 875                 880
Trp Met Pro Ser Glu Pro Ser Asp Ala Gly Phe Cys Gly Ile Leu Ser
                885                 890                 895
Glu Pro Ser Thr Arg Gly Leu Lys Ala Ala Thr Cys Ile Asn Pro Leu
            900                 905                 910
Asn Gly Ser Val Cys Glu Arg Pro Ala Asn His Ser Ala Lys Gln Cys
        915                 920                 925
Arg Thr Pro Cys Ala Leu Arg Thr Ala Cys Gly Glu Cys Thr Ser Ser
    930                 935                 940
Ser Ser Glu Cys Met Trp Cys Ser Asn Met Lys Gln Cys Val Asp Ser
945                 950                 955                 960
Asn Ala Tyr Val Ala Ser Phe Pro Phe Gly Gln Cys Met Glu Trp Tyr
                965                 970                 975
Thr Met Ser Ser Cys Pro Pro Glu Asn Cys Ser Gly Tyr Cys Thr Cys
            980                 985                 990
Ser His Cys Leu Glu Gln Pro Gly Cys Gly Trp Cys Thr Asp Pro Ser
        995                1000                1005
Asn Thr Gly Lys Gly Lys Cys Ile Glu Gly Ser Tyr Lys Gly Pro Val
    1010                1015                1020
Lys Met Pro Ser Gln Ala Ser Ala Gly Asn Val Tyr Pro Gln Pro Leu
1025                1030                1035                1040
Leu Asn Ser Ser Met Cys Leu Glu Asp Ser Arg Tyr Asn Trp Ser Phe
                1045                1050                1055
Ile His Cys Pro Ala Cys Gln Cys Asn Gly His Ser Lys Cys Ile Asn
            1060                1065                1070
Gln Ser Val Cys Glu Lys Cys Glu Asp Leu Thr Thr Gly Lys His Cys
        1075                1080                1085
Glu Thr Cys Ile Ser Gly Phe Tyr Gly Asp Pro Thr Asn Gly Gly Lys
    1090                1095                1100
```

-continued

```
Cys Gln Pro Cys Lys Cys Asn Gly His Ala Ser Leu Cys Asn Thr Asn
1105                1110                1115                1120

Thr Gly Lys Cys Phe Cys Thr Thr Lys Gly Val Lys Gly Asp Glu Cys
            1125                1130                1135

Gln Leu Cys Lys Val Glu Asn Arg Tyr Gln Gly Asn Pro Leu Lys Gly
        1140                1145                1150

Thr Cys Tyr Tyr Thr Leu Leu Ile Asp Tyr Gln Phe Thr Phe Ser Leu
    1155                1160                1165

Ser Gln Gly Asp Asp Arg Tyr Tyr Thr Ala Ile Asn Phe Val Ala Thr
1170                1175                1180

Pro Asp Glu Gln Asn Arg Asp Phe Asp Met Phe Ile Asn Ala Ser Lys
1185                1190                1195                1200

Lys Phe Asn Leu Asn Ile Thr Trp Ala Thr Ser Phe Pro Ala Gly Thr
            1205                1210                1215

Gln Thr Gly Glu Glu Val Pro Val Val Ser Lys Thr Asn Ile Lys Glu
        1220                1225                1230

Tyr Lys Asp Ser Phe Ser Asn Glu Lys Phe Asp Phe Arg Asn His Pro
    1235                1240                1245

Asn Ile Thr Phe Phe Val Tyr Val Ser Asn Phe Thr Trp Pro Ile Lys
1250                1255                1260

Ile Gln Ile Ala Phe Ser Gln His Ser Asn Phe Met Asp Leu Val Gln
1265                1270                1275                1280

Phe Phe Val Thr Phe Phe Ser Cys Phe Leu Ser Leu Leu Val Ala
            1285                1290                1295

Ala Val Val Trp Lys Ile Lys Gln Ser Cys Trp Ala Ser Arg Arg Arg
        1300                1305                1310

Glu Gln Leu Leu Arg Glu Met Gln Gln Met Ala Ser Arg Pro Phe Ala
    1315                1320                1325

Ser Val Asn Val Ala Leu Glu Thr Asp Glu Glu Pro Pro Asp Leu Ile
1330                1335                1340

Gly Gly Ser Ile Lys Thr Val Pro Lys Pro Ile Ala Leu Glu Pro Cys
1345                1350                1355                1360

Phe Gly Asn Lys Ala Ala Val Leu Ser Val Phe Val Arg Leu Pro Arg
            1365                1370                1375

Gly Leu Gly Gly Ile Pro Pro Gly Gln Ser Gly Leu Ala Val Ala
        1380                1385                1390

Ser Ala Leu Val Asp Ile Ser Gln Gln Met Pro Ile Val Tyr Lys Glu
    1395                1400                1405

Lys Ser Gly Ala Val Arg Asn Arg Lys Gln Gln Pro Pro Ala Gln Pro
1410                1415                1420

Gly Thr Cys Ile
1425
```

<210> SEQ ID NO 34
<211> LENGTH: 1428
<212> TYPE: PRT
<213> ORGANISM: Mus musculus

<400> SEQUENCE: 34

```
Met Val Ala Val Ala Ala Ala Ala Thr Glu Ala Arg Leu Arg Gly
1               5                   10                  15

Ser Thr Thr Thr Ala Ala Pro Ala Gly Arg Lys Gly Arg Gln His
            20                  25                  30

Arg Pro Cys Thr Ala Thr Gly Ala Trp Arg Pro Gly Pro Arg Ala Arg
        35                  40                  45
```

-continued

```
Leu Cys Leu Pro Arg Val Leu Ser Arg Ala Leu Pro Pro Pro Leu
     50                  55                  60

Leu Pro Leu Leu Phe Ser Leu Leu Leu Pro Leu Pro Arg Glu Ala
 65                  70                  75                  80

Glu Ala Ala Ala Val Ala Ala Val Ser Gly Ser Ala Ala Ala Glu
                 85                  90                  95

Ala Lys Glu Cys Asp Arg Pro Cys Val Asn Gly Arg Cys Asn Pro
            100                 105                 110

Gly Thr Gly Gln Cys Val Cys Pro Thr Gly Trp Val Gly Glu Gln Cys
        115                 120                 125

Gln His Cys Gly Gly Arg Phe Arg Leu Thr Gly Ser Ser Gly Phe Val
    130                 135                 140

Thr Asp Gly Pro Gly Asn Tyr Lys Tyr Lys Thr Lys Cys Thr Trp Leu
145                 150                 155                 160

Ile Glu Gly Gln Pro Asn Arg Ile Met Arg Leu Arg Phe Asn His Phe
                165                 170                 175

Ala Thr Glu Cys Ser Trp Asp His Leu Tyr Val Tyr Asp Gly Asp Ser
            180                 185                 190

Ile Tyr Ala Pro Leu Ile Ala Ala Phe Ser Gly Leu Ile Val Pro Glu
        195                 200                 205

Arg Asp Gly Asn Glu Thr Ala Pro Glu Val Thr Val Thr Ser Gly Tyr
210                 215                 220

Ala Leu Leu His Phe Phe Ser Asp Ala Ala Tyr Asn Leu Thr Gly Phe
225                 230                 235                 240

Asn Ile Thr Tyr Asn Phe Asp Met Cys Pro Asn Asn Cys Ser Gly Arg
                245                 250                 255

Gly Glu Cys Lys Ser Ser Asn Ser Ser Ser Ala Val Glu Cys Glu Cys
            260                 265                 270

Ser Glu Asn Trp Lys Gly Glu Ser Cys Asp Ile Pro His Cys Thr Asp
        275                 280                 285

Asn Cys Gly Phe Pro His Arg Gly Ile Cys Asn Ala Ser Asp Thr Arg
    290                 295                 300

Gly Cys Ser Cys Phe Pro His Trp Gln Gly Pro Gly Cys Ser Ile Pro
305                 310                 315                 320

Val Pro Ala Asn Gln Ser Phe Trp Thr Arg Glu Glu Tyr Ser Asp Leu
                325                 330                 335

Lys Leu Pro Arg Ala Ser His Lys Ala Val Asn Gly Asn Ile Met
            340                 345                 350

Trp Val Val Gly Gly Tyr Met Phe Asn His Ser Asp Tyr Ser Met Val
        355                 360                 365

Leu Ala Tyr Asp Leu Thr Ser Arg Glu Trp Leu Pro Leu Asn His Ser
    370                 375                 380

Val Asn Ser Val Val Arg Tyr Gly His Ser Leu Ala Leu His Lys
385                 390                 395                 400

Asp Lys Ile Tyr Met Tyr Gly Gly Lys Ile Asp Ser Thr Gly Asn Val
                405                 410                 415

Thr Asn Glu Leu Arg Val Phe His Ile His Asn Glu Ser Trp Val Leu
            420                 425                 430

Leu Thr Pro Lys Ala Lys Asp Gln Tyr Ala Val Val Gly His Ser Ala
        435                 440                 445

His Ile Val Thr Leu Ala Ser Gly Arg Val Val Met Leu Val Ile Phe
    450                 455                 460
```

-continued

```
Gly His Cys Pro Leu Tyr Gly Tyr Ile Ser Val Val Gln Glu Tyr Asp
465                 470                 475                 480

Leu Glu Lys Asn Thr Trp Ser Ile Leu His Thr Gln Gly Ala Leu Val
            485                 490                 495

Gln Gly Gly Tyr Gly His Ser Ser Val Tyr Asp Asp Arg Thr Lys Ala
                500                 505                 510

Leu Tyr Val His Gly Gly Tyr Lys Ala Phe Ser Ala Asn Lys Tyr Arg
            515                 520                 525

Leu Ala Asp Asp Leu Tyr Arg Tyr Asp Val Asp Thr Gln Met Trp Thr
    530                 535                 540

Ile Leu Lys Asp Ser Arg Phe Phe Arg Tyr Leu His Thr Ala Val Ile
545                 550                 555                 560

Val Ser Gly Thr Met Leu Val Phe Gly Gly Asn Thr His Asn Asp Thr
                565                 570                 575

Ser Met Ser His Gly Ala Lys Cys Phe Ser Ser Asp Phe Met Ala Tyr
            580                 585                 590

Asp Ile Ala Cys Asp Arg Trp Ser Val Leu Pro Arg Pro Glu Leu His
    595                 600                 605

His Asp Val Asn Arg Phe Gly His Ser Ala Val Leu Tyr Asn Ser Thr
    610                 615                 620

Met Tyr Val Phe Gly Gly Phe Asn Ser Leu Leu Leu Ser Asp Val Leu
625                 630                 635                 640

Val Phe Thr Ser Glu Gln Cys Asp Ala His Arg Ser Glu Ala Ala Cys
                645                 650                 655

Val Ala Ala Gly Pro Gly Ile Arg Cys Leu Trp Asp Thr Gln Ser Ser
                660                 665                 670

Arg Cys Thr Ser Trp Glu Leu Ala Thr Glu Glu Gln Ala Glu Lys Leu
            675                 680                 685

Lys Ser Glu Cys Phe Ser Lys Arg Thr Leu Asp His Asp Arg Cys Asp
690                 695                 700

Gln His Thr Asp Cys Tyr Ser Cys Thr Ala Asn Thr Asn Asp Cys His
705                 710                 715                 720

Trp Cys Asn Asp His Cys Val Pro Val Asn His Ser Cys Thr Glu Gly
            725                 730                 735

Gln Ile Ser Ile Ala Lys Tyr Glu Ser Cys Pro Lys Asp Asn Pro Met
            740                 745                 750

Tyr Tyr Cys Asn Lys Lys Thr Ser Cys Arg Ser Cys Ala Leu Asp Gln
            755                 760                 765

Asn Cys Gln Trp Glu Pro Arg Asn Gln Glu Cys Ile Ala Leu Pro Glu
    770                 775                 780

Asn Ile Cys Gly Asn Gly Trp His Leu Val Gly Asn Ser Cys Leu Lys
785                 790                 795                 800

Ile Thr Thr Ala Lys Glu Asn Tyr Asp Asn Ala Lys Leu Ser Cys Arg
                805                 810                 815

Asn His Asn Ala Phe Leu Ala Ser Leu Thr Ser Gln Lys Lys Val Glu
            820                 825                 830

Phe Val Leu Lys Gln Leu Arg Leu Met Gln Ser Ser Gln Ser Met Ser
            835                 840                 845

Lys Leu Thr Leu Thr Pro Trp Val Gly Leu Arg Lys Ile Asn Val Ser
    850                 855                 860

Tyr Trp Cys Trp Glu Asp Met Ser Pro Phe Thr Asn Ser Leu Leu Gln
865                 870                 875                 880

Trp Met Pro Ser Glu Pro Ser Asp Ala Gly Phe Cys Gly Ile Leu Ser
```

-continued

```
                885                 890                 895
Glu Pro Ser Thr Arg Gly Leu Lys Ala Ala Thr Cys Ile Asn Pro Leu
        900                 905                 910
Asn Gly Ser Val Cys Glu Arg Pro Ala Asn His Ser Ala Lys Gln Cys
        915                 920                 925
Arg Thr Pro Cys Ala Leu Arg Thr Ala Cys Gly Glu Cys Thr Ser Ser
        930                 935                 940
Ser Ser Glu Cys Met Trp Cys Ser Asn Met Lys Gln Cys Val Asp Ser
945                 950                 955                 960
Asn Ala Tyr Val Ala Ser Phe Pro Phe Gly Gln Cys Met Glu Trp Tyr
        965                 970                 975
Thr Met Ser Ser Cys Pro Pro Glu Asn Cys Ser Gly Tyr Cys Thr Cys
        980                 985                 990
Ser His Cys Leu Glu Gln Pro Gly Cys Gly Trp Cys Thr Asp Pro Ser
        995                 1000                1005
Asn Thr Gly Lys Gly Lys Cys Ile Glu Gly Ser Tyr Lys Gly Pro Val
        1010                1015                1020
Lys Met Pro Ser Gln Ala Ser Ala Gly Asn Val Tyr Pro Gln Pro Leu
1025                1030                1035                1040
Leu Asn Ser Ser Met Cys Leu Glu Asp Ser Arg Tyr Asn Trp Ser Phe
        1045                1050                1055
Ile His Cys Pro Ala Cys Gln Cys Asn Gly His Ser Lys Cys Ile Asn
        1060                1065                1070
Gln Ser Ile Cys Glu Lys Cys Glu Asp Leu Thr Thr Gly Lys His Cys
        1075                1080                1085
Glu Thr Cys Ile Ser Gly Phe Tyr Gly Asp Pro Thr Asn Gly Gly Lys
        1090                1095                1100
Cys Gln Pro Cys Lys Cys Asn Gly His Ala Ser Leu Cys Asn Thr Asn
1105                1110                1115                1120
Thr Gly Lys Cys Phe Cys Thr Thr Lys Gly Val Lys Gly Asp Glu Cys
        1125                1130                1135
Gln Leu Cys Glu Val Glu Asn Arg Tyr Gln Gly Asn Pro Leu Lys Gly
        1140                1145                1150
Thr Cys Tyr Tyr Thr Leu Leu Ile Asp Tyr Gln Phe Thr Phe Ser Leu
        1155                1160                1165
Ser Gln Glu Asp Asp Arg Tyr Tyr Thr Ala Ile Asn Phe Val Ala Thr
        1170                1175                1180
Pro Asp Glu Gln Asn Arg Asp Leu Asp Met Phe Ile Asn Ala Ser Lys
1185                1190                1195                1200
Asn Phe Asn Leu Asn Ile Thr Trp Ala Thr Ser Phe Pro Ala Gly Thr
        1205                1210                1215
Gln Thr Gly Glu Glu Val Pro Val Val Ser Lys Thr Asn Ile Lys Glu
        1220                1225                1230
Tyr Lys Asp Ser Phe Ser Asn Glu Lys Phe Asp Phe Arg Asn His Pro
        1235                1240                1245
Asn Ile Thr Phe Phe Val Tyr Val Ser Asn Phe Thr Trp Pro Ile Lys
        1250                1255                1260
Ile Gln Ile Ala Phe Ser Gln His Ser Asn Phe Met Asp Leu Val Gln
1265                1270                1275                1280
Phe Phe Val Thr Phe Phe Ser Cys Phe Leu Ser Leu Leu Leu Val Ala
        1285                1290                1295
Ala Val Val Trp Lys Ile Lys Gln Ser Cys Trp Ala Ser Arg Arg Arg
        1300                1305                1310
```

```
Glu Gln Leu Leu Arg Glu Met Gln Met Ala Ser Arg Pro Phe Ala
    1315                1320                1325

Ser Val Asn Val Ala Leu Glu Thr Asp Glu Pro Pro Asp Leu Ile
    1330                1335                1340

Gly Gly Ser Ile Lys Thr Val Pro Lys Pro Ile Ala Leu Glu Pro Cys
1345                1350                1355                1360

Phe Gly Asn Lys Ala Ala Val Leu Ser Val Phe Val Arg Leu Pro Arg
            1365                1370                1375

Gly Leu Gly Gly Ile Pro Pro Gly Gln Ser Gly Leu Ala Val Ala
            1380                1385                1390

Ser Ala Leu Val Asp Ile Ser Gln Gln Met Pro Ile Val Tyr Lys Glu
    1395                1400                1405

Lys Ser Gly Ala Val Arg Asn Arg Lys Gln Gln Pro Pro Ala Gln Pro
    1410                1415                1420

Gly Thr Cys Ile
1425

<210> SEQ ID NO 35
<211> LENGTH: 1198
<212> TYPE: PRT
<213> ORGANISM: Homo sapiens

<400> SEQUENCE: 35

Met Val Ala Ala Ala Ala Thr Glu Ala Arg Leu Arg Arg Thr
1               5                   10                  15

Ala Ala Thr Ala Ala Leu Ala Gly Arg Ser Gly Gly Pro His Cys Val
                20                  25                  30

Asn Gly Gly Arg Cys Asn Pro Gly Thr Gly Gln Cys Val Cys Pro Ala
            35                  40                  45

Gly Trp Val Gly Glu Gln Cys Gln His Cys Gly Gly Arg Phe Arg Leu
        50                  55                  60

Thr Gly Ser Ser Gly Phe Val Thr Asp Gly Pro Gly Asn Tyr Lys Tyr
65                  70                  75                  80

Lys Thr Lys Cys Thr Trp Leu Ile Glu Gly Gln Pro Asn Arg Ile Met
                85                  90                  95

Arg Leu Arg Phe Asn His Phe Ala Thr Glu Cys Ser Trp Asp His Leu
            100                 105                 110

Tyr Val Tyr Asp Gly Asp Ser Ile Tyr Ala Pro Leu Val Ala Ala Phe
        115                 120                 125

Ser Gly Leu Ile Val Pro Glu Arg Asp Gly Asn Glu Thr Val Pro Glu
    130                 135                 140

Val Val Ala Thr Ser Gly Tyr Ala Leu Leu His Phe Ser Asp Ala
145                 150                 155                 160

Ala Tyr Asn Leu Thr Gly Phe Asn Ile Thr Tyr Ser Phe Asp Met Cys
                165                 170                 175

Pro Asn Asn Cys Ser Gly Arg Gly Glu Cys Lys Ile Ser Asn Ser Ser
            180                 185                 190

Asp Thr Val Glu Cys Glu Cys Ser Glu Asn Trp Lys Gly Glu Ala Cys
        195                 200                 205

Asp Ile Pro His Cys Thr Asp Asn Cys Gly Phe Pro His Arg Gly Ile
    210                 215                 220

Cys Asn Ser Ser Asp Val Arg Gly Cys Ser Cys Phe Ser Asp Trp Gln
225                 230                 235                 240

Gly Pro Gly Cys Ser Val Pro Val Pro Ala Asn Gln Ser Phe Trp Thr
```

-continued

```
                245                 250                 255
Arg Glu Glu Tyr Ser Asn Leu Lys Leu Pro Arg Ala Ser His Lys Ala
            260                 265                 270
Val Val Asn Gly Asn Ile Met Trp Val Val Gly Gly Tyr Met Phe Asn
            275                 280                 285
His Ser Asp Tyr Asn Met Val Leu Ala Tyr Asp Leu Ala Ser Arg Glu
            290                 295                 300
Trp Leu Pro Leu Asn Arg Ser Val Asn Asn Val Val Arg Tyr Gly
305                 310                 315                 320
His Ser Leu Ala Leu Tyr Lys Asp Lys Ile Tyr Met Tyr Gly Gly Lys
            325                 330                 335
Ile Asp Ser Thr Gly Asn Val Thr Asn Glu Leu Arg Val Phe His Ile
            340                 345                 350
His Asn Glu Ser Trp Val Leu Leu Thr Pro Lys Ala Lys Glu Gln Tyr
            355                 360                 365
Ala Val Val Gly His Ser Ala His Ile Val Thr Leu Lys Asn Gly Arg
            370                 375                 380
Val Val Met Leu Val Ile Phe Gly His Cys Pro Leu Tyr Gly Tyr Ile
385                 390                 395                 400
Ser Asn Val Gln Glu Tyr Asp Leu Asp Lys Asn Thr Trp Ser Ile Leu
            405                 410                 415
His Thr Gln Gly Ala Leu Val Gln Gly Gly Tyr Gly His Ser Ser Val
            420                 425                 430
Tyr Asp His Arg Thr Arg Ala Leu Tyr Val His Gly Gly Tyr Lys Ala
            435                 440                 445
Phe Ser Ala Asn Lys Tyr Arg Leu Ala Asp Asp Leu Tyr Arg Tyr Asp
450                 455                 460
Val Asp Thr Gln Met Trp Thr Ile Leu Lys Asp Ser Arg Phe Phe Arg
465                 470                 475                 480
Tyr Leu His Thr Ala Val Ile Val Ser Gly Thr Met Leu Val Phe Gly
            485                 490                 495
Gly Asn Thr His Asn Asp Thr Ser Met Ser His Gly Ala Lys Cys Phe
            500                 505                 510
Ser Ser Asp Phe Met Ala Tyr Asp Ile Ala Cys Asp Arg Trp Ser Val
            515                 520                 525
Leu Pro Arg Pro Asp Ser Thr Met Met Ser Thr Asp Leu Ala Ile Pro
            530                 535                 540
Ala Val Leu His Asn Ser Thr Met Tyr Val Phe Gly Gly Phe Asn Ser
545                 550                 555                 560
Leu Leu Leu Ser Asp Ile Leu Val Phe Thr Ser Glu Gln Cys Asp Ala
            565                 570                 575
His Arg Ser Glu Ala Ala Cys Leu Ala Ala Gly Pro Gly Ile Arg Cys
            580                 585                 590
Val Trp Asn Thr Gly Ser Ser Gln Cys Ile Ser Trp Ala Leu Ala Thr
            595                 600                 605
Asp Glu Gln Glu Glu Lys Leu Lys Ser Glu Cys Phe Ser Lys Arg Thr
            610                 615                 620
Leu Asp His Asp Arg Cys Asp Gln His Thr Asp Cys Tyr Ser Cys Thr
625                 630                 635                 640
Ala Asn Thr Asn Asp Cys His Trp Cys Asn Asp His Cys Val Pro Arg
            645                 650                 655
Asn His Ser Cys Ser Glu Gly Gln Ile Ser Ile Phe Arg Tyr Glu Asn
            660                 665                 670
```

```
Cys Pro Lys Asp Asn Pro Met Tyr Tyr Cys Asn Lys Lys Thr Ser Cys
            675                 680                 685

Arg Ser Cys Ala Leu Asp Gln Asn Cys Gln Trp Glu Pro Arg Asn Gln
        690                 695                 700

Glu Cys Ile Ala Leu Pro Glu Asn Ile Cys Gly Ile Gly Trp His Leu
705                 710                 715                 720

Val Gly Asn Ser Cys Leu Lys Ile Thr Thr Ala Lys Glu Asn Tyr Asp
                725                 730                 735

Asn Ala Lys Leu Phe Cys Arg Asn His Asn Ala Leu Leu Ala Ser Leu
            740                 745                 750

Thr Thr Gln Lys Lys Val Glu Phe Val Leu Lys Gln Leu Arg Ile Met
        755                 760                 765

Gln Ser Ser Gln Ser Met Ser Lys Leu Thr Leu Thr Pro Trp Val Gly
            770                 775                 780

Leu Arg Lys Ile Asn Val Ser Tyr Trp Cys Trp Glu Asp Met Ser Pro
785                 790                 795                 800

Phe Thr Asn Ser Leu Leu Gln Trp Met Pro Ser Glu Pro Ser Asp Ala
                805                 810                 815

Gly Phe Cys Gly Ile Leu Ser Glu Pro Ser Thr Arg Gly Leu Lys Ala
            820                 825                 830

Ala Thr Cys Ile Asn Pro Leu Asn Gly Ser Val Cys Glu Arg Pro Ala
        835                 840                 845

Asn His Ser Ala Lys Gln Cys Arg Thr Pro Cys Ala Leu Arg Thr Ala
            850                 855                 860

Cys Gly Asp Cys Thr Ser Gly Ser Ser Glu Cys Met Trp Cys Ser Asn
865                 870                 875                 880

Met Lys Gln Cys Val Asp Ser Asn Ala Tyr Val Ala Ser Phe Pro Phe
                885                 890                 895

Gly Gln Cys Met Glu Trp Tyr Thr Met Ser Thr Cys Pro Pro Glu Asn
            900                 905                 910

Cys Ser Gly Tyr Cys Thr Cys Ser His Cys Leu Glu Gln Pro Gly Cys
        915                 920                 925

Gly Trp Cys Thr Asp Pro Ser Asn Thr Gly Lys Gly Lys Cys Ile Glu
    930                 935                 940

Gly Ser Tyr Lys Gly Pro Val Lys Met Pro Ser Gln Ala Pro Thr Gly
945                 950                 955                 960

Asn Phe Tyr Pro Gln Pro Leu Leu Asn Ser Ser Met Cys Leu Glu Asp
                965                 970                 975

Ser Arg Tyr Asn Trp Ser Phe Ile His Cys Pro Ala Cys Gln Cys Asn
            980                 985                 990

Gly His Ser Lys Cys Ile Asn Gln Ser Ile Cys Glu Lys Cys Glu Asn
        995                 1000                1005

Leu Thr Thr Gly Lys His Cys Glu Thr Cys Ile Ser Gly Phe Tyr Gly
    1010                1015                1020

Asp Pro Thr Asn Gly Gly Lys Cys Gln Pro Cys Lys Cys Asn Gly His
1025                1030                1035                1040

Ala Ser Leu Cys Asn Thr Asn Thr Gly Lys Cys Phe Cys Thr Thr Lys
                1045                1050                1055

Gly Val Lys Gly Asp Glu Cys Gln Leu Cys Glu Val Glu Asn Arg Tyr
            1060                1065                1070

Gln Gly Asn Pro Leu Arg Gly Thr Cys Tyr Tyr Thr Leu Leu Ile Asp
        1075                1080                1085
```

-continued

```
Tyr Gln Phe Thr Phe Ser Leu Ser Gln Glu Asp Asp Arg Tyr Tyr Thr
    1090                1095                1100

Ala Ile Asn Phe Val Ala Thr Pro Asp Glu Gln Asn Arg Asp Leu Asp
1105                1110                1115                1120

Met Phe Ile Asn Ala Ser Lys Asn Phe Asn Leu Asn Ile Thr Trp Ala
            1125                1130                1135

Ala Ser Phe Ser Ala Gly Thr Gln Ala Gly Glu Glu Met Pro Val Val
            1140                1145                1150

Ser Lys Thr Asn Ile Lys Glu Tyr Lys Asp Ser Phe Ser Asn Glu Lys
        1155                1160                1165

Phe Asp Phe Arg Asn His Pro Asn Ile Thr Phe Phe Val Tyr Val Ser
    1170                1175                1180

Asn Phe Thr Trp Pro Ile Lys Ile Gln Val Gln Thr Glu Gln
1185                1190                1195

<210> SEQ ID NO 36
<211> LENGTH: 1275
<212> TYPE: PRT
<213> ORGANISM: Rattus norvegicus

<400> SEQUENCE: 36

Met Val Ala Ala Ala Ala Ala Glu Ala Thr Glu Ala Arg Leu Arg
 1               5                  10                  15

Gly Tyr Thr Thr Ala Thr Ala Ala Pro Ala Gly Trp Lys Glu Arg Gln
                20                  25                  30

His Arg Pro Cys Ala Ala Thr Gly Ala Trp Arg Pro Trp Pro Arg Ala
            35                  40                  45

Gly Leu Cys Leu Pro Arg Val Leu Ser Arg Ala Leu Ser Pro Pro Pro
        50                  55                  60

Leu Leu Pro Leu Leu Pro Leu Leu Phe Ser Leu Leu Leu Pro Leu
 65                  70                  75                  80

Pro Arg Glu Ala Glu Ala Ala Val Ala Ala Val Ser Gly Ser
                85                  90                  95

Ala Ala Glu Ala Lys Glu Cys Asp Arg Pro Cys Val Asn Gly Gly
            100                 105                 110

Arg Cys Asn Pro Gly Thr Gly Gln Cys Val Cys Pro Thr Gly Trp Val
        115                 120                 125

Gly Glu Gln Cys Gln His Cys Gly Gly Arg Phe Arg Leu Thr Gly Ser
    130                 135                 140

Ser Gly Phe Val Thr Asp Gly Pro Gly Asn Tyr Lys Tyr Lys Thr Lys
145                 150                 155                 160

Cys Thr Trp Leu Ile Glu Gly Gln Pro Asn Lys Ile Met Arg Leu Arg
                165                 170                 175

Phe Asn His Phe Ala Thr Glu Cys Ser Trp Asp His Leu Tyr Val Tyr
            180                 185                 190

Asp Gly Asp Ser Ile Tyr Ala Pro Leu Ile Ala Ala Phe Ser Gly Leu
        195                 200                 205

Ile Val Pro Glu Arg Asp Gly Asn Glu Thr Ala Pro Glu Val Thr Val
    210                 215                 220

Thr Ser Gly Tyr Ala Leu Leu His Phe Phe Ser Asp Ala Ala Tyr Asn
225                 230                 235                 240

Leu Thr Gly Phe Asn Ile Thr Tyr Asn Phe Asp Met Cys Pro Asn Asn
                245                 250                 255

Cys Ser Gly Arg Gly Glu Cys Lys Ser Ser Asn Ser Ser Thr Val
            260                 265                 270
```

```
Glu Cys Glu Cys Ser Glu Asn Trp Lys Gly Glu Ser Cys Asp Ile Pro
        275                 280                 285
His Cys Thr Asp Asn Cys Gly Phe Pro His Arg Gly Ile Cys Asn Ala
        290                 295                 300
Ser Asp Thr Arg Gly Cys Ser Cys Phe Pro His Trp Gln Gly Pro Gly
305                 310                 315                 320
Cys Ser Ile Pro Val Pro Ala Asn Gln Ser Phe Trp Thr Arg Glu Glu
                325                 330                 335
Tyr Ser Asp Leu Lys Leu Pro Arg Ala Ser His Lys Ala Glu Val Asn
            340                 345                 350
Gly Asn Ile Met Trp Val Val Gly Tyr Met Phe Asn His Ser Asp
        355                 360                 365
Tyr Ser Met Val Leu Ala Tyr Asp Leu Ala Ser Arg Glu Trp Leu Ser
        370                 375                 380
Leu Asn His Ser Val Asn Ser Val Val Arg Tyr Gly His Ser Leu
385                 390                 395                 400
Ala Leu His Lys Asp Lys Ile Tyr Met Tyr Gly Gly Lys Ile Asp Ser
            405                 410                 415
Thr Gly Asn Val Thr Asn Glu Leu Arg Val Phe His Ile His Asn Glu
            420                 425                 430
Ser Trp Val Leu Leu Thr Pro Lys Ala Lys Asp Gln Tyr Ala Val Val
        435                 440                 445
Gly His Ser Ala His Ile Val Thr Leu Ser Ser Gly Arg Val Val Met
        450                 455                 460
Leu Val Ile Phe Gly His Cys Pro Leu Tyr Gly Tyr Ile Ser Val Val
465                 470                 475                 480
Gln Glu Tyr Asp Leu Glu Lys Asn Thr Trp Ser Ile Leu Gln Thr Gln
                485                 490                 495
Gly Ala Leu Val Gln Gly Gly Tyr Gly His Ser Ser Val Tyr Asp His
                500                 505                 510
Arg Thr Lys Ala Leu Tyr Val His Gly Gly Tyr Lys Ala Phe Ser Ala
        515                 520                 525
Asn Lys Tyr Arg Leu Ala Asp Asp Leu Tyr Arg Tyr His Val Asp Thr
530                 535                 540
Gln Met Trp Thr Ile Leu Lys Asp Ser Arg Phe Arg Tyr Leu His
545                 550                 555                 560
Thr Ala Val Ile Val Ser Gly Thr Met Leu Val Phe Gly Gly Asn Thr
                565                 570                 575
His Asn Asp Thr Ser Met Ser His Gly Ala Lys Cys Phe Ser Ser Asp
            580                 585                 590
Phe Met Ala Tyr Asp Ile Ala Cys Asp Arg Trp Ser Val Leu Pro Arg
        595                 600                 605
Pro Glu Leu His His Asp Val Asn Arg Phe Gly His Ser Ala Val Leu
        610                 615                 620
His Asn Ser Thr Met Tyr Val Phe Gly Gly Phe Asn Ser Leu Leu Leu
625                 630                 635                 640
Ser Asp Val Leu Val Phe Thr Ser Glu Gln Cys Asp Ala His Arg Ser
                645                 650                 655
Glu Ala Ala Cys Val Ala Ala Gly Pro Gly Ile Arg Cys Leu Trp Asp
            660                 665                 670
Thr Gln Ser Ser Arg Cys Thr Ser Trp Glu Leu Ala Thr Glu Glu Gln
        675                 680                 685
```

-continued

```
Ala Glu Lys Leu Lys Ser Glu Cys Phe Ser Lys Arg Thr Leu Asp His
    690                 695                 700

Asp Arg Cys Asp Gln His Thr Asp Cys Tyr Ser Cys Thr Ala Asn Thr
705                 710                 715                 720

Asn Asp Cys His Trp Cys Asn Asp His Cys Val Pro Val Asn His Ser
            725                 730                 735

Cys Thr Glu Gly Gln Ile Ser Ile Ala Lys Tyr Asp Asn Cys Pro Lys
            740                 745                 750

Asp Asn Pro Met Tyr Tyr Cys Asn Lys Lys Thr Ser Cys Arg Ser Cys
            755                 760                 765

Ala Leu Asp Gln Asn Cys Gln Trp Glu Pro Arg Asn Gln Glu Cys Ile
    770                 775                 780

Ala Leu Pro Glu Asn Ile Cys Gly Ile Gly Trp His Leu Val Gly Asn
785                 790                 795                 800

Ser Cys Leu Lys Ile Thr Thr Ala Lys Glu Asn Tyr Asp Asn Ala Lys
            805                 810                 815

Leu Ser Cys Arg Asn His Asn Ala Phe Leu Ala Ser Leu Thr Ser Gln
            820                 825                 830

Lys Lys Val Glu Phe Val Leu Lys Gln Leu Arg Leu Met Gln Ser Ser
    835                 840                 845

Gln Ser Thr Ser Lys Leu Thr Leu Thr Pro Trp Val Gly Leu Arg Lys
850                 855                 860

Ile Asn Val Ser Tyr Trp Cys Trp Glu Asp Met Ser Pro Phe Thr Asn
865                 870                 875                 880

Ser Leu Leu Gln Trp Met Pro Ser Glu Pro Ser Asp Ala Gly Phe Cys
            885                 890                 895

Gly Ile Leu Ser Glu Pro Ser Thr Arg Gly Leu Lys Ala Ala Thr Cys
            900                 905                 910

Ile Asn Pro Leu Asn Gly Ser Val Cys Glu Arg Pro Ala Asn His Ser
    915                 920                 925

Ala Lys Gln Cys Arg Thr Pro Cys Ala Leu Arg Thr Ala Cys Gly Glu
    930                 935                 940

Cys Thr Ser Ser Ser Glu Cys Met Trp Cys Ser Asn Met Lys Gln
945                 950                 955                 960

Cys Val Asp Ser Asn Ala Tyr Val Ala Ser Phe Pro Phe Gly Gln Cys
            965                 970                 975

Met Glu Trp Tyr Thr Met Ser Ser Cys Pro Pro Glu Asn Cys Ser Gly
            980                 985                 990

Tyr Cys Thr Cys Ser His Cys Leu Glu Gln Pro Gly Cys Gly Trp Cys
            995                 1000                1005

Thr Asp Pro Ser Asn Thr Gly Lys Gly Lys Cys Ile Glu Gly Ser Tyr
    1010                1015                1020

Lys Gly Pro Val Lys Met Pro Ser His Ala Ser Thr Gly Asn Val Tyr
1025                1030                1035                1040

Pro Gln Pro Leu Leu Asn Ser Ser Met Cys Leu Glu Asp Ser Arg Tyr
            1045                1050                1055

Asn Trp Ser Phe Ile His Cys Pro Ala Cys Gln Cys Asn Gly His Ser
            1060                1065                1070

Lys Cys Ile Asn Gln Ser Ile Cys Glu Lys Cys Glu Asp Leu Thr Thr
    1075                1080                1085

Gly Lys His Cys Glu Thr Cys Ile Ser Gly Phe Tyr Gly Asp Pro Thr
    1090                1095                1100

Asn Gly Gly Lys Cys Gln Pro Cys Lys Cys Asn Gly His Ala Ser Leu
```

```
                1105                1110                1115                1120
Cys Asn Thr Asn Thr Gly Lys Cys Phe Cys Thr Thr Lys Gly Val Lys
                    1125                1130                1135
Gly Glu Glu Cys Gln Leu Cys Glu Val Glu Asn Arg Tyr Gln Gly Asn
            1140                1145                1150
Pro Leu Lys Gly Thr Cys Tyr Tyr Thr Leu Leu Ile Asp Tyr Gln Phe
        1155                1160                1165
Thr Phe Ser Leu Ser Gln Glu Asp Asp Arg Tyr Tyr Thr Ala Ile Asn
    1170                1175                1180
Phe Val Ala Thr Pro Asp Glu Gln Asn Arg Asp Leu Asp Met Phe Ile
1185                1190                1195                1200
Asn Ala Ser Lys Asn Phe Asn Leu Asn Ile Thr Trp Ala Thr Ser Phe
                1205                1210                1215
Pro Ala Gly Thr Gln Thr Gly Glu Glu Val Pro Val Val Ser Lys Thr
            1220                1225                1230
Asn Ile Lys Glu Tyr Lys Asp Ser Phe Ser Asn Glu Lys Phe Asp Phe
        1235                1240                1245
Arg Asn His Pro Asn Ile Thr Phe Phe Val Tyr Val Ser Asn Phe Thr
    1250                1255                1260
Trp Pro Ile Lys Ile Gln Val Arg Val Thr Ser
1265                1270                1275

<210> SEQ ID NO 37
<211> LENGTH: 883
<212> TYPE: PRT
<213> ORGANISM: Homo sapiens

<400> SEQUENCE: 37

Met Leu Glu Met Asn Ala Arg Ser Leu Gln Gln Lys Leu Glu Thr Glu
 1               5                   10                  15
Arg Glu Leu Lys Gln Arg Leu Leu Glu Glu Ala Lys Leu Gln Gln
            20                  25                  30
Gln Met Asp Leu Gln Lys Asn His Ile Phe Arg Leu Thr Gln Gly Leu
        35                  40                  45
Gln Glu Ala Leu Asp Arg Ala Asp Leu Leu Lys Thr Glu Arg Ser Asp
    50                  55                  60
Leu Glu Tyr Gln Leu Glu Asn Ile Gln Val Leu Tyr Ser His Glu Lys
65                  70                  75                  80
Val Lys Met Glu Gly Thr Ile Ser Gln Gln Thr Lys Leu Ile Asp Phe
                85                  90                  95
Leu Gln Ala Lys Met Asp Gln Pro Ala Lys Lys Lys Val Pro Leu
            100                 105                 110
Gln Tyr Asn Glu Leu Lys Leu Ala Leu Glu Lys Glu Lys Ala Arg Cys
        115                 120                 125
Ala Glu Leu Glu Glu Ala Leu Gln Lys Thr Arg Ile Glu Leu Arg Ser
    130                 135                 140
Ala Arg Glu Glu Ala Ala His Arg Lys Ala Thr Asp His Pro His Pro
145                 150                 155                 160
Ser Thr Pro Ala Thr Ala Arg Gln Gln Ile Ala Met Ser Ala Ile Val
                165                 170                 175
Arg Ser Pro Glu His Gln Pro Ser Ala Met Ser Leu Leu Ala Pro Pro
            180                 185                 190
Ser Ser Arg Arg Lys Glu Ser Ser Thr Pro Glu Glu Phe Ser Arg Arg
        195                 200                 205
```

-continued

```
Leu Lys Glu Arg Met His His Asn Ile Pro His Arg Phe Asn Val Gly
210                 215                 220
Leu Asn Met Arg Ala Thr Lys Cys Ala Val Cys Leu Asp Thr Val His
225                 230                 235                 240
Phe Gly Arg Gln Ala Ser Lys Cys Leu Glu Cys Gln Val Met Cys His
                    245                 250                 255
Pro Lys Cys Ser Thr Cys Leu Pro Ala Thr Cys Gly Leu Pro Ala Glu
                260                 265                 270
Tyr Ala Thr His Phe Thr Glu Ala Phe Cys Arg Asp Lys Met Asn Ser
            275                 280                 285
Pro Gly Leu Gln Thr Lys Glu Pro Ser Ser Leu His Leu Glu Gly
290                 295                 300
Trp Met Lys Val Pro Arg Asn Asn Lys Arg Gly Gln Gln Gly Trp Asp
305                 310                 315                 320
Arg Lys Tyr Ile Val Leu Glu Gly Ser Lys Val Leu Ile Tyr Asp Asn
                    325                 330                 335
Glu Ala Arg Glu Ala Gly Gln Arg Pro Val Glu Glu Phe Glu Leu Cys
                340                 345                 350
Leu Pro Asp Gly Asp Val Ser Ile His Gly Ala Val Gly Ala Ser Glu
            355                 360                 365
Leu Ala Asn Thr Ala Lys Ala Asp Val Pro Tyr Ile Leu Lys Met Glu
370                 375                 380
Ser His Pro His Thr Thr Cys Trp Pro Gly Arg Thr Leu Tyr Leu Leu
385                 390                 395                 400
Ala Pro Ser Phe Pro Asp Lys Gln Arg Trp Val Thr Ala Leu Glu Ser
                    405                 410                 415
Val Val Ala Gly Gly Arg Val Ser Arg Glu Lys Ala Glu Ala Asp Ala
                420                 425                 430
Lys Leu Leu Gly Asn Ser Leu Leu Lys Leu Glu Gly Asp Asp Arg Leu
            435                 440                 445
Asp Met Asn Cys Thr Leu Pro Phe Ser Asp Gln Val Val Leu Val Gly
450                 455                 460
Thr Glu Glu Gly Leu Tyr Ala Leu Asn Val Leu Lys Asn Ser Leu Thr
465                 470                 475                 480
His Val Pro Gly Ile Gly Ala Val Phe Gln Ile Tyr Ile Ile Lys Asp
                    485                 490                 495
Leu Glu Lys Leu Leu Met Ile Ala Gly Glu Glu Arg Ala Leu Cys Leu
                500                 505                 510
Val Asp Val Lys Lys Val Lys Gln Ser Leu Ala Gln Ser His Leu Pro
            515                 520                 525
Ala Gln Pro Asp Ile Ser Pro Asn Ile Phe Glu Ala Val Lys Gly Cys
530                 535                 540
His Leu Phe Gly Ala Gly Lys Ile Glu Asn Gly Leu Cys Ile Cys Ala
545                 550                 555                 560
Ala Met Pro Ser Lys Val Val Ile Leu Arg Tyr Asn Glu Asn Leu Ser
                    565                 570                 575
Lys Tyr Cys Ile Arg Lys Glu Ile Glu Thr Ser Glu Pro Cys Ser Cys
                580                 585                 590
Ile His Phe Thr Asn Tyr Ser Ile Leu Ile Gly Thr Asn Lys Phe Tyr
            595                 600                 605
Glu Ile Asp Met Lys Gln Tyr Thr Leu Glu Glu Phe Leu Asp Lys Asn
610                 615                 620
Asp His Ser Leu Ala Pro Ala Val Phe Ala Ala Ser Ser Asn Ser Phe
```

```
                625                 630                 635                 640
Pro Val Ser Ile Val Gln Val Asn Ser Ala Gly Gln Arg Glu Glu Tyr
                    645                 650                 655
Leu Leu Cys Phe His Glu Phe Gly Val Phe Val Asp Ser Tyr Gly Arg
                660                 665                 670
Arg Ser Arg Thr Asp Asp Leu Lys Trp Ser Arg Leu Pro Leu Ala Phe
            675                 680                 685
Ala Tyr Arg Glu Pro Tyr Leu Phe Val Thr His Phe Asn Ser Leu Glu
        690                 695                 700
Val Ile Glu Ile Gln Ala Arg Ser Ser Ala Gly Thr Pro Ala Arg Ala
705                 710                 715                 720
Tyr Leu Asp Ile Pro Asn Pro Arg Tyr Leu Gly Pro Ala Ile Ser Ser
                    725                 730                 735
Gly Ala Ile Tyr Leu Ala Ser Ser Tyr Gln Asp Lys Leu Arg Val Ile
                740                 745                 750
Cys Cys Lys Gly Asn Leu Val Lys Glu Ser Gly Thr Glu His His Arg
            755                 760                 765
Gly Pro Ser Thr Ser Arg Ser Ser Pro Asn Lys Arg Gly Pro Pro Thr
        770                 775                 780
Tyr Asn Glu His Ile Thr Lys Arg Val Ala Ser Ser Pro Ala Pro Pro
785                 790                 795                 800
Glu Gly Pro Ser His Pro Arg Glu Pro Ser Thr Pro His Arg Tyr Arg
                    805                 810                 815
Glu Gly Arg Thr Glu Leu Arg Arg Asp Lys Ser Pro Gly Arg Pro Leu
                820                 825                 830
Glu Arg Glu Lys Ser Pro Gly Arg Met Leu Ser Thr Arg Arg Glu Arg
            835                 840                 845
Ser Pro Gly Arg Leu Phe Glu Asp Ser Ser Arg Gly Arg Leu Pro Ala
        850                 855                 860
Gly Ala Val Arg Thr Pro Leu Ser Gln Val Asn Lys Val Trp Asp Gln
865                 870                 875                 880
Ser Ser Val

<210> SEQ ID NO 38
<211> LENGTH: 1286
<212> TYPE: PRT
<213> ORGANISM: Homo sapiens

<400> SEQUENCE: 38

Val Leu Asp Asn Gln Ile Lys Lys Asp Leu Ala Asp Lys Glu Thr Leu
  1               5                  10                  15
Glu Asn Met Met Gln Arg His Glu Glu Ala His Glu Lys Gly Lys
                20                  25                  30
Ile Leu Ser Glu Gln Lys Ala Met Ile Asn Ala Met Asp Ser Lys Ile
            35                  40                  45
Arg Ser Leu Glu Gln Arg Ile Val Glu Leu Ser Glu Ala Asn Lys Leu
        50                  55                  60
Ala Ala Asn Ser Ser Leu Phe Thr Gln Arg Asn Met Lys Ala Gln Glu
 65                  70                  75                  80
Glu Met Ile Ser Glu Leu Arg Gln Gln Lys Phe Tyr Leu Glu Thr Gln
                85                  90                  95
Ala Gly Lys Leu Glu Ala Gln Asn Arg Lys Leu Glu Glu Gln Leu Glu
            100                 105                 110
Lys Ile Ser His Gln Asp His Ser Asp Lys Asn Arg Leu Leu Glu Leu
```

```
                115                 120                 125
Glu Thr Arg Leu Arg Glu Val Ser Leu Glu His Glu Glu Gln Lys Leu
    130                 135                 140
Glu Leu Lys Arg Gln Leu Thr Glu Leu Gln Leu Ser Leu Gln Glu Arg
145                 150                 155                 160
Glu Ser Gln Leu Thr Ala Leu Gln Ala Ala Arg Ala Ala Leu Glu Ser
                165                 170                 175
Gln Leu Arg Gln Ala Lys Thr Glu Leu Glu Glu Thr Thr Ala Glu Ala
            180                 185                 190
Glu Glu Glu Ile Gln Ala Leu Thr Ala His Arg Asp Glu Ile Gln Arg
        195                 200                 205
Lys Phe Asp Ala Leu Arg Asn Ser Cys Thr Val Ile Thr Asp Leu Glu
    210                 215                 220
Glu Gln Leu Asn Gln Leu Thr Glu Asp Asn Ala Glu Leu Asn Asn Gln
225                 230                 235                 240
Asn Phe Tyr Leu Ser Lys Gln Leu Asp Glu Ala Ser Gly Ala Asn Asp
                245                 250                 255
Glu Ile Val Gln Leu Arg Ser Glu Val Asp His Leu Arg Arg Glu Ile
            260                 265                 270
Thr Glu Arg Glu Met Gln Leu Thr Ser Gln Lys Gln Thr Met Glu Ala
        275                 280                 285
Leu Lys Thr Thr Cys Thr Met Leu Glu Glu Gln Val Met Asp Leu Glu
    290                 295                 300
Ala Leu Asn Asp Glu Leu Leu Glu Lys Glu Arg Gln Trp Glu Ala Trp
305                 310                 315                 320
Arg Ser Val Leu Gly Asp Glu Lys Ser Gln Phe Glu Cys Arg Val Arg
                325                 330                 335
Glu Leu Gln Arg Met Leu Asp Thr Glu Lys Gln Ser Arg Ala Arg Ala
            340                 345                 350
Asp Gln Arg Ile Thr Glu Ser Arg Gln Val Val Glu Leu Ala Val Lys
        355                 360                 365
Glu His Lys Ala Glu Ile Leu Ala Leu Gln Gln Ala Leu Lys Glu Gln
    370                 375                 380
Lys Leu Lys Ala Glu Ser Leu Ser Asp Lys Leu Asn Asp Leu Glu Lys
385                 390                 395                 400
Lys His Ala Met Leu Glu Met Asn Ala Arg Ser Leu Gln Gln Lys Leu
                405                 410                 415
Glu Thr Glu Arg Glu Leu Lys Gln Arg Leu Leu Glu Glu Gln Ala Lys
            420                 425                 430
Leu Gln Gln Gln Met Asp Leu Gln Lys Asn His Ile Phe Arg Leu Thr
        435                 440                 445
Gln Gly Leu Gln Glu Ala Leu Asp Arg Ala Asp Leu Leu Lys Thr Glu
    450                 455                 460
Arg Ser Asp Leu Glu Tyr Gln Leu Glu Asn Ile Gln Val Leu Tyr Ser
465                 470                 475                 480
His Glu Lys Val Lys Met Glu Gly Thr Ile Ser Gln Gln Thr Lys Leu
                485                 490                 495
Ile Asp Phe Leu Gln Ala Lys Met Asp Gln Pro Ala Lys Lys Lys Lys
            500                 505                 510
Val Pro Leu Gln Tyr Asn Glu Leu Lys Leu Ala Leu Glu Lys Glu Lys
        515                 520                 525
Ala Arg Cys Ala Glu Leu Glu Glu Ala Leu Gln Lys Thr Arg Ile Glu
    530                 535                 540
```

-continued

```
Leu Arg Ser Ala Arg Glu Glu Ala Ala His Arg Lys Ala Thr Asp His
545                 550                 555                 560

Pro His Pro Ser Thr Pro Ala Thr Ala Arg Gln Gln Ile Ala Met Ser
            565                 570                 575

Ala Ile Val Arg Ser Pro Glu His Gln Pro Ser Ala Met Ser Leu Leu
                580                 585                 590

Ala Pro Pro Ser Ser Arg Arg Lys Glu Ser Ser Thr Pro Glu Glu Phe
            595                 600                 605

Ser Arg Arg Leu Lys Glu Arg Met His His Asn Ile Pro His Arg Phe
    610                 615                 620

Asn Val Gly Leu Asn Met Arg Ala Thr Lys Cys Ala Val Cys Leu Asp
625                 630                 635                 640

Thr Val His Phe Gly Arg Gln Ala Ser Lys Cys Leu Glu Cys Gln Val
                645                 650                 655

Met Cys His Pro Lys Cys Ser Thr Cys Leu Pro Ala Thr Cys Gly Leu
            660                 665                 670

Pro Ala Glu Tyr Ala Thr His Phe Thr Glu Ala Phe Cys Arg Asp Lys
            675                 680                 685

Met Asn Ser Pro Gly Leu Gln Thr Lys Glu Pro Ser Ser Ser Leu His
690                 695                 700

Leu Glu Gly Trp Met Lys Val Pro Arg Asn Asn Lys Arg Gly Gln Gln
705                 710                 715                 720

Gly Trp Asp Arg Lys Tyr Ile Val Leu Glu Gly Ser Lys Val Leu Ile
            725                 730                 735

Tyr Asp Asn Glu Ala Arg Glu Ala Gly Gln Arg Pro Val Glu Glu Phe
            740                 745                 750

Glu Leu Cys Leu Pro Asp Gly Asp Val Ser Ile His Gly Ala Val Gly
    755                 760                 765

Ala Ser Glu Leu Ala Asn Thr Ala Lys Ala Asp Val Pro Tyr Ile Leu
770                 775                 780

Lys Met Glu Ser His Pro His Thr Thr Cys Trp Pro Gly Arg Thr Leu
785                 790                 795                 800

Tyr Leu Leu Ala Pro Ser Phe Pro Asp Lys Gln Arg Trp Val Thr Ala
            805                 810                 815

Leu Glu Ser Val Val Ala Gly Arg Val Ser Arg Glu Lys Ala Glu
            820                 825                 830

Ala Asp Ala Lys Leu Leu Gly Asn Ser Leu Leu Lys Leu Glu Gly Asp
    835                 840                 845

Asp Arg Leu Asp Met Asn Cys Thr Leu Pro Phe Ser Asp Gln Val Val
850                 855                 860

Leu Val Gly Thr Glu Glu Gly Leu Tyr Ala Leu Asn Val Leu Lys Asn
865                 870                 875                 880

Ser Leu Thr His Val Pro Gly Ile Gly Ala Val Phe Gln Ile Tyr Ile
            885                 890                 895

Ile Lys Asp Leu Glu Lys Leu Leu Met Ile Ala Gly Glu Glu Arg Ala
            900                 905                 910

Leu Cys Leu Val Asp Val Lys Val Lys Gln Ser Leu Ala Gln Ser
    915                 920                 925

His Leu Pro Ala Gln Pro Asp Ile Ser Pro Asn Ile Phe Glu Ala Val
    930                 935                 940

Lys Gly Cys His Leu Phe Gly Ala Gly Lys Ile Glu Asn Gly Leu Cys
945                 950                 955                 960
```

```
Ile Cys Ala Ala Met Pro Ser Lys Val Val Ile Leu Arg Tyr Asn Glu
                965                 970                 975
Asn Leu Ser Lys Tyr Cys Ile Arg Lys Glu Ile Glu Thr Ser Glu Pro
            980                 985                 990
Cys Ser Cys Ile His Phe Thr Asn Tyr Ser Ile Leu Ile Gly Thr Asn
        995                 1000                1005
Lys Phe Tyr Glu Ile Asp Met Lys Gln Tyr Thr Leu Glu Glu Phe Leu
    1010                1015                1020
Asp Lys Asn Asp His Ser Leu Ala Pro Ala Val Phe Ala Ala Ser Ser
1025                1030                1035                1040
Asn Ser Phe Pro Val Ser Ile Val Gln Val Asn Ser Ala Gly Gln Arg
                1045                1050                1055
Glu Glu Tyr Leu Leu Cys Phe His Glu Phe Gly Val Phe Val Asp Ser
            1060                1065                1070
Tyr Gly Arg Arg Ser Arg Thr Asp Asp Leu Lys Trp Ser Arg Leu Pro
        1075                1080                1085
Leu Ala Phe Ala Tyr Arg Glu Pro Tyr Leu Phe Val Thr His Phe Asn
    1090                1095                1100
Ser Leu Glu Val Ile Glu Ile Gln Ala Arg Ser Ser Ala Gly Thr Pro
1105                1110                1115                1120
Ala Arg Ala Tyr Leu Asp Ile Pro Asn Pro Arg Tyr Leu Gly Pro Ala
                1125                1130                1135
Ile Ser Ser Gly Ala Ile Tyr Leu Ala Ser Ser Tyr Gln Asp Lys Leu
            1140                1145                1150
Arg Val Ile Cys Cys Lys Gly Asn Leu Val Lys Glu Ser Gly Thr Glu
        1155                1160                1165
His His Arg Gly Pro Ser Thr Ser Arg Ser Ser Pro Asn Lys Arg Gly
    1170                1175                1180
Pro Pro Thr Tyr Asn Glu His Ile Thr Lys Arg Val Ala Ser Ser Pro
1185                1190                1195                1200
Ala Pro Pro Glu Gly Pro Ser His Pro Arg Glu Pro Ser Thr Pro His
                1205                1210                1215
Arg Tyr Arg Glu Gly Arg Thr Glu Leu Arg Arg Asp Lys Ser Pro Gly
            1220                1225                1230
Arg Pro Leu Glu Arg Glu Lys Ser Pro Gly Arg Met Leu Ser Thr Arg
        1235                1240                1245
Arg Glu Arg Ser Pro Gly Arg Leu Phe Glu Asp Ser Ser Arg Gly Arg
    1250                1255                1260
Leu Pro Ala Gly Ala Val Arg Thr Pro Leu Ser Gln Val Asn Lys Val
1265                1270                1275                1280
Trp Asp Gln Ser Ser Val
            1285

<210> SEQ ID NO 39
<211> LENGTH: 940
<212> TYPE: PRT
<213> ORGANISM: Homo sapiens

<400> SEQUENCE: 39

Gln Ser Arg Ala Arg Ala Asp Gln Arg Ile Thr Glu Ser Arg Gln Val
 1               5                  10                  15
Val Glu Leu Ala Val Lys Glu His Lys Ala Glu Ile Leu Ala Leu Gln
            20                  25                  30
Gln Ala Leu Lys Glu Gln Lys Leu Lys Ala Glu Ser Leu Ser Asp Lys
        35                  40                  45
```

```
Leu Asn Asp Leu Glu Lys Lys His Ala Met Leu Glu Met Asn Ala Arg
 50                  55                  60

Ser Leu Gln Gln Lys Leu Glu Thr Glu Arg Glu Leu Lys Gln Arg Leu
 65                  70                  75                  80

Leu Glu Glu Gln Ala Lys Leu Gln Gln Met Asp Leu Gln Lys Asn
                 85                  90                  95

His Ile Phe Arg Leu Thr Gln Gly Leu Gln Ala Leu Asp Arg Ala
            100                 105                 110

Asp Leu Leu Lys Thr Glu Arg Ser Asp Leu Glu Tyr Gln Leu Glu Asn
            115                 120                 125

Ile Gln Val Leu Tyr Ser His Glu Lys Val Lys Met Glu Gly Thr Ile
    130                 135                 140

Ser Gln Gln Thr Lys Leu Ile Asp Phe Leu Gln Ala Lys Met Asp Gln
145                 150                 155                 160

Pro Ala Lys Lys Lys Val Pro Leu Gln Tyr Asn Glu Leu Lys Leu
                165                 170                 175

Ala Leu Glu Lys Glu Lys Ala Arg Cys Ala Glu Leu Glu Glu Ala Leu
            180                 185                 190

Gln Lys Thr Arg Ile Glu Leu Arg Ser Ala Arg Glu Glu Ala Ala His
    195                 200                 205

Arg Lys Ala Thr Asp His Pro His Pro Ser Thr Pro Ala Thr Ala Arg
210                 215                 220

Gln Gln Ile Ala Met Ser Ala Ile Val Arg Ser Pro Glu His Gln Pro
225                 230                 235                 240

Ser Ala Met Ser Leu Leu Ala Pro Pro Ser Ser Arg Arg Lys Glu Ser
                245                 250                 255

Ser Thr Pro Glu Glu Phe Ser Arg Arg Leu Lys Glu Arg Met His His
            260                 265                 270

Asn Ile Pro His Arg Phe Asn Val Gly Leu Asn Met Arg Ala Thr Lys
            275                 280                 285

Cys Ala Val Cys Leu Asp Thr Val His Phe Gly Arg Gln Ala Ser Lys
290                 295                 300

Cys Leu Glu Cys Gln Val Met Cys His Pro Lys Cys Ser Thr Cys Leu
305                 310                 315                 320

Pro Ala Thr Cys Gly Leu Pro Ala Glu Tyr Ala Thr His Phe Thr Glu
                325                 330                 335

Ala Phe Cys Arg Asp Lys Met Asn Ser Pro Gly Leu Gln Thr Lys Glu
            340                 345                 350

Pro Ser Ser Ser Leu His Leu Glu Gly Trp Met Lys Val Pro Arg Asn
            355                 360                 365

Asn Lys Arg Gly Gln Gln Gly Trp Asp Arg Lys Tyr Ile Val Leu Glu
    370                 375                 380

Gly Ser Lys Val Leu Ile Tyr Asp Asn Glu Ala Arg Glu Ala Gly Gln
385                 390                 395                 400

Arg Pro Val Glu Glu Phe Glu Leu Cys Leu Pro Asp Gly Asp Val Ser
                405                 410                 415

Ile His Gly Ala Val Gly Ala Ser Glu Leu Ala Asn Thr Ala Lys Ala
            420                 425                 430

Asp Val Pro Tyr Ile Leu Lys Met Glu Ser His Pro His Thr Thr Cys
            435                 440                 445

Trp Pro Gly Arg Thr Leu Tyr Leu Leu Ala Pro Ser Phe Pro Asp Lys
450                 455                 460
```

-continued

```
Gln Arg Trp Val Thr Ala Leu Glu Ser Val Val Ala Gly Gly Arg Val
465                 470                 475                 480

Ser Arg Glu Lys Ala Glu Ala Asp Ala Lys Leu Leu Gly Asn Ser Leu
            485                 490                 495

Leu Lys Leu Glu Gly Asp Asp Arg Leu Asp Met Asn Cys Thr Leu Pro
            500                 505                 510

Phe Ser Asp Gln Val Val Leu Val Gly Thr Glu Glu Gly Leu Tyr Ala
            515                 520                 525

Leu Asn Val Leu Lys Asn Ser Leu Thr His Val Pro Gly Ile Gly Ala
            530                 535                 540

Val Phe Gln Ile Tyr Ile Lys Asp Leu Glu Lys Leu Leu Met Ile
545                 550                 555                 560

Ala Gly Glu Glu Arg Ala Leu Cys Leu Val Asp Val Lys Lys Val Lys
                565                 570                 575

Gln Ser Leu Ala Gln Ser His Leu Pro Ala Gln Pro Asp Ile Ser Pro
            580                 585                 590

Asn Ile Phe Glu Ala Val Lys Gly Cys His Leu Phe Gly Ala Gly Lys
            595                 600                 605

Ile Glu Asn Gly Leu Cys Ile Cys Ala Ala Met Pro Ser Lys Val Val
            610                 615                 620

Ile Leu Arg Tyr Asn Glu Asn Leu Ser Lys Tyr Cys Ile Arg Lys Glu
625                 630                 635                 640

Ile Glu Thr Ser Glu Pro Cys Ser Cys Ile His Phe Thr Asn Tyr Ser
                645                 650                 655

Ile Leu Ile Gly Thr Asn Lys Phe Tyr Glu Ile Asp Met Lys Gln Tyr
            660                 665                 670

Thr Leu Glu Glu Phe Leu Asp Lys Asn Asp His Ser Leu Ala Pro Ala
            675                 680                 685

Val Phe Ala Ala Ser Ser Asn Ser Phe Pro Val Ser Ile Val Gln Val
690                 695                 700

Asn Ser Ala Gly Gln Arg Glu Glu Tyr Leu Leu Cys Phe His Glu Phe
705                 710                 715                 720

Gly Val Phe Val Asp Ser Tyr Gly Arg Arg Ser Arg Thr Asp Asp Leu
                725                 730                 735

Lys Trp Ser Arg Leu Pro Leu Ala Phe Ala Tyr Arg Glu Pro Tyr Leu
            740                 745                 750

Phe Val Thr His Phe Asn Ser Leu Glu Val Ile Glu Ile Gln Ala Arg
            755                 760                 765

Ser Ser Ala Gly Thr Pro Ala Arg Ala Tyr Leu Asp Ile Pro Asn Pro
770                 775                 780

Arg Tyr Leu Gly Pro Ala Ile Ser Ser Gly Ala Ile Tyr Leu Ala Ser
785                 790                 795                 800

Ser Tyr Gln Asp Lys Leu Arg Val Ile Cys Cys Lys Gly Asn Leu Val
                805                 810                 815

Lys Glu Ser Gly Thr Glu His His Arg Gly Pro Ser Thr Ser Arg Ser
            820                 825                 830

Ser Pro Asn Lys Arg Gly Pro Pro Thr Tyr Asn Glu His Ile Thr Lys
            835                 840                 845

Arg Val Ala Ser Ser Pro Ala Pro Pro Glu Gly Pro Ser His Pro Arg
850                 855                 860

Glu Pro Ser Thr Pro His Arg Tyr Arg Glu Gly Arg Thr Glu Leu Arg
865                 870                 875                 880

Arg Asp Lys Ser Pro Gly Arg Pro Leu Glu Arg Glu Lys Ser Pro Gly
```

-continued

```
                   885                 890                 895
Arg Met Leu Ser Thr Arg Arg Glu Arg Ser Pro Gly Arg Leu Phe Glu
            900                 905                 910

Asp Ser Ser Arg Gly Arg Leu Pro Ala Gly Ala Val Arg Thr Pro Leu
            915                 920                 925

Ser Gln Val Asn Lys Val Trp Asp Gln Ser Ser Val
            930                 935                 940

<210> SEQ ID NO 40
<211> LENGTH: 1641
<212> TYPE: PRT
<213> ORGANISM: Mus musculus

<400> SEQUENCE: 40

Pro Phe Val Pro Thr Leu Lys Ser Asp Asp Thr Ser Asn Phe Asp
 1               5                  10                  15

Glu Pro Glu Lys Asn Ser Trp Val Ser Ser Val Cys Gln Leu Ser
                20                  25                  30

Pro Ser Gly Phe Ser Gly Glu Glu Leu Pro Phe Val Gly Phe Ser Tyr
            35                  40                  45

Ser Lys Ala Leu Gly Tyr Leu Gly Arg Ser Glu Ser Val Val Ser Ser
        50                  55                  60

Leu Asp Ser Pro Ala Lys Val Ser Ser Met Glu Lys Lys Leu Leu Ile
 65                  70                  75                  80

Lys Ser Lys Glu Leu Gln Asp Ser Gln Asp Lys Cys His Lys Met Glu
                85                  90                  95

Gln Glu Met Thr Arg Leu His Arg Arg Val Ser Glu Val Glu Ala Val
            100                 105                 110

Leu Ser Gln Lys Glu Val Glu Leu Lys Ala Ser Glu Thr Gln Arg Ser
        115                 120                 125

Leu Leu Glu Gln Asp Leu Ala Thr Tyr Ile Thr Glu Cys Ser Ser Leu
    130                 135                 140

Lys Arg Ser Leu Glu Gln Ala Arg Met Glu Val Ser Gln Glu Asp Asp
145                 150                 155                 160

Lys Ala Leu Gln Leu Leu His Asp Ile Arg Glu Gln Ser Arg Lys Leu
                165                 170                 175

Gln Glu Ile Lys Glu Gln Glu Tyr Gln Ala Gln Val Glu Glu Met Arg
            180                 185                 190

Leu Met Met Asn Gln Leu Glu Glu Asp Leu Val Ser Ala Arg Arg Arg
        195                 200                 205

Ser Asp Leu Tyr Glu Ser Glu Leu Arg Glu Ser Arg Leu Ala Ala Glu
    210                 215                 220

Glu Phe Lys Arg Lys Ala Asn Glu Cys Gln His Lys Leu Met Lys Ala
225                 230                 235                 240

Lys Asp Gln Gly Lys Pro Glu Val Gly Glu Tyr Ser Lys Leu Glu Lys
                245                 250                 255

Ile Asn Ala Glu Gln Gln Leu Lys Ile Gln Glu Leu Gln Glu Lys Leu
            260                 265                 270

Glu Lys Ala Val Lys Ala Ser Thr Glu Ala Thr Glu Leu Leu Gln Asn
        275                 280                 285

Ile Arg Gln Ala Lys Glu Arg Ala Glu Arg Glu Leu Glu Lys Leu His
    290                 295                 300

Asn Arg Glu Asp Ser Ser Glu Gly Ile Lys Lys Lys Leu Val Glu Ala
305                 310                 315                 320
```

-continued

```
Glu Glu Leu Glu Glu Lys His Arg Glu Ala Gln Val Ser Ala Gln His
                325                 330                 335

Leu Glu Val His Leu Lys Gln Lys Glu Gln His Tyr Glu Glu Lys Ile
                340                 345                 350

Lys Val Leu Asp Asn Gln Ile Lys Lys Asp Leu Ala Asp Lys Glu Ser
                355                 360                 365

Leu Glu Asn Met Met Gln Arg His Glu Glu Ala His Glu Lys Gly
        370                 375                 380

Lys Ile Leu Ser Glu Gln Lys Ala Met Ile Asn Ala Met Asp Ser Lys
385                 390                 395                 400

Ile Arg Ser Leu Glu Gln Arg Ile Val Glu Leu Ser Glu Ala Asn Lys
                405                 410                 415

Leu Ala Ala Asn Ser Ser Leu Phe Thr Gln Arg Asn Met Lys Ala Gln
                420                 425                 430

Glu Glu Met Ile Ser Glu Leu Arg Gln Gln Lys Phe Tyr Leu Glu Thr
                435                 440                 445

Gln Ala Gly Lys Leu Glu Ala Gln Asn Arg Lys Leu Glu Glu Gln Leu
        450                 455                 460

Glu Lys Ile Ser His Gln Asp His Ser Asp Lys Ser Arg Leu Leu Glu
465                 470                 475                 480

Leu Glu Thr Arg Leu Arg Glu Val Ser Leu Glu His Glu Glu Gln Lys
                485                 490                 495

Leu Glu Leu Lys Arg Gln Leu Thr Glu Leu Gln Leu Ser Leu Gln Glu
                500                 505                 510

Arg Glu Ser Gln Leu Thr Ala Leu Gln Ala Ala Arg Ala Ala Leu Glu
                515                 520                 525

Ser Gln Leu Arg Gln Ala Lys Thr Glu Leu Glu Glu Thr Thr Ala Glu
        530                 535                 540

Ala Glu Glu Glu Ile Gln Ala Leu Thr Ala His Arg Asp Glu Ile Gln
545                 550                 555                 560

Arg Lys Phe Asp Ala Leu Arg Asn Ser Cys Thr Val Ile Thr Asp Leu
                565                 570                 575

Glu Glu Gln Leu Asn Gln Leu Thr Glu Asp Asn Ala Glu Leu Asn Asn
                580                 585                 590

Gln Asn Phe Tyr Leu Ser Lys Gln Leu Asp Glu Ala Ser Gly Ala Asn
        595                 600                 605

Asp Glu Ile Val Gln Leu Arg Ser Glu Val Asp His Leu Arg Arg Glu
        610                 615                 620

Ile Thr Glu Arg Glu Met Gln Leu Thr Ser Gln Lys Gln Thr Met Glu
625                 630                 635                 640

Ala Leu Lys Thr Thr Cys Thr Met Leu Glu Glu Gln Val Leu Asp Leu
                645                 650                 655

Glu Ala Leu Asn Asp Glu Leu Leu Glu Lys Glu Arg Gln Trp Glu Ala
                660                 665                 670

Trp Arg Ser Val Leu Gly Asp Glu Lys Ser Gln Phe Glu Cys Arg Val
                675                 680                 685

Arg Glu Leu Gln Arg Met Leu Asp Thr Glu Lys Gln Ser Arg Ala Arg
        690                 695                 700

Ala Asp Gln Arg Ile Thr Glu Ser Arg Gln Val Val Glu Leu Ala Val
705                 710                 715                 720

Lys Glu His Lys Ala Glu Ile Leu Ala Leu Gln Gln Ala Leu Lys Glu
                725                 730                 735

Gln Lys Leu Lys Ala Glu Ser Leu Ser Asp Lys Leu Asn Asp Leu Glu
```

-continued

```
            740                 745                 750
Lys Lys His Ala Met Leu Glu Met Asn Ala Arg Ser Leu Gln Gln Lys
        755                 760                 765
Leu Glu Thr Glu Arg Glu Leu Lys Gln Arg Leu Leu Glu Glu Gln Ala
770                 775                 780
Lys Leu Gln Gln Gln Met Asp Leu Gln Lys Asn His Ile Phe Arg Leu
785                 790                 795                 800
Thr Gln Gly Leu Gln Glu Ala Leu Asp Arg Ala Asp Leu Leu Lys Thr
                805                 810                 815
Glu Arg Ser Asp Leu Glu Tyr Gln Leu Glu Asn Ile Gln Val Leu Tyr
            820                 825                 830
Ser His Glu Lys Val Lys Met Glu Gly Thr Ile Ser Gln Gln Thr Lys
        835                 840                 845
Leu Ile Asp Phe Leu Gln Ala Lys Met Asp Gln Pro Ala Lys Lys Lys
850                 855                 860
Lys Val Pro Leu Gln Tyr Asn Glu Leu Lys Leu Ala Leu Glu Lys Glu
865                 870                 875                 880
Lys Ala Arg Cys Ala Glu Leu Glu Glu Ala Leu Gln Lys Thr Arg Ile
                885                 890                 895
Glu Leu Arg Ser Ala Arg Glu Glu Ala Ala His Arg Lys Ala Thr Asp
            900                 905                 910
His Pro His Pro Ser Thr Pro Ala Thr Ala Arg Gln Gln Ile Ala Met
        915                 920                 925
Ser Ala Ile Val Arg Ser Pro Glu His Gln Pro Ser Ala Met Ser Leu
        930                 935                 940
Leu Ala Pro Pro Ser Ser Arg Arg Lys Glu Ser Ser Thr Pro Glu Glu
945                 950                 955                 960
Phe Ser Arg Arg Leu Lys Glu Arg Met His His Asn Ile Pro His Arg
                965                 970                 975
Phe Asn Val Gly Leu Asn Met Arg Ala Thr Lys Cys Ala Val Cys Leu
            980                 985                 990
Asp Thr Val His Phe Gly Arg Gln Ala Ser Lys Cys Leu Glu Cys Gln
        995                 1000                1005
Val Met Cys His Pro Lys Cys Ser Thr Cys Leu Pro Ala Thr Cys Gly
    1010                1015                1020
Leu Pro Ala Glu Tyr Ala Thr His Phe Thr Glu Ala Phe Cys Arg Asp
1025                1030                1035                1040
Lys Met Asn Ser Pro Gly Leu Gln Ser Lys Glu Pro Gly Ser Ser Leu
                1045                1050                1055
His Leu Glu Gly Trp Met Lys Val Pro Arg Asn Asn Lys Arg Gly Gln
            1060                1065                1070
Gln Gly Trp Asp Arg Lys Tyr Ile Val Leu Glu Gly Ser Lys Val Leu
        1075                1080                1085
Ile Tyr Asp Asn Glu Ala Arg Glu Ala Gly Gln Arg Pro Val Glu Glu
    1090                1095                1100
Phe Glu Leu Cys Leu Pro Asp Gly Asp Val Ser Ile His Gly Ala Val
1105                1110                1115                1120
Gly Ala Ser Glu Leu Ala Asn Thr Ala Lys Ala Asp Val Pro Tyr Ile
                1125                1130                1135
Leu Lys Met Glu Ser His Pro His Thr Thr Cys Trp Pro Gly Arg Thr
            1140                1145                1150
Leu Tyr Leu Leu Ala Pro Ser Phe Pro Asp Lys Gln Arg Trp Val Thr
        1155                1160                1165
```

-continued

Ala Leu Glu Ser Val Val Ala Gly Gly Arg Val Ser Arg Glu Lys Ala
    1170                1175                1180

Glu Ala Asp Ala Lys Leu Leu Gly Asn Ser Leu Leu Lys Leu Glu Gly
1185                1190                1195                1200

Asp Asp Arg Leu Asp Met Asn Cys Thr Leu Pro Phe Ser Asp Gln Val
                1205                1210                1215

Val Leu Val Gly Thr Glu Glu Gly Leu Tyr Ala Leu Asn Val Leu Lys
            1220                1225                1230

Asn Ser Leu Thr His Ile Pro Gly Ile Gly Ala Val Phe Gln Ile Tyr
        1235                1240                1245

Ile Ile Lys Asp Leu Glu Lys Leu Leu Met Ile Ala Gly Glu Glu Arg
    1250                1255                1260

Ala Leu Cys Leu Val Asp Val Lys Lys Val Lys Gln Ser Leu Ala Gln
1265                1270                1275                1280

Ser His Leu Pro Ala Gln Pro Asp Val Ser Pro Asn Ile Phe Glu Ala
                1285                1290                1295

Val Lys Gly Cys His Leu Phe Ala Ala Gly Lys Ile Glu Asn Ser Leu
            1300                1305                1310

Cys Ile Cys Ala Ala Met Pro Ser Lys Val Val Ile Leu Arg Tyr Asn
        1315                1320                1325

Asp Asn Leu Ser Lys Tyr Cys Ile Arg Lys Glu Ile Glu Thr Ser Glu
    1330                1335                1340

Pro Cys Ser Cys Ile His Phe Thr Asn Tyr Ser Ile Leu Ile Gly Thr
1345                1350                1355                1360

Asn Lys Phe Tyr Glu Ile Asp Met Lys Gln Tyr Thr Leu Asp Glu Phe
                1365                1370                1375

Leu Asp Lys Asn Asp His Ser Leu Ala Pro Ala Val Phe Ala Ser Ser
            1380                1385                1390

Ser Asn Ser Phe Pro Val Ser Ile Val Gln Ala Asn Ser Ala Gly Gln
        1395                1400                1405

Arg Glu Glu Tyr Leu Leu Cys Phe His Glu Phe Gly Val Phe Val Asp
    1410                1415                1420

Ser Tyr Gly Arg Arg Ser Arg Thr Asp Asp Leu Lys Trp Ser Arg Leu
1425                1430                1435                1440

Pro Leu Ala Phe Ala Tyr Arg Glu Pro Tyr Leu Phe Val Thr His Phe
                1445                1450                1455

Asn Ser Leu Glu Val Ile Glu Ile Gln Ala Arg Ser Ser Leu Gly Ser
            1460                1465                1470

Pro Ala Arg Ala Tyr Leu Glu Ile Pro Asn Pro Arg Tyr Leu Gly Pro
        1475                1480                1485

Ala Ile Ser Ser Gly Ala Ile Tyr Leu Ala Ser Ser Tyr Gln Asp Lys
    1490                1495                1500

Leu Arg Val Ile Cys Cys Lys Gly Asn Leu Val Lys Glu Ser Gly Thr
1505                1510                1515                1520

Glu Gln His Arg Val Pro Ser Thr Ser Arg Ser Ser Pro Asn Lys Arg
                1525                1530                1535

Gly Pro Pro Thr Tyr Asn Glu His Ile Thr Lys Arg Val Ala Ser Ser
            1540                1545                1550

Pro Ala Pro Pro Glu Gly Pro Ser His Pro Arg Glu Pro Ser Thr Pro
        1555                1560                1565

His Arg Tyr Arg Asp Arg Glu Gly Arg Thr Glu Leu Arg Arg Asp Lys
    1570                1575                1580

-continued

```
Ser Pro Gly Arg Pro Leu Glu Arg Glu Lys Ser Pro Gly Arg Met Leu
1585                1590                1595                1600

Ser Thr Arg Arg Glu Arg Ser Pro Gly Arg Leu Phe Glu Asp Ser Ser
            1605                1610                1615

Arg Gly Arg Leu Pro Ala Gly Ala Val Arg Thr Pro Leu Ser Gln Val
        1620                1625                1630

Asn Lys Val Trp Asp Gln Ser Ser Val
        1635                1640

<210> SEQ ID NO 41
<211> LENGTH: 1597
<212> TYPE: PRT
<213> ORGANISM: Mus musculus

<400> SEQUENCE: 41

Met Leu Leu Gly Glu Glu Ala Met Met Glu Gln Met Thr Arg Leu
 1               5                  10                  15

His Arg Arg Val Ser Glu Val Glu Ala Val Leu Ser Gln Lys Glu Val
            20                  25                  30

Glu Leu Lys Ala Ser Glu Thr Gln Arg Ser Leu Leu Glu Gln Asp Leu
        35                  40                  45

Ala Thr Tyr Ile Thr Glu Cys Ser Ser Leu Lys Arg Ser Leu Glu Gln
    50                  55                  60

Ala Arg Met Glu Val Ser Gln Glu Asp Asp Lys Ala Leu Gln Leu Leu
65                  70                  75                  80

His Asp Ile Arg Glu Gln Ser Arg Lys Leu Gln Glu Ile Lys Glu Gln
                85                  90                  95

Glu Tyr Gln Ala Gln Val Glu Glu Met Arg Leu Met Met Asn Gln Leu
            100                 105                 110

Glu Glu Asp Leu Val Ser Ala Arg Arg Arg Ser Asp Leu Tyr Glu Ser
        115                 120                 125

Glu Leu Arg Glu Ser Arg Leu Ala Ala Glu Glu Phe Lys Arg Lys Ala
    130                 135                 140

Asn Glu Cys Gln His Lys Leu Met Lys Ala Lys Asp Gln Gly Lys Pro
145                 150                 155                 160

Glu Val Gly Glu Tyr Ser Lys Leu Glu Lys Ile Asn Ala Glu Gln Gln
                165                 170                 175

Leu Lys Ile Gln Glu Leu Gln Glu Lys Leu Glu Lys Ala Val Lys Ala
            180                 185                 190

Ser Thr Glu Ala Thr Glu Leu Leu Gln Asn Ile Arg Gln Ala Lys Glu
        195                 200                 205

Arg Ala Glu Arg Glu Leu Glu Lys Leu His Asn Arg Glu Asp Ser Ser
    210                 215                 220

Glu Gly Ile Lys Lys Lys Leu Val Glu Ala Glu Arg Arg His Ser
225                 230                 235                 240

Leu Glu Asn Lys Val Lys Arg Leu Glu Thr Met Glu Arg Arg Glu Asn
                245                 250                 255

Arg Leu Lys Asp Asp Ile Gln Thr Lys Ser Glu Gln Ile Gln Gln Met
            260                 265                 270

Ala Asp Lys Ile Leu Glu Leu Glu Glu Lys His Arg Glu Ala Gln Val
        275                 280                 285

Ser Ala Gln His Leu Glu Val His Leu Lys Gln Lys Glu Gln His Tyr
    290                 295                 300

Glu Glu Lys Ile Lys Val Leu Asp Asn Gln Ile Lys Lys Asp Leu Ala
305                 310                 315                 320
```

-continued

```
Asp Lys Glu Ser Leu Glu Asn Met Met Gln Arg His Glu Glu Ala
            325                 330                 335

His Glu Lys Gly Lys Ile Leu Ser Glu Gln Lys Ala Met Ile Asn Ala
            340                 345                 350

Met Asp Ser Lys Ile Arg Ser Leu Glu Gln Arg Ile Val Glu Leu Ser
            355                 360                 365

Glu Ala Asn Lys Leu Ala Ala Asn Ser Ser Leu Phe Thr Gln Arg Asn
        370                 375                 380

Met Lys Ala Gln Glu Glu Met Ile Ser Glu Leu Arg Gln Gln Lys Phe
385                 390                 395                 400

Tyr Leu Glu Thr Gln Ala Gly Lys Leu Glu Ala Gln Asn Arg Lys Leu
                405                 410                 415

Glu Glu Gln Leu Glu Lys Ile Ser His Gln Asp His Ser Asp Lys Ser
            420                 425                 430

Arg Leu Leu Glu Leu Glu Thr Arg Leu Arg Glu Val Ser Leu Glu His
            435                 440                 445

Glu Glu Gln Lys Leu Glu Leu Lys Arg Gln Leu Thr Glu Leu Gln Leu
        450                 455                 460

Ser Leu Gln Glu Arg Glu Ser Gln Leu Thr Ala Leu Gln Ala Ala Arg
465                 470                 475                 480

Ala Ala Leu Glu Ser Gln Leu Arg Gln Ala Lys Thr Glu Leu Glu Glu
                485                 490                 495

Thr Thr Ala Glu Ala Glu Glu Ile Gln Ala Leu Thr Ala His Arg
            500                 505                 510

Asp Glu Ile Gln Arg Lys Phe Asp Ala Leu Arg Asn Ser Cys Thr Val
            515                 520                 525

Ile Thr Asp Leu Glu Glu Gln Leu Asn Gln Leu Thr Glu Asp Asn Ala
        530                 535                 540

Glu Leu Asn Asn Gln Asn Phe Tyr Leu Ser Lys Gln Leu Asp Glu Ala
545                 550                 555                 560

Ser Gly Ala Asn Asp Glu Ile Val Gln Leu Arg Ser Glu Val Asp His
                565                 570                 575

Leu Arg Arg Glu Ile Thr Glu Arg Glu Met Gln Leu Thr Ser Gln Lys
            580                 585                 590

Gln Thr Met Glu Ala Leu Lys Thr Thr Cys Thr Met Leu Glu Glu Gln
            595                 600                 605

Val Leu Asp Leu Glu Ala Leu Asn Asp Glu Leu Leu Glu Lys Glu Arg
        610                 615                 620

Gln Trp Glu Ala Trp Arg Ser Val Leu Gly Asp Glu Lys Ser Gln Phe
625                 630                 635                 640

Glu Cys Arg Val Arg Glu Leu Gln Arg Met Leu Asp Thr Glu Lys Gln
                645                 650                 655

Ser Arg Ala Arg Ala Asp Gln Arg Ile Thr Glu Ser Arg Gln Val Val
            660                 665                 670

Glu Leu Ala Val Lys Glu His Lys Ala Glu Ile Leu Ala Leu Gln Gln
            675                 680                 685

Ala Leu Lys Glu Gln Lys Leu Lys Ala Glu Ser Leu Ser Asp Lys Leu
        690                 695                 700

Asn Asp Leu Glu Lys Lys His Ala Met Leu Glu Met Asn Ala Arg Ser
705                 710                 715                 720

Leu Gln Gln Lys Leu Glu Thr Glu Arg Glu Leu Lys Gln Arg Leu Leu
                725                 730                 735
```

```
Glu Glu Gln Ala Lys Leu Gln Gln Met Asp Leu Gln Lys Asn His
            740                 745                 750

Ile Phe Arg Leu Thr Gln Gly Leu Gln Glu Ala Leu Asp Arg Ala Asp
        755                 760                 765

Leu Leu Lys Thr Glu Arg Ser Asp Leu Glu Tyr Gln Leu Glu Asn Ile
    770                 775                 780

Gln Val Leu Tyr Ser His Glu Lys Val Lys Met Glu Gly Thr Ile Ser
785                 790                 795                 800

Gln Gln Thr Lys Leu Ile Asp Phe Leu Gln Ala Lys Met Asp Gln Pro
                805                 810                 815

Ala Lys Lys Lys Lys Val Pro Leu Gln Tyr Asn Glu Leu Lys Leu Ala
            820                 825                 830

Leu Glu Lys Glu Lys Ala Arg Cys Ala Glu Leu Glu Glu Ala Leu Gln
        835                 840                 845

Lys Thr Arg Ile Glu Leu Arg Ser Ala Arg Glu Glu Ala Ala His Arg
    850                 855                 860

Lys Ala Thr Asp His Pro His Pro Ser Thr Pro Ala Thr Ala Arg Gln
865                 870                 875                 880

Gln Ile Ala Met Ser Ala Ile Val Arg Ser Pro Glu His Gln Pro Ser
                885                 890                 895

Ala Met Ser Leu Leu Ala Pro Pro Ser Ser Arg Arg Lys Glu Ser Ser
            900                 905                 910

Thr Pro Glu Glu Phe Ser Arg Arg Leu Lys Glu Arg Met His His Asn
        915                 920                 925

Ile Pro His Arg Phe Asn Val Gly Leu Asn Met Arg Ala Thr Lys Cys
    930                 935                 940

Ala Val Cys Leu Asp Thr Val His Phe Gly Arg Gln Ala Ser Lys Cys
945                 950                 955                 960

Leu Glu Cys Gln Val Met Cys His Pro Lys Cys Ser Thr Cys Leu Pro
                965                 970                 975

Ala Thr Cys Gly Leu Pro Ala Glu Tyr Ala Thr His Phe Thr Glu Ala
            980                 985                 990

Phe Cys Arg Asp Lys Met Asn Ser Pro Gly Leu Gln Ser Lys Glu Pro
        995                 1000                1005

Gly Ser Ser Leu His Leu Glu Gly Trp Met Lys Val Pro Arg Asn Asn
    1010                1015                1020

Lys Arg Gly Gln Gln Gly Trp Asp Arg Lys Tyr Ile Val Leu Glu Gly
1025                1030                1035                1040

Ser Lys Val Leu Ile Tyr Asp Asn Glu Ala Arg Glu Ala Gly Gln Arg
                1045                1050                1055

Pro Val Glu Glu Phe Glu Leu Cys Leu Pro Asp Gly Asp Val Ser Ile
            1060                1065                1070

His Gly Ala Val Gly Ala Ser Glu Leu Ala Asn Thr Ala Lys Ala Asp
        1075                1080                1085

Val Pro Tyr Ile Leu Lys Met Glu Ser His Pro His Thr Thr Cys Trp
    1090                1095                1100

Pro Gly Arg Thr Leu Tyr Leu Leu Ala Pro Ser Phe Pro Asp Lys Gln
1105                1110                1115                1120

Arg Trp Val Thr Ala Leu Glu Ser Val Val Ala Gly Gly Arg Val Ser
                1125                1130                1135

Arg Glu Lys Ala Glu Ala Asp Ala Lys Leu Leu Gly Asn Ser Leu Leu
            1140                1145                1150

Lys Leu Glu Gly Asp Asp Arg Leu Asp Met Asn Cys Thr Leu Pro Phe
```

```
                1155                1160                1165
Ser Asp Gln Val Val Leu Val Gly Thr Glu Glu Gly Leu Tyr Ala Leu
    1170                1175                1180

Asn Val Leu Lys Asn Ser Leu Thr His Ile Pro Gly Ile Gly Ala Val
1185                1190                1195                1200

Phe Gln Ile Tyr Ile Ile Lys Asp Leu Glu Lys Leu Met Ile Ala
            1205                1210                1215

Gly Glu Glu Arg Ala Leu Cys Leu Val Asp Val Lys Val Lys Gln
        1220                1225                1230

Ser Leu Ala Gln Ser His Leu Pro Ala Gln Pro Asp Val Ser Pro Asn
    1235                1240                1245

Ile Phe Glu Ala Val Lys Gly Cys His Leu Phe Ala Ala Gly Lys Ile
    1250                1255                1260

Glu Asn Ser Leu Cys Ile Cys Ala Ala Met Pro Ser Lys Val Val Ile
1265                1270                1275                1280

Leu Arg Tyr Asn Asp Asn Leu Ser Lys Tyr Cys Ile Arg Lys Glu Ile
            1285                1290                1295

Glu Thr Ser Glu Pro Cys Ser Cys Ile His Phe Thr Asn Tyr Ser Ile
        1300                1305                1310

Leu Ile Gly Thr Asn Lys Phe Tyr Glu Ile Asp Met Lys Gln Tyr Thr
    1315                1320                1325

Leu Asp Glu Phe Leu Asp Lys Asn Asp His Ser Leu Ala Pro Ala Val
    1330                1335                1340

Phe Ala Ser Ser Ser Asn Ser Phe Pro Val Ser Ile Val Gln Ala Asn
1345                1350                1355                1360

Ser Ala Gly Gln Arg Glu Glu Tyr Leu Leu Cys Phe His Glu Phe Gly
            1365                1370                1375

Val Phe Val Asp Ser Tyr Gly Arg Arg Ser Arg Thr Asp Asp Leu Lys
        1380                1385                1390

Trp Ser Arg Leu Pro Leu Ala Phe Ala Tyr Arg Glu Pro Tyr Leu Phe
    1395                1400                1405

Val Thr His Phe Asn Ser Leu Glu Val Ile Glu Ile Gln Ala Arg Ser
    1410                1415                1420

Ser Leu Gly Ser Pro Ala Arg Ala Tyr Leu Glu Ile Pro Asn Pro Arg
1425                1430                1435                1440

Tyr Leu Gly Pro Ala Ile Ser Ser Gly Ala Ile Tyr Leu Ala Ser Ser
            1445                1450                1455

Tyr Gln Asp Lys Leu Arg Val Ile Cys Cys Lys Gly Asn Leu Val Lys
        1460                1465                1470

Glu Ser Gly Thr Glu Gln His Arg Val Pro Ser Thr Ser Arg Ser Ser
    1475                1480                1485

Pro Asn Lys Arg Gly Pro Pro Thr Tyr Asn Glu His Ile Thr Lys Arg
    1490                1495                1500

Val Ala Ser Ser Pro Ala Pro Pro Glu Gly Pro Ser His Pro Arg Glu
1505                1510                1515                1520

Pro Ser Thr Pro His Arg Tyr Arg Asp Arg Glu Gly Arg Thr Glu Leu
            1525                1530                1535

Arg Arg Asp Lys Ser Pro Gly Arg Pro Leu Glu Arg Glu Lys Ser Pro
        1540                1545                1550

Gly Arg Met Leu Ser Thr Arg Arg Glu Arg Ser Pro Gly Arg Leu Phe
    1555                1560                1565

Glu Asp Ser Ser Arg Gly Arg Leu Pro Ala Gly Ala Val Arg Thr Pro
    1570                1575                1580
```

```
Leu Ser Gln Val Asn Lys Val Trp Asp Gln Ser Ser Val
1585                1590                1595

<210> SEQ ID NO 42
<211> LENGTH: 1871
<212> TYPE: PRT
<213> ORGANISM: Homo sapiens

<400> SEQUENCE: 42

Met Pro Ser Val Cys Leu Leu Leu Leu Phe Leu Ala Val Gly Gly
  1               5                  10                  15

Ala Leu Gly Asn Arg Pro Phe Arg Ala Phe Val Thr Asp Thr Thr
             20                  25                  30

Leu Thr His Leu Ala Val His Arg Val Thr Gly Glu Val Phe Val Gly
         35                  40                  45

Ala Val Asn Arg Val Phe Lys Leu Ala Pro Asn Leu Thr Glu Leu Arg
 50                  55                  60

Ala His Val Thr Gly Pro Val Glu Asp Asn Ala Arg Cys Tyr Pro Pro
 65                  70                  75                  80

Pro Ser Met Arg Val Cys Ala His Arg Leu Ala Pro Val Asp Asn Ile
             85                  90                  95

Asn Lys Leu Leu Leu Ile Asp Tyr Ala Ala Arg Arg Leu Val Ala Cys
            100                 105                 110

Gly Ser Ile Trp Gln Gly Ile Cys Gln Phe Leu Arg Leu Asp Asp Leu
            115                 120                 125

Phe Lys Leu Gly Glu Pro His His Arg Lys Glu His Tyr Leu Ser Gly
        130                 135                 140

Ala Gln Glu Pro Asp Ser Met Ala Gly Val Ile Val Glu Gln Gly Gln
145                 150                 155                 160

Gly Pro Ser Lys Leu Phe Val Gly Thr Ala Val Asp Gly Lys Ser Glu
                165                 170                 175

Tyr Phe Pro Thr Leu Ser Ser Arg Lys Leu Ile Ser Asp Glu Asp Ser
            180                 185                 190

Ala Asp Met Phe Ser Leu Val Tyr Gln Asp Glu Phe Val Ser Ser Gln
            195                 200                 205

Ile Lys Ile Pro Ser Asp Thr Leu Ser Leu Tyr Pro Ala Phe Asp Ile
        210                 215                 220

Tyr Tyr Ile Tyr Gly Phe Val Ser Ala Ser Phe Val Tyr Phe Leu Thr
225                 230                 235                 240

Leu Gln Leu Asp Thr Gln Gln Thr Leu Leu Asp Thr Ala Gly Glu Lys
                245                 250                 255

Phe Phe Thr Ser Lys Ile Val Arg Met Cys Ala Gly Asp Ser Glu Phe
            260                 265                 270

Tyr Ser Tyr Val Glu Phe Pro Ile Gly Cys Ser Trp Arg Gly Val Glu
        275                 280                 285

Tyr Arg Leu Val Gln Ser Ala His Leu Ala Lys Pro Gly Leu Leu Leu
    290                 295                 300

Ala Gln Ala Leu Gly Val Pro Ala Asp Glu Asp Val Leu Phe Thr Ile
305                 310                 315                 320

Phe Ser Gln Gly Gln Lys Asn Arg Ala Ser Pro Pro Arg Gln Thr Ile
                325                 330                 335

Leu Cys Leu Phe Thr Leu Ser Asn Ile Asn Ala His Ile Arg Arg Arg
            340                 345                 350

Ile Gln Ser Cys Tyr Arg Gly Glu Gly Thr Leu Ala Leu Pro Trp Leu
```

-continued

```
              355                 360                 365
Leu Asn Lys Glu Leu Pro Cys Ile Asn Thr Pro Met Gln Ile Asn Gly
    370                 375                 380

Asn Phe Cys Gly Leu Val Leu Asn Gln Pro Leu Gly Gly Leu His Val
385                 390                 395                 400

Ile Glu Gly Leu Pro Leu Leu Ala Asp Ser Thr Asp Gly Met Ala Ser
                405                 410                 415

Val Ala Ala Tyr Thr Tyr Arg Gln His Ser Val Val Phe Ile Gly Thr
                420                 425                 430

Arg Ser Gly Ser Leu Lys Val Arg Val Asp Gly Phe Gln Asp Ala
                435                 440                 445

His Leu Tyr Glu Thr Val Pro Val Val Asp Gly Ser Pro Ile Leu Arg
    450                 455                 460

Asp Leu Leu Phe Ser Pro Asp His Arg His Ile Tyr Leu Leu Ser Glu
465                 470                 475                 480

Lys Gln Val Ser Gln Leu Pro Val Glu Thr Cys Glu Gln Tyr Gln Ser
                485                 490                 495

Cys Ala Ala Cys Leu Gly Ser Gly Asp Pro His Cys Gly Trp Cys Val
                500                 505                 510

Leu Arg His Arg Cys Cys Arg Glu Gly Ala Cys Leu Gly Ala Ser Ala
    515                 520                 525

Pro His Gly Phe Ala Glu Glu Leu Ser Lys Cys Val Gln Val Arg Val
    530                 535                 540

Arg Pro Asn Asn Val Ser Val Thr Ser Pro Gly Val Gln Leu Thr Val
545                 550                 555                 560

Thr Leu His Asn Val Pro Asp Leu Ser Ala Gly Val Ser Cys Ala Phe
                565                 570                 575

Glu Ala Ala Ala Glu Asn Glu Ala Val Leu Pro Ser Gly Glu Leu
                580                 585                 590

Leu Cys Pro Ser Pro Ser Leu Gln Glu Leu Arg Ala Leu Thr Arg Gly
    595                 600                 605

His Gly Ala Thr Arg Thr Val Arg Leu Gln Leu Leu Ser Lys Glu Thr
    610                 615                 620

Gly Val Arg Phe Ala Gly Ala Asp Phe Val Phe Tyr Asn Cys Ser Val
625                 630                 635                 640

Leu Gln Ser Cys Met Ser Cys Val Gly Ser Pro Tyr Pro Cys His Trp
                645                 650                 655

Cys Lys Tyr Arg His Thr Cys Thr Ser Arg Pro His Glu Cys Ser Phe
                660                 665                 670

Gln Glu Gly Arg Val His Ser Pro Glu Gly Cys Pro Glu Ile Leu Pro
                675                 680                 685

Ser Gly Asp Leu Leu Ile Pro Val Gly Val Met Gln Pro Leu Thr Leu
    690                 695                 700

Arg Ala Lys Asn Leu Pro Gln Pro Gln Ser Gly Gln Lys Asn Tyr Glu
705                 710                 715                 720

Cys Val Val Arg Val Gln Gly Arg Gln Gln Arg Val Pro Ala Val Arg
                725                 730                 735

Phe Asn Ser Ser Ser Val Gln Cys Gln Asn Ala Ser Tyr Ser Tyr Glu
                740                 745                 750

Gly Asp Glu His Gly Asp Thr Glu Leu Asp Phe Ser Val Val Trp Asp
    755                 760                 765

Gly Asp Phe Pro Ile Asp Lys Pro Pro Ser Phe Arg Ala Leu Leu Tyr
    770                 775                 780
```

-continued

```
Lys Cys Trp Ala Gln Arg Pro Ser Cys Gly Leu Cys Leu Lys Ala Asp
785                 790                 795                 800

Pro Arg Phe Asn Cys Gly Trp Cys Ile Ser Glu His Arg Cys Gln Leu
                805                 810                 815

Arg Thr His Cys Pro Ala Pro Lys Thr Asn Trp Met His Leu Ser Gln
            820                 825                 830

Lys Gly Thr Arg Cys Ser His Pro Arg Ile Thr Gln Ile His Pro Leu
        835                 840                 845

Val Gly Pro Lys Glu Gly Thr Arg Val Thr Ile Val Gly Asp Asn
850                 855                 860

Leu Gly Leu Leu Ser Arg Glu Val Gly Leu Arg Val Ala Gly Val Arg
865                 870                 875                 880

Cys Asn Ser Ile Pro Ala Glu Tyr Ile Ser Ala Glu Arg Ile Val Cys
                885                 890                 895

Glu Met Glu Glu Ser Leu Val Pro Ser Pro Pro Gly Pro Val Glu
            900                 905                 910

Leu Cys Val Gly Asp Cys Ser Ala Asp Phe Arg Thr Gln Ser Glu Gln
        915                 920                 925

Val Tyr Ser Phe Val Thr Pro Thr Phe Asp Gln Val Ser Pro Ser Arg
    930                 935                 940

Gly Pro Ala Ser Gly Thr Arg Leu Thr Ile Ser Gly Ser Ser Leu
945                 950                 955                 960

Asp Ala Gly Ser Arg Val Thr Val Thr Val Arg Asp Ser Glu Cys Gln
                965                 970                 975

Phe Val Arg Arg Asp Ala Lys Ala Ile Val Cys Ile Ser Pro Leu Ser
            980                 985                 990

Thr Leu Gly Pro Ser Gln Ala Pro Ile Thr Leu Ala Ile Asp Arg Ala
        995                 1000                1005

Asn Ile Ser Ser Pro Gly Leu Ile Tyr Thr Tyr Thr Gln Asp Pro Thr
    1010                1015                1020

Val Thr Arg Leu Glu Pro Thr Trp Ser Ile Ile Asn Gly Ser Thr Ala
1025                1030                1035                1040

Ile Thr Val Ser Gly Thr His Leu Leu Thr Val Gln Glu Pro Arg Val
                1045                1050                1055

Arg Ala Lys Tyr Arg Gly Ile Glu Thr Thr Asn Thr Cys Gln Val Ile
            1060                1065                1070

Asn Asp Thr Ala Met Leu Cys Lys Ala Pro Gly Ile Phe Leu Gly Arg
        1075                1080                1085

Pro Gln Pro Arg Ala Gln Gly Glu His Pro Asp Glu Phe Gly Phe Leu
    1090                1095                1100

Leu Asp His Val Gln Thr Ala Arg Ser Leu Asn Arg Ser Ser Phe Thr
1105                1110                1115                1120

Tyr Tyr Pro Asp Pro Ser Phe Glu Pro Leu Gly Pro Ser Gly Val Leu
                1125                1130                1135

Asp Val Lys Pro Gly Ser His Val Val Leu Lys Gly Lys Asn Leu Ile
            1140                1145                1150

Pro Ala Ala Ala Gly Ser Ser Arg Leu Asn Tyr Thr Val Leu Ile Gly
        1155                1160                1165

Gly Gln Pro Cys Ser Leu Thr Val Ser Asp Thr Gln Leu Leu Cys Asp
    1170                1175                1180

Ser Pro Ser Gln Thr Gly Arg Gln Pro Val Met Val Leu Val Gly Gly
1185                1190                1195                1200
```

-continued

```
Leu Glu Phe Trp Leu Gly Thr Leu His Ile Ser Ala Glu Arg Ala Leu
            1205                1210                1215

Thr Leu Pro Ala Met Met Gly Leu Ala Ala Gly Gly Leu Leu Leu
        1220                1225                1230

Leu Ala Ile Thr Ala Val Leu Val Ala Tyr Lys Arg Lys Thr Gln Asp
            1235                1240                1245

Ala Asp Arg Thr Leu Lys Arg Leu Gln Leu Gln Met Asp Asn Leu Glu
    1250                1255                1260

Ser Arg Val Ala Leu Glu Cys Lys Glu Ala Phe Ala Glu Leu Gln Thr
1265                1270                1275                1280

Asp Ile Asn Glu Leu Thr Asn His Met Asp Glu Val Gln Ile Pro Phe
            1285                1290                1295

Leu Asp Tyr Arg Thr Tyr Ala Val Arg Val Leu Phe Pro Gly Ile Glu
            1300                1305                1310

Ala His Pro Val Leu Lys Glu Leu Asp Thr Pro Pro Asn Val Glu Lys
        1315                1320                1325

Ala Leu Arg Leu Phe Gly Gln Leu Leu His Ser Arg Ala Phe Val Leu
    1330                1335                1340

Thr Phe Ile His Thr Leu Glu Ala Gln Ser Ser Phe Ser Met Arg Asp
1345                1350                1355                1360

Arg Gly Thr Val Ala Ser Leu Thr Met Val Ala Leu Gln Ser Arg Leu
            1365                1370                1375

Asp Tyr Ala Thr Gly Leu Leu Lys Gln Leu Leu Ala Asp Leu Ile Glu
            1380                1385                1390

Lys Asn Leu Glu Ser Lys Asn His Pro Lys Leu Leu Leu Arg Arg Thr
        1395                1400                1405

Glu Ser Val Ala Glu Lys Met Leu Thr Asn Trp Phe Thr Phe Leu Leu
    1410                1415                1420

His Lys Phe Leu Lys Glu Cys Ala Gly Glu Pro Leu Phe Leu Leu Tyr
1425                1430                1435                1440

Cys Ala Ile Lys Gln Gln Met Glu Lys Gly Pro Ile Asp Ala Ile Thr
            1445                1450                1455

Gly Glu Ala Arg Tyr Ser Leu Ser Glu Asp Lys Leu Ile Arg Gln Gln
            1460                1465                1470

Ile Asp Tyr Lys Thr Leu Thr Leu His Cys Val Cys Pro Glu Asn Glu
        1475                1480                1485

Gly Ser Ala Gln Val Pro Val Lys Val Leu Asn Cys Asp Ser Ile Thr
    1490                1495                1500

Gln Ala Lys Asp Lys Leu Leu Asp Thr Val Tyr Lys Gly Ile Pro Tyr
1505                1510                1515                1520

Ser Gln Arg Pro Lys Ala Glu Asp Met Asp Leu Glu Trp Arg Gln Gly
            1525                1530                1535

Arg Met Thr Arg Ile Ile Leu Gln Asp Glu Asp Val Thr Thr Lys Ile
            1540                1545                1550

Glu Cys Asp Trp Lys Arg Leu Asn Ser Leu Ala His Tyr Gln Val Thr
        1555                1560                1565

Asp Gly Ser Leu Val Ala Leu Val Pro Lys Gln Val Ser Ala Tyr Asn
    1570                1575                1580

Met Ala Asn Ser Phe Thr Phe Thr Arg Ser Leu Ser Arg Tyr Glu Ser
1585                1590                1595                1600

Leu Leu Arg Thr Ala Ser Ser Pro Asp Ser Leu Arg Ser Arg Ala Pro
            1605                1610                1615

Met Ile Thr Pro Asp Gln Glu Thr Gly Thr Lys Leu Trp His Leu Val
```

-continued

```
                  1620                1625                1630
Lys Asn His Asp His Ala Asp His Arg Glu Gly Asp Arg Gly Ser Lys
            1635                1640                1645

Met Val Ser Glu Ile Tyr Leu Thr Arg Leu Leu Ala Thr Lys Gly Thr
        1650                1655                1660

Leu Gln Lys Phe Val Asp Asp Leu Phe Glu Thr Val Phe Ser Thr Ala
1665                1670                1675                1680

His Arg Gly Ser Ala Leu Pro Leu Ala Ile Lys Tyr Met Phe Asp Phe
            1685                1690                1695

Leu Asp Glu Gln Ala Asp Gln Arg Gln Ile Ser Asp Pro Asp Val Arg
        1700                1705                1710

His Thr Trp Lys Ser Asn Cys Leu Pro Leu Arg Phe Trp Val Asn Val
    1715                1720                1725

Ile Lys Asn Pro Gln Phe Val Phe Asp Ile His Lys Asn Ser Ile Thr
        1730                1735                1740

Asp Ala Cys Leu Ser Val Ala Gln Thr Phe Met Asp Ser Cys Ser
1745                1750                1755                1760

Thr Ser Glu His Arg Leu Gly Lys Asp Ser Pro Ser Asn Lys Leu Leu
            1765                1770                1775

Tyr Ala Lys Asp Ile Pro Asn Tyr Lys Ser Trp Val Glu Arg Tyr Tyr
        1780                1785                1790

Arg Asp Ile Ala Lys Met Ala Ser Ile Ser Asp Gln Asp Met Asp Ala
    1795                1800                1805

Tyr Leu Val Glu Gln Ser Arg Leu His Ala Ser Asp Phe Ser Val Leu
    1810                1815                1820

Ser Ala Leu Asn Glu Leu Tyr Phe Tyr Val Thr Lys Tyr Arg Gln Glu
1825                1830                1835                1840

Ile Leu Thr Ala Leu Asp Arg Asp Ala Ser Cys Arg Lys His Lys Leu
            1845                1850                1855

Arg Gln Lys Leu Glu Gln Ile Ile Ser Leu Val Ser Ser Asp Ser
        1860                1865                1870

<210> SEQ ID NO 43
<211> LENGTH: 1963
<212> TYPE: PRT
<213> ORGANISM: Homo sapiens

<400> SEQUENCE: 43

Gly Phe Gly Arg Leu Pro Asp Ser Glu Leu Arg Ala Gly Arg Gly Ala
1               5                   10                  15

Ser Arg Arg Pro Gln Gln Pro Ala Ala Glu Val Asp Arg Ala Gly
            20                  25                  30

Thr Glu Gly Gln Thr Asp Val Ala Glu Leu Glu Ser Cys Glu Gly Gln
        35                  40                  45

Pro Gly Lys Val Glu Gln Met Ser Thr His Arg Ser Arg Leu Leu Thr
    50                  55                  60

Ala Ala Pro Leu Ser Met Glu Gln Arg Pro Trp Pro Arg Ala Leu
65                  70                  75                  80

Glu Val Asp Ser Arg Ser Val Val Leu Leu Ser Val Val Trp Val Leu
                85                  90                  95

Leu Ala Pro Pro Ala Ala Gly Met Pro Gln Phe Ser Thr Phe His Ser
            100                 105                 110

Glu Asn Arg Asp Trp Thr Phe Asn His Leu Thr Val His Gln Gly Thr
        115                 120                 125
```

-continued

```
Gly Ala Val Tyr Val Gly Ala Ile Asn Arg Val Tyr Lys Leu Thr Gly
130                 135                 140

Asn Leu Thr Ile Gln Val Ala His Lys Thr Gly Pro Glu Glu Asp Asn
145                 150                 155                 160

Lys Ser Cys Tyr Pro Pro Leu Ile Val Gln Pro Cys Ser Glu Val Leu
                165                 170                 175

Thr Leu Thr Asn Asn Val Asn Lys Leu Leu Ile Ile Asp Tyr Ser Glu
                180                 185                 190

Asn Arg Leu Leu Ala Cys Gly Ser Leu Tyr Gln Gly Val Cys Lys Leu
            195                 200                 205

Leu Arg Leu Asp Asp Leu Phe Ile Leu Val Glu Pro Ser His Lys Lys
    210                 215                 220

Glu His Tyr Leu Ser Ser Val Asn Lys Thr Gly Thr Met Tyr Gly Val
225                 230                 235                 240

Ile Val Arg Ser Glu Gly Glu Asp Gly Lys Leu Phe Ile Gly Thr Ala
                245                 250                 255

Val Asp Gly Lys Gln Asp Tyr Phe Pro Thr Leu Ser Ser Arg Lys Leu
                260                 265                 270

Pro Arg Asp Pro Glu Ser Ser Ala Met Leu Asp Tyr Glu Leu His Ser
            275                 280                 285

Asp Phe Val Ser Ser Leu Ile Lys Ile Pro Ser Asp Thr Leu Ala Leu
    290                 295                 300

Val Ser His Phe Asp Ile Phe Tyr Ile Tyr Gly Phe Ala Ser Gly Gly
305                 310                 315                 320

Phe Val Tyr Phe Leu Thr Val Gln Pro Glu Thr Pro Glu Gly Val Ala
                325                 330                 335

Ile Asn Ser Ala Gly Asp Leu Phe Tyr Thr Ser Arg Ile Val Arg Leu
            340                 345                 350

Cys Lys Asp Asp Pro Lys Phe His Ser Tyr Val Ser Leu Pro Phe Gly
    355                 360                 365

Cys Thr Arg Ala Gly Val Glu Tyr Arg Leu Leu Gln Ala Ala Tyr Leu
370                 375                 380

Ala Lys Pro Gly Asp Ser Leu Ala Gln Ala Phe Asn Ile Thr Ser Gln
385                 390                 395                 400

Asp Asp Val Leu Phe Ala Ile Phe Ser Lys Gly Gln Lys Gln Tyr His
                405                 410                 415

His Pro Pro Asp Asp Ser Ala Leu Cys Ala Phe Pro Ile Arg Ala Ile
                420                 425                 430

Asn Leu Gln Ile Lys Gly Arg Leu Gln Ser Cys Tyr Gln Gly Glu Gly
            435                 440                 445

Asn Leu Glu Leu Asn Trp Leu Leu Gly Lys Asp Val Gln Cys Thr Lys
    450                 455                 460

Ala Pro Val Pro Ile Asp Asp Asn Phe Cys Gly Leu Asp Ile Asn Gln
465                 470                 475                 480

Pro Leu Gly Gly Ser Thr Pro Val Glu Gly Leu Thr Leu Tyr Thr Thr
                485                 490                 495

Ser Arg Asp Arg Met Thr Ser Val Ala Ser Tyr Val Tyr Asn Gly Tyr
                500                 505                 510

Ser Val Val Phe Val Gly Thr Lys Ser Gly Lys Leu Lys Lys Ile Arg
            515                 520                 525

Ala Asp Gly Pro Pro His Gly Gly Val Gln Tyr Glu Met Val Ser Val
    530                 535                 540

Leu Lys Asp Gly Ser Pro Ile Leu Arg Asp Met Ala Phe Ser Ile Asp
```

```
           545                 550                 555                 560
Gln Arg Tyr Leu Tyr Val Met Ser Glu Arg Gln Val Thr Arg Val Pro
                565                 570                 575
Val Glu Ser Cys Glu Gln Tyr Thr Thr Cys Gly Glu Cys Leu Ser Ser
                580                 585                 590
Gly Asp Pro His Cys Gly Trp Cys Ala Leu His Asn Met Cys Ser Arg
                595                 600                 605
Arg Asp Lys Cys Gln Gln Ala Trp Glu Pro Asn Arg Phe Ala Ala Ser
            610                 615                 620
Ile Ser Gln Cys Val Ser Leu Ala Val His Pro Ser Ser Ile Ser Val
625                 630                 635                 640
Ser Glu His Ser Arg Leu Leu Ser Leu Val Val Ser Asp Ala Pro Asp
                645                 650                 655
Leu Ser Ala Gly Ile Ala Cys Ala Phe Gly Asn Leu Thr Glu Val Glu
                660                 665                 670
Gly Gln Val Ser Gly Ser Gln Val Ile Cys Ile Ser Pro Gly Pro Lys
                675                 680                 685
Asp Val Pro Val Ile Pro Leu Asp Gln Asp Trp Phe Gly Leu Glu Leu
            690                 695                 700
Gln Leu Arg Ser Lys Glu Thr Gly Lys Ile Phe Val Ser Thr Glu Phe
705                 710                 715                 720
Lys Phe Tyr Asn Cys Ser Ala His Gln Leu Cys Leu Ser Cys Val Asn
                725                 730                 735
Ser Ala Phe Arg Cys His Trp Cys Lys Tyr Arg Asn Leu Cys Thr His
                740                 745                 750
Asp Pro Thr Thr Cys Ser Phe Gln Glu Gly Arg Ile Asn Ile Ser Glu
            755                 760                 765
Asp Cys Pro Gln Leu Val Pro Thr Glu Glu Ile Leu Ile Pro Val Gly
            770                 775                 780
Glu Val Lys Pro Ile Thr Leu Lys Ala Arg Asn Leu Pro Gln Pro Gln
785                 790                 795                 800
Ser Gly Gln Arg Gly Tyr Glu Cys Val Leu Asn Ile Gln Gly Ala Ile
                805                 810                 815
His Arg Val Pro Ala Leu Arg Phe Asn Ser Ser Ser Val Gln Cys Gln
                820                 825                 830
Asn Ser Ser Tyr Gln Tyr Asp Gly Met Asp Ile Ser Asn Leu Ala Val
            835                 840                 845
Asp Phe Ala Val Val Trp Asn Gly Asn Phe Ile Ile Asp Asn Pro Gln
            850                 855                 860
Asp Leu Lys Val His Leu Tyr Lys Cys Ala Ala Gln Arg Glu Ser Cys
865                 870                 875                 880
Gly Leu Cys Leu Lys Ala Asp Arg Lys Phe Glu Cys Gly Trp Cys Ser
                885                 890                 895
Gly Glu Arg Arg Cys Thr Leu His Gln His Cys Thr Ser Pro Ser Ser
                900                 905                 910
Pro Trp Leu Asp Trp Ser Ser His Asn Val Lys Cys Ser Asn Pro Gln
            915                 920                 925
Ile Thr Glu Ile Leu Thr Val Ser Gly Pro Pro Glu Gly Gly Thr Arg
            930                 935                 940
Val Thr Ile His Gly Val Asn Leu Gly Leu Asp Phe Ser Glu Ile Ala
945                 950                 955                 960
His His Val Gln Val Ala Gly Val Pro Cys Thr Pro Leu Pro Gly Glu
                965                 970                 975
```

-continued

```
Tyr Ile Ile Ala Glu Gln Ile Val Cys Glu Met Gly His Ala Leu Val
            980                 985                 990

Gly Thr Thr Ser Gly Pro Val Arg Leu Cys Ile Gly Glu Cys Lys Pro
        995                 1000                1005

Glu Phe Met Thr Lys Ser His Gln Gln Tyr Thr Phe Val Asn Pro Ser
1010                1015                1020

Val Leu Ser Leu Asn Pro Ile Arg Gly Pro Glu Ser Gly Gly Thr Met
1025                1030                1035                1040

Val Thr Ile Thr Gly His Tyr Leu Gly Ala Gly Ser Ser Val Ala Val
            1045                1050                1055

Tyr Leu Gly Asn Gln Thr Cys Glu Phe Tyr Gly Arg Ser Met Ser Glu
            1060                1065                1070

Ile Val Cys Val Ser Pro Pro Ser Asn Gly Leu Gly Pro Val Pro
            1075                1080                1085

Val Ser Val Ser Val Asp Arg Ala His Val Asp Ser Asn Leu Gln Phe
    1090                1095                1100

Glu Tyr Ile Asp Asp Pro Arg Val Gln Arg Ile Glu Pro Glu Trp Ser
1105                1110                1115                1120

Ile Ala Ser Gly His Thr Pro Leu Thr Ile Thr Gly Phe Asn Leu Asp
            1125                1130                1135

Val Ile Gln Glu Pro Arg Ile Arg Val Lys Phe Asn Gly Lys Glu Ser
            1140                1145                1150

Val Asn Val Cys Lys Val Val Asn Thr Thr Thr Leu Thr Cys Leu Ala
            1155                1160                1165

Pro Ser Leu Thr Thr Asp Tyr Arg Pro Gly Leu Asp Thr Val Glu Arg
            1170                1175                1180

Pro Asp Glu Phe Gly Phe Val Phe Asn Asn Val Gln Ser Leu Leu Ile
1185                1190                1195                1200

Tyr Asn Asp Thr Lys Phe Ile Tyr Tyr Pro Asn Pro Thr Phe Glu Leu
            1205                1210                1215

Leu Ser Pro Thr Gly Val Leu Asp Gln Lys Pro Gly Ser Pro Ile Ile
        1220                1225                1230

Leu Lys Gly Lys Asn Leu Cys Pro Pro Ala Ser Gly Gly Ala Lys Leu
        1235                1240                1245

Asn Tyr Thr Val Leu Ile Gly Glu Thr Pro Cys Ala Val Thr Val Ser
        1250                1255                1260

Glu Thr Gln Leu Leu Cys Glu Pro Pro Asn Leu Thr Gly Gln His Lys
1265                1270                1275                1280

Val Met Val His Val Gly Gly Met Val Phe Ser Pro Gly Ser Val Ser
            1285                1290                1295

Val Ile Ser Asp Ser Leu Leu Thr Leu Pro Ala Ile Val Ser Ile Ala
        1300                1305                1310

Ala Gly Gly Ser Leu Leu Leu Ile Ile Val Ile Ile Val Leu Ile Ala
        1315                1320                1325

Tyr Lys Arg Lys Ser Arg Glu Asn Asp Leu Thr Leu Lys Arg Leu Gln
    1330                1335                1340

Met Gln Met Asp Asn Leu Glu Ser Arg Val Ala Leu Glu Cys Lys Glu
1345                1350                1355                1360

Ala Phe Ala Glu Leu Gln Thr Asp Ile Asn Glu Leu Thr Ser Asp Leu
            1365                1370                1375

Asp Arg Ser Gly Ile Pro Tyr Leu Asp Tyr Arg Thr Tyr Ala Met Arg
            1380                1385                1390
```

-continued

```
Val Leu Phe Pro Gly Ile Glu Asp His Pro Val Leu Arg Glu Leu Glu
    1395                1400                1405

Val Gln Gly Asn Gly Gln Gln His Val Glu Lys Ala Leu Lys Leu Phe
    1410                1415                1420

Ala Gln Leu Ile Asn Asn Lys Val Phe Leu Leu Thr Phe Ile Arg Thr
1425                1430                1435                1440

Leu Glu Leu Gln Arg Ser Phe Ser Met Arg Asp Arg Gly Asn Val Ala
                1445                1450                1455

Ser Leu Ile Met Thr Gly Leu Gln Gly Arg Leu Glu Tyr Ala Thr Asp
            1460                1465                1470

Val Leu Lys Gln Leu Leu Ser Asp Leu Ile Asp Lys Asn Leu Glu Asn
    1475                1480                1485

Lys Asn His Pro Lys Leu Leu Leu Arg Arg Thr Glu Ser Val Ala Glu
    1490                1495                1500

Lys Met Leu Thr Asn Trp Phe Ala Phe Leu Leu His Lys Phe Leu Lys
1505                1510                1515                1520

Glu Cys Ala Gly Glu Pro Leu Phe Met Leu Tyr Cys Ala Ile Lys Gln
                1525                1530                1535

Gln Met Glu Lys Gly Pro Ile Asp Ala Ile Thr Gly Glu Ala Arg Tyr
            1540                1545                1550

Ser Leu Ser Glu Asp Lys Leu Ile Arg Gln Gln Ile Glu Tyr Lys Thr
    1555                1560                1565

Leu Ile Leu Asn Cys Val Asn Pro Asp Asn Glu Asn Ser Pro Glu Ile
    1570                1575                1580

Pro Val Lys Val Leu Asn Cys Asp Thr Ile Thr Gln Val Lys Glu Lys
1585                1590                1595                1600

Ile Leu Asp Ala Val Tyr Lys Asn Val Pro Tyr Ser Gln Arg Pro Arg
                1605                1610                1615

Ala Val Asp Met Asp Leu Glu Trp Arg Gln Gly Arg Ile Ala Arg Val
            1620                1625                1630

Val Leu Gln Asp Glu Asp Ile Thr Thr Lys Ile Glu Gly Asp Trp Lys
    1635                1640                1645

Arg Leu Asn Thr Leu Met His Tyr Gln Val Ser Asp Arg Ser Val Val
    1650                1655                1660

Ala Leu Val Pro Lys Gln Thr Ser Ser Tyr Asn Ile Pro Ala Ser Ala
1665                1670                1675                1680

Ser Ile Ser Arg Thr Ser Ile Ser Arg Tyr Asp Ser Ser Phe Arg Tyr
                1685                1690                1695

Thr Gly Ser Pro Asp Ser Leu Arg Ser Arg Ala Pro Met Ile Thr Pro
            1700                1705                1710

Asp Leu Glu Ser Gly Val Lys Val Trp His Leu Val Lys Asn His Asp
    1715                1720                1725

His Gly Asp Gln Lys Glu Gly Asp Arg Gly Ser Lys Met Val Ser Glu
    1730                1735                1740

Ile Tyr Leu Thr Arg Leu Leu Ala Thr Lys Gly Thr Leu Gln Lys Phe
1745                1750                1755                1760

Val Asp Asp Leu Phe Glu Thr Leu Phe Ser Thr Val His Arg Gly Ser
                1765                1770                1775

Ala Leu Pro Leu Ala Ile Lys Tyr Met Phe Asp Phe Leu Asp Glu Gln
            1780                1785                1790

Ala Asp Arg His Ser Ile His Asp Thr Asp Val Arg His Thr Trp Lys
    1795                1800                1805

Ser Asn Cys Leu Pro Leu Arg Phe Trp Val Asn Val Ile Lys Asn Pro
```

```
                1810                1815                1820
Gln Phe Val Phe Asp Ile His Lys Gly Ser Ile Thr Asp Ala Cys Leu
1825                1830                1835                1840

Ser Val Val Ala Gln Thr Phe Met Asp Ser Cys Ser Thr Ser Glu His
                1845                1850                1855

Arg Leu Gly Lys Asp Ser Pro Ser Asn Lys Leu Leu Tyr Ala Lys Asp
                1860                1865                1870

Ile Pro Ser Tyr Lys Ser Trp Val Glu Arg Tyr Tyr Ala Asp Ile Ala
            1875                1880                1885

Lys Leu Pro Ala Ile Ser Asp Gln Asp Met Asn Ala Tyr Leu Ala Glu
            1890                1895                1900

Gln Ser Arg Leu His Ala Val Glu Phe Asn Met Leu Ser Ala Leu Asn
1905                1910                1915                1920

Glu Ile Tyr Ser Tyr Val Ser Lys Tyr Ser Glu Leu Ile Gly Ala
                1925                1930                1935

Leu Glu Gln Asp Glu Gln Ala Arg Arg Gln Arg Leu Ala Tyr Lys Val
            1940                1945                1950

Glu Gln Leu Ile Asn Ala Met Ser Ile Glu Ser
            1955                1960

<210> SEQ ID NO 44
<211> LENGTH: 1905
<212> TYPE: PRT
<213> ORGANISM: Xenopus laevis

<400> SEQUENCE: 44

Met Leu Leu His Ala Glu Arg Pro Leu Pro Phe His Leu Trp Thr Phe
1               5                   10                  15

Leu Val Leu Leu Gly Ser Trp Ile Ala Thr Gly Asp Gly Ser Pro Lys
                20                  25                  30

Asp Phe Arg Thr Phe Thr Gly Ser Asp Trp Ser Leu Thr His Leu Val
            35                  40                  45

Val His Asn Lys Thr Gly Glu Val Tyr Val Gly Ala Ile Asn Arg Ile
    50                  55                  60

Tyr Lys Leu Ser Asn Asn Leu Thr Leu Leu Arg Thr His Val Thr Gly
65                  70                  75                  80

Pro Val Glu Asp Asn Glu Lys Cys Tyr Pro Pro Ser Val Gln Ser
                85                  90                  95

Cys Pro His Gly Leu Ile Thr Thr Asn Asn Val Asn Lys Leu Leu Leu
            100                 105                 110

Ile Asp Tyr Ser Asp Asn Arg Leu Ile Ala Cys Gly Ser Ala Ser Gln
        115                 120                 125

Gly Ile Cys Gln Phe Leu Arg Leu Asp Asp Leu Phe Lys Leu Gly Glu
    130                 135                 140

Pro His His Arg Lys Glu His Tyr Leu Ser Ser Val Asn Glu Ser Gly
145                 150                 155                 160

Thr Met Ser Gly Val Ile Ile Glu Val Pro Asn Gly Gln Asn Lys Leu
                165                 170                 175

Phe Val Gly Thr Pro Ile Asp Gly Lys Ser Glu Tyr Phe Pro Thr Leu
            180                 185                 190

Ser Ser Arg Lys Leu Leu Gly Asn Glu Glu Asn Ala Glu Met Phe Gly
        195                 200                 205

Phe Val Tyr Gln Asp Glu Phe Val Ser Ser Gln Leu Lys Ile Pro Ser
    210                 215                 220
```

-continued

```
Asp Thr Leu Ser Lys Phe Pro Thr Phe Asp Ile Tyr Tyr Val Tyr Ser
225                 230                 235                 240

Phe Ser Ser Glu Gln Phe Val Tyr Tyr Leu Thr Leu Gln Leu Asp Thr
            245                 250                 255

Gln Leu Thr Ser Pro Asp Ser Thr Gly Glu Gln Phe Phe Thr Ser Lys
        260                 265                 270

Ile Val Arg Leu Cys Val Asp Asp Pro Lys Phe Tyr Ser Tyr Val Glu
    275                 280                 285

Phe Pro Ile Gly Cys Met Lys Asp Gly Val Glu Tyr Arg Leu Ile Gln
290                 295                 300

Asp Ala Tyr Leu Ser Lys Pro Gly Lys Arg Leu Ala Lys Glu Leu Gly
305                 310                 315                 320

Ile Ser Glu Arg Glu Asp Ile Leu Phe Thr Val Phe Ser Gln Gly Gln
            325                 330                 335

Lys Asn Arg Ile Lys Pro Pro Lys Glu Ser Val Leu Cys Leu Phe Thr
        340                 345                 350

Leu Lys Lys Ile Lys Asp Lys Ile Lys Glu Arg Ile Gln Ser Cys Tyr
    355                 360                 365

Arg Gly Asp Gly Lys Leu Ser Leu Pro Trp Leu Leu Asn Lys Glu Leu
370                 375                 380

Gly Cys Ile Asn Ser Pro Leu Gln Ile Asp Asp Asn Phe Cys Gly Gln
385                 390                 395                 400

Asp Phe Asn Gln Pro Leu Gly Gly Thr Val Thr Ile Glu Gly Thr Pro
            405                 410                 415

Leu Phe Leu Asp Lys Glu Asp Gly Met Thr Ser Val Ala Ala Tyr Asp
        420                 425                 430

Tyr Arg Gly His Thr Val Val Phe Ala Gly Thr Arg Ser Gly Arg Val
    435                 440                 445

Lys Lys Ile Leu Val Asp Leu Ser Ala Ser Ser His Leu Val Gln
450                 455                 460

Gln Tyr Glu Asn Val Val His Glu Gly Asn Ala Ile Leu Arg Asp
465                 470                 475                 480

Leu Val Leu Ser Pro Asp Arg Gln Tyr Ile Tyr Ala Met Thr Glu Lys
            485                 490                 495

Gln Val Thr Arg Val Pro Val Glu Ser Cys Glu Gln Tyr Glu Ser Cys
        500                 505                 510

Asp Thr Cys Leu Gly Ser Arg Asp Pro His Cys Gly Trp Cys Val Leu
    515                 520                 525

His Asn Met Cys Ser Arg Lys Asp Lys Cys Glu Arg Ala Asp Glu Leu
530                 535                 540

His Arg Phe Thr Ser Asp Gln Arg Gln Cys Val Gln Leu Thr Val His
545                 550                 555                 560

Pro Lys Asn Ile Ser Val Thr Val Ser Glu Val Pro Met Val Leu Gln
            565                 570                 575

Ala Trp Asn Val Pro Asp Leu Ser Ala Gly Val Asn Cys Ser Phe Glu
        580                 585                 590

Asp Phe Thr Glu Met Glu Gly Arg Ile Leu Asp Gly Lys Ile Tyr Cys
    595                 600                 605

Thr Ser Pro Ser Ala Lys Glu Val Ile Pro Ile Thr Arg Gly His Gly
610                 615                 620

Asp Lys Arg Val Val Lys Leu Tyr Leu Lys Ser Lys Glu Thr Gly Lys
625                 630                 635                 640

Lys Phe Ala Ser Val Asp Phe Val Phe Tyr Asn Cys Ser Val His Gln
```

-continued

```
                645                 650                 655
Ser Cys Leu Ser Cys Val Asn Gly Ser Phe Pro Cys His Trp Cys Lys
            660                 665                 670
Tyr Arg His Val Cys Thr His Asn Ala Ala Asp Cys Ser Phe Gln Glu
        675                 680                 685
Gly Arg Val Asn Met Ser Glu Asp Cys Pro Gln Ile Leu Pro Ser Ser
    690                 695                 700
Gln Ile Tyr Ile Pro Val Gly Val Lys Pro Ile Thr Leu Thr Ala
705                 710                 715                 720
Lys Asn Leu Pro Gln Pro Gln Ser Gly Gln Arg Asn Tyr Glu Cys Ile
                725                 730                 735
Phe His Ile Pro Gly Ser Val Thr Arg Val Thr Ala Leu Arg Phe Asn
            740                 745                 750
Ser Thr Ser Ile Gln Cys Gln Asn Thr Ser Tyr Asn Tyr Glu Gly Asn
        755                 760                 765
Asp Ile Ser Asp Leu Pro Val Asn Leu Ser Val Val Trp Asn Gly His
    770                 775                 780
Phe Val Ile Asp Asn Pro Gln Asn Ile Gln Ala His Leu Tyr Lys Cys
785                 790                 795                 800
Ser Ala Leu Arg Glu Ser Cys Gly Leu Cys Leu Lys Ser Asp Arg Arg
                805                 810                 815
Phe Glu Cys Gly Trp Cys Val Ser Glu Lys Lys Cys Thr Leu Arg Gln
            820                 825                 830
Asn Cys Pro Thr Leu Glu Asn Pro Trp Met His Ala Ser Thr Ala Asn
        835                 840                 845
Ser Arg Cys Thr Asp Pro Lys Ile Thr Lys Leu Phe Pro Glu Thr Gly
    850                 855                 860
Pro Arg Gln Gly Gly Thr Arg Leu Thr Ile Thr Gly Glu Asn Leu Gly
865                 870                 875                 880
Leu Arg Phe Glu Asp Ile Arg Phe Gly Val Arg Val Gly His Val Met
                885                 890                 895
Cys Val Pro Val Glu Ser Glu Tyr Ile Ser Ala Glu Gln Ile Val Cys
            900                 905                 910
Glu Ile Asn Asp Ala Gly Arg Thr Arg Val His Glu Ala Gln Val Glu
        915                 920                 925
Val Cys Val Lys Asp Cys Ser Gln Asp Tyr Arg Ala Ile Ser Pro Lys
    930                 935                 940
Ser Phe Thr Phe Val Leu Pro Ser Phe Asn Arg Val Thr Pro Ser Arg
945                 950                 955                 960
Gly Pro Leu Ser Gly Gly Thr Trp Ile Ser Ile Glu Gly Asn Tyr Leu
                965                 970                 975
Asn Ala Gly Ser Asp Val Ser Val Ala Ile Gly Gly Arg Pro Cys Met
            980                 985                 990
Phe Ser Trp Arg Thr Ala Lys Glu Ile Arg Cys Lys Thr Pro Gln Gly
        995                 1000                1005
Pro Ser Thr Gly Lys Ala Glu Ile Gln Ile Leu Ile Asn Arg Ala Thr
    1010                1015                1020
Met Asn Asn Ser Glu Val His Tyr Asn Tyr Thr Glu Asp Pro Thr Val
1025                1030                1035                1040
Gln Lys Ile Glu Pro Glu Trp Ser Ile Ala Ser Gly Gly Thr Pro Leu
                1045                1050                1055
Ile Val Thr Gly Met Asn Leu Ala Thr Ile Lys Glu Pro Lys Ile Arg
            1060                1065                1070
```

-continued

```
Ala Lys Tyr Gly Asp Val Glu Lys Glu Asn Asn Cys Thr Leu Tyr Asn
    1075                1080                1085
Asp Thr Thr Met Val Cys Leu Ala Pro Ser Val Asp Asn Pro Leu Arg
    1090                1095                1100
Ser Pro Pro Glu Asn Gly Asp Arg Pro Asp Glu Ile Gly Phe Ile Met
1105                1110                1115                1120
Asp Asn Val His Ala Leu Leu Ile Val Asn Thr Thr Ser Phe Leu Tyr
            1125                1130                1135
Tyr Pro Asp Pro Val Phe Glu Pro Leu Thr Ala Ser Gly Asn Leu Glu
        1140                1145                1150
Leu Lys Pro Ser Ser Pro Leu Ile Ile Lys Gly Arg Asn Leu Ile Pro
    1155                1160                1165
Ala Ala Pro Gly Asn Phe Arg Leu Asn Tyr Thr Val Leu Ile Gly Asp
    1170                1175                1180
Thr Pro Cys Ala Leu Thr Val Ser Glu Thr Gln Leu Leu Cys Glu Ser
1185                1190                1195                1200
Pro Asn Leu Thr Gly Gln His Lys Val Thr Ile Lys Ala Gly Gly Phe
            1205                1210                1215
Glu Tyr Ser Pro Gly Thr Leu Gln Ile Tyr Ser Asp Ser Leu Leu Thr
        1220                1225                1230
Leu Pro Ala Ile Ile Gly Ile Gly Gly Gly Gly Leu Leu Leu Leu
    1235                1240                1245
Ile Ile Ile Ile Val Leu Ile Ala Tyr Lys Arg Lys Ser Arg Asp Ala
    1250                1255                1260
Asp Arg Thr Leu Lys Arg Leu Gln Leu Gln Met Asp Asn Leu Glu Ser
1265                1270                1275                1280
Arg Val Ala Leu Glu Cys Lys Glu Ala Phe Ala Glu Leu Gln Thr Asp
            1285                1290                1295
Ile His Glu Leu Thr Asn Asp Leu Asp Gly Ala Gly Ile Pro Phe Leu
        1300                1305                1310
Glu Tyr Arg Thr Tyr Ala Met Arg Val Leu Phe Pro Gly Ile Glu Asp
    1315                1320                1325
His Pro Val Leu Lys Glu Met Glu Val Gln Ala Asn Val Glu Lys Ser
    1330                1335                1340
Leu Thr Leu Phe Gly Gln Leu Leu Thr Lys Lys His Phe Leu Leu Thr
1345                1350                1355                1360
Phe Ile Arg Thr Leu Glu Ala Gln Arg Ser Phe Ser Met Arg Asp Arg
            1365                1370                1375
Gly Asn Val Ala Ser Leu Ile Met Thr Ala Leu Gln Gly Glu Met Glu
        1380                1385                1390
Tyr Ala Thr Gly Val Leu Lys Gln Leu Leu Ser Asp Leu Ile Glu Lys
    1395                1400                1405
Asn Leu Glu Ser Lys Asn His Pro Lys Leu Leu Leu Arg Arg Thr Glu
    1410                1415                1420
Ser Val Ala Glu Lys Met Leu Thr Asn Trp Phe Thr Phe Leu Leu Tyr
1425                1430                1435                1440
Lys Phe Leu Lys Glu Cys Ala Gly Glu Pro Leu Phe Met Leu His Cys
            1445                1450                1455
Ala Ile Lys Gln Gln Met Glu Lys Gly Pro Ile Asp Ala Ile Thr Gly
        1460                1465                1470
Glu Ala Arg Tyr Ser Leu Ser Glu Asp Lys Leu Ile Arg Gln Gln Ile
    1475                1480                1485
```

```
Asp Tyr Lys Thr Leu Asn Pro Cys Ala Asp Asp Val Gly Leu Ser Asp
    1490                1495                1500

Glu Ser Cys Cys Arg Ser Pro Gln Thr Leu Asn Cys Val Asn Pro Glu
1505                1510                1515                1520

Asn Glu Asn Ala Pro Glu Ile Pro Val Lys Val Leu Asn Cys Asp Thr
            1525                1530                1535

Ile Thr Gln Val Lys Glu Lys Leu Leu Asp Ala Val Tyr Lys Gly Val
        1540                1545                1550

Pro Tyr Ser Gln Arg Pro Lys Ala Gly Asp Met Asp Leu Glu Trp Arg
    1555                1560                1565

Gln Gly Arg Met Ala Arg Ile Ile Leu Gln Asp Glu Asp Val Thr Thr
1570                1575                1580

Lys Ile Asp Asn Asp Trp Lys Arg Leu Asn Thr Leu Ala His Tyr Gln
1585                1590                1595                1600

Val Thr Asp Gly Ser Ser Val Ala Leu Val Pro Lys Gln Asn Ser Ala
            1605                1610                1615

Tyr Asn Ile Ser Asn Ser Ser Thr Phe Thr Lys Ser Leu Ser Arg Tyr
        1620                1625                1630

Glu Ser Met Leu Arg Thr Ala Ser Ser Pro Asp Ser Leu Arg Ser Arg
    1635                1640                1645

Thr Pro Met Ile Thr Pro Asp Leu Glu Ser Gly Thr Lys Leu Trp His
1650                1655                1660

Leu Val Lys Asn His Asp His Leu Asp Gln Arg Glu Gly Asp Arg Gly
1665                1670                1675                1680

Ser Lys Met Val Ser Glu Ile Tyr Leu Thr Arg Leu Leu Ala Thr Lys
            1685                1690                1695

Gly Thr Leu Gln Lys Phe Val Asp Asp Leu Phe Glu Thr Ile Phe Ser
        1700                1705                1710

Thr Ala His Arg Gly Ser Ala Leu Pro Leu Ala Ile Lys Tyr Met Phe
    1715                1720                1725

Asp Phe Leu Asp Glu Gln Ala Asp Lys His Gln Ile Thr Asp Tyr Asp
1730                1735                1740

Val Arg His Thr Trp Lys Ser Asn Cys Leu Pro Leu Arg Phe Trp Val
1745                1750                1755                1760

Asn Val Ile Lys Asn Pro Gln Phe Val Phe Asp Ile His Lys Asn Ser
            1765                1770                1775

Ile Thr Asp Ala Cys Leu Ser Val Val Ala Gln Thr Phe Met Asp Ser
        1780                1785                1790

Cys Ser Thr Ser Glu His Lys Leu Gly Lys Asp Ser Pro Ser Asn Lys
    1795                1800                1805

Leu Leu Tyr Ala Lys Asp Ile Pro Asn Tyr Lys Ser Trp Val Glu Arg
    1810                1815                1820

Tyr Tyr Ala Asp Ile Ala Lys Met Pro Val Ile Ser Asp Gln Asp Met
1825                1830                1835                1840

Ser Ala Tyr Leu Ala Glu Gln Ser Arg Leu His Leu Ser Gln Phe Asn
            1845                1850                1855

Ser Met Ser Ala Leu His Glu Ile Tyr Ser Tyr Ile Thr Lys Tyr Arg
        1860                1865                1870

Asp Glu Ile Leu Thr Ala Leu Glu Lys Asp Glu Gln Ala Arg Arg Gln
    1875                1880                1885

Arg Leu Arg Ser Lys Leu Glu Gln Val Ile Asp Thr Met Ala Gln Ser
    1890                1895                1900

Ser
```

-continued

1905

<210> SEQ ID NO 45
<211> LENGTH: 813
<212> TYPE: PRT
<213> ORGANISM: Homo sapiens

<400> SEQUENCE: 45

```
Gly Thr Arg Val Val Cys Lys Val Val Asn Thr Thr Leu Thr Cys
 1               5                  10                  15

Leu Ala Pro Ser Leu Thr Thr Asp Tyr Arg Pro Gly Leu Asp Thr Val
                20                  25                  30

Glu Arg Pro Asp Glu Phe Gly Phe Val Phe Asn Asn Val Gln Ser Leu
            35                  40                  45

Leu Ile Tyr Asn Asp Thr Lys Phe Ile Tyr Tyr Pro Asn Pro Thr Phe
        50                  55                  60

Glu Leu Leu Ser Pro Thr Gly Val Leu Asp Gln Lys Pro Gly Ser Pro
65                  70                  75                  80

Ile Ile Leu Lys Gly Lys Asn Leu Cys Pro Pro Ala Ser Gly Gly Ala
                85                  90                  95

Lys Leu Asn Tyr Thr Val Leu Ile Gly Glu Thr Pro Cys Ala Val Thr
            100                 105                 110

Val Ser Glu Thr Gln Leu Leu Cys Glu Pro Pro Asn Leu Thr Gly Gln
        115                 120                 125

His Lys Val Met Val His Val Gly Gly Met Val Phe Ser Pro Gly Ser
    130                 135                 140

Val Ser Val Ile Ser Asp Ser Leu Leu Thr Leu Pro Ala Ile Val Ser
145                 150                 155                 160

Ile Ala Ala Gly Gly Ser Leu Leu Leu Ile Val Ile Ile Val Leu
                165                 170                 175

Ile Ala Tyr Lys Arg Lys Ser Arg Glu Asn Asp Leu Thr Leu Lys Arg
            180                 185                 190

Leu Gln Met Gln Met Asp Asn Leu Glu Ser Arg Val Ala Leu Glu Cys
        195                 200                 205

Lys Glu Ala Phe Ala Glu Leu Gln Thr Asp Ile Asn Glu Leu Thr Ser
    210                 215                 220

Asp Leu Asp Arg Ser Gly Ile Pro Tyr Leu Asp Tyr Arg Thr Tyr Ala
225                 230                 235                 240

Met Arg Val Leu Phe Pro Gly Ile Glu Asp His Pro Val Leu Arg Glu
                245                 250                 255

Leu Glu Val Gln Gly Asn Gly Gln Gln His Val Glu Lys Ala Leu Lys
            260                 265                 270

Leu Phe Ala Gln Leu Ile Asn Asn Lys Val Phe Leu Leu Thr Phe Ile
        275                 280                 285

Arg Thr Leu Glu Leu Gln Arg Ser Phe Ser Met Arg Asp Arg Gly Asn
    290                 295                 300

Val Ala Ser Leu Ile Met Thr Gly Leu Gln Gly Arg Leu Glu Tyr Ala
305                 310                 315                 320

Thr Asp Val Leu Lys Gln Leu Ser Asp Leu Ile Asp Lys Asn Leu
                325                 330                 335

Glu Asn Lys Asn His Pro Lys Leu Leu Leu Arg Arg Thr Glu Ser Val
            340                 345                 350

Ala Glu Lys Met Leu Thr Asn Trp Phe Ala Phe Leu Leu His Lys Phe
        355                 360                 365
```

-continued

```
Leu Lys Glu Cys Ala Gly Glu Pro Leu Phe Met Leu Tyr Cys Ala Ile
    370                 375                 380

Lys Gln Gln Met Glu Lys Gly Pro Ile Asp Ala Ile Thr Gly Glu Ala
385                 390                 395                 400

Arg Tyr Ser Leu Ser Glu Asp Lys Leu Ile Arg Gln Gln Ile Glu Tyr
                405                 410                 415

Lys Thr Leu Ile Leu Asn Cys Val Asn Pro Asp Asn Glu Asn Ser Pro
            420                 425                 430

Glu Ile Pro Val Lys Val Leu Asn Cys Asp Thr Ile Thr Gln Val Lys
                435                 440                 445

Glu Lys Ile Leu Asp Ala Val Tyr Lys Asn Val Pro Tyr Ser Gln Arg
    450                 455                 460

Pro Arg Ala Val Asp Met Asp Leu Glu Trp Arg Gln Gly Arg Ile Ala
465                 470                 475                 480

Arg Val Val Leu Gln Asp Glu Asp Ile Thr Thr Lys Ile Glu Gly Asp
                485                 490                 495

Trp Lys Arg Leu Asn Thr Leu Met His Tyr Gln Val Ser Asp Arg Ser
            500                 505                 510

Val Val Ala Leu Val Pro Lys Gln Thr Ser Ser Tyr Asn Ile Pro Ala
            515                 520                 525

Ser Ala Ser Ile Ser Arg Thr Ser Ile Ser Arg Tyr Asp Ser Ser Phe
530                 535                 540

Arg Tyr Thr Gly Ser Pro Asp Ser Leu Arg Ser Arg Ala Pro Met Ile
545                 550                 555                 560

Thr Pro Asp Leu Glu Ser Gly Val Lys Val Trp His Leu Val Lys Asn
                565                 570                 575

His Asp His Gly Asp Gln Lys Glu Gly Asp Arg Gly Ser Lys Met Val
            580                 585                 590

Ser Glu Ile Tyr Leu Thr Arg Leu Leu Ala Thr Lys Gly Thr Leu Gln
            595                 600                 605

Lys Phe Val Asp Asp Leu Phe Glu Thr Leu Leu Ser Thr Val His Arg
610                 615                 620

Gly Ser Ala Leu Pro Leu Ala Ile Lys Tyr Met Phe Asp Phe Leu Asp
625                 630                 635                 640

Glu Gln Ala Asp Arg His Ser Ile His Asp Thr Asp Val Arg His Thr
                645                 650                 655

Trp Lys Ser Asn Cys Leu Pro Leu Arg Phe Trp Val Asn Val Ile Lys
            660                 665                 670

Asn Pro Gln Phe Val Phe Asp Ile His Lys Gly Ser Ile Thr Asp Ala
            675                 680                 685

Cys Leu Ser Val Val Ala Gln Thr Phe Met Asp Ser Cys Ser Thr Ser
    690                 695                 700

Glu His Arg Leu Gly Lys Asp Ser Pro Ser Asn Lys Leu Leu Tyr Ala
705                 710                 715                 720

Lys Asp Ile Pro Ser Tyr Lys Ser Trp Val Glu Arg Tyr Tyr Ala Asp
                725                 730                 735

Ile Ala Lys Leu Pro Ala Ile Ser Asp Gln Asp Met Asn Ala Tyr Leu
            740                 745                 750

Ala Glu Gln Ser Arg Leu His Ala Val Glu Phe Asn Met Leu Ser Ala
            755                 760                 765

Leu Asn Glu Ile Tyr Ser Tyr Val Ser Lys Tyr Ser Glu Glu Leu Ile
770                 775                 780

Gly Ala Leu Glu Gln Asp Glu Gln Ala Arg Arg Gln Arg Leu Ala Tyr
```

```
                    785              790              795              800
Lys Val Glu Gln Leu Ile Asn Ala Met Ser Ile Glu Ser
                805              810

<210> SEQ ID NO 46
<211> LENGTH: 593
<212> TYPE: PRT
<213> ORGANISM: Homo sapiens

<400> SEQUENCE: 46

Val Glu Leu Thr Val Val Trp Asn Gly His Phe Asn Ile Asp Asn Pro
 1               5                  10                  15

Ala Gln Asn Lys Val His Leu Tyr Lys Cys Gly Ala Met Arg Glu Ser
                20                  25                  30

Cys Gly Leu Cys Leu Lys Ala Asp Pro Asp Phe Ala Cys Gly Trp Cys
            35                  40                  45

Gln Gly Pro Gly Gln Cys Thr Leu Arg Gln His Cys Pro Ala Gln Glu
        50                  55                  60

Ser Gln Trp Leu Glu Leu Ser Gly Ala Lys Ser Lys Cys Thr Asn Pro
65                  70                  75                  80

Arg Ile Thr Glu Ile Ile Pro Val Thr Gly Pro Arg Glu Gly Gly Thr
                85                  90                  95

Lys Val Thr Ile Arg Gly Glu Asn Leu Gly Leu Glu Phe Arg Asp Ile
                100                 105                 110

Ala Ser His Val Lys Val Ala Gly Val Glu Cys Ser Pro Leu Val Asp
            115                 120                 125

Gly Tyr Ile Pro Ala Glu Gln Ile Val Cys Glu Met Gly Glu Ala Lys
        130                 135                 140

Pro Ser Gln His Ala Gly Phe Val Glu Ile Cys Val Ala Val Cys Arg
145                 150                 155                 160

Pro Glu Phe Met Ala Arg Ser Ser Gln Leu Tyr Tyr Phe Met Thr Leu
                165                 170                 175

Thr Leu Ser Asp Leu Lys Pro Ser Arg Gly Pro Met Ser Gly Gly Thr
            180                 185                 190

Gln Val Thr Ile Thr Gly Thr Asn Leu Asn Ala Gly Ser Asn Val Val
        195                 200                 205

Val Met Phe Gly Lys Gln Pro Cys Leu Phe His Arg Arg Ser Pro Ser
    210                 215                 220

Tyr Ile Val Cys Asn Thr Thr Ser Ser Asp Glu Val Leu Glu Met Lys
225                 230                 235                 240

Val Ser Val Gln Val Asp Arg Ala Lys Ile His Gln Asp Leu Val Phe
                245                 250                 255

Gln Tyr Val Glu Asp Pro Thr Ile Val Arg Ile Glu Pro Glu Trp Ser
            260                 265                 270

Ile Val Ser Gly Asn Thr Pro Ile Ala Val Trp Gly Thr His Leu Asp
        275                 280                 285

Leu Ile Gln Asn Pro Gln Ile Arg Ala Lys His Gly Gly Lys Glu His
    290                 295                 300

Ile Asn Ile Cys Glu Val Leu Asn Ala Thr Glu Met Thr Cys Gln Ala
305                 310                 315                 320

Pro Ala Leu Ala Leu Gly Pro Asp His Gln Ser Asp Leu Thr Glu Arg
                325                 330                 335

Pro Glu Glu Phe Gly Phe Ile Leu Asp Asn Val Gln Ser Leu Leu Ile
            340                 345                 350
```

```
Leu Asn Lys Thr Asn Phe Thr Tyr Tyr Pro Asn Pro Val Phe Glu Ala
            355                 360                 365

Phe Gly Pro Ser Gly Ile Leu Glu Leu Lys Pro Gly Thr Pro Ile Ile
        370                 375                 380

Leu Lys Gly Lys Asn Leu Ile Pro Pro Val Ala Gly Asn Val Lys
385                 390                 395                 400

Leu Asn Tyr Thr Val Leu Val Gly Lys Pro Cys Thr Val Thr Val
                405                 410                 415

Ser Asp Val Gln Leu Leu Cys Glu Ser Pro Asn Leu Ile Gly Arg His
                420                 425                 430

Lys Val Met Ala Arg Val Gly Gly Met Glu Tyr Ser Pro Gly Met Val
            435                 440                 445

Tyr Ile Ala Pro Asp Ser Pro Leu Ser Leu Pro Ala Ile Val Ser Ile
        450                 455                 460

Ala Val Ala Gly Gly Leu Leu Ile Ile Phe Ile Val Ala Val Leu Ile
465                 470                 475                 480

Ala Tyr Lys Arg Lys Ser Arg Glu Ser Asp Leu Thr Leu Lys Arg Leu
                485                 490                 495

Gln Met Gln Met Asp Asn Leu Glu Ser Arg Val Ala Leu Glu Cys Lys
            500                 505                 510

Glu Gly Thr Glu Trp Pro His Ala Gly Gly His Val Cys Val Arg Val
        515                 520                 525

Cys Ile Cys Val Cys Met His Ile Cys Val Cys Val Cys Ile Cys Phe
        530                 535                 540

Ile Tyr Lys Gln Ala Gly Trp Ala Ala Val Gly Ser Ala Gly Gly Trp
545                 550                 555                 560

Arg Cys Val Cys Leu Cys Glu Cys Val Cys Val His Val Cys Val Cys
                565                 570                 575

Thr Ser Val Cys Ile Tyr Val Ser Tyr Thr Ser Lys Gln Ala Gly Gln
            580                 585                 590

Gln

<210> SEQ ID NO 47
<211> LENGTH: 477
<212> TYPE: PRT
<213> ORGANISM: Homo sapiens

<400> SEQUENCE: 47

Met Leu Pro Pro Gly Ser Asn Gly Thr Ala Tyr Pro Gly Gln Phe Ala
  1               5                  10                  15

Leu Tyr Gln Gln Leu Ala Gln Gly Asn Ala Val Gly Gly Ser Ala Gly
                20                  25                  30

Ala Pro Pro Leu Gly Pro Ser Gln Val Val Thr Ala Cys Leu Leu Thr
            35                  40                  45

Leu Leu Ile Ile Trp Thr Leu Leu Gly Asn Val Leu Val Cys Ala Ala
        50                  55                  60

Ile Val Arg Ser Arg His Leu Arg Ala Asn Met Thr Asn Val Phe Ile
 65                  70                  75                  80

Val Ser Leu Ala Val Ser Asp Leu Phe Val Ala Leu Leu Val Met Pro
                85                  90                  95

Trp Lys Ala Val Ala Glu Val Ala Gly Tyr Trp Pro Phe Gly Ala Phe
            100                 105                 110

Cys Asp Val Trp Val Ala Phe Asp Ile Met Cys Ser Thr Ala Ser Ile
        115                 120                 125
```

```
Leu Asn Leu Cys Val Ile Ser Val Asp Arg Tyr Trp Ala Ile Ser Arg
            130                 135                 140

Pro Phe Arg Tyr Lys Arg Lys Met Thr Gln Arg Met Ala Leu Val Met
145                 150                 155                 160

Val Gly Leu Ala Trp Thr Leu Ser Ile Leu Ile Ser Phe Ile Pro Val
                165                 170                 175

Gln Leu Asn Trp His Arg Asp Gln Ala Ala Ser Trp Gly Gly Leu Asp
            180                 185                 190

Leu Pro Asn Asn Leu Ala Asn Trp Thr Pro Trp Glu Glu Asp Phe Trp
            195                 200                 205

Glu Pro Asp Val Asn Ala Glu Asn Cys Asp Ser Ser Leu Asn Arg Thr
            210                 215                 220

Tyr Ala Ile Ser Ser Ser Leu Ile Ser Phe Tyr Ile Pro Val Ala Ile
225                 230                 235                 240

Met Ile Val Thr Tyr Thr Arg Ile Tyr Arg Ile Ala Gln Val Gln Ile
                245                 250                 255

Arg Arg Ile Ser Ser Leu Glu Arg Ala Ala Glu His Ala Gln Ser Cys
            260                 265                 270

Arg Ser Ser Ala Ala Cys Ala Pro Asp Thr Ser Leu Arg Ala Ser Ile
            275                 280                 285

Lys Lys Glu Thr Lys Val Leu Lys Thr Leu Ser Val Ile Met Gly Val
            290                 295                 300

Phe Val Cys Cys Trp Leu Pro Phe Phe Ile Leu Asn Cys Met Val Pro
305                 310                 315                 320

Phe Cys Ser Gly His Pro Glu Gly Pro Pro Ala Gly Phe Pro Cys Val
                325                 330                 335

Ser Glu Thr Thr Phe Asp Val Phe Val Trp Phe Gly Trp Ala Asn Ser
            340                 345                 350

Ser Leu Asn Pro Val Ile Tyr Ala Phe Asn Ala Asp Phe Gln Lys Val
            355                 360                 365

Phe Ala Gln Leu Leu Gly Cys Ser His Phe Cys Ser Arg Thr Pro Val
            370                 375                 380

Glu Thr Val Asn Ile Ser Asn Glu Leu Ile Ser Tyr Asn Gln Asp Ile
385                 390                 395                 400

Val Phe His Lys Glu Ile Ala Ala Ala Tyr Ile His Met Met Pro Asn
                405                 410                 415

Ala Val Thr Pro Gly Asn Arg Glu Val Asp Asn Asp Glu Glu Glu Gly
                420                 425                 430

Pro Phe Asp Arg Met Phe Gln Ile Tyr Gln Thr Ser Pro Asp Gly Asp
            435                 440                 445

Pro Val Ala Glu Ser Val Trp Glu Leu Asp Cys Glu Gly Glu Ile Ser
            450                 455                 460

Leu Asp Lys Ile Thr Pro Phe Thr Pro Asn Gly Phe His
465                 470                 475

<210> SEQ ID NO 48
<211> LENGTH: 475
<212> TYPE: PRT
<213> ORGANISM: Homo sapiens

<400> SEQUENCE: 48

Met Leu Pro Pro Gly Arg Asn Arg Thr Ala Gln Pro Ala Arg Leu Gly
  1               5                  10                  15

Leu Gln Arg Gln Leu Ala Gln Val Asp Ala Pro Ala Gly Ser Ala Thr
             20                  25                  30
```

```
Pro Leu Gly Pro Ala Gln Val Val Thr Ala Gly Leu Leu Thr Leu Leu
         35                  40                  45

Ile Val Trp Thr Leu Leu Gly Asn Val Leu Val Cys Ala Ala Ile Val
         50                  55                  60

Arg Ser Arg His Leu Arg Ala Lys Met Thr Asn Ile Phe Ile Val Ser
 65              70                  75                      80

Leu Ala Val Ser Asp Leu Phe Val Ala Leu Leu Val Met Pro Trp Lys
                 85                  90                  95

Ala Val Ala Glu Val Ala Gly Tyr Trp Pro Phe Gly Thr Phe Cys Asp
             100                 105                 110

Ile Trp Val Ala Phe Asp Ile Met Cys Ser Thr Ala Ser Ile Leu Asn
             115                 120                 125

Leu Cys Ile Ile Ser Val Asp Arg Tyr Trp Ala Ile Ser Arg Pro Phe
         130                 135                 140

Arg Tyr Glu Arg Lys Met Thr Gln Arg Val Ala Leu Val Met Val Gly
145                 150                 155                 160

Leu Ala Trp Thr Leu Ser Ile Leu Ile Ser Phe Ile Pro Val Gln Leu
                 165                 170                 175

Asn Trp His Arg Asp Lys Ala Gly Ser Gln Gly Gln Glu Gly Leu Leu
             180                 185                 190

Ser Asn Gly Thr Pro Trp Glu Glu Gly Trp Glu Leu Glu Gly Arg Thr
         195                 200                 205

Glu Asn Cys Asp Ser Ser Leu Asn Arg Thr Tyr Ala Ile Ser Ser Ser
210                 215                 220

Leu Ile Ser Phe Tyr Ile Pro Val Ala Ile Met Ile Val Thr Tyr Thr
225                 230                 235                 240

Arg Ile Tyr Arg Ile Ala Gln Val Gln Ile Arg Arg Ile Ser Ser Leu
                 245                 250                 255

Glu Arg Ala Ala Glu His Ala Gln Ser Cys Arg Ser Arg Gly Ala Tyr
             260                 265                 270

Glu Pro Asp Pro Ser Leu Arg Ala Ser Ile Lys Lys Glu Thr Lys Val
             275                 280                 285

Phe Lys Thr Leu Ser Met Ile Met Gly Val Phe Val Cys Cys Trp Leu
290                 295                 300

Pro Phe Phe Ile Leu Asn Cys Met Val Pro Phe Cys Ser Ser Gly Asp
305                 310                 315                 320

Ala Glu Gly Pro Lys Thr Gly Phe Pro Cys Val Ser Glu Thr Thr Phe
                 325                 330                 335

Asp Ile Phe Val Trp Phe Gly Trp Ala Asn Ser Ser Leu Asn Pro Ile
             340                 345                 350

Ile Tyr Ala Phe Asn Ala Asp Phe Arg Lys Val Phe Ala Gln Leu Leu
             355                 360                 365

Gly Cys Ser His Phe Cys Phe Arg Thr Pro Val Gln Thr Val Asn Ile
         370                 375                 380

Ser Asn Glu Leu Ile Ser Tyr Asn Gln Asp Thr Val Phe His Lys Glu
385                 390                 395                 400

Ile Ala Thr Ala Tyr Val His Met Ile Pro Asn Ala Val Ser Ser Gly
                 405                 410                 415

Asp Arg Glu Val Gly Glu Glu Glu Glu Gly Pro Phe Asp His Met
             420                 425                 430

Ser Gln Ile Ser Pro Thr Thr Pro Asp Gly Asp Leu Ala Ala Glu Ser
             435                 440                 445
```

```
Val Trp Glu Leu Asp Cys Glu Glu Val Ser Leu Gly Lys Ile Ser
    450                 455                 460

Pro Leu Thr Pro Asn Cys Phe Asp Lys Thr Ala
465                 470                 475

<210> SEQ ID NO 49
<211> LENGTH: 457
<212> TYPE: PRT
<213> ORGANISM: Homo sapiens

<400> SEQUENCE: 49

Met Tyr Gln Pro Phe Gln His Leu Asp Ser Asp Gln Val Ala Ser Trp
  1               5                  10                  15

Gln Ser Pro Glu Met Leu Met Asn Lys Ser Val Ser Arg Glu Ser Gln
                 20                  25                  30

Arg Arg Lys Glu Leu Val Ala Gly Gln Ile Val Thr Gly Ser Leu Leu
             35                  40                  45

Leu Leu Leu Ile Phe Trp Thr Leu Phe Gly Asn Ile Leu Val Cys Thr
 50                  55                  60

Ala Val Met Arg Phe Arg His Leu Arg Ser Arg Val Thr Asn Ile Phe
 65                  70                  75                  80

Ile Val Ser Leu Ala Val Ser Asp Leu Leu Val Ala Leu Leu Val Met
                 85                  90                  95

Pro Trp Lys Ala Val Ala Glu Val Ala Gly His Trp Pro Phe Gly Ala
            100                 105                 110

Phe Cys Asp Ile Trp Val Ala Phe Asp Ile Met Cys Ser Thr Ala Ser
        115                 120                 125

Ile Leu Asn Leu Cys Val Ile Ser Val Asp Arg Tyr Trp Ala Ile Ser
    130                 135                 140

Ser Pro Phe Arg Tyr Glu Arg Lys Met Thr Gln Arg Val Ala Leu Leu
145                 150                 155                 160

Met Ile Ser Thr Ala Trp Ala Leu Ser Val Leu Ile Ser Phe Ile Pro
                165                 170                 175

Val Gln Leu Ser Trp His Lys Ser Glu Thr Glu Asp His Leu Leu Ser
            180                 185                 190

Asn His Ser Thr Gly Asn Cys Asp Ser Ser Leu Asn Arg Thr Tyr Ala
        195                 200                 205

Ile Ser Ser Ser Leu Ile Ser Phe Tyr Ile Pro Val Ala Ile Met Ile
    210                 215                 220

Val Thr Tyr Thr Arg Ile Tyr Arg Ile Ala Gln Ile Gln Ile Lys Arg
225                 230                 235                 240

Ile Ser Thr Leu Glu Arg Ala Ala Glu His Ala Gln Ser Cys Arg Ser
                245                 250                 255

Asn Arg Val Asp Ser Cys Ser Arg His His Gln Thr Ser Leu Arg Thr
            260                 265                 270

Ser Ile Lys Lys Glu Thr Lys Val Leu Lys Thr Leu Ser Ile Ile Met
        275                 280                 285

Gly Val Phe Val Cys Cys Trp Leu Pro Phe Phe Ile Leu Asn Cys Met
    290                 295                 300

Val Pro Phe Cys Asp Arg Ser Pro Gly His Pro Gln Ala Gly Leu Pro
305                 310                 315                 320

Cys Val Ser Glu Thr Thr Phe Asp Ile Phe Val Trp Phe Gly Trp Ala
                325                 330                 335

Asn Ser Ser Leu Asn Pro Ile Ile Tyr Ala Phe Asn Ala Asp Phe Arg
            340                 345                 350
```

-continued

```
Lys Val Phe Ser Ser Leu Leu Gly Cys Gly His Trp Cys Ser Thr Thr
            355                 360                 365
Pro Val Glu Thr Val Asn Ile Ser Asn Glu Leu Ile Ser Tyr Asn Gln
            370                 375                 380
Asp Thr Leu Phe His Lys Asp Ile Val Thr Ala Tyr Val Asn Met Ile
385                 390                 395                 400
Pro Asn Val Val Asp Cys Ile Asp Asn Glu Asp Ala Phe Asp His
                405                 410                 415
Met Ser Gln Ile Ser Gln Thr Ser Ala Asn Asn Glu Leu Ala Thr Asp
            420                 425                 430
Ser Met Cys Glu Leu Asp Ser Glu Val Asp Ile Ser Leu His Lys Ile
            435                 440                 445
Thr Pro Ser Met Ser Asn Gly Ile His
            450                 455

<210> SEQ ID NO 50
<211> LENGTH: 486
<212> TYPE: PRT
<213> ORGANISM: Gallus gallus

<400> SEQUENCE: 50

Met Leu Arg Gly Gly Arg Ser Pro Leu Pro Pro Ala Gly Pro Pro
1               5                   10                  15
Gly Gly Ala Arg Gly Gln Ala Gly Ala Ala Gln Val Ala Ala
            20                  25                  30
Gly Ser Leu Leu Ala Leu Leu Ile Leu Trp Thr Leu Phe Gly Asn Val
            35                  40                  45
Leu Val Cys Ala Ala Ile Val Arg Tyr Arg His Leu Arg Ser Lys Val
        50                  55                  60
Thr Asn Ile Phe Ile Val Ser Leu Ala Val Ser Asp Leu Leu Val Ala
65                  70                  75                  80
Val Leu Val Met Pro Trp Lys Ala Val Ala Glu Val Ala Gly Tyr Trp
                85                  90                  95
Pro Phe Gly Ala Phe Gln Asn Val Trp Val Ala Phe Asp Ile Met Cys
            100                 105                 110
Ser Thr Ala Ser Ile Leu Asn Leu Cys Val Ile Ser Val Asp Arg Tyr
            115                 120                 125
Trp Ala Ile Ser Ser Pro Phe Arg Tyr Glu Arg Lys Met Thr Gln Arg
        130                 135                 140
Leu Ala Leu Val Met Ile Gly Val Ala Trp Ala Leu Ser Val Leu Ile
145                 150                 155                 160
Ser Phe Ile Pro Val Gln Leu Asn Trp His Arg Gly Gly Asp Ala Ala
                165                 170                 175
Thr Ala Ala Ala Ala Gly Asp Ile Glu Asp Gly Phe Asp Thr Gly Trp
            180                 185                 190
Glu Ala Ala Gly Ala Phe Thr Thr Trp Ala Glu Asp Met Ser Thr Thr
            195                 200                 205
Trp Val Ala Leu Ala Ala Met Thr Pro Ser Glu Gly Thr Ser Gly Ser
        210                 215                 220
Asn Asn Thr Val Pro Gly Pro Ser Glu Ser Cys Asp Ser Ser Leu Asn
225                 230                 235                 240
Arg Thr Tyr Ala Ile Ser Ser Ser Leu Ile Ser Phe Tyr Ile Pro Val
                245                 250                 255
Ala Ile Met Ile Val Thr Tyr Thr Arg Ile Tyr Arg Ile Ala Gln Val
```

```
                    260                 265                 270
Gln Ile Arg Arg Ile Ser Ser Leu Glu Arg Ala Ala Glu His Ala Gln
            275                 280                 285
Ser Cys Arg Cys Asn His Val Asp Cys His His Thr Ser Leu Lys
    290                 295                 300
Ser Ser Ile Arg Lys Glu Thr Lys Val Leu Lys Thr Leu Ser Ile Ile
305                 310                 315                 320
Met Gly Val Phe Val Cys Cys Trp Leu Pro Phe Ile Leu Asn Cys
                325                 330                 335
Met Val Pro Phe Cys Glu Ser Pro Pro Ser Asp Pro Arg Ala Gly Leu
            340                 345                 350
Pro Cys Val Ser Glu Thr Thr Phe Asn Ile Phe Val Trp Phe Gly Trp
        355                 360                 365
Ala Asn Ser Ser Leu Asn Pro Ile Ile Tyr Ala Phe Asn Ala Asp Phe
        370                 375                 380
Arg Lys Val Phe Ser Asn Leu Leu Gly Cys Gly Gln Phe Cys Ser Ser
385                 390                 395                 400
Thr Pro Val Glu Thr Val Asn Ile Ser Asn Glu Leu Ile Ser Tyr His
                405                 410                 415
Gln Asp Thr Phe His Lys Glu Ile Val Thr Ala Tyr Val Asn Met Ile
            420                 425                 430
Pro Asn Val Val Asp Cys Glu Glu Asn Arg Glu Asp Pro Phe Asp Arg
        435                 440                 445
Met Ser Gln Ile Ser Pro Asp Pro Glu Val Ala Thr Asp Ser Val Cys
    450                 455                 460
Glu Leu Asp Cys Glu Gly Glu Ile Ser Leu Gly Lys Ile Thr Pro Phe
465                 470                 475                 480
Thr Pro Asn Gly Leu His
                485

<210> SEQ ID NO 51
<211> LENGTH: 458
<212> TYPE: PRT
<213> ORGANISM: Anguilla anguilla

<400> SEQUENCE: 51

Met Gly Ser Pro Ala Lys Tyr Leu Ser Val His Glu Thr Gln Ser Val
  1               5                  10                  15
Pro Phe Phe Ile Gly Glu Ile Met Trp Asn Thr Ser Glu Ser Ala Glu
             20                  25                  30
Lys Thr Asp Gly Lys Lys Glu Leu Ile Val Arg Thr Val Thr Gly Cys
         35                  40                  45
Leu Leu Ser Leu Leu Ile Leu Trp Thr Leu Leu Gly Asn Ile Leu Val
     50                  55                  60
Cys Ser Ala Val Leu Lys Phe Arg His Leu Arg Thr Lys Val Thr Asn
 65                  70                  75                  80
Ile Phe Ile Val Ser Leu Ala Val Ser Asp Leu Phe Val Ala Val Leu
                 85                  90                  95
Val Met Pro Trp Lys Ala Val Ala Glu Val Ala Gly Tyr Trp Pro Phe
            100                 105                 110
Gly Pro Phe Cys Asn Ile Trp Val Ala Phe Asp Ile Met Cys Ser Thr
        115                 120                 125
Ala Ser Ile Leu Asn Leu Cys Ile Ile Ser Val Asp Arg Tyr Trp Ala
    130                 135                 140
```

```
Ile Ser Ser Pro Phe Arg Tyr Glu Arg Lys Met Thr Gln Arg Val Ala
145                 150                 155                 160

Phe Val Met Ile Ser Val Thr Trp Thr Leu Ser Val Leu Ile Ser Phe
                165                 170                 175

Ile Pro Val Gln Leu Asn Trp His Lys Ala Ser Asp Glu Glu Val Trp
            180                 185                 190

Ile Asn Gly Thr Ser Phe Gly Glu Lys Ser Glu Asn Cys Asp Ser Ser
        195                 200                 205

Leu Asn Arg Glu Tyr Ala Ile Ser Ser Leu Ile Ser Phe Tyr Ile
    210                 215                 220

Pro Val Ala Ile Met Ile Val Thr Tyr Thr Arg Ile Tyr Arg Ile Ala
225                 230                 235                 240

Gln Ile Gln Ile Arg Arg Ile Ser Ser Leu Glu Arg Ala Ala Glu His
                245                 250                 255

Ala Gln Ser Cys Arg Thr Asn Arg Leu Glu Cys Gln His His Asn Thr
            260                 265                 270

Leu Lys Thr Ser Ile Lys Arg Glu Thr Lys Val Phe Lys Thr Leu Ser
        275                 280                 285

Val Ile Met Gly Val Phe Val Cys Cys Trp Leu Pro Phe Phe Ile Leu
    290                 295                 300

Asn Cys Ile Val Pro Phe Cys Asp Arg Pro Thr Asp His Thr Ala
305                 310                 315                 320

Gly Leu Pro Cys Val Ser Asp Thr Thr Phe Asp Val Phe Val Trp Phe
                325                 330                 335

Gly Trp Thr Asn Ser Ser Leu Asn Pro Ile Ile Tyr Ala Phe Asn Ala
            340                 345                 350

Asp Phe Arg Lys Ala Phe Ala Ser Leu Leu Gly Cys Arg Asn Phe Cys
        355                 360                 365

Ser Arg Thr Pro Val Glu Thr Val Asn Ile Ser Asn Glu Leu Val Ser
370                 375                 380

Tyr Asn Gln Asp Thr Leu Phe His Lys Glu Ile Val Thr Ala Tyr Val
385                 390                 395                 400

Asn Met Ile Pro Asn Val Val Asp Cys Ile Asp Asp Asn Glu Asp Thr
                405                 410                 415

Phe Asp Arg Ile Ser Gln Phe Ser His Asn Asn Glu Ile Ala Thr Asp
            420                 425                 430

Ser Val Cys Asp Leu Asp Asp Cys Glu Ala Asp Ile Cys Leu Asp Arg
        435                 440                 445

Leu Ala Pro Phe Thr Pro Asn Gly Leu His
    450                 455

<210> SEQ ID NO 52
<211> LENGTH: 879
<212> TYPE: PRT
<213> ORGANISM: Rattus norvegicus

<400> SEQUENCE: 52

Met Lys Met Leu Thr Arg Leu Gln Ile Leu Met Leu Ala Leu Phe Ser
1               5                   10                  15

Lys Gly Phe Leu Leu Ser Leu Gly Asp His Asn Phe Met Arg Arg Glu
                20                  25                  30

Ile Lys Ile Glu Gly Asp Leu Val Leu Gly Gly Leu Phe Pro Ile Asn
            35                  40                  45

Glu Lys Gly Thr Gly Thr Glu Glu Cys Gly Arg Ile Asn Glu Asp Arg
        50                  55                  60
```

-continued

```
Gly Ile Gln Arg Leu Glu Ala Met Leu Phe Ala Ile Asp Glu Ile Asn
 65                  70                  75                  80

Lys Asp Asn Tyr Leu Leu Pro Gly Val Lys Leu Gly Val His Ile Leu
                 85                  90                  95

Asp Thr Cys Ser Arg Asp Thr Tyr Ala Leu Glu Gln Ser Leu Glu Phe
            100                 105                 110

Val Arg Ala Ser Leu Thr Lys Val Asp Glu Ala Glu Tyr Met Cys Pro
        115                 120                 125

Asp Gly Ser Tyr Ala Ile Gln Glu Asn Ile Pro Leu Leu Ile Ala Gly
    130                 135                 140

Val Ile Gly Gly Ser Tyr Ser Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Phe Phe
        195                 200                 205

Asn Trp Thr Tyr Val Ser Thr Val Ala Ser Glu Gly Asp Tyr Gly Glu
    210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
            260                 265                 270

Val Leu Phe Met Arg Ser Asp Ser Arg Glu Leu Ile Ala Ala Ala
        275                 280                 285

Asn Arg Val Asn Ala Ser Phe Thr Trp Val Ala Ser Asp Gly Trp Gly
    290                 295                 300

Ala Gln Glu Ser Ile Val Lys Gly Ser Glu His Val Ala Tyr Gly Ala
305                 310                 315                 320

Ile Thr Leu Glu Leu Ala Ser His Pro Val Arg Gln Phe Asp Arg Tyr
                325                 330                 335

Phe Gln Ser Leu Asn Pro Tyr Asn Asn His Arg Asn Pro Trp Phe Arg
            340                 345                 350

Asp Phe Trp Glu Gln Lys Phe Gln Cys Ser Leu Gln Asn Lys Arg Asn
        355                 360                 365

His Arg Gln Val Cys Asp Lys His Leu Ala Ile Asp Ser Ser Asn Tyr
    370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                405                 410                 415

Lys Leu Cys Asp Ala Met Lys Ile Leu Asp Gly Lys Lys Leu Tyr Lys
            420                 425                 430

Glu Tyr Leu Leu Lys Ile Asn Phe Thr Ala Pro Phe Asn Pro Asn Lys
        435                 440                 445

Gly Ala Asp Ser Ile Val Lys Phe Asp Thr Phe Gly Asp Gly Met Gly
    450                 455                 460

Arg Tyr Asn Val Phe Asn Leu Gln Gln Thr Gly Gly Lys Tyr Ser Tyr
465                 470                 475                 480
```

-continued

```
Leu Lys Val Gly His Trp Ala Glu Thr Leu Ser Leu Asp Val Asp Ser
                485                 490                 495
Ile His Trp Ser Arg Asn Ser Val Pro Thr Ser Gln Cys Ser Asp Pro
            500                 505                 510
Cys Ala Pro Asn Glu Met Lys Asn Met Gln Pro Gly Asp Val Cys Cys
        515                 520                 525
Trp Ile Cys Ile Pro Cys Glu Pro Tyr Glu Tyr Leu Val Asp Glu Phe
    530                 535                 540
Thr Cys Met Asp Cys Gly Pro Gly Gln Trp Pro Thr Ala Asp Leu Ser
545                 550                 555                 560
Gly Cys Tyr Asn Leu Pro Glu Asp Tyr Ile Lys Trp Glu Asp Ala Trp
                565                 570                 575
Ala Ile Gly Pro Val Thr Ile Ala Cys Leu Gly Phe Leu Cys Thr Cys
            580                 585                 590
Ile Val Ile Thr Val Phe Ile Lys His Asn Asn Thr Pro Leu Val Lys
        595                 600                 605
Ala Ser Gly Arg Glu Leu Cys Tyr Ile Leu Leu Phe Gly Val Ser Leu
    610                 615                 620
Ser Tyr Cys Met Thr Phe Phe Phe Ile Ala Lys Pro Ser Pro Val Ile
625                 630                 635                 640
Cys Ala Leu Arg Arg Leu Gly Leu Gly Thr Ser Phe Ala Ile Cys Tyr
                645                 650                 655
Ser Ala Leu Leu Thr Lys Thr Asn Cys Ile Ala Arg Ile Phe Asp Gly
            660                 665                 670
Val Lys Asn Gly Ala Gln Arg Pro Lys Phe Ile Ser Pro Ser Ser Gln
        675                 680                 685
Val Phe Ile Cys Leu Gly Leu Ile Leu Val Gln Ile Val Met Val Ser
    690                 695                 700
Val Trp Leu Ile Leu Glu Thr Pro Gly Thr Arg Arg Tyr Thr Leu Pro
705                 710                 715                 720
Glu Lys Arg Glu Thr Val Ile Leu Lys Cys Asn Val Lys Asp Ser Ser
                725                 730                 735
Met Leu Ile Ser Leu Thr Tyr Asp Val Leu Val Ile Leu Cys Thr
            740                 745                 750
Val Tyr Ala Phe Lys Thr Arg Lys Cys Pro Glu Asn Phe Asn Glu Ala
        755                 760                 765
Lys Phe Ile Gly Phe Thr Met Tyr Thr Thr Cys Ile Ile Trp Leu Ala
    770                 775                 780
Phe Leu Pro Ile Phe Tyr Val Thr Ser Ser Asp Tyr Arg Val Gln Thr
785                 790                 795                 800
Thr Thr Met Cys Ile Ser Val Ser Leu Ser Gly Phe Val Val Leu Gly
                805                 810                 815
Cys Leu Phe Ala Pro Lys Val His Ile Val Leu Phe Gln Pro Gln Lys
            820                 825                 830
Asn Val Val Thr His Arg Leu His Leu Asn Arg Phe Ser Val Ser Gly
        835                 840                 845
Thr Ala Thr Thr Tyr Ser Gln Ser Ser Ala Ser Thr Tyr Val Pro Thr
    850                 855                 860
Val Cys Asn Gly Arg Glu Val Leu Asp Ser Thr Thr Ser Ser Leu
865                 870                 875
```

<210> SEQ ID NO 53
<211> LENGTH: 879
<212> TYPE: PRT

<213> ORGANISM: Mus musculus

<400> SEQUENCE: 53

Met Lys Met Leu Thr Arg Leu Gln Val Leu Met Leu Ala Leu Phe Ser
1               5                   10                  15

Lys Gly Phe Leu Val Ser Leu Gly Asp His Asn Phe Met Arg Arg Glu
            20                  25                  30

Ile Lys Ile Glu Gly Asp Leu Val Leu Gly Gly Leu Phe Pro Ile Asn
        35                  40                  45

Glu Lys Gly Thr Gly Thr Glu Glu Cys Gly Arg Ile Asn Glu Asp Arg
    50                  55                  60

Gly Ile Gln Arg Leu Glu Ala Met Leu Phe Ala Ile Asp Glu Ile Asn
65                  70                  75                  80

Lys Asp Asn Tyr Leu Leu Pro Gly Val Lys Leu Gly Val His Ile Leu
                85                  90                  95

Asp Thr Cys Ser Arg Asp Thr Tyr Ala Leu Glu Gln Ser Leu Glu Phe
            100                 105                 110

Val Arg Ala Ser Leu Thr Lys Val Asp Glu Ala Glu Tyr Met Cys Pro
        115                 120                 125

Asp Gly Ser Tyr Ala Ile Gln Glu Asn Ile Pro Leu Leu Ile Ala Gly
    130                 135                 140

Val Ile Gly Gly Ser Tyr Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Tyr Phe
        195                 200                 205

Asn Trp Thr Tyr Val Ser Thr Val Ala Ser Glu Gly Asp Tyr Gly Glu
    210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
            260                 265                 270

Val Leu Phe Met Arg Ser Asp Asp Ser Arg Glu Leu Ile Ala Ala Ala
        275                 280                 285

Ser Arg Val Asn Ala Ser Phe Thr Trp Val Ala Ser Asp Gly Trp Gly
    290                 295                 300

Ala Gln Glu Ser Ile Val Lys Gly Ser Glu His Val Ala Tyr Gly Ala
305                 310                 315                 320

Ile Thr Leu Glu Leu Ala Ser His Pro Val Arg Gln Phe Asp Arg Tyr
                325                 330                 335

Phe Gln Ser Leu Asn Pro Tyr Asn Asn His Arg Asn Pro Trp Phe Arg
            340                 345                 350

Asp Phe Trp Glu Gln Lys Phe Gln Cys Ser Leu Gln Asn Lys Arg Asn
        355                 360                 365

His Arg Gln Ile Cys Asp Lys His Leu Ala Ile Asp Ser Ser Asn Tyr
    370                 375                 380

Glu Gln Glu Ser Lys Ile Met Phe Val Val Asn Ala Val Tyr Ala Met
385                 390                 395                 400

-continued

```
Ala His Ala Leu His Lys Met Gln Arg Thr Leu Cys Pro Asn Thr Thr
            405                 410                 415
Lys Leu Cys Asp Ala Met Lys Ile Leu Asp Gly Lys Lys Leu Tyr Lys
            420                 425                 430
Asp Tyr Leu Leu Lys Ile Asn Phe Thr Ala Pro Phe Asn Pro Asn Lys
            435                 440                 445
Gly Ala Asp Ser Ile Val Lys Phe Asp Thr Tyr Gly Asp Gly Met Gly
            450                 455                 460
Arg Tyr Asn Val Phe Asn Phe Gln His Ile Gly Gly Lys Tyr Ser Tyr
465                 470                 475                 480
Leu Lys Val Gly His Trp Ala Glu Thr Leu Tyr Leu Asp Val Asp Ser
                485                 490                 495
Ile His Trp Ser Arg Asn Ser Val Pro Thr Ser Gln Cys Ser Asp Pro
            500                 505                 510
Cys Ala Pro Asn Glu Met Lys Asn Met Gln Pro Gly Asp Val Cys Cys
            515                 520                 525
Trp Ile Cys Ile Pro Cys Glu Pro Tyr Glu Tyr Leu Val Asp Glu Phe
            530                 535                 540
Thr Cys Met Asp Cys Gly Pro Gly Gln Trp Pro Thr Ala Asp Leu Ser
545                 550                 555                 560
Gly Cys Tyr Asn Leu Pro Glu Asp Tyr Ile Arg Trp Glu Asp Ala Trp
                565                 570                 575
Ala Ile Gly Pro Val Thr Ile Ala Cys Leu Gly Phe Met Cys Thr Cys
            580                 585                 590
Ile Val Ile Thr Val Phe Ile Lys His Asn Asn Thr Pro Leu Val Lys
            595                 600                 605
Ala Ser Gly Arg Glu Leu Cys Tyr Ile Leu Leu Phe Gly Val Ser Leu
            610                 615                 620
Ser Tyr Cys Met Thr Phe Phe Phe Ile Ala Lys Pro Ser Pro Val Ile
625                 630                 635                 640
Cys Ala Leu Arg Arg Leu Gly Leu Gly Thr Ser Phe Ala Ile Cys Tyr
                645                 650                 655
Ser Ala Leu Leu Thr Lys Thr Asn Cys Ile Ala Arg Ile Phe Asp Gly
            660                 665                 670
Val Lys Asn Gly Ala Gln Arg Pro Lys Phe Ile Ser Pro Ser Ser Gln
            675                 680                 685
Val Phe Ile Cys Leu Gly Leu Ile Leu Val Gln Ile Val Met Val Ser
            690                 695                 700
Val Trp Leu Ile Leu Glu Thr Pro Gly Thr Arg Arg Tyr Thr Leu Pro
705                 710                 715                 720
Glu Lys Arg Glu Thr Val Ile Leu Lys Cys Asn Val Lys Asp Ser Ser
                725                 730                 735
Met Leu Ile Ser Leu Thr Tyr Asp Val Val Leu Val Ile Leu Cys Thr
            740                 745                 750
Val Tyr Ala Phe Lys Thr Arg Lys Cys Pro Glu Asn Phe Asn Glu Ala
            755                 760                 765
Lys Phe Ile Gly Phe Thr Met Tyr Thr Thr Cys Ile Ile Trp Leu Ala
            770                 775                 780
Phe Leu Pro Ile Phe Tyr Val Thr Ser Ser Asp Tyr Arg Val Gln Thr
785                 790                 795                 800
Thr Thr Met Cys Ile Ser Val Ser Leu Ser Gly Phe Val Val Leu Gly
                805                 810                 815
Cys Leu Phe Ala Pro Lys Val His Ile Val Leu Phe Gln Pro Gln Lys
```

```
                    820                 825                 830
Asn Val Val Thr His Arg Leu His Leu Asn Arg Phe Ser Val Ser Gly
            835                 840                 845

Thr Ala Thr Thr Tyr Ser Gln Ser Ser Ala Ser Thr Tyr Val Pro Thr
850                 855                 860

Val Cys Asn Gly Arg Glu Val Leu Asp Ser Thr Thr Ser Ser Leu
865                 870                 875

<210> SEQ ID NO 54
<211> LENGTH: 879
<212> TYPE: PRT
<213> ORGANISM: Mus musculus

<400> SEQUENCE: 54

Met Lys Met Leu Thr Arg Leu Gln Val Leu Met Leu Ala Leu Phe Ser
 1               5                  10                  15

Lys Gly Phe Leu Val Ser Leu Gly Asp His Asn Phe Met Arg Arg Glu
            20                  25                  30

Ile Lys Ile Glu Gly Asp Leu Val Leu Gly Gly Leu Phe Pro Ile Asn
        35                  40                  45

Glu Lys Gly Thr Gly Thr Glu Glu Cys Arg Gly Ile Asn Glu Asp Arg
    50                  55                  60

Gly Ile Gln Arg Leu Glu Ala Met Leu Phe Ala Ile Asp Glu Ile Asn
65                  70                  75                  80

Lys Asp Asn Tyr Leu Leu Pro Gly Val Lys Leu Gly Val His Ile Leu
                85                  90                  95

Asp Thr Cys Ser Arg Asp Thr Tyr Ala Leu Glu Gln Ser Leu Glu Phe
            100                 105                 110

Val Arg Ala Ser Leu Thr Lys Val Asp Glu Ala Glu Tyr Met Cys Pro
        115                 120                 125

Asp Gly Ser Tyr Ala Ile Gln Glu Asn Ile Pro Leu Leu Ile Ala Gly
    130                 135                 140

Val Ile Gly Gly Ser Tyr Ser Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Tyr Phe
        195                 200                 205

Asn Trp Thr Tyr Val Ser Thr Val Ala Ser Glu Gly Asp Tyr Gly Glu
    210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
            260                 265                 270

Val Leu Phe Met Arg Ser Asp Asp Ser Arg Glu Leu Ile Ala Ala Ala
        275                 280                 285

Ser Arg Val Asn Ala Ser Phe Thr Trp Val Ala Ser Asp Gly Trp Gly
    290                 295                 300

Ala Gln Glu Ser Ile Val Lys Gly Ser Glu His Val Ala Tyr Gly Ala
305                 310                 315                 320
```

-continued

```
Ile Thr Leu Glu Leu Ala Ser His Pro Val Arg Gln Phe Asp Arg Tyr
            325                 330                 335

Phe Gln Ser Leu Asn Pro Tyr Asn Asn His Arg Asn Pro Trp Phe Arg
            340                 345                 350

Asp Phe Trp Glu Gln Lys Phe Gln Cys Ser Leu Gln Asn Lys Arg Asn
            355                 360                 365

His Arg Gln Ile Cys Asp Lys His Leu Ala Ile Asp Ser Ser Asn Tyr
            370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                    405                 410                 415

Lys Leu Cys Asp Ala Met Lys Ile Leu Asp Gly Lys Lys Leu Tyr Lys
                420                 425                 430

Asp Tyr Leu Leu Lys Ile Asn Phe Thr Ala Pro Phe Asn Pro Asn Lys
            435                 440                 445

Gly Ala Asp Ser Ile Val Lys Phe Asp Thr Tyr Gly Asp Gly Met Gly
    450                 455                 460

Arg Tyr Asn Val Phe Asn Phe Gln His Ile Gly Gly Lys Tyr Ser Tyr
465                 470                 475                 480

Leu Lys Val Gly His Trp Ala Glu Thr Leu Tyr Leu Asp Val Asp Ser
                485                 490                 495

Ile His Trp Ser Arg Asn Ser Val Pro Thr Ser Gln Cys Ser Asp Pro
            500                 505                 510

Cys Ala Pro Asn Glu Met Lys Asn Met Gln Pro Gly Asp Val Cys Cys
            515                 520                 525

Trp Ile Cys Ile Pro Cys Glu Pro Tyr Glu Tyr Leu Val Asp Glu Phe
            530                 535                 540

Thr Cys Met Asp Cys Gly Pro Gly Gln Trp Pro Thr Ala Asp Leu Ser
545                 550                 555                 560

Gly Cys Tyr Asn Leu Pro Glu Asp Tyr Ile Arg Trp Glu Asp Ala Trp
                565                 570                 575

Ala Ile Gly Pro Val Thr Ile Ala Cys Leu Gly Phe Met Cys Thr Cys
            580                 585                 590

Ile Val Ile Thr Val Phe Ile Lys His Asn Asn Thr Pro Leu Val Lys
            595                 600                 605

Ala Ser Gly Arg Glu Leu Cys Tyr Ile Leu Leu Phe Gly Val Ser Leu
    610                 615                 620

Ser Tyr Cys Met Thr Phe Phe Ile Ala Lys Pro Ser Pro Val Ile
625                 630                 635                 640

Cys Ala Leu Arg Arg Leu Gly Leu Gly Thr Ser Phe Ala Ile Cys Tyr
                645                 650                 655

Ser Ala Leu Leu Thr Lys Thr Asn Cys Ile Ala Arg Ile Phe Asp Gly
            660                 665                 670

Val Lys Asn Gly Ala Gln Arg Pro Lys Phe Ile Ser Pro Ser Ser Gln
            675                 680                 685

Val Phe Ile Cys Leu Gly Leu Ile Leu Val Gln Ile Val Met Val Ser
            690                 695                 700

Val Trp Leu Ile Leu Glu Thr Pro Gly Thr Arg Arg Tyr Thr Leu Pro
705                 710                 715                 720

Glu Lys Arg Glu Thr Val Ile Leu Lys Cys Asn Val Lys Asp Ser Ser
                725                 730                 735

Met Leu Ile Ser Leu Thr Tyr Asp Val Val Leu Val Ile Leu Cys Thr
```

```
                    740                 745                 750
Val Tyr Ala Phe Lys Thr Arg Lys Cys Pro Glu Asn Phe Asn Glu Ala
        755                 760                 765

Lys Phe Ile Gly Phe Thr Met Tyr Thr Thr Cys Ile Ile Trp Leu Ala
        770                 775                 780

Phe Leu Pro Ile Phe Tyr Val Thr Ser Ser Asp Tyr Arg Val Gln Thr
785                 790                 795                 800

Thr Thr Met Cys Ile Ser Val Ser Leu Ser Gly Phe Val Val Leu Gly
                805                 810                 815

Cys Leu Phe Ala Pro Lys Val His Ile Val Leu Phe Gln Pro Gln Lys
            820                 825                 830

Asn Val Val Thr His Arg Leu His Leu Asn Arg Phe Ser Val Ser Gly
                835                 840                 845

Thr Ala Thr Thr Tyr Ser Gln Ser Ser Ala Ser Thr Tyr Val Pro Thr
    850                 855                 860

Val Cys Asn Gly Arg Glu Val Leu Asp Ser Thr Thr Ser Ser Leu
865                 870                 875

<210> SEQ ID NO 55
<211> LENGTH: 442
<212> TYPE: PRT
<213> ORGANISM: Homo sapiens

<400> SEQUENCE: 55

Met Gly Leu Ala Met Glu His Gly Gly Ser Tyr Ala Arg Ala Gly Gly
1               5                   10                  15

Ser Ser Arg Gly Cys Trp Tyr Tyr Leu Arg Tyr Phe Leu Phe Val
            20                  25                  30

Ser Leu Ile Gln Phe Leu Ile Ile Leu Gly Leu Val Leu Phe Met Val
        35                  40                  45

Tyr Gly Asn Val His Val Ser Thr Glu Ser Asn Leu Gln Ala Thr Glu
    50                  55                  60

Arg Arg Ala Glu Gly Leu Tyr Ser Gln Leu Leu Gly Leu Thr Ala Ser
65                  70                  75                  80

Gln Ser Asn Leu Thr Lys Glu Leu Asn Phe Thr Thr Arg Ala Lys Asp
                85                  90                  95

Ala Ile Met Gln Met Trp Leu Asn Ala Arg Arg Asp Leu Asp Arg Ile
            100                 105                 110

Asn Ala Ser Phe Arg Gln Cys Gln Gly Asp Arg Val Ile Tyr Thr Asn
        115                 120                 125

Asn His Arg Tyr Met Ala Ala Ile Ile Leu Ser Glu Lys Gln Cys Arg
    130                 135                 140

Asp Gln Phe Lys Asp Met Asn Lys Ser Cys Asp Ala Leu Leu Phe Met
145                 150                 155                 160

Leu Asn Gln Lys Val Lys Thr Leu Glu Val Glu Ile Ala Lys Glu Lys
                165                 170                 175

Thr Ile Cys Thr Lys Asp Lys Glu Ser Val Leu Leu Asn Lys Arg Val
            180                 185                 190

Ala Glu Glu Gln Leu Val Glu Cys Val Lys Thr Arg Glu Leu Gln His
        195                 200                 205

Gln Glu Arg Gln Leu Ala Lys Glu Gln Leu Gln Lys Val Gln Ala Leu
    210                 215                 220

Cys Leu Pro Leu Asp Lys Asp Lys Phe Glu Met Asp Leu Arg Asn Leu
225                 230                 235                 240
```

```
Trp Arg Asp Ser Ile Ile Pro Arg Ser Leu Asp Asn Leu Gly Tyr Asn
            245                 250                 255

Leu Tyr His Pro Leu Gly Ser Glu Leu Ala Ser Ile Arg Arg Ala Cys
        260                 265                 270

Asp His Met Pro Ser Leu Met Ser Ser Lys Val Glu Glu Leu Ala Arg
    275                 280                 285

Ser Leu Arg Ala Asp Ile Glu Arg Val Ala Arg Glu Asn Ser Asp Leu
290                 295                 300

Gln Arg Gln Lys Leu Glu Ala Gln Gln Gly Leu Arg Ala Ser Gln Glu
305                 310                 315                 320

Ala Lys Gln Lys Val Glu Lys Glu Ala Gln Ala Arg Glu Ala Lys Leu
                325                 330                 335

Gln Ala Glu Cys Ser Arg Gln Thr Gln Leu Ala Leu Glu Glu Lys Ala
            340                 345                 350

Val Leu Arg Lys Glu Arg Asp Asn Leu Ala Lys Glu Leu Glu Glu Lys
        355                 360                 365

Lys Arg Glu Ala Glu Gln Leu Arg Met Glu Leu Ala Ile Arg Asn Ser
    370                 375                 380

Ala Leu Asp Thr Cys Ile Lys Thr Lys Ser Gln Pro Met Met Pro Val
385                 390                 395                 400

Ser Arg Pro Met Gly Pro Val Pro Asn Pro Gln Pro Ile Asp Pro Ala
                405                 410                 415

Ser Leu Glu Glu Phe Lys Arg Lys Ile Leu Glu Ser Gln Arg Pro Pro
            420                 425                 430

Ala Gly Ile Pro Val Ala Pro Ser Ser Gly
            435                 440

<210> SEQ ID NO 56
<211> LENGTH: 442
<212> TYPE: PRT
<213> ORGANISM: Homo sapiens

<400> SEQUENCE: 56

Met Gly Leu Ala Met Glu His Gly Gly Ser Tyr Ala Arg Ala Gly Gly
1               5                   10                  15

Ser Ser Arg Gly Cys Trp Tyr Tyr Leu Arg Tyr Phe Phe Leu Phe Val
            20                  25                  30

Ser Leu Ile Gln Phe Leu Ile Ile Leu Gly Leu Val Leu Phe Met Val
        35                  40                  45

Tyr Gly Asn Val His Val Ser Thr Glu Ser Asn Leu Gln Ala Thr Glu
    50                  55                  60

Arg Arg Ala Glu Gly Leu Tyr Ser Gln Leu Leu Gly Leu Thr Ala Ser
65                  70                  75                  80

Gln Ser Asn Leu Thr Lys Glu Leu Asn Phe Thr Thr Arg Ala Lys Asp
                85                  90                  95

Ala Ile Met Gln Met Trp Leu Asn Ala Arg Arg Asp Leu Asp Arg Ile
            100                 105                 110

Asn Ala Ser Phe Arg Gln Cys Gln Gly Asp Arg Val Ile Tyr Thr Asn
        115                 120                 125

Asn Gln Arg Tyr Met Ala Ala Ile Ile Leu Ser Glu Lys Gln Cys Arg
    130                 135                 140

Asp Gln Phe Lys Asp Met Asn Lys Ser Cys Asp Ala Leu Leu Phe Met
145                 150                 155                 160

Leu Asn Gln Lys Val Lys Thr Leu Glu Val Glu Ile Ala Lys Glu Lys
                165                 170                 175
```

```
Thr Ile Cys Thr Lys Asp Lys Glu Ser Val Leu Leu Asn Lys Arg Val
            180                 185                 190

Ala Glu Glu Gln Leu Val Glu Cys Val Lys Thr Arg Glu Leu Gln His
        195                 200                 205

Gln Glu Arg Gln Leu Ala Lys Glu Gln Leu Gln Lys Val Gln Ala Leu
        210                 215                 220

Cys Leu Pro Leu Asp Lys Asp Lys Phe Glu Met Asp Leu Arg Asn Leu
225                 230                 235                 240

Trp Arg Asp Ser Ile Ile Pro Arg Ser Leu Asp Asn Leu Gly Tyr Asn
                245                 250                 255

Leu Tyr His Pro Leu Gly Ser Glu Leu Ala Ser Ile Arg Arg Ala Cys
        260                 265                 270

Asp His Met Pro Ser Leu Met Ser Ser Lys Val Glu Glu Leu Ala Arg
        275                 280                 285

Ser Leu Arg Ala Asp Ile Glu Arg Val Ala Arg Glu Asn Ser Asp Leu
        290                 295                 300

Gln Arg Gln Lys Leu Glu Ala Gln Gln Gly Leu Arg Ala Ser Gln Glu
305                 310                 315                 320

Ala Lys Gln Lys Val Glu Lys Glu Ala Gln Ala Arg Glu Ala Lys Leu
                325                 330                 335

Gln Ala Glu Cys Ser Arg Gln Thr Gln Leu Ala Leu Glu Glu Lys Ala
        340                 345                 350

Val Leu Arg Lys Glu Arg Asp Asn Leu Ala Lys Glu Leu Glu Glu Lys
        355                 360                 365

Lys Arg Glu Ala Glu Gln Leu Arg Met Glu Leu Ala Ile Arg Asn Ser
        370                 375                 380

Ala Leu Asp Thr Cys Ile Lys Thr Lys Ser Gln Pro Met Met Pro Val
385                 390                 395                 400

Ser Arg Pro Met Gly Pro Val Pro Asn Pro Gln Pro Ile Asp Pro Ala
                405                 410                 415

Ser Leu Glu Glu Phe Lys Arg Lys Ile Leu Glu Ser Gln Arg Pro Pro
        420                 425                 430

Ala Gly Ile Pro Val Ala Pro Ser Ser Gly
        435                 440

<210> SEQ ID NO 57
<211> LENGTH: 438
<212> TYPE: PRT
<213> ORGANISM: Rattus norvegicus

<400> SEQUENCE: 57

Met Gly Leu Ser Met Asp Arg Ser Pro Tyr Ser Arg Thr Gly Asp Arg
1               5                   10                  15

Asp Arg Gly Cys Trp Tyr Tyr Leu Arg Tyr Phe Phe Leu Phe Val Ser
                20                  25                  30

Leu Ile Gln Phe Leu Ile Ile Leu Gly Leu Val Leu Phe Met Ile Tyr
            35                  40                  45

Gly Asn Val His Ala Thr Thr Glu Ser Ser Leu Arg Ala Thr Glu Ile
        50                  55                  60

Arg Ala Asp Asn Leu Tyr Ser Gln Val Gly Leu Ser Ala Ala Gln
65                  70                  75                  80

Ala Asn Leu Ser Lys Gln Leu Asn Ile Ser Thr Leu Val Lys Asp Thr
                85                  90                  95

Val Met Gln Gln Leu Leu Thr Thr Arg Arg Glu Val Glu Arg Ile Asn
```

-continued

```
                100                 105                 110
Ala Ser Phe Arg Gln Cys Gln Gly Asp Leu Ile Thr Tyr Ile Asn Tyr
            115                 120                 125

Asn Arg Phe Ile Ala Ala Ile Ile Leu Ser Glu Lys Gln Cys Gln Glu
        130                 135                 140

Gln Leu Lys Glu Gly Asn Lys Thr Cys Glu Ala Leu Leu Phe Lys Leu
145                 150                 155                 160

Gly Glu Lys Val Lys Thr Leu Glu Met Glu Val Lys Glu Lys Ala
                165                 170                 175

Val Cys Ser Lys Asp Lys Asp Ser Leu Leu Ala Gly Lys Arg Gln Ala
            180                 185                 190

Glu Met Gln Gln Glu Ala Cys Gly Lys Ala Arg Glu Gln Gln Lys Gln
            195                 200                 205

Asp Gln Gln Val Thr Glu Gln Leu Arg Lys Val Gln Ser Leu Cys
        210                 215                 220

Leu Pro Leu Asp Gln Glu Lys Phe Gln Ala Asp Val Leu Asn Val Trp
225                 230                 235                 240

Arg Asp Ser Leu Val Tyr Arg Ser Leu Asp Asn Ile Gly Tyr His Tyr
                245                 250                 255

Ser Leu Met Pro Glu Phe Ser Ser Leu Arg Arg Thr Cys Glu Ser Leu
            260                 265                 270

Pro Gly Ile Met Thr Thr Lys Val Glu Glu Leu Ala Arg Gly Leu Arg
            275                 280                 285

Ala Gly Ile Glu Arg Val Thr Arg Glu Asn Gly Glu Leu Arg Arg Gln
        290                 295                 300

Lys Leu Glu Leu Glu Arg Ala Ile Gln Gly Glu Arg Glu Ala Arg Thr
305                 310                 315                 320

Arg Ala Gly Thr Glu Ala Gln Ala Arg Glu Thr Gln Leu Arg Thr Glu
                325                 330                 335

Cys Ala Arg Gln Thr Gln Leu Ala Leu Glu Glu Lys Ala Ala Leu Arg
            340                 345                 350

Thr Gln Arg Asp Asp Leu Glu Arg Gln Leu Glu Ala Arg Lys Arg Glu
        355                 360                 365

Leu Glu Gln Leu Arg Thr Glu Val Asp Val Arg Ile Ser Ala Leu Asp
        370                 375                 380

Thr Cys Val Lys Ala Lys Ser Leu Pro Ala Ile Gln Pro Arg Leu Pro
385                 390                 395                 400

Gly Pro Pro Asn Pro Pro Ile Asp Pro Ala Ser Leu Glu Glu
                405                 410                 415

Phe Lys Lys Arg Ile Leu Glu Ser Gln Arg Pro Pro Leu Val Asn Pro
            420                 425                 430

Ala Val Pro Pro Ser Gly
        435

<210> SEQ ID NO 58
<211> LENGTH: 438
<212> TYPE: PRT
<213> ORGANISM: Mus musculus

<400> SEQUENCE: 58

Met Gly Leu Ser Met Asp Arg Ser Pro Tyr Ala Arg Thr Gly Asp Gln
1               5                   10                  15

Gln Arg Gly Cys Trp Tyr Tyr Leu Arg Tyr Phe Phe Leu Phe Val Ser
            20                  25                  30
```

```
Leu Ile Gln Phe Leu Ile Ile Leu Gly Leu Val Leu Phe Met Ile Tyr
            35                  40                  45

Gly Asn Val His Ala Thr Thr Glu Ser Ser Leu Arg Ala Thr Glu Ile
    50                  55                  60

Arg Ala Asp Ser Leu Tyr Ser Gln Val Val Gly Leu Ser Ala Ser Gln
65                  70                  75                  80

Ala Asn Leu Ser Lys Gln Leu Asn Ile Ser Leu Leu Val Lys Glu Thr
                85                  90                  95

Val Met Gln Gln Leu Leu Thr Thr Arg Arg Glu Met Glu Arg Ile Asn
            100                 105                 110

Ala Ser Phe Arg Gln Cys Gln Gly Asp Leu Ile Thr Tyr Ile Asn Tyr
            115                 120                 125

Asn Arg Phe Ile Ala Ala Ile Ile Leu Ser Glu Lys Gln Cys Gln Glu
    130                 135                 140

Gln Leu Lys Glu Val Asn Lys Thr Cys Glu Ala Leu Leu Phe Lys Leu
145                 150                 155                 160

Gly Glu Lys Val Lys Thr Leu Glu Met Glu Val Ala Lys Glu Lys Ala
                165                 170                 175

Val Cys Ser Lys Asp Lys Glu Ser Leu Leu Ala Gly Lys Arg Gln Thr
            180                 185                 190

Glu Glu Gln Leu Glu Ala Cys Gly Lys Ala Arg Glu Arg Gln Gln Gln
            195                 200                 205

Glu Gln Gln Val Thr Glu Glu Asn Leu Arg Lys Val Gln Ser Leu Cys
            210                 215                 220

Ile Pro Leu Asp Gln Glu Lys Phe Gln Ala Asp Val Leu Ser Ala Trp
225                 230                 235                 240

Arg Asp Ser Leu Ile Tyr Arg Thr Leu Glu Thr Leu Pro Tyr His Tyr
                245                 250                 255

Gln Leu Met Pro Glu Tyr Ala Ser Leu Arg Arg Thr Cys Glu Ser Leu
            260                 265                 270

Pro Gly Ile Met Thr Thr Lys Ile Glu Glu Leu Ala Arg Gly Leu Arg
    275                 280                 285

Ala Gly Ile Glu Arg Val Thr Arg Glu Asn Ala Glu Leu Arg Arg Gln
    290                 295                 300

Lys Leu Glu Leu Glu Arg Ala Ala Gln Ala Ala Gln Glu Ala Arg Ala
305                 310                 315                 320

Arg Ala Gly Thr Glu Ala Gln Ala Arg Glu Thr Gln Leu Arg Ala Glu
                325                 330                 335

Cys Ala Arg Gln Thr Gln Leu Ala Leu Glu Lys Ala Ala Leu Arg
            340                 345                 350

Ala Gln Arg Asp Asn Leu Glu Arg Glu Leu Glu Ala Arg Lys Arg Glu
    355                 360                 365

Leu Glu Gln Leu Arg Thr Glu Val Asp Val Arg Ile Ser Ala Leu Asp
    370                 375                 380

Thr Cys Val Lys Ala Lys Ser Leu Pro Ala Val Pro Pro Arg Val Ser
385                 390                 395                 400

Gly Pro Pro Pro Asn Pro Pro Ile Asp Pro Ala Ser Leu Glu Glu
                405                 410                 415

Phe Lys Lys Arg Ile Leu Glu Ser Gln Arg Leu Pro Val Val Asn Pro
            420                 425                 430

Ala Ala Gln Pro Ser Gly
            435
```

<210> SEQ ID NO 59
<211> LENGTH: 438
<212> TYPE: PRT
<213> ORGANISM: Mus musculus

<400> SEQUENCE: 59

Met Gly Leu Ser Met Asp Arg Ser Pro Tyr Ala Arg Thr Gly Asp Gln
1               5                   10                  15

Gln Arg Gly Cys Trp Tyr Tyr Leu Arg Tyr Phe Phe Leu Phe Val Ser
            20                  25                  30

Leu Ile Gln Phe Leu Ile Ile Leu Gly Leu Val Leu Phe Met Ile Tyr
        35                  40                  45

Gly Asn Val His Ala Thr Thr Glu Ser Ser Leu Arg Ala Thr Glu Ile
    50                  55                  60

Arg Ala Asp Ser Leu Tyr Ser Gln Val Val Gly Leu Ser Ala Ser Gln
65                  70                  75                  80

Ala Asn Leu Ser Lys Gln Leu Asn Ile Ser Leu Leu Val Lys Glu Thr
                85                  90                  95

Val Met Gln Gln Leu Leu Thr Thr Arg Arg Glu Met Glu Arg Ile Asn
            100                 105                 110

Ala Ser Phe Arg Gln Cys Gln Gly Asp Leu Ile Thr Tyr Ile Asn Tyr
        115                 120                 125

Asn Arg Phe Ile Ala Ala Ile Ile Leu Ser Glu Lys Gln Cys Gln Glu
    130                 135                 140

Gln Leu Lys Glu Val Asn Lys Thr Cys Glu Ala Leu Leu Phe Lys Leu
145                 150                 155                 160

Gly Glu Lys Val Lys Thr Leu Glu Met Glu Val Ala Lys Glu Lys Ala
                165                 170                 175

Val Cys Ser Lys Asp Lys Glu Ser Leu Leu Ala Gly Lys Arg Gln Ala
            180                 185                 190

Glu Glu Gln Leu Glu Ala Cys Gly Lys Ala Arg Glu Arg Gln Gln Gln
        195                 200                 205

Glu Gln Gln Val Thr Glu Glu Asn Leu Arg Lys Val Gln Ser Leu Cys
    210                 215                 220

Ile Pro Leu Asp Gln Glu Lys Phe Gln Ala Asp Val Leu Ser Ala Trp
225                 230                 235                 240

Arg Asp Ser Leu Ile Tyr Arg Thr Leu Glu Thr Leu Pro Tyr His Tyr
                245                 250                 255

Gln Leu Met Pro Glu Tyr Ala Ser Leu Arg Arg Thr Cys Glu Ser Leu
            260                 265                 270

Pro Gly Ile Met Pro Pro Lys Ile Glu Glu Met Ala Arg Gly Val Arg
        275                 280                 285

Ala Gly Ile Glu Arg Val Thr Arg Glu Asn Ala Glu Leu Arg Arg Gln
    290                 295                 300

Lys Leu Glu Leu Glu Arg Ala Ala Gln Arg Ala Gln Glu Ala Arg Ala
305                 310                 315                 320

Arg Ala Gly Thr Glu Ala Gln Ala Arg Glu Thr Gln Leu Arg Ala Glu
                325                 330                 335

Cys Ala Arg Gln Thr Gln Leu Ala Leu Glu Glu Lys Ala Ala Leu Arg
            340                 345                 350

Ala Gln Arg Asp Asn Leu Glu Arg Glu Leu Glu Ala Arg Lys Arg Glu
        355                 360                 365

Leu Glu Gln Leu Arg Thr Glu Val Asp Val Arg Ile Ser Ala Leu Asp
    370                 375                 380

-continued

```
Thr Cys Val Lys Ala Lys Ser Leu Pro Ala Val Pro Pro Arg Val Ser
385                 390                 395                 400

Gly Pro Pro Pro Asn Pro Pro Ile Asp Pro Ala Ser Leu Glu Glu
                405                 410                 415

Phe Lys Lys Arg Ile Leu Glu Ser Gln Arg Leu Pro Val Val Asn Pro
                420                 425                 430

Ala Ala Gln Pro Ser Gly
            435

<210> SEQ ID NO 60
<211> LENGTH: 1788
<212> TYPE: PRT
<213> ORGANISM: Rattus norvegicus

<400> SEQUENCE: 60

Met Leu Arg Pro Met Gln Pro Thr Ser Arg Thr Leu Gln Arg Pro Pro
  1               5                  10                  15

Arg Gly Ala Leu Glu Ala Gly Arg Arg Asn Cys Gln Asp Gln Val
                 20                  25                  30

Ala His Pro Asn Trp Asn Thr Gln Ser Val Gln Thr Pro Arg Val Arg
             35                  40                  45

Arg Thr Leu Gly Ala Pro Val Pro Pro Ser Arg Lys Val Lys Ala Trp
         50                  55                  60

Ala Pro Gly Thr Asp Gln Trp Pro Gly Val Ser Pro His Cys Lys Arg
 65                  70                  75                  80

Ser Glu Ala Glu Ala Lys Pro Ser Gly Ser Gln Thr Val Asn Leu Thr
                 85                  90                  95

Gly Arg Ala Asn Asp Pro Cys Asp Leu Asp Ser Arg Val Gln Ala Thr
                100                 105                 110

Ser Val Lys Val Thr Val Ala Gly Phe Gln Pro Gly Gly Ala Val Glu
            115                 120                 125

Lys Leu Cys Gln Glu Ser Leu Gly Lys Leu Thr Thr Gly Asp Ala Cys
130                 135                 140

Val Ser Thr Ser Cys Glu Leu Ala Ser Ala Leu Ser His Leu Asp Ala
145                 150                 155                 160

Ser His Leu Thr Glu Asn Leu Pro Lys Ala Ala Ser Glu Leu Gly Gln
                165                 170                 175

Gln Pro Met Thr Ser Ser Asp Leu Ile Ser Ser Pro Gly Lys Lys Gly
            180                 185                 190

Ala Ala His Pro Asp Pro Ser Lys Thr Ser Val Asp Thr Gly Gln Val
            195                 200                 205

Ser Arg Pro Glu Asn Pro Ser Gln Pro Ala Ser Pro Arg Val Thr Lys
210                 215                 220

Cys Lys Ala Arg Ser Pro Val Arg Leu Pro His Glu Gly Ser Pro Ser
225                 230                 235                 240

Pro Gly Glu Lys Ala Ala Pro Pro Asp Tyr Ser Lys Thr Arg Ser
                245                 250                 255

Ala Ser Glu Thr Ser Thr Pro His Asn Thr Arg Arg Val Ala Ala Leu
            260                 265                 270

Arg Gly Ala Gly Pro Gly Ala Glu Gly Met Thr Pro Ala Gly Ala Val
            275                 280                 285

Leu Pro Gly Asp Pro Leu Thr Ser Gln Glu Gln Arg Gln Gly Ala Pro
290                 295                 300

Gly Asn His Ser Lys Ala Leu Glu Met Thr Gly Ile His Ala Pro Glu
305                 310                 315                 320
```

-continued

```
Ser Ser Gln Glu Pro Ser Leu Leu Gly Ala Asp Ser Val Ser Ser
            325                 330                 335

Arg Ala Pro Gln Ala Ser Leu Ser Met Leu Pro Ser Thr Asp Asn Thr
            340                 345                 350

Lys Glu Ala Cys Gly His Val Ser Gly His Cys Cys Pro Gly Gly Ser
            355                 360                 365

Arg Glu Ser Pro Val Thr Asp Ile Asp Ser Phe Ile Lys Glu Leu Asp
            370                 375                 380

Ala Ser Ala Ala Arg Ser Pro Ser Ser Gln Thr Gly Asp Ser Gly Ser
385                 390                 395                 400

Gln Glu Gly Ser Ala Gln Gly His Pro Pro Ala Gly Ala Gly Gly Gly
            405                 410                 415

Ser Ser Cys Arg Ala Glu Pro Val Pro Gly Gly Gln Thr Ser Ser Pro
            420                 425                 430

Arg Arg Ala Trp Ala Ala Gly Ala Pro Ala Tyr Pro Gln Trp Ala Ser
            435                 440                 445

Gln Pro Ser Val Leu Asp Ser Ile Asn Pro Asp Lys His Phe Thr Val
            450                 455                 460

Asn Lys Asn Phe Leu Ser Asn Tyr Ser Arg Asn Phe Ser Ser Phe His
465                 470                 475                 480

Glu Asp Ser Thr Ser Leu Ser Gly Leu Gly Asp Ser Thr Glu Pro Ser
            485                 490                 495

Leu Ser Ser Met Tyr Gly Asp Ala Glu Asp Ser Ser Ser Asp Pro Glu
            500                 505                 510

Ser Leu Thr Glu Ala Pro Arg Ala Ser Ala Arg Asp Gly Trp Ser Pro
            515                 520                 525

Pro Arg Ser Arg Val Ser Leu His Lys Glu Asp Pro Ser Glu Ser Glu
            530                 535                 540

Glu Glu Gln Ile Glu Ile Cys Ser Thr Arg Gly Cys Pro Asn Pro Pro
545                 550                 555                 560

Ser Ser Pro Ala His Leu Pro Thr Gln Ala Ala Ile Cys Pro Ala Ser
            565                 570                 575

Ala Lys Val Leu Ser Leu Lys Tyr Ser Thr Pro Arg Glu Ser Val Ala
            580                 585                 590

Ser Pro Arg Glu Lys Ala Ala Cys Leu Pro Gly Ser Tyr Thr Ser Gly
            595                 600                 605

Pro Asp Ser Ser Gln Pro Ser Ser Leu Leu Glu Met Ser Ser Gln Glu
            610                 615                 620

His Glu Thr His Ala Asp Ile Ser Thr Ser Gln Asn His Arg Pro Ser
625                 630                 635                 640

Cys Ala Glu Glu Thr Thr Glu Val Thr Ser Ala Ser Ser Ala Met Glu
            645                 650                 655

Asn Ser Pro Leu Ser Lys Val Ala Arg His Phe His Ser Pro Pro Ile
            660                 665                 670

Ile Leu Ser Ser Pro Asn Met Val Asn Gly Leu Glu His Asp Leu Leu
            675                 680                 685

Asp Asp Glu Thr Leu Asn Gln Tyr Glu Thr Ser Ile Asn Ala Ala Ala
            690                 695                 700

Ser Leu Ser Ser Phe Ser Val Asp Val Pro Lys Asn Gly Glu Ser Val
705                 710                 715                 720

Leu Glu Asn Leu His Ile Ser Glu Ser Gln Asp Leu Asp Asp Leu Leu
            725                 730                 735
```

-continued

```
Gln Lys Pro Lys Met Ile Ala Arg Arg Pro Ile Met Ala Trp Phe Lys
            740                 745                 750

Glu Ile Asn Lys His Asn Gln Gly Thr His Leu Arg Ser Lys Thr Glu
            755                 760                 765

Lys Glu Gln Pro Leu Met Pro Ala Arg Ser Pro Asp Ser Lys Ile Gln
    770                 775                 780

Met Val Ser Ser Ser Gln Lys Lys Gly Val Thr Val Pro His Ser Pro
785                 790                 795                 800

Pro Gln Pro Lys Thr Asn Leu Glu Asn Lys Asp Leu Ser Lys Lys Ser
                805                 810                 815

Pro Ala Glu Met Leu Leu Thr Asn Gly Gln Lys Ala Lys Cys Gly Pro
            820                 825                 830

Lys Leu Lys Arg Leu Ser Leu Lys Gly Lys Ala Lys Val Asn Ser Glu
            835                 840                 845

Ala Pro Ala Ala Asn Ala Val Lys Ala Gly Gly Thr Asp His Arg Lys
    850                 855                 860

Pro Leu Ile Ser Pro Gln Thr Ser His Lys Thr Leu Ser Lys Ala Val
865                 870                 875                 880

Ser Gln Arg Leu His Val Ala Asp His Glu Asp Pro Asp Arg Asn Thr
                885                 890                 895

Thr Ala Ala Pro Arg Ser Pro Gln Cys Val Leu Glu Ser Lys Pro Pro
            900                 905                 910

Leu Ala Thr Ser Gly Pro Leu Lys Pro Ser Val Ser Asp Thr Ser Ile
            915                 920                 925

Arg Thr Phe Val Ser Pro Leu Thr Ser Pro Lys Pro Val Pro Glu Gln
    930                 935                 940

Gly Met Trp Ser Arg Phe His Met Ala Val Leu Ser Glu Pro Asp Arg
945                 950                 955                 960

Gly Cys Pro Thr Thr Pro Lys Ser Pro Lys Cys Arg Ala Glu Gly Arg
                965                 970                 975

Ala Pro Arg Ala Asp Ser Gly Pro Val Ser Pro Ala Ala Ser Arg Asn
            980                 985                 990

Gly Met Ser Val Ala Gly Asn Arg Gln Ser Glu Pro Arg Leu Ala Ser
            995                 1000                1005

His Val Ala Ala Asp Thr Ala Gln Pro Arg Pro Thr Gly Glu Lys Gly
    1010                1015                1020

Gly Asn Ile Met Ala Ser Asp Arg Leu Glu Arg Thr Asn Gln Leu Lys
1025                1030                1035                1040

Ile Val Glu Ile Ser Ala Glu Ala Val Ser Glu Thr Val Cys Gly Asn
                1045                1050                1055

Lys Pro Ala Glu Ser Asp Arg Arg Gly Gly Cys Leu Ala Gln Gly Asn
            1060                1065                1070

Cys Gln Glu Lys Ser Glu Ile Arg Leu Tyr Arg Gln Val Ala Glu Ser
        1075                1080                1085

Ser Thr Ser His Pro Ser Ser Leu Pro Ser His Ala Ser Gln Ala Glu
    1090                1095                1100

Gln Glu Met Ser Arg Ser Phe Ser Met Ala Lys Leu Ala Ser Ser Ser
1105                1110                1115                1120

Ser Ser Leu Gln Thr Ala Ile Arg Lys Ala Glu Tyr Ser Gln Gly Lys
            1125                1130                1135

Ser Ser Leu Met Ser Asp Ser Arg Gly Val Pro Arg Asn Ser Ile Pro
            1140                1145                1150

Gly Gly Pro Ser Gly Glu Asp His Leu Tyr Phe Thr Pro Arg Pro Ala
```

-continued

```
          1155                1160                1165
Thr Arg Thr Tyr Ser Met Pro Ala Gln Phe Ser Ser His Phe Gly Arg
      1170                1175                1180
Glu Gly His Pro Pro His Ser Leu Gly Arg Ser Arg Asp Ser Gln Val
1185                1190                1195                1200
Pro Val Thr Ser Ser Val Val Pro Glu Ala Lys Ala Ser Arg Gly Gly
              1205                1210                1215
Leu Pro Ser Leu Ala Asn Gly Gln Gly Ile Tyr Ser Val Lys Pro Leu
          1220                1225                1230
Leu Asp Thr Ser Arg Asn Leu Pro Ala Thr Asp Glu Gly Asp Ile Ile
      1235                1240                1245
Ser Val Gln Glu Thr Ser Cys Leu Val Thr Asp Lys Ile Lys Val Thr
  1250                1255                1260
Arg Arg His Tyr Cys Tyr Glu Gln Asn Trp Pro His Glu Ser Thr Ser
1265                1270                1275                1280
Phe Phe Ser Val Lys Gln Arg Ile Lys Ser Phe Glu Asn Leu Ala Asn
              1285                1290                1295
Ala Asp Arg Pro Val Ala Lys Ser Gly Ala Ser Pro Phe Leu Ser Val
          1300                1305                1310
Ser Ser Lys Pro Pro Ile Gly Arg Arg Ser Ser Gly Ser Ile Val Ser
      1315                1320                1325
Gly Ser Leu Gly His Pro Gly Asp Ala Ala Ala Arg Leu Leu Arg Arg
  1330                1335                1340
Ser Leu Ser Ser Cys Ser Glu Asn Gln Ser Glu Ala Gly Thr Leu Leu
1345                1350                1355                1360
Pro Gln Met Ala Lys Ser Pro Ser Ile Met Thr Leu Thr Ile Ser Arg
              1365                1370                1375
Gln Asn Pro Pro Glu Thr Ser Ser Lys Gly Ser Asp Ser Glu Leu Lys
          1380                1385                1390
Lys Ser Leu Gly Pro Leu Gly Ile Pro Thr Pro Thr Met Thr Leu Ala
      1395                1400                1405
Ser Pro Val Lys Arg Asn Lys Ser Ser Val Arg His Thr Gln Pro Ser
  1410                1415                1420
Pro Val Ser Arg Ser Lys Leu Gln Glu Leu Arg Ala Leu Ser Met Pro
1425                1430                1435                1440
Asp Leu Asp Lys Leu Cys Ser Glu Asp Tyr Ser Ala Gly Pro Ser Ala
              1445                1450                1455
Val Leu Phe Lys Thr Glu Leu Glu Ile Thr Pro Arg Arg Ser Pro Gly
          1460                1465                1470
Pro Pro Ala Gly Gly Val Ser Cys Pro Glu Lys Gly Gly Asn Arg Ala
      1475                1480                1485
Cys Pro Gly Gly Ser Gly Pro Lys Thr Ser Ala Ala Glu Thr Pro Ser
  1490                1495                1500
Ser Ala Ser Asp Thr Gly Glu Ala Ala Gln Asp Leu Pro Phe Arg Arg
1505                1510                1515                1520
Ser Trp Ser Val Lys Leu Asp Gln Leu Leu Val Ser Ala Gly Asp Gln
              1525                1530                1535
Gln Arg Leu Gln Ser Val Leu Ser Ser Val Gly Ser Lys Ser Thr Ile
          1540                1545                1550
Leu Thr Leu Ile Gln Glu Ala Lys Ala Gln Ser Glu Asn Glu Glu Asp
      1555                1560                1565
Val Cys Phe Ile Val Leu Asn Arg Lys Glu Gly Ser Gly Leu Gly Phe
  1570                1575                1580
```

```
Ser Val Ala Gly Gly Thr Asp Val Glu Pro Lys Ser Ile Thr Val His
1585                1590                1595                1600

Arg Val Phe Ser Gln Gly Ala Ala Ser Gln Glu Gly Thr Met Asn Arg
            1605                1610                1615

Gly Asp Phe Leu Leu Ser Val Asn Gly Ala Ser Leu Ala Gly Leu Ala
        1620                1625                1630

His Gly Asn Val Leu Lys Val Leu His Gln Ala Gln Leu His Lys Asp
    1635                1640                1645

Ala Leu Val Val Ile Lys Lys Gly Met Asp Gln Pro Arg Pro Ser Ala
1650                1655                1660

Arg Gln Glu Pro Pro Thr Ala Asn Gly Lys Gly Leu Leu Ser Arg Lys
1665                1670                1675                1680

Thr Ile Pro Leu Glu Pro Gly Ile Gly Arg Ser Val Ala Val His Asp
            1685                1690                1695

Ala Leu Cys Val Glu Val Leu Lys Thr Ser Ala Gly Leu Gly Leu Ser
        1700                1705                1710

Leu Asp Gly Gly Lys Ser Ser Val Thr Gly Asp Gly Pro Leu Val Ile
    1715                1720                1725

Lys Arg Val Tyr Lys Gly Gly Ala Ala Glu Gln Ala Gly Ile Ile Glu
1730                1735                1740

Ala Gly Asp Glu Ile Leu Ala Ile Asn Gly Lys Pro Leu Val Gly Leu
1745                1750                1755                1760

Met His Phe Asp Ala Trp Asn Ile Met Lys Ser Val Pro Glu Gly Pro
            1765                1770                1775

Val Gln Leu Leu Ile Arg Lys His Arg Asn Ser Ser
        1780                1785

<210> SEQ ID NO 61
<211> LENGTH: 1608
<212> TYPE: PRT
<213> ORGANISM: Homo sapiens

<400> SEQUENCE: 61

Ser Ser Asp Leu Ile Ser Ser Pro Gly Lys Lys Gly Ala Ala His Pro
1               5                   10                  15

Asp Pro Ser Lys Thr Ser Val Asp Thr Gly Lys Val Ser Arg Pro Glu
            20                  25                  30

Asn Pro Ser Gln Pro Ala Ser Pro Arg Val Ala Lys Cys Lys Ala Arg
        35                  40                  45

Ser Pro Val Arg Leu Pro His Glu Gly Ser Pro Ser Pro Gly Glu Lys
    50                  55                  60

Ala Ala Ala Pro Pro Asp Tyr Ser Lys Thr Arg Ser Ala Ser Glu Thr
65                  70                  75                  80

Ser Thr Pro His Asn Thr Arg Arg Val Ala Ala Leu Arg Gly Ala Gly
            85                  90                  95

Pro Gly Ala Glu Gly Met Thr Pro Ala Gly Ala Val Leu Pro Gly Asp
        100                 105                 110

Pro Leu Thr Ser Gln Glu Gln Arg Gln Gly Ala Pro Gly Asn His Ser
    115                 120                 125

Lys Ala Leu Glu Met Thr Gly Ile His Ala Pro Glu Ser Ser Gln Glu
130                 135                 140

Pro Ser Leu Leu Glu Gly Ala Asp Ser Val Ser Ser Arg Ala Pro Gln
145                 150                 155                 160

Ala Ser Leu Ser Met Leu Pro Ser Thr Asp Asn Thr Lys Glu Ala Cys
```

```
                165                 170                 175
Gly His Val Ser Gly His Cys Cys Pro Gly Gly Ser Arg Glu Ser Pro
            180                 185                 190
Val Thr Asp Ile Asp Ser Phe Ile Lys Glu Leu Asp Ala Ser Ala Ala
            195                 200                 205
Arg Ser Pro Ser Ser Gln Thr Gly Asp Ser Gly Ser Gln Glu Gly Ser
            210                 215                 220
Ala Gln Gly His Pro Ala Gly Ala Gly Gly Ser Ser Cys Arg
225                 230                 235                 240
Ala Glu Pro Val Pro Gly Gly Gln Thr Ser Ser Pro Arg Arg Ala Trp
            245                 250                 255
Ala Ala Gly Ala Pro Ala Tyr Pro Gln Trp Ala Ser Gln Pro Ser Val
            260                 265                 270
Leu Asp Ser Ile Asn Pro Asp Lys His Phe Thr Val Asn Lys Asn Phe
            275                 280                 285
Leu Ser Asn Tyr Ser Arg Asn Phe Ser Ser Phe His Glu Asp Ser Thr
            290                 295                 300
Ser Leu Ser Gly Leu Gly Asp Ser Thr Glu Pro Ser Leu Ser Ser Met
305                 310                 315                 320
Tyr Gly Asp Ala Glu Asp Ser Ser Asp Pro Glu Ser Leu Thr Glu
            325                 330                 335
Ala Pro Arg Ala Ser Ala Arg Asp Gly Trp Ser Pro Pro Arg Ser Arg
            340                 345                 350
Val Ser Leu His Lys Glu Asp Pro Ser Glu Ser Glu Glu Gln Ile
            355                 360                 365
Glu Ile Cys Ser Thr Arg Gly Cys Pro Asn Pro Pro Ser Ser Pro Ala
            370                 375                 380
His Leu Pro Thr Gln Ala Ala Ile Cys Pro Ala Ser Ala Lys Val Leu
385                 390                 395                 400
Ser Leu Lys Tyr Ser Thr Pro Arg Glu Ser Val Ala Ser Pro Arg Glu
            405                 410                 415
Lys Val Ala Cys Leu Pro Gly Ser Tyr Thr Ser Gly Pro Asp Ser Ser
            420                 425                 430
Gln Pro Ser Ser Leu Leu Glu Met Ser Ser Gln Glu His Glu Thr His
            435                 440                 445
Ala Asp Ile Ser Thr Ser Gln Asn His Arg Pro Ser Cys Ala Glu Glu
            450                 455                 460
Thr Thr Glu Val Thr Ser Ala Ser Ser Ala Met Glu Asn Ser Pro Leu
465                 470                 475                 480
Ser Lys Val Ala Arg His Phe His Ser Pro Pro Ile Ile Leu Ser Ser
            485                 490                 495
Pro Asn Met Val Asn Gly Leu Glu His Asp Leu Leu Asp Asp Glu Thr
            500                 505                 510
Leu Asn Gln Tyr Glu Thr Ser Ile Asn Ala Ala Ser Leu Ser Ser
            515                 520                 525
Phe Ser Val Asp Val Pro Lys Asn Gly Glu Ser Val Leu Glu Asn Leu
            530                 535                 540
His Ile Ser Glu Ser Gln Asp Leu Asp Asp Leu Leu Gln Lys Pro Lys
545                 550                 555                 560
Met Ile Ala Arg Arg Pro Ile Met Ala Trp Phe Lys Glu Ile Asn Lys
            565                 570                 575
His Asn Gln Gly Thr His Leu Arg Ser Lys Thr Glu Lys Glu Gln Pro
            580                 585                 590
```

-continued

```
Leu Met Pro Ala Arg Ser Pro Asp Ser Lys Ile Gln Met Val Ser Ser
        595                 600                 605
Ser Gln Lys Lys Gly Val Thr Val Pro His Ser Pro Gln Pro Lys
    610                 615                 620
Thr Asn Leu Glu Asn Lys Asp Leu Ser Lys Lys Ser Pro Ala Glu Met
625                 630                 635                 640
Leu Leu Thr Asn Gly Gln Lys Ala Lys Cys Gly Pro Lys Leu Lys Arg
                645                 650                 655
Leu Ser Leu Lys Gly Lys Ala Lys Val Asn Ser Glu Ala Pro Ala Ala
            660                 665                 670
Asn Ala Val Lys Ala Gly Gly Thr Asp His Arg Lys Pro Leu Ile Ser
        675                 680                 685
Pro Gln Thr Ser His Lys Thr Leu Ser Lys Ala Val Ser Gln Arg Leu
    690                 695                 700
His Val Ala Asp His Glu Asp Pro Asp Arg Asn Thr Thr Ala Ala Pro
705                 710                 715                 720
Arg Ser Pro Gln Cys Val Leu Glu Ser Lys Pro Pro Leu Ala Thr Ser
                725                 730                 735
Gly Pro Leu Lys Pro Ser Val Ser Asp Thr Ser Ile Arg Thr Phe Val
            740                 745                 750
Ser Pro Leu Thr Ser Pro Lys Pro Val Pro Glu Gln Gly Met Trp Ser
        755                 760                 765
Arg Phe His Met Ala Val Leu Ser Glu Pro Asp Arg Gly Cys Pro Thr
    770                 775                 780
Thr Pro Lys Ser Pro Lys Cys Arg Ala Glu Gly Arg Ala Pro Arg Ala
785                 790                 795                 800
Asp Ser Gly Pro Val Ser Pro Ala Ala Ser Arg Asn Gly Met Ser Val
                805                 810                 815
Ala Gly Asn Arg Gln Ser Glu Pro Arg Leu Ala Ser His Val Ala Ala
            820                 825                 830
Asp Thr Ala Gln Pro Arg Pro Thr Gly Glu Lys Gly Gly Asn Ile Met
        835                 840                 845
Ala Ser Asp Arg Leu Glu Arg Thr Asn Gln Leu Lys Ile Val Glu Ile
    850                 855                 860
Ser Ala Glu Ala Val Ser Glu Thr Val Cys Gly Asn Lys Pro Ala Glu
865                 870                 875                 880
Ser Asp Arg Arg Gly Gly Cys Leu Ala Gln Gly Asn Cys Gln Glu Lys
                885                 890                 895
Ser Glu Ile Arg Leu Tyr Arg Gln Val Ala Glu Ser Thr Ser His
            900                 905                 910
Pro Ser Ser Leu Pro Ser His Ala Ser Gln Ala Glu Gln Glu Met Ser
        915                 920                 925
Arg Ser Phe Ser Met Ala Lys Leu Ala Ser Ser Ser Ser Leu Gln
    930                 935                 940
Thr Ala Ile Arg Lys Ala Glu Tyr Ser Gln Gly Lys Ser Ser Leu Met
945                 950                 955                 960
Ser Asp Ser Arg Gly Val Pro Arg Asn Ser Ile Pro Gly Gly Pro Ser
                965                 970                 975
Gly Glu Asp His Leu Tyr Phe Thr Pro Arg Pro Ala Thr Arg Thr Tyr
            980                 985                 990
Ser Met Pro Ala Gln Phe Ser Ser His Phe Gly Arg Glu Gly His Pro
        995                 1000                1005
```

```
Pro His Ser Leu Gly Arg Ser Arg Asp Ser Gln Val Pro Val Thr Ser
    1010                1015                1020
Ser Val Val Pro Glu Ala Lys Ala Ser Arg Gly Gly Leu Pro Ser Leu
1025                1030                1035                1040
Ala Asn Gly Gln Gly Ile Tyr Ser Val Lys Pro Leu Leu Asp Thr Ser
        1045                1050                1055
Arg Asn Leu Pro Ala Thr Asp Glu Gly Asp Ile Ile Ser Val Gln Glu
        1060                1065                1070
Thr Ser Cys Leu Val Thr Asp Lys Ile Lys Val Thr Arg Arg His Tyr
        1075                1080                1085
Cys Tyr Glu Gln Asn Trp Pro His Glu Ser Thr Ser Phe Phe Ser Val
        1090                1095                1100
Lys Gln Arg Ile Lys Ser Phe Glu Asn Leu Ala Asn Ala Asp Arg Pro
1105                1110                1115                1120
Val Ala Lys Ser Gly Ala Ser Pro Phe Leu Ser Val Ser Ser Lys Pro
        1125                1130                1135
Pro Ile Gly Arg Arg Ser Ser Gly Ser Ile Val Ser Gly Ser Leu Gly
        1140                1145                1150
His Pro Gly Asp Ala Ala Ala Arg Leu Leu Arg Arg Ser Leu Ser Ser
        1155                1160                1165
Cys Ser Glu Asn Gln Ser Glu Ala Gly Thr Leu Leu Pro Gln Met Ala
        1170                1175                1180
Lys Ser Pro Ser Ile Met Thr Leu Thr Ile Ser Arg Gln Asn Pro Pro
1185                1190                1195                1200
Glu Thr Ser Ser Lys Gly Ser Asp Ser Glu Leu Lys Lys Ser Leu Gly
        1205                1210                1215
Pro Leu Gly Ile Pro Thr Pro Thr Met Thr Leu Ala Ser Pro Val Lys
        1220                1225                1230
Arg Asn Lys Ser Ser Val Arg His Thr Gln Pro Ser Pro Val Ser Arg
        1235                1240                1245
Ser Lys Leu Gln Glu Leu Arg Ala Leu Ser Met Pro Asp Leu Asp Lys
        1250                1255                1260
Leu Cys Ser Glu Asp Tyr Ser Ala Gly Pro Ser Ala Val Leu Phe Lys
1265                1270                1275                1280
Thr Glu Leu Glu Ile Thr Pro Arg Arg Ser Pro Gly Pro Pro Ala Gly
        1285                1290                1295
Gly Val Ser Cys Pro Glu Lys Gly Gly Asn Arg Ala Cys Pro Gly Gly
        1300                1305                1310
Ser Gly Pro Lys Thr Ser Ala Ala Glu Thr Pro Ser Ser Ala Ser Asp
        1315                1320                1325
Thr Gly Glu Ala Ala Gln Asp Leu Pro Phe Arg Arg Ser Trp Ser Val
        1330                1335                1340
Asn Leu Asp Gln Leu Leu Val Ser Ala Gly Asp Gln Gln Arg Leu Gln
1345                1350                1355                1360
Ser Val Leu Ser Ser Val Gly Ser Lys Ser Thr Ile Leu Thr Leu Ile
        1365                1370                1375
Gln Glu Ala Lys Ala Gln Ser Glu Asn Glu Glu Asp Val Cys Phe Ile
        1380                1385                1390
Val Leu Asn Arg Lys Glu Gly Ser Gly Leu Gly Phe Ser Val Ala Gly
        1395                1400                1405
Gly Thr Asp Val Glu Pro Lys Ser Ile Thr Val His Arg Val Phe Ser
    1410                1415                1420
Gln Gly Ala Ala Ser Gln Glu Gly Thr Met Asn Arg Gly Asp Phe Leu
```

-continued

```
                1425                1430                1435                1440

Leu Ser Val Asn Gly Ala Ser Leu Ala Gly Leu Ala His Gly Asn Val
            1445                1450                1455

Leu Lys Val Leu His Gln Ala Gln Leu His Lys Asp Ala Leu Val Val
        1460                1465                1470

Ile Lys Lys Gly Met Asp Gln Pro Arg Pro Ser Ala Arg Gln Glu Pro
    1475                1480                1485

Pro Thr Ala Asn Gly Lys Gly Leu Leu Ser Arg Lys Thr Ile Pro Leu
1490                1495                1500

Glu Pro Gly Ile Gly Arg Ser Val Ala Val His Asp Ala Leu Cys Val
1505                1510                1515                1520

Glu Val Leu Lys Thr Ser Ala Gly Leu Gly Leu Ser Leu Asp Gly Gly
            1525                1530                1535

Lys Ser Ser Val Thr Gly Asp Gly Pro Leu Val Ile Lys Arg Val Tyr
        1540                1545                1550

Lys Gly Gly Ala Ala Glu Gln Ala Gly Ile Ile Glu Ala Gly Asp Glu
    1555                1560                1565

Ile Leu Ala Ile Asn Gly Lys Pro Leu Val Gly Leu Met His Phe Asp
    1570                1575                1580

Ala Trp Asn Ile Met Lys Ser Val Pro Glu Gly Pro Val Gln Leu Leu
1585                1590                1595                1600

Ile Arg Lys His Arg Asn Ser Ser
            1605

<210> SEQ ID NO 62
<211> LENGTH: 2766
<212> TYPE: PRT
<213> ORGANISM: Rattus norvegicus

<400> SEQUENCE: 62

Met Pro Ile Thr Gln Asp Asn Ala Leu Leu His Leu Pro Leu Leu Tyr
1               5                   10                  15

Glu Trp Leu Gln Asn Ser Leu Arg Glu Gly Gly Asp Ser Pro Glu Gln
            20                  25                  30

Arg Leu Cys Gln Ala Ala Ile Gln Lys Leu Gln Glu Tyr Ile Gln Leu
        35                  40                  45

Asn Leu Ala Val Asp Glu Ser Thr Val Pro Pro Asp His Ser Pro Pro
    50                  55                  60

Glu Met Glu Ile Cys Thr Val Tyr Leu Thr Lys Gln Leu Gly Asp Thr
65                  70                  75                  80

Glu Thr Val Gly Leu Ser Phe Gly Asn Ile Pro Val Phe Gly Asp Tyr
                85                  90                  95

Gly Glu Lys Arg Arg Gly Gly Lys Lys Arg Lys Thr His Gln Gly Pro
            100                 105                 110

Val Leu Asp Val Gly Cys Ile Trp Val Thr Glu Leu Arg Lys Asn Ser
        115                 120                 125

Pro Ala Gly Lys Ser Gly Lys Val Arg Leu Arg Asp Glu Ile Leu Ser
    130                 135                 140

Leu Asn Gly Gln Leu Met Val Gly Val Asp Val Thr Gly Ala Ser Tyr
145                 150                 155                 160

Leu Ala Glu Gln Cys Trp Asn Gly Gly Phe Ile Tyr Leu Ile Met Leu
                165                 170                 175

Arg Arg Phe Lys Gln Lys Ala His Val Thr Tyr Asn Gly Asn Ser Gly
            180                 185                 190
```

```
Asn Ser Ser Glu Pro Gly Glu Thr Pro Thr Leu Glu Leu Gly Asp Gln
        195                 200                 205

Thr Ser Lys Lys Gly Lys Arg Thr Lys Phe Gly Val Ile Ser Arg
210                 215                 220

Pro Ser Ile Ser Lys Thr Pro Glu Asp Ser Lys Ser Ser Gly Cys
225                 230                 235                 240

Asp Thr Ala Asp Asp Pro Asn Ser Glu Leu Glu Asn Gly Ala Asp Pro
                245                 250                 255

Glu Leu Gly Asn Gly His Ala Phe Glu Leu Glu Asn Gly Pro His Ser
            260                 265                 270

Leu Lys Asp Val Ala Gly Pro His Leu Glu Arg Ser Glu Ala Asp Ser
        275                 280                 285

Glu Val Glu Leu Arg Val Pro Lys Thr Glu Ala Pro Leu Ser Asp Ser
290                 295                 300

Asn Asp Lys Arg Arg Phe Ser Lys Thr Gly Lys Thr Asp Phe Gln Ser
305                 310                 315                 320

Ser Asp Cys Leu Ala Arg Glu Val Gly Arg Ile Trp Lys Met Glu
                325                 330                 335

Leu Leu Lys Glu Ser Asp Gly Leu Gly Ile Gln Val Ser Gly Gly Arg
            340                 345                 350

Gly Ser Lys Arg Ser Pro His Ala Ile Val Val Thr Gln Val Lys Glu
        355                 360                 365

Gly Gly Ala Ala His Arg Asp Gly Arg Leu Ser Leu Gly Asp Glu Leu
370                 375                 380

Leu Val Ile Asn Gly His Leu Leu Val Gly Leu Ser His Glu Glu Ala
385                 390                 395                 400

Val Ala Ile Leu Arg Ser Ala Thr Gly Met Val Gln Leu Val Val Ala
                405                 410                 415

Ser Lys Met Pro Gly Ser Glu Glu Ser Gln Asp Val Gly Ser Ser Glu
            420                 425                 430

Glu Ser Lys Gly Asn Leu Glu Ser Pro Lys Gln Gly Asn Cys Lys Thr
        435                 440                 445

Lys Leu Lys Ser Arg Leu Ser Gly Gly Val His Arg Leu Glu Ser Val
450                 455                 460

Glu Glu Tyr Asn Glu Leu Met Val Arg Asn Gly Asp Pro Arg Ile Arg
465                 470                 475                 480

Met Leu Glu Val Ser Arg Asp Gly Arg Lys His Ser Leu Pro Gln Leu
                485                 490                 495

Leu Asp Ser Thr Gly Thr Ser Gln Glu Tyr His Ile Val Lys Lys Ser
            500                 505                 510

Thr Arg Ser Leu Ser Thr His Val Glu Ser Pro Trp Arg Leu Ile
        515                 520                 525

Arg Pro Ser Val Ile Ser Ile Gly Leu Tyr Lys Glu Lys Gly Lys
530                 535                 540

Gly Leu Gly Phe Ser Ile Ala Gly Gly Arg Asp Cys Ile Arg Gly Gln
545                 550                 555                 560

Met Gly Ile Phe Val Lys Thr Ile Phe Pro Asn Gly Ser Ala Ala Glu
                565                 570                 575

Asp Gly Arg Leu Lys Glu Gly Asp Glu Ile Leu Asp Val Asn Gly Ile
            580                 585                 590

Pro Ile Lys Gly Leu Thr Phe Gln Glu Ala Ile His Thr Phe Lys Gln
        595                 600                 605

Ile Arg Ser Gly Leu Phe Val Leu Thr Val Arg Thr Lys Leu Leu Ser
```

-continued

```
            610                 615                 620
Pro Ser Leu Thr Pro Cys Ser Thr Pro Thr His Met Ser Arg Ser Ser
625                 630                 635                 640

Ser Pro Ser Phe Asn Thr Asn Ser Gly Gly Thr Pro Ala Gly Gly Gly
                645                 650                 655

Gln Glu Glu Gly Gly Ser Ser Ser Leu Gly Arg Lys Ala Pro Gly Pro
                660                 665                 670

Lys Asp Arg Ile Val Met Glu Val Thr Leu Asn Lys Glu Pro Arg Val
                675                 680                 685

Gly Leu Gly Ile Gly Ala Cys Cys Leu Ala Leu Glu Asn Ser Pro Pro
690                 695                 700

Gly Ile Tyr Ile His Ser Leu Ala Pro Gly Ser Val Ala Lys Met Glu
705                 710                 715                 720

Ser Asn Leu Ser Arg Gly Asp Gln Ile Leu Glu Val Asn Ser Val Asn
                725                 730                 735

Val Arg His Ala Ala Leu Ser Lys Val His Ala Ile Leu Ser Lys Cys
                740                 745                 750

Pro Pro Gly Pro Val Arg Leu Val Ile Gly Arg His Pro Asn Pro Lys
                755                 760                 765

Val Ser Glu Gln Glu Met Asp Glu Val Ile Ala Arg Ser Thr Tyr Gln
770                 775                 780

Glu Ser Arg Glu Ala Asn Ser Ser Pro Gly Leu Gly Thr Pro Leu Lys
785                 790                 795                 800

Ser Pro Ser Leu Ala Lys Lys Asp Ser Leu Leu Ser Glu Ser Glu Leu
                805                 810                 815

Ser Gln Tyr Phe Val His Asp Gly Gln Gly Ser Leu Ser Asp Phe Val
                820                 825                 830

Val Ala Gly Ser Glu Asp Glu Asp His Pro Gly Ser Gly Tyr Glu Thr
                835                 840                 845

Ser Glu Asp Gly Ser Leu Leu Pro Val Pro Ser Ala His Lys Ala Arg
850                 855                 860

Ala Asn Ser Leu Val Thr Leu Gly Ser Gln Arg Thr Ser Gly Leu Leu
865                 870                 875                 880

His Lys Gln Val Thr Val Ala Arg Gln Ala Ser Leu Pro Gly Ser Pro
                885                 890                 895

Gln Val Leu Arg Asn Pro Leu Leu Arg Gln Arg Val Arg Cys Tyr
                900                 905                 910

Asp Ser Asn Gly Gly Ser Asp Asp Glu Asp Phe Asp Gly Glu Gly Asp
                915                 920                 925

Cys Ile Ser Leu Pro Gly Val Leu Pro Gly Pro Gly Lys Pro Leu Val
930                 935                 940

Glu Asp Asp Thr Arg Pro Ala Leu Thr Thr Ser Ser Lys Ser Ile Asp
945                 950                 955                 960

Val Asn Lys Gln Glu Glu Arg Leu Gln Lys Pro Leu Val Ser Lys Ala
                965                 970                 975

Cys Ser Val Pro Leu Leu Gly Ser Ser Leu Asp Ser Glu His Ser Ile
                980                 985                 990

Leu Asn Gly Ala Gly Gly Thr Pro Pro Lys Val Ala Ser Leu Pro Gly
                995                 1000                1005

Ser Gly Glu Thr Pro Lys Asn Gly Pro Arg Gly Ser Gly Arg Lys Glu
    1010                1015                1020

Met Ser Gly Ser Arg Ser Ser Pro Lys Leu Glu Tyr Arg Val Pro Thr
1025                1030                1035                1040
```

```
Asp Thr Gln Ser Pro Arg Ser Pro Glu Asn His Thr Ser Pro Pro Gln
            1045                1050                1055

Lys Ser Glu Asn Leu Val Ser Arg His Lys Pro Val Ala Arg Ile Ser
        1060                1065                1070

Pro His Tyr Lys Arg Ser Asp Ala Glu Glu Ala Pro Gly Gly Thr Ala
    1075                1080                1085

Asn Gly Pro Cys Ala Gln Asp Leu Lys Val Gln Ala Ser Pro Val Lys
    1090                1095                1100

Asp Pro Val Thr Ser Arg Gln Pro Gly Gly Thr Ala Glu Lys Glu Leu
1105                1110                1115                1120

Arg Gly Asn Pro Thr Pro Gly Asp Ser Ser Val Pro Thr Asn Cys Gly
            1125                1130                1135

Pro Ala Ser Thr Pro Cys His Pro Asn Ile Gly Leu Pro Thr Glu Asn
        1140                1145                1150

Pro Gln Gly Ala Ala Pro Glu Cys Gly Pro His Pro Gly Thr Gly Trp
    1155                1160                1165

Asp Gly Ser Ser Glu His Leu Cys Ser Pro Gly Lys Ser Arg Glu Val
    1170                1175                1180

His Pro Asp Ser Ser Glu Thr Pro Thr Val Ala Glu Gln Val His Gln
1185                1190                1195                1200

Pro Glu Ser Leu Ser Gln Pro Val Ser Pro Arg Thr Ser Glu Pro Glu
            1205                1210                1215

Ser Gln Gly Ile Ser Lys Met Lys Pro Pro Ser Gln Arg Cys Val Ser
        1220                1225                1230

Pro Arg Glu Lys Ala Ser Thr Pro Pro Asp Ser Ser Arg Ala Trp Ala
    1235                1240                1245

Ala Pro Gly Asp Ser Ser Pro Ser Thr Arg Arg Ile Ala Val Pro Met
    1250                1255                1260

Ser Thr Gly Ala Ala Pro Ala Thr Ala Ile Pro Gln Ala Ser Leu Val
1265                1270                1275                1280

Ser Gln Glu Arg Ser Arg Gly Leu Ser Gly Pro Ser Lys Gly Leu Gly
            1285                1290                1295

Thr Lys Glu Leu Cys Ile Pro Lys Ser Leu Lys Asp Gly Ala Leu Leu
        1300                1305                1310

Glu Asp Thr Ala Pro Ala Ser Gly Lys Met Ser His Ala Ser Ser Pro
    1315                1320                1325

Ser Gly Pro Val Ala Thr Glu Arg Thr Leu Ser Gly Ser Pro Glu Asn
    1330                1335                1340

Pro Val Thr Asp Ile Asp Asn Phe Ile Glu Glu Ala Ser Glu Ala Arg
1345                1350                1355                1360

Leu Ser Gln Ser Pro Gln Lys Ala Asp Cys Arg Ala His Gly Asp Thr
            1365                1370                1375

Phe Glu Ser Gln Pro Pro Gly Gly Ala Gly Ser Ser Ser His His
        1380                1385                1390

Ala Gln Met Val Arg Ser Asp Gln Thr Ser Ser Pro Arg Lys Thr Gly
    1395                1400                1405

Gly Thr Gly Ser Pro Pro Pro Gln Gln Trp Ala Leu Gln Pro Ser Val
    1410                1415                1420

Leu Asp Ser Ile His Pro Asp Lys His Leu Ala Val Asn Lys Thr Phe
1425                1430                1435                1440

Leu Asn Asn Tyr Ser Arg Asn Phe Ser Asn Phe His Glu Asp Ser Ile
            1445                1450                1455
```

```
Ser Leu Ser Gly Pro Gly Gly Ser Ser Glu Pro Ser Pro Ser Ser Met
            1460                1465                1470

Tyr Gly Asn Ala Glu Asp Ser Ser Asp Pro Glu Ser Leu Ala Glu
        1475                1480                1485

Asp Pro Gly Ala Ala Arg Asn Asn Trp Ser Pro Leu Ser Pro
    1490                1495                1500

Glu Ser Ser Pro Lys Glu Gly Ser Ser Glu Ser Glu Asp Glu Arg Ile
1505                1510                1515                1520

Glu Ile Cys Ser Thr Asp Gly Cys Pro Gly Thr Pro Val Thr Ala Pro
                1525                1530                1535

Pro Pro Thr Gln Val Ala Leu Cys Pro Val Leu Pro Val Gln Gln Arg
            1540                1545                1550

Ala Val Cys Lys Pro Val Gly Asp Ile Cys Glu Arg Ala Cys Phe Val
        1555                1560                1565

Pro Gly Ala Ser Arg Thr Ser Ile Pro Asp Ser Ser Gln Pro Phe Ser
    1570                1575                1580

Phe Leu Asp Val Ser Ser Glu Glu Pro Glu Thr Trp Ala Ser Ile Asn
1585                1590                1595                1600

Ala Ser Gln Asn His Met Pro Val Cys Thr Glu Gly Ile Met Asp Val
                1605                1610                1615

Thr Ser Thr Ser Ser Asn Met Gly Asp Ser Gln Ser Ser Gln Met Thr
            1620                1625                1630

Arg His Cys Arg Asn Ala Pro Phe Val Leu Gly Asn Pro Asp Met Val
        1635                1640                1645

Asn Asp Leu Gly Arg Asp Leu Leu Asp Glu Gly Ala Pro Lys Glu Gly
1650                1655                1660

Ala Ala Ala Ser Val Met Arg Ser Val Phe Ala Leu Gly Ala Glu
1665                1670                1675                1680

Gly Pro Lys Asn Gly Glu Ala Val Leu Ala Asp Leu His Ile Ala Glu
            1685                1690                1695

Arg Gly Asn Leu Glu Asp Leu Leu Gln Lys Pro Lys Thr Ile Ser Arg
        1700                1705                1710

Arg Pro Ile Leu Thr Trp Phe Lys Glu Ile Asn Lys Asp Ser Gln Gly
    1715                1720                1725

Ser His Leu Arg Ser Thr Ser Glu Lys Glu Gln Ser Ser Met Leu Ala
1730                1735                1740

Leu Gly Pro Gly Ser Lys Ala Asn Met Val Asn Thr Gly His Arg Lys
1745                1750                1755                1760

Gly Val Thr Val Pro Lys Ser Pro Ser Arg Gln Lys Ser Gln Glu
            1765                1770                1775

Asn Lys Asp Leu Pro Pro Lys Ser Pro Val Glu Thr Leu Gly Asn Cys
        1780                1785                1790

Gln Lys Pro Lys Cys Ser Pro Lys Leu Lys Arg Leu Asn Ser Lys Gly
    1795                1800                1805

Lys Ala Ser Pro Glu Val Pro Val Ala Ile Ser Thr Lys Gly Ser Arg
    1810                1815                1820

Asn Asp His Arg Lys Thr Leu Pro Ser Pro Gln Ala Ser His Lys Met
1825                1830                1835                1840

Phe Ser Lys Ala Val Ser His Arg Leu His Ile Ala Asp Gln Glu Glu
                1845                1850                1855

Pro Lys Asn Thr Ala Gly Asp Thr Pro Lys Pro Pro Gln Cys Val Pro
            1860                1865                1870

Glu Ser Lys Pro Pro Gln Ala Ala Leu Gly Ser Leu Arg Thr Ser Ala
```

-continued

```
                1875                1880                1885
Ser Asp Thr Ser Ile Arg Thr Phe Thr Ser Pro Leu Thr Ser Pro Lys
    1890                1895                1900

Leu Leu Pro Glu Gln Gly Ala Asn Ser Arg Phe His Met Ala Val Tyr
1905                1910                1915                1920

Leu Glu Ser Asp Thr Ser Cys Pro Thr Thr Ser Arg Ser Pro Arg Ser
                1925                1930                1935

Gly Pro Glu Gly Lys Ala Pro His Ala Asn Ser Gly Ser Ala Ser Pro
            1940                1945                1950

Pro Ala Ser Arg Ala Ser Leu Ala Leu Ala Gly Ile Arg Gln Ser Lys
    1955                1960                1965

Gln Phe Thr Pro Gly Arg Ala Asp Leu Leu Val Ser Glu Ala Thr Gln
    1970                1975                1980

Pro Gln Gly Ile Cys Glu Lys Gly Ala Glu Lys Val Ser Asp Pro
1985                1990                1995                2000

Pro Gln Arg Thr Asn Gln Leu Lys Ile Val Glu Ile Ser Ser Glu Arg
                2005                2010                2015

Val Pro Lys Asn Ala Cys Gly Asp Arg Pro Pro Glu Ser Asp Arg Lys
    2020                2025                2030

Gly Gly Phe Leu Thr Gln Asn Asn Cys Gln Glu Lys Ser Ala Ile Arg
    2035                2040                2045

Leu Arg Gln Ser Glu Glu Ser Ser Pro Glu His Thr Pro Phe Pro Pro
2050                2055                2060

Ser Gln Ala Ser Gln Val Glu Arg Glu Ile Arg Trp Ser Phe Ser Met
2065                2070                2075                2080

Ala Lys Pro Ala Thr Ser Ser Ser Ser Leu Gln Leu Pro Ala Lys
    2085                2090                2095

Leu Pro Glu Ser Phe Gln Gly Lys Ser Ser Gln Met Pro Ala Ser Val
        2100                2105                2110

Gly Val Pro Lys Asn Gly Val Pro Ile Gly Leu Ala Gly Glu Glu Ser
    2115                2120                2125

Pro Tyr Phe Thr Pro Arg Pro Ala Thr Arg Thr Tyr Ser Met Pro Ala
    2130                2135                2140

Gln Phe Ser Ser His Phe Gly Arg Glu Gly Pro Ser Pro His Ser Pro
2145                2150                2155                2160

Ser His Ser Pro Gln Asp Pro Gln Val Pro Ala Met Gly Gly Lys Leu
            2165                2170                2175

Ser Glu Lys Thr Ala Lys Gly Val Thr Asn Gly Gln Gly Val Tyr Ser
            2180                2185                2190

Val Lys Pro Leu Leu Glu Thr Ser Lys Asn Leu Ser Pro Val Asp Gly
        2195                2200                2205

Arg Asp Val Ser Ala Asp Pro Glu Thr Ser Cys Leu Ile Pro Asp Lys
    2210                2215                2220

Val Lys Val Thr Arg Arg Gln Tyr Cys Cys Glu Gln Ser Trp Pro His
2225                2230                2235                2240

Glu Ser Thr Ser Phe Phe Ser Val Lys Gln Arg Ile Lys Ser Phe Glu
            2245                2250                2255

Asn Leu Ala Asn Ser Asp Arg Pro Thr Ala Lys Cys Ala Thr Ser Pro
        2260                2265                2270

Phe Leu Ser Val Ser Ser Lys Pro Pro Ile Asn Arg Arg Ser Ser Gly
    2275                2280                2285

Ser Ile Pro Ser Gly Ser Pro Ser Asp Met Thr Ser Arg Ser Leu Arg
    2290                2295                2300
```

-continued

```
Arg Ser Leu Ser Ser Cys Ser Glu Ser Gln Ser Glu Ala Ser Ser Leu
2305                2310                2315                2320

Leu Pro Gln Met Thr Lys Ser Pro Ser Ser Met Thr Leu Thr Val Ser
            2325                2330                2335

Arg Gln Asn Pro Pro Asp Thr Ser Asn Lys Gly Pro Ser Pro Asp Pro
        2340                2345                2350

Lys Lys Ser Leu Val Pro Val Gly Ile Pro Thr Ser Thr Val Ser Pro
        2355                2360                2365

Ala Ser Pro Ser Lys Arg Asn Lys Ser Ser Val Arg His Ala Gln Pro
    2370                2375                2380

Ser Pro Val Ser Arg Ser Lys Leu Gln Glu Arg Arg Thr Leu Ser Met
2385                2390                2395                2400

Pro Asp Leu Asp Lys Leu Cys Asn Gly Glu Asp Asp Ser Ala Ser Pro
            2405                2410                2415

Gly Ala Val Leu Phe Lys Thr Gln Leu Glu Ile Thr Pro Arg Arg Ser
        2420                2425                2430

Lys Gly Ser Gln Ala Thr Ser Pro Ala Gly Ser Pro Ala Arg Gly His
        2435                2440                2445

Ala Asp Phe Asn Gly Ser Thr Phe Leu Ser Cys Pro Met Asn Gly Gly
    2450                2455                2460

Thr Arg Ala Tyr Thr Lys Gly Asn Ser Pro Pro Ala Ser Glu Pro Ala
2465                2470                2475                2480

Ile Ala Thr Gly Ser Arg Glu Glu Gly Glu Ser Val Trp Ala Thr Pro
            2485                2490                2495

Ser Gly Lys Ser Trp Ser Val Ser Leu Asp Arg Leu Leu Ala Ser Val
        2500                2505                2510

Gly Asn Gln Gln Arg Leu Gln Gly Ile Leu Ser Leu Val Gly Ser Lys
        2515                2520                2525

Ser Pro Ile Leu Thr Leu Ile Gln Glu Ala Lys Ala Gln Ser Glu Thr
    2530                2535                2540

Lys Glu Asp Ile Cys Phe Ile Val Leu Asn Lys Lys Glu Gly Ser Gly
2545                2550                2555                2560

Leu Gly Phe Ser Val Ala Gly Gly Ala Asp Val Glu Pro Lys Ser Val
            2565                2570                2575

Met Val His Arg Val Phe Ser Gln Gly Val Ala Ser Gln Glu Gly Thr
            2580                2585                2590

Val Ser Arg Gly Asp Phe Leu Leu Ser Val Asn Gly Thr Ser Leu Ala
        2595                2600                2605

Gly Leu Ala His Ser Glu Val Thr Lys Val Leu His Gln Ala Glu Leu
    2610                2615                2620

His Lys His Ala Leu Met Ile Ile Lys Lys Gly Asn Asp Gln Pro Gly
2625                2630                2635                2640

Pro Ser Phe Lys Gln Glu Pro Pro Ser Ala Asn Gly Lys Gly Pro Phe
            2645                2650                2655

Pro Arg Arg Thr Leu Pro Leu Glu Pro Gly Ala Gly Arg Asn Gly Ala
        2660                2665                2670

Ala His Asp Ala Leu Cys Val Glu Val Leu Lys Thr Ser Ala Gly Leu
    2675                2680                2685

Gly Leu Ser Leu Asp Gly Gly Lys Ser Ser Val Ser Gly Glu Gly Pro
    2690                2695                2700

Leu Val Ile Lys Arg Val Tyr Lys Gly Gly Ala Ala Glu Arg Ala Gly
2705                2710                2715                2720
```

Thr Ile Glu Ala Gly Asp Glu Ile Leu Ala Ile Asn Gly Lys Pro Leu
                2725                2730                2735

Val Gly Leu Val His Phe Asp Ala Trp Asn Ile Met Lys Ser Val Pro
            2740                2745                2750

Glu Gly Pro Val Gln Leu Val Ile Arg Lys His Arg Asp Ser
        2755                2760                2765

<210> SEQ ID NO 63
<211> LENGTH: 2641
<212> TYPE: PRT
<213> ORGANISM: Homo sapiens

<400> SEQUENCE: 63

Met Pro Ile Thr Gln Asp Asn Ala Val Leu His Leu Pro Leu Leu Tyr
 1               5                   10                  15

Gln Trp Leu Gln Asn Ser Leu Gln Glu Gly Gly Asp Gly Pro Glu Gln
            20                  25                  30

Arg Leu Cys Gln Ala Ala Ile Gln Lys Leu Gln Glu Tyr Ile Gln Leu
        35                  40                  45

Asn Phe Ala Val Asp Glu Ser Thr Val Pro Pro Asp His Ser Pro Pro
    50                  55                  60

Glu Met Glu Ile Cys Thr Val Tyr Leu Thr Lys Glu Leu Gly Asp Thr
65                  70                  75                  80

Glu Thr Val Gly Leu Ser Phe Gly Asn Ile Pro Val Phe Gly Asp Tyr
                85                  90                  95

Gly Glu Lys Arg Arg Gly Gly Lys Lys Arg Lys Thr His Gln Gly Pro
            100                 105                 110

Val Leu Asp Val Gly Cys Ile Trp Val Thr Glu Leu Arg Lys Asn Ser
        115                 120                 125

Pro Ala Gly Lys Ser Gly Lys Val Arg Leu Arg Asp Glu Ile Leu Ser
    130                 135                 140

Leu Asn Gly Gln Leu Met Val Gly Val Asp Val Ser Gly Ala Ser Tyr
145                 150                 155                 160

Leu Ala Glu Gln Cys Trp Asn Gly Gly Phe Ile Tyr Leu Ile Met Leu
                165                 170                 175

Arg Arg Phe Lys His Lys Ala His Ser Thr Tyr Asn Gly Asn Ser Ser
            180                 185                 190

Asn Ser Ser Glu Pro Gly Glu Thr Pro Thr Leu Glu Leu Gly Asp Arg
        195                 200                 205

Thr Ala Lys Lys Gly Lys Arg Thr Arg Lys Phe Gly Val Ile Ser Arg
    210                 215                 220

Pro Pro Ala Asn Lys Ala Pro Glu Glu Ser Lys Gly Ser Ala Gly Cys
225                 230                 235                 240

Glu Val Ser Ser Asp Pro Ser Thr Glu Leu Glu Asn Gly Ala Asp Pro
                245                 250                 255

Glu Leu Gly Asn Gly His Val Phe Gln Leu Glu Asn Gly Pro Asp Ser
            260                 265                 270

Leu Lys Glu Val Ala Gly Pro His Leu Glu Arg Ser Glu Val Asp Arg
        275                 280                 285

Gly Thr Glu His Arg Ile Pro Lys Thr Asp Ala Pro Leu Thr Thr Ser
    290                 295                 300

Asn Asp Lys Arg Arg Phe Ser Lys Gly Gly Lys Thr Asp Phe Gln Ser
305                 310                 315                 320

Ser Asp Cys Leu Ala Arg Gln Glu Glu Val Gly Arg Ile Trp Lys Met
                325                 330                 335

-continued

```
Glu Leu Leu Lys Glu Ser Asp Gly Leu Gly Ile Gln Val Ser Gly Gly
                340                 345                 350

Arg Gly Ser Lys Arg Ser Pro His Ala Ile Val Val Thr Gln Val Lys
            355                 360                 365

Glu Gly Gly Ala Ala His Arg Glu Tyr His Ile Val Lys Lys Ser Thr
        370                 375                 380

Arg Ser Leu Ser Thr Thr Gln Val Glu Ser Pro Trp Arg Leu Ile Arg
385                 390                 395                 400

Pro Ser Val Ile Ser Ile Ile Gly Leu Tyr Lys Glu Lys Gly Lys Gly
                405                 410                 415

Leu Gly Phe Ser Ile Ala Gly Gly Arg Asp Cys Ile Arg Gly Gln Met
            420                 425                 430

Gly Ile Phe Val Lys Thr Ile Phe Pro Asn Gly Ser Ala Ala Glu Asp
        435                 440                 445

Gly Arg Leu Lys Glu Gly Asp Glu Ile Leu Asp Val Asn Gly Ile Pro
    450                 455                 460

Ile Lys Gly Leu Thr Phe Gln Glu Ala Ile His Thr Phe Lys Gln Ile
465                 470                 475                 480

Arg Ser Gly Leu Phe Val Leu Thr Val Arg Thr Lys Leu Val Ser Pro
                485                 490                 495

Ser Leu Thr Pro Cys Ser Thr Pro Thr His Met Ser Arg Ser Ala Ser
            500                 505                 510

Pro Asn Phe Asn Thr Ser Gly Gly Ala Ser Ala Gly Gly Ser Asp Glu
        515                 520                 525

Gly Ser Ser Ser Leu Gly Arg Lys Thr Pro Gly Pro Lys Asp Arg
    530                 535                 540

Ile Val Met Glu Val Thr Leu Asn Lys Glu Pro Arg Val Gly Leu Gly
545                 550                 555                 560

Ile Gly Ala Cys Cys Leu Ala Leu Glu Asn Ser Pro Pro Gly Ile Tyr
                565                 570                 575

Ile His Ser Leu Ala Pro Gly Ser Val Ala Lys Met Glu Ser Asn Leu
            580                 585                 590

Ser Arg Gly Asp Gln Ile Leu Glu Val Asn Ser Val Asn Val Arg His
        595                 600                 605

Ala Ala Leu Ser Lys Val His Ala Ile Leu Ser Lys Cys Pro Val Ser
    610                 615                 620

Glu Gln Glu Met Asp Glu Val Ile Ala Arg Ser Thr Tyr Gln Glu Ser
625                 630                 635                 640

Lys Glu Ala Asn Ser Ser Pro Gly Leu Gly Thr Pro Leu Lys Ser Pro
                645                 650                 655

Ser Leu Ala Lys Lys Asp Ser Leu Ile Ser Glu Ser Glu Leu Ser Gln
            660                 665                 670

Tyr Phe Ala His Asp Val Pro Gly Pro Leu Ser Asp Phe Met Val Ala
        675                 680                 685

Gly Ser Glu Asp Glu Asp His Pro Gly Ser Gly Cys Ser Thr Ser Glu
    690                 695                 700

Glu Gly Ser Leu Pro Pro Ser Thr Ser Ser Glu Pro Gly Lys Pro Arg
705                 710                 715                 720

Ala Asn Ser Leu Val Thr Leu Gly Ser His Arg Ala Ser Gly Leu Phe
                725                 730                 735

His Lys Gln Val Thr Val Ala Arg Gln Ala Ser Leu Pro Gly Ser Pro
            740                 745                 750
```

-continued

Gln Ala Leu Arg Asn Pro Leu Leu Arg Gln Arg Lys Val Gly Cys Tyr
            755                 760                 765

Asp Ala Asn Asp Ala Ser Asp Glu Glu Glu Phe Asp Arg Glu Gly Asp
        770                 775                 780

Cys Ile Ser Leu Pro Gly Ala Leu Pro Gly Pro Ile Arg Pro Leu Ser
785                 790                 795                 800

Glu Asp Asp Pro Arg Arg Val Ser Ile Ser Ser Ser Lys Gly Met Asp
                805                 810                 815

Val His Asn Gln Glu Glu Arg Pro Arg Lys Thr Leu Val Ser Lys Ala
            820                 825                 830

Ile Ser Ala Pro Leu Leu Gly Ser Ser Val Asp Leu Glu Glu Ser Ile
        835                 840                 845

Pro Glu Gly Met Val Asp Ala Ala Ser Tyr Ala Ala Asn Leu Thr Asp
    850                 855                 860

Ser Ala Glu Ala Pro Lys Gly Ser Pro Gly Ser Trp Trp Lys Lys Glu
865                 870                 875                 880

Leu Ser Gly Ser Ser Ser Ala Pro Lys Leu Glu Tyr Thr Val Arg Thr
                885                 890                 895

Asp Thr Gln Ser Pro Thr Asn Thr Gly Ser Pro Ser Ser Pro Gln Gln
            900                 905                 910

Lys Ser Glu Gly Leu Gly Ser Arg His Arg Pro Val Ala Arg Val Ser
        915                 920                 925

Pro His Cys Lys Arg Ser Glu Ala Glu Ala Lys Pro Ser Gly Ser Gln
    930                 935                 940

Thr Val Asn Leu Thr Gly Arg Ala Asn Asp Pro Cys Asp Leu Asp Ser
945                 950                 955                 960

Arg Val Gln Ala Thr Ser Val Lys Val Thr Val Ala Gly Phe Gln Pro
                965                 970                 975

Gly Gly Ala Val Glu Lys Leu Cys Gln Glu Ser Leu Gly Lys Leu Thr
            980                 985                 990

Thr Gly Asp Ala Cys Val Ser Thr Ser Cys Glu Leu Ala Ser Ala Leu
        995                 1000                1005

Ser His Leu Asp Ala Ser His Leu Thr Glu Asn Leu Pro Lys Ala Ala
    1010                1015                1020

Ser Glu Leu Gly Gln Gln Pro Met Thr Ser Ser Asp Leu Ile Ser Ser
1025                1030                1035                1040

Pro Gly Lys Lys Gly Ala Ala His Pro Asp Pro Ser Lys Thr Ser Val
                1045                1050                1055

Asp Thr Gly Gln Val Ser Arg Pro Glu Asn Pro Ser Gln Pro Ala Ser
            1060                1065                1070

Pro Arg Val Thr Lys Cys Lys Ala Arg Ser Pro Val Arg Leu Pro His
        1075                1080                1085

Glu Gly Ser Pro Ser Pro Gly Glu Lys Ala Ala Ala Pro Pro Asp Tyr
    1090                1095                1100

Ser Lys Thr Arg Ser Ala Ser Glu Thr Ser Thr Pro His Asn Thr Arg
1105                1110                1115                1120

Arg Val Ala Ala Leu Arg Gly Ala Gly Pro Ala Glu Gly Met Thr
                1125                1130                1135

Pro Ala Gly Ala Val Leu Pro Gly Asp Pro Leu Thr Ser Gln Glu Gln
            1140                1145                1150

Arg Gln Gly Ala Pro Gly Asn His Ser Lys Ala Leu Glu Met Thr Gly
        1155                1160                1165

Ile His Ala Pro Glu Ser Ser Gln Glu Pro Ser Leu Leu Glu Gly Ala

-continued

```
                1170                1175                1180
Asp Ser Val Ser Ser Arg Ala Pro Gln Ala Ser Leu Ser Met Leu Pro
1185                1190                1195                1200

Ser Thr Asp Asn Thr Lys Glu Ala Cys Gly His Val Ser Gly His Cys
                1205                1210                1215

Cys Pro Gly Gly Ser Arg Glu Ser Pro Val Thr Asp Ile Asp Ser Phe
                1220                1225                1230

Ile Lys Glu Leu Asp Ala Ser Ala Ala Arg Ser Pro Ser Ser Gln Thr
                1235                1240                1245

Gly Asp Ser Gly Ser Gln Glu Gly Ser Ala Gln Gly His Pro Pro Ala
                1250                1255                1260

Gly Ala Gly Gly Ser Ser Cys Arg Ala Glu Pro Val Pro Gly Gly
                1265                1270                1275                1280

Gln Thr Ser Ser Pro Arg Arg Ala Trp Ala Ala Gly Ala Pro Ala Tyr
                1285                1290                1295

Pro Gln Trp Ala Ser Gln Pro Ser Val Leu Asp Ser Ile Asn Pro Asp
                    1300                1305                1310

Lys His Phe Thr Val Asn Lys Asn Phe Leu Ser Asn Tyr Ser Arg Asn
            1315                1320                1325

Phe Ser Ser Phe His Glu Asp Ser Thr Ser Leu Ser Gly Leu Gly Asp
    1330                1335                1340

Ser Thr Glu Pro Ser Leu Ser Ser Met Tyr Gly Asp Ala Glu Asp Ser
1345                1350                1355                1360

Ser Ser Asp Pro Glu Ser Leu Thr Glu Ala Pro Arg Ala Ser Ala Arg
                1365                1370                1375

Asp Gly Trp Ser Pro Pro Arg Ser Arg Val Ser Leu His Lys Glu Asp
            1380                1385                1390

Pro Ser Glu Ser Glu Glu Gln Ile Glu Ile Cys Ser Thr Arg Gly
            1395                1400                1405

Cys Pro Asn Pro Pro Ser Ser Pro Ala His Leu Pro Thr Gln Ala Ala
    1410                1415                1420

Ile Cys Pro Ala Ser Ala Lys Val Leu Ser Leu Lys Tyr Ser Thr Pro
1425                1430                1435                1440

Arg Glu Ser Val Ala Ser Pro Arg Glu Lys Ala Ala Cys Leu Pro Gly
                1445                1450                1455

Ser Tyr Thr Ser Gly Pro Asp Ser Ser Gln Pro Ser Ser Leu Leu Glu
        1460                1465                1470

Met Ser Ser Gln Glu His Glu Thr His Ala Asp Ile Ser Thr Ser Gln
            1475                1480                1485

Asn His Arg Pro Ser Cys Ala Glu Glu Thr Thr Glu Val Thr Ser Ala
    1490                1495                1500

Ser Ser Ala Met Glu Asn Ser Pro Leu Ser Lys Val Ala Arg His Phe
1505                1510                1515                1520

His Ser Pro Pro Ile Ile Leu Ser Ser Pro Asn Met Val Asn Gly Leu
                1525                1530                1535

Glu His Asp Leu Leu Asp Asp Glu Thr Leu Asn Gln Tyr Glu Thr Ser
            1540                1545                1550

Ile Asn Ala Ala Ala Ser Leu Ser Ser Phe Ser Val Asp Val Pro Lys
    1555                1560                1565

Asn Gly Glu Ser Val Leu Glu Asn Leu His Ile Ser Glu Ser Gln Asp
    1570                1575                1580

Leu Asp Asp Leu Leu Gln Lys Pro Lys Met Ile Ala Arg Arg Pro Ile
1585                1590                1595                1600
```

-continued

```
Met Ala Trp Phe Lys Glu Ile Asn Lys His Asn Gln Gly Thr His Leu
            1605                1610                1615

Arg Ser Lys Thr Glu Lys Glu Gln Pro Leu Met Pro Ala Arg Ser Pro
            1620                1625                1630

Asp Ser Lys Ile Gln Met Val Ser Ser Gln Lys Lys Gly Val Thr
        1635                1640                1645

Val Pro His Ser Pro Pro Gln Pro Lys Thr Asn Leu Glu Asn Lys Asp
    1650                1655                1660

Leu Ser Lys Lys Ser Pro Ala Glu Met Leu Leu Thr Asn Gly Gln Lys
1665                1670                1675                1680

Ala Lys Cys Gly Pro Lys Leu Lys Arg Leu Ser Leu Lys Gly Lys Ala
            1685                1690                1695

Lys Val Asn Ser Glu Ala Pro Ala Ala Asn Ala Val Lys Ala Gly Gly
            1700                1705                1710

Thr Asp His Arg Lys Pro Leu Ile Ser Pro Gln Thr Ser His Lys Thr
        1715                1720                1725

Leu Ser Lys Ala Val Ser Gln Arg Leu His Val Ala Asp His Glu Asp
    1730                1735                1740

Pro Asp Arg Asn Thr Thr Ala Ala Pro Arg Ser Pro Gln Cys Val Leu
1745                1750                1755                1760

Glu Ser Lys Pro Pro Leu Ala Thr Ser Gly Pro Leu Lys Pro Ser Val
            1765                1770                1775

Ser Asp Thr Ser Ile Arg Thr Phe Val Ser Pro Leu Thr Ser Pro Lys
            1780                1785                1790

Pro Val Pro Glu Gln Gly Met Trp Ser Arg Phe His Met Ala Val Leu
        1795                1800                1805

Ser Glu Pro Asp Arg Gly Cys Pro Thr Thr Pro Lys Ser Pro Lys Cys
    1810                1815                1820

Arg Ala Glu Gly Arg Ala Pro Arg Ala Asp Ser Gly Pro Val Ser Pro
1825                1830                1835                1840

Ala Ala Ser Arg Asn Gly Met Ser Val Ala Gly Asn Arg Gln Ser Glu
            1845                1850                1855

Pro Arg Leu Ala Ser His Val Ala Ala Asp Thr Ala Gln Pro Arg Pro
            1860                1865                1870

Thr Gly Glu Lys Gly Gly Asn Ile Met Ala Ser Asp Arg Leu Glu Arg
        1875                1880                1885

Thr Asn Gln Leu Lys Ile Val Glu Ile Ser Ala Glu Ala Val Ser Glu
    1890                1895                1900

Thr Val Cys Gly Asn Lys Pro Ala Glu Ser Asp Arg Arg Gly Gly Cys
1905                1910                1915                1920

Leu Ala Gln Gly Asn Cys Gln Glu Lys Ser Glu Ile Arg Leu Tyr Arg
            1925                1930                1935

Gln Val Ala Glu Ser Ser Thr Ser His Pro Ser Ser Leu Pro Ser His
            1940                1945                1950

Ala Ser Gln Ala Glu Gln Glu Met Ser Arg Ser Phe Ser Met Ala Lys
        1955                1960                1965

Leu Ala Ser Ser Ser Ser Ser Leu Gln Thr Ala Ile Arg Lys Ala Glu
    1970                1975                1980

Tyr Ser Gln Gly Lys Ser Ser Leu Met Ser Asp Ser Arg Gly Val Pro
1985                1990                1995                2000

Arg Asn Ser Ile Pro Gly Gly Pro Ser Gly Glu Asp His Leu Tyr Phe
            2005                2010                2015
```

-continued

```
Thr Pro Arg Pro Ala Thr Arg Thr Tyr Ser Met Pro Ala Gln Phe Ser
            2020                2025                2030

Ser His Phe Gly Arg Glu Gly His Pro Pro His Ser Leu Gly Arg Ser
        2035                2040                2045

Arg Asp Ser Gln Val Pro Val Thr Ser Ser Val Val Pro Glu Ala Lys
    2050                2055                2060

Ala Ser Arg Gly Gly Leu Pro Ser Leu Ala Asn Gly Gln Gly Ile Tyr
2065                2070                2075                2080

Ser Val Lys Pro Leu Leu Asp Thr Ser Arg Asn Leu Pro Ala Thr Asp
            2085                2090                2095

Glu Gly Asp Ile Ile Ser Val Gln Glu Thr Ser Cys Leu Val Thr Asp
            2100                2105                2110

Lys Ile Lys Val Thr Arg Arg His Tyr Cys Tyr Glu Gln Asn Trp Pro
    2115                2120                2125

His Glu Ser Thr Ser Phe Phe Ser Val Lys Gln Arg Ile Lys Ser Phe
    2130                2135                2140

Glu Asn Leu Ala Asn Ala Asp Arg Pro Val Ala Lys Ser Gly Ala Ser
2145                2150                2155                2160

Pro Phe Leu Ser Val Ser Ser Lys Pro Pro Ile Gly Arg Arg Ser Ser
            2165                2170                2175

Gly Ser Ile Val Ser Gly Ser Leu Gly His Pro Gly Asp Ala Ala Ala
            2180                2185                2190

Arg Leu Leu Arg Arg Ser Leu Ser Ser Cys Ser Glu Asn Gln Ser Glu
        2195                2200                2205

Ala Gly Thr Leu Leu Pro Gln Met Ala Lys Ser Pro Ser Ile Met Thr
    2210                2215                2220

Leu Thr Ile Ser Arg Gln Asn Pro Pro Glu Thr Ser Ser Lys Gly Ser
2225                2230                2235                2240

Asp Ser Glu Leu Lys Lys Ser Leu Gly Pro Leu Gly Ile Pro Thr Pro
            2245                2250                2255

Thr Met Thr Leu Ala Ser Pro Val Lys Arg Asn Lys Ser Ser Val Arg
        2260                2265                2270

His Thr Gln Pro Ser Pro Val Ser Arg Ser Lys Leu Gln Glu Leu Arg
    2275                2280                2285

Ala Leu Ser Met Pro Asp Leu Asp Lys Leu Cys Ser Glu Asp Tyr Ser
    2290                2295                2300

Ala Gly Pro Ser Ala Val Leu Phe Lys Thr Glu Leu Glu Ile Thr Pro
2305                2310                2315                2320

Arg Arg Ser Pro Gly Pro Pro Ala Gly Gly Val Ser Cys Pro Glu Lys
            2325                2330                2335

Gly Gly Asn Arg Ala Cys Pro Gly Gly Ser Gly Pro Lys Thr Ser Ala
        2340                2345                2350

Ala Glu Thr Pro Ser Ser Ala Ser Asp Thr Gly Glu Ala Ala Gln Asp
    2355                2360                2365

Leu Pro Phe Arg Arg Ser Trp Ser Val Lys Leu Asp Gln Leu Leu Val
    2370                2375                2380

Ser Ala Gly Asp Gln Gln Arg Leu Gln Ser Val Leu Ser Ser Val Gly
2385                2390                2395                2400

Ser Lys Ser Thr Ile Leu Thr Leu Ile Gln Glu Ala Lys Ala Gln Ser
            2405                2410                2415

Glu Asn Glu Glu Asp Val Cys Phe Ile Val Leu Asn Arg Lys Glu Gly
            2420                2425                2430

Ser Gly Leu Gly Phe Ser Val Ala Gly Gly Thr Asp Val Glu Pro Lys
```

-continued

```
                2435                2440                2445
Ser Ile Thr Val His Arg Val Phe Ser Gln Gly Ala Ala Ser Gln Glu
    2450                2455                2460

Gly Thr Met Asn Arg Gly Asp Phe Leu Leu Ser Val Asn Gly Ala Ser
2465                2470                2475                2480

Leu Ala Gly Leu Ala His Gly Asn Val Leu Lys Val Leu His Gln Ala
            2485                2490                2495

Gln Leu His Lys Asp Ala Leu Val Val Ile Lys Lys Gly Met Asp Gln
        2500                2505                2510

Pro Arg Pro Ser Ala Arg Gln Glu Pro Pro Thr Ala Asn Gly Lys Gly
    2515                2520                2525

Leu Leu Ser Arg Lys Thr Ile Pro Leu Glu Pro Gly Ile Gly Arg Ser
    2530                2535                2540

Val Ala Val His Asp Ala Leu Cys Val Glu Val Leu Lys Thr Ser Ala
2545                2550                2555                2560

Gly Leu Gly Leu Ser Leu Asp Gly Gly Lys Ser Ser Val Thr Gly Asp
            2565                2570                2575

Gly Pro Leu Val Ile Lys Arg Val Tyr Lys Gly Gly Ala Ala Glu Gln
        2580                2585                2590

Ala Gly Ile Ile Glu Ala Gly Asp Glu Ile Leu Ala Ile Asn Gly Lys
        2595                2600                2605

Pro Leu Val Gly Leu Met His Phe Asp Ala Trp Asn Ile Met Lys Ser
    2610                2615                2620

Val Pro Glu Gly Pro Val Gln Leu Leu Ile Arg Lys His Arg Asn Ser
2625                2630                2635                2640

Ser
```

<210> SEQ ID NO 64
<211> LENGTH: 364
<212> TYPE: PRT
<213> ORGANISM: Mus musculus

<400> SEQUENCE: 64

```
Met Leu Arg Arg Phe Lys Gln Lys Ala His Leu Thr Tyr Asn Gly Asn
  1               5                  10                  15

Ser Gly Asn Ser Ser Glu Pro Gly Glu Thr Pro Thr Leu Glu Leu Gly
             20                  25                  30

Asp Gln Thr Ser Lys Lys Gly Lys Arg Thr Lys Phe Gly Val Ile
         35                  40                  45

Ser Arg Pro Ala Ile Ile Lys Ala Pro Glu Asp Ser Lys Ser Asn Ser
     50                  55                  60

Gly Cys Asp Thr Ala Asp Asp Pro Ser Ser Glu Leu Glu Asn Gly Thr
 65                  70                  75                  80

Asp Ser Glu Leu Gly Asn Gly His Ala Phe Glu Leu Glu Asn Gly Pro
                 85                  90                  95

Asn Ser Leu Lys Asp Val Ala Gly Pro His Leu Glu Arg Ser Glu Ala
            100                 105                 110

Asp Arg Glu Ala Glu Leu Arg Val Pro Lys Thr Glu Ala Pro Leu Ser
        115                 120                 125

Asp Ser Asn Asp Lys Arg Arg Phe Ser Lys Thr Gly Lys Thr Asn Phe
    130                 135                 140

Gln Ser Ser Asp Ser Leu Ala Arg Glu Glu Val Gly Arg Ile Trp Glu
145                 150                 155                 160

Met Glu Leu Leu Lys Glu Ser Asp Gly Leu Gly Ile Gln Val Ser Gly
```

```
                165                 170                 175
Gly Arg Gly Ser Lys Arg Ser Pro His Ala Ile Val Val Thr Gln Val
            180                 185                 190
Lys Glu Gly Gly Ala Ala His Arg Asp Gly Arg Leu Ser Leu Gly Asp
        195                 200                 205
Glu Leu Val Ile Asn Gly His Leu Leu Val Gly Leu Ser His Glu
    210                 215                 220
Glu Ala Val Ala Ile Leu Arg Ser Ala Thr Gly Met Val Gln Leu Val
225                 230                 235                 240
Val Ala Ser Lys Met Leu Gly Ser Glu Glu Ser Gln Asp Val Gly Ser
            245                 250                 255
Ser Glu Glu Ser Lys Gly Asn Asn Leu Glu Ser Pro Lys Gln Gly Asn
            260                 265                 270
Ser Lys Met Lys Leu Lys Ser Arg Leu Ser Gly Gly Val His Arg Leu
        275                 280                 285
Glu Ser Val Glu Glu Tyr Asn Glu Leu Met Val Arg Asn Gly Asp Pro
    290                 295                 300
Arg Ile Arg Met Leu Glu Val Ser Arg Asp Gly Arg Lys His Ser Leu
305                 310                 315                 320
Pro Gln Leu Leu Asp Ser Thr Gly Thr Ser Gln Glu Tyr His Ile Val
            325                 330                 335
Lys Lys Ser Thr Arg Ser Leu Ser Thr Thr His Val Glu Ser Pro Trp
            340                 345                 350
Arg Leu Ile Arg Pro Ser Val Ile Ser Ile Gly
        355                 360

<210> SEQ ID NO 65
<211> LENGTH: 51
<212> TYPE: PRT
<213> ORGANISM: Artificial Sequence
<220> FEATURE:
<223> OTHER INFORMATION: Description of Artificial Sequence: LRRCT
      Consensus Sequence

<400> SEQUENCE: 65

Asn Pro Phe Ile Cys Asp Cys Glu Leu Arg Trp Leu Leu Arg Trp Leu
  1               5                  10                  15
Gln Ala Asn Arg His Leu Gln Asp Pro Val Asp Leu Arg Cys Ala Ser
            20                  25                  30
Pro Glu Ser Leu Arg Gly Pro Leu Leu Leu Leu Pro Ser Ser Phe
        35                  40                  45
Lys Cys Pro
    50

<210> SEQ ID NO 66
<211> LENGTH: 51
<212> TYPE: PRT
<213> ORGANISM: Artificial Sequence
<220> FEATURE:
<223> OTHER INFORMATION: Description of Artificial Sequence: LRRCT
      Consensus Sequence

<400> SEQUENCE: 66

Asn Pro Phe Ile Cys Asp Cys Glu Leu Arg Trp Leu Leu Arg Trp Leu
  1               5                  10                  15
Arg Glu Pro Arg Arg Leu Glu Asp Pro Glu Asp Leu Arg Cys Ala Ser
            20                  25                  30
Pro Glu Ser Leu Arg Gly Pro Leu Leu Glu Leu Leu Pro Ser Asp Phe
```

-continued

```
               35                  40                  45

Ser Cys Pro
    50

<210> SEQ ID NO 67
<211> LENGTH: 124
<212> TYPE: PRT
<213> ORGANISM: Artificial Sequence
<220> FEATURE:
<223> OTHER INFORMATION: Description of Artificial Sequence: CLECT
      Consensus Sequence

<400> SEQUENCE: 67

Cys Pro Ser Gly Trp Val Ser Tyr Pro Gly Gly Lys Cys Tyr Lys Phe
  1               5                  10                  15

Ser Thr Glu Lys Lys Thr Trp Ala Asp Ala Gln Ala Phe Cys Gln Ser
                 20                  25                  30

Leu Gly Ala His Leu Ala Ser Ile His Ser Glu Glu Glu Asn Asp Phe
             35                  40                  45

Leu Leu Ser Leu Leu Lys Asn Ser Asn Ser Asp Tyr Tyr Trp Ile Gly
     50                  55                  60

Leu Ser Arg Pro Asp Ser Asn Gly Ser Trp Gln Trp Ser Asp Gly Ser
 65                  70                  75                  80

Gly Pro Val Asp Tyr Ser Asn Trp Ala Pro Gly Glu Pro Gly Gly Ser
                 85                  90                  95

Gly Asn Cys Val Val Leu Ser Thr Ser Gly Gly Gly Lys Trp Asn Asp
            100                 105                 110

Val Ser Cys Thr Ser Lys Leu Pro Phe Ile Cys Glu
        115                 120

<210> SEQ ID NO 68
<211> LENGTH: 114
<212> TYPE: PRT
<213> ORGANISM: Artificial Sequence
<220> FEATURE:
<223> OTHER INFORMATION: Description of Artificial Sequence: CUB
      Consensus Sequence

<400> SEQUENCE: 68

Cys Gly Gly Thr Leu Thr Ala Ser Ser Gly Thr Ile Thr Ser Pro Asn
  1               5                  10                  15

Tyr Pro Asn Ser Tyr Pro Asn Asn Leu Asn Cys Val Trp Thr Ile Ser
                 20                  25                  30

Ala Pro Pro Gly Tyr Arg Ile Glu Leu Lys Phe Thr Asp Phe Asp Leu
             35                  40                  45

Glu Ser Ser Asp Asn Cys Thr Tyr Asp Tyr Val Glu Ile Tyr Asp Gly
     50                  55                  60

Pro Ser Thr Ser Ser Pro Leu Leu Gly Arg Phe Cys Gly Ser Glu Leu
 65                  70                  75                  80

Pro Pro Pro Ile Ile Ser Ser Ser Asn Ser Met Thr Val Thr Phe
                 85                  90                  95

Val Ser Asp Ser Ser Val Gln Lys Arg Gly Phe Ser Ala Arg Tyr Ser
            100                 105                 110

Ala Val

<210> SEQ ID NO 69
<211> LENGTH: 110
<212> TYPE: PRT
<213> ORGANISM: Artificial Sequence
```

-continued

```
<220> FEATURE:
<223> OTHER INFORMATION: Description of Artificial Sequence: CUB
      Consensus Sequence

<400> SEQUENCE: 69

Cys Gly Gly Val Leu Thr Glu Ser Ser Gly Ser Ile Ser Pro Asn
 1               5                  10                  15

Tyr Pro Asn Asp Tyr Pro Pro Asn Lys Glu Cys Val Trp Thr Ile Arg
                 20                  25                  30

Ala Pro Pro Gly Tyr Arg Val Glu Leu Thr Phe Gln Asp Phe Asp Leu
            35                  40                  45

Glu Asp His Thr Gly Cys Arg Tyr Asp Tyr Val Glu Ile Arg Asp Gly
 50                  55                  60

Asp Gly Ser Ser Pro Leu Leu Gly Lys Phe Cys Gly Ser Gly Pro
 65                  70                  75                  80

Pro Glu Asp Ile Val Ser Ser Asn Arg Met Thr Ile Lys Phe Val
                 85                  90                  95

Ser Asp Ala Ser Val Ser Lys Arg Gly Phe Lys Ala Thr Tyr
            100                 105                 110

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Lectin
      C-type domain Consensus Sequence

<400> SEQUENCE: 70

Glu Ser Lys Thr Trp Ala Glu Ala Gln Ala Ala Cys Gln Lys Leu Gly
 1               5                  10                  15

Gly Gly Leu Val Ser Ile Gln Ser Ala Glu Glu Gln Asp Phe Leu Thr
                 20                  25                  30

Ser Leu Thr Lys Ala Ser Asn Ser Tyr Ala Trp Ile Gly Leu Thr Asp
            35                  40                  45

Ile Asn Thr Glu Gly Thr Trp Val Trp Thr Asp Gly Ser Pro Val Asn
 50                  55                  60

Tyr Thr Asn Trp Ala Pro Gly Glu Pro Asn Asn Arg Gly Asn Lys Glu
 65                  70                  75                  80

Asp Cys Val Glu Ile Tyr Thr Asp Gly Asn Lys Trp Asn Asp Glu Pro
                 85                  90                  95

Cys Gly Ser Lys Leu Pro Tyr Val Cys Glu Phe
            100                 105

<210> SEQ ID NO 71
<211> LENGTH: 304
<212> TYPE: PRT
<213> ORGANISM: Artificial Sequence
<220> FEATURE:
<223> OTHER INFORMATION: Description of Artificial Sequence: CNH domain
      Consensus Sequence

<400> SEQUENCE: 71

Tyr Thr Ala Lys Cys Asn His Pro Ile Thr Cys Asp Ala Lys Asn Leu
 1               5                  10                  15

Leu Val Gly Thr Glu Glu Gly Leu Tyr Val Leu Asn Arg Ser Asp Gln
                 20                  25                  30

Gly Gly Thr Leu Glu Lys Ile Ile Ser Arg Arg Ser Val Thr Gln Ile
            35                  40                  45
```

```
Trp Val Leu Glu Glu Asn Asn Val Leu Leu Met Ile Ser Gly Lys Lys
     50                  55                  60

Pro Tyr Leu Tyr Ala His Pro Leu Ser Gly Leu Arg Glu Lys Asp Ala
 65                  70                  75                  80

Leu Gly Ser Ala Arg Leu Val Ile Arg Lys Asn Val Trp Val Lys Ile
                 85                  90                  95

Glu Asp Val Lys Gly Cys His Leu Phe Ala Val Val Asn Gly Lys Arg
            100                 105                 110

Ile Leu Phe Leu Cys Ala Ala Leu Pro Ser Ser Val Gln Leu Leu Gln
        115                 120                 125

Trp Tyr Asn Pro Leu Lys Lys Phe Lys Leu Phe Lys Ser Lys Phe Leu
    130                 135                 140

Lys Lys Leu Ile Val Pro Val Pro Leu Phe Val Leu Leu Thr Ser Ser
145                 150                 155                 160

Ser Phe Glu Leu Pro Lys Ile Cys Ile Gly Val Asp Lys Asn Gly Phe
                165                 170                 175

Asp Val Val Gln Phe His Gln Thr Ser Leu Val Ser Lys Glu Asp Leu
            180                 185                 190

Ser Leu Pro Asn Leu Asn Glu Glu Thr Ser Lys Lys Pro Ile Pro Val
        195                 200                 205

Ile Gln Val Pro Gln Ser Asp Asp Glu Leu Leu Leu Cys Phe Asp Glu
    210                 215                 220

Phe Gly Val Phe Val Asn Leu Gln Gly Met Arg Arg Ser Arg Lys Pro
225                 230                 235                 240

Ile Leu Thr Trp Glu Phe Met Pro Glu Tyr Phe Ala Tyr His Glu Pro
                245                 250                 255

Tyr Leu Leu Ala Phe His Ser Asn Gly Ile Glu Ile Arg Ser Ile Glu
            260                 265                 270

Thr Gly Glu Leu Leu Gln Glu Leu Ala Asp Arg Glu Ala Arg Lys Ile
        275                 280                 285

Arg Val Leu Gly Ser Ser Asp Arg Lys Ile Leu Val Ser Ser Ser Pro
    290                 295                 300
```

<210> SEQ ID NO 72
<211> LENGTH: 256
<212> TYPE: PRT
<213> ORGANISM: Artificial Sequence
<220> FEATURE:
<223> OTHER INFORMATION: Description of Artificial Sequence:
      Serine/Threoniune protein kinase Consensus
      Sequence

<400> SEQUENCE: 72

```
Tyr Glu Leu Leu Glu Val Leu Gly Lys Gly Ala Phe Gly Lys Val Tyr
 1               5                  10                  15

Leu Ala Arg Asp Lys Lys Thr Gly Lys Leu Val Ala Ile Lys Val Ile
                20                  25                  30

Lys Lys Glu Lys Leu Lys Lys Lys Arg Glu Arg Ile Leu Arg Glu
         35                  40                  45

Ile Lys Ile Leu Lys Lys Leu Asp His Pro Asn Ile Val Lys Leu Tyr
    50                  55                  60

Asp Val Phe Glu Asp Asp Lys Leu Tyr Leu Val Met Glu Tyr Cys
 65                  70                  75                  80

Glu Gly Gly Asp Leu Phe Asp Leu Leu Lys Lys Arg Gly Arg Leu Ser
                85                  90                  95

Glu Asp Glu Ala Arg Phe Tyr Ala Arg Gln Ile Leu Ser Ala Leu Glu
```

```
                    100                 105                 110
Tyr Leu His Ser Gln Gly Ile Ile His Arg Asp Leu Lys Pro Glu Asn
            115                 120                 125

Ile Leu Leu Asp Ser Asp Gly His Val Lys Leu Ala Asp Phe Gly Leu
130                 135                 140

Ala Lys Gln Leu Asp Ser Gly Gly Thr Leu Thr Thr Phe Val Gly
145                 150                 155                 160

Thr Pro Glu Tyr Met Ala Pro Glu Val Leu Leu Gly Lys Gly Tyr Gly
                165                 170                 175

Lys Ala Val Asp Ile Trp Ser Leu Gly Val Ile Leu Tyr Glu Leu Leu
                180                 185                 190

Thr Gly Lys Pro Pro Phe Pro Gly Asp Asp Gln Leu Leu Ala Leu Phe
            195                 200                 205

Lys Lys Ile Gly Lys Pro Pro Pro Phe Pro Pro Glu Trp Lys
210                 215                 220

Ile Ser Pro Glu Ala Lys Asp Leu Ile Lys Leu Leu Val Lys Asp
225                 230                 235                 240

Pro Glu Lys Arg Leu Thr Ala Glu Glu Ala Leu Glu His Pro Phe Phe
                245                 250                 255

<210> SEQ ID NO 73
<211> LENGTH: 301
<212> TYPE: PRT
<213> ORGANISM: Artificial Sequence
<220> FEATURE:
<223> OTHER INFORMATION: Description of Artificial Sequence: CNH domain
      Consensus Sequence

<400> SEQUENCE: 73

Asn Thr Ala Lys Trp Asn His Pro Ile Thr Cys Asp Ala Lys Ile Leu
1               5                   10                  15

Leu Val Gly Thr Glu Glu Gly Leu Tyr Val Leu Asn Ile Ser Asp Gln
                20                  25                  30

His Gly Thr Leu Glu Lys Leu Ile Gly Arg Arg Ser Val Thr Gln Ile
            35                  40                  45

Trp Val Leu Glu Glu Asn Asn Val Leu Leu Met Ile Ser Gly Lys Lys
        50                  55                  60

Pro Gln Leu Tyr Ser His Pro Leu Ser Ala Leu Thr Glu Lys Asp Ala
65                  70                  75                  80

Leu Gly Ser Ala Arg Leu Val Ile Arg Lys Asn Val Leu Thr Lys Ile
                85                  90                  95

Pro Asp Val Lys Gly Cys His Leu Cys Ala Val Val Asn Gly Lys Arg
            100                 105                 110

Ile Leu Phe Leu Cys His Ala Leu Gln Ser Ser Val Leu Leu Gln
        115                 120                 125

Trp Tyr Asn Pro Leu Lys Lys Phe Lys Leu Phe Lys Ser Lys Phe Leu
        130                 135                 140

Phe Pro Leu Ile Ser Pro Val Pro Val Phe Glu Leu Val Ser Ser
145                 150                 155                 160

Ser Phe Glu Leu Pro Gly Ile Cys Ile Gly Ser Asp Lys Asn Gly Gly
                165                 170                 175

Asp Val Val Gln Phe His Gln Ser Leu Val Ser Lys Glu Asp Leu Ser
            180                 185                 190

Leu Pro Phe Leu Ser Glu Glu Thr Ser Ser Lys Pro Ile Ser Val Val
        195                 200                 205
```

-continued

```
Gln Val Pro Ala Asp Glu Leu Leu Cys Tyr Asp Glu Phe Gly Val
    210                 215                 220

Phe Val Asn Leu Tyr Gly Met Arg Arg Ser Arg Asn Pro Ile Leu His
225                 230                 235                 240

Trp Glu Phe Met Pro Glu Ser Phe Ala Tyr His Ser Pro Tyr Leu Leu
                245                 250                 255

Ala Phe His Asp Asn Gly Ile Glu Ile Arg Ser Ile Lys Thr Gly Glu
                260                 265                 270

Leu Leu Gln Glu Leu Ala Asp Arg Lys Thr Arg Lys Ile Arg Leu Leu
            275                 280                 285

Gly Ser Ser Asp Arg Lys Ile Leu Leu Ser Ser Pro
            290                 295                 300

<210> SEQ ID NO 74
<211> LENGTH: 256
<212> TYPE: PRT
<213> ORGANISM: Artificial Sequence
<220> FEATURE:
<223> OTHER INFORMATION: Description of Artificial Sequence: Protein
      kinase domain Consensus Sequence

<400> SEQUENCE: 74

Tyr Glu Leu Gly Glu Lys Leu Gly Ser Gly Ala Phe Gly Lys Val Tyr
  1               5                  10                  15

Lys Gly Lys His Lys Asp Thr Gly Glu Ile Val Ala Ile Lys Ile Leu
                 20                  25                  30

Lys Lys Arg Ser Leu Ser Glu Lys Lys Arg Phe Leu Arg Glu Ile
             35                  40                  45

Gln Ile Leu Arg Arg Leu Ser His Pro Asn Ile Val Arg Leu Leu Gly
         50                  55                  60

Val Phe Glu Glu Asp Asp His Leu Tyr Leu Val Met Glu Tyr Met Glu
 65                  70                  75                  80

Gly Gly Asp Leu Phe Asp Tyr Leu Arg Arg Asn Gly Leu Leu Leu Ser
                 85                  90                  95

Glu Lys Glu Ala Lys Lys Ile Ala Leu Gln Ile Leu Arg Gly Leu Glu
                100                 105                 110

Tyr Leu His Ser Arg Gly Ile Val His Arg Asp Leu Lys Pro Glu Asn
            115                 120                 125

Ile Leu Leu Asp Glu Asn Gly Thr Val Lys Ile Ala Asp Phe Gly Leu
        130                 135                 140

Ala Arg Lys Leu Glu Ser Ser Ser Tyr Glu Lys Leu Thr Thr Phe Val
145                 150                 155                 160

Gly Thr Pro Glu Tyr Met Ala Pro Glu Val Leu Glu Gly Arg Gly Tyr
                165                 170                 175

Ser Ser Lys Val Asp Val Trp Ser Leu Gly Val Ile Leu Tyr Glu Leu
            180                 185                 190

Leu Thr Gly Lys Leu Pro Phe Pro Gly Ile Asp Pro Leu Glu Glu Leu
        195                 200                 205

Phe Arg Ile Lys Glu Arg Pro Arg Leu Arg Leu Pro Leu Pro Pro Asn
    210                 215                 220

Cys Ser Glu Glu Leu Lys Asp Leu Ile Lys Lys Cys Leu Asn Lys Asp
225                 230                 235                 240

Pro Glu Lys Arg Pro Thr Ala Lys Glu Ile Leu Asn His Pro Trp Phe
                245                 250                 255

<210> SEQ ID NO 75
```

-continued

```
<211> LENGTH: 258
<212> TYPE: PRT
<213> ORGANISM: Artificial Sequence
<220> FEATURE:
<223> OTHER INFORMATION: Description of Artificial Sequence: Tyrosine
      Kinase Consensus Sequence

<400> SEQUENCE: 75

Leu Thr Leu Gly Lys Lys Leu Gly Glu Gly Ala Phe Gly Glu Val Tyr
1               5                   10                  15

Lys Gly Thr Leu Lys Gly Lys Gly Val Glu Val Glu Val Ala Val
            20                  25                  30

Lys Thr Leu Lys Glu Asp Ala Ser Glu Gln Gln Ile Glu Glu Phe Leu
        35                  40                  45

Arg Glu Ala Arg Leu Met Arg Lys Leu Asp His Pro Asn Ile Val Lys
    50                  55                  60

Leu Leu Gly Val Cys Thr Glu Glu Pro Leu Met Ile Val Met Glu
65                  70                  75                  80

Tyr Met Glu Gly Gly Asp Leu Leu Asp Tyr Leu Arg Lys Asn Arg Pro
                85                  90                  95

Lys Glu Leu Ser Leu Ser Asp Leu Leu Ser Phe Ala Leu Gln Ile Ala
            100                 105                 110

Arg Gly Met Glu Tyr Leu Glu Ser Lys Asn Phe Val His Arg Asp Leu
        115                 120                 125

Ala Ala Arg Asn Cys Leu Val Gly Glu Asn Lys Thr Val Lys Ile Ala
    130                 135                 140

Asp Phe Gly Leu Ala Arg Asp Leu Tyr Asp Asp Tyr Tyr Arg Lys
145                 150                 155                 160

Lys Lys Ser Pro Arg Leu Pro Ile Arg Trp Met Ala Pro Glu Ser Leu
                165                 170                 175

Lys Asp Gly Lys Phe Thr Ser Lys Ser Asp Val Trp Ser Phe Gly Val
            180                 185                 190

Leu Leu Trp Glu Ile Phe Thr Leu Gly Glu Ser Pro Tyr Pro Gly Met
        195                 200                 205

Ser Asn Glu Glu Val Leu Glu Tyr Leu Lys Lys Gly Tyr Arg Leu Pro
    210                 215                 220

Gln Pro Pro Asn Cys Pro Asp Glu Ile Tyr Asp Leu Met Leu Gln Cys
225                 230                 235                 240

Trp Ala Glu Asp Pro Glu Asp Arg Pro Thr Phe Ser Glu Leu Val Glu
                245                 250                 255

Arg Leu

<210> SEQ ID NO 76
<211> LENGTH: 430
<212> TYPE: PRT
<213> ORGANISM: Artificial Sequence
<220> FEATURE:
<223> OTHER INFORMATION: Description of Artificial Sequence: Sema domain
      Consensus Sequence

<400> SEQUENCE: 76

Leu Gln Asn Leu Leu Leu Asp Glu Asp Asn Gly Thr Leu Tyr Val Gly
1               5                   10                  15

Ala Arg Asn Arg Leu Tyr Val Leu Ser Leu Asn Leu Ile Ser Glu Ala
            20                  25                  30

Glu Val Lys Thr Gly Pro Val Leu Ser Ser Pro Asp Cys Glu Glu Cys
        35                  40                  45
```

```
Val Ser Lys Gly Lys Asp Pro Thr Asp Cys Val Asn Phe Ile Arg
     50                  55                  60
Leu Leu Leu Asp Tyr Asn Ala Asp His Leu Val Cys Gly Thr Asn
 65                  70                  75                  80
Ala Phe Gln Pro Val Cys Arg Leu Ile Asn Leu Gly Asn Leu Asp Arg
                 85                  90                  95
Leu Glu Val Gly Arg Glu Ser Gly Arg Gly Arg Cys Pro Phe Asp Pro
                100                 105                 110
Gln His Asn Ser Thr Ala Val Leu Val Asp Gly Glu Leu Tyr Val Gly
                115                 120                 125
Thr Val Ala Asp Phe Ser Gly Ser Asp Pro Ala Ile Tyr Arg Ser Leu
    130                 135                 140
Ser Val Arg Arg Leu Lys Gly Thr Ser Gly Pro Ser Leu Arg Thr Val
145                 150                 155                 160
Leu Tyr Asp Ser Arg Trp Leu Asn Glu Pro Asn Phe Val Tyr Ala Phe
                165                 170                 175
Glu Ser Gly Asp Phe Val Tyr Phe Phe Arg Glu Thr Ala Val Glu
                180                 185                 190
Asp Glu Asn Cys Gly Lys Ala Val Val Ser Arg Val Ala Arg Val Cys
                195                 200                 205
Lys Asn Asp Val Gly Gly Pro Arg Ser Leu Ser Lys Lys Trp Thr Ser
    210                 215                 220
Phe Leu Lys Ala Arg Leu Glu Cys Ser Val Pro Gly Glu Phe Pro Phe
225                 230                 235                 240
Tyr Phe Asn Glu Leu Gln Ala Ala Phe Leu Leu Pro Ala Gly Ser Glu
                245                 250                 255
Ser Asp Asp Val Leu Tyr Gly Val Phe Ser Thr Ser Ser Asn Pro Ile
                260                 265                 270
Pro Gly Ser Ala Val Cys Ala Phe Ser Leu Ser Asp Ile Asn Ala Val
    275                 280                 285
Phe Asn Glu Pro Phe Lys Glu Cys Glu Thr Gly Asn Ser Gln Trp Leu
290                 295                 300
Pro Tyr Pro Arg Gly Leu Val Pro Phe Pro Arg Pro Gly Thr Cys Pro
305                 310                 315                 320
Asn Thr Pro Leu Ser Ser Lys Asp Leu Pro Asp Asp Val Leu Asn Phe
                325                 330                 335
Ile Lys Thr His Pro Leu Met Asp Glu Val Val Gln Pro Leu Thr Gly
                340                 345                 350
Arg Pro Leu Phe Val Lys Thr Asp Ser Asn Tyr Leu Leu Thr Ser Ile
    355                 360                 365
Ala Val Asp Arg Val Arg Thr Asp Gly Gly Asn Tyr Thr Val Leu Phe
    370                 375                 380
Leu Gly Thr Ser Asp Gly Arg Ile Leu Lys Val Val Leu Ser Arg Ser
385                 390                 395                 400
Ser Ser Ser Ser Glu Ser Val Val Leu Glu Glu Ile Ser Val Phe Asp
                405                 410                 415
Pro Gly Ser Pro Val Ser Asp Leu Val Leu Ser Pro Lys Lys
                420                 425                 430

<210> SEQ ID NO 77
<211> LENGTH: 433
<212> TYPE: PRT
<213> ORGANISM: Artificial Sequence
<220> FEATURE:
<223> OTHER INFORMATION: Description of Artificial Sequence: Sema domain
```

Consensus Sequence

<400> SEQUENCE: 77

```
Phe Val Thr Leu Leu Asp Glu Asp Arg Gly Arg Leu Tyr Val Gly
  1               5                  10                  15

Ala Arg Asn Arg Val Tyr Val Leu Asn Leu Glu Asp Leu Ser Glu Val
             20                  25                  30

Leu Asn Leu Lys Thr Gly Trp Pro Gly Ser Cys Glu Thr Cys Glu Glu
         35                  40                  45

Cys Asn Met Lys Gly Lys Ser Pro Leu Thr Glu Cys Thr Asn Phe Ile
     50                  55                  60

Arg Val Leu Gln Ala Tyr Asn Asp Thr His Leu Tyr Val Cys Gly Thr
 65                  70                  75                  80

Asn Ala Phe Gln Pro Val Cys Thr Leu Ile Asn Leu Gly Asp Leu Phe
                 85                  90                  95

Ser Leu Asp Val Asp Asn Glu Glu Asp Gly Cys Gly Asp Cys Pro Tyr
                100                 105                 110

Asp Pro Leu Gly Asn Thr Thr Ser Val Leu Val Gln Gly Gly Glu Leu
            115                 120                 125

Tyr Ser Gly Thr Val Ile Asp Phe Ser Gly Arg Asp Pro Ser Ile Arg
        130                 135                 140

Arg Leu Leu Gly Ser His Asp Gly Leu Arg Thr Glu Phe His Asp Ser
145                 150                 155                 160

Lys Trp Leu Asn Leu Pro Asn Phe Val Asp Ser Tyr Pro Ile His Tyr
                165                 170                 175

Val His Ser Phe Ser Asp Asp Lys Val Tyr Phe Phe Arg Glu Thr
                180                 185                 190

Ala Val Glu Asp Ser Asn Cys Lys Thr Ile His Ser Arg Val Ala Arg
            195                 200                 205

Val Cys Lys Asn Asp Pro Gly Gly Arg Ser Tyr Leu Glu Leu Asn Lys
210                 215                 220

Trp Thr Thr Phe Leu Lys Ala Arg Leu Asn Cys Ser Ile Pro Gly Glu
225                 230                 235                 240

Gly Thr Pro Phe Tyr Phe Asn Glu Leu Gln Ala Ala Phe Val Leu Pro
                245                 250                 255

Thr Gly Ala Asp Thr Asp Pro Val Leu Tyr Gly Val Phe Thr Thr Ser
            260                 265                 270

Ser Asn Ser Ser Ala Gly Ser Ala Val Cys Ala Phe Ser Met Ser Asp
        275                 280                 285

Ile Asn Gln Val Phe Glu Gly Pro Phe Lys His Gln Ser Pro Asn Ser
    290                 295                 300

Lys Trp Leu Pro Tyr Arg Gly Lys Val Pro Gln Pro Arg Pro Gly Gln
305                 310                 315                 320

Cys Pro Asn Ala Ser Gly Leu Asn Leu Pro Asp Asp Thr Leu Asn Phe
                325                 330                 335

Ile Arg Cys His Pro Leu Met Asp Glu Val Val Pro Pro Leu His Asn
            340                 345                 350

Val Pro Leu Phe Val Gly Gln Ser Gly Asn Tyr Arg Leu Thr Ser Ile
        355                 360                 365

Ala Val Asp Arg Val Arg Ala Gly Asp Gly Gln Ile Tyr Thr Val Leu
    370                 375                 380

Phe Leu Gly Thr Asp Asp Gly Arg Val Leu Lys Gln Val Val Leu Ser
385                 390                 395                 400
```

-continued

```
Arg Ser Ser Ala Ser Tyr Leu Val Val Leu Glu Glu Ser Leu
            405                 410                 415

Val Phe Pro Asp Gly Glu Pro Val Gln Arg Met Val Ile Ser Ser Lys
            420                 425                 430

Asn

<210> SEQ ID NO 78
<211> LENGTH: 85
<212> TYPE: PRT
<213> ORGANISM: Artificial Sequence
<220> FEATURE:
<223> OTHER INFORMATION: Description of Artificial Sequence: TIG domain
      Consensus Sequence

<400> SEQUENCE: 78

Pro Val Ile Thr Ser Ile Ser Pro Ser Ser Gly Pro Leu Ser Gly Gly
  1               5                  10                  15

Thr Glu Ile Thr Ile Thr Gly Ser Asn Leu Gly Ser Gly Glu Asp Ile
             20                  25                  30

Lys Val Thr Phe Gly Gly Thr Glu Cys Asp Val Val Ser Gln Glu Ala
         35                  40                  45

Ser Gln Ile Val Cys Lys Thr Pro Pro Tyr Ala Asn Gly Gly Pro Gln
     50                  55                  60

Pro Val Thr Val Ser Leu Asp Gly Gly Gly Leu Ser Ser Ser Pro Val
 65                  70                  75                  80

Thr Phe Thr Tyr Val
             85

<210> SEQ ID NO 79
<211> LENGTH: 85
<212> TYPE: PRT
<213> ORGANISM: Artificial Sequence
<220> FEATURE:
<223> OTHER INFORMATION: Description of Artificial Sequence: TIG
      Consensus Sequence

<400> SEQUENCE: 79

Pro Val Ile Thr Ser Ile Ser Pro Ser Ser Gly Pro Leu Ser Gly Gly
  1               5                  10                  15

Thr Glu Ile Thr Ile Thr Gly Ser Asn Leu Gly Ser Gly Glu Asp Ile
             20                  25                  30

Lys Val Thr Phe Gly Gly Thr Glu Cys Asp Val Val Ser Gln Glu Ala
         35                  40                  45

Ser Gln Ile Val Cys Lys Thr Pro Pro Tyr Ala Asn Gly Gly Pro Gln
     50                  55                  60

Pro Val Thr Val Ser Leu Asp Gly Gly Gly Leu Ser Ser Ser Pro Val
 65                  70                  75                  80

Thr Phe Thr Tyr Val
             85

<210> SEQ ID NO 80
<211> LENGTH: 85
<212> TYPE: PRT
<213> ORGANISM: Artificial Sequence
<220> FEATURE:
<223> OTHER INFORMATION: Description of Artificial Sequence: TIG
      Consensus Sequence

<400> SEQUENCE: 80

Pro Val Ile Thr Ser Ile Ser Pro Ser Ser Gly Pro Leu Ser Gly Gly
  1               5                  10                  15
```

-continued

Thr Glu Ile Thr Ile Thr Gly Ser Asn Leu Gly Ser Gly Glu Asp Ile
                20                  25                  30

Lys Val Thr Phe Gly Gly Thr Glu Cys Asp Val Val Ser Gln Glu Ala
            35                  40                  45

Ser Gln Ile Val Cys Lys Thr Pro Pro Tyr Ala Asn Gly Gly Pro Gln
        50                  55                  60

Pro Val Thr Val Ser Leu Asp Gly Gly Leu Ser Ser Ser Pro Val
65                  70                  75                  80

Thr Phe Thr Tyr Val
                85

<210> SEQ ID NO 81
<211> LENGTH: 47
<212> TYPE: PRT
<213> ORGANISM: Artificial Sequence
<220> FEATURE:
<223> OTHER INFORMATION: Description of Artificial Sequence: PSI domain
      Consensus Sequence

<400> SEQUENCE: 81

Arg Cys Ser Ala Tyr Thr Ser Cys Ser Glu Cys Leu Leu Ala Arg Asp
1               5                   10                  15

Pro Tyr Cys Ala Trp Cys Ser Ser Gln Gly Arg Cys Thr Ser Gly Glu
            20                  25                  30

Arg Cys Asp Ser Leu Arg Gln Asn Trp Ser Ser Gly Gln Cys Pro
        35                  40                  45

<210> SEQ ID NO 82
<211> LENGTH: 93
<212> TYPE: PRT
<213> ORGANISM: Artificial Sequence
<220> FEATURE:
<223> OTHER INFORMATION: Description of Artificial Sequence: IPT
      Consensus Sequence

<400> SEQUENCE: 82

Asp Pro Val Ile Thr Arg Ile Ser Pro Asn Ser Gly Pro Leu Ser Gly
1               5                   10                  15

Gly Thr Arg Ile Thr Leu Cys Gly Lys Asn Leu Asp Ser Ile Ser Val
            20                  25                  30

Val Phe Val Glu Val Gly Val Gly Glu Val Pro Cys Thr Phe Leu Pro
        35                  40                  45

Ser Asp Val Ser Gln Thr Ala Ile Val Cys Lys Thr Pro Pro Tyr His
    50                  55                  60

Asn Ile Pro Gly Ser Val Pro Val Arg Val Glu Val Gly Leu Arg Asn
65                  70                  75                  80

Gly Gly Val Pro Gly Glu Pro Ser Pro Phe Thr Tyr Val
                85                  90

<210> SEQ ID NO 83
<211> LENGTH: 254
<212> TYPE: PRT
<213> ORGANISM: Artificial Sequence
<220> FEATURE:
<223> OTHER INFORMATION: Description of Artificial Sequence: 7
      transmembrane receptor Consensus Sequence

<400> SEQUENCE: 83

Gly Asn Leu Leu Val Ile Leu Val Ile Leu Arg Thr Lys Lys Leu Arg
1               5                   10                  15

```
Thr Pro Thr Asn Ile Phe Leu Asn Leu Ala Val Ala Asp Leu Leu
            20                  25                  30

Phe Leu Leu Thr Leu Pro Pro Trp Ala Leu Tyr Tyr Leu Val Gly Gly
        35                  40                  45

Asp Trp Val Phe Gly Asp Ala Leu Cys Lys Leu Val Gly Ala Leu Phe
    50                  55                  60

Val Val Asn Gly Tyr Ala Ser Ile Leu Leu Thr Ala Ile Ser Ile
65                  70                  75                  80

Asp Arg Tyr Leu Ala Ile Val His Pro Leu Arg Tyr Arg Arg Ile Arg
                85                  90                  95

Thr Pro Arg Arg Ala Lys Val Leu Ile Leu Leu Val Trp Val Leu Ala
            100                 105                 110

Leu Leu Leu Ser Leu Pro Pro Leu Leu Phe Ser Trp Leu Arg Thr Val
            115                 120                 125

Glu Glu Gly Asn Thr Thr Val Cys Leu Ile Asp Phe Pro Glu Glu Ser
    130                 135                 140

Val Lys Arg Ser Tyr Val Leu Leu Ser Thr Leu Val Gly Phe Val Leu
145                 150                 155                 160

Pro Leu Leu Val Ile Leu Val Cys Tyr Thr Arg Ile Leu Arg Thr Leu
                165                 170                 175

Arg Lys Arg Ala Arg Ser Gln Arg Ser Leu Lys Arg Ser Ser Ser
            180                 185                 190

Glu Arg Lys Ala Ala Lys Met Leu Leu Val Val Val Val Phe Val
            195                 200                 205

Leu Cys Trp Leu Pro Tyr His Ile Val Leu Leu Asp Ser Leu Cys
    210                 215                 220

Leu Leu Ser Ile Trp Arg Val Leu Pro Thr Ala Leu Leu Ile Thr Leu
225                 230                 235                 240

Trp Leu Ala Tyr Val Asn Ser Cys Leu Asn Pro Ile Ile Tyr
                245                 250
```

<210> SEQ ID NO 84
<211> LENGTH: 402
<212> TYPE: PRT
<213> ORGANISM: Artificial Sequence
<220> FEATURE:
<223> OTHER INFORMATION: Description of Artificial Sequence: ANF
      receptor Consensus Sequence

<400> SEQUENCE: 84

```
Gly Leu Ile Asn Tyr Ala Val Arg Gly Ile Thr Arg Leu Glu Ala Met
1               5                   10                  15

Leu Gly Ala Phe Asp Arg Ile Asn Ala Asp Pro Ala Leu Leu Pro Gly
            20                  25                  30

Leu Ala Leu Gly Leu Ala Ile Leu Asp Ile Asn Ser Leu Arg Asn Val
        35                  40                  45

Ala Leu Glu Gln Ser Phe Thr Phe Val Tyr Gly Leu Leu Ile Lys Cys
    50                  55                  60

Asp Cys Ser Ser Val Arg Cys Ala Gly Gly Asp Leu Ala Leu Thr His
65                  70                  75                  80

Gly Val Ala Gly Val Ile Gly Pro Ser Cys Ser Ser Ala Ile Gln
                85                  90                  95

Val Ala Asn Leu Ala Ser Leu Leu Asn Ile Pro Met Ile Ser Tyr Gly
            100                 105                 110

Ser Thr Ala Pro Glu Leu Ser Asp Lys Thr Arg Tyr Pro Thr Phe Ser
        115                 120                 125
```

```
Arg Thr Ile Pro Ser Asp Ala Phe Gln Gly Leu Ala Met Val Asp Ile
            130                 135                 140

Phe Lys His Phe Asn Trp Asn Tyr Val Ser Val Tyr Ser Asp Gly
145                 150                 155                 160

Thr Tyr Gly Glu Glu Gly Cys Glu Ala Phe Ile Glu Ala Leu Arg Ala
                165                 170                 175

Arg Gly Gly Cys Ile Ala Leu Ser Val Lys Ile Gly Glu Phe Asp Arg
            180                 185                 190

Gly Asp Glu Glu Asp Phe Asp Lys Leu Leu Arg Glu Leu Lys Arg Arg
            195                 200                 205

Ala Arg Val Val Val Met Cys Gly His Gly Glu Thr Leu Arg Glu Leu
210                 215                 220

Leu Glu Ala Ala Leu Arg Leu Gly Leu Thr Gly Glu Asp Tyr Val Phe
225                 230                 235                 240

Ile Ser Asp Asp Leu Phe Asn Lys Ser Leu Pro Ala Glu Pro Gly Ala
                245                 250                 255

Pro Gly Ala Ile Glu Leu Ala Asn Ala Ser Met Leu Arg Phe Ala Tyr
            260                 265                 270

Tyr Phe Val Leu Val Leu Thr Leu Asn Asn Pro Arg Asn Pro Trp Phe
            275                 280                 285

Leu Glu Phe Trp Lys Glu Asn Phe Ile Cys Ala Leu Gln Asp Phe Leu
290                 295                 300

Thr Leu Glu Pro Tyr Glu Gln Glu Gly Lys Ala Gly Phe Val Tyr Asp
305                 310                 315                 320

Ala Val Tyr Leu Tyr Ala His Ala Leu His Asn Thr Thr Leu Ala Leu
                325                 330                 335

Gly Gly Ser Trp Val Asp Gly Glu Lys Leu Val Gln His Leu Arg Asn
            340                 345                 350

Leu Thr Phe Glu Gly Val Thr Gly Pro Val Thr Phe Asp Glu Asn Gly
            355                 360                 365

Asp Arg Asp Gly Asp Tyr Val Leu Leu Asp Thr Gln Asn Thr Glu Thr
370                 375                 380

Gly Gln Leu Lys Val Thr Gly Thr Tyr Asp Gly Val Gly Lys Trp Thr
385                 390                 395                 400

Glu Pro

<210> SEQ ID NO 85
<211> LENGTH: 256
<212> TYPE: PRT
<213> ORGANISM: Artificial Sequence
<220> FEATURE:
<223> OTHER INFORMATION: Description of Artificial Sequence: 7
      transmembrane receptor (metabotrobic E family)
      Consensus Sequence

<400> SEQUENCE: 85

Leu Gly Ile Val Leu Val Ala Leu Ala Val Leu Gly Ile Val Leu Thr
 1               5                  10                  15

Leu Phe Val Leu Val Val Phe Val Lys His Arg Asp Thr Pro Ile Val
                20                  25                  30

Lys Ala Ser Asn Arg Glu Leu Ser Tyr Leu Leu Leu Ile Gly Leu Ile
            35                  40                  45

Leu Cys Tyr Leu Cys Ser Phe Leu Phe Ile Gly Lys Pro Ser Glu Thr
        50                  55                  60

Ser Cys Ile Leu Arg Arg Ile Leu Phe Gly Leu Gly Phe Thr Leu Cys
```

```
                65                  70                  75                  80
Tyr Ser Ala Leu Leu Ala Lys Thr Asn Arg Val Leu Arg Ile Phe Arg
                    85                  90                  95
Ala Lys Lys Pro Gly Ser Gly Lys Pro Lys Phe Ile Ser Pro Trp Ala
                100                 105                 110
Gln Val Leu Ile Val Leu Ile Leu Val Leu Ile Gln Val Ile Ile Cys
                115                 120                 125
Val Ile Trp Leu Val Val Glu Pro Pro Arg Pro Thr Ile Asp Ile Tyr
        130                 135                 140
Ser Glu Lys Glu Lys Ile Ile Leu Glu Cys Asn Lys Gly Ser Met Val
145                 150                 155                 160
Ala Phe Val Val Leu Gly Tyr Asp Gly Leu Leu Ala Val Leu Cys
                165                 170                 175
Thr Phe Leu Ala Phe Leu Thr Arg Asn Leu Pro Glu Asn Phe Asn Glu
                180                 185                 190
Ala Lys Phe Ile Gly Phe Ser Met Leu Thr Phe Cys Ile Val Trp Val
                195                 200                 205
Ala Phe Ile Pro Ile Tyr Leu Ser Thr Pro Gly Lys Val Gln Val Ala
        210                 215                 220
Val Glu Ile Phe Ser Ile Leu Ala Ser Ser Thr Val Leu Leu Gly Cys
225                 230                 235                 240
Leu Phe Val Pro Lys Cys Tyr Ile Ile Leu Phe Arg Pro Glu Lys Asn
                245                 250                 255

<210> SEQ ID NO 86
<211> LENGTH: 86
<212> TYPE: PRT
<213> ORGANISM: Artificial Sequence
<220> FEATURE:
<223> OTHER INFORMATION: Description of Artificial Sequence: PDZ
      domain Consensus Sequence

<400> SEQUENCE: 86

Glu Pro Arg Leu Val Glu Leu Glu Lys Gly Gly Gly Gly Leu Gly Phe
1               5                   10                  15
Ser Leu Val Gly Gly Lys Asp Ser Gly Asp Gly Val Val Val Ser
            20                  25                  30
Ser Val Val Pro Gly Ser Pro Ala Ala Lys Ala Gly Leu Lys Pro Gly
        35                  40                  45
Asp Val Ile Leu Glu Val Asn Gly Thr Ser Val Glu Gly Leu Thr His
    50                  55                  60
Leu Glu Ala Val Asp Leu Leu Lys Glu Ala Gly Gly Lys Val Thr Leu
65                  70                  75                  80
Thr Val Leu Arg Gly Gly
                85

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: NOV1c
      Primer 1

<400> SEQUENCE: 87
tcatcacatg acaacatgaa gctgt                                         25

<210> SEQ ID NO 88
```

```
<211> LENGTH: 26
<212> TYPE: DNA
<213> ORGANISM: Artificial Sequence
<220> FEATURE:
<223> OTHER INFORMATION: Description of Artificial Sequence: NOV1c
      Primer 2

<400> SEQUENCE: 88
gaaagccctc aaactctcca tctatg                                      26

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: NOV7a
      Primer 1

<400> SEQUENCE: 89
ccaatctctg atgccctgcg at                                          22

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: NOV7a
      Primer 2

<400> SEQUENCE: 90
aggtcagtgc cggagcctcc                                             20

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Ag273b
      Forward

<400> SEQUENCE: 91
cggcttgacg atgcttcac                                              19

<210> SEQ ID NO 92
<211> LENGTH: 32
<212> TYPE: DNA
<213> ORGANISM: Artificial Sequence
<220> FEATURE:
<223> OTHER INFORMATION: Description of Artificial Sequence: Ag273b
      Probe

<400> SEQUENCE: 92
tgacttttct gggcttacca atgctatttc aa                               32

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Ag273b
      Reverse

<400> SEQUENCE: 93
gcacctatct caatatctgc aatattg                                     27

<210> SEQ ID NO 94
<211> LENGTH: 20
```

```
<212> TYPE: DNA
<213> ORGANISM: Artificial Sequence
<220> FEATURE:
<223> OTHER INFORMATION: Description of Artificial Sequence: Ag1094
      Forward

<400> SEQUENCE: 94
atggactgga aaacctggaa                                                    20

<210> SEQ ID NO 95
<211> LENGTH: 29
<212> TYPE: DNA
<213> ORGANISM: Artificial Sequence
<220> FEATURE:
<223> OTHER INFORMATION: Description of Artificial Sequence: Ag1094
      Probe

<400> SEQUENCE: 95
tcctgcaagc agataacaat tttatcaca                                          29

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Ag1094
      Reverse

<400> SEQUENCE: 96
tgctaaaggc acttggttca                                                    20

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Ag2100
      Forward

<400> SEQUENCE: 97
agatccctgg aacagaggat t                                                  21

<210> SEQ ID NO 98
<211> LENGTH: 26
<212> TYPE: DNA
<213> ORGANISM: Artificial Sequence
<220> FEATURE:
<223> OTHER INFORMATION: Description of Artificial Sequence: Ag2100
      Probe

<400> SEQUENCE: 98
tgtctgaagc caataaactt gcagca                                             26

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Ag2100
      Reverse

<400> SEQUENCE: 99
ccttcatgtt cctttgggta a                                                  21

<210> SEQ ID NO 100
<211> LENGTH: 22
<212> TYPE: DNA
```

```
<213> ORGANISM: Artificial Sequence
<220> FEATURE:
<223> OTHER INFORMATION: Description of Artificial Sequence: Ag217
      Forward

<400> SEQUENCE: 100
atctgtgctg aggcatgttc ct                                                 22

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Ag217
      Probe

<400> SEQUENCE: 101
atcctcctcc ctccccggct ctc                                                23

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Ag217
      Reverse

<400> SEQUENCE: 102
ctgcatggct ggtgtgatg                                                     19

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Ag850
      Forward

<400> SEQUENCE: 103
cctttcttct cttcctcctc aa                                                 22

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Ag850
      Probe

<400> SEQUENCE: 104
cacctggcga gtgctcctct ctg                                                23

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Ag850
      Reverse

<400> SEQUENCE: 105
ggtggatggc gttgtagag                                                     19

<210> SEQ ID NO 106
<211> LENGTH: 22
<212> TYPE: DNA
<213> ORGANISM: Artificial Sequence
```

```
<220> FEATURE:
<223> OTHER INFORMATION: Description of Artificial Sequence: Ag1469
      Forward

<400> SEQUENCE: 106
cgtacgtctt ccatgatgag tt                                             22

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Ag1469
      Probe

<400> SEQUENCE: 107
cgtggcctcg atgattaaga tccctt                                         26

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Ag1469
      Reverse

<400> SEQUENCE: 108
aagtcaggga tgatggtgaa g                                              21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Ag2976
      Forward

<400> SEQUENCE: 109
accccaaatg gattccatta                                                20

<210> SEQ ID NO 110
<211> LENGTH: 26
<212> TYPE: DNA
<213> ORGANISM: Artificial Sequence
<220> FEATURE:
<223> OTHER INFORMATION: Description of Artificial Sequence: Ag2976
      Probe

<400> SEQUENCE: 110
ccctcatgga tctgcataac cacaca                                         26

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Ag2976
      Reverse

<400> SEQUENCE: 111
cttgtgtgtg catgcttgtc                                                20

<210> SEQ ID NO 112
<211> LENGTH: 22
<212> TYPE: DNA
<213> ORGANISM: Artificial Sequence
<220> FEATURE:
```

<223> OTHER INFORMATION: Description of Artificial Sequence: Ag760
      Forward

<400> SEQUENCE: 112
caccatgaca acgacaccta ta                                            22

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Ag760
      Probe

<400> SEQUENCE: 113
atatggcacc aacatcacat gcacg                                         25

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Ag760
      Reverse

<400> SEQUENCE: 114
tgggtagaaa gtgtgtgtga aa                                            22

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Ag1537
      Forward

<400> SEQUENCE: 115
aaggagctgg aagagaagaa ga                                            22

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Ag1537
      Probe

<400> SEQUENCE: 116
atcagaaact cagccctgga cacctg                                        26

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Ag1537
      Reverse

<400> SEQUENCE: 117
gctgcgactt ggtcttgat                                                19

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Ag147

-continued

```
      Forward

<400> SEQUENCE: 118
tgaagacagc acctccctat ca                                              22

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Ag147
      Probe

<400> SEQUENCE: 119
cggctccgtg ctgtcaccca g                                               21

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Ag147
      Reverse

<400> SEQUENCE: 120
aagaatcctc agcatcgcca ta                                              22

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Ag718
      Forward

<400> SEQUENCE: 121
agaaggaatc tctgggaaag ct                                              22

<210> SEQ ID NO 122
<211> LENGTH: 27
<212> TYPE: DNA
<213> ORGANISM: Artificial Sequence
<220> FEATURE:
<223> OTHER INFORMATION: Description of Artificial Sequence: Ag718
      Probe

<400> SEQUENCE: 122
ccactggaga tgcttgtgtc tctacca                                         27

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Ag718
      Reverse

<400> SEQUENCE: 123
gacagagcac tggctagttc ac                                              22

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Ag3681/
      Ag4085 Forward
```

```
<400> SEQUENCE: 124
gaatcatcca caagtcatcc at                                              22

<210> SEQ ID NO 125
<211> LENGTH: 25
<212> TYPE: DNA
<213> ORGANISM: Artificial Sequence
<220> FEATURE:
<223> OTHER INFORMATION: Description of Artificial Sequence: Ag3681/
      Ag4085 Probe

<400> SEQUENCE: 125
ctcactccca tctcatgcct cccag                                           25

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Ag3681/
      Ag4085 Reverse

<400> SEQUENCE: 126
catgctgaat gatcgtgaca                                                 20

<210> SEQ ID NO 127
<211> LENGTH: 1011
<212> TYPE: PRT
<213> ORGANISM: Homo sapiens

<400> SEQUENCE: 127
```

| Ile | Ser | Asn | Ser | Ser | Asp | Thr | Val | Glu | Cys | Glu | Cys | Ser | Glu | Asn | Trp |
|---|---|---|---|---|---|---|---|---|---|---|---|---|---|---|---|
| 1 | | | | 5 | | | | | 10 | | | | | 15 | |

| Lys | Gly | Glu | Ala | Cys | Asp | Ile | Pro | His | Cys | Thr | Asp | Asn | Cys | Gly | Phe |
|---|---|---|---|---|---|---|---|---|---|---|---|---|---|---|---|
| | | | 20 | | | | | 25 | | | | | 30 | | |

| Pro | His | Arg | Gly | Ile | Cys | Asn | Ser | Ser | Asp | Val | Arg | Gly | Cys | Ser | Cys |
|---|---|---|---|---|---|---|---|---|---|---|---|---|---|---|---|
| | | 35 | | | | | 40 | | | | | 45 | | | |

| Phe | Ser | Asp | Trp | Gln | Gly | Pro | Gly | Cys | Ser | Val | Pro | Val | Pro | Ala | Asn |
|---|---|---|---|---|---|---|---|---|---|---|---|---|---|---|---|
| 50 | | | | | 55 | | | | | 60 | | | | | |

| Gln | Ser | Phe | Trp | Thr | Arg | Glu | Glu | Tyr | Ser | Asn | Leu | Lys | Leu | Pro | Arg |
|---|---|---|---|---|---|---|---|---|---|---|---|---|---|---|---|
| 65 | | | | | 70 | | | | | 75 | | | | | 80 |

| Ala | Ser | His | Lys | Ala | Val | Val | Asn | Gly | Asn | Ile | Met | Trp | Val | Val | Gly |
|---|---|---|---|---|---|---|---|---|---|---|---|---|---|---|---|
| | | | 85 | | | | | 90 | | | | | 95 | | |

| Gly | Tyr | Met | Phe | Asn | His | Ser | Asp | Tyr | Asn | Met | Val | Leu | Ala | Tyr | Asp |
|---|---|---|---|---|---|---|---|---|---|---|---|---|---|---|---|
| | | | 100 | | | | | 105 | | | | | 110 | | |

| Leu | Ala | Ser | Arg | Glu | Trp | Leu | Pro | Leu | Asn | Arg | Ser | Val | Asn | Asn | Val |
|---|---|---|---|---|---|---|---|---|---|---|---|---|---|---|---|
| | | | 115 | | | | | 120 | | | | | 125 | | |

| Val | Val | Arg | Tyr | Gly | His | Ser | Leu | Ala | Leu | Tyr | Lys | Asp | Lys | Ile | Tyr |
|---|---|---|---|---|---|---|---|---|---|---|---|---|---|---|---|
| | 130 | | | | | 135 | | | | | 140 | | | | |

| Met | Tyr | Gly | Gly | Lys | Ile | Asp | Ser | Thr | Gly | Asn | Val | Thr | Asn | Glu | Leu |
|---|---|---|---|---|---|---|---|---|---|---|---|---|---|---|---|
| 145 | | | | | 150 | | | | | 155 | | | | | 160 |

| Arg | Val | Phe | His | Ile | His | Asn | Glu | Ser | Trp | Val | Leu | Leu | Thr | Pro | Lys |
|---|---|---|---|---|---|---|---|---|---|---|---|---|---|---|---|
| | | | | 165 | | | | | 170 | | | | | 175 | |

| Ala | Lys | Glu | Gln | Tyr | Ala | Val | Val | Gly | His | Ser | Ala | His | Ile | Val | Thr |
|---|---|---|---|---|---|---|---|---|---|---|---|---|---|---|---|
| | | | 180 | | | | | 185 | | | | | 190 | | |

| Leu | Lys | Asn | Gly | Arg | Val | Val | Met | Leu | Val | Ile | Phe | Gly | His | Cys | Pro |
|---|---|---|---|---|---|---|---|---|---|---|---|---|---|---|---|
| | | | 195 | | | | | 200 | | | | | 205 | | |

| Leu | Tyr | Gly | Tyr | Ile | Ser | Asn | Val | Gln | Glu | Tyr | Asp | Leu | Asp | Lys | Asn |

-continued

```
            210                 215                 220
Thr Trp Ser Ile Leu His Thr Gln Gly Ala Leu Val Gln Gly Gly Tyr
225                 230                 235                 240

Gly His Ser Ser Val Tyr Asp His Arg Thr Arg Ala Leu Tyr Val His
                245                 250                 255

Gly Gly Tyr Lys Ala Phe Ser Ala Asn Lys Tyr Arg Leu Ala Asp Asp
                260                 265                 270

Leu Tyr Arg Tyr Asp Val Asp Thr Gln Met Trp Thr Ile Leu Lys Asp
                275                 280                 285

Ser Arg Phe Phe Arg Tyr Leu His Thr Ala Val Ile Val Ser Gly Thr
290                 295                 300

Met Leu Val Phe Gly Gly Asn Thr His Asn Asp Thr Ser Met Ser His
305                 310                 315                 320

Gly Ala Lys Cys Phe Ser Asp Phe Met Ala Tyr Asp Ile Ala Cys
                325                 330                 335

Asp Arg Trp Ser Val Leu Pro Arg Pro Asp Leu His His Asp Val Asn
                340                 345                 350

Arg Phe Gly His Ser Ala Val Leu His Asn Ser Thr Met Tyr Val Phe
                355                 360                 365

Gly Gly Phe Asn Ser Leu Leu Leu Ser Asp Ile Leu Val Phe Thr Ser
370                 375                 380

Glu Gln Cys Asp Ala His Arg Ser Glu Ala Ala Cys Leu Ala Ala Gly
385                 390                 395                 400

Pro Gly Ile Arg Cys Val Trp Asn Thr Gly Ser Ser Gln Cys Ile Ser
                405                 410                 415

Trp Ala Leu Ala Thr Asp Glu Gln Glu Glu Lys Leu Lys Ser Glu Cys
                420                 425                 430

Phe Ser Lys Arg Thr Leu Asp His Asp Arg Cys Asp Gln His Thr Asp
                435                 440                 445

Cys Tyr Ser Cys Thr Ala Asn Thr Asn Asp Cys His Trp Cys Asn Asp
                450                 455                 460

His Cys Val Pro Arg Asn His Ser Cys Ser Glu Gly Gln Ile Ser Ile
465                 470                 475                 480

Phe Arg Tyr Glu Asn Cys Pro Lys Asp Asn Pro Met Tyr Tyr Cys Asn
                485                 490                 495

Lys Lys Thr Ser Cys Arg Ser Cys Ala Leu Asp Gln Asn Cys Gln Trp
                500                 505                 510

Glu Pro Arg Asn Gln Glu Cys Ile Ala Leu Pro Glu Asn Ile Cys Gly
                515                 520                 525

Ile Gly Trp His Leu Val Gly Asn Ser Cys Leu Lys Ile Thr Thr Ala
                530                 535                 540

Lys Glu Asn Tyr Asp Asn Ala Lys Leu Phe Cys Arg Asn His Asn Ala
545                 550                 555                 560

Leu Leu Ala Ser Leu Thr Thr Gln Lys Lys Val Glu Phe Val Leu Lys
                565                 570                 575

Gln Leu Arg Ile Met Gln Ser Ser Gln Ser Met Ser Lys Leu Thr Leu
                580                 585                 590

Thr Pro Trp Val Gly Leu Arg Lys Ile Asn Val Ser Tyr Trp Cys Trp
                595                 600                 605

Glu Asp Met Ser Pro Phe Thr Asn Ser Leu Leu Gln Trp Met Pro Ser
                610                 615                 620

Glu Pro Ser Asp Ala Gly Phe Cys Gly Ile Leu Ser Glu Pro Ser Thr
625                 630                 635                 640
```

-continued

```
Arg Gly Leu Lys Ala Ala Thr Cys Ile Asn Pro Leu Asn Gly Ser Val
            645                 650                 655
Cys Glu Arg Pro Ala Asn His Ser Ala Lys Gln Cys Arg Thr Pro Cys
            660                 665                 670
Ala Leu Arg Thr Ala Cys Gly Asp Cys Thr Ser Gly Ser Ser Glu Cys
            675                 680                 685
Met Trp Cys Ser Asn Met Lys Gln Cys Val Asp Ser Asn Ala Tyr Val
            690                 695                 700
Ala Ser Phe Pro Phe Gly Gln Cys Met Glu Trp Tyr Thr Met Ser Thr
705                 710                 715                 720
Cys Pro Pro Glu Asn Cys Ser Gly Tyr Cys Thr Cys Ser His Cys Leu
            725                 730                 735
Glu Gln Pro Gly Cys Gly Trp Cys Thr Asp Pro Ser Asn Thr Gly Lys
            740                 745                 750
Gly Lys Cys Ile Glu Gly Ser Tyr Lys Gly Pro Val Lys Met Pro Ser
            755                 760                 765
Gln Ala Pro Thr Gly Asn Phe Tyr Pro Gln Pro Leu Leu Asn Ser Ser
            770                 775                 780
Met Cys Leu Glu Asp Ser Arg Tyr Asn Trp Ser Phe Ile His Cys Pro
785                 790                 795                 800
Ala Cys Gln Cys Asn Gly His Ser Lys Cys Ile Asn Gln Ser Ile Cys
            805                 810                 815
Glu Lys Cys Glu Asn Leu Thr Thr Gly Lys His Cys Glu Thr Cys Ile
            820                 825                 830
Ser Gly Phe Tyr Gly Asp Pro Thr Asn Gly Gly Lys Cys Gln Pro Cys
            835                 840                 845
Lys Cys Asn Gly His Ala Ser Leu Cys Asn Thr Asn Thr Gly Lys Cys
            850                 855                 860
Phe Cys Thr Thr Lys Gly Val Lys Gly Asp Glu Cys Gln Leu Cys Glu
865                 870                 875                 880
Val Glu Asn Arg Tyr Gln Gly Asn Pro Leu Arg Gly Thr Cys Tyr Tyr
            885                 890                 895
Thr Leu Leu Ile Asp Tyr Gln Phe Thr Phe Ser Leu Ser Gln Glu Asp
            900                 905                 910
Asp Arg Tyr Tyr Thr Ala Ile Asn Phe Val Ala Thr Pro Asp Glu Gln
            915                 920                 925
Asn Arg Asp Leu Asp Met Phe Ile Asn Ala Ser Lys Asn Phe Asn Leu
            930                 935                 940
Asn Ile Thr Trp Ala Ala Ser Phe Ser Ala Gly Thr Gln Ala Gly Glu
945                 950                 955                 960
Glu Met Pro Val Val Ser Lys Thr Asn Ile Lys Glu Tyr Lys Asp Ser
            965                 970                 975
Phe Ser Asn Glu Lys Phe Asp Phe Arg Asn His Pro Asn Ile Thr Phe
            980                 985                 990
Phe Val Tyr Val Ser Asn Phe Thr Trp Pro Ile Lys Ile Gln Val Gln
            995                 1000                1005
Thr Glu Gln
    1010
```